US012735386B2

(12) United States Patent
Nivorozhkin et al.

(10) Patent No.: US 12,735,386 B2
(45) Date of Patent: Sep. 15, 2026

(54) PSILOCYBIN ANALOGS, SALTS, COMPOSITIONS, AND METHODS OF USE

(71) Applicant: Cybin IRL Limited, North Wall Quay (IE)

(72) Inventors: Alex Nivorozhkin, West Roxbury, MA (US); Pradip Pathare, Lexington, MA (US); Kenneth L. Avery, Merrimack, NH (US)

(73) Assignee: Cybin IRL Limited, Dublin (IE)

( * ) Notice: Subject to any disclaimer, the term of this patent is extended or adjusted under 35 U.S.C. 154(b) by 211 days.

(21) Appl. No.: 18/547,100

(22) PCT Filed: Mar. 17, 2022

(86) PCT No.: PCT/EP2022/056991
§ 371 (c)(1),
(2) Date: Aug. 18, 2023

(87) PCT Pub. No.: WO2022/195011
PCT Pub. Date: Sep. 22, 2022

(65) Prior Publication Data

US 2024/0174607 A1 May 30, 2024

Related U.S. Application Data

(60) Provisional application No. 63/276,117, filed on Nov. 5, 2021, provisional application No. 63/162,749, filed on Mar. 18, 2021.

(51) Int. Cl.

| | |
|---|---|
| ***C07D 209/16*** | (2006.01) |
| ***C07B 59/00*** | (2006.01) |
| ***C07C 53/10*** | (2006.01) |
| ***C07C 53/126*** | (2006.01) |
| ***C07C 55/06*** | (2006.01) |
| ***C07C 55/08*** | (2006.01) |
| ***C07C 55/10*** | (2006.01) |
| ***C07C 57/03*** | (2006.01) |
| ***C07C 57/15*** | (2006.01) |
| ***C07C 59/255*** | (2006.01) |
| ***C07C 59/265*** | (2006.01) |
| ***C07C 63/08*** | (2006.01) |
| ***C07C 65/10*** | (2006.01) |
| ***C07C 309/29*** | (2006.01) |

(52) U.S. Cl.

CPC .......... *C07D 209/16* (2013.01); *C07B 59/002* (2013.01); *C07C 53/10* (2013.01); *C07C 53/126* (2013.01); *C07C 55/06* (2013.01); *C07C 55/08* (2013.01); *C07C 55/10* (2013.01); *C07C 57/03* (2013.01); *C07C 57/15* (2013.01); *C07C 59/255* (2013.01); *C07C 59/265* (2013.01); *C07C 63/08* (2013.01); *C07C 65/10* (2013.01); *C07C 309/29* (2013.01)

(58) Field of Classification Search

CPC ..... C07D 209/16; C07B 59/002; C07C 53/10; C07C 53/126; C07C 55/06; C07C 55/08; C07C 55/10; C07C 57/03; C07C 57/15; C07C 59/255; C07C 59/265; C07C 63/08; C07C 65/10; C07C 309/29

See application file for complete search history.

(56) References Cited

U.S. PATENT DOCUMENTS

| | | | |
|---|---|---|---|
| 3,072,530 | A | 1/1963 | Hofmann et al. |
| 3,078,214 | A | 2/1963 | Hofmann et al. |
| 3,192,111 | A | 6/1965 | Hofmann et al. |
| 3,444,174 | A | 5/1969 | Remers et al. |
| 3,686,213 | A | 8/1972 | Poletto et al. |
| 4,855,325 | A | 8/1989 | Naftchi |
| 5,158,956 | A | 10/1992 | Gidda et al. |
| 5,258,379 | A | 11/1993 | Gidda et al. |

(Continued)

FOREIGN PATENT DOCUMENTS

| | | | |
|---|---|---|---|
| AT | 501069 | A1 | 6/2006 |
| AU | 3230299 | A | 12/1999 |

(Continued)

OTHER PUBLICATIONS

Cybin IRL Limited, "A Study of a Psilocybin Analog (CYB003) in Healthy Participants With and Without Major Depressive Disorder", ClinicalTrials.gov ID: NCT05385783, May 18, 2022.

(Continued)

*Primary Examiner* — Kamal A Saeed
*Assistant Examiner* — Quincy McKoy
(74) *Attorney, Agent, or Firm* — Lathrop GPM LLP; Lisa Hillman

(57) ABSTRACT

The present disclosure relates to psilocin compounds and pharmaceutically acceptable salts, polymorphs, stereoisomers, or solvates thereof, to pharmaceutical compositions, and in some embodiments, to serotonin 5-$HT_2$ receptor agonists and uses in the treatment of diseases associated with a 5-$HT_2$ receptor.

(I)

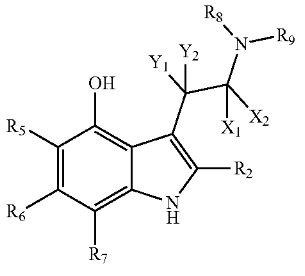

23 Claims, 159 Drawing Sheets

(56) References Cited

U.S. PATENT DOCUMENTS

| | | | |
|---|---|---|---|
| 5,417,987 | A | 5/1995 | Dietz et al. |
| 5,594,034 | A | 1/1997 | Gidda et al. |
| 6,107,499 | A | 8/2000 | Chan et al. |
| 6,207,396 | B1 | 3/2001 | Sigler et al. |
| 6,306,616 | B1 | 10/2001 | Shindelman |
| 6,403,808 | B1 | 6/2002 | Glennon et al. |
| 6,407,137 | B2 | 6/2002 | Shashoua |
| 6,815,212 | B2 | 11/2004 | Ness et al. |
| 7,052,846 | B2 | 5/2006 | Van Ness et al. |
| 7,642,344 | B2 | 1/2010 | Van Ness et al. |
| 8,980,880 | B1 | 3/2015 | King et al. |
| 9,139,821 | B2 | 9/2015 | Nazor et al. |
| 9,226,925 | B1 | 1/2016 | King et al. |
| 10,183,001 | B1 | 1/2019 | King et al. |
| 10,519,175 | B2 | 12/2019 | Londesbrough et al. |
| 10,729,706 | B2 | 8/2020 | Kucuksen et al. |
| 10,738,268 | B2 | 8/2020 | Leo |
| 10,933,073 | B2 | 3/2021 | Chadeayne |
| 11,000,534 | B1 | 5/2021 | Sippy |
| 11,136,293 | B2 | 10/2021 | Protzko |
| 11,312,684 | B1 | 4/2022 | Nichols et al. |
| 11,344,564 | B1 | 5/2022 | Sippy |
| 11,970,447 | B2 | 4/2024 | Schultheiss et al. |
| 2001/0008641 | A1 | 7/2001 | Krotzer |
| 2003/0007961 | A1 | 1/2003 | Wilburn |
| 2003/0078231 | A1 | 4/2003 | Wilburn |
| 2003/0096013 | A1 | 5/2003 | Werling et al. |
| 2004/0105881 | A1 | 6/2004 | Cevc et al. |
| 2004/0132800 | A1 | 7/2004 | Chen et al. |
| 2004/0180147 | A1 | 9/2004 | Parikh et al. |
| 2004/0258617 | A1 | 12/2004 | Weber |
| 2005/0288616 | A1 | 12/2005 | Bozenbury et al. |
| 2006/0192098 | A1 | 8/2006 | Danylewych-May |
| 2008/0194553 | A1 | 8/2008 | Gillessen |
| 2008/0220441 | A1 | 9/2008 | Birnbaum et al. |
| 2008/0221170 | A1 | 9/2008 | Roberts et al. |
| 2008/0227830 | A1 | 9/2008 | Roberts et al. |
| 2008/0241255 | A1 | 10/2008 | Rose et al. |
| 2009/0028796 | A1 | 1/2009 | Bednarek et al. |
| 2009/0093513 | A1 | 4/2009 | Hamann et al. |
| 2009/0197822 | A1 | 8/2009 | Griffin |
| 2009/0286760 | A1 | 11/2009 | Chen |
| 2009/0318527 | A1 | 12/2009 | Sard et al. |
| 2010/0137616 | A1 | 6/2010 | Sard et al. |
| 2010/0292448 | A1 | 11/2010 | Nilssen |
| 2011/0060037 | A1 | 3/2011 | Woldbye et al. |
| 2011/0207627 | A1 | 8/2011 | Liotta et al. |
| 2012/0108510 | A1 | 5/2012 | Young et al. |
| 2012/0183600 | A1 | 7/2012 | Chen |
| 2013/0210167 | A1 | 8/2013 | Benchikh et al. |
| 2013/0303735 | A1 | 11/2013 | Epshtein et al. |
| 2014/0066881 | A1 | 3/2014 | Freeman |
| 2014/0242722 | A1 | 8/2014 | Knop et al. |
| 2014/0256688 | A1 | 9/2014 | Lozinsky |
| 2014/0349976 | A1 | 11/2014 | Hacksell et al. |
| 2015/0343144 | A1 | 12/2015 | Altscul et al. |
| 2016/0067711 | A1 | 3/2016 | Yoon et al. |
| 2016/0338945 | A1 | 11/2016 | Knight |
| 2017/0173262 | A1 | 6/2017 | Veltz |
| 2017/0281652 | A1 | 10/2017 | Altscul et al. |
| 2017/0313666 | A1 | 11/2017 | Wu et al. |
| 2017/0348303 | A1 | 12/2017 | Bosse et al. |
| 2018/0021326 | A1 | 1/2018 | Stamets |
| 2018/0147142 | A1 | 5/2018 | Knight |
| 2018/0221396 | A1 | 8/2018 | Chadeayne |
| 2018/0343812 | A1 | 12/2018 | Leo |
| 2018/0354995 | A1 | 12/2018 | Gudkov et al. |
| 2019/0119310 | A1 | 4/2019 | Londesbrough et al. |
| 2019/0142851 | A1 | 5/2019 | Chadeayne |
| 2019/0246591 | A1 | 8/2019 | Leo |
| 2019/0254988 | A1 | 8/2019 | Archibald |
| 2019/0350949 | A1 | 11/2019 | Kucuksen et al. |
| 2020/0060997 | A1 | 2/2020 | Goren et al. |
| 2020/0114005 | A1 | 4/2020 | Fernandes et al. |
| 2020/0179349 | A1 | 6/2020 | Yun et al. |
| 2020/0229411 | A1 | 7/2020 | Leo |
| 2020/0237683 | A1 | 7/2020 | Whalley et al. |
| 2020/0290992 | A1 | 9/2020 | Zhang |
| 2020/0331939 | A1 | 10/2020 | Londesbrough et al. |
| 2020/0370073 | A1 | 11/2020 | Leo |
| 2020/0375967 | A1 | 12/2020 | Stamets |
| 2020/0397752 | A1 | 12/2020 | Perez et al. |
| 2021/0000803 | A1 | 1/2021 | Sharp et al. |
| 2021/0015738 | A1 | 1/2021 | Larosa et al. |
| 2021/0015833 | A1 | 1/2021 | Larosa et al. |
| 2021/0023052 | A1 | 1/2021 | Chadeayne |
| 2021/0030787 | A1 | 2/2021 | Goren et al. |
| 2021/0069170 | A1 | 3/2021 | Chadeayne |
| 2021/0085671 | A1 | 3/2021 | Chadeayne |
| 2021/0113644 | A1 | 4/2021 | Chadeayne |
| 2021/0137137 | A1 | 5/2021 | Leo |
| 2021/0137854 | A1 | 5/2021 | Goren et al. |
| 2021/0137908 | A1 | 5/2021 | Kristensen et al. |
| 2021/0145851 | A1 | 5/2021 | Stamets |
| 2021/0147888 | A1 | 5/2021 | Vogan et al. |
| 2021/0236523 | A1 | 8/2021 | Schindler et al. |
| 2021/0251157 | A1 | 8/2021 | Leo |
| 2021/0267966 | A1 | 9/2021 | Petcavich |
| 2021/0267985 | A1 | 9/2021 | Horn |
| 2021/0268036 | A1 | 9/2021 | Hsiao et al. |
| 2021/0275618 | A1 | 9/2021 | Davidson et al. |
| 2021/0292278 | A1 | 9/2021 | Chadeayne |
| 2021/0300870 | A1 | 9/2021 | Chadeayne |
| 2021/0308200 | A1 | 10/2021 | Stamets |
| 2021/0322306 | A1 | 10/2021 | Espinoza et al. |
| 2021/0322447 | A1 | 10/2021 | Plakogiannis et al. |
| 2022/0017549 | A1 | 1/2022 | Slassi et al. |
| 2022/0096504 | A1 | 3/2022 | Blumstock et al. |
| 2022/0110955 | A1 | 4/2022 | Sippy |
| 2022/0110956 | A1 | 4/2022 | Sippy |
| 2022/0280482 | A1 | 9/2022 | Barrow et al. |
| 2022/0370413 | A1 | 11/2022 | Barrow et al. |
| 2022/0409584 | A1 | 12/2022 | Bilal et al. |
| 2023/0062523 | A1 | 3/2023 | Sippy |
| 2024/0199545 | A1 | 6/2024 | Schultheiss et al. |
| 2024/0246912 | A1 | 7/2024 | Schultheiss et al. |
| 2025/0213527 | A1 | 7/2025 | Nivorozhkin et al. |

FOREIGN PATENT DOCUMENTS

| | | | |
|---|---|---|---|
| AU | 2007209313 | A1 | 8/2007 |
| AU | 2009214724 | A1 | 8/2009 |
| AU | 2014202047 | A1 | 5/2014 |
| AU | 2015201896 | B2 | 8/2016 |
| AU | 2016208412 | A1 | 8/2016 |
| AU | 2021215274 | A1 | 9/2021 |
| CA | 672478 | A | 10/1963 |
| CA | 2338326 | A1 | 2/2000 |
| CA | 2422730 | A1 | 3/2002 |
| CA | 2487849 | A1 | 1/2004 |
| CA | 2489410 | A1 | 1/2004 |
| CA | 2498938 | A1 | 4/2004 |
| CA | 2686723 | A1 | 11/2008 |
| CA | 3123908 | A1 | 10/2010 |
| CA | 2796883 | A1 | 11/2011 |
| CA | 2816595 | A1 | 4/2012 |
| CA | 2812063 | A1 | 7/2012 |
| CA | 2838667 | A1 | 12/2012 |
| CA | 2909633 | A1 | 9/2014 |
| CA | 2758774 | C | 2/2015 |
| CA | 2952818 | A1 | 11/2016 |
| CA | 3051914 | A1 | 8/2018 |
| CA | 3099293 | A1 | 11/2019 |
| CA | 3127854 | A1 | 8/2020 |
| CA | 3088384 | A1 | 10/2020 |
| CN | 1688288 | A | 10/2005 |
| CN | 1300139 | C | 2/2007 |
| CN | 101427140 | A | 5/2009 |
| CN | 102115455 | A | 7/2011 |
| CN | 101795621 | B | 5/2012 |
| CN | 102724913 | A | 10/2012 |
| CN | 103816150 | A | 5/2014 |
| CN | 204576485 | U | 8/2015 |
| CN | 105706423 | A | 6/2016 |

(56) References Cited

FOREIGN PATENT DOCUMENTS

| | | | |
|---|---|---|---|
| CN | 106692144 | A | 5/2017 |
| CN | 107095680 | A | 8/2017 |
| CN | 107771056 | A | 3/2018 |
| CN | 107949314 | A | 4/2018 |
| CN | 108619214 | A | 10/2018 |
| CN | 108929259 | A | 12/2018 |
| CN | 109069073 | A | 12/2018 |
| CN | 105792942 | B | 4/2019 |
| CN | 109890371 | A | 6/2019 |
| CN | 110049723 | A | 7/2019 |
| CN | 110325954 | A | 10/2019 |
| CN | 209606445 | U | 11/2019 |
| CN | 110996775 | A | 4/2020 |
| CS | 276073 | B6 | 3/1992 |
| CZ | 307719 | B6 | 3/1992 |
| DE | 255749 | A1 | 4/1988 |
| DE | 265636 | A1 | 3/1989 |
| DE | 102016014603 | A1 | 1/2018 |
| EP | 0152379 | A2 | 12/1999 |
| EP | 0850320 | B1 | 12/1999 |
| EP | 0962464 | A2 | 12/1999 |
| EP | 0990047 | A2 | 4/2000 |
| EP | 1693366 | A1 | 8/2006 |
| EP | 0992511 | B1 | 3/2009 |
| EP | 3713568 | A1 | 9/2020 |
| ES | 2355024 | B1 | 10/2009 |
| FI | 34529 | A | 10/1964 |
| FR | 2448540 | A1 | 9/1980 |
| GB | 911946 | A | 12/1962 |
| GB | 912714 | A | 12/1962 |
| GB | 912715 | A | 12/1962 |
| GB | 981192 | A | 1/1965 |
| GB | 982738 | A | 1/1965 |
| GB | 1264610 | A | 2/1972 |
| GB | 2588505 | A | 4/2021 |
| HU | P0400250 | A2 | 1/2003 |
| IL | 271923 | A | 2/2020 |
| IN | 52/2019 | | 12/2019 |
| JP | H0827029 | A | 1/1996 |
| JP | 2005-031029 | A | 2/2005 |
| JP | 2008-183012 | A | 8/2008 |
| JP | 4786653 | B2 | 10/2011 |
| KR | 101730189 | B1 | 8/2010 |
| KR | 20110028361 | A | 3/2011 |
| KR | 20150046994 | A | 5/2015 |
| MX | PA01005905 | A | 9/2002 |
| PT | 879054 | E | 8/1997 |
| RU | 2320663 | C2 | 3/2008 |
| RU | 2340619 | C2 | 12/2008 |
| SG | 10201705968 | R | 8/2017 |
| SG | 10201707484 | U | 10/2017 |
| TW | 201103937 | A | 2/2011 |
| TW | 201242600 | A | 11/2012 |
| TW | 201605856 | A | 2/2016 |
| TW | 202045477 | A | 12/2020 |
| TW | 202103699 | A | 2/2021 |
| TW | 202128610 | A | 8/2021 |
| WO | WO 1991/001756 | A1 | 2/1991 |
| WO | WO 1995/001334 | A1 | 1/1995 |
| WO | WO 1998/026644 | A2 | 6/1998 |
| WO | WO 1999/042840 | A1 | 8/1999 |
| WO | WO 2000/003679 | A2 | 1/2000 |
| WO | WO 2001/095903 | A1 | 12/2001 |
| WO | WO 2002/005851 | A2 | 1/2002 |
| WO | WO 2002/023984 | A2 | 3/2002 |
| WO | WO 2002/036113 | A1 | 5/2002 |
| WO | WO 2002/036114 | A1 | 5/2002 |
| WO | WO 2002/102988 | A2 | 12/2002 |
| WO | WO 2003/000252 | A1 | 1/2003 |
| WO | WO 2003/016903 | A2 | 2/2003 |
| WO | WO 2004/025268 | A1 | 3/2004 |
| WO | WO 2004/054500 | A2 | 7/2004 |
| WO | WO 2007/024741 | A2 | 3/2007 |
| WO | WO 2007/097754 | A1 | 8/2007 |
| WO | WO 2007/110637 | A1 | 10/2007 |
| WO | WO 2008/003028 | A2 | 1/2008 |
| WO | WO 2008/122990 | A1 | 10/2008 |
| WO | WO 2008/130638 | A1 | 10/2008 |
| WO | WO 2009/021055 | A1 | 2/2009 |
| WO | WO 2009/097596 | A1 | 8/2009 |
| WO | WO 2009/140680 | A1 | 11/2009 |
| WO | WO 2010/033724 | A2 | 3/2010 |
| WO | WO 2010/124089 | A2 | 10/2010 |
| WO | WO 2010/151258 | A1 | 12/2010 |
| WO | WO 2011/028875 | A1 | 3/2011 |
| WO | WO 2011/140607 | A1 | 11/2011 |
| WO | WO 2011/140608 | A1 | 11/2011 |
| WO | WO 2012/005951 | A1 | 1/2012 |
| WO | WO 2012/058337 | A2 | 5/2012 |
| WO | WO 2012/058769 | A1 | 5/2012 |
| WO | WO 2012/134436 | A1 | 10/2012 |
| WO | WO 2012/139042 | A1 | 10/2012 |
| WO | WO 2013/022775 | A1 | 2/2013 |
| WO | WO 2013/032940 | A1 | 3/2013 |
| WO | WO 2014/004460 | A1 | 1/2014 |
| WO | WO 2014/026044 | A2 | 2/2014 |
| WO | WO 2014/064703 | A1 | 5/2014 |
| WO | WO 2014/070424 | A1 | 5/2014 |
| WO | WO 2014/078374 | A2 | 5/2014 |
| WO | WO 2014/144130 | A2 | 9/2014 |
| WO | WO 2014/144712 | A1 | 9/2014 |
| WO | WO 2014/146091 | A1 | 9/2014 |
| WO | WO 2014/152663 | A1 | 9/2014 |
| WO | WO 2015/073459 | A1 | 5/2015 |
| WO | WO 2015/073588 | A1 | 5/2015 |
| WO | WO 2015/090583 | A1 | 6/2015 |
| WO | WO 2015/094981 | A1 | 6/2015 |
| WO | WO 2015/122964 | A1 | 8/2015 |
| WO | WO 2015/127556 | A1 | 9/2015 |
| WO | WO 2015/127558 | A1 | 9/2015 |
| WO | WO 2015/164541 | A1 | 10/2015 |
| WO | WO 2016/033204 | A1 | 3/2016 |
| WO | WO 2016/057343 | A1 | 4/2016 |
| WO | WO 2016/138135 | A1 | 9/2016 |
| WO | WO 2016/161138 | A1 | 10/2016 |
| WO | WO 2017/044702 | A1 | 3/2017 |
| WO | WO 2017/112398 | A1 | 6/2017 |
| WO | WO 2017/189528 | A1 | 11/2017 |
| WO | WO 2018/031803 | A1 | 2/2018 |
| WO | WO 2018/049167 | A1 | 3/2018 |
| WO | WO 2018/057576 | A1 | 3/2018 |
| WO | WO 2018/064465 | A1 | 4/2018 |
| WO | WO 2018/089375 | A1 | 5/2018 |
| WO | WO 2018/106738 | A1 | 6/2018 |
| WO | WO 2018/136610 | A1 | 7/2018 |
| WO | WO 2018/195455 | A1 | 10/2018 |
| WO | WO 2018/204764 | A1 | 11/2018 |
| WO | WO 2018/207192 | A1 | 11/2018 |
| WO | WO 2018/223044 | A1 | 12/2018 |
| WO | WO 2019/018735 | A1 | 1/2019 |
| WO | WO 2019/021158 | A1 | 1/2019 |
| WO | WO 2019/058145 | A1 | 3/2019 |
| WO | WO 2019/073379 | A1 | 4/2019 |
| WO | WO 2019/079742 | A1 | 4/2019 |
| WO | WO 2019/081764 | A1 | 5/2019 |
| WO | WO 2019/081942 | A1 | 5/2019 |
| WO | WO 2019/109124 | A1 | 6/2019 |
| WO | WO 2019/122525 | A1 | 6/2019 |
| WO | WO 2019/173797 | A1 | 9/2019 |
| WO | WO 2019/241451 | A1 | 12/2019 |
| WO | WO 2019/246532 | A1 | 12/2019 |
| WO | WO 2020/023084 | A1 | 1/2020 |
| WO | WO 2020/157669 | A1 | 1/2020 |
| WO | WO 2020/024060 | A1 | 2/2020 |
| WO | WO 2020/024071 | A1 | 2/2020 |
| WO | WO 2020/041329 | A1 | 2/2020 |
| WO | WO 2020/053196 | A1 | 3/2020 |
| WO | WO 2020/212948 | A1 | 4/2020 |
| WO | WO 2020/157569 | A1 | 8/2020 |
| WO | WO 2020/181194 | A1 | 9/2020 |
| WO | WO 2020/185581 | A2 | 9/2020 |
| WO | WO 2020/212951 | A1 | 10/2020 |
| WO | WO 2020/219461 | A1 | 10/2020 |
| WO | WO 2020/245133 | A1 | 12/2020 |

(56) References Cited

FOREIGN PATENT DOCUMENTS

| | | | |
|---|---|---|---|
| WO | WO 2020/247632 | A1 | 12/2020 |
| WO | WO 2020/260917 | A1 | 12/2020 |
| WO | WO 2020/264390 | A2 | 12/2020 |
| WO | WO 2021/000053 | A1 | 1/2021 |
| WO | WO 2021/000054 | A1 | 1/2021 |
| WO | WO 2021/000997 | A1 | 1/2021 |
| WO | WO 2021/003467 | A1 | 1/2021 |
| WO | WO 2021/007659 | A1 | 1/2021 |
| WO | WO 2021/007660 | A1 | 1/2021 |
| WO | WO 2021/007661 | A1 | 1/2021 |
| WO | WO 2021/007662 | A1 | 1/2021 |
| WO | WO 2021/007663 | A1 | 1/2021 |
| WO | WO 2021/009374 | A1 | 1/2021 |
| WO | WO 2021/016423 | A1 | 1/2021 |
| WO | WO 2021/016710 | A1 | 2/2021 |
| WO | WO 2021/030571 | A1 | 2/2021 |
| WO | WO 2021/155468 | A1 | 2/2021 |
| WO | WO 2021/038112 | A2 | 3/2021 |
| WO | WO 2021/041407 | A1 | 3/2021 |
| WO | WO 2021/052989 | A1 | 3/2021 |
| WO | WO 2021/062557 | A1 | 4/2021 |
| WO | WO 2021/062559 | A1 | 4/2021 |
| WO | WO 2021/067626 | A2 | 4/2021 |
| WO | WO 2021/072530 | A1 | 4/2021 |
| WO | WO 2021/076572 | A1 | 4/2021 |
| WO | WO 2021/076849 | A1 | 4/2021 |
| WO | WO 2021/081138 | A1 | 4/2021 |
| WO | WO 2021/086513 | A1 | 5/2021 |
| WO | WO 2021/089873 | A1 | 5/2021 |
| WO | WO 2021/102567 | A1 | 6/2021 |
| WO | WO 2021/102568 | A1 | 6/2021 |
| WO | WO 2021/102569 | A1 | 6/2021 |
| WO | WO 2021/108911 | A1 | 6/2021 |
| WO | WO 2021/113958 | A1 | 6/2021 |
| WO | WO 2021/113959 | A1 | 6/2021 |
| WO | WO 2021/116503 | A2 | 6/2021 |
| WO | WO 2021/113986 | A1 | 7/2021 |
| WO | WO 2021/138564 | A1 | 7/2021 |
| WO | WO 2021/142238 | A1 | 7/2021 |
| WO | WO 2021/155467 | A1 | 8/2021 |
| WO | WO 2021/155470 | A1 | 8/2021 |
| WO | WO 2021/159213 | A1 | 8/2021 |
| WO | WO 2021/168082 | A1 | 8/2021 |
| WO | WO 2021/173989 | A1 | 9/2021 |
| WO | WO 2021/178579 | A1 | 9/2021 |
| WO | WO 2021/179091 | A1 | 9/2021 |
| WO | WO 2021/183490 | A2 | 9/2021 |
| WO | WO 2021/188782 | A1 | 9/2021 |
| WO | WO 2021/188812 | A1 | 9/2021 |
| WO | WO 2021/188870 | A1 | 9/2021 |
| WO | WO 2021/207137 | A1 | 10/2021 |
| WO | WO 2021/207824 | A1 | 10/2021 |
| WO | WO 2021/209815 | A1 | 10/2021 |
| WO | WO 2022/076642 | A1 | 10/2021 |
| WO | WO 2022/192097 | A1 | 3/2022 |
| WO | WO 2022/246572 | A1 | 5/2022 |
| WO | WO 2023/023155 | A1 | 8/2022 |
| WO | WO 2022/195011 | A1 | 9/2022 |
| WO | WO 2022/195489 | A2 | 9/2022 |
| WO | WO 2022/251169 | A1 | 12/2022 |
| WO | WO 2023/078604 | A1 | 5/2023 |

OTHER PUBLICATIONS

Cybin, "CYB003 Phase 2 Topline Depression Study Review and R&D Briefing", Nov. 30, 2023.

Cybin, "Cybin R&D Day", Feb. 28, 2023.

Cybin, Poster #361: "In Vitro and In Vivo Profile of CYB003: A Novel, Deuterated Psilocybin Analog for the Potential Treatment of Major Depressive Disorder", American College of Neuropsychopharmacology (ACNP) Annual Meeting, Phoenix, Arizona, Dec. 4-7, 2022.

Cybin, Poster #P362: "Pharmacokinetic Profile Of CYB003: A Novel, Deuterated Psilocybin Analog for the Potential Treatment of Major Depressive Disorder", American College of Neuropsychopharmacology (ACNP) Annual Meeting, Phoenix, Arizona, Dec. 4-7, 2022.

Cybin, Poster: "CYB003: A Novel, Orally Active Analog of Psilocybin for the Potential Treatment of Major Depressive Disorder", Society for Neuroscience (SFN), San Diego, California, Nov. 12-16, 2022.

Cybin, Poster: "Pharmacological and Pharmacokinetic Profile of CYB003, A Novel, Orally Active Analog of Psilocybin", From Research to Reality: Global Summit on Psychedelic-Assisted Therapies and Medicine, Toronto, Canada, May 27-29, 2022.

Cybin, Press Release: "Clinilabs Drug Development Corporation Begins Enrollment for Phase 1/2a Trial Evaluating CYB003 for the Treatment of Major Depressive Disorder", Retrieved from url: <https://ir.cybin.com/investors/news/news-details/2022/Clinilabs-Drug-Development-Corporation-Begins-Enrollment-for-Phase-12a-Trial-Evaluating-CYB003-for-the-Treatment-of-Major-Depressive-Disorder/default.aspx>, Jul. 12, 2022.

Cybin, Press Release: "Cybin Announces Phase 2 Cohort 5 Dosing Completion of CYB003 in Major Depressive Disorder", Retrieved from url: <https://ir.cybin.com/investors/news/news-details/2023/Cybin-Announces-Phase-2-Cohort-5-Dosing-Completion-of-CYB003-in-Major-Depressive-Disorder/default.aspx>, Jul. 24, 2023.

Cybin, Press Release: "Cybin Announces Positive CYB003 Data Demonstrating Significant Advantages Over Oral Psilocybin for Treatment of Mental Health", Retrieved from url: <https://ir.cybin.com/investors/news/news-details/2021/Cybin-Announces-Positive-CYB003-Data-Demonstrating-Significant-Advantages-Over-Oral-Psilocybin-for-Treatment-of-Mental-Health/default.aspx>, Nov. 8, 2021.

Cybin, Press Release: "Cybin Announces Positive Data from its CYB003 Phase 1/2a Trial and Provides Update on its CYB004 Development Program", Retrieved from url: <https://ir.cybin.com/investors/news/news-details/2023/Cybin-Announces-Positive-Data-from-its-CYB003-Phase-12a-Trial-and-Provides-Update-on-its-CYB004-Development-Program/default.aspx>, Feb. 28, 2023.

Cybin, Press Release: "Cybin Announces Publication in Frontiers in Psychology Journal Introducing EMBARK, an Integrative Model of Psychedelic Therapy", Retrieved from url: <https://ir.cybin.com/investors/news/news-details/2022/Cybin-Announces-Publication-in-Frontiers-in-Psychology-Journal-Introducing-EMBARK-an-Integrative-Model-of-Psychedelic-Therapy/default.aspx>, Jun. 2, 2022.

Cybin, Press Release: "Cybin Announces Successful Completion of In Vivo Preclinical Studies for its Deuterated Psilocybin Analog CYB003 Supporting Advancement into Phase 1/2a Clinical Trial", Retrieved from url: <https://ir.cybin.com/investors/news/news-details/2022/Cybin-Announces-Successful-Completion-of-In-Vivo-Preclinical-Studies-for-its-Deuterated-Psilocybin-Analog-CYB003-Supporting-Advancement-into-Phase-12a-Clinical-Trial/default.aspx>, Mar. 29, 2022.

Cybin, Press Release: "Cybin Announces Unprecedented Positive Phase 2 Interim Data for CYB003 in Major Depressive Disorder Meeting Primary Efficacy Endpoint with Rapid and Significant Improvements in Depression Symptoms After Single Dose", Retrieved from url: <https://ir.cybin.com/investors/news/news-details/2023/Cybin-Announces-Unprecedented-Positive-Phase-2-Interim-Data-for-CYB003-in-Major-Depressive-Disorder-Meeting-Primary-Efficacy-Endpoint-with-Rapid-and-Significant-Improvements-in-Depression-Symptoms-After-Single-Dose/default.aspx>, Oct. 31, 2023.

Cybin, Press Release: "Cybin Completes Dosing in Phase 2 Study of CYB003 for the Treatment of Major Depressive Disorder", Retrieved from url: <https://ir.cybin.com/investors/news/news-details/2023/Cybin-Completes-Dosing-in-Phase-2-Study-of-CYB003-for-the-Treatment-of-Major-Depressive-Disorder/default.aspx>, Oct. 3, 2023.

Cybin, Press Release: "Cybin Completes Enrollment in Phase 2 Study of CYB003 in Major Depressive Disorder", Retrieved from url: <https://ir.cybin.com/investors/news/news-details/2023/Cybin-Completes-Enrollment-in-Phase-2-Study-of-CYB003-in-Major-Depressive-Disorder/default.aspx>, Sep. 21, 2023.

Cybin, Press Release: "Cybin Inc. Reports Fiscal Year 2023 Financial Results and Recent Business Highlights", Retrieved from url: <https://ir.cybin.com/investors/news/news-details/2023/Cybin-Inc.-

(56) References Cited

OTHER PUBLICATIONS

Reports-Fiscal-Year-2023-Financial-Results-and-Recent-Business-Highlights/default.aspx>, Jun. 27, 2023.

Cybin, Press Release: "Cybin Initiates Dosing of Final Cohort of its Phase 2 Trial of CYB003 in Major Depressive Disorder", Retrieved from url: <https://ir.cybin.com/investors/news/news-details/2023/Cybin-Initiates-Dosing-of-Final-Cohort-of-its-Phase-2-Trial-of-CYB003-in-Major-Depressive-Disorder/default.aspx>, Aug. 2, 2023.

Cybin, Press Release: "Cybin Prepares for GMP Manufacturing of CYB003 Capsules for Phase 3 Trial", Retrieved from url: <https://ir.cybin.com/investors/news/news-details/2023/Cybin-Prepares-for-GMP-Manufacturing-of-CYB003-Capsules-for-Phase-3-Trial/default.aspx>, Aug. 17, 2023.

Cybin, Press Release: "Cybin Receives FDA IND Clearance for its Phase 1/2a Clinical Trial Evaluating CYB003 for the Potential Treatment of Major Depressive Disorder", Retrieved from url: <https://ir.cybin.com/investors/news/news-details/2022/Cybin-Receives-FDA-IND-Clearance-for-its-Phase-12a-Clinical-Trial-Evaluating-CYB003-for-the-Potential-Treatment-of-Major-Depressive-Disorder/default.aspx>, Jun. 27, 2022.

Cybin, Press Release: "Cybin Reports Positive Topline Data from Phase 2 Study of CYB003 in Major Depressive Disorder with 79% of Patients in Remission after Two 12mg Doses", Retrieved from url: <https://ir.cybin.com/investors/news/news-details/2023/Cybin-Reports-Positive-Topline-Data-from-Phase-2-Study-of-CYB003-in-Major-Depressive-Disorder-with-79-of-Patients-in-Remission-after-Two-12mg-Doses/default.aspx>, Nov. 30, 2023.

Cybin, Press Release: "Cybin Submits IND Application to FDA for its Phase 1/2a First-in-Human Trial of CYB003 for the Treatment of Major Depressive Disorder", Retrieved from url: <https://ir.cybin.com/investors/news/news-details/2022/Cybin-Submits-IND-Application-to-FDA-for-its-Phase-12a-First-in-Human-Trial-of-CYB003-for-the-Treatment-of-Major-Depressive-Disorder/default.aspx>, May 31, 2022.

Cybin, Webcast: "CYB003 Phase 2 Interim Data Conference Call", Nov. 1, 2023, Obtained from url: <https://ir.cybin.com/investors/events-and-presentations/events/event-details/2023/CYB003-Phase-2-Interim-Data-Conference-Call/default.aspx>.

Cybin, Webcast: "CYB003 Phase 2 Topline Depression Study Review and R&D Briefing", Nov. 30, 2023, Obtained from url: <https://ir.cybin.com/investors/events-and-presentations/events/event-details/2023/CYB003-Phase-2-Topline-Depression-Study-Review-and-RD-Briefing/default.aspx>.

Cybin, Webcast: "Cybin Acquisition of Small Pharma Inc.—Conference Call", Aug. 28, 2023, Obtained from url: <https://ir.cybin.com/investors/events-and-presentations/events/event-details/2023/Cybin-Inc-Conference-Call/default.aspx>.

International Search Report and Written Opinion for PCT International Patent Application No. PCT/EP2024/054897, dated Jun. 7, 2024.

U.S. Appl. No. 18/547,100, filed Aug. 18, 2023, Alex Nivorozhkin, Psilocybin Analogs, Salts, Compositions, and Methods of Use.

U.S. Appl. No. 18/588,132, filed Feb. 27, 2024, Alex Nivorozhkin, Methods of Treating Disorders With a Psilocybin Analog.

Abbas et al., "Oregon Psilocybin Advisory Board Rapid Evidence Review and Recommendations", Phase 1 and 2 Clinical Trials Report, Jul. 30, 2021, Retrieved from the internet: https://www.oregon.gov/oha/ph/preventionwellness/pages/psilocybin-scientific-literature-review.aspx.

Aghajanian et al., "Hallucinogenic indoleamines: Preferential action upon presynaptic serotonin receptors", Psychopharmacol. Commun., 1975, 1(6): 619-629.

Barker et al., "Comparison of the brain levels of N,N-dimethyltryptamine and α,α,β,β-tetradeutero-N,N-dimethyltryptamine following intraperitoneal injection: The In Vivo kinetic isotope effect", Biochem. Pharmacol., Aug. 1982, 31(15): 2513-2516.

Barker et al., "In vivo metabolism of α,α,β,β-tetradeutero-n,N-dimethyltryptamine in rodent brain", Biochem Pharmacol., May 1984, 33(9): 1395-400.

Bauer et al., "The State of the Art of Psilacetin (4-AcO-DMT)", Psychedelic Science Review, Sep. 18, 2019, Retrieved from the internet: https://psychedelicreview.com/the-state-of-the-art-of-psilacetin-4-aco-dmt/.

Bauer, "New Toad Venom Compound Synthesized for Clinical Use: 5-MeO-DMT Succinate", Psychedelic Science Review, Jan. 18, 2021, Retrieved on the internet: https://psychedelicreview.com/new-toad-venom-compound-synthesized-for-clinical-use-5-meo-dmt-succinate/.

Bauer, "Two New Crystalline Forms of Norpsilocin", Psychedelic Science Review, Apr. 23, 2020, 11 pages. Retrieved from the internet: https://psychedelicreview.com/two-new-crystalline-forms-of-norpsilocin/.

Brandt et al., "Characterization of the synthesis of N,N-dimethyltryptamine by reductive amination using gas chromatography ion trap mass spectrometry", Drug Testing and Analysis, Jul. 2010, 2(7): 330-338.

Brandt et al., "Microwave-accelerated synthesis of psychoactive deuterated N,N-dialkylated-[a,a,b,b-d4]-tryptamines", Journal of Labelled Compounds and Radiopharmaceuticals, Nov. 3, 2008, 51(14): 423-429.

Brodwin et al., "Denver just became the first city in the US to decriminalize magic mushrooms. Here's what they do to your body and mind.", Business Insider India, May 10, 2019, Retrieved from the internet: https://www.businessinsider.in/denver-just-became-the-first-city-in-the-us-to-decriminalize-magic-mushrooms-heres-what-they-do-to-your-body-and-mind-/articleshow/69258788.cms.

Cameron et al., "A Non-Hallucinogenic Psychedelic Analog with Therapeutic Potential", Nature, 2021, 589: 474-479.

Cayman Chemical, "4-hydroxy DMT", Product Info, Item No. 11864, 2024, Retrieved from the internet: https://www.caymanchem.com/product/11864/4-hydroxy-dmt.

Cayman Chemical, "4-hydroxy DMT-d10", Product Info, Item No. 31734, 2022, Retrieved from the internet: https://www.caymanchem.com/product/31734/psilocin-d10.

Cayman Chemical, "4-hydroxy DMT-d6", Product info, Item No. 34780, 2024, Retrieved from the internet: https://www.caymanchem.com/product/34780/psilocin-d6.

Cayman Chemical, "5-methoxy DMT", Product Info, Item No. 11480, 2024, Retrieved from the internet: https://www.caymanchem.com/product/11480/5-methoxy-dmt.

Cayman Chemical, "N,N-DMT (succinate)", Product Info, Item No. 33586, 2024, Retrieved from the internet: https://www.caymanchem.com/product/33586/n%2Cn-dmt-(succinate)#:~:text=Product%20Description&text=N%2CN%2DDMT%20substitutes%20for,for%20research%20and%20forensic%20applications.

Cayman Chemical, "N,N-DMT(Fumarate)", Product Info, Item No. 9003568, 2024, Retrieved from the internet: https://www.caymanchem.com/product/9003568/n%2Cn-dmt-(fumarate).

Cayman Chemical, "N,N-DMT-d4 (fumarate)", Product Info, Item No. 34354, 2024, Retrieved from the internet: https://www.caymanchem.com/product/34354/n%2Cn-dmt-d4-(fumarate).

Cerilliant, "Psilocin-D10", Item Details, P-099-1ML, 2022, Retrieved from the internet: https://www.cerilliant.com/shoponline/Item_Details.aspx?itemno=4973ed15-d59e-4a94-8cd4-ed45a8b6f249&item=P-099.

Cerilliant, "Psilocin-D10", Certified Reference Material—Certificate of Analysis, Catalog No. P-049, Lot No. FC032610-01, Revision 2, Feb. 2, 2015, 7 pages.

Cerilliant, "Psilocybin", Certified Reference Material, P-097-1ML, 2024, Retrieved from the internet: https://www.cerilliant.com/shoponline/Item_Details.aspx?itemno=d8a0a0a6-a045-4d2a-8f0e-d1172e18454d&item=P-097.

Chadeayne et al., "Active Metabolite of Aeruginascin (4-Hydroxy-N,N,N-trimethyltryptamine): Synthesis, Structure, and Serotonergic Binding Affinity", ACS Omega, Jul. 14, 2020, 5(27): 16940-16943.

Chadeayne et al., "Bis(4-acetoxy-N,N-dimethyltryptammonium) fumarate: a new crystalline form of psilacetin, an alternative to psilocybin as a psilocin prodrug", Acta Crystallogr. E. Crystallogr. Commun., Jun. 2019, 75(Pt 6): 900-902.

Chadeayne et al., "Bis(4-hydroxy-N,N-di-n-propyltryptammonium) fumarate tetrahydrate", IUCrData, 2019, 4(Pt. 11): x191469, 9 pages.

(56) References Cited

OTHER PUBLICATIONS

Chadeayne et al., "Bis(4-hydroxy-N-isopropyl-N-methyltryptammonium) fumarate: a new crystalline form of miprocin", Acta. Crystallogr. E. Crystallogr. Commun., Apr. 2020, 76(Pt 4): 514-517.
Chadeayne et al., "DMT analogues: N-ethyl-N-propyltryptamine and N-allyl-N-methytryptamine as their hydrofumarate salts", Acta Crystallogr. E. Crystallogr. Commun., Aug. 2020; 76(Pt 8): 1201-1205.
Chadeayne et al., "Norpsilocin: freebase and fumarate salt", Acta Crystallogr E Crystallogr Commun., Apr. 2020; 76(Pt 4): 589-593.
Chadeayne et al., "The Crystal Structure of 4-AcO-DMT Fumarate", Psychedelic Science Review, Mar. 25, 2019, Retrieved on the internet: https://psychedelicreview.com/the-crystal-structure-of-4-aco-dmt-fumarate/.
Chadeayne et al., "The fumarate salts of the N-isopropyl-N-methyl derivatives of DMT and psilocin", Acta Crystallogr E Crystallogr Commun., Sep. 2019; 75(Pt 9): 1316-1320.
Chemspider, "N,N-DMT(Fumarate)", Chemical Structure, CSID: 29787037, 2024, Retrieved from the internet: https://www.chemspider.com/Chemical-Structure.29787037.html.
Compass Pathways, "About psilocybin therapy", Retrieved from the internet on Mar. 11, 2024 at: https://compasspathways.com/our-work/about-psilocybin-therapy-and-treatment/.
Compass Pathways, "Compass Pathways announces investigational COMP360 psilocybin treatment was well-tolerated in phase 2 study of post-traumatic stress disorder", Dec. 19, 2023, Retrieved from the internet: https://compasspathways.com/category/articles/compass-news/.
Compass Pathways, "COMPASS Pathways granted patent covering use of its psilocybin formulation in addressing treatment-resistant depression", Jan. 15, 2020, Retrieved from the internet: https://compasspathways.com/compass-pathways-granted-patent-covering-use-of-its-psilocybin-formulation-in-addressing-treatment-resistant-depression/.
Cybin Inc., "Cybin Advances IND-Enabling Studies of Two Psychedelic Molecules, CYB003 and CYB004 for Investigational New Drug Applications", Business Wire, Apr. 13, 2021, Retrieved from the internet: https://www.businesswire.com/news/home/20210413005466/en/Cybin-Advances-IND-Enabling-Studies-of-Two-Psychedelic-Molecules-CYB003-and-CYB004-for-Investigational-New-Drug-Applications.
Cybin Inc., "Cybin Announces Completion of its 51st Pre-Clinical Psychedelic Molecule Study", Business Wire Press Release, Jun. 22, 2021, Retrieved from the internet: https://www.businesswire.com/news/home/20210622005438/en/Cybin-Announces-Completion-of-its-51st-Pre-Clinical-Psychedelic-Molecule-Study.
Cybin Inc., Cybin Stock Info, Graph and Key Stats, Mar. 21, 2024, Retrieved from the internet: https://www.cnbc.com/quotes/CYBN.
European Monitoring Centre for Drugs and Drug Addiction, "Lysergide (LSD) drug profile", Retrieved from the internet Mar. 11, 2024: https://www.emcdda.europa.eu/publications/drug-profiles/lsd_en.
Hasler et al., "Determination of psilocin and 4-hydroxyindole-3-acetic acid in plasma by HPLC-ECD and pharmacokinetic profiles of oral and intravenous psilocybin in man", Pharm. Acta. Helv., Jun. 1997, 72(3): 175-184.
Innovation & Tech Today, "Cybin Advances Psilocybin as Treatment for Depression and Addiction", 2024, Retrieved from the internet: https://innotechtoday.com/cybin-advances-psilocybin-as-treatment-for-depression-and-addiction/.
International Search Report and Written Opinion for PCT International Patent Application No. PCT/EP2022/056991, dated Aug. 19, 2022.
International Search Report and Written Opinion for PCT International Patent Application No. PCT/EP2022/076073, dated Feb. 6, 2023.
Kargbo et al., "Direct Phosphorylation of Psilocin Enables Optimized cGMP Kilogram-Scale Manufacture of Psilocybin", ACS Omega, Jul. 14, 2020, 5(27): 16959-16966.
Kargbo, "Psilocin Derivatives as Serotonergic Psychedelic Agents for the Treatment of CNS Disorders", ACS Med. Chem. Lett., Oct. 14, 2021, 12(10): 1519-1520.
Krempien et al., "Randomized, Double-Blind, Placebo-Controlled Study to Evaluate the Safety and Efficacy of CYB003, a Deuterated Psilocybin Analog an Patients with Major Depressive Disorder", American Society of Neuropharmacology (ACNP), Tampa, Florida, Dec. 3-6, 2023.
Kuhnert-Brandsatter et al., "Polymorphe Modifikationen und Solvate von Psilocin und Psilocybin [Polymorphic Modifications and Solvates of Psilocin and Psilocybin]" Archiv der Pharmazie, 1976, 309: 625-631.
Lennham Pharmaceuticals, "Coupling the therapeutic potential of psilocybin with compound patent protection", Retrieved on the internet on Mar. 11, 2024 at: https://www.lennham.com/dpsilocybin.
Lennham Pharmaceuticals, "Lennham Pharmaceuticals Announces Issuance of U.S. Patent Covering Deuterated Psilocybin Products", May 14, 2021, Retrieved from the internet: https://www.businesswire.com/news/home/20210514005086/en/Lennham-Pharmaceuticals-Announces-Issuance-of-U.S.-Patent-Covering-Deuterated-Psilocybin-Products.
Lowe et al., "The Therapeutic Potential of Psilocybin", Molecules, May 2021; 26(10): 2948, 33 pages.
Martin et al., "Synthesis, hydrolysis and stability of psilocin glucuronide", Forensic Sci. Int., Apr. 2014, 237: 1-6.
Migliaccio et al., "Comparison of Solution Conformational Preferences for the Hallucinogens Bufotenin and Psilocin Using 360-MHz Proton NMR Spectroscopy", J. Med. Chem., Feb. 1981, 24(2): 206-209.
Mindset Pharma Inc., "Mindset Selects its Lead Clinical Candidate, MSP-1014, a Next Generation Psychedelic Medicine", Globe Newswire, Jun. 3, 2021, Retrieved from the internet: https://www.globenewswire.com/en/news-release/2021/06/03/2241140/0/en/Mindset-Selects-its-Lead-Clinical-Candidate-MSP-1014-a-Next-Generation-Psychedelic-Medicine.html.
Mindset Pharma, "Mindset Announces Milestone in New Drug Program with Successful Proof-of-Concept Animal Studies of Its Patent-Pending Psilocybin-Inspired Drug Candidates", Newfile Corp., Feb. 10, 2021, Retrieved from the internet: https://www.newsfilecorp.com/release/74087.
Morris et al., "Indolealkylamine metabolism: synthesis of deuterated indolealkylamines as metabolic probes", Journal of Labelled Compounds and Pharmaceuticals, Jun. 1993, 33(6): 455-466.
Neonmind Biosciences, Neonmind front web page, accessed from The Wayback Machine web archive website on Mar. 22, 2024 at: https://web.archive.org/web/20230527173053/https://neonmindbiosciences.com/.
Nichols, "Improvements to the Synthesis of Psilocybin and a Facile Method for Preparing the O-Acetyl Prodrug of Psilocin", Synthesis, Jun. 1999, 6: 935-938.
Olson, "Psychedelic drugs could treat depression, and other mental illnesses", University of California web page, Jun. 20, 2018, Retrieved from the internet: https://www.universityofcalifornia.edu/news/psychedelic-drugs-could-treat-depression-and-other-mental-illnesses.
Orthogonal Thinker Inc., "Orthogonal Thinker Launches First Psychedelics Lifestyle Brand PsillyLife to Promote Psychedelic Culture and Proprietary Research", Globe Newswire Press Release, Dec. 2, 2019, Retrieved from the internet: https://www.globenewswire.com/news-release/2019/12/02/1954840/0/en/Orthogonal-Thinker-Launches-First-Psychedelics-Lifestyle-Brand-PsillyLife-to-Promote-Psychedelic-Culture-and-Proprietary-Research.html.
Orthogonal Thinker, Inc., "Orthogonal Thinker Front Web Page", Retrieved from the internet on Mar. 21, 2024 at: https://www.orthogonalthinker.com/.
Parkins, "Club to clinic: psychedelic drug trials aim to break new ground in mental health", Clinical Trials Arena, Jun. 11, 2021. Retrieved from the internet: https://www.clinicaltrialsarena.com/features/psychedelics-psychedelic-drug-trials-aim-to-break-new-ground-in-mental-health/?cf-view&cf-closed.

(56) References Cited

OTHER PUBLICATIONS

Pham et al., "5-Methoxy-N,N-di-n-propyltryptamine (5-MeODPT): freebase and fumarate", Acta Crystallogr E Crystallogr Commun., May 2021; 77(Pt 5): 522-526.
Pham et al., "Psilacetin derivatives: fumarate salts of the methyl-ethyl, methyl-allyl and diallyl variants of the psilocin prodrug", Acta Crystallogr E Crystallogr Commun. Feb. 2021; 77(Pt 2): 101-106.
Ray et al., "Tungstate-catalyzed oxidation of triptans with hydrogen peroxide: A novel method for the synthesis of N,N-dimethyltryptamine N-oxides", Indian Journal of Chemistry, Jan. 2009, 48B: 134-136.
Sammeta et al., "The hydrochloride salt of 4-hydroxy-N,N-di-npropyltryptamine (4-HO-DPT)", IUCrdata, Nov. 27, 2020, 5(Pt 11):x201546, 8 pages.
Sherwood et al., "Synthesis and Characterization of 5-MeO-DMT Succinate for Clinical Use", ACS Omega, Dec. 2, 2020, 5(49):32067-32075.
Shoda et al., "Enzyme-assisted synthesis of the glucuronide conjugate of psilocin, an hallucinogenic component of magic mushrooms", Drug Testing and Analysis, Sep. 2011, 3(9):594-596.
Sigma-Aldrich, "New Hydranal® Certified Reference Materials for Water Analysis", Analytix, 2015, 3: 24 pages.
Small Pharma Inc., "Small Pharma Provides Update to Patent Portfolio Including Receipt of an in Order for Grant Notice for its Patent Related to Psychedelic Tryptamines", Globe Newswire Press Release, May 7, 2021, Retrieved from the internet: https://www.globenewswire.com/en/news-release/2021/05/07/2225468/0/en/Small-Pharma-Provides-Update-to-Patent-Portfolio-Including-Receipt-of-an-in-Order-for-Grant-Notice-for-its-Patent-Related-to-Psychedelic-Tryptamines.html.
Small Pharma, "Psychedelic-assisted therapy: a new approach to treating depression", Jun. 2021, B29, Retrieved from the internet: https://www.nature.com/biopharmdeal.
Small Pharma, Clinical Trial: SPL026 (DMT Fumarate) in Healthy Subjects and MDD Patients, Study Details, First posted: Dec. 17, 2020, Retrieved on the internet: https://classic.clinicaltrials.gov/ct2/show/study/NCT04673383.
Speights, "Investing in Psychedelic Stocks", The Motley Fool, Jan. 18, 2024, Retrieved from the internet: https://www.fool.com/investing/stock-market/market-sectors/healthcare/psychedelic-stocks/.
Strassman, "Human psychopharmacology of N,N-dimethyltryptamine", Behav. Brain Res., 1996, 73(1-2): 121-124.
Tirumalaraju, "Cybin gets approval to trial psilocybin for depression", Clinical Trials Arena, May 19, 2021, Retrieved from the internet: https://www.clinicaltrialsarena.com/news/cybin-phase-ii-psilocybin/.
Usona Institute, "Usona Institute Publishes Synthesis and Characterization of cGMP 5-MeO-DMT", Business Wire Press Release, Dec. 8, 2020, Retrieved from the internet: https://www.usonainstitute.org/updates/usona-institute-publishes-synthesis-and-characterization-of-cgmp-5-meo-dmt.
Vaupel et al., "The inhibition of food intake in the dog by LDS, mescaline, psilocin, d-amphetamine and phenylisopropylamine derivatives", Life Sci., Jun. 25, 1979, 24(26): 2427-2431.
Walker et al., "Identification of N,N-dimethyltryptamine as the product of an in vitro enzymic methylation", Analytical Biochem., May 1972, 47(1): 228-234.
Xu et al., "Synthesis of deuterium labeled standards of 5-methoxy-N,N-dimethyltryptamine (5-Meo-DMT)", J. Labelled Compounds Radiopharamaceuticals, 2006, 49(10): 897-902.
European Examination Report for European Patent Application No. 22716857.2, dated Nov. 3, 2025.
Foster et al., "Deuterium isotope effects in the metabolism of drugs and xenobiotics: implications for drug design", Advances in Drug Research, 1986, 14: 1-40.
Ashizawa et al., Chemistry of Pharmaceutical Polymorphism and Crystallization, 2002, pp. 273, 278, and 305-317.
Byrn et al., "Pharmaceutical Solids: A Strategic Approach to Regulatory Considerations", Pharmaceutical Research, 1995, 12(7): 945-954.
Caira, "Crystalline Polymorphism of Organic Compounds", Topics in Current Chemistry, 1998, 198: 163-208.
Hirayama et al., Handbook of Organic Compound Crystallization, 2008, pp. 17-23, 37-40, 45-51, and 57-65.
O'Driscoll L, "Heavyweight drugs", Chemistry & Industry, Mar. 9, 2009, pp. 24-26.
Pirali et al., "Applications of deuterium in medicinal chemistry", Journal of Medicinal Chemistry, 2019, 62(11): 5276-5297.
Savjani et al., "Drug Solubility: Importance and Enhancement Techniques", International Scholarly Research Network ISRN Pharmaceutics, 2012, vol. 2012, pp. 1-10.
Database Registry [Online], Chemical Abstracts Service, "3-(1,1,2,2-Tetradeuterio-2- dimethylaminoethyl)-1H-indol-4-ol", CAS Registry No. 1286546-49-3, Entered STN: Apr. 27, 2011.
Database Registry [Online], Chemical Abstracts Service, "3-[2-[di(methyl-d3)amino]ethyl-1,1,2,2-d4]-1H-Indol-4-ol", CAS Registry No. 1435934-64-7, Entered STN: Jun. 7, 2013.
Wang et al., "Research Progress on Deuterated Drugs", Tianjin Pharmacy, Dec. 31, 2020, 32: 44-46. Machine Google English included.

(A) (B) (C) (I-3)

I-7c Post DVS (pattern 6)

I-7c Pre DVS, scale up, poorly crystalline form (pattern 5)

ED01798-031-001-00_10_1TGA, 09.11.2021 19:13:30
ED01798-031-001-00_10_1TGA, 1.2810 mg

I-3c (pattern 1)
I-7c (pattern 1)
I-7c (pattern 2)
I-7c (pattern 4)
I-7c (pattern 3)

1 mg 50 100 150 200 250 300 350 °C

I-3c (pattern 2, seeded)
I-3c (pattern 1, non-seeded)
I-7c (pattern 4)

ED01798-037-001-00_10_1DSC, 15.11.2021 14:48:34
ED01798-037-001-00_10_1DSC, 1.1600 mg

| | |
|---|---|
| Integral | -355.21 mJ |
| normalized | -306.22 Jg^-1 |
| Onset | 229.64 °C |
| Peak | 232.32 °C |
| Left Limit | 220.49 °C |
| Right Limit | 234.46 °C |

E001798-031-001-00_10_2DSC, 10.11.2021 10:42:16
ED01798-031-001-00_10_2DSC, 1.3800 mg

| | |
|---|---|
| Integral | -120.92 mJ |
| normalized | -87.62 Jg^-1 |
| Onset | 222.62 °C |
| Peak | 229.08 °C |
| Left Limit | 218.51 °C |
| Right Limit | 231.80 °C |

ED01798-015-003-00_10_1DSC, 08.10.2021 13:23:59
ED01798-015-003-00_10_1DSC, 1.1800 mg

| | |
|---|---|
| Integral | -488.15 mJ |
| normalized | -413.69 Jg^-1 |
| Onset | 227.53 °C |
| Peak | 230.75 °C |
| Left Limit | 219.47 °C |
| Right Limit | 235.10°C |

10 mW 40 60 80 100 120 140 160 180 200 220 240 260 280 °C

Acetic acid (AcA), pH 2.90, 40C
0H
4H
24H
Psilocin (%)
100
80
60
40
20
0
PI
PI+0.1M AcA
PI + Fe3+
PI+Fe3+ +AcA
PI + Al3+
PI+Al3+ +AcA

| SH24 |
|---|
|  |
| Minor nodules: 45.0%<br>Major nodules: 32.5%<br>Sunken appearance<br>Moderately defined deboss |

SH24

Minor nodules: 27.5%
Major nodules: 5.0%
Sunken appearance
Slightly shiny base
Moderately defined deboss Minor nodules: 10.0%
Major nodules: 0%
Sunken appearance
Moderately defined deboss Minor nodules: 5.0%
Major nodules: 2.5%
Sunken appearance
Moderately defined deboss

PSILOCYBIN ANALOGS, SALTS, COMPOSITIONS, AND METHODS OF USE

CROSS REFERENCE TO RELATED APPLICATIONS

This application is 35 U.S.C. § 371 national phase application of PCT/EP2022/56991, filed on Mar. 17, 2022, which claims the benefit of U.S. Provisional Application No. 63/162,749 filed Mar. 18, 2021, and U.S. Provisional Application No. 63/276,117 filed Nov. 5, 2021, each incorporated herein by reference in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD

The present disclosure relates generally to psilocin compounds and pharmaceutically acceptable salts, polymorphs, stereoisomers, or solvates thereof, compositions, and, in some embodiments, to serotonin 5-$HT_2$ receptor agonists and uses in the treatment of diseases associated with a 5-$HT_2$ receptor.

BACKGROUND

Psilocybin (PY) and psilocin (PI) are tryptamine alkaloids and structural analogs of the neurotransmitter serotonin. Psilocybin is a prodrug of psilocin. That is, when consumed, psilocybin is rapidly metabolized into the active form, psilocin (4-hydroxy-N,N-dimethyltryptamine). Specifically, a chemical process called dephosphorylation removes the phosphate group on psilocybin, creating psilocin.

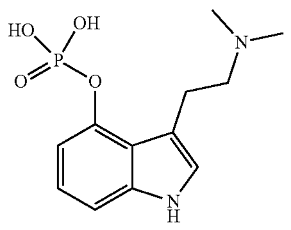

Psilocybin

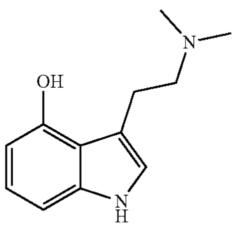

Psilocin

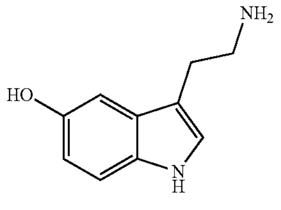

Serotonin

Outside the body, psilocin is reported to be a short-lived and unstable molecule. Therefore, therapeutic applications involving the use of psilocin are generally accomplished by administration of the precursor, psilocybin, or other prodrug approaches. However, psilocybin has slow onset and a long duration of drug action, often requiring 7-8 hours of supervised clinical observation of a patient before discharge. Therefore, there is a need for a stabilized psilocin, that does not rely on breakdown of a prodrug to provide pharmacologically active drug, and that has a faster/quicker therapeutic onset and a shorter duration of drug action (i.e., shorter duration of therapeutic effect) than psilocybin.

SUMMARY

The present disclosure is based at least in part on the identification of novel stabilized forms of psilocin and deuterated psilocin, including novel polymorphs of psilocin/deuterated psilocin, novel salt forms of psilocin/deuterated psilocin and their polymorphs, as well as compositions thereof, which provide a fast therapeutic onset, a shortened duration of drug action, and less variability in drug exposure (e.g., compared to psilocybin or other prodrug approaches), and methods of using the same to treat diseases associated with a serotonin 5-$HT_2$ receptor. More specifically, the present disclosure provides stabilized forms of psilocin and deuterated psilocin and compositions thereof, that can be used to treat neuropsychiatric disorders, central nervous system (CNS) disorders, and other disorders, such as those associated with inflammation, for example, through various dosing regimens (e.g., once-daily, once-weekly, sub-psychedelic dosing, etc.) to selectively engage 5-$HT_{2A}$Rs without producing psychedelic side effects.

The disclosed stabilized forms of psilocin and deuterated psilocin do not rely on prodrug metabolism for release of active agent, as is the case with psilocybin administration or related prodrug approaches, and thus have a faster/quicker therapeutic onset, a shorter duration of drug action (i.e., short duration of therapeutic effect), and less inter-subject variability. Further, certain dosage forms of these stabilized forms of psilocin and deuterated psilocin, such as oral disintegrating tablets (ODT) and immediate release (IR) tablets, have also been found to enhance these stability and/or fast onset characteristics, as they provide for immediate disintegration and rapid release of the compounds/salts herein—particularly ODT and related dosage forms which allow for pre-gastric absorption of the compounds/salts herein, e.g., when administered through the mucosal linings of the oral cavity.

Thus, the present disclosure provides:

(1) A pharmaceutically acceptable salt of a compound of Formula (I), or a polymorph, stereoisomer, or solvate thereof, (I)

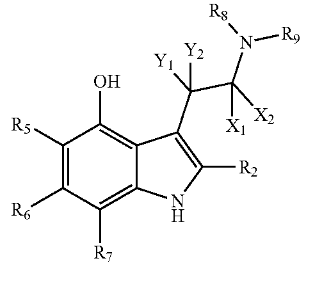

wherein:

$R_2$, $R_5$, $R_6$, and $R_7$ are independently selected from the group consisting of hydrogen or deuterium, $R_8$ and $R_9$ are independently selected from the group consisting of —$CH_3$ and —$CD_3$, and $X_1$, $X_2$, $Y_1$, and $Y_2$ are independently selected from the group consisting of hydrogen or deuterium.

(2) The pharmaceutically acceptable salt of (1), wherein $R_2$, $R_5$, $R_6$, and $R_7$ are hydrogen.

(3) The pharmaceutically acceptable salt of (1), wherein at least one of $R_2$, $R_5$, $R_6$, and $R_7$ is deuterium.

(4) The pharmaceutically acceptable salt of any one of (1) to (3), wherein $R_8$ and $R_9$ are —$CH_3$.

(5) The pharmaceutically acceptable salt of any one of (1) to (3), wherein $R_8$ and $R_9$ are —$CD_3$.

(6) The pharmaceutically acceptable salt of any one of (1) to (5), wherein $X_1$, $X_2$, $Y_1$, and $Y_2$ are deuterium.

(7) The pharmaceutically acceptable salt of any one of (1) to (6), wherein $X_1$ and $X_2$ are deuterium.

(8) The pharmaceutically acceptable salt of any one of (1) to (7), wherein $Y_1$ and $Y_2$ are deuterium.

(9) The pharmaceutically acceptable salt of any one of (1) to (5) or (7), wherein $Y_1$ and $Y_2$ are hydrogen.

(10) The pharmaceutically acceptable salt of any one of (1) to (9), wherein the compound of Formula (I) is selected from the group consisting of:

(I-1)

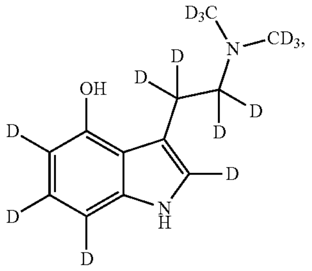

(I-2)

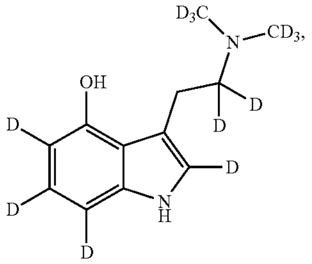

(I-3)

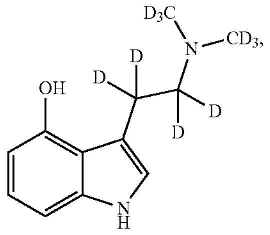

(I-4)

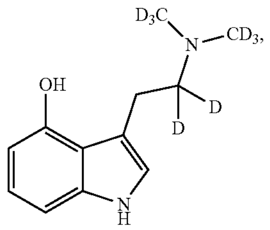

-continued (I-5)

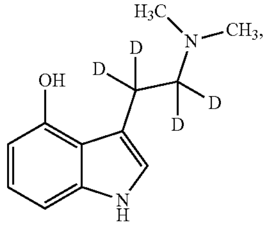

(I-6)

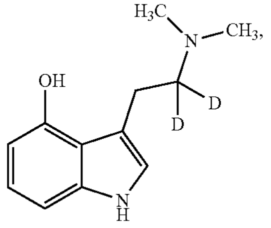

(I-7)

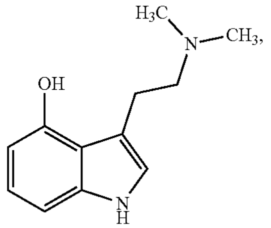

(I-8)

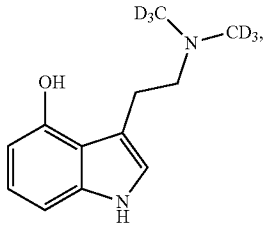

(I-9)

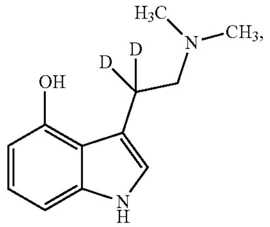

and (I-10)

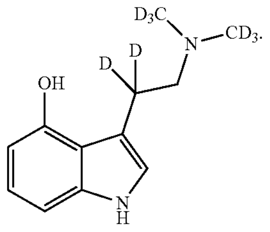

(11) The pharmaceutically acceptable salt of any one of (1) to (10), wherein the compound of Formula (I) is (I-3)

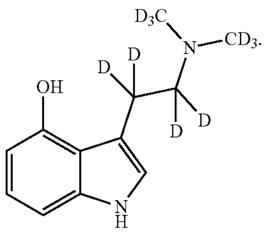

(12) The pharmaceutically acceptable salt of any one of (1) to (10), wherein the compound of Formula (I) is (I-7)

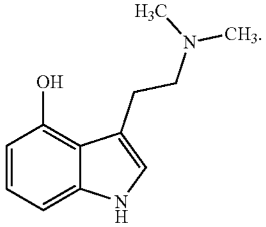

(13) The pharmaceutically acceptable salt of any one of (1) to (12), wherein the compound of Formula (I) is an agonist of a serotonin 5-$HT_2$ receptor.

(14) The pharmaceutically acceptable salt of any one of (1) to (13), wherein the compound of Formula (I) is an agonist of a serotonin 5-$HT_{2A}$ receptor.

(15) The pharmaceutically acceptable salt of any one of (1) to (14), which is a benzenesulfonate salt, a tartrate salt, a hemi-fumarate salt, an acetate salt, a citrate salt, a malonate salt, a fumarate salt, a succinate salt, an oxalate salt, a benzoate salt, a salicylate salt, an ascorbate salt, a hydrochloride salt, a maleate salt, a malate salt, a methanesulfonate salt, a toluenesulfonate salt, a glucuronate salt, or a glutarate salt of the compound of Formula (I).

(16) The pharmaceutically acceptable salt of any one of (1) to (15), which is a benzenesulfonate salt, a tartrate salt, a hemi-fumarate salt, an acetate salt, a citrate salt, a malonate salt, a fumarate salt, a succinate salt, an oxalate salt, a benzoate salt, or a salicylate salt of the compound of Formula (I).

(17) The pharmaceutically acceptable salt of any one of (1) to (16), which is a benzenesulfonate salt or a benzoate salt of the compound of Formula (I).

(18) The pharmaceutically acceptable salt of any one of (1) to (17), which is a benzenesulfonate salt of the compound of Formula (I).

(19) The pharmaceutically acceptable salt of any one of (1) to (17), which is a benzoate salt of the compound of Formula (I).

(20) The pharmaceutically acceptable salt of any one of (1) to (16), which is a citrate salt of the compound of Formula (I).

(21) The pharmaceutically acceptable salt of any one of (1) to (16), which is a tartrate salt of the compound of Formula (I).

(22) The pharmaceutically acceptable salt of any one of (1) to (18), which is a benzenesulfonate salt of 3-(2-(bis(methyl-$d_3$)amino)ethyl-1,1,2,2-$d_4$)-1H-indol-4-ol (I-3a).

(23) The pharmaceutically acceptable salt of (22), wherein the benzenesulfonate salt of 3-(2-(bis(methyl-$d_3$)amino)ethyl-1,1,2,2-$d_4$)-1H-indol-4-ol (1-3a) is crystalline and characterized by an X-ray powder diffraction pattern containing at least three characteristic peaks at diffraction angles ($2\theta=0.2°$) selected from the group consisting of 7.023°, 7.767°, 11.822°, 12.550°, 12.860°, 13.994°, 15.521°, 18.436°, 19.503°, 20.760°, 21.070°, 22.007°, 22.745°, 23.340°, 24.187°, 25.532°, 26.880°, 27.856°, 28.163°, 31.267°, 33.024°, 35.030°, 36.835°, 39.312°, 40.545°, and 40.9880.

(24) The pharmaceutically acceptable salt of any one of (1) to (18), which is a benzenesulfonate salt of 3-(2-(dimethylamino)ethyl)-1H-indol-4-ol (I-7a).

(25) The pharmaceutically acceptable salt of (24), wherein the benzenesulfonate salt of 3-(2-(dimethylamino)ethyl)-1H-indol-4-ol (I-7a) is crystalline and characterized by an X-ray powder diffraction pattern containing at least three characteristic peaks at diffraction angles ($2\theta=0.2°$) selected from the group consisting of 7.002°, 7.733°, 11.768°, 12.516°, 12.882°, 13.546°, 13.968°, 14.788°, 15.225°, 15.474°, 18.370°, 19.737°, 20.703°, 21.050°, 21.873°, 21.982°, 22.315°, 22.639°, 23.282°, 23.775°, 24.125°, 25.193°, 25.475°, 25.931°, 26.813°, 27.778°, 28.127°, 30.866°, 31.207°, 32.941°, 33.222°, 33.698°, 36.803°, 38.668°, and 39.289°.

(26) The pharmaceutically acceptable salt of any one of (1) to (17) or (19), which is a benzoate salt of 3-(2-(bis(methyl-$d_3$)amino)ethyl-1,1,2,2-$d_4$)-1H-indol-4-ol (I-3j).

(27) The pharmaceutically acceptable salt of (26), wherein the benzoate salt of 3-(2-(bis(methyl-$d_3$) amino)ethyl-1,1,2,2-$d_4$)-1H-indol-4-ol (I-3j) is crystalline and characterized by an X-ray powder diffraction pattern containing at least three characteristic peaks at diffraction angles ($2\theta\pm0.2°$) selected from the group consisting of 9.486°, 11.006°, 12.379°, 13.428°, 14.608°, 15.446°, 16.389°, 18.247°, 18.977°, 19.346°, 19.831°, 20.868°, 21.447°, 22.860°, 23.878°, 24.944°, 25.737°, 26.144°, 26.341°, 26.990°, 27.708°, 28.595°, 30.048°, 30.763°, 31.127°, 31.839°, 32.800°, 34.460°, 35.444°, 37.725°, and 38.597°.

(28) The pharmaceutically acceptable salt of any one of (1) to (17) or (19), which is a benzoate salt of 3-(2-(dimethylamino)ethyl)-1H-indol-4-ol (I-7j).

(29) The pharmaceutically acceptable salt of (28), wherein benzoate salt of 3-(2-(dimethylamino)ethyl)-1H-indol-4-ol (I-7j) is crystalline and characterized by an X-ray powder diffraction pattern containing at least three characteristic peaks at diffraction angles ($2\theta\pm0.2°$) selected from the group consisting of 9.492°, 11.011°, 12.391°, 13.440°, 14.609°, 15.432°, 16.394°, 18.259°, 18.967°, 19.356°, 19.827°, 20.843°, 21.476°, 22.062°, 22.805°, 23.862°, 24.963°, 25.734°, 26.170°, 26.992°, 27.738°, 28.593°, 30.073°, 30.746°, 31.041°, 31.799°, 32.794°, 33.551°, 34.480°, 35.430°, 37.685°, and 38.643°.

(30) The pharmaceutically acceptable salt of anyone of (1) to (16) or (20), which is a citrate salt of 3-(2-(bis (methyl-$d_3$)amino)ethyl-1,1,2,2-$d_4$)-1H-indol-4-ol (I-3e).

(31) The pharmaceutically acceptable salt of (30), wherein the citrate salt of 3-(2-(bis(methyl-$d_3$)amino) ethyl-1,1,2,2-$d_4$)-1H-indol-4-ol (I-3e) is amorphous by X-ray powder diffraction.

(32) The pharmaceutically acceptable salt of any one of (1) to (16) or (20), which is a citrate salt of 3-(2-(dimethylamino)ethyl)-1H-indol-4-ol (I-7e).

(33) The pharmaceutically acceptable salt of (32), wherein citrate salt of 3-(2-(dimethylamino)ethyl)-1H-indol-4-ol (I-7e) is amorphous by X-ray powder diffraction.

(34) The pharmaceutically acceptable salt of any one of (1) to (16) or (21), which is a tartrate salt of 3-(2-(bis(methyl-$d_3$)amino)ethyl-1,1,2,2-$d_4$)-1H-indol-4-ol (I-3b).

(35) The pharmaceutically acceptable salt of (34), wherein the tartrate salt of 3-(2-(bis(methyl-$d_3$)amino)ethyl-1,1,2,2-$d_4$)-1H-indol-4-ol (I-3b) is crystalline and characterized by an X-ray powder diffraction pattern containing at least three characteristic peaks at diffraction angles (2θ±0.2°) selected from the group consisting of 6.732°, 12.708°, 13.470°, 14.774°, 15.921°, 16.268°, 17.295°, 18.869°, 20.079°, 20.208°, 20.877°, 21.894°, 22.657°, 23.491°, 23.702°, 24.636°, 24.882°, 25.569°, 26.685°, 27.060°, 27.502°, 28.179°, 28.597°, 29.035°, 29.257°, 29.527°, 31.017°, 31.527°, 32.059°, 32.307°, 33.012°, 34.024°, 34.388°, 34.905°, 35.361°, 36.183°, 37.372°, 37.764°, 38.657°, 41.049°.

(36) The pharmaceutically acceptable salt of any one of (1) to (16) or (21), which is a tartrate salt of 3-(2-(dimethylamino)ethyl)-1H-indol-4-ol (I-7b).

(37) The pharmaceutically acceptable salt of (36), wherein the tartrate salt of 3-(2-(dimethylamino)ethyl)-1H-indol-4-ol (I-7b) is crystalline and characterized by an X-ray powder diffraction pattern containing at least three characteristic peaks at diffraction angles (2θ±0.2°) selected from the group consisting of 6.798°, 11.360°, 12.764°, 13.535°, 14.837°, 15.973°, 16.351°, 17.367°, 18.937°, 20.168°, 20.929°, 21.946°, 22.719°, 23.604°, 23.814°, 24.874°, 25.609°, 26.745°, 27.111°, 27.558°, 28.653°, 29.630°, 31.129°, 31.567°, 32.180°, 33.073°, 34.096°, 34.460°, 36.226°, 37.497°, 38.727°.

(38) The pharmaceutically acceptable salt of any one of (1) to (37), wherein the pharmaceutically acceptable salt of the compound of Formula (I) has a water solubility from about 1 mg/mL to about 400 mg/mL.

(39) The pharmaceutically acceptable salt of any one of (1) to (14), which is a fatty acid salt of the compound of Formula (I).

(40) The pharmaceutically acceptable salt of (39), which is an adipate salt, a laurate salt, a linoleate salt, a myristate salt, a caprate salt, a stearate salt, an oleate salt, a caprylate salt, a palmitate salt, a sebacate salt, an undecylenate salt, or a caproate salt of the compound of Formula (I).

(41) The pharmaceutically acceptable salt of (39) or (40), which is an adipate salt, a laurate salt, a linoleate salt, a myristate salt, a caprate salt, a stearate salt, an oleate salt, or a caprylate salt of the compound of Formula (I).

(42) The pharmaceutically acceptable salt of any one of (39) to (41), which is a laurate salt, a linoleate salt, a myristate salt, a caprate salt, a stearate salt, an oleate salt, or a caprylate salt of the compound of Formula (I).

(43) The pharmaceutically acceptable salt of any one of (39) to (42), which is a laurate salt, a linoleate salt, a caprate salt, or a caprylate salt of the compound of Formula (I).

(44) A pharmaceutical composition comprising the pharmaceutically acceptable salt of any one of (1) to (43), and a pharmaceutically acceptable vehicle.

(45) The pharmaceutical composition of (44), which is adapted for intraoral administration.

(46) The pharmaceutical composition of (44) or (45), wherein the pharmaceutical composition is in an orodispersible dosage form.

(47) The pharmaceutical composition of any one of (44) to (46), wherein the pharmaceutical composition is in a form of an orally disintegrating tablet (ODT).

(48) The pharmaceutical composition of any one of (44) to (47), wherein the pharmaceutically acceptable vehicle comprises a water-soluble polymer and a matrix material, filler, or diluent.

(49) The pharmaceutical composition of (48), wherein the water-soluble polymer is gelatin, and the matrix material, filler, or diluent is mannitol.

(50) The pharmaceutical composition of (48) or (49), wherein the pharmaceutically acceptable vehicle further comprises an acid.

(51) The pharmaceutical composition of (50), wherein the acid is citric acid and/or tartaric acid.

(52) The pharmaceutical composition of any one of (44) to (46), wherein the pharmaceutical composition is in a form of an orodispersible film (ODF).

(53) The pharmaceutical composition of (44), wherein the pharmaceutical composition is in an immediate release (IR) dosage form.

(54) The pharmaceutical composition of (53), wherein the immediate release (IR) dosage form is an immediate release (IR) tablet.

(55) The pharmaceutical composition of (54), wherein the immediate release (IR) tablet comprises microcrystalline cellulose, sodium carboxymethylcellulose, and magnesium stearate.

(56) The pharmaceutical composition of (54), wherein the immediate release (IR) tablet comprises mannitol, crospovidone, and sodium stearyl fumarate.

(57) A method of treating a subject with a disease or disorder, comprising: administering to the subject a therapeutically effective amount of the pharmaceutically acceptable salt of any one of (1) to (43).

(58) A method of treating a subject with a disease or disorder associated with a serotonin 5-$HT_2$ receptor, comprising:

administering to the subject a therapeutically effective amount of the pharmaceutically acceptable salt of any one of (1) to (43).

(59) The method of (58), wherein the disease or disorder is a neuropsychiatric disease or disorder or an inflammatory disease or disorder.

(60) The method of (58), wherein the disease or disorder is a central nervous system (CNS) disorder.

(61) The method of (60), wherein the central nervous system (CNS) disorder is at least one selected from the group consisting of major depressive disorder (MDD), treatment-resistant depression (TRD), post-traumatic stress disorder (PTSD), bipolar and related disorders, obsessive-compulsive disorder (OCD), generalized anxiety disorder (GAD), social anxiety disorder, a substance use disorder, an eating disorder, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, suicidal ideation, suicidal behavior, major depressive disorder with suicidal ideation or suicidal behavior, melancholic depression, atypical depression, dysthymia, non-suicidal self-injury disorder (NSSID), chronic fatigue syndrome, Lyme's disease, gambling disorder, a paraphilic disorder, sexual dysfunction, peripheral neuropathy, and obesity.

(62) The method of (60), wherein the central nervous system (CNS) disorder is major depressive disorder (MDD).

(63) The method of (60), wherein the central nervous system (CNS) disorder is treatment-resistant depression (TRD).

(64) The method of (60), wherein the central nervous system (CNS) disorder is generalized anxiety disorder (GAD).

(65) The method of (60), wherein the central nervous system (CNS) disorder is social anxiety disorder.

(66) The method of (60), wherein the central nervous system (CNS) disorder is obsessive-compulsive disorder (OCD).

(67) The method of (60), wherein the central nervous system (CNS) disorder is a substance use disorder.

(68) The method of (67), wherein the central nervous system (CNS) disorder is alcohol use disorder.

(69) The method of (58), wherein the disease or disorder is an autonomic nervous system (ANS) condition.

(70) The method of (58), wherein the disease or disorder is a pulmonary disorder.

(71) The method of (58), wherein the disease or disorder is a cardiovascular disorder.

(72) The method of any one of (58) to (71), wherein the pharmaceutically acceptable salt is administered orally to the subject.

(73) The method of any one of (58) to (72), wherein the pharmaceutically acceptable salt is administered intraorally to the subject.

(74) The method of any one of (58) to (71), wherein the pharmaceutically acceptable salt is administered transdermally to the subject.

(75) The method of any one of (58) to (71), wherein the pharmaceutically acceptable salt is administered subcutaneously to the subject.

(76) The method of any one of (58) to (75), wherein the pharmaceutically acceptable salt is administered at a psychedelic dose of about 0.083 mg/kg to about 1 mg/kg.

(77) The method of (76), wherein the pharmaceutically acceptable salt is administered at the psychedelic dose once per week or less over a treatment course.

(78) The method of any one of (57) to (75), wherein the pharmaceutically acceptable salt is administered at a sub-psychedelic dose of about 0.00001 mg/kg to less than about 0.083 mg/kg.

(79) The method of (78), wherein the pharmaceutically acceptable salt is administered at the sub-psychedelic dose once per day or more over a treatment course.

(80) A method for stabilizing the compound of Formula (I) comprising preparing the pharmaceutically acceptable salt of the compound of Formula (I) of any one of (1) to (43).

(81) A method for decreasing time of therapeutic onset relative to a psilocybin-based drug, comprising:

administering a therapeutically effective amount of the pharmaceutically acceptable salt of the compound of Formula (I) of any one of (1) to (43) to a subject in need thereof.

(82) A method of reducing psychedelic side effects relative to a psilocybin-based drug, comprising:

administering a therapeutically effective amount of the pharmaceutically acceptable salt of the compound of Formula (I) of any one of (1) to (43) to a subject in need thereof.

(83) A method of decreasing duration of therapeutic effect relative to a psilocybin-based drug, comprising:

administering a therapeutically effective amount of the pharmaceutically acceptable salt of the compound of Formula (I) of any one of (1) to (43) to a subject in need thereof.

(84) A solution-phase composition, comprising:

the pharmaceutically acceptable salt of the compound of Formula (I) of any one of (1) to (43), in solvated form.

(85) The solution-phase composition of (84), which is an aqueous solution-phase composition comprising the pharmaceutically acceptable salt of the compound of Formula (I), in solvated form.

(86) A crystalline polymorph of a compound of Formula (I), or a stereoisomer or a solvate thereof, (I)

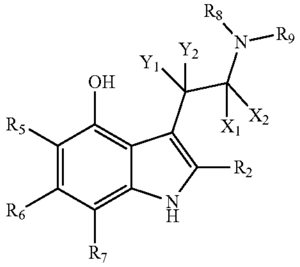

wherein:

$R_2$, $R_5$, $R_6$, and $R_7$ are independently selected from the group consisting of hydrogen or deuterium, $R_8$ and $R_9$ are independently selected from the group consisting of —$CH_3$ and —$CD_3$, and $X_1$, $X_2$, $Y_1$, and $Y_2$ are independently selected from the group consisting of hydrogen or deuterium.

(87) The crystalline polymorph of (86), which is a crystalline form of 3-(2-(bis(methyl-$d_3$)amino)ethyl-1,1,2,2-$d_4$)-1H-indol-4-ol (I-3) characterized by an X-ray powder diffraction pattern containing at least three characteristic peaks at diffraction angles (2θ±0.2°) selected from the group consisting of 7.582°, 8.395°, 9.647°, 10.444°, 11.319°, 12.614°, 13.372°, 14.222°, 15.157°, 16.524°, 16.787°, 17.693°, 19.468°, 19.699°, 20.901°, 21.132°, 21.859°, 22.547°, 23.699°, 24.630°, 25.034°, 25.264°, 26.867°, 27.399°, 27.929°, 28.219°, 28.871°, 29.430°, 30.120°, 30.675°, 31.373°, 32.365°, 33.880°, 34.418°, 34.792°, 35.884°, 36.254°, 37.156°, 38.200°, and 38.417°.

(88) The crystalline polymorph of (86), which is a crystalline form of 3-(2-(bis(methyl-$d_3$)amino)ethyl-1,1,2,2-$d_4$)-1H-indol-4-ol (I-3) characterized by an X-ray powder diffraction pattern containing at least three characteristic peaks at diffraction angles (2θ=0.2°) selected from the group consisting of 8.124°, 8.357°, 10.059°, 12.630°, 13.420°, 13.743°, 14.053°, 15.220°, 16.272°, 16.763°, 16.954°, 17.328°, 17.662°, 18.062°, 18.742°, 19.413°, 19.658°, 20.172°, 20.836°, 21.267°, 21.833°, 22.213°, 22.504°, 23.334°, 23.701°, 24.385°, 25.431°, 25.721°, 26.049°, 27.291°, 28.368°, 30.349°, 30.656°, 31.337°, 31.538°, 32.091°, 35.870°, 38.514°, and 41.361°.

(89) The crystalline polymorph of (86), which is a crystalline form of 3-(2-(dimethylamino)ethyl)-1H-indol-4-ol (I-7) characterized by an X-ray powder diffraction pattern containing at least three characteristic peaks at diffraction angles (2θ±0.2°) selected from the group consisting of 7.563°, 8.375°, 12.626°, 13.383°, 15.211°, 16.753°, 17.671°, 19.668°, 21.112°, 21.863°, 22.201°, 22.560°, 23.711°, 24.592°, 25.415°, 26.820°, 27.357°, 27.921°, 28.228°, 29.253°, 30.653°, 31.364°, 32.401°, 33.797°, 34.445°, 39.867°

(90) A pharmaceutical composition comprising the crystalline polymorph of any one of (86) to (89), and a pharmaceutically acceptable vehicle.

(91) The pharmaceutical composition of (90), wherein the pharmaceutically acceptable vehicle comprises an acid.

(92) The pharmaceutical composition of (91), wherein the acid is citric acid and/or tartaric acid.

(93) A method of treating a subject with a disease or disorder associated with a serotonin 5-$HT_2$ receptor, comprising:

administering to the subject a therapeutically effective amount of the crystalline polymorph of any one of (86) to (89).

(94) An amorphous compound of Formula (I), or a stereoisomer or a solvate thereof, (I)

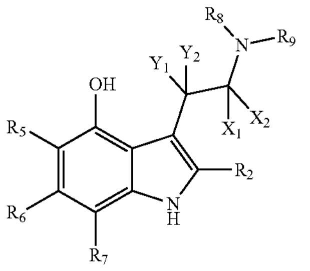

wherein:

$R_2$, $R_5$, $R_6$, and $R_7$ are independently selected from the group consisting of hydrogen or deuterium, $R_8$ and $R_9$ are independently selected from the group consisting of —$CH_3$ and —$CD_3$, and $X_1$, $X_2$, $Y_1$, and $Y_2$ are independently selected from the group consisting of hydrogen or deuterium.

(95) The amorphous compound of (94), which is an amorphous form of 3-(2-(bis(methyl-$d_3$)amino)ethyl-1,1,2,2-$d_4$)-1H-indol-4-ol (I-3), as determined by X-ray powder diffraction.

(96) The amorphous compound of (94), which is an amorphous form of 3-(2-(dimethylamino)ethyl)-1H-indol-4-ol (I-7), as determined by X-ray powder diffraction.

(97) The amorphous compound of any one of (94) to (96), which has a glass transition temperature of about 26° C. to about 30° C. as determined by differential scanning calorimetry (DSC).

(98) The amorphous compound of any one of (94) to (97), which is prepared by melting a crystalline form of the compound of Formula (I) to beyond a melting point of the crystalline form, and then rapidly cooling to a glass transition temperature.

(99) A pharmaceutical composition comprising the amorphous compound of any one of (94) to (98), and a pharmaceutically acceptable vehicle.

(100) A method of treating a subject with a disease or disorder associated with a serotonin 5-$HT_2$ receptor, comprising:

administering to the subject a therapeutically effective amount of the amorphous compound of any one of (94) to (98).

(101) Use of the pharmaceutically acceptable salt of any one of (1) to (43), the pharmaceutical composition of any one of (44) to (56), the solution-phase composition of (84) or (85), the crystalline polymorph of any one of (86) to (89), the pharmaceutical composition of any one of (90) to (92), the amorphous compound of any one of (94) to (98), or the pharmaceutical composition of (99) for treating a subject with a disease or disorder associated with a serotonin 5-$HT_2$ receptor.

(102) The pharmaceutically acceptable salt of any one of (1) to (43), which is at least 10% more stable as both a solid and an aqueous solution, in terms of % (active) remaining after being subject to 40° C. for 24 hours, compared to the compound of Formula (I) (free base) prepared in substantially the same way as a solid or aqueous solution.

BRIEF DESCRIPTION OF THE DRAWINGS

The forgoing paragraphs have been provided by way of general introduction and are not intended to limit the scope of the following claims. The described embodiments, together with further advantages, will be best understood by reference to the following detailed description when considered in conjunction with the accompanying drawings, wherein:

FIG. 4 shows a differential scanning calorimetry (DSC) curve of I-7a;

FIG. 5 shows a thermogravimetric analysis (TGA) curve of I-7a;

FIGS. 6A and 6B show a $^1H$ NMR spectrum of I-7a;

FIG. 7 shows the ultra performance liquid chromatogram (UPLC) of I-7a;

FIG. 8 shows a DVS isotherm plot of I-7a;

(FIG. 108A), 23° C. (FIG. 108B), 40° C. (FIG. 108C);

FIG. 119 shows the stability of I-7 (PI-$d_0$) over 24 hours in 1% w/w solutions of CAVITRON® W7 HP7, with or without metal ions, compared to those solutions without CAVITRON® W7 HP7, at 40° C.;

Figure 120:
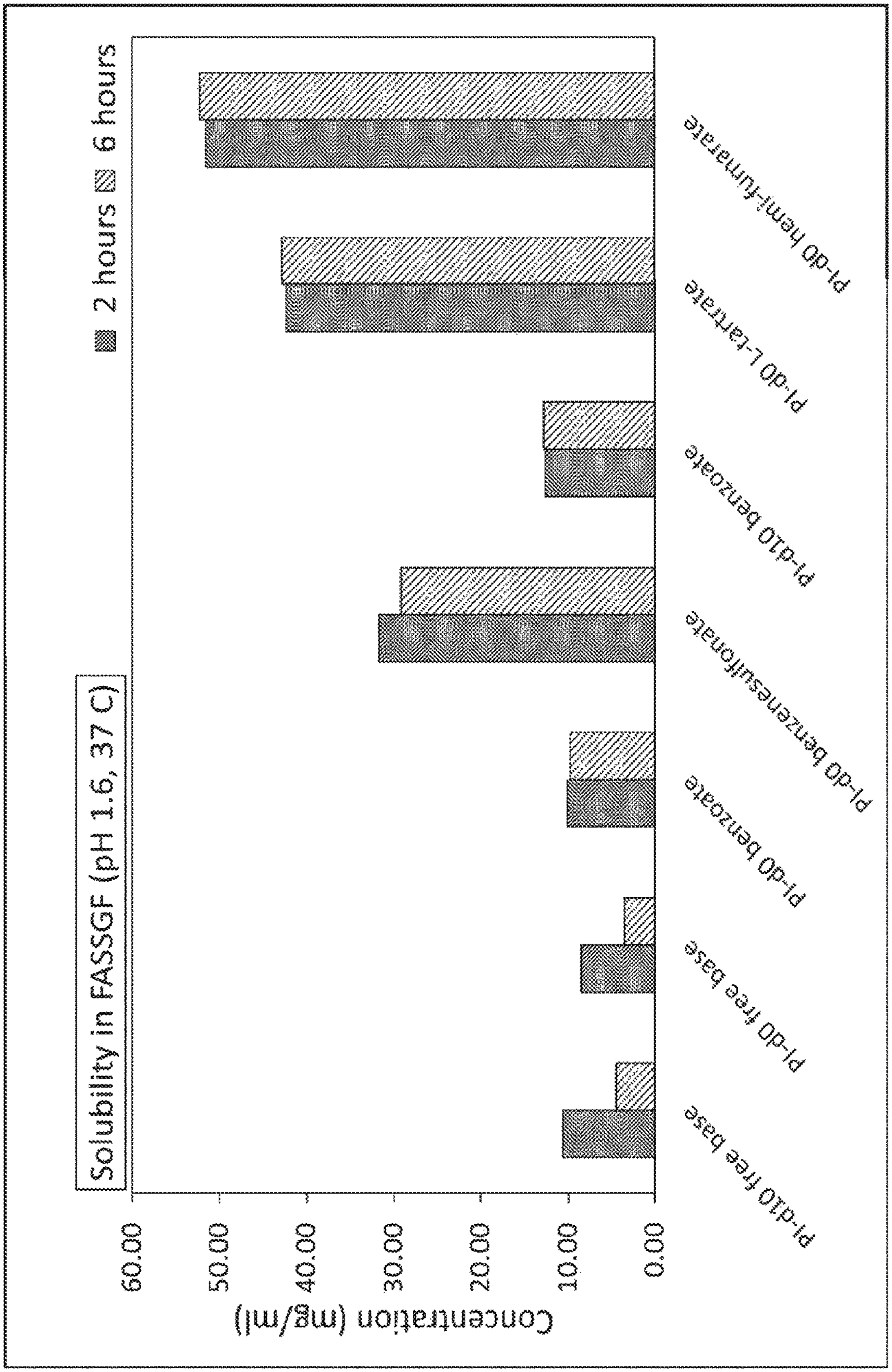
Figure 121:
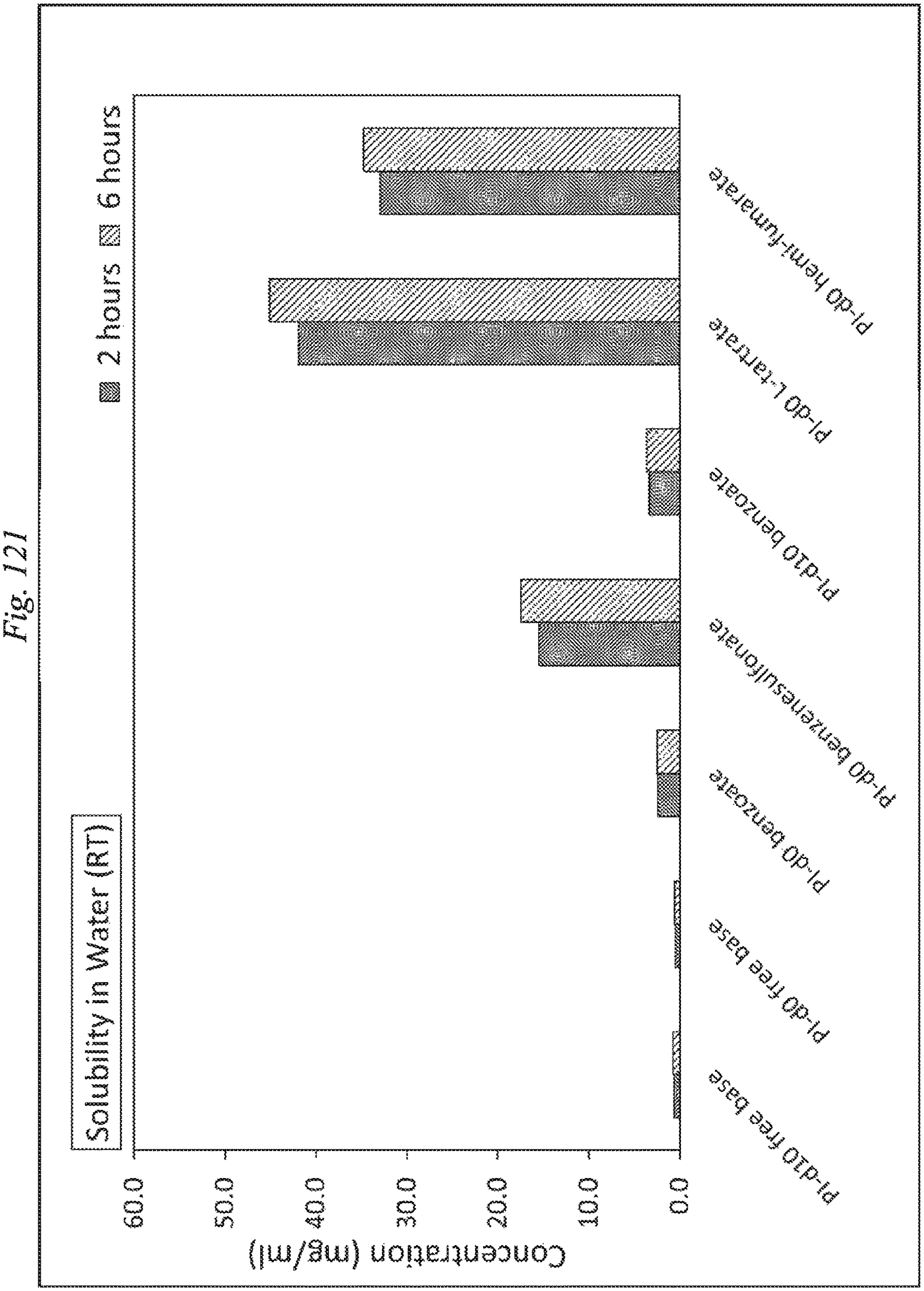
Figure 122:
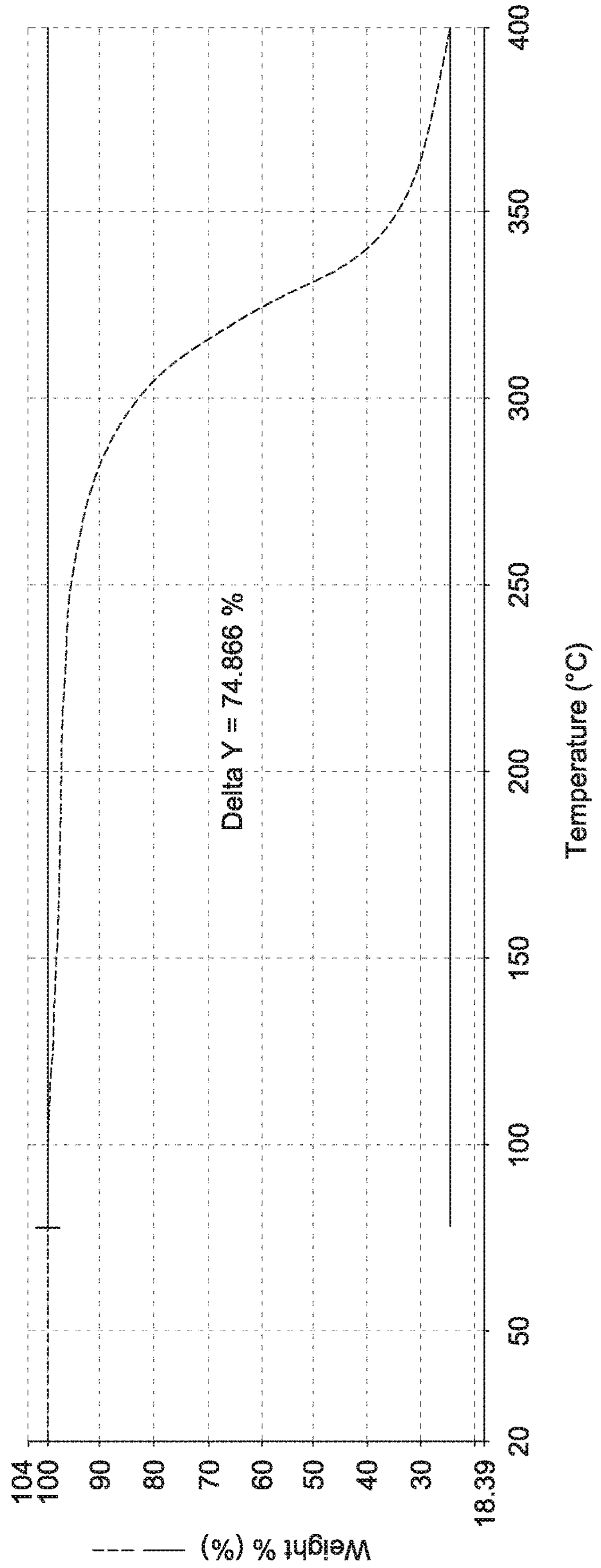
Figure 123:
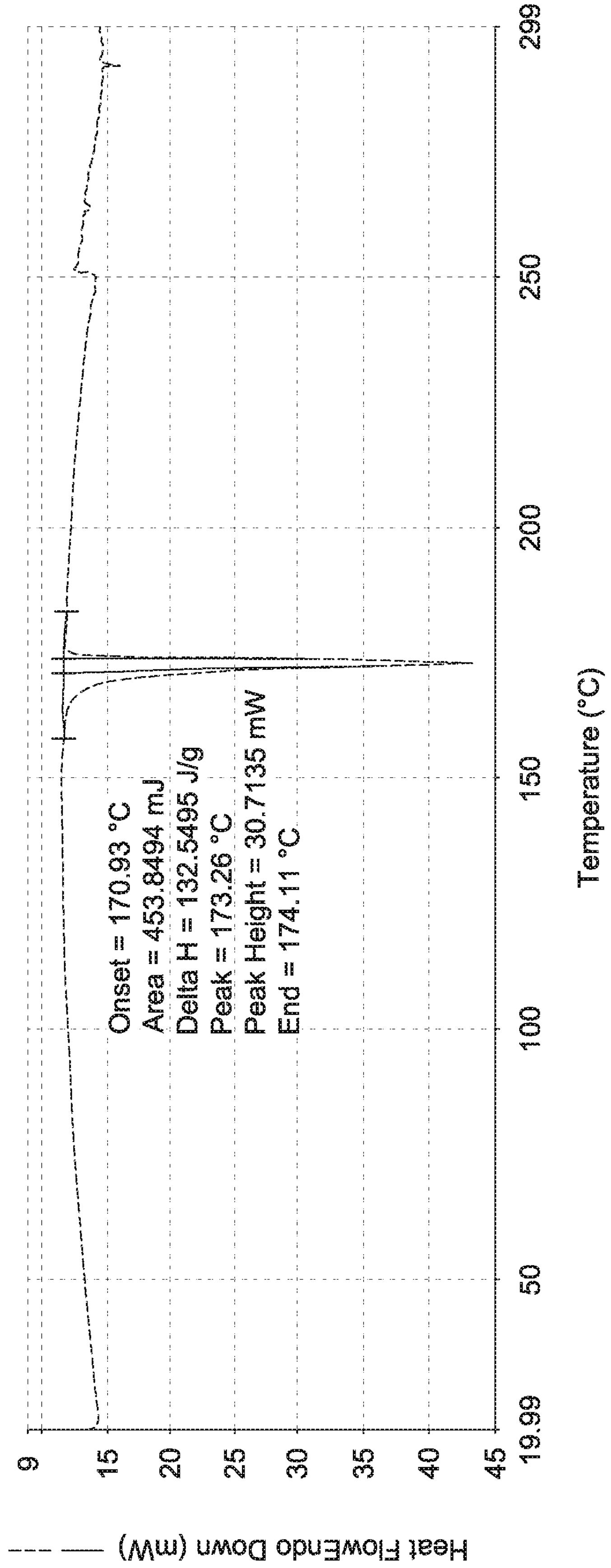
Figure 124:
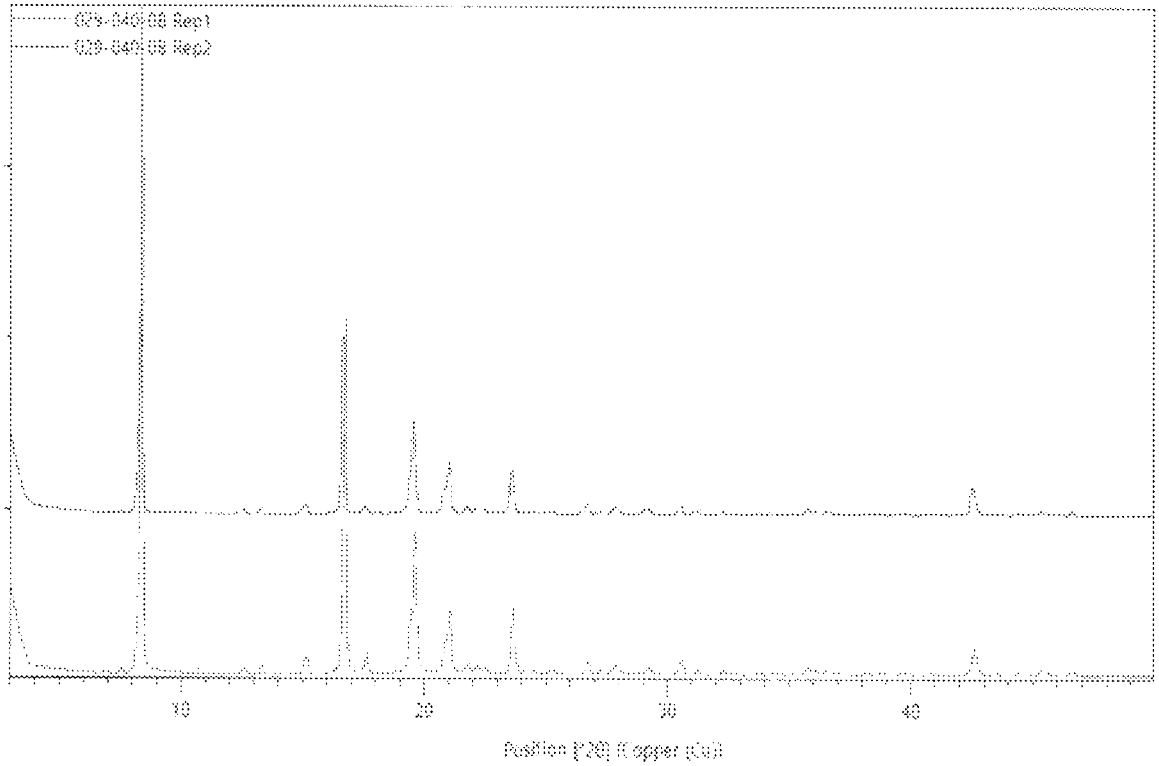
Figure 125:
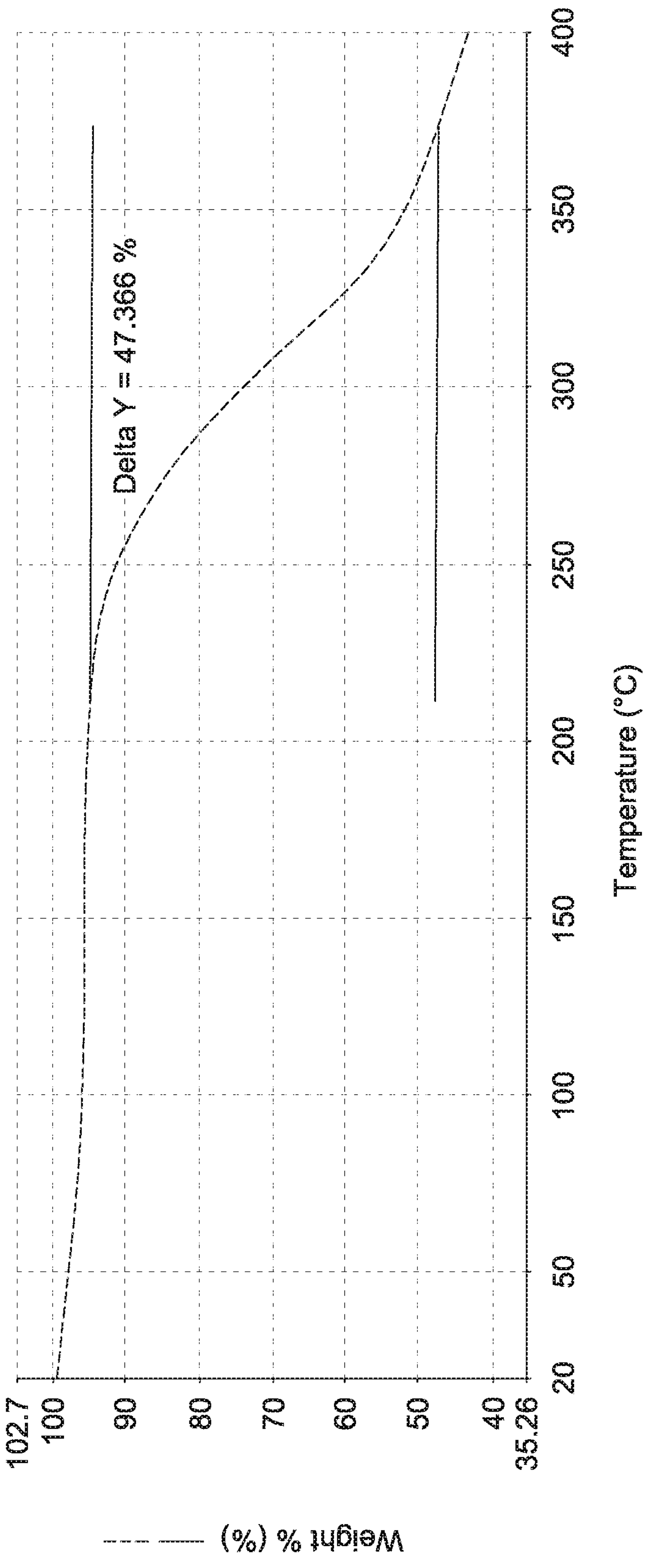
Figure 126:
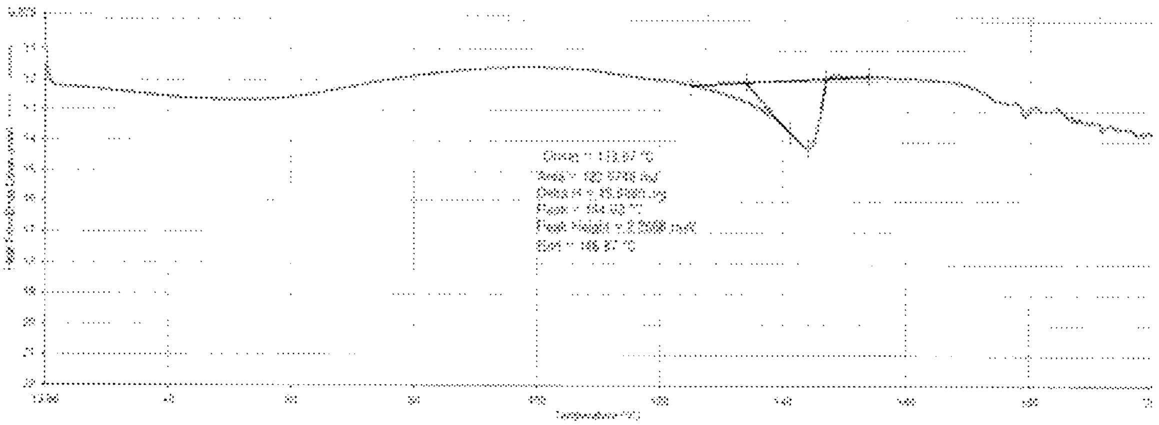
Figure 127:
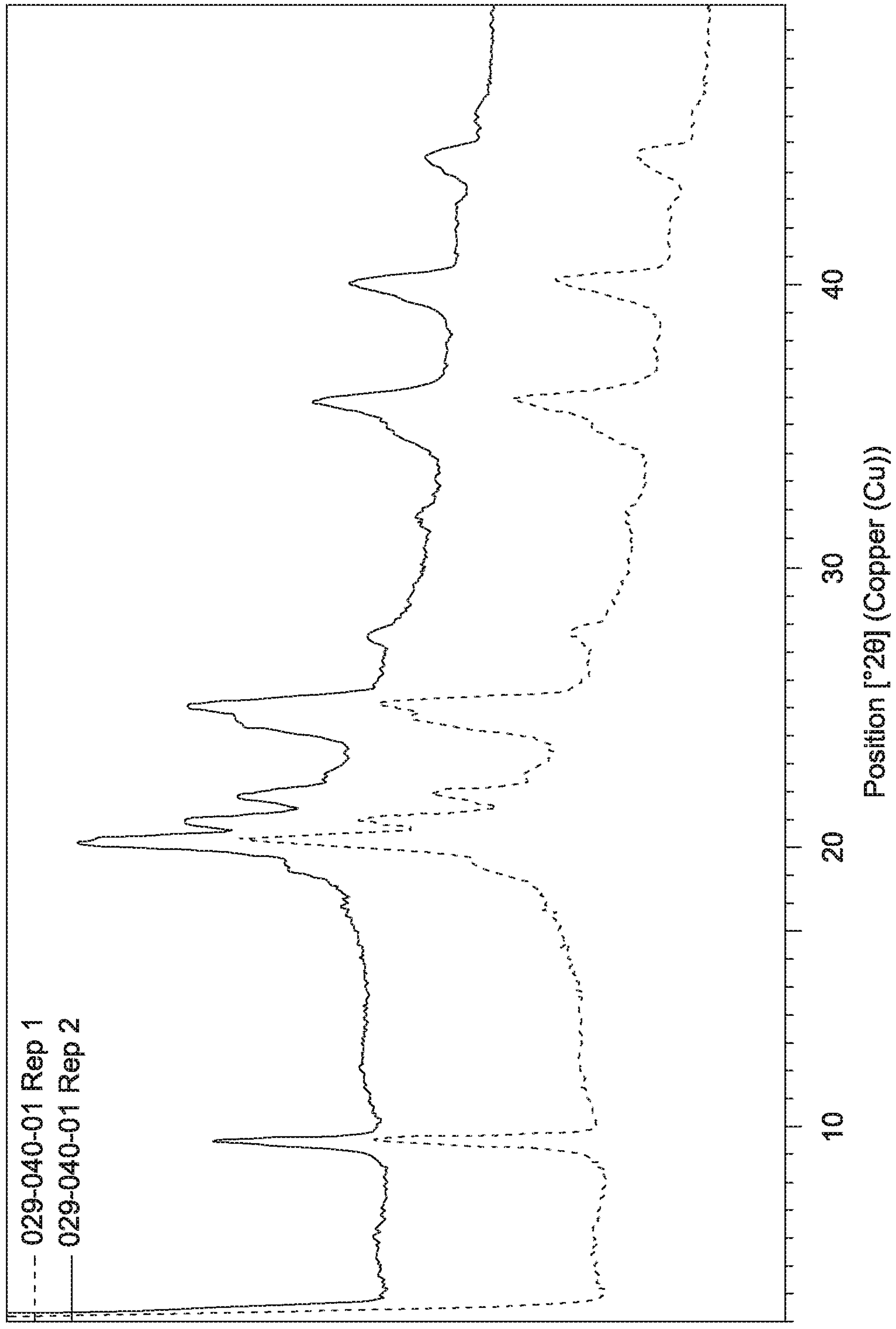
Figure 128:
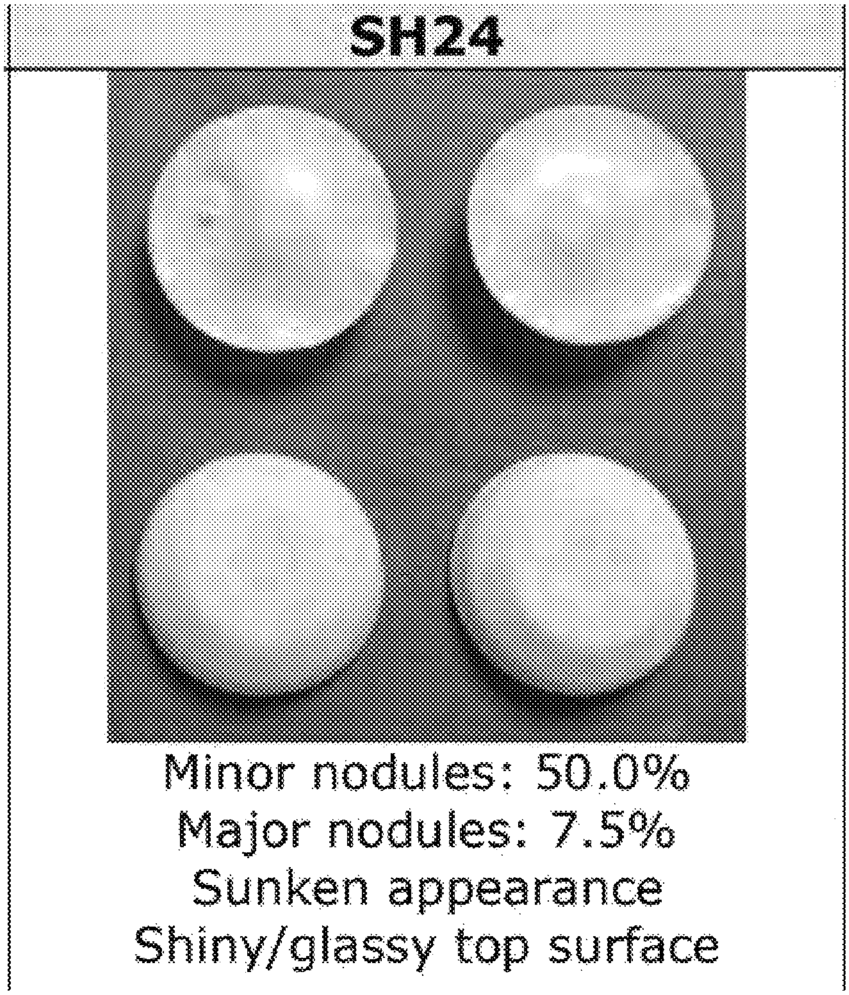
Figure 129:
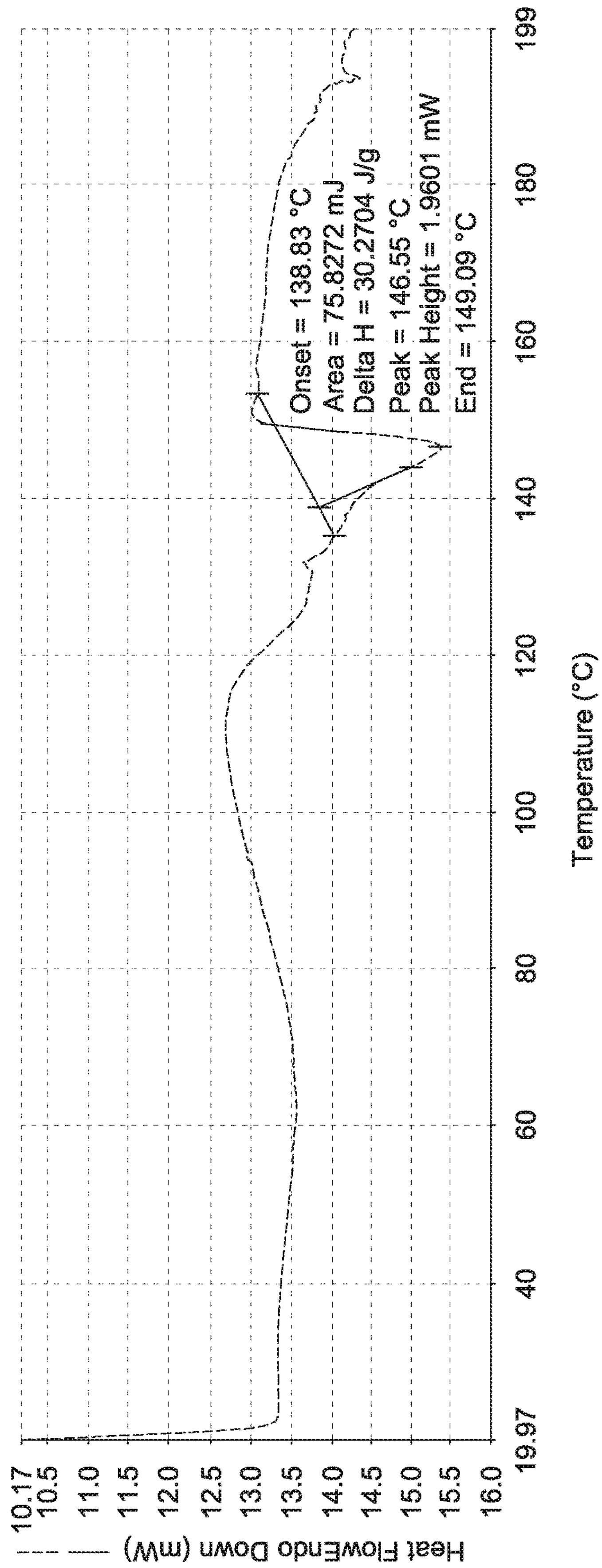
Figure 130:
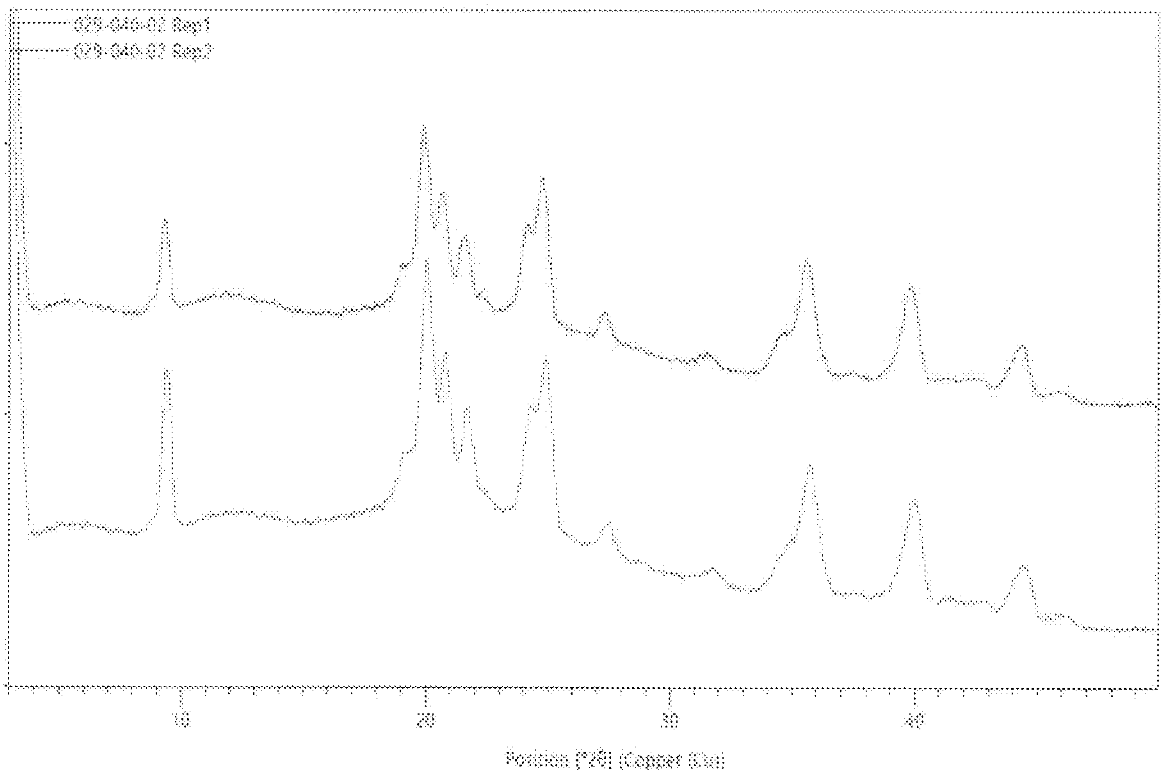
Figure 131:
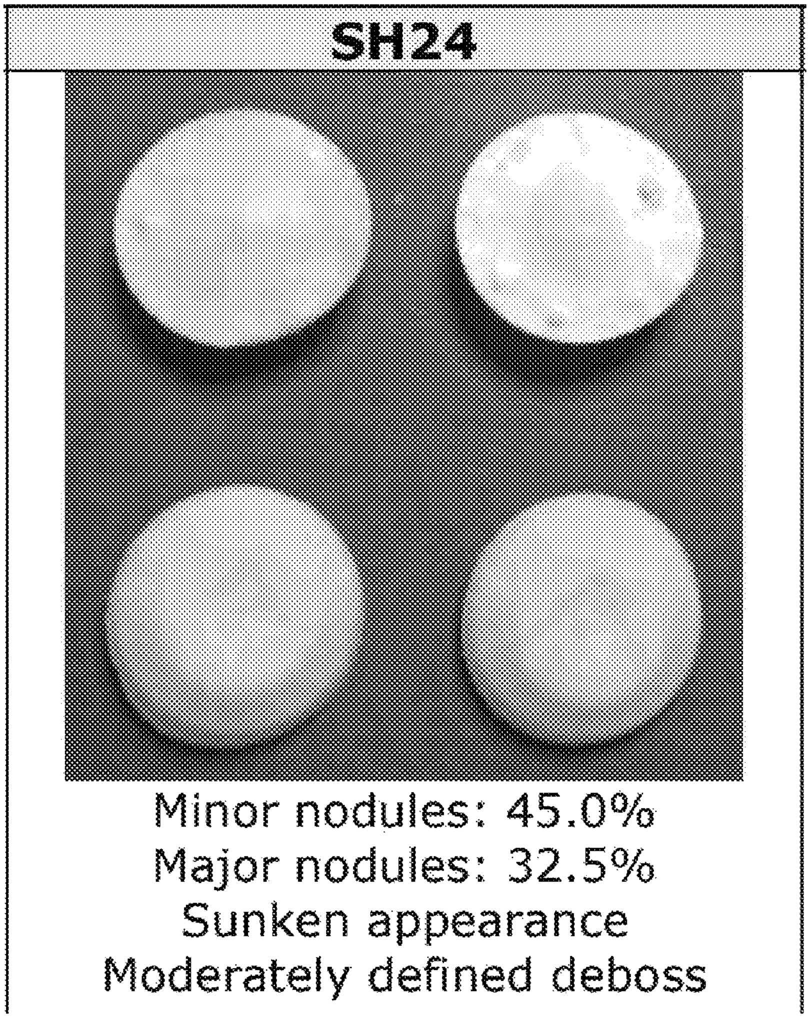
Figure 132:
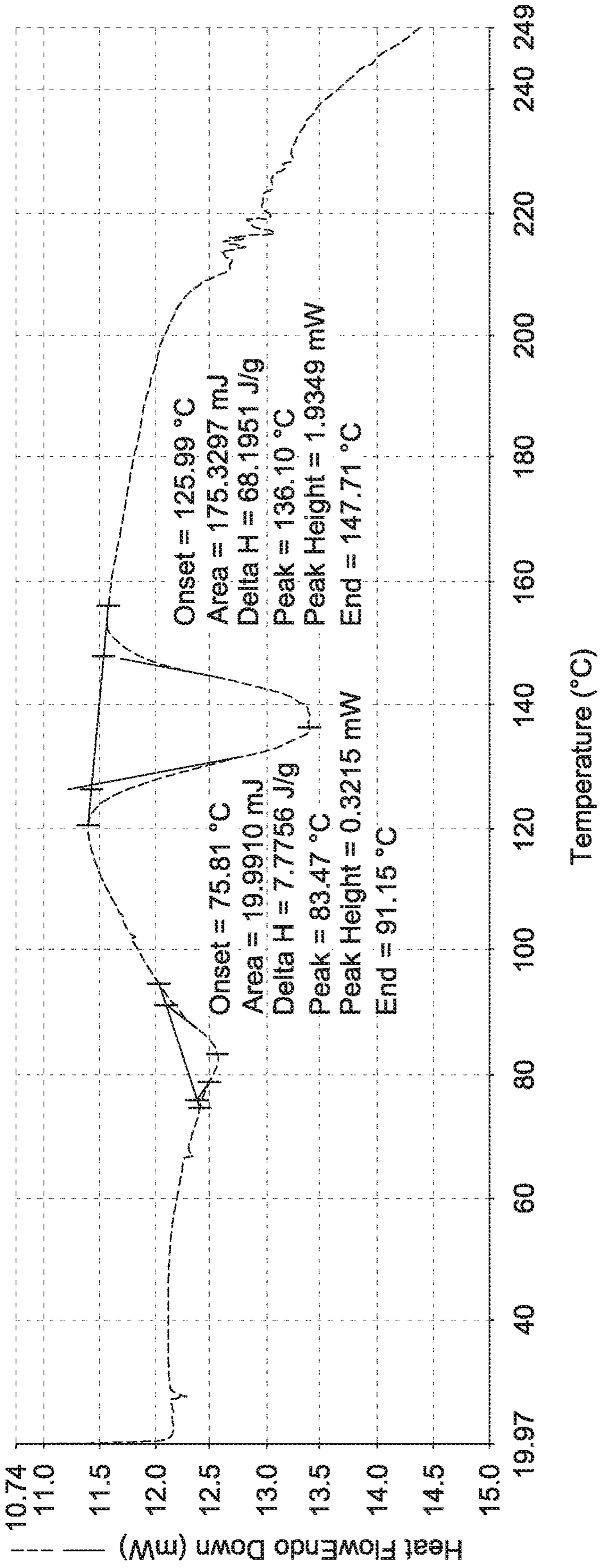
Figure 133:
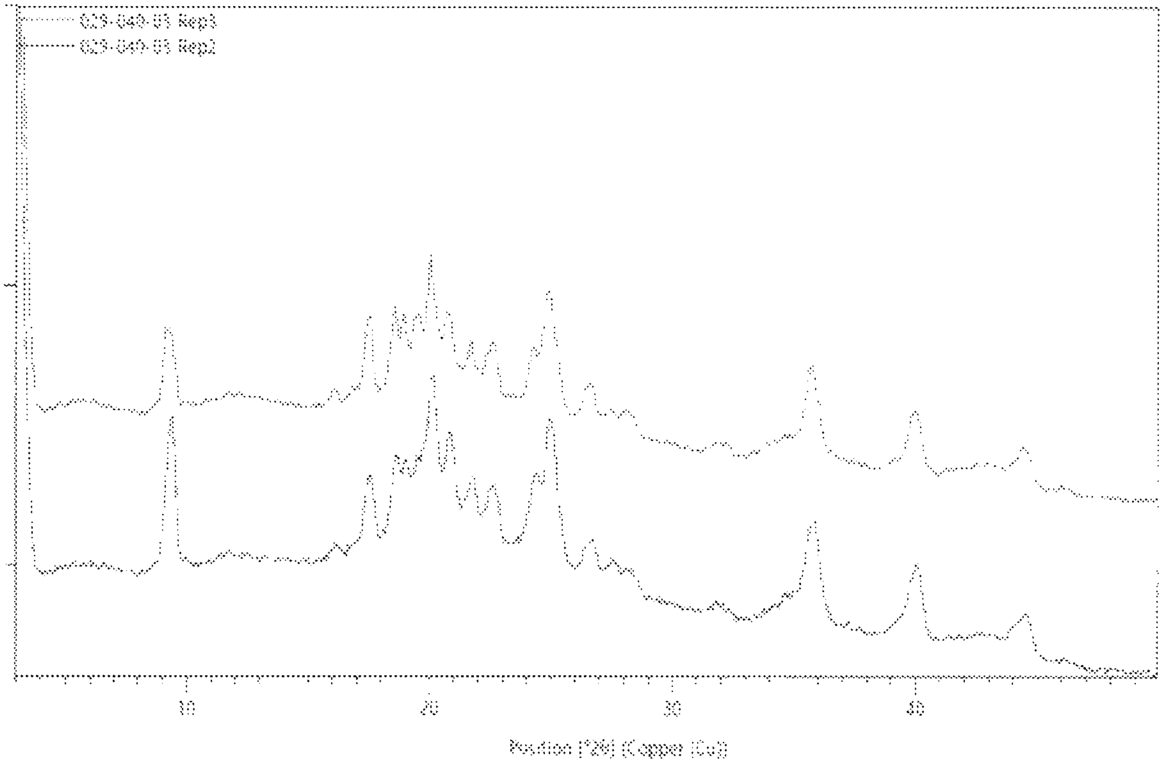
Figure 134:
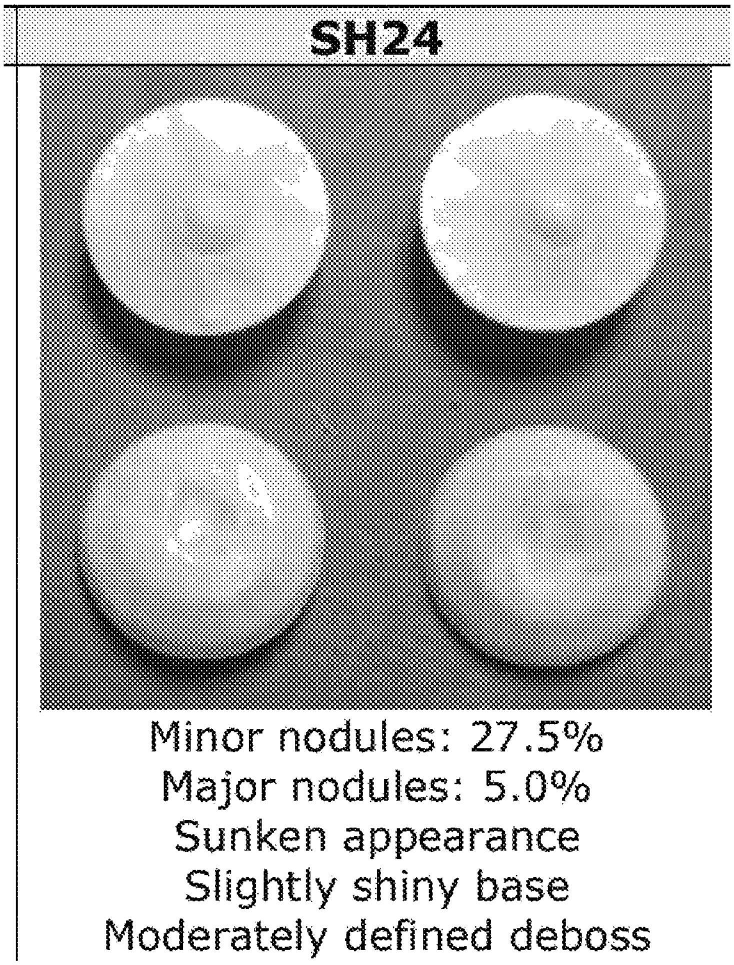
Figure 135:
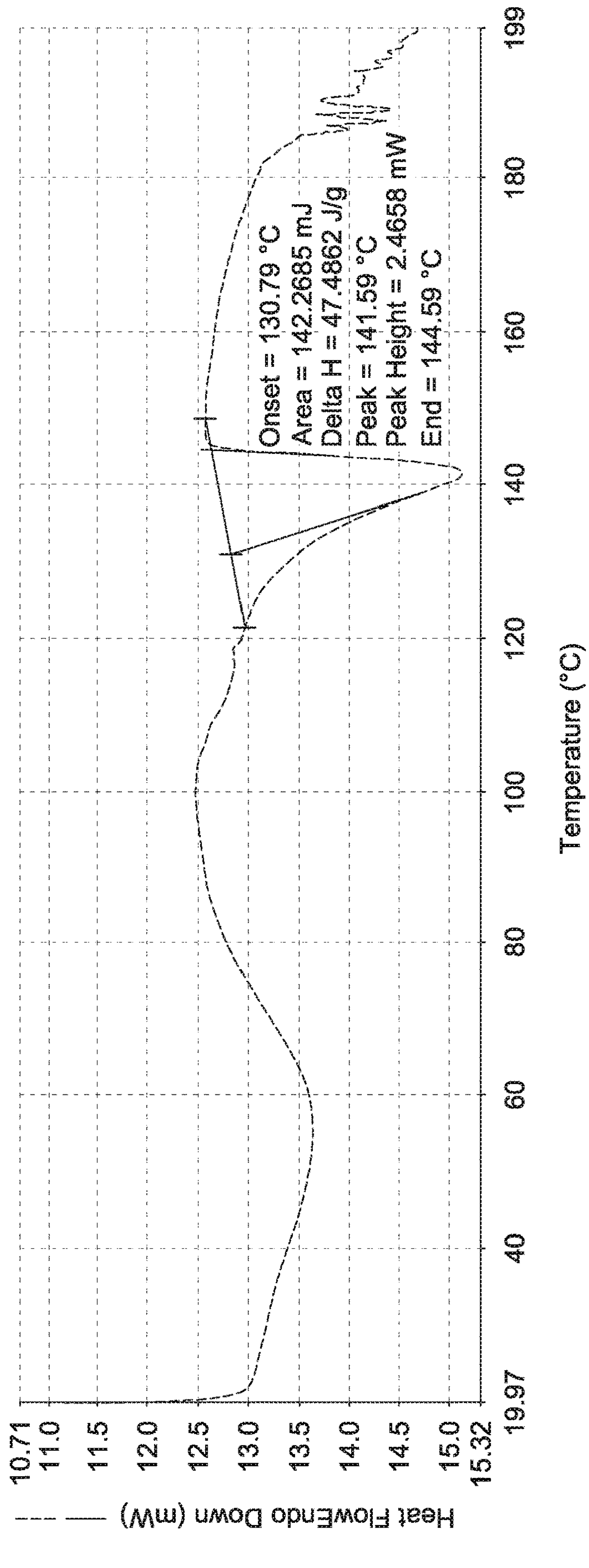
Figure 136:
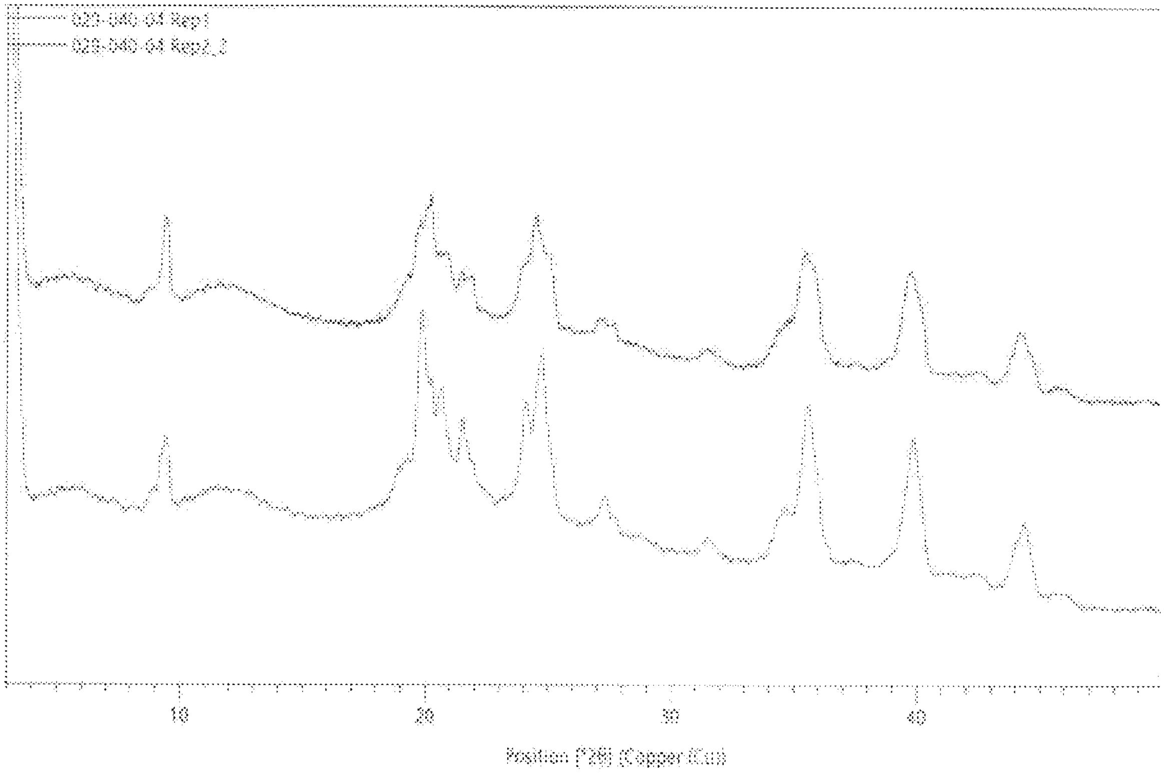
Figure 137:
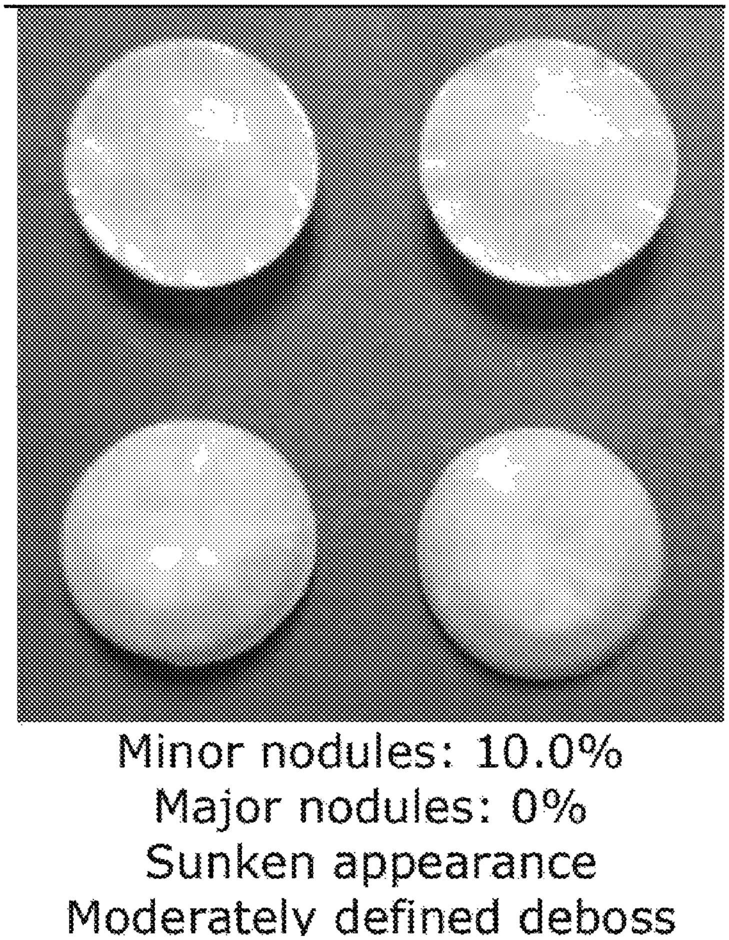
Figure 138:
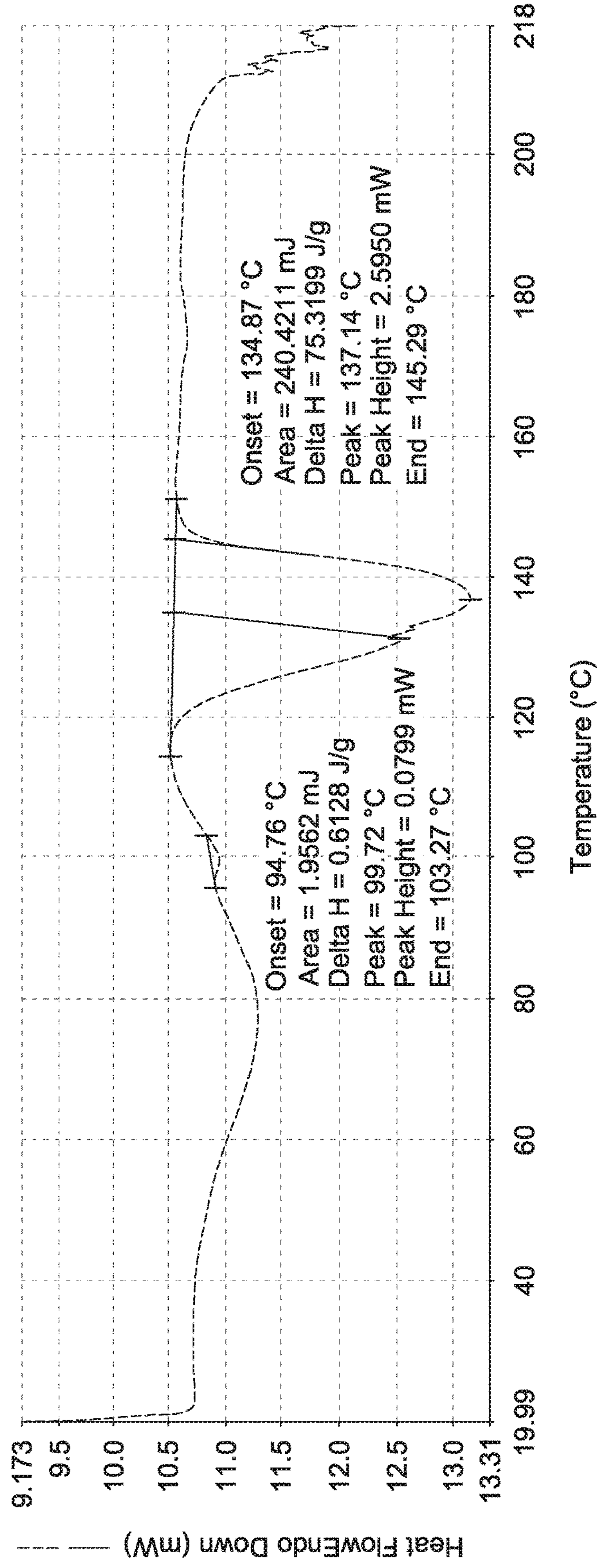
Figure 139:
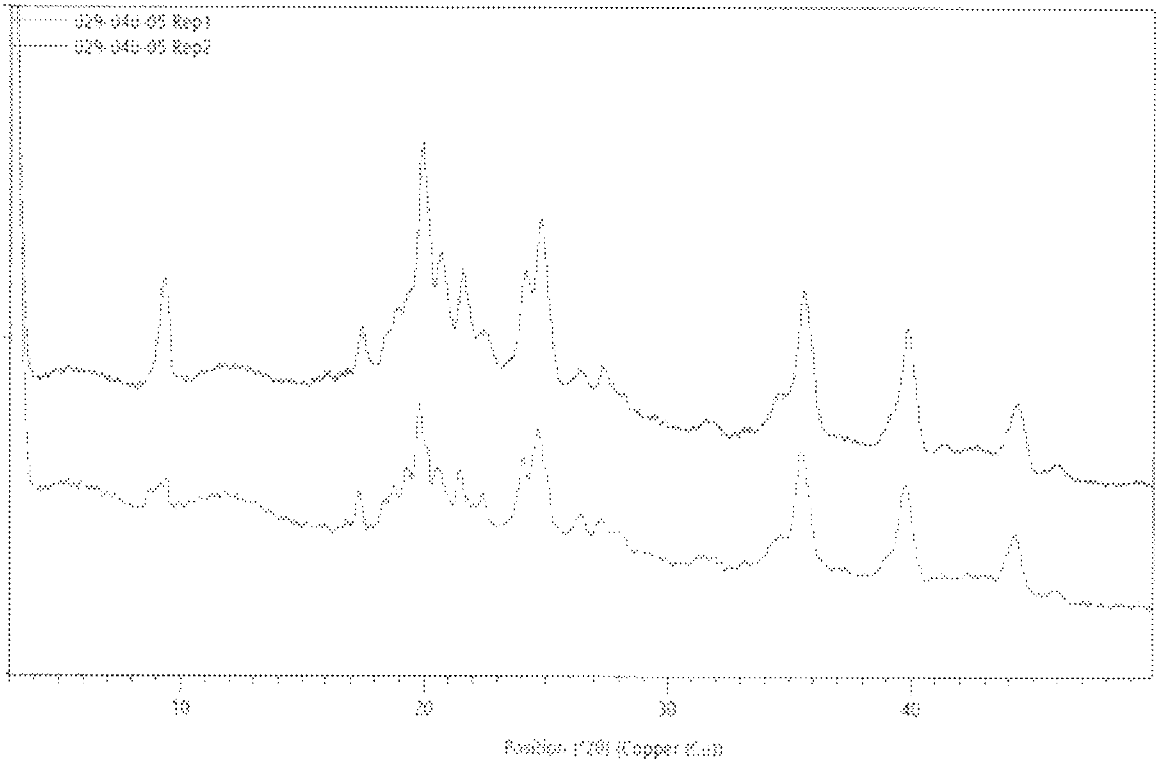
Figure 140:
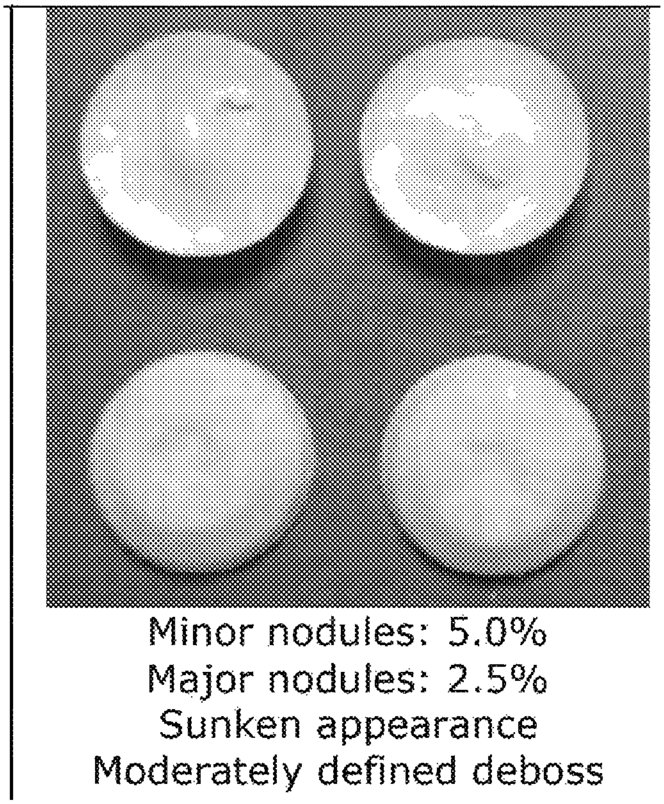
Figure 141:
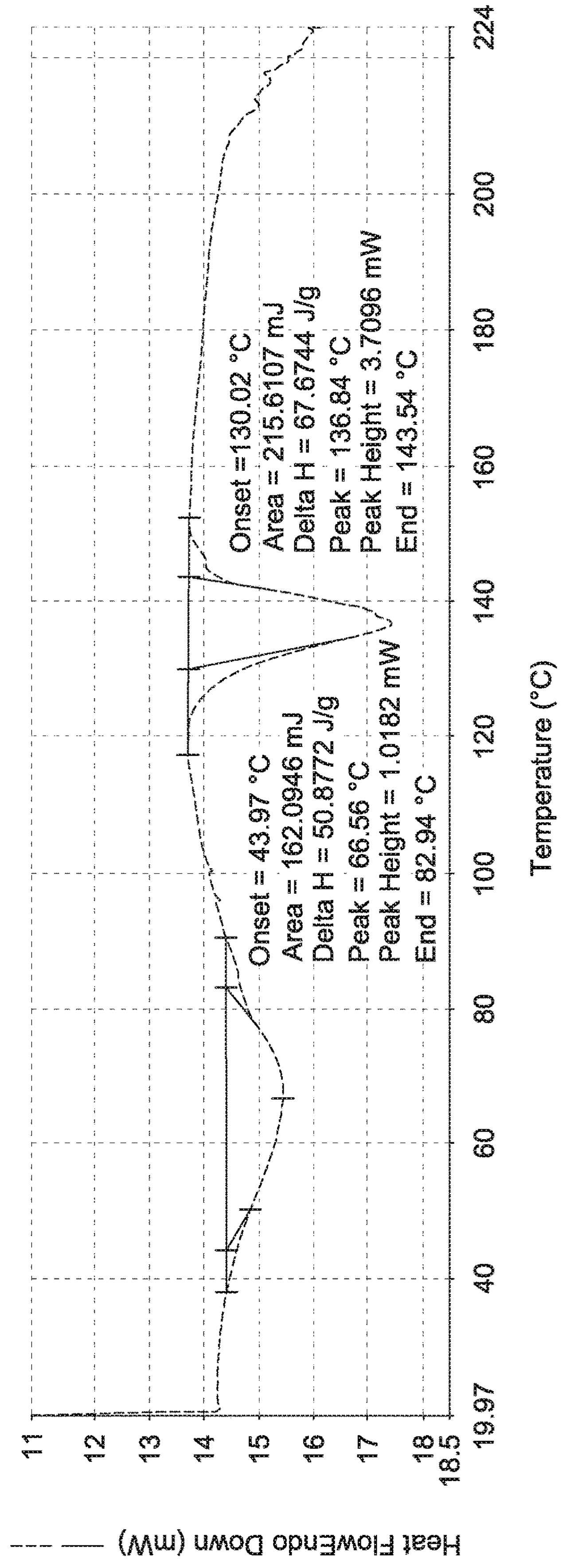
Figure 142:
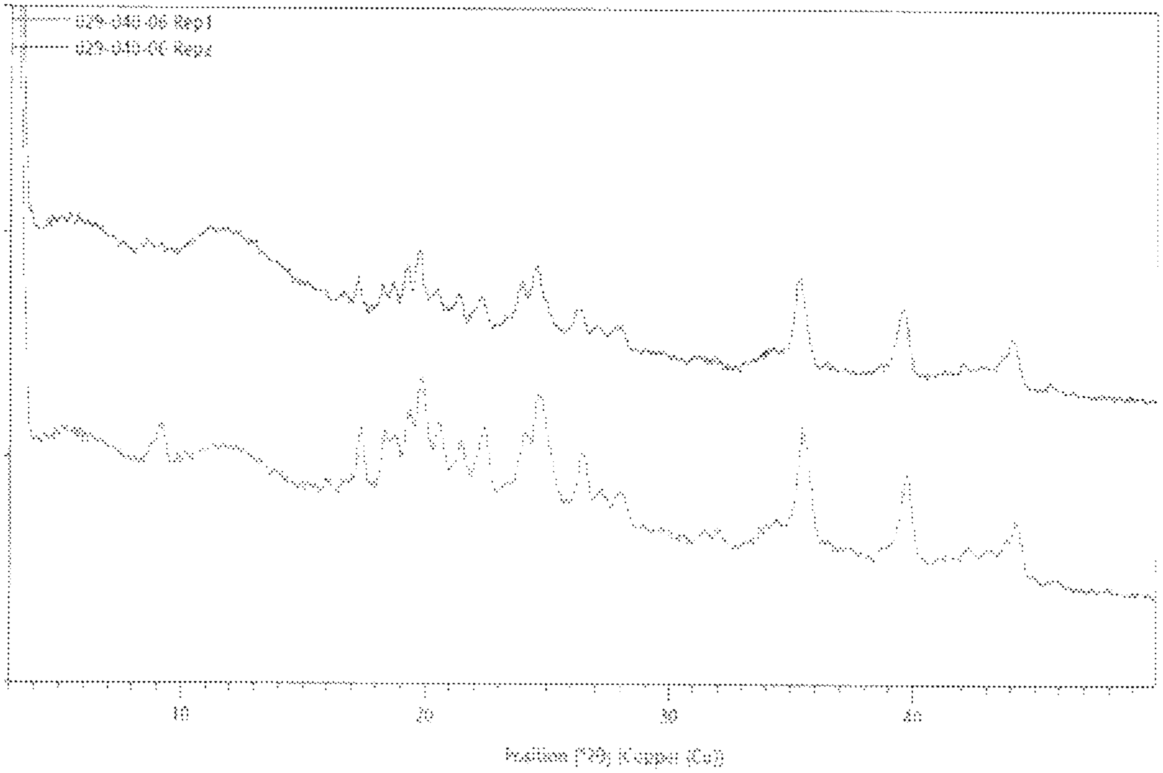
Figure 143:
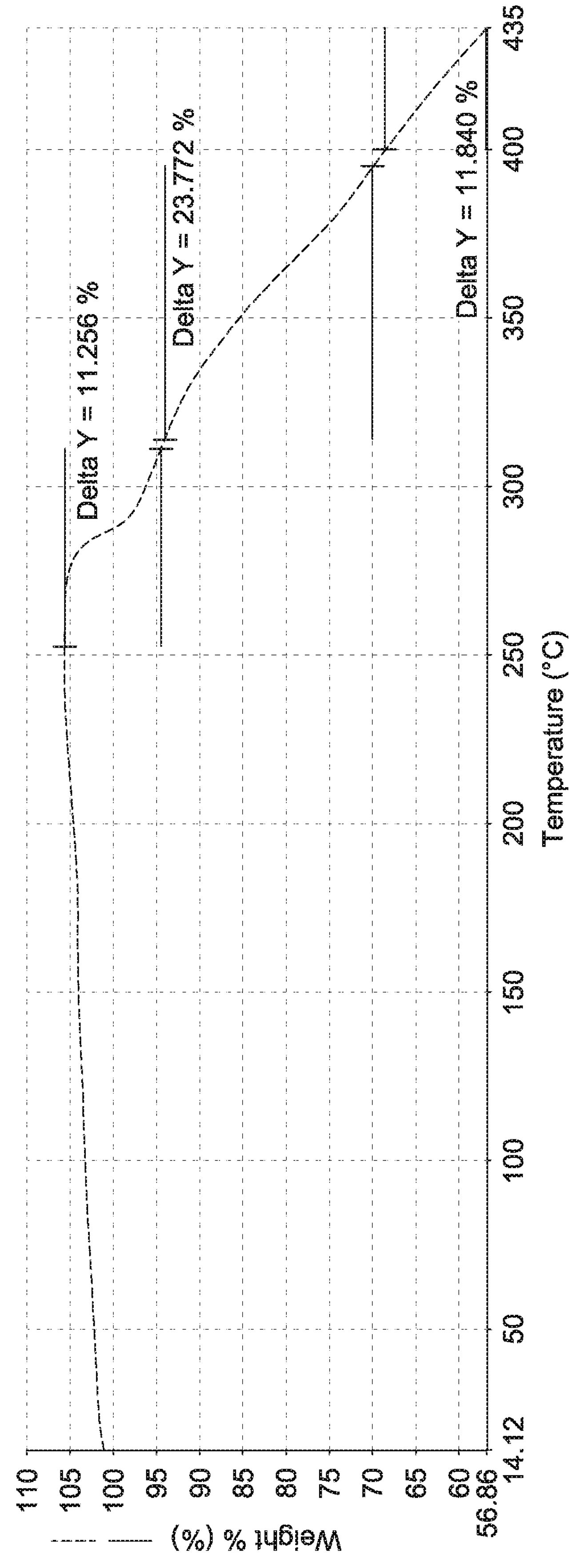
Figure 144:
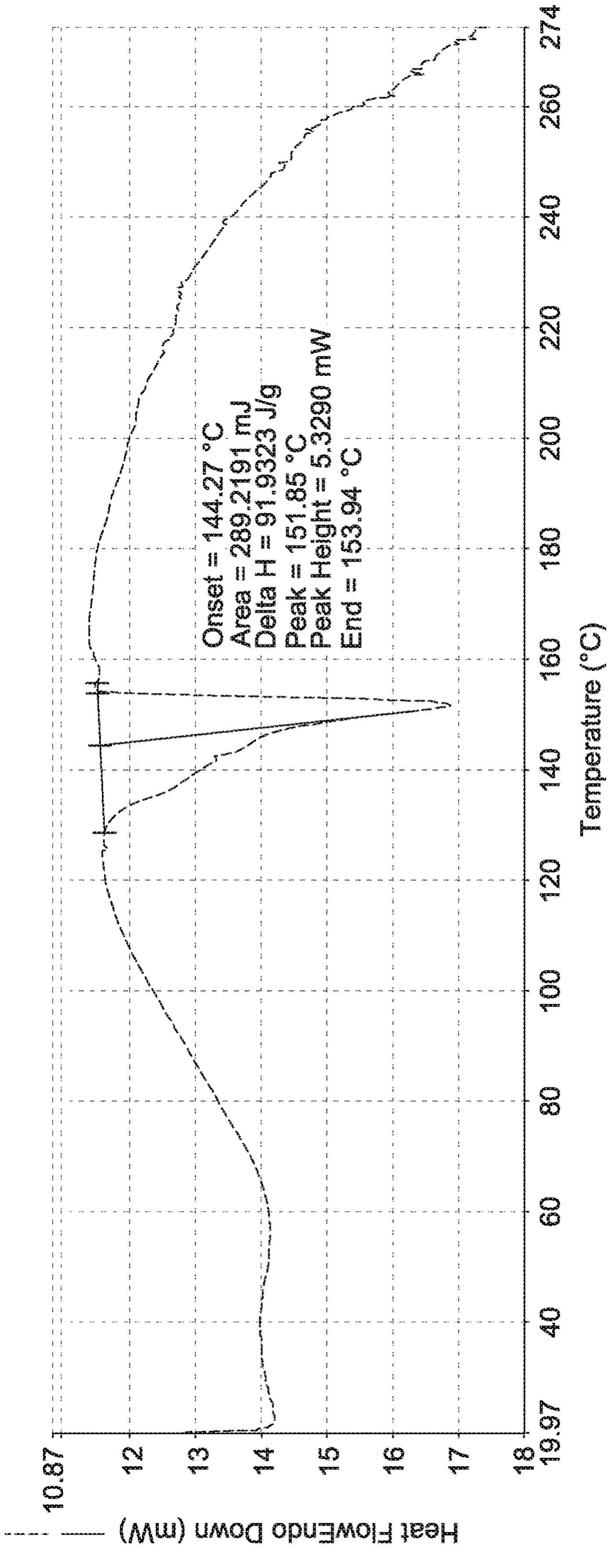
Figure 145:
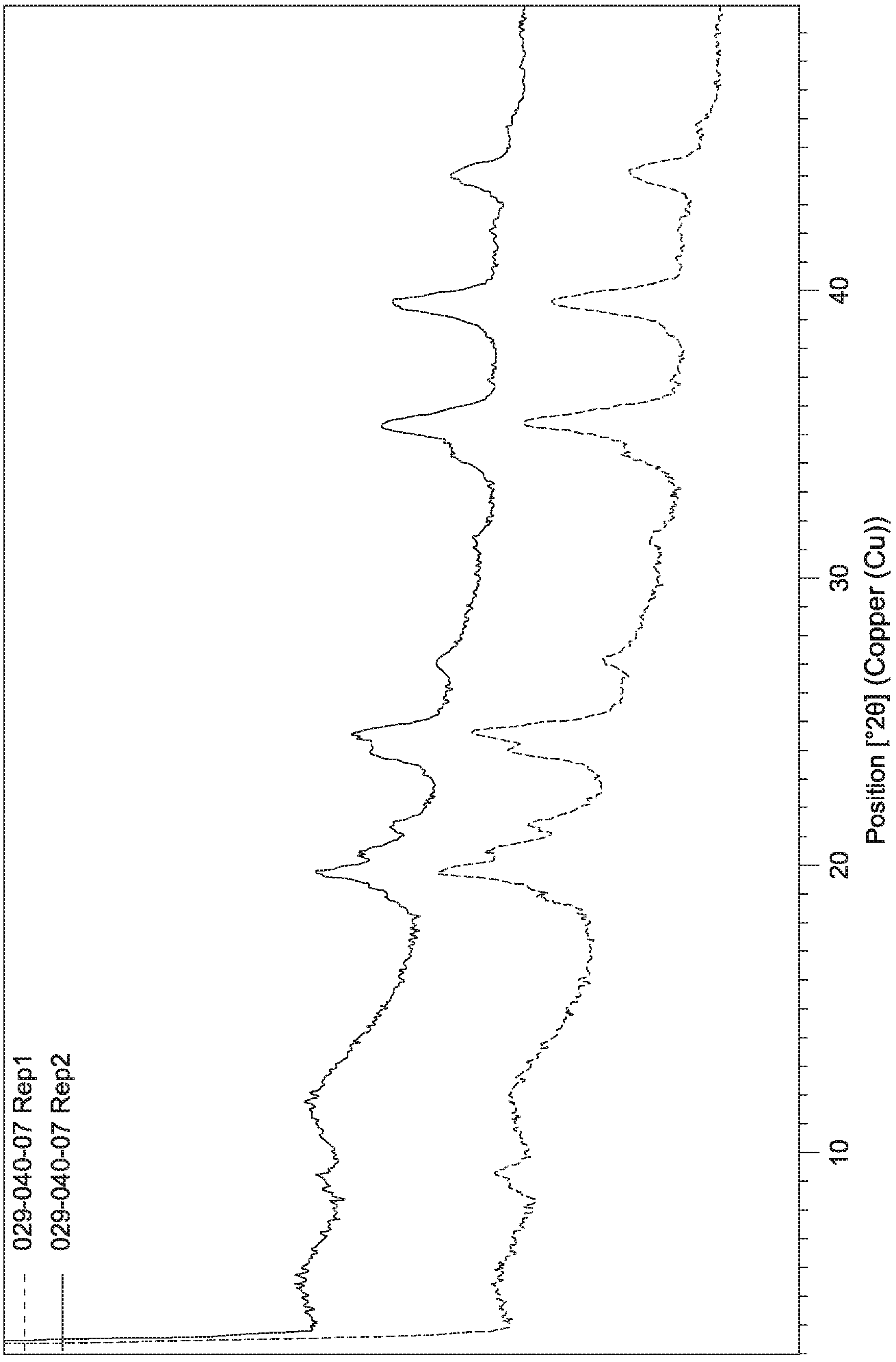
Figure 146:
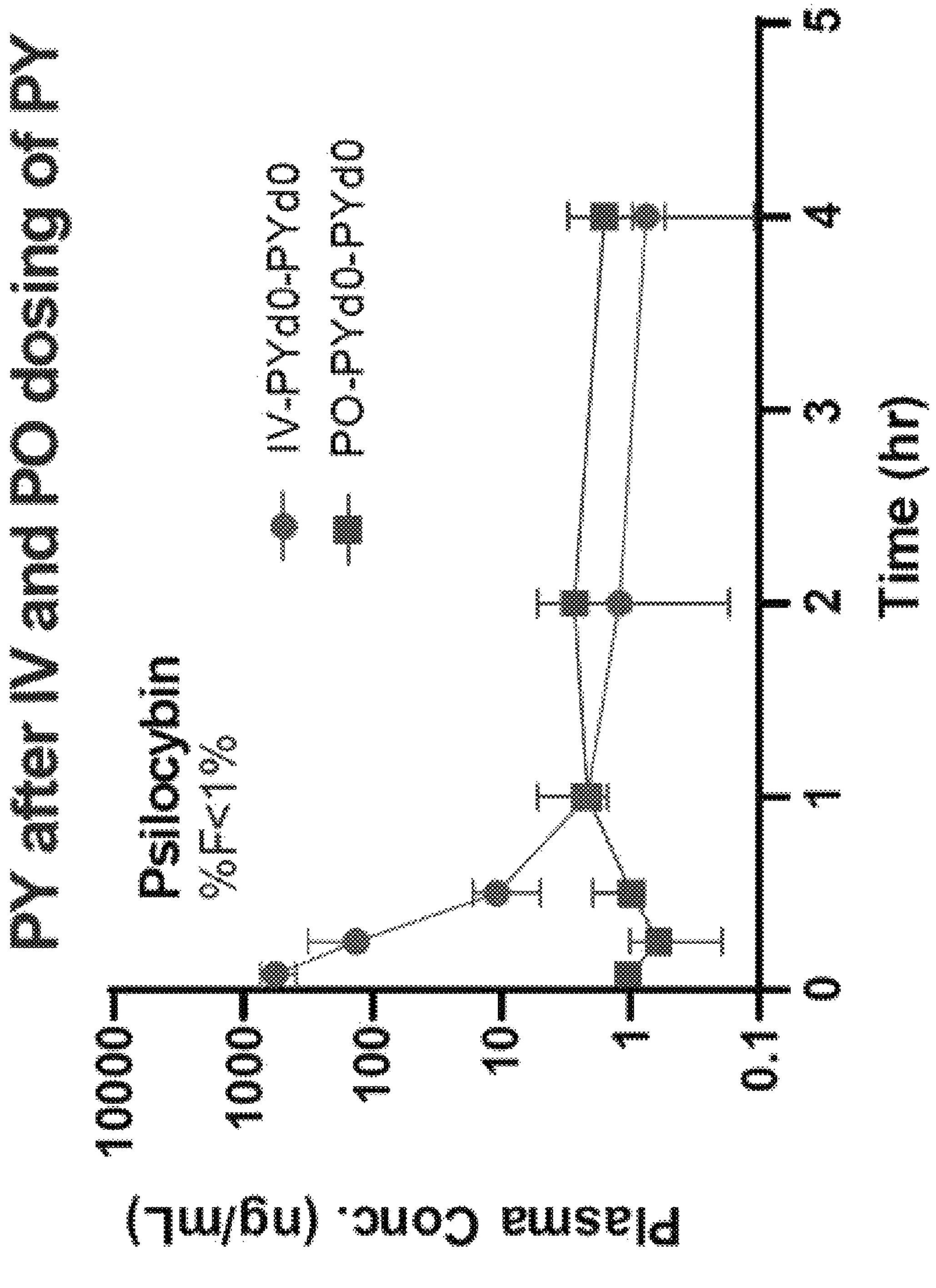
Figure 147:
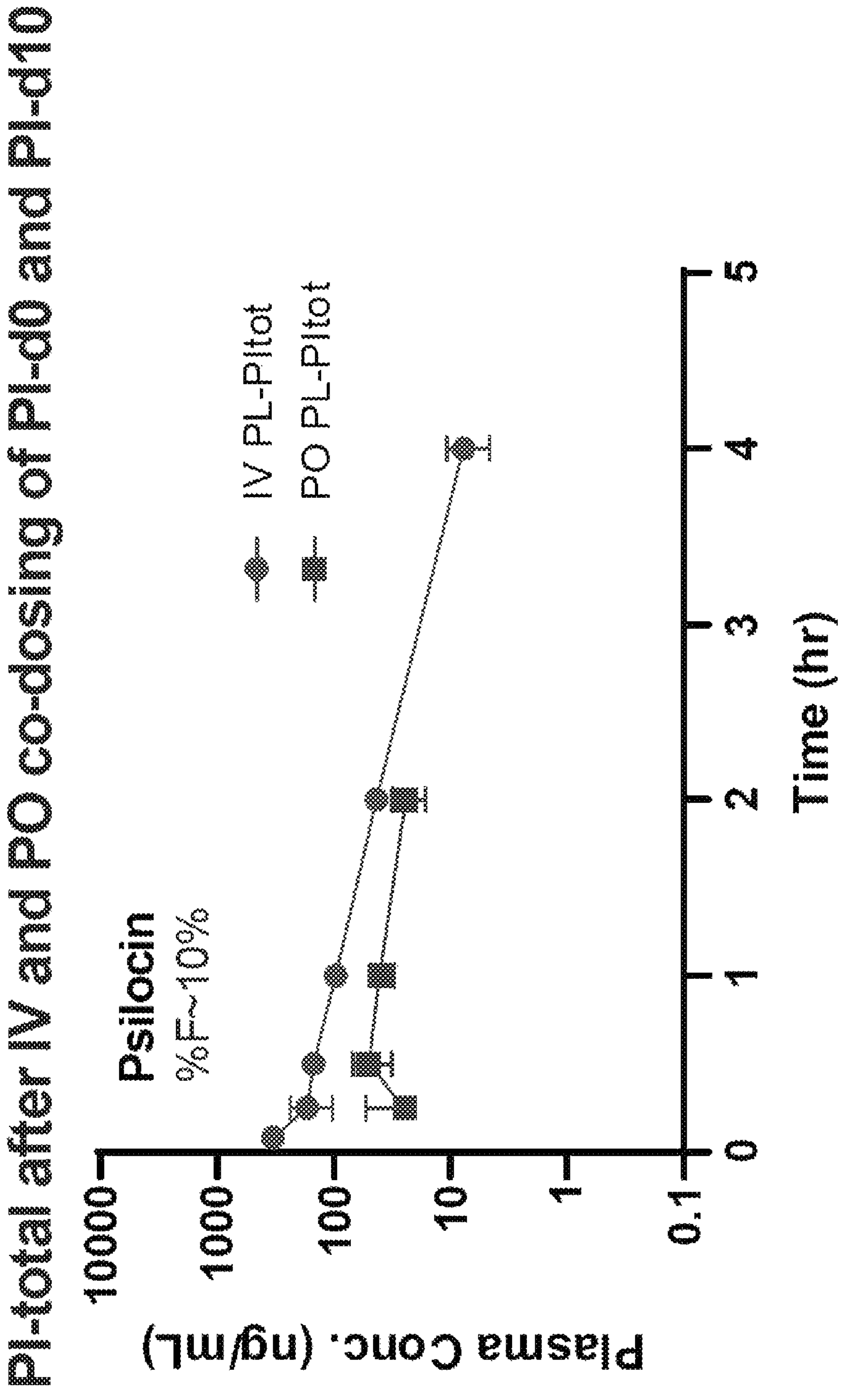
Figure 148:
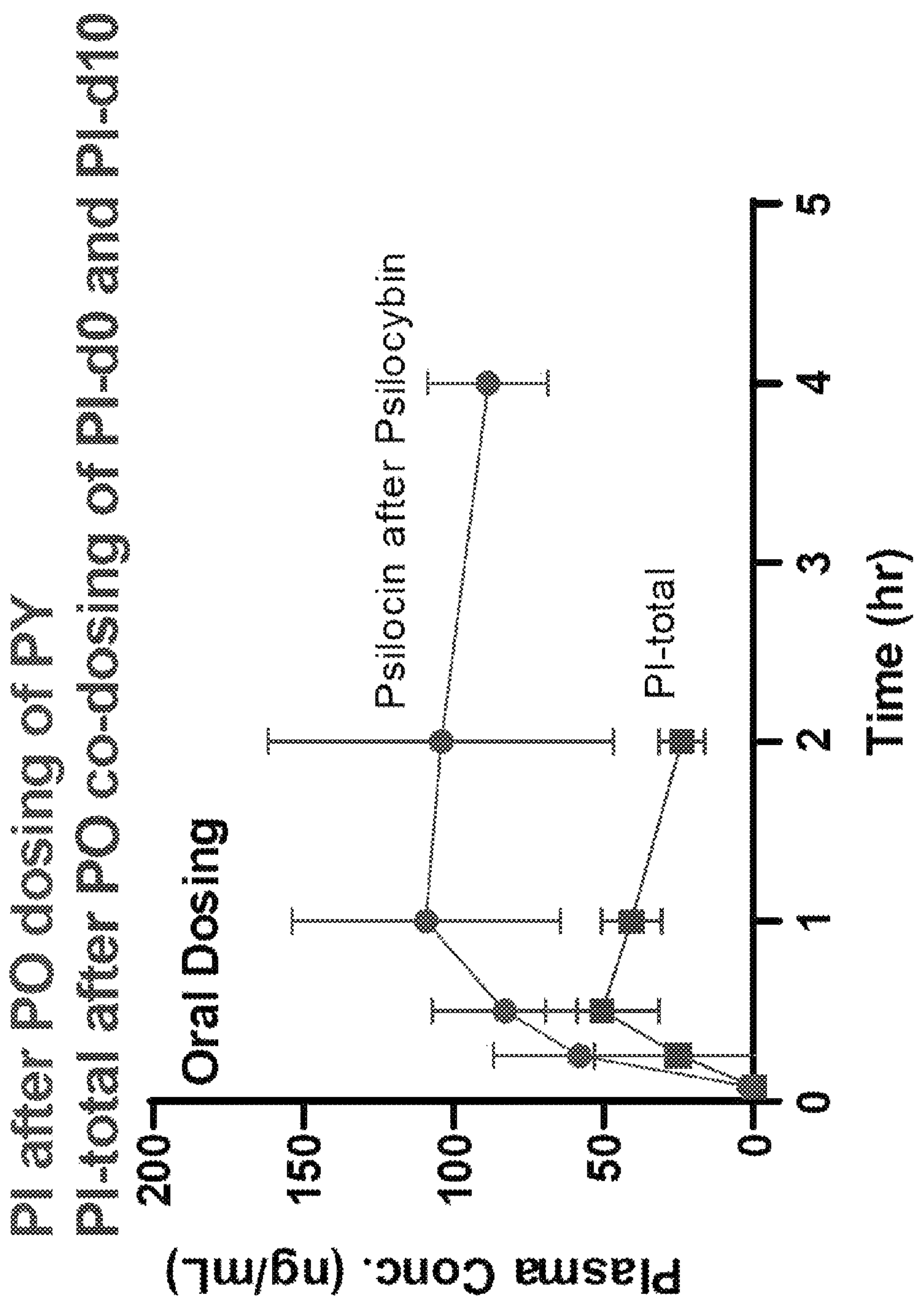
Figure 149:
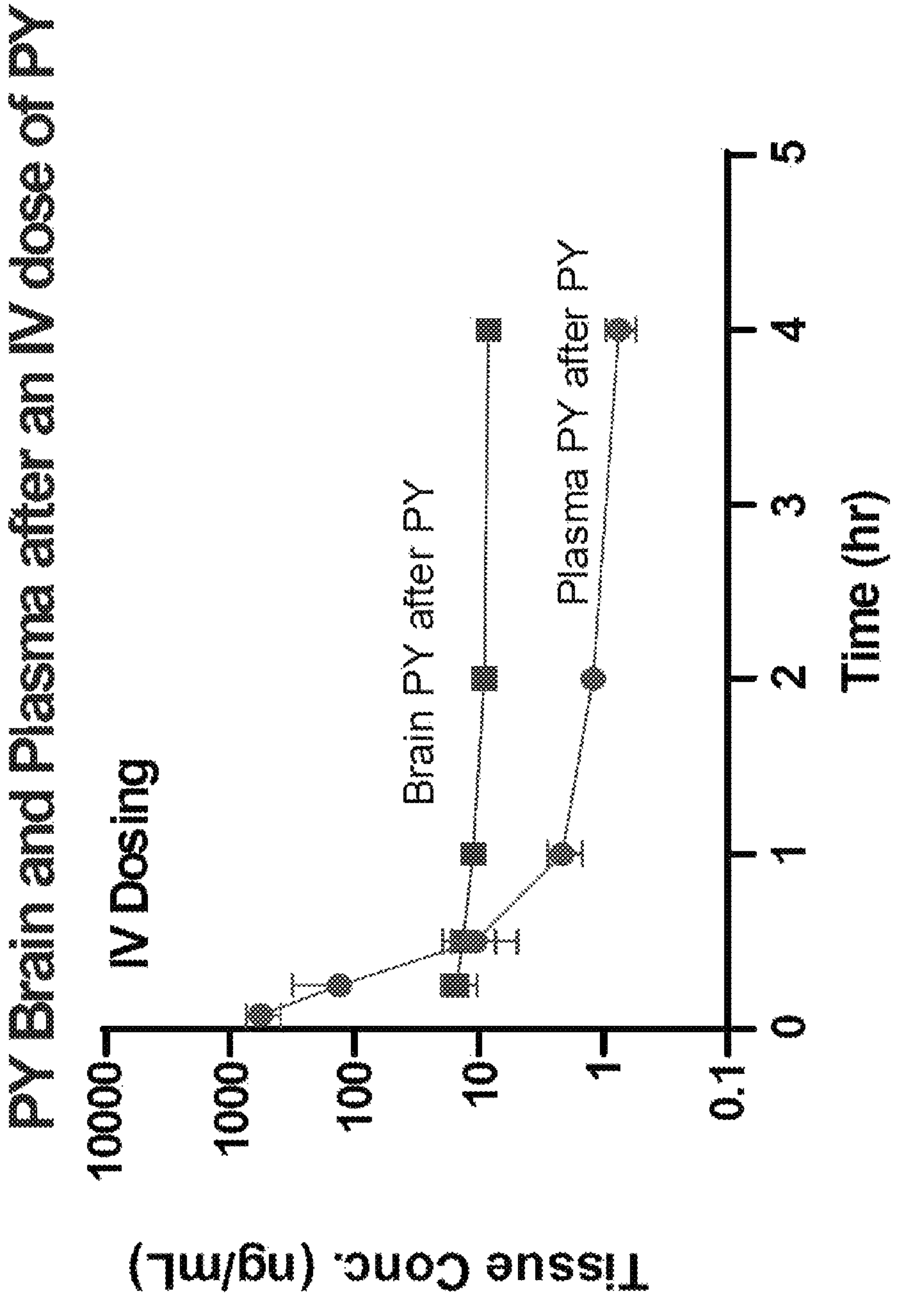
Figure 150:
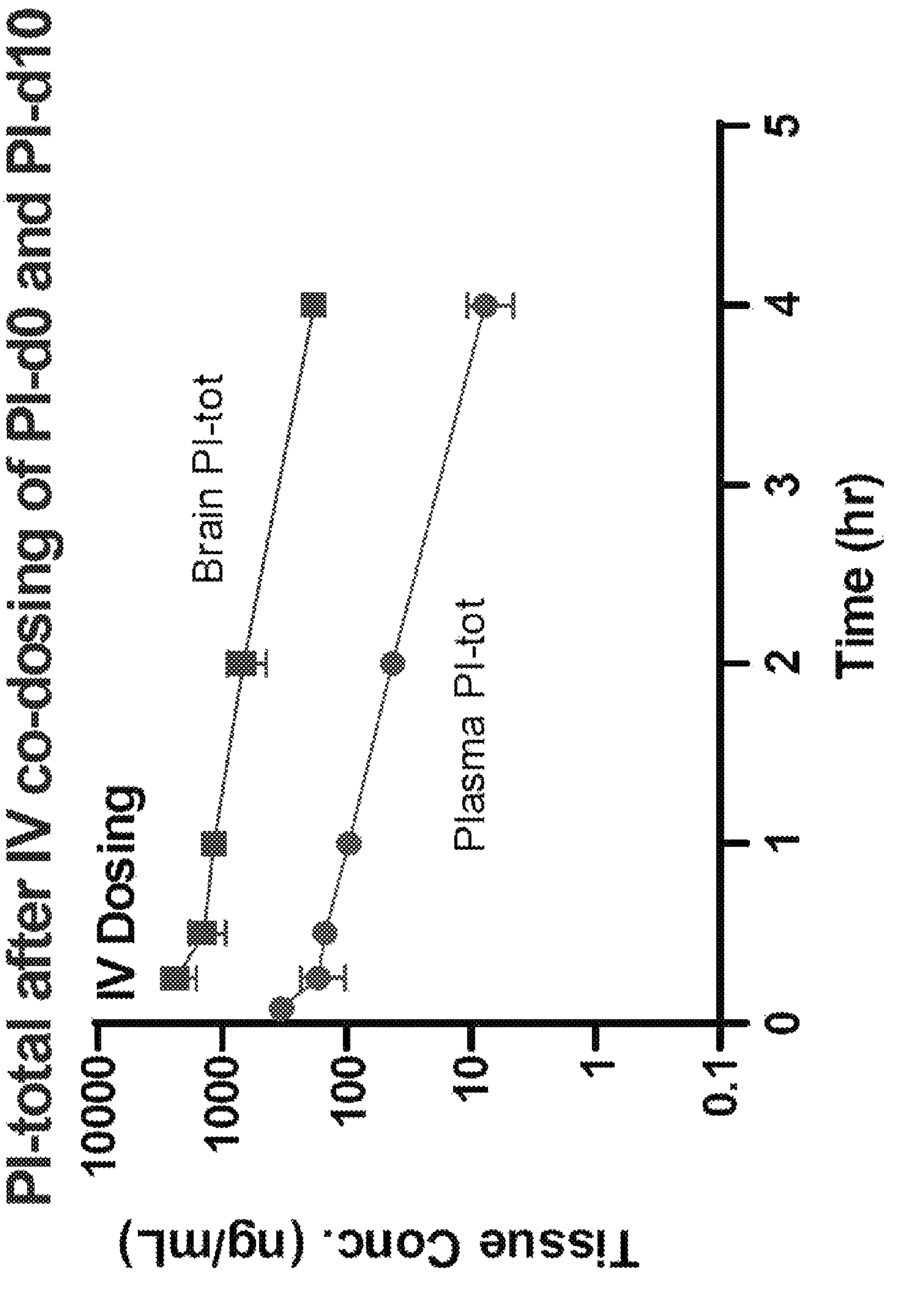
Figure 151:
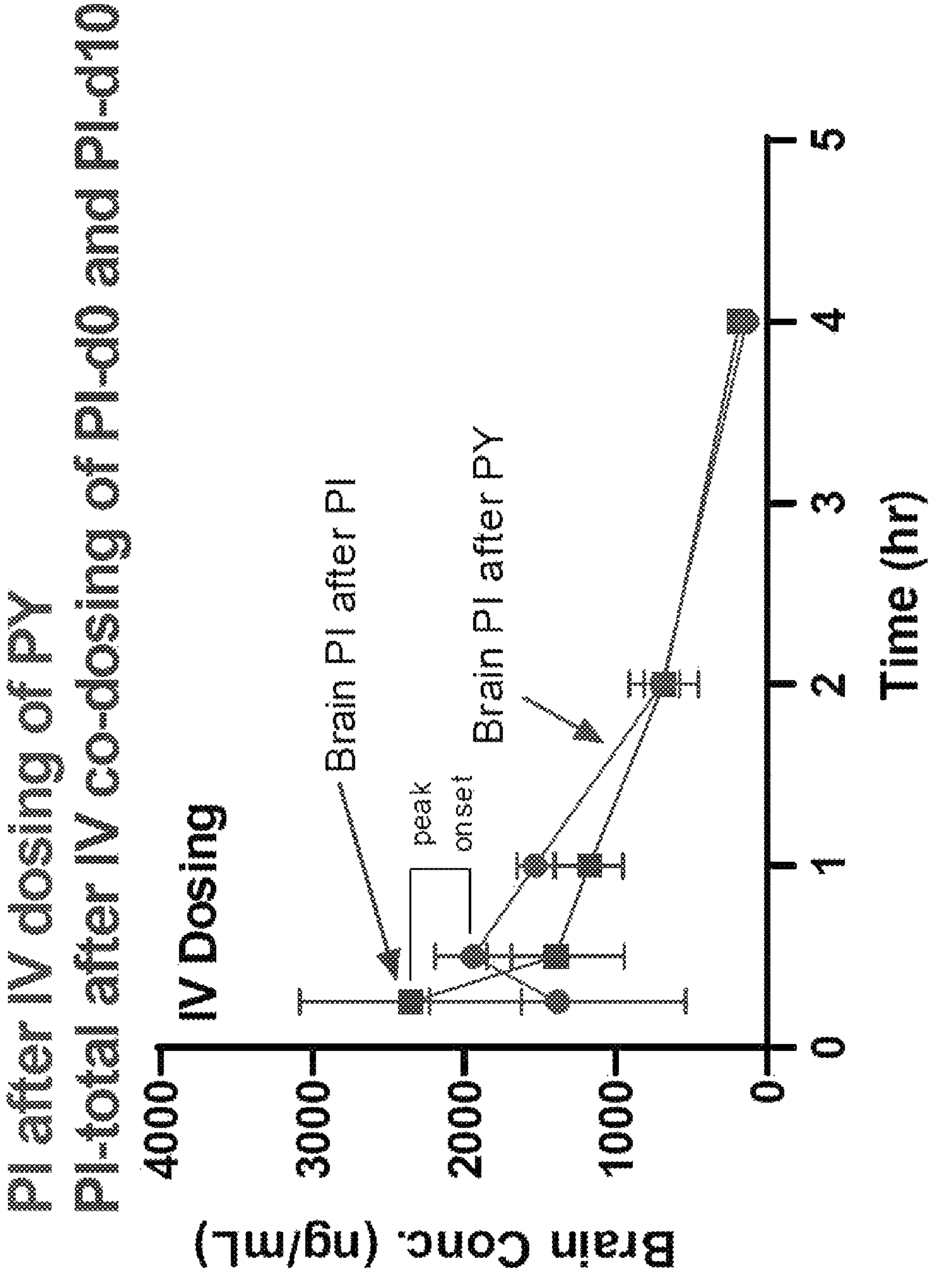
Figure 152A:
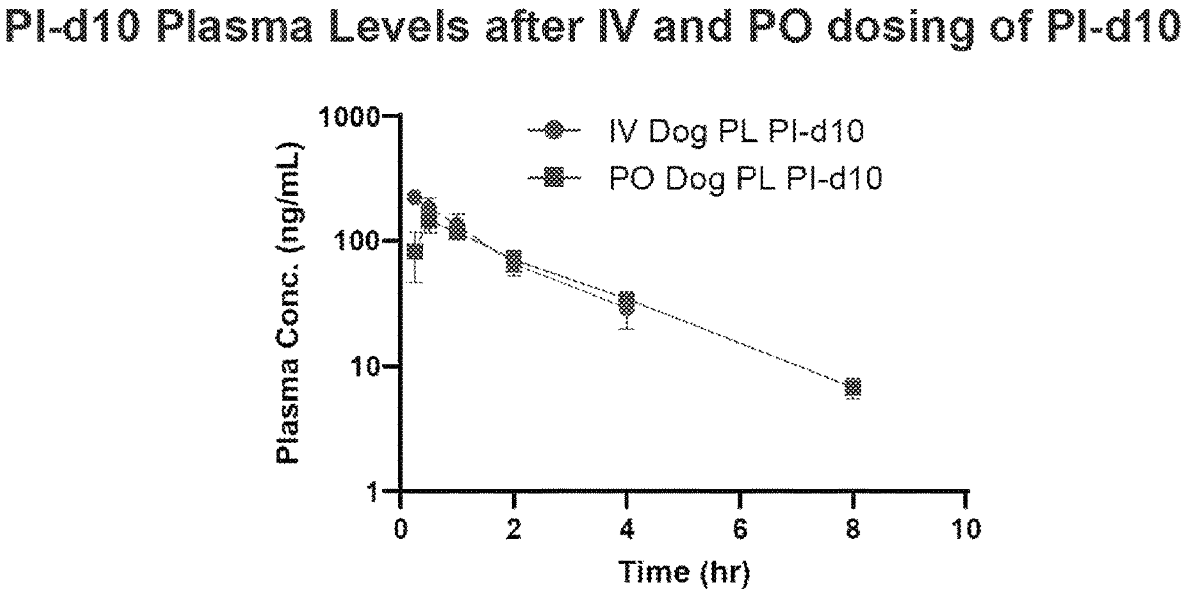
Figure 152B:
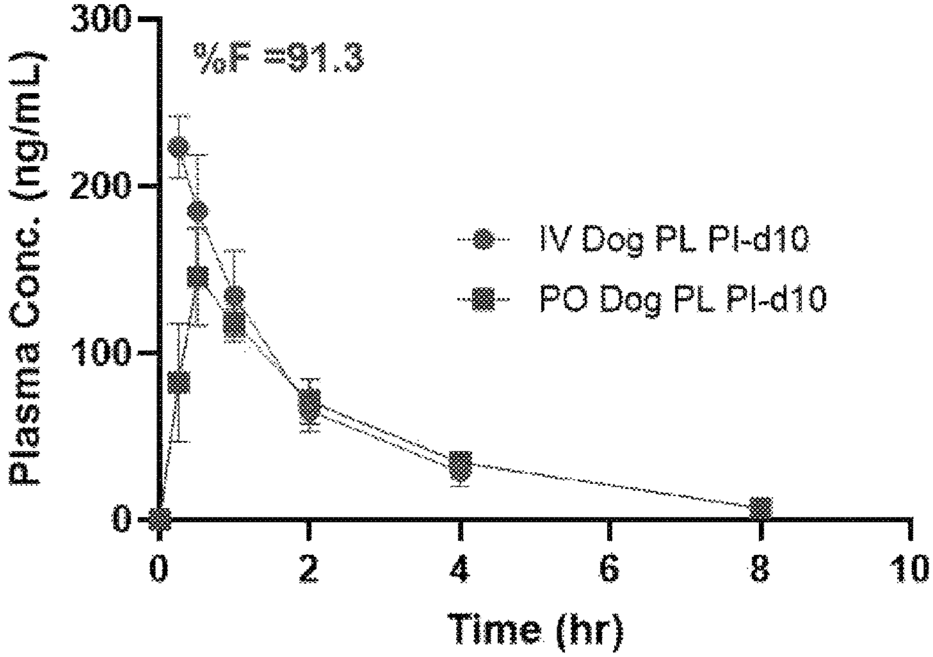
Figure 153A:
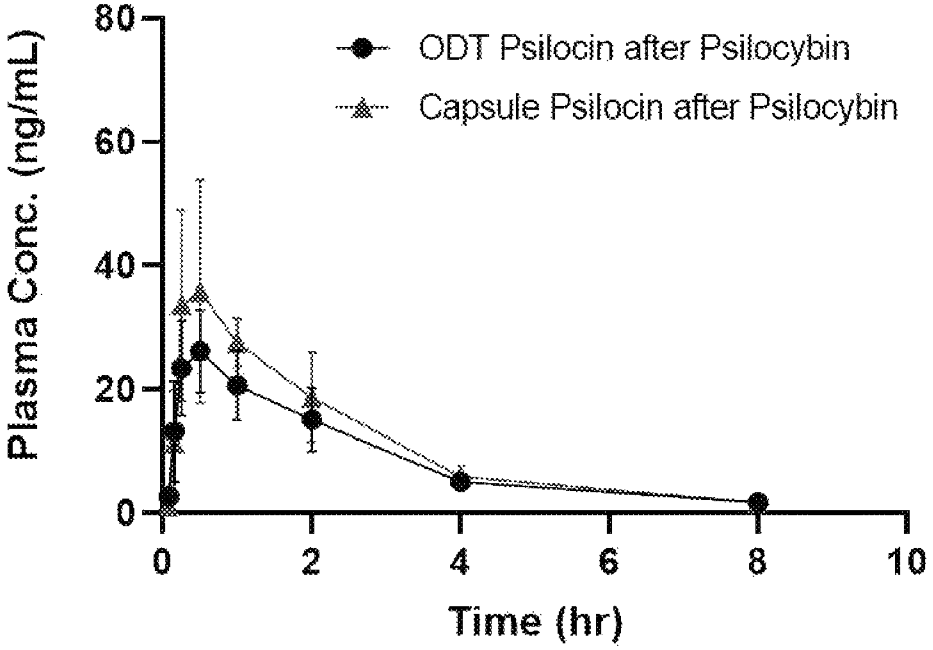
Figure 153B:
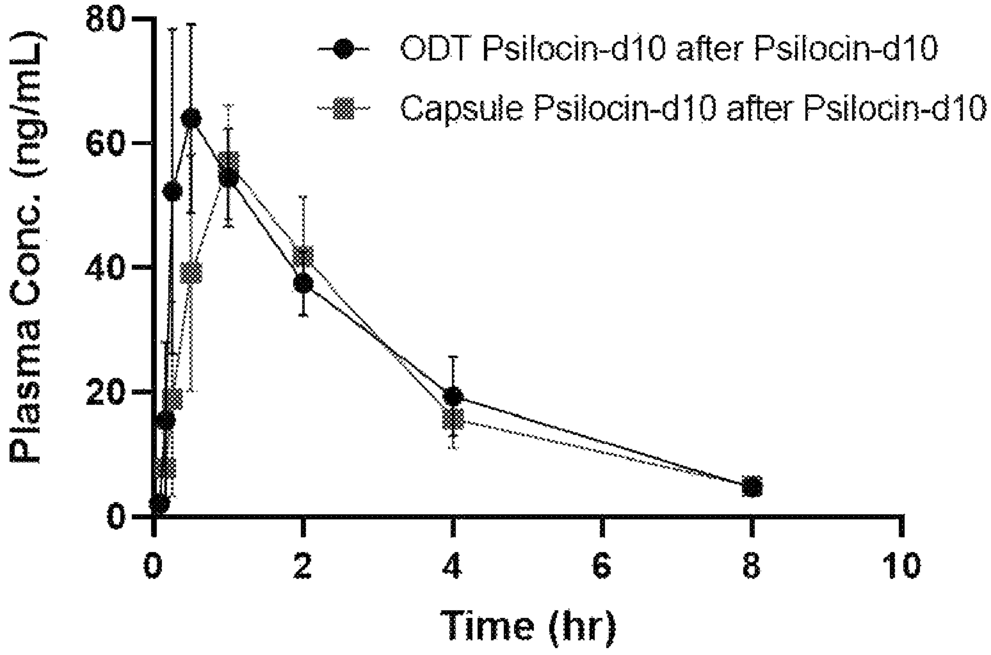
Figure 154:
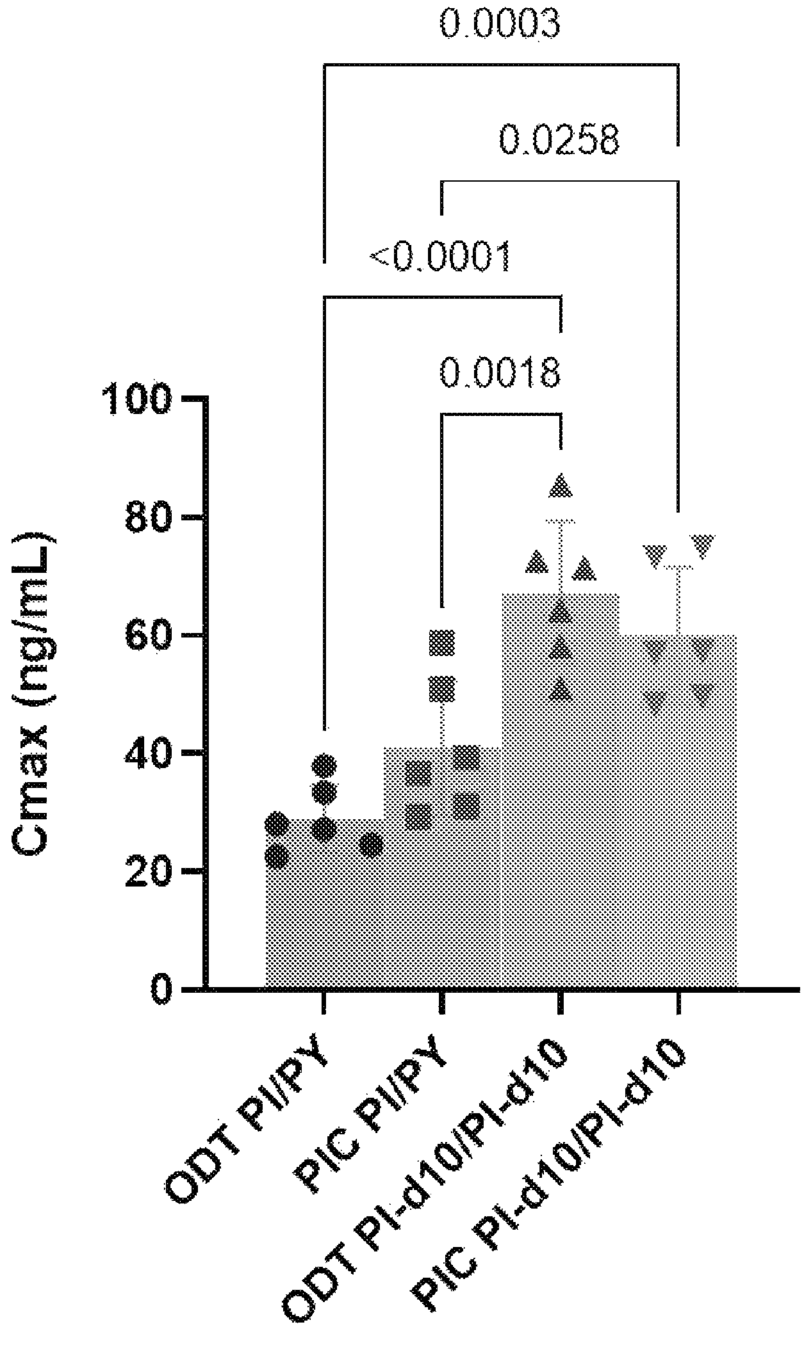
Figure 155:
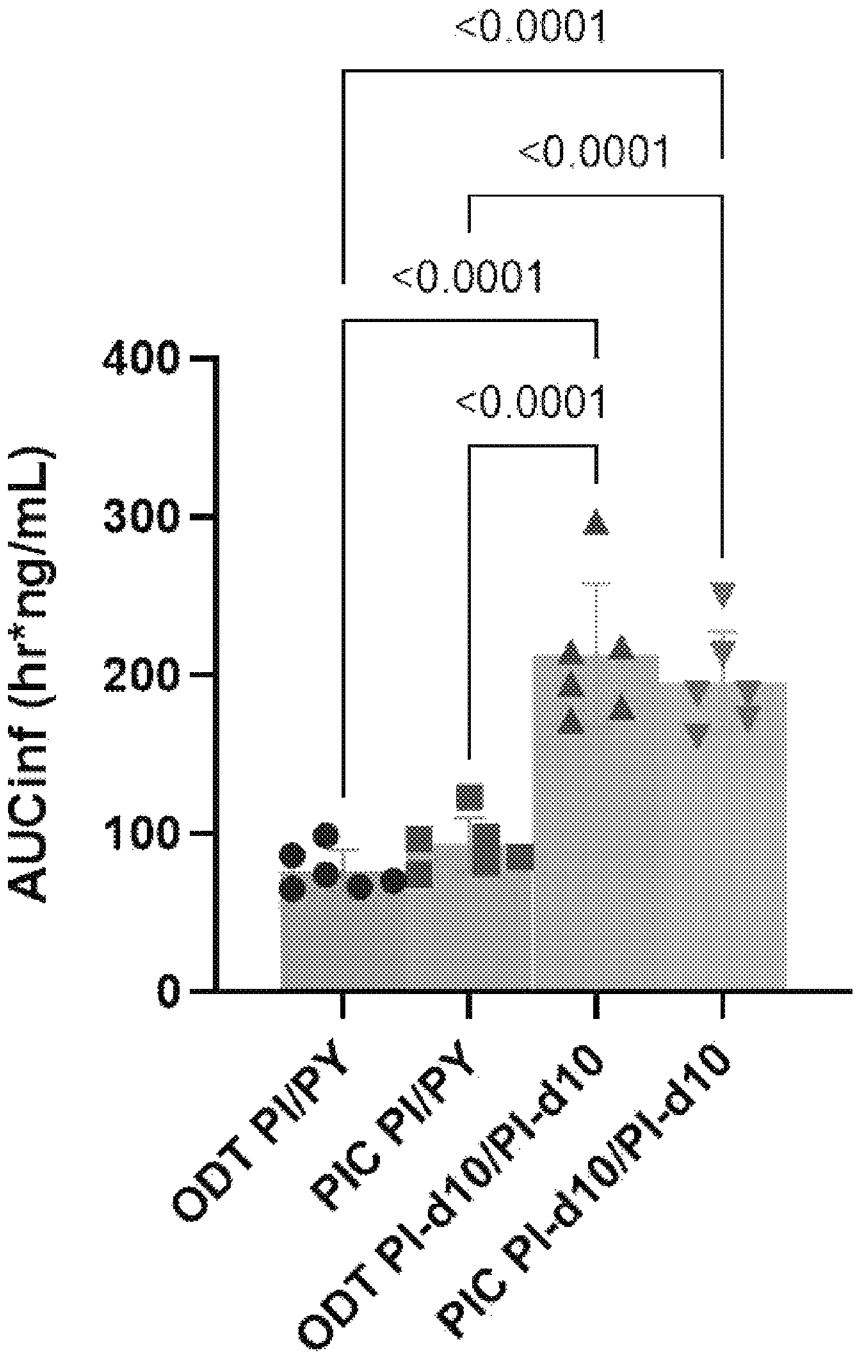

FIG. 120 shows the solubility of I-3 (PI-$d_{10}$)(pattern 1), I-7 (PI-$d_0$)(pattern1), I-3j (pattern 1), I-7a (pattern 1), I-7b (pattern 1), I-7c (pattern 5), and I-7j (pattern 1) in FaSSGF (Fasted State Simulated Gastric Fluid)(pH 1.6), at 37° C. for 2 and 6 hours;

FIG. 121 shows the solubility of I-3 (PI-$d_{10}$)(pattern 1), I-7 (PI-$d_0$)(pattern1), I-3j (pattern 1), I-7a (pattern 1), I-7b (pattern 1), I-7c (pattern 5), and I-7j (pattern 1) in water at room temperature for 2 and 6 hours;

FIG. 122 shows the TGA plot of I-7 (API) used in the ODT formulations;

FIG. 123 show the DSC curve of I-7 (API) used in the ODT formulations;

FIG. 124 shows the XRPD pattern of I-7 (pattern 1)(API) used in the ODT formulations;

FIG. 125 shows the TGA plot of the ODT dosage form formed from batch 1a (SH24) formulated with the citrate salt of psilocin at pH 3.55;

FIG. 126 shows the DSC curve of the ODT dosage form formed from batch 1a (SH24) formulated with the citrate salt of psilocin at pH 3.55;

FIG. 127 shows the XRPD pattern of the ODT dosage form formed from batch 1a (SH24) formulated with the citrate salt of psilocin at pH 3.55;

FIG. 128 shows the appearance of the ODT dosage form formed from batch 1a (SH24) formulated with the citrate salt of psilocin at pH 3.55;

FIG. 129 shows the DSC plot of the ODT dosage form formed from batch 1b (SH24) formulated with the citrate salt of psilocin at pH 4.50;

FIG. 130 shows the XRPD pattern of the ODT dosage form formed from batch 1b (SH24) formulated with the citrate salt of psilocin at pH 4.50;

FIG. 131 shows the appearance of the ODT dosage form formed from batch 1b (SH24) formulated with the citrate salt of psilocin at pH 4.50;

FIG. 132 shows the DSC plot of the ODT dosage form formed from batch 1c (SH24) formulated with the citrate salt of psilocin at pH 7.56;

FIG. 133 shows the XRPD pattern of the ODT dosage form formed from batch 1c (SH24) formulated with the citrate salt of psilocin at pH 7.56;

FIG. 134 shows the appearance of the ODT dosage form formed from batch 1c (SH24) formulated with the citrate salt of psilocin at pH 7.56;

FIG. 135 shows the DSC curve of the ODT dosage form formed from batch 2a (SH24) formulated with the tartrate salt of psilocin at pH 3.13;

FIG. 136 shows the XRPD pattern of the ODT dosage form formed from batch 2a (SH24) formulated with the tartrate salt of psilocin at pH 3.13;

FIG. 137 shows the appearance of the ODT dosage form formed from batch 2a (SH24) formulated with the tartrate salt of psilocin at pH 3.13;

FIG. 138 shows the DSC plot of the ODT dosage form formed from batch 2b (SH24) formulated with the tartrate salt of psilocin at pH 4.33;

FIG. 139 shows the XRPD pattern of the ODT dosage form formed from batch 2b (SH24) formulated with the tartrate salt of psilocin at pH 4.33;

FIG. 140 shows the appearance of the ODT dosage form formed from batch 2b (SH24) formulated with the tartrate salt of psilocin at pH 4.33;

FIG. 141 shows the DSC curve of the ODT dosage form formed from batch 2c (SH24) formulated with the tartrate salt of psilocin at pH 7.94;

FIG. 142 shows the XRPD pattern of the ODT dosage form formed from batch 2c (SH24) formulated with the tartrate salt of psilocin at pH 7.94;

FIG. 143 shows the TGA plot of the placebo ODT dosage form;

FIG. 144 shows the DSC curve of the placebo ODT dosage form;

FIG. 145 shows the XRPD pattern of the placebo ODT dosage form;

FIG. 146 shows a plasma concentration-time curve of psilocybin dosed orally and intravenously in rats;

FIG. 147 is a plasma concentration-time curve of PI-$d_0$+PI-$d_{10}$ (PI-tot) from co-dosing PI-do and PI-$d_{10}$ orally and intravenously in rats;

FIG. 148 is a plasma concentration-time curve comparing PI-tot plasma levels after oral PI-$d_0$+PI-$d_{10}$ and oral psilocybin in rats;

FIG. 149 is a tissue concentration-time curve comparing brain and plasma psilocybin levels after intravenous dosing of psilocybin in rats;

FIG. 150 is a tissue concentration-time curve comparing brain and plasma PI-tot levels after intravenous co-dosing of PI-$d_0$ and PI-$d_{10}$ in rats;

FIG. 151 is a brain concentration-time curve comparing brain PI levels after intravenous dosing of psilocybin and PI-tot levels after intravenous co-dosing of PI-$d_0$ and PI-$d_{10}$ in rats;

FIGS. 152A-152B show a plasma concentration-time curve following intravenous and oral administration of psilocin-$d_{10}$ to dogs (FIG. 152A), and a bioavailability profile of psilocin-$d_{10}$ to dogs of 91.3% (FIG. 152B);

FIGS. 153A-153B show the plasma concentration-time profiles for PI-$d_0$ after psilocybin dosing (FIG. 153A) and for PI-$d_{10}$ after PI-$d_{10}$ (FIG. 153B) with orally disintegrating tablets (ODT) and powder in capsule (PIC) dosage forms;

FIG. 154 shows the exposure comparison between PI-$d_0$ after psilocybin dosing and PI-$d_{10}$ after PI-$d_{10}$ dosing for both ODT and PIC dosage forms as assessed by Cmax; and FIG. 155 shows the exposure comparison between PI-$d_0$ after psilocybin dosing and PI-$d_{10}$ after PI-$d_{10}$ dosing for both ODT and PIC dosage forms as assessed by AUCinf.

DETAILED DESCRIPTION

In the following detailed description of the embodiments of the instant disclosure, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the instant disclosure.

Definitions

Unless defined otherwise, all technical and scientific terms used herein have the same meaning as is commonly understood by one of skill in the art to which this disclosure belongs.

When it is stated that a substituent or group "comprise(s) deuterium" or is "comprising deuterium," it is to be understood that the substituent or group may itself be deuterium, or the substituent or group may contain at least one deuterium substitution in its chemical structure. For example, when substituent "—R" is defined to comprise deuterium, it is to be understood that —R may be -D (-deuterium), or a group such as —$CD_3$ that is consistent with the other requirements set forth of —R.

As used herein, the term "fatty" describes a compound with a long-chain (linear) hydrophobic portion made up of hydrogen and anywhere from 4 to 26 carbon atoms, which may be fully saturated or partially unsaturated.

The phrases "pharmaceutically acceptable," "physiologically acceptable," and the like, are employed herein to refer to those compounds, materials, compositions, and/or dosage forms which are, within the scope of sound medical judgment, suitable for use in contact with the tissues of human beings without excessive toxicity, irritation, allergic response, or other problem or complication, commensurate with a reasonable benefit/risk ratio. When referencing salts, the phrases "pharmaceutically acceptable salt," "physiologically acceptable salt," and the like, means a salt which is acceptable for administration to a patient, such as a mammal (salts with counterions having acceptable mammalian safety for a given dosage regime). As is well known in the art, such salts can be derived from pharmaceutically acceptable inorganic or organic bases, by way of example, sodium, potassium, calcium, magnesium, ammonium, and tetraalkylammonium salts, and the like, and when the molecule contains a basic functionality, addition salts with inorganic acids, such as hydrochloride, hydrobromide, sulfate, sulfamate, phosphate, nitrate, perchlorate salts, and the like, and addition salts with organic acids, such as formate, tartrate, besylate, mesylate, acetate, maleate, malonate, oxalate, fumarate, benzoate, salicylate, succinate, oxalate, glycolate, hemi-oxalate, hemi-fumarate, propionate, stearate, lactate, citrate, ascorbate, pamoate, hydroxymaleate, phenylacetate, glutamate, 2-acetoxybenzoate, tosylate, ethanedisulfonate, isethionate salts, and the like. The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a physical association of a compound or salt of the present disclosure with one or more solvent molecules, whether organic, inorganic, or a mixture of both. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Some examples of solvents include, but are not limited to, methanol, ethanol, isopropanol, N,N-dimethylformamide, tetrahydrofuran, dimethylsulfoxide, and water. When the solvent is water, the solvate formed is a hydrate (e.g., monohydrate, dihydrate, etc.). Exemplary solvates thus include, but are not limited to, hydrates, methanolates, ethanolates, isopropanolates, etc. Methods of solvation are generally known in the art.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. Other tautomeric ring atom arrangements are also possible.

It will be appreciated that the compounds herein can exist in different salt, solvate, and stereoisomer forms, and the present disclosure is intended to include all permutations of salts, solvates and stereoisomers, such as a solvate of a pharmaceutically acceptable salt of a stereoisomer of the subject compound.

As used herein, the term "steady" describes the stable or steady-state level of a molecule concentration, e.g., concentration of any compound described herein.

The term "stable," "stability," and the like, as used herein includes chemical stability and solid state (physical) stability. The term "chemical stability" means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition. "Solid-state stability" means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g., hydration, dehydration, solvatization, desolvatization, crystallization, recrystallization or solid-state phase transition).

A "psilocybin-based" drug is any prodrug of a psilocin-type compound, such as an alkyl/aryl ester, an α-amino ester (e.g., an amino acid ester), a hemi-ester, a bis-ester, a phosphate ester, a sulfate ester, etc., that when administered releases psilocin or a deuterated analog thereof (e.g., a compound of Formula (I)) as the active component. A psilocybin-based drug includes psilocybin itself.

As used herein, the term "composition" is equivalent to the term "formulation."

References to X-ray powder diffraction (XRPD) patterns of compounds/salts of the present disclosure being characterized by an X-ray powder diffraction pattern containing "at least three characteristic peaks" should be understood to include those compounds/salts characterized as having 3, 4, 5, 6, 7, 8, 9, 10, 11, 12, 13, 14, 15 or more (including all) of the recited characteristic XRPD diffraction peaks.

As used herein, the language "administration event" describes the administration of a subject a given dose, within any suitable window of time, e.g., less than about 60 minutes, 50, minutes, 40 minutes, 30 minutes, 20 minutes, 10 minutes, 5 minutes, or 2 minutes.

The term "treating" or "treatment" as used herein means the treating or treatment of a disease or medical condition in a patient, such as a mammal (particularly a human) that includes: ameliorating the disease or medical condition, such as, eliminating or causing regression of the disease or medical condition in a patient; suppressing the disease or medical condition, for example by, slowing or arresting the development of the disease or medical condition in a patient; or alleviating one or more symptoms of the disease or medical condition in a patient. In an embodiment, prophylactic treatment can result in preventing the disease or medical condition from occurring, in a subject.

A "patient" or "subject," used interchangeably herein, can be any mammal including, for example, a human and non-human subjects. A patient or subject can have a condition to be treated or can be susceptible to a condition to be treated.

As used herein, and unless otherwise specified, the terms "prevent," "preventing" and "prevention" refer to the prevention of the onset, recurrence or spread of a disease, disorder, or condition, or of one or more symptoms thereof. The terms encompass the inhibition or reduction of a symptom of the particular disease, disorder, or condition. Subjects with familial history of a disease, disorder, or condition, in particular, are candidates for preventive regimens in certain embodiments. In addition, subjects who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease, disorder, or condition, or of one or more symptoms thereof. Often, the beneficial effects that a subject derives from a prophylactic and/or therapeutic agent do not result in a cure of the disease, disorder, or condition. In this regard, the term "managing" encompasses treating a subject who had suffered from the particular disease, disorder, or condition in an attempt to prevent or minimize the recurrence of the disease, disorder, or condition.

"Therapeutically effective amount" refers to an amount of a compound(s) or its salt form sufficient to treat a specified disorder or disease or one or more of its symptoms and/or to prevent the occurrence of the disease or disorder (prophylactically effective amount).

As used herein, and unless otherwise specified, a "prophylactically effective amount" of an active agent, is an amount sufficient to prevent a disease, disorder, or condition, or prevent its recurrence. The term "prophylactically effective amount" can encompass an amount that improves overall prophylaxis or enhances the prophylactic efficacy of another prophylactic agent.

The term "administration schedule" is a plan in which the type, amount, period, procedure, etc. of the drug in the drug treatment are shown in time series, and the dosage, administration method, administration order, administration date, and the like of each drug are indicated. The date specified to be administered is determined before the start of the drug administration. The administration is continued by repeating the course with the set of administration schedules as "courses". A "continuous" administration schedule means administration every day without interruption during the treatment course. If the administration schedule follows an "intermittent" administration schedule, then days of administration may be followed by "rest days" or days of non-administration of drug within the course. A "drug holiday" indicates that the drug is not administered in a predetermined administration schedule. For example, after undergoing several courses of treatment, a subject may be prescribed a regulated drug holiday as part of the administration schedule, e.g., prior to re-recommencing active treatment.

The language "toxic spikes" is used herein to describe neurological spikes in concentration of any compound described herein that would produce side-effects of sedation or psychotomimetic effects, e.g., hallucination, dizziness, and nausea; which can not only have immediate repercussions, but also effect treatment compliance. In particular, side effects may become more pronounced at blood concentration levels of about 250, 300, 400, 500 ng/L or more.

As used herein, and unless otherwise specified, a "neuropsychiatric disease or disorder" is a behavioral or psychological problem associated with a known neurological condition, and typically defined as a cluster of symptoms that co-exist. Examples of neuropsychiatric disorders include, but are not limited to, attention deficit disorder, attention deficit hyperactivity disorder, bipolar and manic disorders, depression or any combinations thereof.

"Inflammatory conditions," "inflammatory disease," or "inflammatory disorder" as used herein, refers broadly to chronic or acute inflammatory diseases, including but are not limited to rheumatic diseases (e.g., rheumatoid arthritis, osteoarthritis, psoriatic arthritis) spondyloarthropathies (e.g., ankylosing spondylitis, reactive arthritis, Reiter's syndrome), crystal arthropathies (e.g., gout, pseudogout, calcium pyrophosphate deposition disease), multiple sclerosis, Lyme disease, polymyalgia rheumatica; connective tissue diseases (e.g., systemic lupus erythematosus, systemic sclerosis, polymyositis, dermatomyositis, Sjogren's syndrome); vasculitides (e.g., polyarteritis nodosa, Wegener's granulomatosis, Churg-Strauss syndrome); inflammatory conditions including consequences of trauma or ischaemia, sarcoidosis; vascular diseases including atherosclerotic vascular disease, atherosclerosis, and vascular occlusive disease (e.g., atherosclerosis, ischaemic heart disease, myocardial infarction, stroke, peripheral vascular disease), and vascular stent restenosis; ocular diseases including uveitis, corneal disease, iritis, iridocyclitis, and cataracts.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

Compounds

Disclosed herein is a compound of Formula (I), or a pharmaceutically acceptable salt, a polymorph, stereoisomer, or solvate thereof, (I)

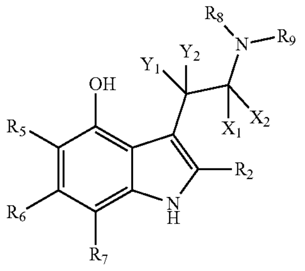

wherein:

$R_2$, $R_5$, $R_6$, and $R_7$ are independently selected from the group consisting of hydrogen or deuterium, $R_8$ and $R_9$ are independently selected from the group consisting of $—CH_3$, $—CH_2D$, $—CHD_2$, and $—CD_3$, and $X_1$, $X_2$, $Y_1$, and $Y_2$ are independently selected from the group consisting of hydrogen or deuterium.

In some embodiments, $R_2$, $R_5$, $R_6$, and $R_7$ are independently selected from the group consisting of hydrogen or deuterium. In some embodiments, $R_2$ is deuterium. In some embodiments, $R_2$ is hydrogen. In some embodiments, $R_5$ is deuterium. In some embodiments, $R_5$ is hydrogen. In some embodiments, $R_6$ is deuterium. In some embodiments, $R_6$ is hydrogen. In some embodiments, $R_7$ is deuterium. In some embodiments, $R_7$ is hydrogen.

$R_2$, $R_5$, $R_6$, and $R_7$ may be the same, for example, $R_2$, $R_5$, $R_6$, and $R_7$ may each be hydrogen, or alternatively, $R_2$, $R_5$, $R_6$, and $R_7$ may each be deuterium. In some embodiments, at least one of $R_2$, $R_5$, $R_6$, and $R_7$ is deuterium. In some embodiments, at least two of $R_2$, $R_5$, $R_6$, and $R_7$ are deuterium. In some embodiments, at least three of $R_2$, $R_5$, $R_6$, and $R_7$ are deuterium.

In some embodiments, $R_8$ and $R_9$ are independently selected from the group consisting of $—CH_3$, $—CH_2D$, $—CHD_2$, and $—CD_3$. $R_8$ and $R_9$ may be the same, or different. In some embodiments, $R_8$ and $R_9$ are the same. In some embodiments, $R_8$ and $R_9$ are independently selected from the group consisting of $—CH_3$ and $—CD_3$. In some embodiments, $R_8$ and $R_9$ are methyl ($—CH_3$). In some embodiments, $R_8$ and $R_9$ are a partially deuterated methyl group, i.e., $—CDH_2$ or $—CD_2H$. In some embodiments, $R_8$ and $R_9$ are a fully deuterated methyl group ($—CD_3$). In some embodiments, at least one of $R_8$ and $R_9$ is $—CD_3$.

In some embodiments, $X_1$, $X_2$, $Y_1$, and $Y_2$ are independently selected from the group consisting of hydrogen or deuterium. $X_1$ and $X_2$ may be the same, or different. In some embodiments, $X_1$ and $X_2$ are the same. In some embodiments, $X_1$ and $X_2$ are hydrogen. In some embodiments, $X_1$ and $X_2$ are deuterium.

$Y_1$ and $Y_2$ may be the same, or different. In some embodiments, $Y_1$ and $Y_2$ are the same. In some embodiments, $Y_1$ and $Y_2$ are hydrogen. In some embodiments, $Y_1$ and $Y_2$ are deuterium. In some embodiments, $X_1$, $X_2$, $Y_1$, and $Y_2$ are hydrogen. In some embodiments, $X_1$, $X_2$, $Y_1$, and $Y_2$ are deuterium.

In some embodiments, $X_1$, $X_2$, $Y_1$, $Y_2$, $R_2$, $R_5$, $R_6$, $R_7$, $R_8$, and $R_9$ are each hydrogen. In some embodiments, at least one of $X_1$, $X_2$, $Y_1$, $Y_2$, $R_2$, $R_5$, $R_6$, $R_7$, $R_8$, and $R_9$ comprises deuterium. In some embodiments, at least $X_1$, $X_2$, $R_8$, and $R_9$ comprise deuterium. In some embodiments, at least $X_1$, $X_2$, $Y_1$, $Y_2$, $R_8$, and $R_9$ comprise deuterium. In some embodiments, $X_1$, $X_2$, $Y_1$, and $Y_2$ are deuterium, and $R_8$ and $R_9$ are a fully deuterated methyl group ($—CD_3$).

The compounds of Formula (I) may contain a stereogenic center. In such cases, the compounds may exist as different stereoisomeric forms, even though Formula (I) is drawn without reference to stereochemistry. Accordingly, the present disclosure includes all possible stereoisomers and includes not only racemic compounds but the individual enantiomers (enantiomerically pure compounds), individual diastereomers (diastereomerically pure compounds), and their non-racemic mixtures as well. When a compound is desired as a single enantiomer, such may be obtained by, e.g., stereospecific synthesis, as is known in the art.

In some embodiments, the compounds described herein, e.g., compounds of Formula (I), are non-stereogenic. In some embodiments, the compounds described herein, e.g., compounds of Formula (I), are racemic. In some embodiments, the compounds described herein, e.g., compounds of Formula (I), are enantiomerically enriched (one enantiomer is present in a higher percentage), including enantiomerically pure. In some embodiments, the compounds described herein, e.g., compounds of Formula (I), are provided as a single diastereomer. In some embodiments, the compounds described herein, e.g., compounds of Formula (I), are provided as a mixture of diastereomers. When provided as a mixture of diastereomers, the mixtures may include equal mixtures, or mixtures which are enriched with a particular diastereomer (one diastereomer is present in a higher percentage than another).

In some embodiments, the compound of Formula (I) is an agonist of a serotonin 5-$HT_2$ receptor.

In some embodiments, the compound of Formula (I) is an agonist of a serotonin 5-$HT_{2A}$ receptor.

In some embodiments, the compound of Formula (I) is selected from the group consisting of:

(I-1)

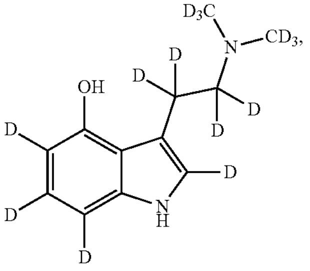

(I-2)

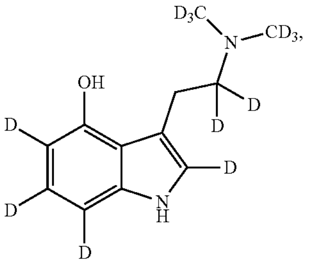

(I-3)

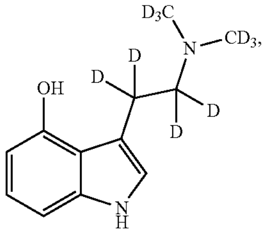

(I-4)

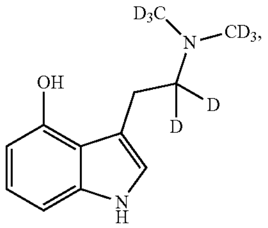

(I-5)

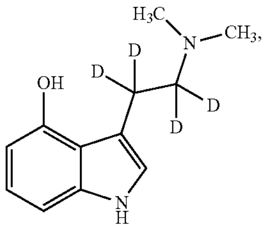

-continued (I-6)

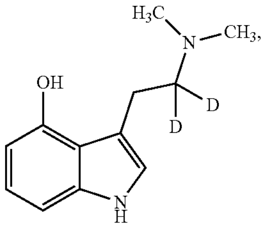

(I-7)

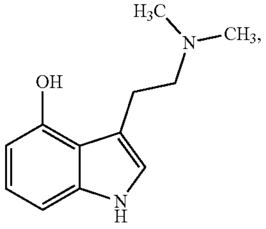

(I-8)

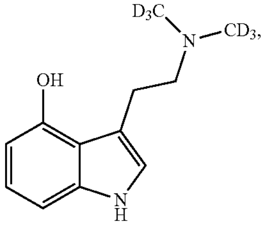

(I-9)

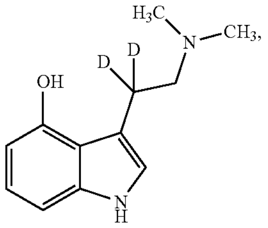

and (I-10)

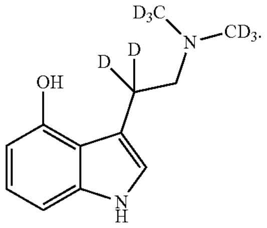

The compound number, IUPAC name, and substituent listing for the above-identified compounds are provided in Table 1.

TABLE 1

Exemplary compounds of Formula (I)

| | | Formula (I) | | | | | | |
|---|---|---|---|---|---|---|---|---|
| | Compound identifier and name | $X_1$, $X_2$ | $Y_1$, $Y_2$ | $R_2$ | $R_5$ | $R_6$ | $R_7$ | $R_8$, $R_9$ |
| I-1 | 3-(2-(bis(methyl-$d_3$)amino)ethyl-1,1,2,2-$d_4$)-1H-indol-2,5,6,7-$d_4$-4-ol | D, D | D, D | D | D | D | D | $-CD_3$, $-CD_3$ |
| I-2 | 3-(2-(bis(methyl-$d_3$)amino)ethyl-2,2-$d_2$)-1H-indol-2,5,6,7-$d_4$-4-ol | D, D | H, H | D | D | D | D | $-CD_3$, $-CD_3$ |
| I-3 | 3-(2-(bis(methyl-$d_3$)amino)ethyl-1,1,2,2-$d_4$)-1H-indol-4-ol | D, D | D, D | H | H | H | H | $-CD_3$, $-CD_3$ |
| I-4 | 3-(2-(bis(methyl-$d_3$)amino)ethyl-2,2-$d_2$)-1H-indol-4-ol | D, D | H, H | H | H | H | H | $-CD_3$, $-CD_3$ |

TABLE 1-continued

| Exemplary compounds of Formula (I) | | | | | | | | |
|---|---|---|---|---|---|---|---|---|
| | | Formula (I) | | | | | | |
| | Compound identifier and name | $X_1$, $X_2$ | $Y_1$, $Y_2$ | $R_2$ | $R_5$ | $R_6$ | $R_7$ | $R_8$, $R_9$ |
| I-5 | 3-(2-(dimethylamino)ethyl-1,1,2,2-$d_4$)-1H-indol-4-ol | D, D | D, D | H | H | H | H | $-CH_3$, $-CH_3$ |
| I-6 | 3-(2-(dimethylamino)ethyl-2,2-$d_2$)-1H-indol-4-o1 | D, D | H, H | H | H | H | H | $-CH_3$, $-CH_3$ |
| I-7 | 3-(2-(dimethylamino)ethyl)-1H-indol-4-ol | H, H | H, H | H | H | H | H | $-CH_3$, $-CH_3$ |
| I-8 | 3-(2-(bis(methyl-$d_3$)amino)ethyl)-1H-indol-4-ol | H, H | H, H | H | H | H | H | $-CD_3$, $-CD_3$ |
| I-9 | 3-(2-(dimethylamino)ethyl-1,1-$d_2$)-1H-indol-4-ol | H, H | D, D | H | H | H | H | $-CH_3$, $-CH_3$ |
| I-10 | 3-(2-(bis(methyl-$d_3$)amino)ethyl-1,1-$d_2$)-1H-indol-4-ol | H, H | D, D | H | H | H | H | $-CD_3$, $-CD_3$ |

In some embodiments, the compounds of the present disclosure are provided as a free base in crystalline form, e.g., as determined by XRPD. Accordingly, pharmaceutical compositions may be prepared from compounds of Formula (I) as a free base, in one or more polymorphic forms, and may be used for treatment as set forth herein.

In some embodiments, the compound of Formula (I) is a crystalline form of 3-(2-(bis(methyl-$d_3$)amino)ethyl-1,1,2,2-$d_4$)-1H-indol-2,5,6,7-$d_4$-4-ol (I-1), as determined by X-ray powder diffraction.

In some embodiments, the compound of Formula (I) is a crystalline form of 3-(2-(bis(methyl-$d_3$)amino)ethyl-2,2-$d_2$)-1H-indol-2,5,6,7-$d_4$-4-ol (I-2), as determined by X-ray powder diffraction.

Figure 2A:
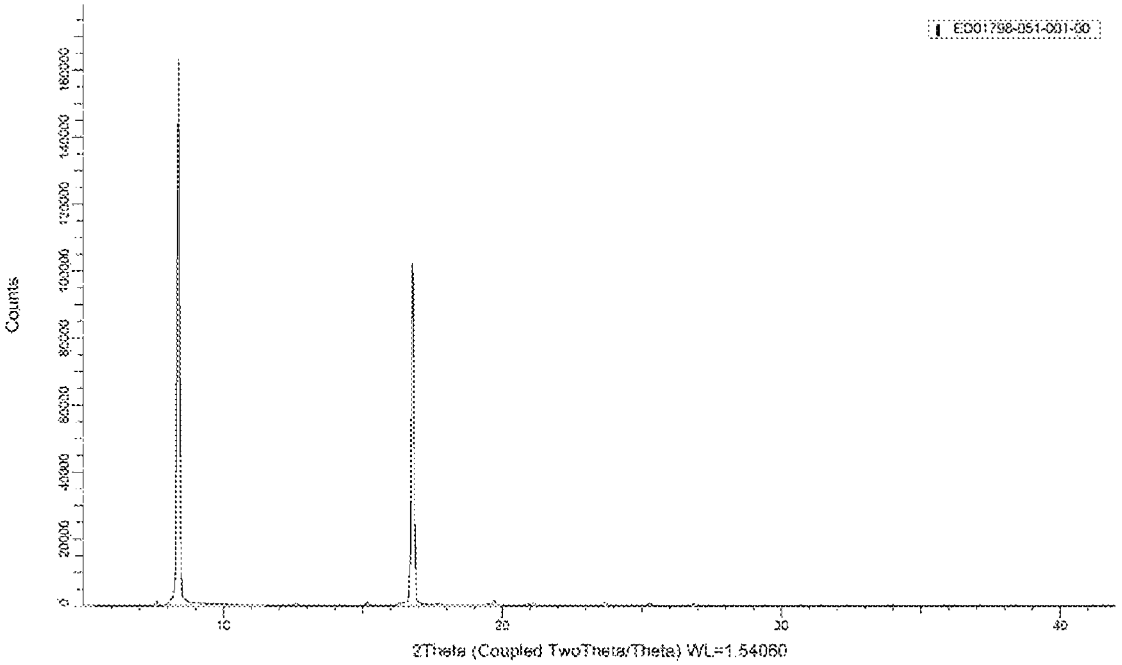
FIGS. 2A-2C show the X-ray powder diffraction (XRPD) pattern (pattern 1) of compound I-3, with FIGS. 2B and 2C being zoomed in and annotated.
Figure 2B:
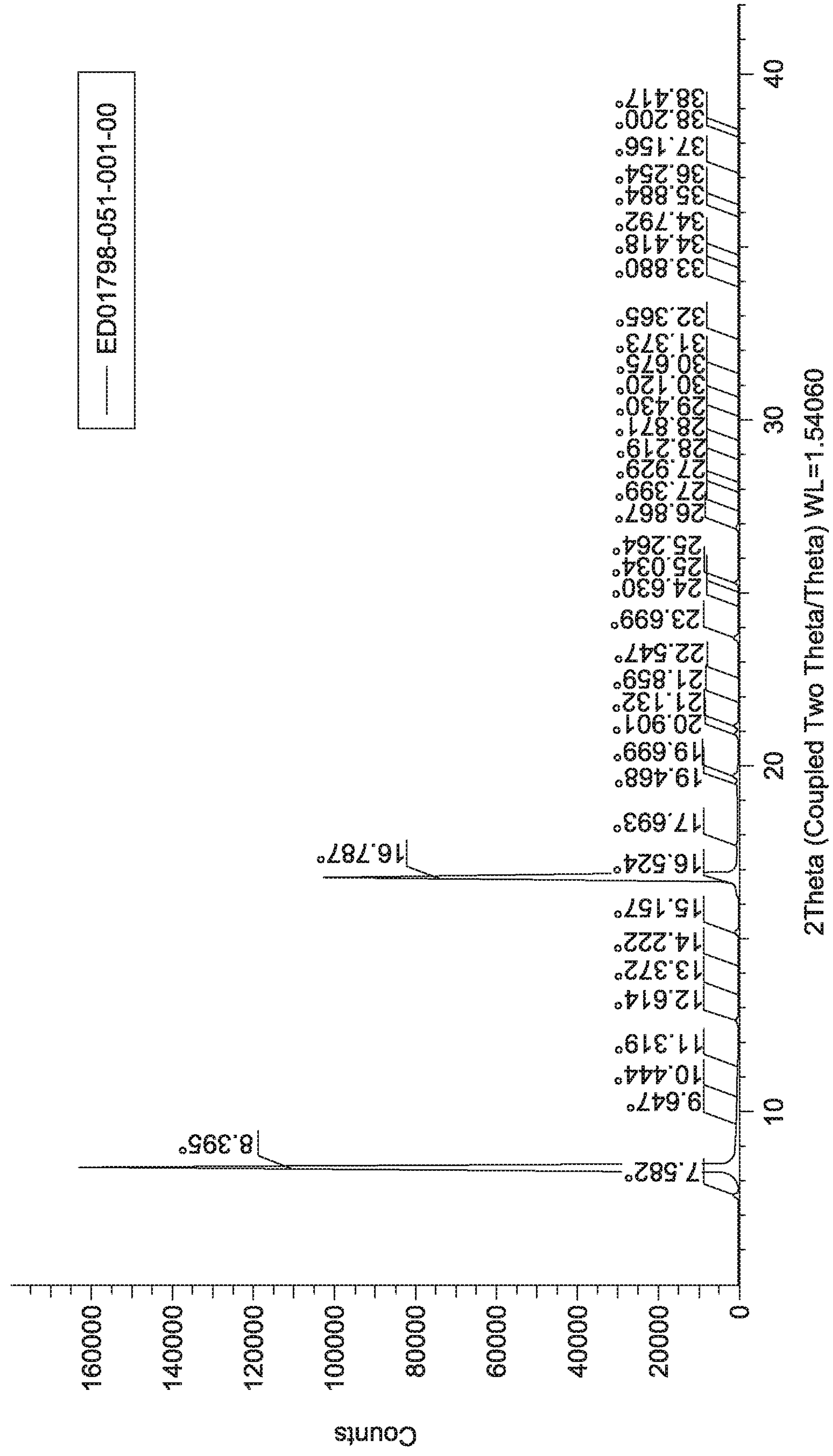
Figure 2C:
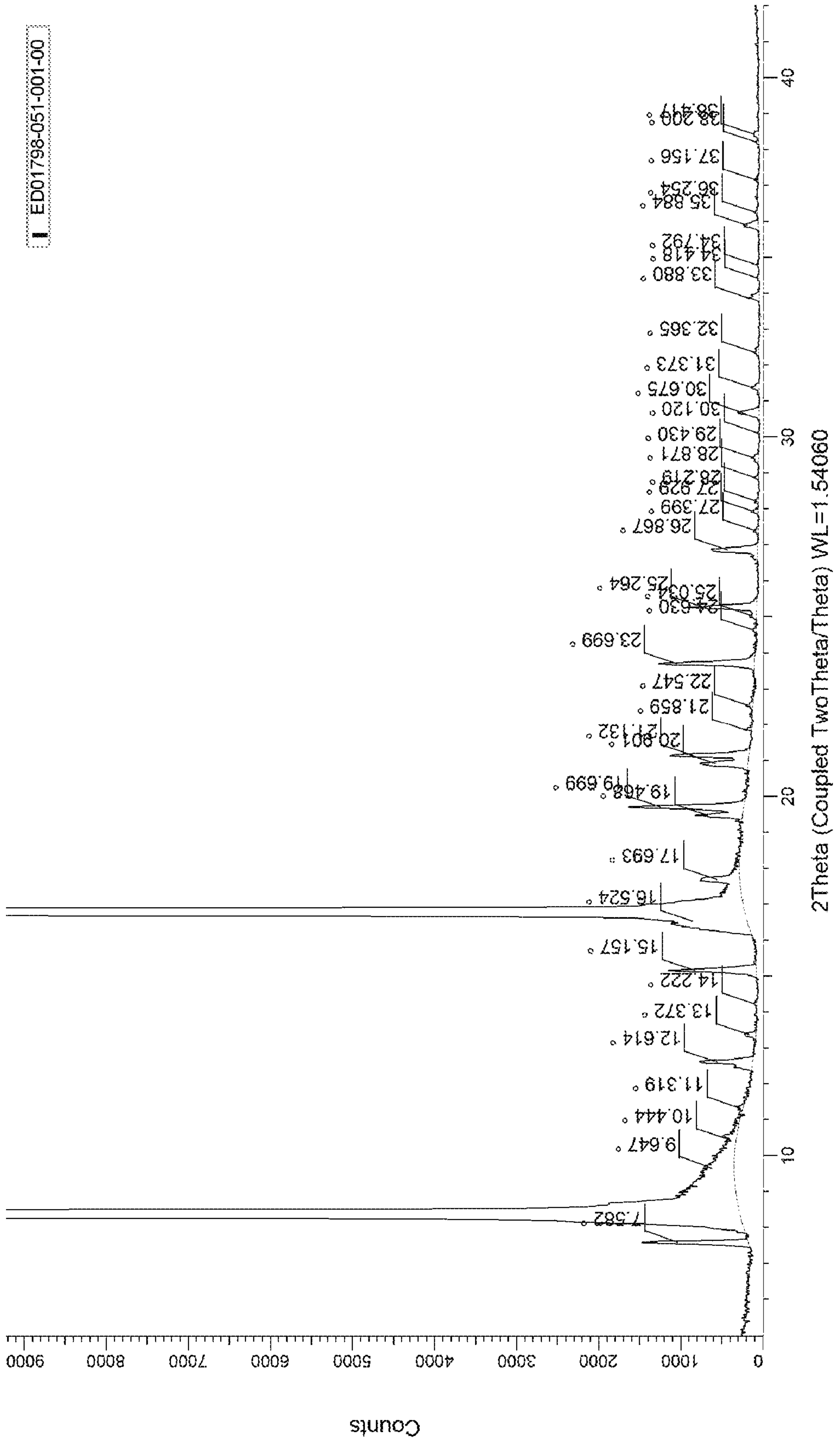
Figure 88:
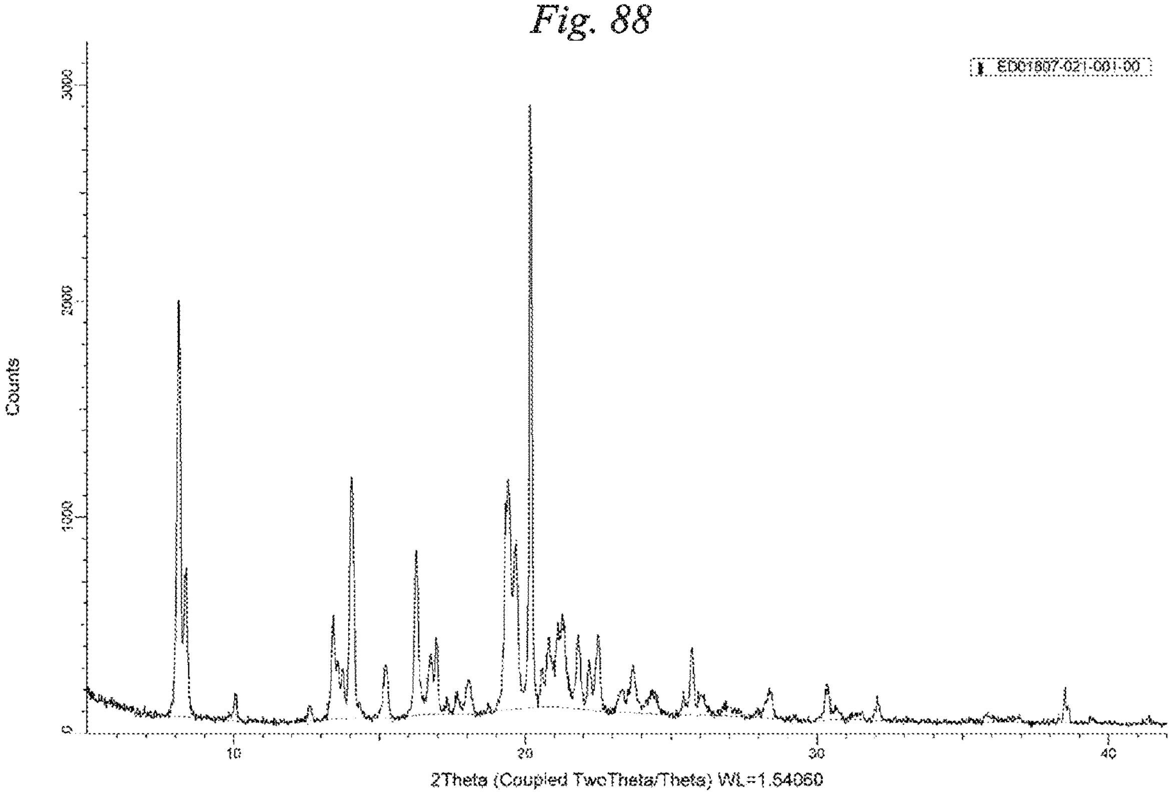
FIG. 88 shows the XRPD pattern of I-3 (pattern 2) obtained from DSC scale-up experiments.
Figure 89:
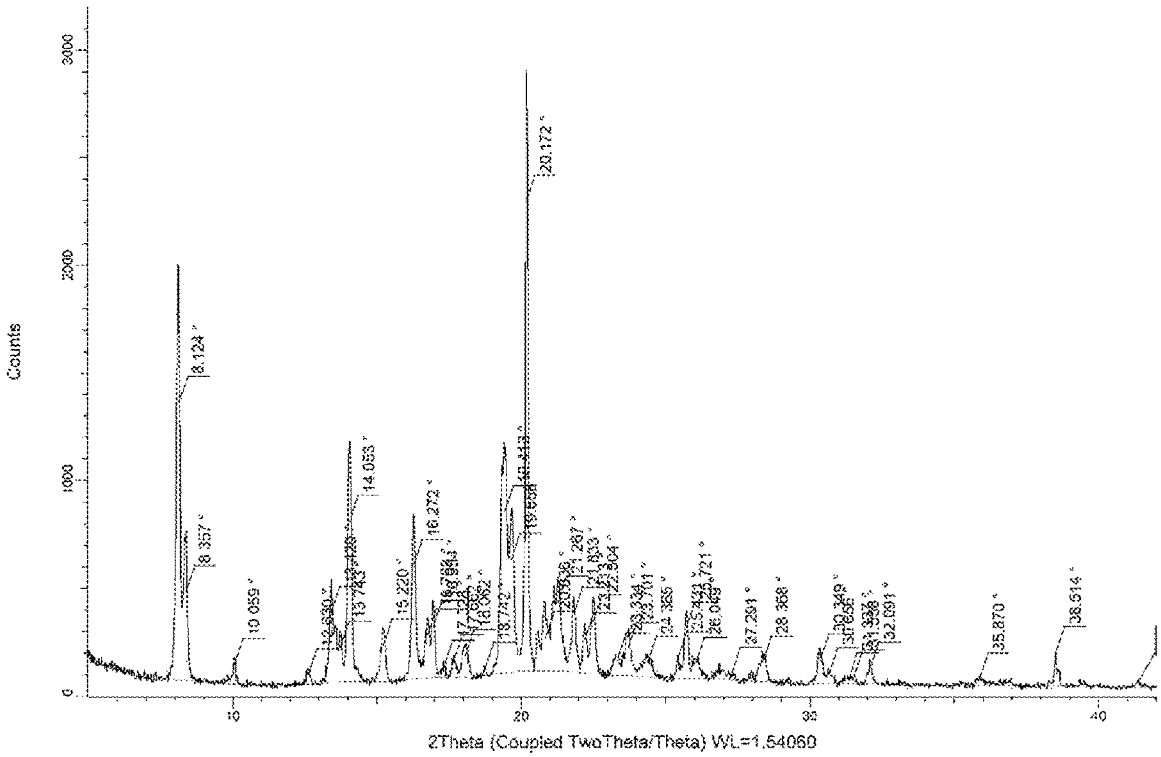
FIG. 89 shows the annotated XRPD pattern of I-3 (pattern 2) obtained from DSC scale-up experiments.

In some embodiments, the compound of Formula (I) is a crystalline form of 3-(2-(bis(methyl-$d_3$)amino)ethyl-1,1,2,2-$d_4$)-1H-indol-4-ol (I-3), as determined by X-ray powder diffraction. In some embodiments, I-3 is a crystalline solid form (polymorph of pattern 1) characterized by an X-ray powder diffraction pattern containing at least three characteristic peaks at diffraction angles (2θ±0.2°) selected from the group consisting of 7.582°, 8.395°, 9.647°, 10.444°, 11.319°, 12.614°, 13.372°, 14.222°, 15.157°, 16.524°, 16.787°, 17.693°, 19.468°, 19.699°, 20.901°, 21.132°, 21.859°, 22.547°, 23.699°, 24.630°, 25.034°, 25.264°, 26.867°, 27.399°, 27.929°, 28.219°, 28.871°, 29.430°, 30.120°, 30.675°, 31.373°, 32.365°, 33.880°, 34.418°, 34.792°, 35.884°, 36.254°, 37.156°, 38.200°, and 38.417°, as determined by XRPD using a CuKα radiation source, for example, as shown in FIGS. 2A-2C. In some embodiments, I-3 is a crystalline solid form (polymorph of pattern 2) characterized by an X-ray powder diffraction pattern containing at least three characteristic peaks at diffraction angles (2θ±0.2°) selected from the group consisting of 8.124°, 8.357°, 10.059°, 12.630°, 13.420°, 13.743°, 14.053°, 15.220°, 16.272°, 16.763°, 16.954°, 17.328°, 17.662°, 18.062°, 18.742°, 19.413°, 19.658°, 20.172°, 20.836°, 21.267°, 21.833°, 22.213°, 22.504°, 23.334°, 23.701°, 24.385°, 25.431°, 25.721°, 26.049°, 27.291°, 28.368°, 30.349°, 30.656°, 31.337°, 31.538°, 32.091°, 35.870°, 38.514°, and 41.361°, as determined by XRPD using a CuKα radiation source, for example, as shown in FIGS. 88-89.

In some embodiments, the compound of Formula (I) is a crystalline form of 3-(2-(bis(methyl-$d_3$)amino)ethyl-2,2-$d_2$)-1H-indol-4-ol (I-4), as determined by X-ray powder diffraction.

In some embodiments, the compound of Formula (I) is a crystalline form of 3-(2-(dimethylamino)ethyl-1,1,2,2-$d_4$)-1H-indol-4-ol (I-5), as determined by X-ray powder diffraction.

In some embodiments, the compound of Formula (I) is a crystalline form of 3-(2-(dimethylamino)ethyl-2,2-$d_2$)-1H-indol-4-ol (I-6), as determined by X-ray powder diffraction.

Figure 3A:
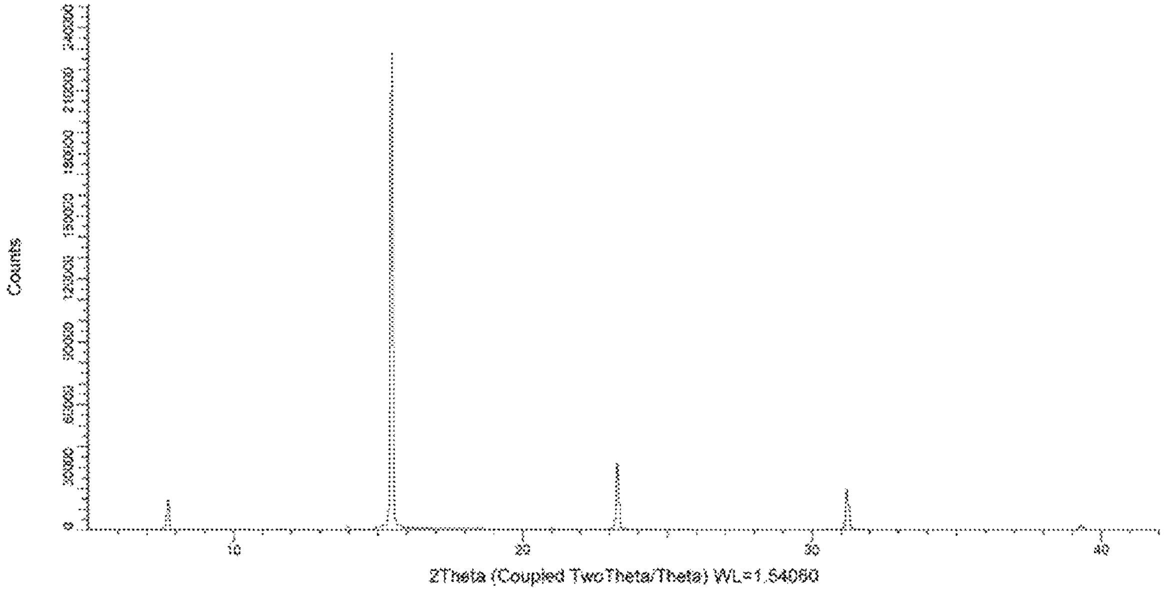
FIGS. 3A-3D show the X-ray powder diffraction (XRPD) pattern of I-7a (pattern 1)(FIG. 3A), with FIG. 3B being zoomed in and annotated, the XRPD pattern of I-7 (PI-$d_0$, free base)(pattern 1)(FIG. 3C), and a comparison between the XRPD patterns of I-7a (benzenesulfonate salt) and I-7 (PI-$d_0$, free base)(pattern 1)(FIG. 3D)
Figure 3B:
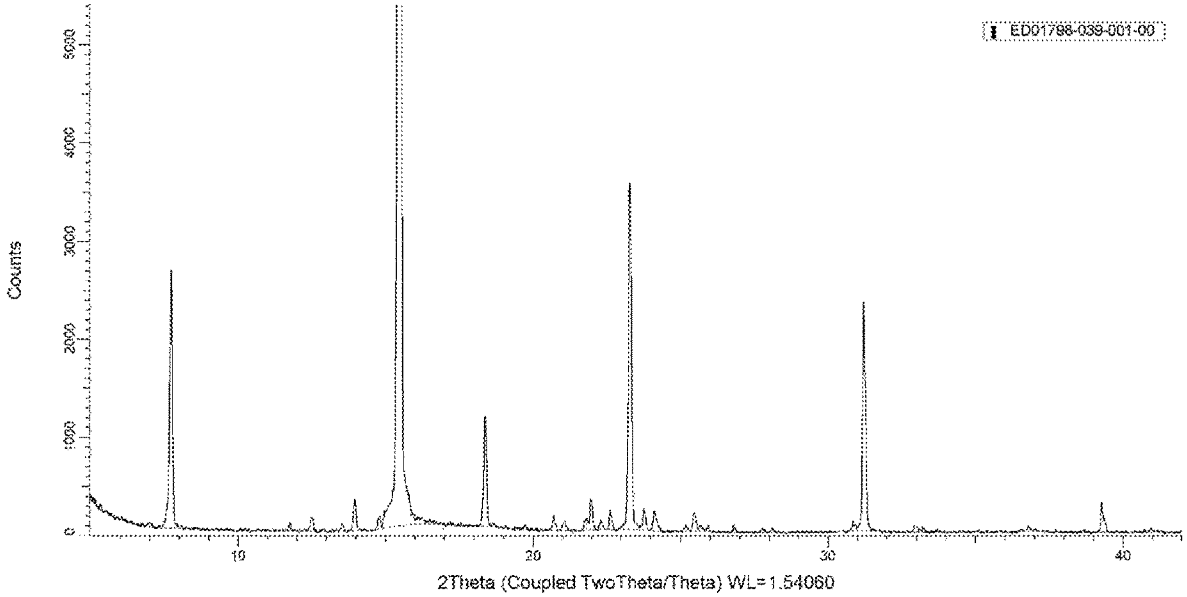
Figure 3C:
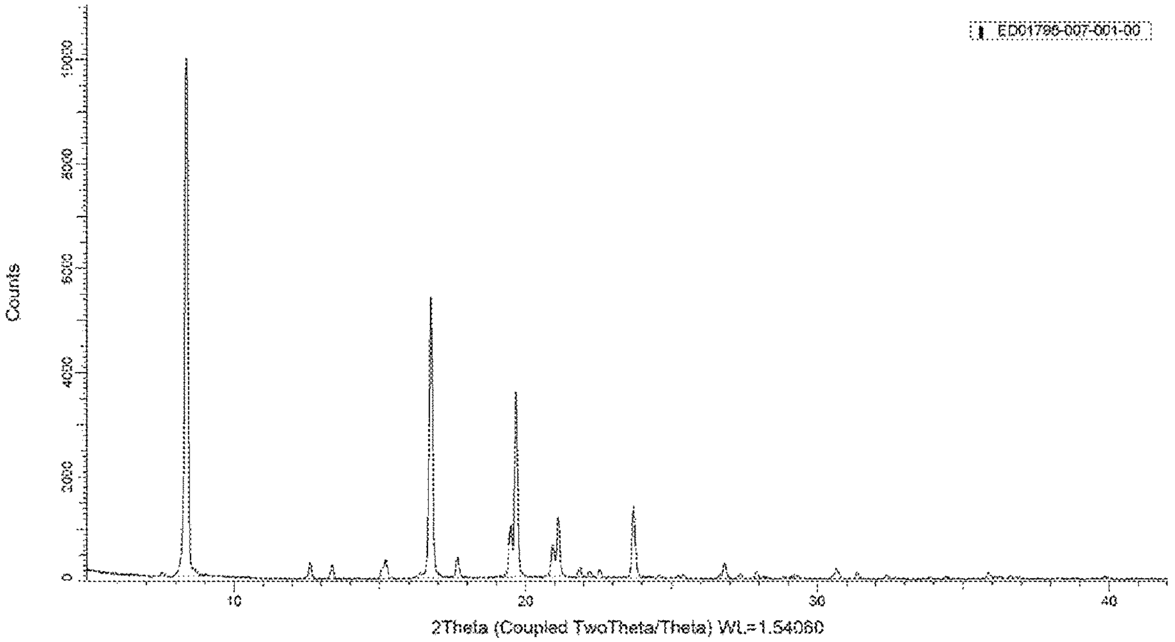

In some embodiments, the compound of Formula (I) is a crystalline form of 3-(2-(dimethylamino)ethyl)-1H-indol-4-ol (I-7), as determined by X-ray powder diffraction. In some embodiments, I-7 is a crystalline solid form (polymorph of pattern 1) characterized by an X-ray powder diffraction pattern containing at least three characteristic peaks at diffraction angles (2θ: 0.2°) selected from the group consisting of 7.563°, 8.375°, 12.626°, 13.383°, 15.211°, 16.753°, 17.671°, 19.668°, 21.112°, 21.863°, 22.201°, 22.560°, 23.711°, 24.592°, 25.415°, 26.820°, 27.357°, 27.921°, 28.228°, 29.253°, 30.653°, 31.364°, 32.401°, 33.797°, 34.445°, 39.867°, as determined by XRPD using a CuKα radiation source, for example, as shown in FIG. 3C.

In some embodiments, the compounds of the present disclosure are provided as a free base in amorphous form, e.g., as determined by XRPD. Accordingly, pharmaceutical compositions may be prepared from compounds of Formula (I) as a free base, in one or more amorphic forms, and may be used for treatment as set forth herein.

Numerous attempts to make an amorphous form of the compounds of the present disclosure proved unsuccessful, including crash cooling/freeze drying, fast evaporation from numerous organic solvents, and anti-solvent precipitation. Crash cooling/freeze drying and fast evaporation techniques each gave only crystalline material, while anti-solvent precipitation failed to produce solid material. After significant experimentation, it has been discovered that amorphous forms of the compounds of Formula (I), e.g., compound I-3 (psilocin-$d_{10}$) can be prepared through a melt/crash cooling procedure. Briefly, crystalline free base material may be heated beyond its melting point, e.g., to at least 180° C., at least 181° C., at least 182° C., at least 183° C., at least 184° C., at least 185° C. using DSC or similar technique, followed by rapid cooling to near the glass transition of the material, e.g., to about 26° C., about 27° C., about 28° C., about 29° C., about 30° C., as determined by differential scanning calorimetry (DSC). For example, it has been found that amorphous I-3 (PI-$d_{10}$, free base) can be prepared by a melt/crash cooling procedure in DSC in which crystalline I-3 is heated to beyond the melting point (to 185° C.) and then rapidly cooled to 30° C. (glass transition temperature of 27° C.). The amorphous nature of the compound of Formula (I) can be determined e.g., by XRPD.

In some embodiments, the compound of Formula (I) is an amorphous form of 3-(2-(bis(methyl-$d_3$)amino)ethyl-1,1,2,2-$d_4$)-1H-indol-2,5,6,7-$d_4$-4-ol (I-1), as determined by X-ray powder diffraction. In some embodiments, the compound of Formula (I) is an amorphous form of 3-(2-(bis(methyl-$d_3$)amino)ethyl-2,2-$d_2$)-1H-indol-2,5,6,7-$d_4$-4-ol (I-2), as determined by X-ray powder diffraction. In some embodiments, the compound of Formula (I) is an amorphous form of 3-(2-(bis(methyl-$d_3$)amino)ethyl-1,1,2,2-$d_4$)-1H-indol-4-ol (I-3), as determined by X-ray powder diffraction. In some embodiments, the compound of Formula (I) is an amorphous form of 3-(2-(bis(methyl-$d_3$)amino)ethyl-2,2-$d_2$)-1H-indol-4-ol (I-4), as determined by X-ray powder diffraction. In some embodiments, the compound of Formula (I) is an amorphous form of 3-(2-(dimethylamino)ethyl-1,1,2,2-$d_4$)-1H-indol-4-ol (I-5), as determined by X-ray powder diffraction. In some embodiments, the compound of Formula (I) is an amorphous form of 3-(2-(dimethylamino)ethyl-2,2-$d_2$)-1H-indol-4-ol (I-6), as determined by X-ray powder diffraction. In some embodiments, the compound of Formula (I) is an amorphous form of 3-(2-(dimethylamino)ethyl)-1H-indol-4-ol (I-7), as determined by X-ray powder diffraction.

Such amorphous forms of the compounds of Formula (I) (free base) may be advantageous in terms of dissolution rates in water, compared to crystalline forms, thereby enabling rapid systemic absorption for quick therapeutic onset and a short duration of drug action. Further, in some embodiments, pharmaceutical compositions may be prepared which comprise the amorphous forms of the compounds of Formula (I) (free base). The pharmaceutical compositions of the present disclosure, such as those set forth herein, may act to stabilize the amorphous forms of the compounds of Formula (I), which tend to be unstable and have a tendency to crystallize. Accordingly, the pharmaceutical compositions can be used to stabilize and deliver these amorphous forms to subjects in need of treatment, e.g., for the treatment of a condition or disease associate with a serotonin 5-$HT_2$ receptor.

Salt Forms

Also disclosed herein is a pharmaceutically acceptable salt of the compound of Formula (I), or a pharmaceutically acceptable polymorph, stereoisomer, or solvate thereof. The acid used to form the pharmaceutically acceptable salt of the compound of Formula (I) may be a monoacid, a diacid, a triacid, a tetraacid, or may contain a higher number of acid groups. The acid groups may be, e.g., a carboxylic acid, a sulfonic acid, a phosphonic acid, or other acidic moieties containing at least one replaceable hydrogen atom. Examples of acids for use in the preparation of the pharmaceutically acceptable (acid addition) salts disclosed herein include, but are not limited to, acetic acid, 2,2-dichloroacetic acid, phenylacetic acid, acylated amino acids, alginic acid, ascorbic acid, L-aspartic acid, sulfonic acids (e.g., benzenesulfonic acid, camphorsulfonic acid, (+)-(1S)-camphor-10-sulfonic acid, ethane-1,2-disulfonic acid, ethanesulfonic acid, 2-hydroxy-ethanesulfonic acid, methanesulfonic acid, naphthalene-2-sulfonic acid, naphthalene-1,5-disulfonic acid, p-toluenesulfonic acid, ethanedisulfonic acid, etc.), benzoic acids (e.g., benzoic acid, 4-acetamidobenzoic acid, 2-acetoxybenzoic acid, salicylic acid, 4-amino-salicylic acid, gentisic acid, etc.), boric acid, (+)-camphoric acid, cinnamic acid, citric acid, cyclamic acid, cyclohexanesulfamic acid, dodecylsulfuric acid, formic acid, fumaric acid, galactaric acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (−)-D-lactic acid, (±)-DL-lactic acid, lactobionic acid, maleic acid, malic acid, (−)-L-malic acid, (+)-D-malic acid, hydroxymaleic acid, malonic acid, (±)-DL-mandelic acid, isethionic acid, 1-hydroxy-2-naphthoic acid, nicotinic acid, nitric acid, orotic acid, oxalic acid, pamoic acid, perchloric acid, phosphoric acid, L-pyroglutamic acid, saccharic acid, succinic acid, sulfuric acid, sulfamic acid, tannic acid, tartaric acids (e.g., DL-tartaric acid, (+)-L-tartaric acid, (−)-D-tartaric acid), thiocyanic acid, propionic acid, valeric acid, and fatty acids (including fatty mono- and di-acids, e.g., adipic (hexandioic) acid, lauric (dodecanoic) acid, linoleic acid, myristic (tetradecanoic) acid, capric (decanoic) acid, stearic (octadecanoic) acid, oleic acid, caprylic (octanoic) acid, palmitic (hexadecenoic) acid, sebacic acid, undecylenic acid, caproic acid, etc.)

Certain salts are preferred among the list above because they possess physical and pharmaceutical characteristics/properties which make them suitable for pharmaceutical preparation and administration. For example, preferred salt forms of the compounds disclosed herein (e.g., compounds of Formula (I)) are those that possess one or more of the following characteristics: are easy to prepare in high yield with a propensity towards salt formation; are stable and have well-defined physical properties such as crystallinity, lack of polymorphism, and high melting/enthalpy of fusion; have slight or no hygroscopicity; are free flowing, do not cohere/adhere to surfaces, and possess a regular morphology; have acceptable aqueous solubility and rate of dissolution for the intended dosage form; and/or are physiologically acceptable, e.g., do not cause excessive irritation.

Crystallinity

The pharmaceutically acceptable salt of the compound of Formula (I) may be crystalline or amorphous, as determined e.g., by X-ray powder diffraction (XRPD). In some embodiments, the salt of the compound of Formula (I) is amorphous. Amorphous forms typically possess higher aqueous solubility and rates of dissolution compared to their crystalline counterparts, and thus may be well suited for quick acting dosage forms adapted to rapidly release the active agent, such as for orodispersible dosage forms (ODxs), immediate release (IR) dosage forms, and the like. In some embodiments, the salt of the compound of Formula (I) is crystalline. Crystalline forms are advantageous in terms of stability and providing well-defined physical properties, which is desirable for pharmaceutical preparation and administration. The salts of the compound of Formula (I) can be in a stable crystalline or amorphous form. In some embodiments, the pharmaceutically acceptable salt of the compound of Formula (I) has a percent crystallinity of at least 50%, at least 60%, at least 70%, at least 80%, at least 90%, at least 95%, at least 99%, or at least 99.5%, and up to 100%, as determined by XRPD analysis. Preference is given to salt forms with high crystallinity, as determined e.g., by discrete and sharp Bragg diffractions in the X-ray diffractograms.

XRPD analyses can be carried out, e.g., on a Bruker AXS D2 diffractometer using CuKα radiation. The instrument may be equipped with a fine focus X-ray tube. The tube voltage and amperage can be set to 30 kV and 10 mA, respectively, and a θ-θ geometry can be used, using a LynxEye detector from 5-42° 2θ, with a step size of 0.024° 2θ and a collection time of 0.1 seconds per step.

In terms of pharmaceutical production processes, advantageous salt forms of the compounds of Formula (I) are those that readily afford a solid material, either a crystalline solid or an amorphous solid, in acceptable yield without proceeding via an oil, and with favorable volume factors, making them suitable for mass production.

Salts forms of the compound of Formula (I) can exist in different polymorphs (i.e., forms having a different crystal structure), however, preferred salt forms of the present disclosure are those which can be generated as a single crystalline form or single polymorph (including a single amorphous form), as determined by XRPD and/or differential scanning calorimetry (DSC). It is also generally desirable for the salts to be free flowing, not cohere/adhere to surfaces, and possess a regular morphology.

Chemical/Solid-State Stability

In some embodiments, the pharmaceutically acceptable salt of the compound of Formula (I) has a melt onset of from about 90° C., from about 100° C., from about 110° C., from about 120° C., from about 130° C., from about 140° C., from about 150° C., from about 160° C., from about 170° C., from about 180° C., from about 190° C., and up to about 250° C., up to about 240° C., up to about 230° C., up to about 225° C., up to about 210° C., up to about 200° C., as determined by DSC.

Pharmaceutically acceptable salts of the compound of Formula (I) may also be characterized as non-hygroscopic or slightly hygroscopic, preferably non-hygroscopic. The hygroscopicity may be measured herein by performing a moisture adsorption-desorption isotherm using a dynamic vapor sorption (DVS) analyzer with a starting exposure of 40% relative humidity (RH), increasing humidity up to 90% RH, decreasing humidity to 0% RH, increasing humidity to 90% RH, decreasing humidity to 0% RH, and finally increasing the humidity back to the starting 40% RH, and classified according to the following:

non-hygroscopic: <0.2%; slightly hygroscopic: ≥0.2% and <2%; hygroscopic: ≥2% and <15%; very hygroscopic: ≥15%; deliquescent: sufficient water is absorbed to form a liquid; all values measured as weight increase (w/w due to acquisition of water) at >90% RH and 25° C.

In some embodiments, the pharmaceutically acceptable salt of the compound of Formula (I) has a weight increase at >90% RH of less than 1% w/w, less than 0.8% w/w, less than 0.6% w/w, less than 0.5% w/w, less than 0.4% w/w, less than 0.3% w/w, less than 0.2% w/w, less than 0.1% w/w, less than 0.08% w/w, less than 0.06% w/w, less than 0.05% w/w, less than 0.02% w/w, as determined by DVS.

Dry powder samples of free base and salts can be maintained/stored in open or closed environments, such as in open or closed flasks/vials, under ambient or stress conditions e.g., 25° C./90+% RH, 40° C./75% RH, etc. without appreciable degradation or physical changes (e.g., changed forms, deliquesced, etc.). For example, dry powder samples of free base and salts forms disclosed herein may have a purity or form change of less than 10%, less than 5%, less than 1%, when stored under ambient conditions or stress conditions (e.g., increased temperature, e.g., 40° C., and/or humidity).

Solution-phase samples of the free base and salts can be maintained/stored in open or closed environments, such as in open or closed flasks/vials, under ambient or stress conditions e.g., 25° C./90+% RH, 40° C./75% RH, etc. without appreciable degradation. Thus, in some embodiments, the present disclosure provides stable solution-phase compositions of salts of the compounds of Formula (I) (e.g., stable solvates of salt forms of compounds of Formula (I) which are in solvated form, preferably fully solvated form), which can be stored as a solution, such as in the form of an aqueous solution, an organic solvent solution, or a mixed aqueous-organic solvent solution, for prolonged periods of time without appreciable degradation or physical changes, such as oiling out of solution. Solvents which can be used to form the solution-phase compositions can be any one or more solvents set forth herein, e.g., water, ethanol, etc. In some embodiments, the solution-phase composition is an aqueous solution-phase composition comprising the pharmaceutically acceptable salt of the compound of Formula (I) solvated with water. The identification of stable solution-phase compositions of compounds of Formula (I) and their salts is advantageous at least because such compositions do not require use immediately after being prepared, such as within 5 minutes, within 4 minutes, within 3 minutes, within 2 minutes, within 1 minute, within 45 seconds, within 30 seconds, within 15 seconds, within 10 seconds of being prepared. Instead, the stable solution-phase compositions of the compounds of Formula (I) and salts thereof described herein can be prepared in advance, when desired, optionally stored, and can be administered hours, days, or even weeks after being prepared, without materially effecting efficacy, e.g., without appreciable degradation of the psilocin or psilocin-type active.

In some embodiments, aqueous solutions formed from the pharmaceutically acceptable salt of the compound of Formula (I) is characterized by increased stability compared to aqueous solutions that are prepared from the compound of Formula (I) (free base) but are otherwise substantially the same. For example, the pharmaceutically acceptable salt of the compound of Formula (I) may be at least 5%, at least 10%, at least 15%, at least 20%, at least 25%, at least 30%, at least 35%, at least 40%, at least 45%, at least 50%, at least 55%, at least 60%, at least 65%, at least 70% more stable in aqueous solution subjected to 40° C. for 24 hours, with or without the presence of metal ions, in terms of % (active) remaining, compared to aqueous solutions prepared with the compound of Formula (I) (free base) but are otherwise substantially the same. Such improved stability behavior can also be found in pharmaceutical compositions of the present disclosure.

Samples can be pulled at pre-determined time-points and analyzed for stability, changes in form, etc. for example, by $^{1}$H NMR, XRPD, HPLC with UV-visible multiple wavelength detector, UPLC, etc.

Physiologically Acceptability

Suitable salt forms of the compounds of Formula (I) are physiologically acceptable. Accordingly, preferred addition salts of the compound of Formula (I) are those formed with an organic acid, preferably an organic acid with a medium or mild acidity, for example an organic acid with a p$K_a$ in water of no less than −3.0, no less than −2.0, no less than −1.0, no less than 0, no less than 1.0, no less than 1.5, no less than 2.0, no less than 2.5, no less than 3.0, no less than 3.5, no less than 4.0, no less than 4.5, for example, from 3.0 to 6.5. Further, it may also be desirable to use acid addition salts that impart a pleasant taste profile (e.g., sweet, citrus flavored, etc.), although poor tasting salt forms (e.g., bitter, harsh, etc.) may still be acceptable depending on, for example, the route of administration and the optional use of taste masking agents such as sweetening agents, flavoring agents, etc.

Solubility

The aqueous solubility of the salt forms of the compounds of Formula (I) can be determined by equilibrating excess solid with 1 mL of water for 24 hours at 22° C. A 200 uL aliquot can be centrifuged at 15,000 rpm for 15 minutes. The supernatant can be analyzed by HPLC and the solubility can be expressed as its free base equivalent (mg FB/mL). For example, pharmaceutically acceptable salts of compound of Formula (I) can be prepared and the solubility and solution pH can be measured.

In some embodiments, the pharmaceutically acceptable salt of the compound of Formula (I) has a water solubility at 22° C. of from about 1 mg/mL to about 400 mg/mL. In some embodiments, the pharmaceutically acceptable salt of the compound of Formula (I) has a water solubility of from about 1 mg/mL, from about 2 mg/mL, from about 3 mg/mL, from about 5 mg/mL, from about 10 mg/mL, from about 20 mg/mL, from about 30 mg/mL, from about 40 mg/mL, from about 50 mg/mL, from about 60 mg/mL, from about 70 mg/mL, from about 80 mg/mL, from about 90 mg/mL, from about 100 mg/mL, from about 110 mg/mL, from about 120 mg/mL, from about 130 mg/mL, from about 140 mg/mL, from about 150 mg/mL, and up to about 400 mg/mL, up to about 380 mg/mL, up to about 360 mg/mL, up to about 340 mg/mL, up to about 320 mg/mL, up to about 300 mg/mL, up to about 280 mg/mL, up to about 260 mg/mL, up to about 250 mg/mL. Several salt forms of the compounds described herein can exhibit the above solubilities, yielding a final water pH approximately between pH 3 to 6 without gelling.

In some embodiments, the salt of the compound of Formula (I) has a water solubility from about 200 mg/mL to about 400 mg/mL. In some embodiments, the salt of the compound of Formula (I) has a water solubility from about 150 mg/mL to about 250 mg/mL. In some embodiments, the salt of the compound of Formula (I) has a water solubility of greater than about 1 mg/mL, 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 110 mg/mL, 120 mg/mL, 130 mg/mL, 140 mg/mL, or 150 mg/mL.

In some embodiments, salt forms of the compounds of Formula (I) possess dissolution rates which enable rapid systemic absorption for quick therapeutic onset and a short duration of drug action. In some embodiments, the salt of the compound of Formula (I) is capable of dissolution in an aqueous medium below about pH 7.5, such as from pH 1-7, from pH 3-7, or from pH 4-7.

In some embodiments, the pharmaceutically acceptable salt of the compound of Formula (I) is a benzenesulfonate salt, a tartrate salt, a hemi-fumarate salt, an acetate salt, a citrate salt, a malonate salt, a fumarate salt, a succinate salt, an oxalate salt, a benzoate salt, a salicylate salt, an ascorbate salt, a hydrochloride salt, a maleate salt, a malate salt, a methanesulfonate salt, a toluenesulfonate salt, a glucuronate salt, or a glutarate salt of the compound of Formula (I). In some embodiments, the pharmaceutically acceptable salt of the compound of Formula (I) is a salt formed from a sulfonic acid (e.g., benzenesulfonic acid, camphorsulfonic acid, (+)-(1 S)-camphor-10-sulfonic acid, ethane-1,2-disulfonic acid, ethanesulfonic acid, 2-hydroxy-ethanesulfonic acid, methanesulfonic acid, naphthalene-2-sulfonic acid, naphthalene-1,5-disulfonic acid, p-toluenesulfonic acid, ethanedisulfonic acid, etc.). In some embodiments, the pharmaceutically acceptable salt of the compound of Formula (I) is a salt formed from a benzoic acid (e.g., benzoic acid, 4-acetamidobenzoic acid, 2-acetoxybenzoic acid, salicylic acid, 4-amino-salicylic acid, etc.).

In some embodiments, the pharmaceutically acceptable salt of the compound of Formula (I) is a benzenesulfonate salt. In some embodiments, the pharmaceutically acceptable salt of the compound of Formula (I) is a tartrate salt. In some embodiments, the pharmaceutically acceptable salt of the compound of Formula (I) is a hemi-fumarate salt. In some embodiments, the pharmaceutically acceptable salt of the compound of Formula (I) is an acetate salt. In some embodiments, the pharmaceutically acceptable salt of the compound of Formula (I) is a citrate salt. In some embodiments, the pharmaceutically acceptable salt of the compound of Formula (I) is a malonate salt. In some embodiments, the pharmaceutically acceptable salt of the compound of Formula (I) is a fumarate salt. In some embodiments, the pharmaceutically acceptable salt of the compound of Formula (I) is a succinate salt. In some embodiments, the pharmaceutically acceptable salt of the compound of Formula (I) is an oxalate salt. In some embodiments, the pharmaceutically acceptable salt of the compound of Formula (I) is a benzoate salt. In some embodiments, the pharmaceutically acceptable salt of the compound of Formula (I) is a salicylate salt. In some embodiments, the pharmaceutically acceptable salt of the compound of Formula (I) is an ascorbate salt. In some embodiments, the pharmaceutically acceptable salt of the compound of Formula (I) is a hydrochloride salt. In some embodiments, the pharmaceutically acceptable salt of the compound of Formula (I) is a maleate salt. In some embodiments, the pharmaceutically acceptable salt of the compound of Formula (I) is a malate salt. In some embodiments, the pharmaceutically acceptable salt of the compound of Formula (I) is a methanesulfonate salt. In some embodiments, the pharmaceutically acceptable salt of the compound of Formula (I) is a toluenesulfonate salt. In some embodiments, the pharmaceutically acceptable salt of the compound of Formula (I) is a glucuronate salt. In some embodiments, the pharmaceutically acceptable salt of the compound of Formula (I) is a glutarate salt.

In some embodiments, the pharmaceutically acceptable salt of the compound of Formula (I) is a benzenesulfonate salt, a tartrate salt, a hemi-fumarate salt, an acetate salt, a citrate salt, a malonate salt, a fumarate salt, a succinate salt, an oxalate salt, a benzoate salt, or a salicylate salt of the compound of Formula (I), with a benzenesulfonate salt, a succinate salt, or a benzoate salt of the compound of Formula (I) being preferred, and with a benzenesulfonate salt or a benzoate salt of the compound of Formula (I) being particularly preferred.

Exemplary pharmaceutically acceptable salt forms (i.e., addition salt forms) of the above-identified compounds are provided in Table 2.

TABLE 2

Exemplary pharmaceutically acceptable salts of compounds of Formula (I)

| Salt form identifier | Salt type of compound |
|---|---|
| I-1a | Benzenesulfonate of I-1 |
| I-1b | Tartrate of I-1 |
| I-1c | Hemi-fumarate of I-1 |
| I-1d | Acetate of I-1 |
| I-1e | Citrate of I-1 |
| I-1f | Malonate of I-1 |
| I-1g | Fumarate of I-1 |
| I-1h | Succinate of I-1 |
| I-1i | Oxalate of I-1 |
| I-1j | Benzoate of I-1 |
| I-1k | Salicylate of I-1 |
| I-2a | Benzenesulfonate of I-2 |
| I-2b | Tartrate of I-2 |
| I-2c | Hemi-fumarate of I-2 |
| I-2d | Acetate of I-2 |
| I-2e | Citrate of I-2 |
| I-2f | Malonate of I-2 |
| I-2g | Fumarate of I-2 |
| I-2h | Succinate of I-2 |

TABLE 2-continued

| Exemplary pharmaceutically acceptable salts of compounds of Formula (I) | |
|---|---|
| Salt form identifier | Salt type of compound |
| I-2i | Oxalate of I-2 |
| I-2j | Benzoate of I-2 |
| I-2k | Salicylate of I-2 |
| I-3a | Benzenesulfonate of I-3 |
| I-3b | Tartrate of I-3 |
| I-3c | Hemi-fumarate of I-3 |
| I-3d | Acetate of I-3 |
| I-3e | Citrate of I-3 |
| I-3f | Malonate of I-3 |
| I-3g | Fumarate of I-3 |
| I-3h | Succinate of I-3 |
| I-3i | Oxalate of I-3 |
| I-3j | Benzoate of I-3 |
| I-3k | Salicylate of I-3 |
| I-4a | Benzenesulfonate of I-4 |
| I-4b | Tartrate of I-4 |
| I-4c | Hemi-fumarate of I-4 |
| I-4d | Acetate of I-4 |
| I-4e | Citrate of I-4 |
| I-4f | Malonate of I-4 |
| I-4g | Fumarate of I-4 |
| I-4h | Succinate of I-4 |
| I-4i | Oxalate of I-4 |
| I-4j | Benzoate of I-4 |
| I-4k | Salicylate of I-4 |
| I-5a | Benzenesulfonate of I-5 |
| I-5b | Tartrate of I-5 |
| I-5c | Hemi-fumarate of I-5 |
| I-5d | Acetate of I-5 |
| I-5e | Citrate of I-5 |
| I-5f | Malonate of I-5 |
| I-5g | Fumarate of I-5 |
| I-5h | Succinate of I-5 |
| I-5i | Oxalate of I-5 |
| I-5j | Benzoate of I-5 |
| I-5k | Salicylate of I-5 |
| I-6a | Benzenesulfonate of I-6 |
| I-6b | Tartrate of I-6 |
| I-6c | Hemi-fumarate of I-6 |
| I-6d | Acetate of I-6 |
| I-6e | Citrate of I-6 |
| I-6f | Malonate of I-6 |
| I-6g | Fumarate of I-6 |
| I-6h | Succinate of I-6 |
| I-6i | Oxalate of I-6 |
| I-6j | Benzoate of I-6 |
| I-6k | Salicylate of I-6 |
| I-7a | Benzenesulfonate of I-7 |
| I-7b | Tartrate of I-7 |
| I-7c | Hemi-fumarate of I-7 |
| I-7d | Acetate of I-7 |
| I-7e | Citrate of I-7 |
| I-7f | Malonate of I-7 |
| I-7g | Fumarate of I-7 |
| I-7h | Succinate of I-7 |
| I-7i | Oxalate of I-7 |
| I-7j | Benzoate of I-7 |
| I-7k | Salicylate of I-7 |
| I-8a | Benzenesulfonate of I-8 |
| I-8b | Tartrate of I-8 |
| I-8c | Hemi-fumarate of I-8 |
| I-8d | Acetate of I-8 |
| I-8e | Citrate of I-8 |
| I-8f | Malonate of I-8 |
| I-8g | Fumarate of I-8 |
| I-8h | Succinate of I-8 |
| I-8i | Oxalate of I-8 |
| I-8j | Benzoate of I-8 |
| I-8k | Salicylate of I-8 |
| I-9a | Benzenesulfonate of I-9 |
| I-9b | Tartrate of I-9 |
| I-9c | Hemi-fumarate of I-9 |
| I-9d | Acetate of I-9 |
| I-9e | Citrate of I-9 |
| I-9f | Malonate of I-9 |

TABLE 2-continued

| Exemplary pharmaceutically acceptable salts of compounds of Formula (I) | |
|---|---|
| Salt form identifier | Salt type of compound |
| I-9g | Fumarate of I-9 |
| I-9h | Succinate of I-9 |
| I-9i | Oxalate of I-9 |
| I-9j | Benzoate of I-9 |
| I-9k | Salicylate of I-9 |
| I-10a | Benzenesulfonate of I-10 |
| I-10b | Tartrate of I-10 |
| I-10c | Hemi-fumarate of I-10 |
| I-10d | Acetate of I-10 |
| I-10e | Citrate of I-10 |
| I-10f | Malonate of I-10 |
| I-10g | Fumarate of I-10 |
| I-10h | Succinate of I-10 |
| I-10i | Oxalate of I-10 |
| I-10j | Benzoate of I-10 |
| I-10k | Salicylate of I-10 |

In some embodiments, the pharmaceutically acceptable salt is a benzenesulfonate salt of 3-(2-(bis(methyl-$d_3$)amino)ethyl-1,1,2,2-$d_4$)-1H-indol-4-ol (I-3a). In some embodiments, salt I-3a is in a crystalline solid form characterized by an X-ray powder diffraction pattern containing at least three characteristic peaks at diffraction angles (2θ±0.20) selected from the group consisting of 7.0230, 7.7670, 11.8220, 12.5500, 12.8600, 13.9940, 15.5210, 18.4360, 19.5030, 20.7600, 21.0700, 22.0070, 22.7450, 23.3400, 24.1870, 25.5320, 26.8800, 27.8560, 28.1630, 31.2670, 33.0240, 35.0300, 36.8350, 39.3120, 40.5450, and 40.9880, as determined by XRPD using a CuKα radiation source, for example, as shown in FIGS. 63A-63D (pattern 1).

In some embodiments, the pharmaceutically acceptable salt is a benzenesulfonate salt of 3-(2-(dimethylamino)ethyl)-1H-indol-4-ol (I-7a). In some embodiments, salt I-7a is in a crystalline solid form characterized by an X-ray powder diffraction pattern containing at least three characteristic peaks at diffraction angles (2θ=+0.20) selected from the group consisting of 7.0020, 7.7330, 11.7680, 12.5160, 12.8820, 13.5460, 13.9680, 14.7880, 15.2250, 15.4740, 18.3700, 19.7370, 20.703°, 21.050°, 21.873°, 21.982°, 22.315°, 22.639°, 23.282°, 23.775°, 24.125°, 25.193°, 25.475°, 25.931°, 26.813°, 27.778°, 28.127°, 30.866°, 31.207°, 32.941°, 33.222°, 33.698°, 36.803°, 38.668°, and 39.289°, as determined by XRPD using a CuKα radiation source, for example, as shown in FIGS. 3A-3B (pattern 1).

Figure 78A:
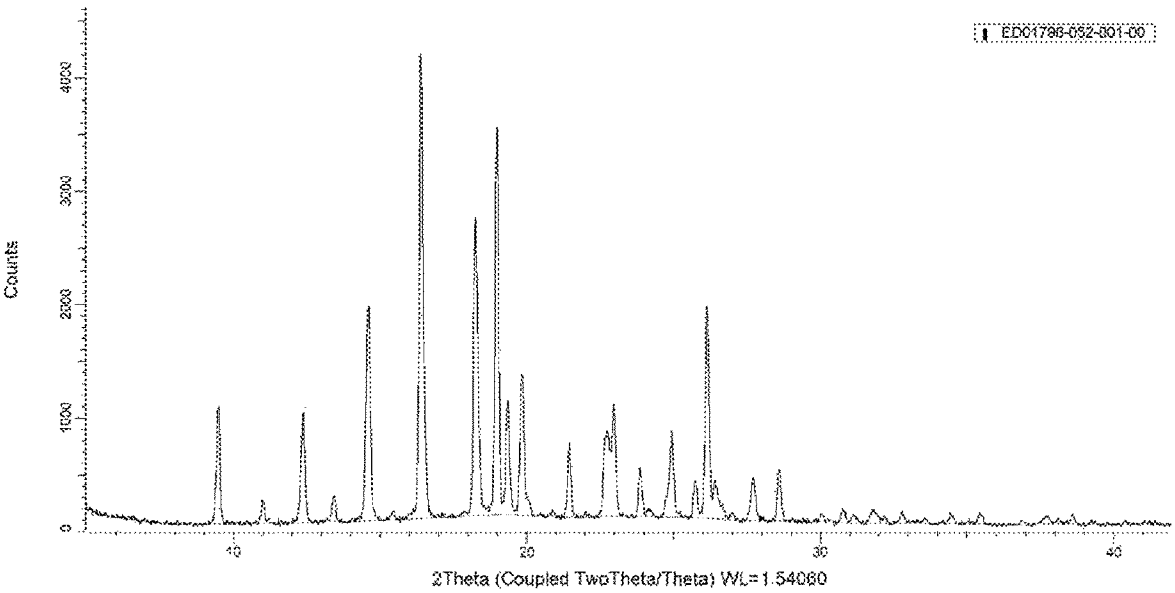
FIGS. 78A-78E shows the XRPD pattern of I-3j (pattern 1) (FIG. 78A), a zoomed in and annotated version (FIG. 78B), a comparison of the XRPD pattern of I-3j (pattern 1) to that of the I-7j seed (FIG. 78C), a single crystal X-ray structure of I-3j (pattern 1) (FIGS. 78D-78E)
Figure 78B:
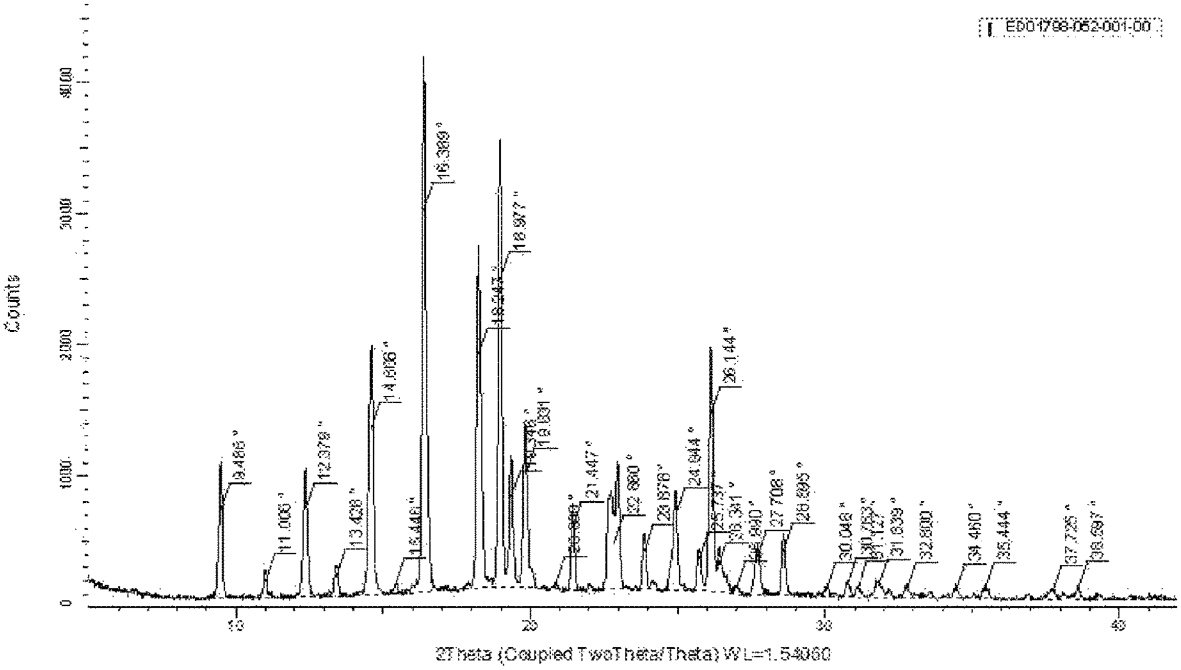
Figure 78C:
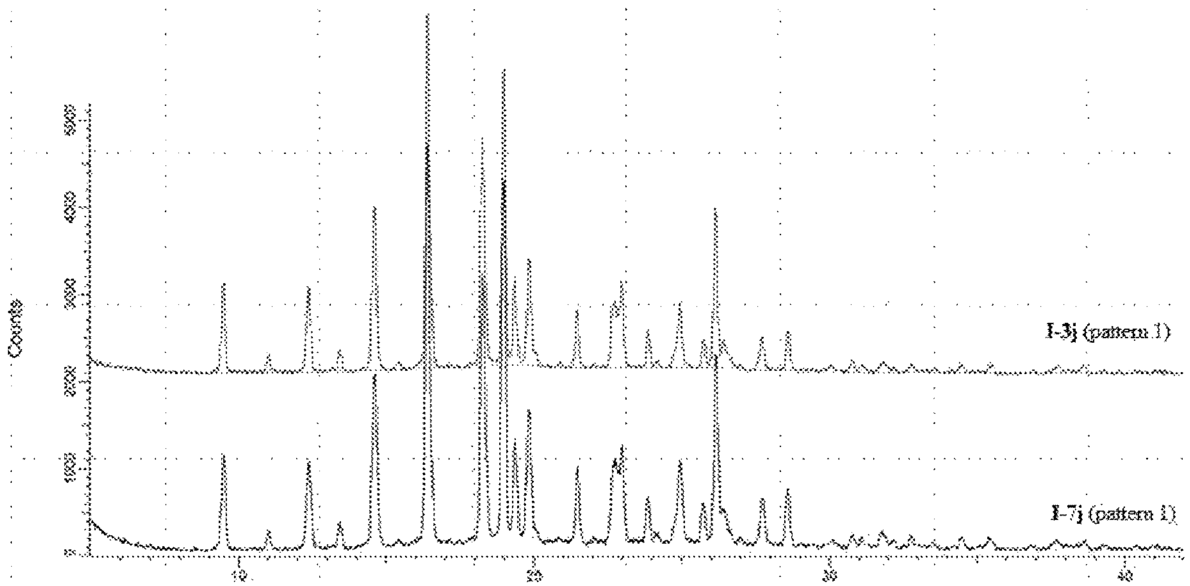

In some embodiments, the pharmaceutically acceptable salt is a benzoate salt of 3-(2-(bis(methyl-$d_3$)amino)ethyl-1,1,2,2-$d_4$)-1H-indol-4-ol (I-3j). In some embodiments, salt I-3j is in a crystalline solid form characterized by an X-ray powder diffraction pattern containing at least three characteristic peaks at diffraction angles (2θ±0.2°) selected from the group consisting of 9.486°, 11.006°, 12.379°, 13.428°, 14.608°, 15.446°, 16.389°, 18.247°, 18.977°, 19.346°, 19.831°, 20.868°, 21.447°, 22.860°, 23.878°, 24.944°, 25.737°, 26.144°, 26.341°, 26.990°, 27.708°, 28.595°, 30.048°, 30.763°, 31.127°, 31.839°, 32.800°, 34.460°, 35.444°, 37.725°, and 38.597°, as determined by XRPD using a CuKα radiation source, for example, as shown in FIGS. 78A-78C (pattern 1).

Figure 53A:
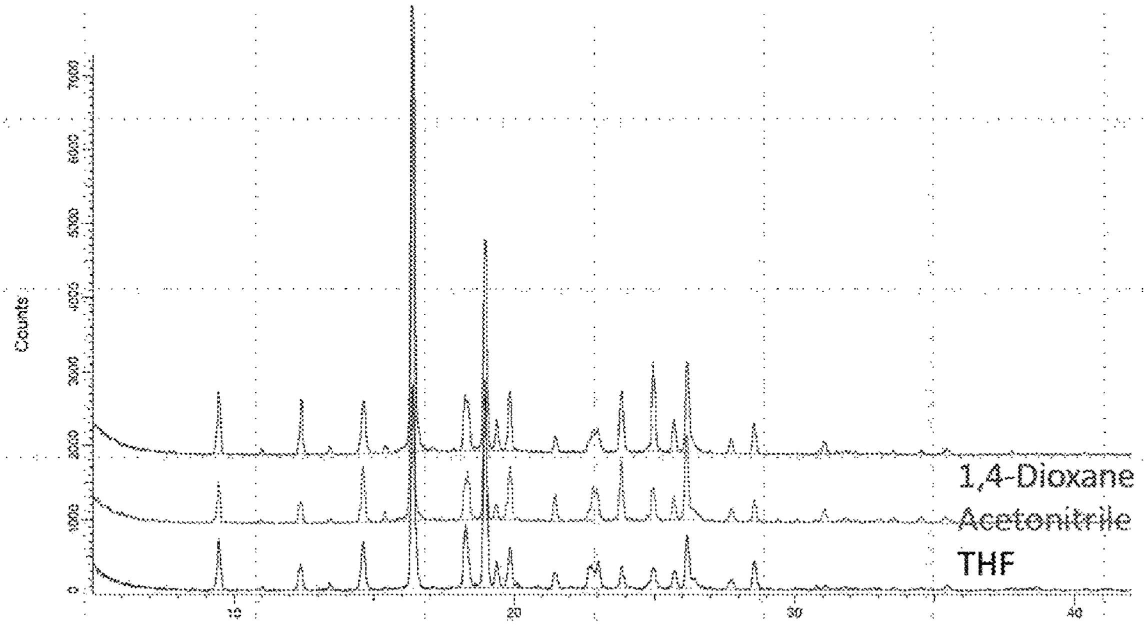
FIGS. 53A-53B show the XRPD pattern of I-7j (polymorph of pattern 1), with FIG. 53B being zoomed in and annotated.
Figure 53B:
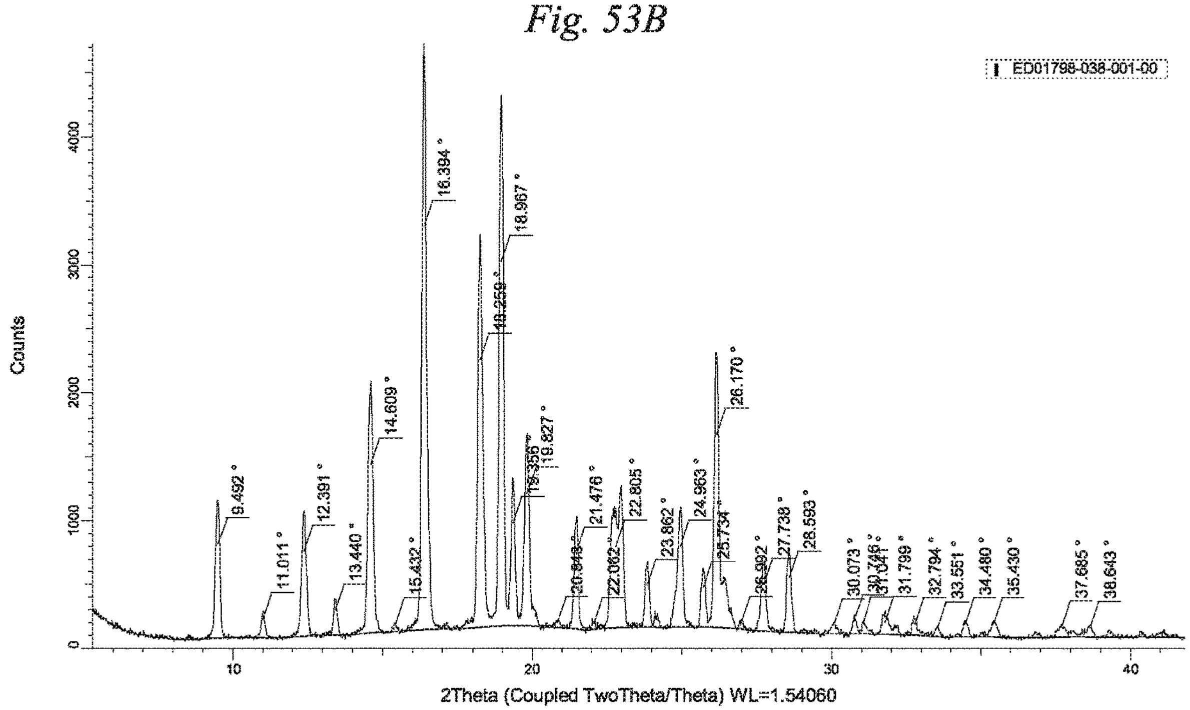

In some embodiments, the pharmaceutically acceptable salt is a benzoate salt of 3-(2-(dimethylamino)ethyl)-1H-indol-4-ol (I-7j). In some embodiments, salt I-7j is in a crystalline solid form characterized by an X-ray powder diffraction pattern containing at least three characteristic peaks at diffraction angles (2θ=0.2°) selected from the group consisting of 9.492°, 11.0110, 12.391°, 13.440°, 14.609°, 15.432°, 16.394°, 18.259°, 18.967°, 19.356°, 19.827°, 20.843°, 21.476°, 22.062°, 22.805°, 23.862°, 24.963°, 25.734°, 26.170°, 26.992°, 27.738°, 28.593°, 30.073°, 30.746°, 31.041°, 31.799°, 32.794°, 33.551°, 34.480°, 35.430°, 37.685°, and 38.643°, as determined by XRPD using a CuKα radiation source, for example, as shown in FIGS. 53A-53B (pattern 1).

In some embodiments, the pharmaceutically acceptable salt is a citrate salt of 3-(2-(bis(methyl-$d_3$)amino)ethyl-1,1,2,2-$d_4$)-1H-indol-4-ol (I-3e). In some embodiments, salt I-3e is in the form of an amorphous solid as characterized by an X-ray powder diffraction (XRPD).

Figure 37:
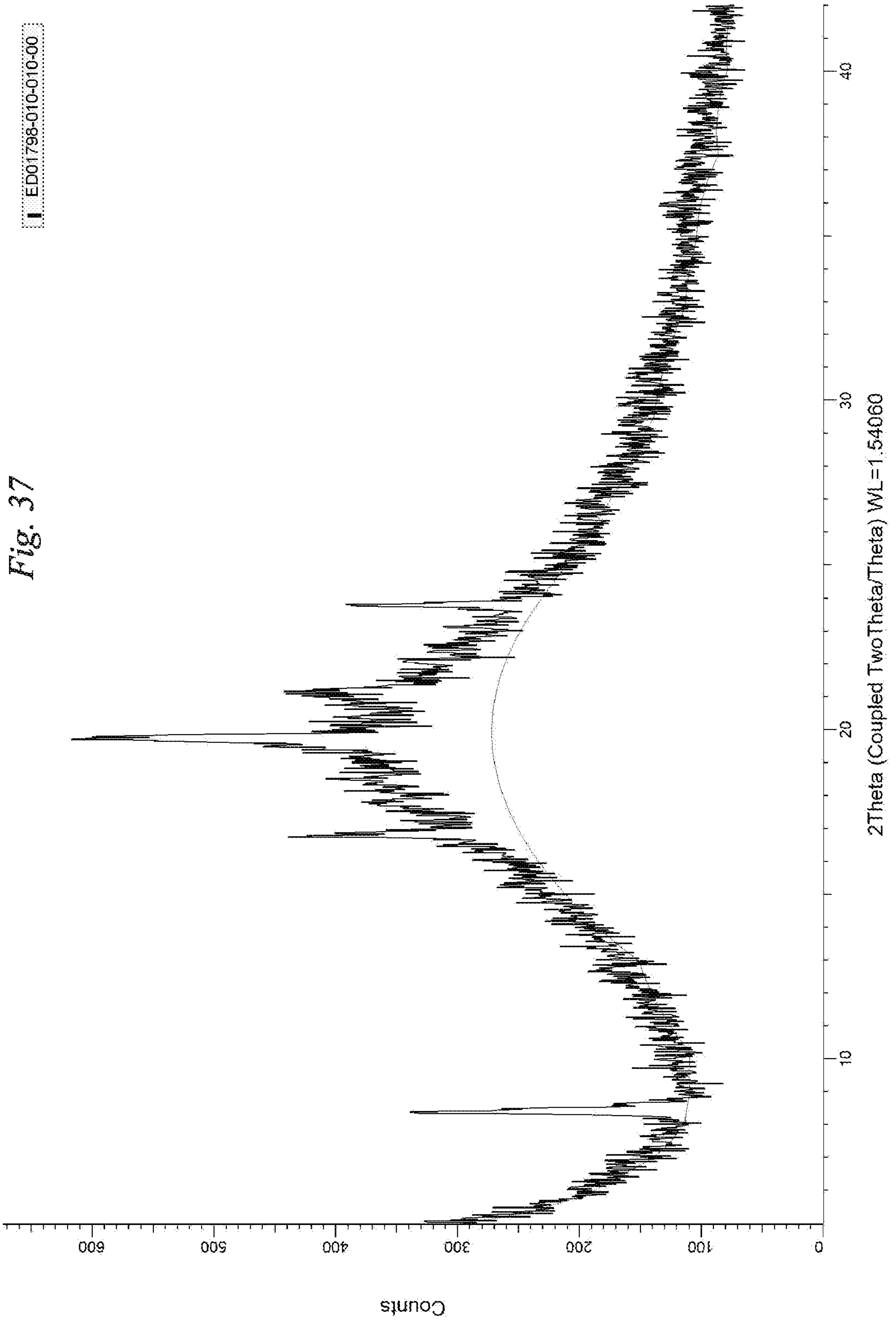
FIG. 37 shows the XRPD pattern of I-7e (amorphous)

In some embodiments, the pharmaceutically acceptable salt is a citrate salt of 3-(2-(dimethylamino)ethyl)-1H-indol-4-ol (I-7e). In some embodiments, salt I-7e is in the form of an amorphous solid as characterized by an X-ray powder diffraction (XRPD), for example, as shown in FIG. 37.

Figure 69A:
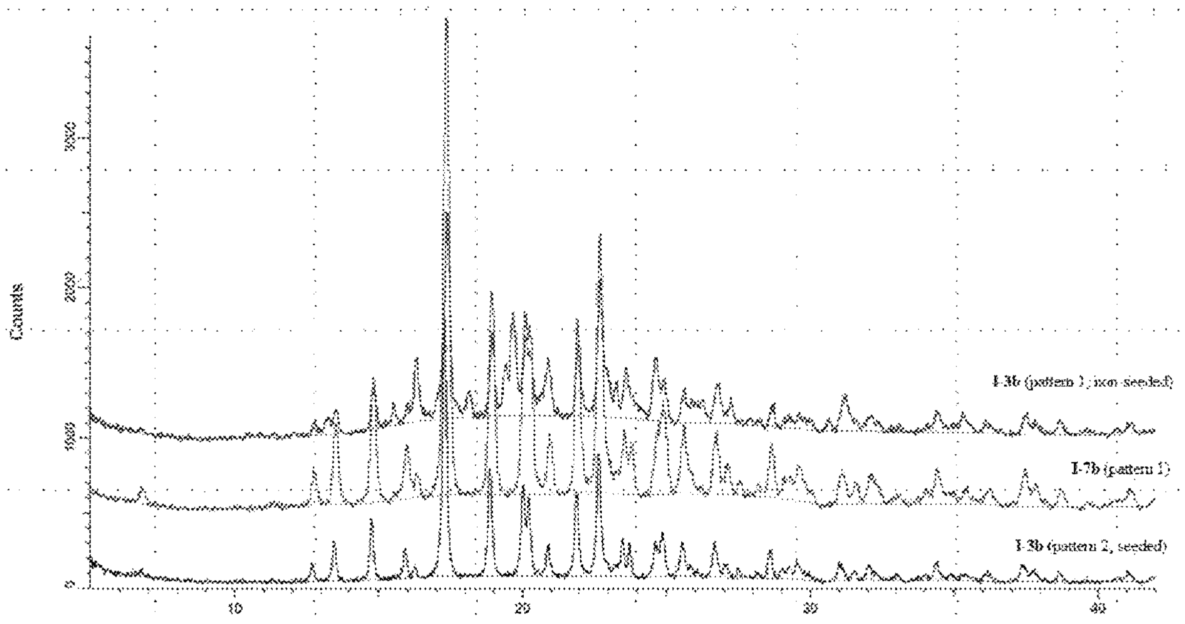
FIGS. 69A-69B show the XRPD pattern of I-3b (pattern 2, obtained from seeded experiments), compared to the seeds of crystalline polymorph of I-7b of pattern 1, and the crystalline polymorph of I-3b of pattern 1 obtained from the non-seeded experiments (FIG. 69A), and the zoomed in and annotated XRPD of I-3b (pattern 2, obtained from seeded experiments)(FIG. 69B)
Figure 69B:
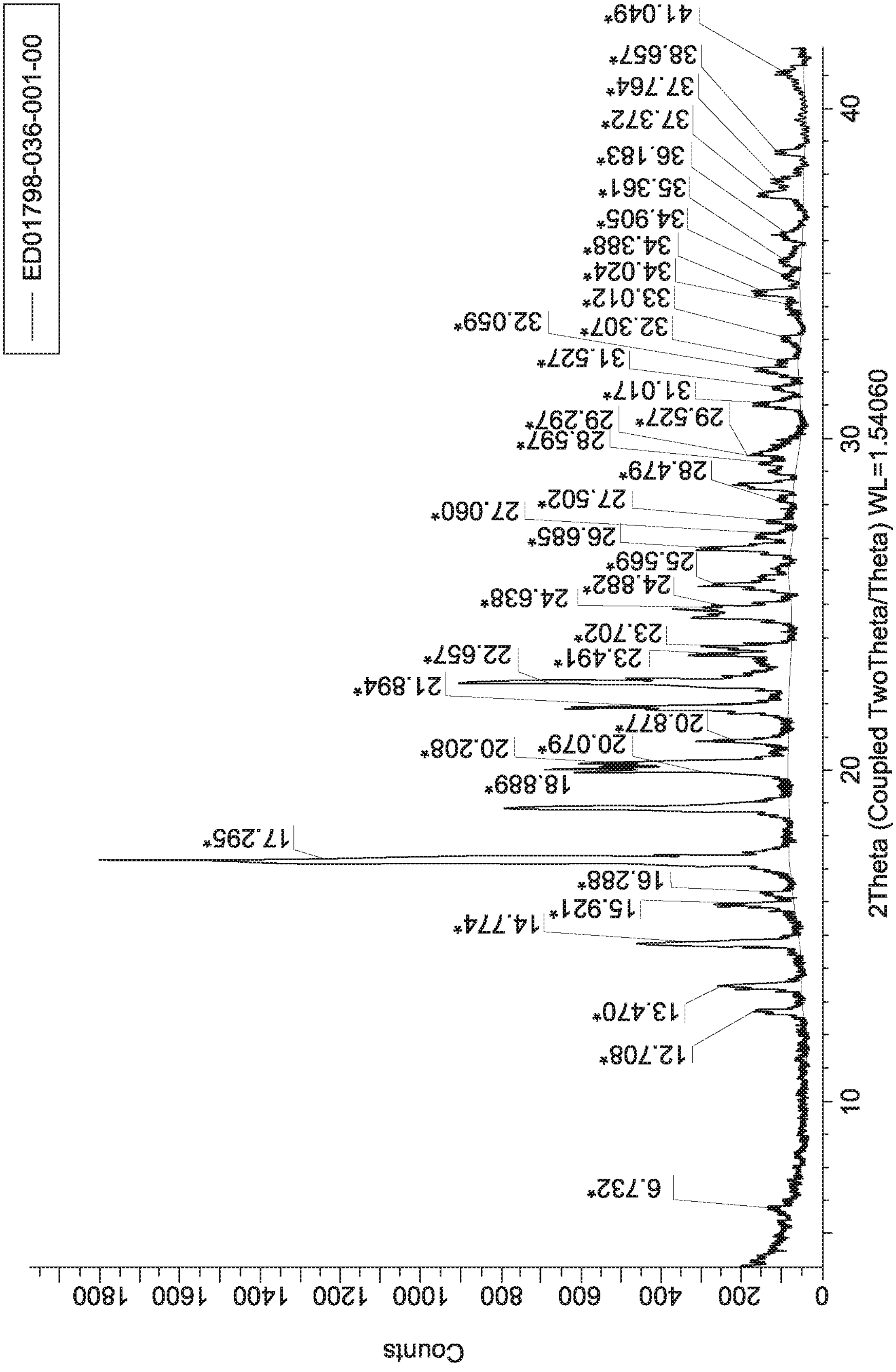

In some embodiments, the pharmaceutically acceptable salt is a tartrate salt of 3-(2-(bis(methyl-$d_3$)amino)ethyl-1,1,2,2-$d_4$)-1H-indol-4-ol (I-3b). In some embodiments, salt I-3b is in a crystalline solid form characterized by an X-ray powder diffraction pattern containing at least three characteristic peaks at diffraction angles (2θ±0.2°) selected from the group consisting of 6.732°, 12.708°, 13.470°, 14.774°, 15.921°, 16.268°, 17.295°, 18.869°, 20.079°, 20.208°, 20.877°, 21.894°, 22.657°, 23.491°, 23.702°, 24.636°, 24.882°, 25.569°, 26.685°, 27.060°, 27.502°, 28.179°, 28.597°, 29.035°, 29.257°, 29.527°, 31.017°, 31.527°, 32.059°, 32.307°, 33.012°, 34.024°, 34.388°, 34.905°, 35.361°, 36.183°, 37.372°, 37.764°, 38.657°, 41.049°, as determined by XRPD using a CuKα radiation source, for example, as shown in FIGS. 69A-69B (pattern 2).

Figure 12:
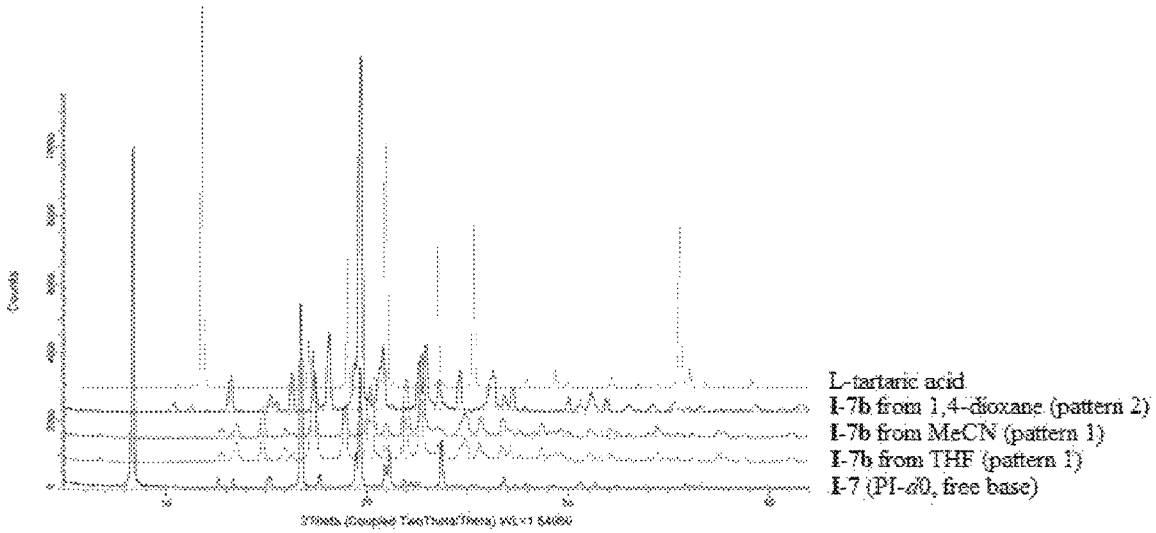
FIG. 12 shows the XRPD pattern of two different crystalline polymorphs of I-7b, pattern 1 (made from acetonitrile or THF), and pattern 2 (made from 1,4-dioxane)

In some embodiments, the pharmaceutically acceptable salt is a tartrate salt of 3-(2-(dimethylamino)ethyl)-1H-indol-4-ol (I-7b). In some embodiments, salt I-7b is in a crystalline solid form characterized by an X-ray powder diffraction pattern containing at least three characteristic peaks at diffraction angles (2θ±0.2°) selected from the group consisting of 6.798°, 11.360°, 12.764°, 13.535°, 14.837°, 15.973°, 16.351°, 17.367°, 18.937°, 20.168°, 20.929°, 21.946°, 22.719°, 23.604°, 23.814°, 24.874°, 25.609°, 26.745°, 27.111°, 27.558°, 28.653°, 29.630°, 31.129°, 31.567°, 32.180°, 33.073°, 34.096°, 34.460°, 36.226°, 37.497°, 38.727°, and 41.126°, as determined by XRPD using a CuKα radiation source, for example, as shown in FIG. 12 (pattern 1). In some embodiments, salt I-7b is in a crystalline solid form of pattern 2 characterized by an X-ray powder diffraction as shown in FIG. 12.

Figure 28:
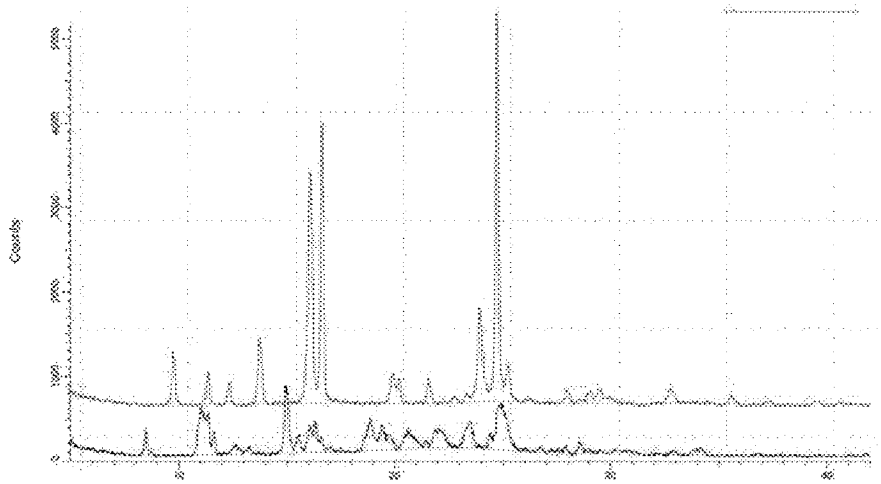
FIG. 28 shows the XRPD pattern of I-7c pre-DVS (polymorph of pattern 5, obtained from scale-up using 1 eq fumaric acid in acetonitrile) and post-DVS (pattern 6)

In some embodiments, the pharmaceutically acceptable salt is a hemi-fumarate salt of 3-(2-(dimethylamino)ethyl)-1H-indol-4-ol (I-7c). In some embodiments, salt I-7c is in a crystalline solid form characterized by an X-ray powder diffraction pattern containing at least three characteristic peaks at diffraction angles (2θ±0.2°) selected from the group consisting of 8.483°, 8.733°, 11.080°, 11.351°, 11.622°, 12.615°, 13.258, 14.977°, 15.557°, 16.089°, 16.319°, 16.606°, 17.013°, 18.928°, 18.884°, 19.429°, 19.734°, 20.643°, 21.484°, 22.067°, 23.433°, 24.466°, 24.885°, 26.740°, 27.900°, 28.557°, 29.523°, 32.888°, 34.183°, and 36.808°, as determined by XRPD using a CuKα radiation source, for example, as shown in FIG. 28 (pattern 5).

Without being bound to any particular theory, it is believed that the novel salts of the compounds of Formula (I) are stable and have a faster/quicker therapeutic onset, a shorter duration of drug action (i.e., short duration of therapeutic effect), and less variability in exposures than psilocybin-based drugs (e.g., psilocybin).

In some embodiments, the pharmaceutically acceptable salt of the compound of Formula (I) is a fatty acid salt. The fatty acid used to make the fatty acid salt of the compound of Formula (I) may be a fatty monoacid or a fatty diacid, and may contain a fatty hydrocarbon portion made up of hydrogen and anywhere from 4, from 6, from 8, from 10, from 12, from 14, from 16, and up to 26, up to 24, up to 22, up to 20, up to 18 carbon atoms, which may be fully saturated or partially unsaturated. In some embodiments, the pharmaceutically acceptable salt of the compound of Formula (I) is an adipate salt, a laurate salt, a linoleate salt, a myristate salt, a caprate salt, a stearate salt, an oleate salt, a caprylate salt, a palmitate salt, a sebacate salt, an undecylenate salt, or a caproate salt of the compound of Formula (I). In some embodiments, the pharmaceutically acceptable salt of the compound of Formula (I) is an adipate salt, a laurate salt, a linoleate salt, a myristate salt, a caprate salt, a stearate salt, an oleate salt, or a caprylate salt of the compound of Formula (I), with a laurate salt, a linoleate salt, a caprate salt, or a caprylate salt of the compound of Formula (I) being preferred.

Exemplary pharmaceutically acceptable fatty acid salt forms (i.e., addition salt forms) of the above-identified compounds are provided in Table 3.

TABLE 3

Exemplary pharmaceutically acceptable fatty acid salts of compounds of Formula (I)

| Salt form identifier | Salt type of compound |
|---|---|
| I-1l | Adipate of I-1 |
| I-1m | Laurate of I-1 |
| I-1n | Linoleate of I-1 |
| I-1o | Myristate of I-1 |
| I-1p | Caprate of I-1 |
| I-1q | Stearate of I-1 |
| I-1r | Oleate of I-1 |
| I-1s | Caprylate of I-1 |
| I-2l | Adipate of I-2 |
| I-2m | Laurate of I-2 |
| I-2n | Linoleate of I-2 |
| I-2o | Myristate of I-2 |
| I-2p | Caprate of I-2 |
| I-2q | Stearate of I-2 |
| I-2r | Oleate of I-2 |
| I-2s | Caprylate of I-2 |
| I-3l | Adipate of I-3 |
| I-3m | Laurate of I-3 |
| I-3n | Linoleate of I-3 |
| I-3o | Myristate of I-3 |
| I-3p | Caprate of I-3 |
| I-3g | Stearate of I-3 |
| I-3r | Oleate of I-3 |
| I-3s | Caprylate of I-3 |
| I-4l | Adipate of I-4 |
| I-4m | Laurate of I-4 |
| I-4n | Linoleate of I-4 |
| I-4o | Myristate of I-4 |
| I-4p | Caprate of I-4 |
| I-4g | Stearate of I-4 |
| I-4r | Oleate of I-4 |
| I-4s | Caprylate of I-4 |
| I-5l | Adipate of I-5 |
| I-5m | Laurate of I-5 |
| I-5n | Linoleate of I-5 |
| I-5o | Myristate of I-5 |
| I-5p | Caprate of I-5 |
| I-5q | Stearate of I-5 |
| I-5r | Oleate of I-5 |
| I-5s | Caprylate of I-5 |
| I-6l | Adipate of I-6 |

TABLE 3-continued

| Exemplary pharmaceutically acceptable fatty acid salts of compounds of Formula (I) | |
|---|---|
| Salt form identifier | Salt type of compound |
| I-6m | Laurate of I-6 |
| I-6n | Linoleate of I-6 |
| I-6o | Myristate of I-6 |
| I-6p | Caprate of I-6 |
| I-6g | Stearate of I-6 |
| I-6r | Oleate of I-6 |
| I-6s | Caprylate of I-6 |
| I-7l | Adipate of I-7 |
| I-7m | Laurate of I-7 |
| I-7n | Linoleate of I-7 |
| I-7o | Myristate of I-7 |
| I-7p | Caprate of I-7 |
| I-7g | Stearate of I-7 |
| I-7r | Oleate of I-7 |
| I-7s | Caprylate of I-7 |
| I-8l | Adipate of I-8 |
| I-8m | Laurate of I-8 |
| I-8n | Linoleate of I-8 |
| I-8o | Myristate of I-8 |
| I-8p | Caprate of I-8 |
| I-8g | Stearate of I-8 |
| I-8r | Oleate of I-8 |
| I-8s | Caprylate of I-8 |
| I-9l | Adipate of I-9 |
| I-9m | Laurate of I-9 |
| I-9n | Linoleate of I-9 |
| I-90 | Myristate of I-9 |
| I-9p | Caprate of I-9 |
| I-9o | Stearate of I-9 |
| I-9r | Oleate of I-9 |
| I-9s | Caprylate of I-9 |
| I-10l | Adipate of I-10 |
| I-10m | Laurate of I-10 |
| I-10n | Linoleate of I-10 |
| I-10o | Myristate of I-10 |
| I-10p | Caprate of I-10 |
| I-10g | Stearate of I-10 |
| I-10r | Oleate of I-10 |
| I-10s | Caprylate of I-10 |

In some embodiments, the pharmaceutically acceptable salt of the compound of Formula (I) has a solubility in corn oil at 22° C. of from about 0.4 mg/mL, from about 0.5 mg/mL, from about 0.6 mg/mL, from about 0.7 mg/mL, from about 0.8 mg/mL, from about 0.9 mg/mL, from about 1 mg/mL, and up to about 2 mg/mL, up to about 1.9 mg/mL, up to about 1.8 mg/mL, up to about 1.7 mg/mL, up to about 1.6 mg/mL, up to about 1.5 mg/mL, up to about 1.4 mg/mL, up to about 1.3 mg/mL, up to about 1.2 mg/mL.

In some embodiments, the pharmaceutically acceptable salt of the compound of Formula (I) has a solubility in Crodamol® GTCC (medium chain glyceride, from Croda) at 22° C. of from about 0.4 mg/mL, from about 0.6 mg/mL, from about 0.8 mg/mL, from about 1 mg/mL, from about 1.2 mg/mL, from about 1.4 mg/mL, from about 1.6 mg/mL, and up to about 4 mg/mL, up to about 3.8 mg/mL, up to about 3.6 mg/mL, up to about 3.4 mg/mL, up to about 3.2 mg/mL, up to about 3 mg/mL, up to about 2.8 mg/mL, up to about 2.6 mg/mL, up to about 2.4 mg/mL, up to about 2.2 mg/mL.

In some embodiments, the pharmaceutically acceptable salt of the compound of Formula (I) has a solubility in Maisine® CC (mixture of unsaturated mono-, di-, and triglycerides, from Gattefosse) at 22° C. of from about 0.8 mg/mL, from about 1 mg/mL, from about 1.2 mg/mL, from about 1.4 mg/mL, from about 1.6 mg/mL, from about 1.8 mg/mL, from about 2 mg/mL, and up to about 5 mg/mL, up to about 4.8 mg/mL, up to about 4.6 mg/mL, up to about 4.4 mg/mL, up to about 4.2 mg/mL, up to about 4 mg/mL, up to about 3.8 mg/mL, up to about 3.6 mg/mL, up to about 3.4 mg/mL, up to about 3.2 mg/mL, up to about 3 mg/mL, up to about 2.8 mg/mL, up to about 2.6 mg/mL, up to about 2.4 mg/mL, up to about 2.2 mg/mL.

Owing to their relatively hydrophobic nature, fatty acid salts of the compounds of Formula (I) may be advantageous when used in medications adapted for a modified, controlled, slow, or extended release profile. As a result, the fatty acid salts of the compounds of Formula (I) may be well suited for routes of administration (e.g., subcutaneous, transdermal, etc.) and/or dosage forms adapted for providing low doses of API over extended periods of time, as may be the case for sub-psychedelic dosing regimens. Non-limiting examples of such dosage forms include, but are not limited to, depots, patches including microneedle patches, liposomes, micelles, microspheres, nanosystems, or other controlled release devices, such as those set forth herein.

Also disclosed herein is a method for stabilizing a compound of Formula (I). The method includes preparing a pharmaceutically acceptable salt of the compound of Formula (I).

Also disclosed herein is a method for preparing a pharmaceutically acceptable salt of the compound of Formula (I). In some embodiments, the method includes:

(a) suspending the free base of the compound of Formula (I) in a solvent or mixture of solvents;

(b) contacting an acid with the compound of Formula (I) to provide a mixture;

(c) optionally heating the mixture;

(d) optionally cooling the mixture; and (e) isolating the salt.

Various solvents may be used in the disclosed methods, including one or more protic solvents, one or more aprotic solvents, or mixtures thereof. In some embodiments, the solvent(s) used in the method of preparing the salt is/are a protic solvent(s). In some embodiments, the solvent used in the method of preparing the salt is selected from the group consisting of methanol, ethanol, propanol, isopropanol, butanol, 2-butanol, acetone, butanone, dioxanes (1,4-dioxane), water, tetrahydrofuran (THF), acetonitrile (MeCN), ether solvents (e.g., t-butylmethyl ether (TBME)), hexane, heptane, octane, and combinations thereof. In some embodiments, the solvent is ethanol. In some embodiments, the solvent is 1,4-dioxane. In some embodiments, the solvent is acetonitrile. In some embodiments, the solvent is tetrahydrofuran.

Suitable acids for use in the preparation of pharmaceutically acceptable acid addition salts may include those described heretofore. The acid may be an inorganic acid such as hydrochloric acid, or an organic acid, with organic acids being preferred. In some embodiments, the acid is an organic acid selected from the group consisting of ascorbic acid, citric acid, fumaric acid, maleic acid, malonic acid, (−)-L-malic acid, (+)-L-tartaric acid, methanesulfonic acid, benzenesulfonic acid, toluenesulfonic acid, benzoic acid, salicylic acid, succinic acid, oxalic acid, D-glucuronic acid, glutaric acid salt, and acetic acid. In some embodiments, the acid is an organic acid selected from the group consisting of benzenesulfonic acid, (+)-L-tartaric acid, fumaric acid, acetic acid, citric acid, malonic acid, succinic acid, oxalic acid, benzoic acid, and salicylic acid, with benzenesulfonic acid, succinic acid, and benzoic acid being preferred. In some embodiments, the acid is a fatty acid, such as adipic (hexandioic) acid, lauric (dodecanoic) acid, linoleic acid, myristic (tetradecanoic) acid, capric (decanoic) acid, stearic (octadecanoic) acid, oleic acid, caprylic (octanoic) acid, palmitic (hexadecenoic) acid, sebacic acid, undecylenic acid, caproic acid, etc., with particular mention being made to adipic (hexandioic) acid, lauric (dodecanoic) acid, linoleic acid, myristic (tetradecanoic) acid, capric (decanoic) acid, stearic (octadecanoic) acid, oleic acid, and caprylic (octanoic) acid.

In some embodiments, a stoichiometric (or superstoichiometric) quantity of the acid is contacted with the compound of Formula (I). In some embodiments, a sub-stoichiometric (e.g., 0.5 molar equivalents) quantity of the acid is contacted with the compound of Formula (I). The use of sub-stoichiometric quantities of the acid may be desirable when, for example, the acid contains at least two acidic protons (e.g., two or more carboxylic acid groups) and the target salt is a hemi-acid salt.

In some embodiments, the mixture is heated, e.g., refluxed, prior to cooling.

In some embodiments, the mixture is cooled and the salt is precipitated out of the solution. In some embodiments, the salt is precipitated out of solution in crystalline form. In some embodiments, the salt is precipitated out of solution in amorphous form.

Isolation of the salt may be performed by various well-known isolation techniques, such as filtration, decantation, and the like. In some embodiments, the isolating step includes filtering the mixture.

After isolation, additional crystallization and/or recrystallization steps may also optionally be performed, if desired, for example to increase purity, crystallinity, etc.

Pharmaceutical Compositions

Also disclosed herein is a pharmaceutical composition comprising a compound of Formula (I), or a pharmaceutically acceptable salt, polymorph, stereoisomer, or solvate thereof, and a pharmaceutically acceptable vehicle. The pharmaceutical compositions may contain one, or more than one, compound, salt form, polymorph, and/or solvate of the present disclosure.

"Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound or salt thereof of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be water, saline, gum acacia, gelatin, starch paste, talc, keratin, colloidal silica, urea, and the like. In addition, auxiliary, stabilizing, solubilizing, thickening, lubricating, coloring agents, sweetening agents, and other pharmaceutical additives may be included in the disclosed compositions, for example those set forth hereinafter. The pharmaceutical vehicle can include an acid, such as those described heretofore for use in forming the pharmaceutically acceptable salt forms of the present disclosure, with specific mention being made to citric acid and/or tartaric acid.

The pharmaceutical composition may comprise a single compound of Formula (I), or a pharmaceutically acceptable salt, a polymorph, stereoisomer, or solvate thereof, or a mixture of compounds of Formula (I), in either free base or salt form, including one or more polymorphs of such materials. The pharmaceutical composition may be formed from an isotopologue mixture of the disclosed compounds. In some embodiments, a subject compound of Formula (I) may be present in the pharmaceutical composition at a purity of at least 50% by weight, at least 60% by weight, at least 70% by weight, at least 80% by weight, at least 90% by weight, at least 95% by weight, at least 99% by weight, based on a total weight of isotopologues of the compound of Formula (I) present in the pharmaceutical composition. For example, a pharmaceutical composition formulated with a salt form of psilocin d-10 (compound I-3; 3-(2-(bis(methyl-$d_3$)amino) ethyl-1,1,2,2-$d_4$)-1H-indol-4-ol), as the subject compound, may additionally contain isotopologues of the subject compound, e.g., psilocin d-9, psilocin d-8, etc., as free-base or salt forms, polymorphs, stereoisomers, solvates, or mixtures thereof. In some embodiments, the composition is substantially free of other isotopologues of the compound, in either free base or salt form, e.g., the composition has less than 20, 15, 10, 9, 8, 7, 6, 5, 4, 3, 2 or 1 or 0.5 mole percent of other isotopologues of the compound.

In some embodiments, any position in the compound having deuterium has a minimum deuterium incorporation of at least 10 atom %, at least 20 atom %, at least 25 atom %, at least 30 atom %, at least 40 atom %, at least 45 atom %, at least 50 atom %, at least 60 atom %, at least 70 atom %, at least 80 atom %, at least 90 atom %, at least 95 atom %, at least 99 atom % at the site of deuteration.

The pharmaceutical composition may be formulated with an enantiomerically pure compound of the present disclosure, e.g., a compound of Formula (I), or a racemic mixture of the compounds. As described herein, a racemic compound of Formula (I) may contain about 50% of the R- and S-stereoisomers based on a molar ratio (about 48 to about 52 mol %, or about a 1:1 ratio)) of one of the isomers. In some embodiments, a composition, medicament, or method of treatment may involve combining separately produced compounds of the R- and S-stereoisomers in an approximately equal molar ratio (e.g., about 48 to 52%). In some embodiments, a medicament or pharmaceutical composition may contain a mixture of separate compounds of the R- and S-stereoisomers in different ratios. In some embodiments, the pharmaceutical composition contains an excess (greater than 50%) of the R-enantiomer. Suitable molar ratios of R/S may be from about 1.5:1, 2:1, 3:1, 4:1, 5:1, 10:1, or higher. In some embodiments, a pharmaceutical composition may contain an excess of the S-enantiomer, with the ratios provided for R/S reversed. Other suitable amounts of R/S may be selected. For example, the R-enantiomer may be enriched, e.g., may be present in amounts of at least about 55% to 100%, or at least 65%, at least 75%, at least 80%, at least 85%, at least 90%, about 95%, about 98%, or 100%. In other embodiments, the S-enantiomer may be enriched, e.g., in amounts of at least about 55% to 100%, or at least 65%, at least 75%, at least 80%, at least 85%, at least 90%, about 95%, about 98%, or 100%. Ratios between all these exemplary embodiments as well as greater than and less than them while still within the disclosure, all are included. Compositions may contain a mixture of the racemate and a separate compound of Formula (I), or a pharmaceutically acceptable salt, a polymorph, stereoisomer, or solvate thereof.

The pharmaceutical composition may be formulated with one or more polymorphs of the compounds of Formula (I) and/or their salt forms, including crystalline and/or amorphous polymorphs of the compounds or salts thereof.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of vehicle will be determined in part by the particular compound, salt form, as well as by the particular method used to administer the composition. Accordingly, there is a wide variety of suitable formulations of the subject pharmaceutical compositions.

Pharmaceutical compositions may be generally provided herein which comprise about 0.1 to about 1000 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg of one or more compounds as disclosed herein, in either free base or salt form, as active pharmaceutical ingredient (API). The quantity of compound of Formula (I) (on active basis) in a unit dose preparation may be varied or adjusted within the above ranges as deemed appropriate using sound medical judgment, according to the particular application, administration route, potency of the active component, etc. The composition can, if desired, also contain other compatible therapeutic agents.

The pharmaceutical compositions disclosed herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Pharmaceutical compositions comprising a compound disclosed herein may be formulated in various dosage forms, such as those for oral, parenteral, and topical administration. The pharmaceutical compositions may also be formulated as a modified release dosage form, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, Rathbone et al., Eds., Drugs and the Pharmaceutical Science, Marcel Dekker, Inc.: New York, N.Y., 2002; Vol. 126).

Any of the pharmaceutical compositions described herein can comprise (as the active component) at least one of compounds of Formula (I), or a pharmaceutically acceptable salt, polymorph, stereoisomer, or solvate thereof.

A. Oral Administration

The pharmaceutical compositions disclosed herein may be provided in solid, semisolid, or liquid dosage forms for oral administration. As used herein, oral administration includes gastric (enteral) delivery, for example whereby the medication is taken by mouth and swallowed, as well as intraoral administration such as through the mucosal linings of the oral cavity, e.g., buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, films, sprinkles, elixirs, and syrups. In addition to the active ingredient(s), the pharmaceutical compositions may contain one or more pharmaceutically acceptable vehicles (e.g., carriers or excipients), including, but not limited to, binders, fillers, diluents, disintegrants, wetting agents, lubricants, glidants, coloring agents, dye-migration inhibitors, sweetening agents, preservatives, antioxidants, lyoprotectants, stabilizing agents, solubilizing agents, complexing agents, and flavoring agents.

In some embodiments, pharmaceutical compositions of the present disclosure may be in orodispersible dosage forms (ODxs), including orally disintegrating tablets (ODTs) (also sometimes referred to as fast disintegrating tablets, orodispersible tablets, or fast dispersible tablets) or orodispersible films (ODFs) (or wafers). Such dosage forms may be particularly advantageous in the present disclosure as they allow for pre-gastric absorption of the compounds/salts herein, e.g., when administered intraorally through the mucosal linings of the oral cavity, e.g., buccal, lingual, and sublingual administration, for increased bioavailability and faster onset compared to oral administration through the gastrointestinal tract.

Orally disintegrating tablets can be prepared by different techniques, such as freeze drying (lyophilization), molding, spray drying, mass extrusion or compressing. Preferably, the orally disintegrating tablets are prepared by lyophilization. In some embodiments, orally disintegrating tablet refers to forms which disintegrate in less than about 90 seconds, in less than about 60 seconds, in less than about 30 seconds, in less than about 20, in less than about 10 seconds, in less than about 5 seconds, or in less than about 2 seconds after being received in the oral cavity. In some embodiments, orally disintegrating tablet refers to forms which dissolve in less than about 90 seconds, in less than about 60 seconds, or in less than about 30 seconds after being received in the oral cavity. In some embodiments, orally disintegrating tablet refers to forms which disperse in less than about 90 seconds, in less than about 60 seconds, in less than about 30 seconds, in less than about 20, in less than about 10 seconds, in less than about 5 seconds, or in less than about 2 seconds after being received in the oral cavity. In some embodiments, the pharmaceutical compositions are in the form of orodispersible dosage forms, such as oral disintegrating tablets (ODTs), having a disintegration time according to the United States Phamacopeia (USP) disintegration test <701> of not more than about 30 seconds, not more than about 20, not more than about 10 seconds, not more than about 5 seconds, not more than about 2 seconds. Orodispersible dosage forms having longer disintegration times according to the United States Phamacopeia (USP) disintegration test <701>, such as when adapted for extended release, for example on the order of 30 minutes or less, 20 minutes or less, 10 minutes or less, 5 minutes or less, 4 minutes or less, 3 minutes or less, 2 minutes or less, are also contemplated.

In some embodiments, the pharmaceutical compositions are in the form of lyophilized orodispersible dosage forms, such as lyopholized ODTs. In some embodiments, the lyophilized orodispersible dosage forms (e.g., lyophilized ODTs) are created by creating a porous matrix by subliming the water from pre-frozen aqueous formulation of the drug containing matrix-forming agents and other vehicles such as those set forth herein, e.g., one or more lyoprotectants, preservatives, antioxidants, stabilizing agents, solubilizing agents, flavoring agents, etc. In some embodiments, the orodispersible dosage forms comprise two component frameworks of a lyophilized matrix system that work together to ensure the development of a successful formulation. In some embodiments, the first component is a water-soluble polymer such as gelatin, dextran, alginate, and maltodextrin. This component maintains the shape and provides mechanical strength to the dosage form (binder). In some embodiments, the second constituent is a matrix-supporting/disintegration-enhancing agent such as sucrose, lactose, mannitol, xylitol, microcrystalline cellulose, calcium diphosphate, and/or starch, which acts by cementing the porous framework, provided by the water-soluble polymer and accelerates the disintegration of the orodispersible dosage forms. In some embodiments, the lyophilized orodispersible dosage form (e.g., lyophilized ODT) includes gelatin and mannitol. In some embodiments, the lyophilized orodispersible dosage form (e.g., lyophilized ODT) includes gelatin, mannitol, and one or more of a lyoprotectant, a preservative, an antioxidant, a stabilizing agent, a solubilizing agent, a flavoring agent, etc., with particular mention being made to citric acid. A non-limiting example of an ODT formulation is Zydis® orally dispersible tablets (available from Catalent). In some embodiments, the ODT formulation (e.g., Zydis® orally dispersible tablets) includes one or more water-soluble polymers, such as gelatin, one or more matrix materials, fillers, or diluents, such as mannitol, a compound of Formula (I), or a pharmaceutically acceptable salt, polymorph, stereoisomer, or solvate thereof, and optionally a lyoprotectant, a preservative, an antioxidant, a stabilizing agent, a solubilizing agent, and/or a flavoring agent. In some embodiments, the ODT formulation (e.g., Zydis® orally dispersible tablets) includes gelatin, mannitol, a compound of Formula (I), or a pharmaceutically acceptable salt, polymorph, stereoisomer, or solvate thereof, and citric acid and/or tartaric acid.

In some embodiments, the pharmaceutical compositions are in the form of lyophilized orodispersible films (ODFs) (or wafers). In some embodiments, the pharmaceutical compositions are in the form of lyophilized ODFs protected for the long-term storage by a specialty packaging excluding moisture, oxygen, and light. In some embodiments, the lyophilized ODFs are created by creating a porous matrix by subliming the water from pre-frozen aqueous formulation of the drug containing matrix-forming agents and other vehicles such as those set forth herein, e.g., one or more of a lyoprotectant, a preservative, an antioxidant, a stabilizing agent, a solubilizing agent, a flavoring agent, etc. In some embodiments, the lyophilized ODF includes a thin water-soluble film matrix. In some embodiments, the ODFs comprise two component frameworks of a lyophilized matrix system that work together to ensure the development of a successful formulation. In some embodiments, the first component is water-soluble polymers such as gelatin, dextran, alginate, and maltodextrin. This component maintains the shape and provides mechanical strength to the film/wafer (binder). In some embodiments, the second constituent is matrix-supporting/disintegration-enhancing agents such as sucrose and mannitol, which acts by cementing the porous framework, provided by the water-soluble polymer and accelerates the disintegration of the wafer. In some embodiments, the lyophilized ODFs include gelatin and mannitol. In some embodiments, the lyophilized ODFs include gelatin, mannitol, and one or more of a lyoprotectant, a preservative, an antioxidant, a stabilizing agent, a solubilizing agent, a flavoring agent, etc., with particular mention being made to citric acid.

In some embodiments, the ODF (or wafer) can comprise a monolayer, bilayer, or trilayer. In some embodiments, the monolayer ODF contains an active agent and one or more pharmaceutically acceptable vehicles (e.g., carrier or excipients). In some embodiments, the bilayer ODF contains one or more excipients, such as a solubilizing agent, in a first layer and an active agent in the second layer. This configuration allows the active agent to be stored separately from the excipients and can increase the stability of the active agent and optionally increase the shelf life of the composition compared to the case where the excipients and the active agent were contained in a single layer. For tri-layer ODFs, each of the layers may be different or two of the layers, such as the upper and lower layers, may have substantially the same composition. In some embodiments, the lower and upper layers surround a core layer containing the active agent. In some embodiments, the lower and upper layers may contain one or more excipients, such as a solubilizing agent. In some embodiments, the lower and upper layers have the same composition. Alternatively, the lower and upper layers may contain different excipients or different amounts of the same excipient. The core layer typically contains the active agent, optionally with one or more excipients.

In some embodiments, in addition to the active ingredient(s), the pharmaceutical compositions in orodispersible dosage forms (ODxs) may contain one or more pharmaceutically acceptable vehicles (e.g., carriers or excipients). For example, in some embodiments, pharmaceutical compositions in orodispersible dosage forms include one or more of pharmaceutically acceptable a lyoprotectant, a preservative, an antioxidant, a stabilizing agent, a solubilizing agent, a flavoring agent, etc.

Examples of pharmaceutically acceptable lyoprotectants include, but are not limited to, disaccharides such as sucrose and trehalose, anionic polymers such as sulfobutylether-3-cyclodextrin (SBECD) and hyaluronic acid, and hydroxylated cyclodextrins.

Examples of pharmaceutically acceptable preservatives include, but are not limited to, glycerin, methyl and propylparaben, benzoic acid, sodium benzoate and alcohol.

Examples of pharmaceutically acceptable antioxidants, which may act to further enhance stability of the composition, include: (1) water soluble antioxidants, such as ascorbic acid, cysteine or salts thereof (cysteine hydrochloride), sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of pharmaceutically acceptable stabilizing agents include, but are not limited to, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, glycerol, methionine, monothioglycerol, ascorbic acid, citric acid, polysorbate, arginine, cyclodextrins, microcrystalline cellulose, modified celluloses (e.g., carboxymethylcellulose, sodium salt), sorbitol, and cellulose gel.

Examples of pharmaceutically acceptable solubilizing agents (or dissolution aids) include, but are not limited to, citric acid, hydroxypropylcellulose, hydroxypropylmethylcellulose, sodium stearyl fumarate, methacrylic acid copolymer LD, methylcellulose, sodium lauryl sulfate, polyoxyl 40 stearate, purified shellac, sodium dehydroacetate, fumaric acid, DL-malic acid, L-ascorbyl stearate, L-asparagine acid, adipic acid, aminoalkyl methacrylate copolymer E, propylene glycol alginate, casein, casein sodium, a carboxyvinyl polymer, carboxymethylethylcellulose, powdered agar, guar gum, succinic acid, copolyvidone, cellulose acetate phthalate, tartaric acid, dioctylsodium sulfosuccinate, zein, powdered skim milk, sorbitan trioleate, lactic acid, aluminum lactate, ascorbyl palmitate, hydroxyethylmethylcellulose, hydroxypropylmethylcelluloseacetate succinate, polyoxyethylene (105) polyoxypropylene (5) glycol, polyoxyethylene hydrogenated castor oil 60, polyoxyl 35 castor oil, poly(sodium 4-styrenesulfonate), polyvinylacetaldiethylamino acetate, polyvinyl alcohol, maleic acid, methacrylic acid copolymer S, lauromacrogol, sulfuric acid, aluminum sulfate, phosphoric acid, calcium dihydrogen phosphate, sodium dodecylbenzenesulfonate, a vinyl pyrrolidone-vinyl acetate copolymer, sodium lauroyl sarcosinate, acetyl tryptophan, sodium methyl sulfate, sodium ethyl sulfate, sodium butyl sulfate, sodium octyl sulfate, sodium decyl sulfate, sodium tetradecyl sulfate, sodium hexadecyl sulfate, and sodium octadecyl sulfate. Of these, in some embodiments, such as in ODT formulation, citric acid is preferred.

Flavoring agents include natural flavors extracted from plants, such as fruits, and synthetic blends of compounds which produce a pleasant taste sensation or taste masking effect. Examples of flavoring agents include, but are not limited to, aspartame, saccharin (as sodium, potassium or calcium saccharin), cyclamate (as a sodium, potassium or calcium salt), sucralose, acesulfame-K, thaumatin, neohisperidin, dihydrochalcone, ammoniated glycyrrhizin, dextrose, maltodextrin, fructose, levulose, sucrose, glucose, wild orange peel, citric acid, tartaric acid, oil of wintergreen, oil of peppermint, methyl salicylate, oil of spearmint, oil of *sassafras*, oil of clove, cinnamon, anethole, menthol, thymol, eugenol, eucalyptol, lemon, lime, and lemon-lime.

Cyclodextrins such as α-cyclodextrin, β-cyclodextrin, γ-cyclodextrin, methyl-β-cyclodextrin, hydroxyethyl β-cyclodextrin, hydroxypropyl-β-cyclodextrin, hydroxypropyl γ-cyclodextrin, sulfated β-cyclodextrin, sulfated α-cyclodextrin, sulfobutyl ether β-cyclodextrin, or other solubilized derivatives can also be advantageously used to enhance delivery of compositions described herein.

Disclosed herein are pharmaceutical compositions in modified release dosage forms, which comprise a compound as disclosed herein and one or more release controlling excipients or carriers as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions may also comprise non-release controlling excipients or carriers.

Further disclosed herein are pharmaceutical compositions in enteric coated dosage forms, which comprise a compound as disclosed herein and one or more release controlling excipients or carriers for use in an enteric coated dosage form. The pharmaceutical compositions may also comprise non-release controlling excipients or carriers.

Further disclosed herein are pharmaceutical compositions in effervescent dosage forms, which comprise a compound as disclosed herein and one or more release controlling excipients or carriers for use in an effervescent dosage form. The pharmaceutical compositions may also comprise non-release controlling excipients or carriers.

Additionally disclosed are pharmaceutical compositions in a dosage form that has an instant releasing component and at least one delayed releasing component, and is capable of giving a discontinuous release of the compound in the form of at least two consecutive pulses separated in time from about 0.1 up to about 24 hours (e.g., about 0.1, 0.5, 1, 2, 4, 6, 8, 10, 12, 14, 16, 18, 10, 22, or 24 hours). The pharmaceutical compositions comprise a compound as disclosed herein and one or more release controlling and non-release controlling excipients or carriers, such as those excipients or carriers suitable for a disruptable semipermeable membrane and as swellable substances.

Disclosed herein also are pharmaceutical compositions in a dosage form for oral administration to a subject, which comprise a compound, salt, or solvate as disclosed herein and one or more pharmaceutically acceptable vehicles (e.g., excipients or carriers), enclosed in an intermediate reactive layer comprising a gastric juice-resistant polymeric layered material partially neutralized with alkali and having cation exchange capacity and a gastric juice-resistant outer layer.

Pharmaceutical compositions adapted for oral administration, e.g., via compressed tablets, may be formulated with various vehicles such as those set forth herein. Examples of suitable vehicles may include, but are not limited to, binders, fillers, diluents, disintegrants, wetting agents, lubricants, glidants, coloring agents, dye-migration inhibitors, sweetening agents, preservatives, antioxidants, stabilizing agents, solubilizing agents, and flavoring agents.

Binders or granulators impart cohesiveness to a tablet to ensure the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions disclosed herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions disclosed herein varies upon the type of formulation, and is readily discernible to those of ordinary skill in the art. The pharmaceutical compositions disclosed herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; sodium stearyl fumarate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, Md.) and CAB-O-SIL® (Cabot Co. of Boston, Mass.); and mixtures thereof. The pharmaceutical compositions disclosed herein may contain about 0.1 to about 5% by weight of a lubricant.

Suitable glidants include colloidal silicon dioxide, CAB-O-SIL® (Cabot Co. of Boston, Mass.), and asbestos-free talc.

Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye.

Sweetening agents include sucrose, lactose, mannitol, syrups, glycerin, and artificial sweeteners, such as saccharin and aspartame.

Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate.

Suspending and dispersing agents include sodium carboxymethylcellulose, pectin, tragacanth, Veegum, acacia, sodium carbomethylcellulose, hydroxypropyl methylcellulose, and polyvinylpyrolidone.

Preservatives include glycerin, methyl and propylparaben, benzoic add, sodium benzoate and alcohol.

Wetting agents include propylene glycol monostearate, sorbitan monooleate, diethylene glycol monolaurate, and polyoxyethylene lauryl ether.

Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many vehicles (carriers, excipients, etc.) may serve several functions, even within the same formulation. Particular mention is made to pharmaceutical compositions herein containing citric acid, which may play multiple roles as a stabilizing agent, e.g., to stabilize the psilocin compound of the present disclosure in free base or salt form, as a solubilizing agent to provide fast dissolution of the active for rapid onset, etc., particularly for dosage forms adapted for rapid onset and a shorter duration of drug action, such as orodispersible dosage forms (e.g., ODTs and ODFs).

The pharmaceutical compositions herein may be in the form of compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more vehicles (e.g., carriers or excipients) described herein, including binders, disintegrants, controlled-release polymers, lubricants, diluents, and/or colorants. Flavoring and sweetening agents are especially useful in the formation of chewable tablets and lozenges.

The dosage form may be an immediate release (IR) dosage form, examples of which include, but are not limited to, an immediate release (IR) tablets or an immediate release (IR) capsule. In addition to the API, dosage forms adapted for immediate release may include one or more pharmaceutically acceptable vehicles which readily disperse, dissolve, or otherwise breakdown in the gastric environment so as not to delay or prolong dissolution/absorption of the API. Examples of pharmaceutically acceptable vehicles for immediate release dosage forms include, but are not limited to, one or more binders/granulators, matrix materials, fillers, diluents, disintegrants, dispersing agents, solubilizing agents, lubricants, and/or performance modifiers. In some embodiments, the immediate release (IR) dosage form is an immediate release (IR) tablet comprising one or more of microcrystalline cellulose, sodium carboxymethylcellulose, magnesium stearate, mannitol, crospovidone, and sodium stearyl fumarate. In some embodiments, the immediate release (IR) dosage form comprises microcrystalline cellulose, sodium carboxymethylcellulose, and magnesium stearate. In some embodiments, the immediate release (IR) dosage form comprises mannitol, crospovidone, and sodium stearyl fumarate.

The pharmaceutical compositions disclosed herein may be disclosed as soft or hard capsules, which can be made from gelatin, methylcellulose, starch, or calcium alginate. The hard gelatin capsule, also known as dry-filled capsule (DFC) or powder in capsule (PIC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms disclosed herein may be encapsulated in a capsule. Suitable liquid and semisolid dosage forms include solutions and suspensions in propylene carbonate, vegetable oils, or triglycerides. The capsules may also be coated as known by those of skill in the art in order to modify or sustain dissolution of the active ingredient.

In some embodiments, the pharmaceutical compositions are in the form of immediate-release capsules for oral administration, and may further comprise cellulose, iron oxides, lactose, magnesium stearate, and sodium starch glycolate.

In some embodiments, the pharmaceutical compositions are in the form of delayed-release capsules for oral administration, and may further comprise cellulose, ethylcellulose, gelatin, hypromellose, iron oxide, and titanium dioxide.

In some embodiments, the pharmaceutical compositions are in the form of enteric coated delayed-release tablets for oral administration, and may further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In some embodiments, the pharmaceutical compositions are in the form of enteric coated delayed-release tablets for oral administration, and may further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The pharmaceutical compositions disclosed herein may be disclosed in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) disclosed herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates. In some embodiments, examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Cyclodextrins such as α-cyclodextrin, β-cyclodextrin, γ-cyclodextrin, methyl-β-cyclodextrin, hydroxyethyl β-cyclodextrin, hydroxypropyl-β-cyclodextrin, hydroxypropyl γ-cyclodextrin, sulfated β-cyclodextrin, sulfated α-cyclodextrin, sulfobutyl ether β-cyclodextrin, or other solubilized derivatives can also be advantageously used to enhance delivery of compositions described herein.

The pharmaceutical compositions disclosed herein for oral administration may be also disclosed in the forms of liposomes, micelles, microspheres, or nanosystems.

The pharmaceutical compositions disclosed herein may be disclosed as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions disclosed herein may be co-formulated with other active ingredients which do not impair the desired therapeutic action, or with substances that supplement the desired action, such as drotrecogin-α, and hydrocortisone.

B. Parenteral Administration

The pharmaceutical compositions disclosed herein may be administered parenterally by injection, infusion, or implantation, for local or systemic administration. Parenteral administration, as used herein, includes, but is not limited to, intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable vehicles (e.g., carriers and excipients), including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, methyl-β-cyclodextrin, hydroxypropyl-3-cyclodextrin/hydroxypropyl-β-cyclodextrin, sulfobutylether-β-cyclodextrin, and sulfobutylether 7-O-cyclodextrin (CAPTISOL®, CyDex, Lenexa, Kans.).

The pharmaceutical compositions disclosed herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In some embodiments, the pharmaceutical compositions are disclosed as ready-to-use sterile solutions. In some embodiments, the pharmaceutical compositions are disclosed as sterile dry soluble products, including lyophilized powders and hypodermic tablets, to be reconstituted with a vehicle prior to use. In some embodiments, the pharmaceutical compositions are disclosed as ready-to-use sterile suspensions. In some embodiments, the pharmaceutical compositions are disclosed as sterile dry insoluble products to be reconstituted with a vehicle prior to use. In some embodiments, the pharmaceutical compositions are disclosed as ready-to-use sterile emulsions.

The pharmaceutical compositions may be formulated as a suspension, solid, semi-solid, or thixotropic liquid, for administration as an implanted depot. In some embodiments, the pharmaceutical compositions disclosed herein are dispersed in a solid inner matrix, which is surrounded by an outer polymeric membrane that is insoluble in body fluids but allows the active ingredient in the pharmaceutical compositions diffuse through. Fatty acid salts of the compounds of Formula (I) may be well-suited for such dosage forms.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions disclosed herein may be administered topically to the skin, orifices, or mucosa. Topical administration, as described herein, includes, but is not limited to, (intra)dermal, conjuctival, intracorneal, intraocular, ophthalmic, auricular, transdermal, nasal, vaginal, uretheral, respiratory, and rectal administration.

The pharmaceutical compositions disclosed herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions disclosed herein may also comprise liposomes, micelles, microspheres, nanosystems, and mixtures thereof.

Pharmaceutically acceptable vehicles (e.g., carriers and excipients) suitable for use in the topical formulations disclosed herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions disclosed herein may be disclosed in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions disclosed herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions disclosed herein; and antioxidants as described herein, including bisulfite and sodium metabisulfite. Suitable vehicles include, but are not limited to, cocoa butter (*Theobroma* oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions disclosed herein may be administered ophthalmically in the forms of solutions, suspensions, ointments, emulsions, gel-forming solutions, powders for solutions, gels, ocular inserts, and implants.

The pharmaceutical compositions disclosed herein may be administered intranasally or by inhalation to the respiratory tract. The pharmaceutical compositions may be disclosed in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be disclosed as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient disclosed herein, a propellant as solvent; and/or an surfactant, such as sorbitan trioleate, oleic acid, or an oligolactic acid.

The pharmaceutical compositions disclosed herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions disclosed herein; a suitable powder base, such as lactose or starch; and a performance modifier, such as 1-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions disclosed herein for inhaled/intranasal administration may further comprise a suitable flavor, such as menthol and levomenthol, or sweeteners, such as saccharin or saccharin sodium.

The pharmaceutical compositions disclosed herein for topical administration may be formulated to be immediate release or modified release, including delayed-, sustained-, pulsed-, controlled-, targeted, and programmed release.

D. Modified Release

The pharmaceutical compositions disclosed herein may be formulated as a modified release dosage form. As used herein, the term "modified release" refers to a dosage form in which the rate or place of release of the active ingredient(s) is different from that of an immediate dosage form when administered by the same route. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

1. Matrix Controlled Release Devices

The pharmaceutical compositions disclosed herein in a modified release dosage form may be fabricated using a matrix controlled release device known to those skilled in the art (see, Takada et al in "Encyclopedia of Controlled Drug Delivery," Vol. 2, Mathiowitz ed., Wiley, 1999).

In one embodiment, the pharmaceutical compositions disclosed herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate, and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions disclosed herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions disclosed herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol, organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the composition.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In some embodiments, the pharmaceutical compositions disclosed herein are formulated as AMT controlled-release dosage forms, which comprises an asymmetric osmotic membrane that coats a core comprising the active ingredient (s) and other pharmaceutically acceptable vehicles (e.g., excipients or carriers). The AMT controlled-release dosage forms can be prepared according to conventional methods and techniques known to those skilled in the art, including direct compression, dry granulation, wet granulation, and a dip-coating method.

In some embodiments, the pharmaceutical compositions disclosed herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions disclosed herein in a modified release dosage form may be fabricated a multiparticulate controlled release device, which comprises a multiplicity of particles, granules, or pellets, ranging from about 10 m to about 3 mm, about 50 m to about 2.5 mm, or from about 100 m to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions disclosed herein may also be formulated to be targeted to a particular tissue, receptor, or other area of the body of the subject to be treated, including liposome-, resealed erythrocyte-, and antibody-based delivery systems.

Any of the delivery devices above, e.g., controlled release device, implant, patch, pump, depot, etc., can be optionally manufactured with smart technology enabling remote activation of the drug delivery. The remote activation can be performed via computer or mobile app. To ensure security, the remote activation device can be password encoded. This technology enables a healthcare provider to perform telehealth sessions with a patient, during which the healthcare provider can remotely activate and administer the compound of Formula (I), or a pharmaceutically acceptable salt, polymorph, stereoisomer, or solvate thereof, via the desired delivery device while supervising the patient on the televisit.

Pharmacokinetics

In some embodiments, the pharmacologic half-life ($T½$) of the compound of Formula (I), when administered orally to a subject via the pharmaceutical composition disclosed herein, is less than 180 minutes, less than 160 minutes, less than 140 minutes, less than 120 minutes.

In some embodiments, the time for the compound of Formula (I) to reach the maximum serum concentration (Tmax), after being administered orally to a subject via the pharmaceutical composition disclosed herein, is less than 180 minutes, less than 160 minutes, less than 140 minutes, less than 120 minutes, less than 100 minutes, less than 80 minutes, less than 60 minutes, less than 50 minutes, less than 40 minutes, less than 30 minutes. In some embodiments, the time for the compound of Formula (I) to reach the maximum serum concentration (Tmax), after being administered orally to a subject via an orally disintegrating tablet (ODT) dosage form is at least 20% lower, at least 25% lower, at least 30% lower, at least 35% lower, at least 40% lower, at least 45% lower, or at least 50% lower than oral administration of the same compound of Formula (I) via a powder in capsule (PIC) dosage form.

In some embodiments, oral administration of the pharmaceutical composition disclosed herein comprising the compound of Formula (I) provides a maximum serum concentration (Cmax) of the compound of Formula (I) which is at least 20% higher, at least 40% higher, at least 60% higher, at least 80% higher, at least 100% higher, at least 120% higher, at least 130% higher than oral administration of psilocybin in substantially the same dosage form.

In some embodiments, oral administration of the pharmaceutical composition disclosed herein comprising the compound of Formula (I), or a pharmaceutically acceptable salt, polymorph, stereoisomer, or solvate thereof, provides an exposure of the compound of Formula (I)-represented as area under the concentration time curve from the time of dosing to the time of last measurable concentration (AUClast) or area under the concentration time curve from the time of dosing extrapolated to infinity (AUCINF_obs)—which is at least 50% higher, at least 70% higher, at least 90% higher, at least 100% higher, at least 120% higher, at least 140% higher, at least 160% higher, at least 170% higher than oral administration of psilocybin in substantially the same dosage form.

In some embodiments, the volume of distribution of the compound of Formula (I) observed (Vz_F_obs) after being administered orally to a subject is at least 20% lower, at least 25% lower, at least 30% lower, at least 35% lower, at least 40% lower, at least 45% lower, at least 50% lower, at least 55% lower, at least 60% lower, than oral administration of psilocybin in substantially the same dosage form.

In some embodiments, the clearance of the compound of Formula (I) observed (Cl_F_obs; mL/kg/hr) after being administered orally to a subject via the pharmaceutical composition disclosed herein, is from 1,500, from 1,600, from 1,700, from 1,800, from 1,900, from 2,000, from 2,100, from 2,200, from 2,300, from 2,400, and up to 3,500, to 3,400, to 3,300, to 3,200, to 3,100, to 3,000, to 2,900, to 2,800, to 2,700, to 2,600 mL/kg/hr.

In some embodiments, the pharmaceutical composition has an onset of therapeutic action of 60 minutes or less, 50 minutes or less, 40 minutes or less, 30 minutes or less, 20 minutes or less, 10 minutes or less, or 5 minutes or less. In some embodiments, the pharmaceutical composition has an acute effects duration of 240 minutes or less, 180 minutes or less, 120 minutes or less, 60 minutes or less, 50 minutes or less, 40 minutes or less, 30 minutes or less, 20 minutes or less, 10 minutes or less, or 5 minutes or less. In some embodiments, the pharmaceutical composition has a drug dissolution time of 120 seconds or less, 90 seconds or less, 60 seconds or less, 50 seconds or less, 40 seconds or less, 30 seconds or less, 20 seconds or less, 10 seconds or less, or 5 seconds or less.

Stabilized Compositions

In some embodiments, pharmaceutical compositions are provided which include the compound of Formula (I), or a pharmaceutically acceptable salt, polymorph, stereoisomer, or solvate thereof, in a stabilized form with a pharmaceutically acceptable vehicle. For example, an amorphous form of the compound of Formula (I) may be stabilized in the disclosed pharmaceutical compositions. In some embodiments, formulations of the compound of Formula (I) in which the compound of Formula (I) exists stably in amorphous form may be accomplished, for example, by immobilizing the compound within a matrix formed by a polymer, e.g., as a solid dispersion or solid molecular complex of the compound of Formula (I) and a polymer.

Provided are solid dispersions and solid molecular complexes that include the compound of Formula (I), or a pharmaceutically acceptable salt, polymorph, stereoisomer, or solvate thereof. For example, the compound of Formula (I), or a pharmaceutically acceptable salt, polymorph, stereoisomer, or solvate thereof, may be dispersed within a matrix formed by a polymer in its solid state such that it is immobilized in its amorphous form. In some embodiments, the polymer may prevent intramolecular hydrogen bonding or weak dispersion forces between two or more drug molecules of the compound of Formula (I). In some embodiments, the solid dispersion provides for a large surface area, thus further allowing for improved dissolution and bioavailability of the compound of Formula (I). In some embodiments, a solid dispersion or solid molecular complex includes a therapeutically effective amount of the compound of Formula (I), or a pharmaceutically acceptable salt, polymorph, stereoisomer, or solvate thereof.

In some embodiments, the compound of Formula (I), or a pharmaceutically acceptable salt, polymorph, stereoisomer, or solvate thereof, is present in the solid dispersion in an amount of from about 1% to about 50%, by weight; or from about 10% to about 40% by weight; or from about 20% to about 35% by weight; or from about 25% to about 30% by weight. In related embodiments, a polymer is present in the solid dispersion in an amount of from about 0% to about 50% by weight; or from about 5% to about 60% by weight; or from 10% to about 70% by weight. In some embodiments, a polymer is present in the solid dispersion in an amount greater than about 10% by weight; or greater than about 20% by weight; or greater than about 30% by weight; or greater than about 40% by weight; or greater than about 50% by weight. In some embodiments, the solid dispersion is about 30% by weight of the compound of Formula (I), or a pharmaceutically acceptable salt, polymorph, stereoisomer, or solvate thereof, and about 70% by weight polymer.

The solid dispersion may comprise the compound of Formula (I), or a pharmaceutically acceptable salt, polymorph, stereoisomer, or solvate thereof dispersed in a non-ionic polymer. This may be accomplished by, for example, melting the polymer and dissolving the compound in the polymer and then cooling the mixture. The resulting solid dispersion may comprise the compound dispersed in the polymer in amorphous form.

A solid dispersion may be formed by dispersing the compound of Formula (I), or a pharmaceutically acceptable salt, polymorph, stereoisomer, or solvate thereof in an ionic polymer. Such solid dispersion may result in increased stability of the compound of Formula (I), or a pharmaceutically acceptable salt, polymorph, stereoisomer, or solvate thereof. This may be accomplished by various means, including the methods described above for use in forming a dispersion in a non-ionic polymer. Because ionic polymers have pH dependent solubility in aqueous systems, the resulting solid dispersion of the compound of Formula (I) and the polymer may be stable at low pH in the stomach and release the compound of Formula (I) in the intestine at higher pH. In some embodiments, the compound of Formula (I), or a pharmaceutically acceptable salt, polymorph, stereoisomer, or solvate thereof in such solid dispersions with an ionic polymer may thus be less capable of separating from the polymer and may be immobilized by the polymer in its amorphous form. Examples of such ionic polymers include, but are not limited to, hydroxypropylmethyl cellulose acetate succinate (HPMC-AS), hydroxypropylmethyl cellulose phthalate (HPMCP), and methacrylic acid copolymers. In some embodiments, a polymer is used that is capable of immobilizing the compound of Formula (I), or a pharmaceutically acceptable salt, polymorph, stereoisomer, or solvate thereof so that it exists primarily in one particular polymorph, e.g., an amorphous form, for an extended period of time.

In some embodiments, the polymer may be linear, branched, or crosslinked. In some embodiments, the polymer may be a homopolymer or copolymer. In some embodiments, the polymer may be a synthetic polymer derived from vinyl, acrylate, methacrylate, urethane, ester and oxide monomers. In some embodiments, the polymer can be a derivative of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulose polymers. In some embodiments, the cellulose polymer is selected from the group consisting of ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In some embodiments, the polymer may be selected from the group consisting of gelatin, polyvinyl alcohol, polyvinylpyrrolidone, pullulan, and the cellulose polymers already disclosed herein. In some embodiments, the cellulose polymer comprises various grades of low viscosity, e.g., MW less than or equal to 50,000 daltons.

In some embodiments, the composition can include solid dispersions and solid molecular complexes that include the compound of Formula (I), or a pharmaceutically acceptable salt, polymorph, stereoisomer, or solvate thereof dispersed within a matrix formed by gelatin. In some embodiments, the composition can include solid dispersions and solid molecular complexes that include the compound of Formula (I), or a pharmaceutically acceptable salt, polymorph, stereoisomer, or solvate thereof dispersed within a matrix formed by gelatin and a non-reducing sugar, e.g., mannitol. In some embodiments, the composition can include solid dispersions and solid molecular complexes that include the compound of Formula (I), or a pharmaceutically acceptable salt, polymorph, stereoisomer, or solvate thereof dispersed within a matrix formed by a cellulose polymer described herein. In some embodiments, the composition can include solid dispersions and solid molecular complexes that include the compound of Formula (I), or a pharmaceutically acceptable salt, polymorph, stereoisomer, or solvate thereof dispersed within a matrix formed by a cellulose polymer described herein and polyvinylpyrrolidone.

In some embodiments, the ratio of the amount by weight of the compound of Formula (I), or a pharmaceutically acceptable salt, polymorph, stereoisomer, or solvate thereof within the solid complex to the amount by weight of the polymer therein is from about 1:9 to about 1:1. In some embodiments, the ratio of the amount by weight of the compound of Formula (I), or a pharmaceutically acceptable salt, polymorph, stereoisomer, or solvate thereof, within the solid complex to the amount by weight of the polymer therein is from about 2:8 to about 4:6. In some embodiments, the ratio of the amount by weight of the compound of Formula (I), or a pharmaceutically acceptable salt, polymorph, stereoisomer, or solvate thereof within the solid complex to the amount by weight of the polymer therein is about 3:7.

In some embodiments, the composition can further include solubilizing agents for the compound of Formula (I), or a pharmaceutically acceptable salt, polymorph, stereoisomer, or solvate thereof. Solubilizing agents include those set forth herein, such as citric acid, sodium phosphate, and natural amino acids. Other solubilizing agents include, but are not limited to, acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, and emulsifying wax.

Various additives can be mixed, ground or granulated with the solid dispersion as described herein to form a material suitable for the above dosage forms. Potentially beneficial additives may fall generally into the following classes: other matrix materials or diluents, surface active agents, drug complexing agents or solubilizers, fillers, disintegrants, binders, lubricants, and pH modifiers (e.g., acids, bases, or buffers). Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids.

The composition may, in addition to the solid dispersion or solid molecular complex, also comprise therapeutically inert, inorganic or organic vehicles, such as those set forth herein.

Therapeutic Applications and Methods

Also disclosed is a method of treating a subject with a disease or disorder comprising administering to the subject a therapeutically effective amount of a compound of Formula (I), or a pharmaceutically acceptable salt, polymorph, stereoisomer, or solvate thereof. In some embodiments, the disease or disorder is associated with a serotonin 5-$HT_2$ receptor.

The dosage and frequency (single or multiple doses) of the compounds herein administered can vary depending upon a variety of factors, including, but not limited to, the salt form/compound/polymorph to be administered; the disease/condition being treated; route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds/salt forms disclosed herein.

Therapeutically effective amounts for use in humans may be determined from animal models. For example, a dose for humans can be formulated to achieve a concentration that has been found to be effective in animals. The dosage in humans can be adjusted by monitoring response to the treatment and adjusting the dosage upwards or downwards.

Dosages may be varied depending upon the requirements of the subject and the compound, salt form, and/or polymorph being employed. The dose administered to a subject, in the context of the pharmaceutical compositions presented herein, should be sufficient to affect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Routes of administration may include oral routes (e.g., enteral/gastric delivery, intraoral administration such buccal, lingual, and sublingual routes), parenteral routes (e.g., intravenous, intraarterial, intraperitoneal, intrathecal, intraventricular, intraurethral, intrasternal, intracranial, intramuscular, intrasynovial, and subcutaneous administration), and topical routes (e.g., (intra)dermal, conjuctival, intracorneal, intraocular, ophthalmic, auricular, transdermal, nasal, vaginal, uretheral, respiratory, and rectal administration), or others sufficient to affect a beneficial therapeutic response.

Administration may follow a continuous administration schedule, or an intermittent administration schedule. The administration schedule may be varied depending on the drug employed, the condition being treated, the administration route, etc. For example, administration may be performed once a day (QD), or in divided dosages throughout the day, such as 2-times a day (BID), 3-times a day (TID), 4-times a day (QID), or more. In some embodiments administration may be performed nightly (QHS). In some embodiments, the compounds/pharmaceutical compositions may be administered as needed (PRN). Administration may also be performed on a weekly basis, e.g., once a week, twice a week, three times a week, four times a week, every other week, or other administration schedules deemed appropriate using sound medical judgement.

The dosing can be continuous (7 days of administration in a week) or intermittent, for example, depending on the pharmacokinetics and a particular subject's clearance/accumulation of the drug. If intermittently, the schedule may be, for example, 4 days of administration and 3 days off (rest days) in a week or any other intermittent dosing schedule deemed appropriate using sound medical judgement. The dosing whether continuous or intermittent is continued for a particular treatment course, typically at least a 28-day cycle (1 month), which can be repeated with or without a drug holiday. Longer or shorter courses can also be used such as 14 days, 18 days, 21 days, 24 days, 35 days, 42 days, 48 days, or longer, or any range therebetween. The course may be repeated without a drug holiday or with a drug holiday depending upon the subject. Other schedules are possible depending upon the presence or absence of adverse events, response to the treatment, patient convenience, and the like.

In some embodiments, the use of compositions of the disclosure may be used as a standalone therapy. In some embodiments, the use of compositions of the disclosure may be used as an adjuvant/combination therapy.

Utilizing the teachings provided herein, an effective prophylactic or therapeutic treatment regimen can be planned that does not cause substantial toxicity or adverse side effects (e.g., caused by sedative or psychotomimetic toxic spikes in plasma concentration of any of the compounds Formula (I)), and yet is entirely effective to treat the clinical symptoms demonstrated by the particular patient. This planning should involve the careful choice of active compound and salt form by considering factors such as compound potency, relative bioavailability, patient body weight, presence and severity of adverse side effects, preferred mode of administration, and the toxicity profile of the selected agent.

A therapeutically effective dose of the compounds, salt forms, polymorphs, solvates, compositions, disclosed herein may vary depending on the variety of factors described above, but is typically that which provides the compound of Formula (I) in an amount of about 0.00001 mg to about 10 mg per kilogram body weight of the recipient per day, or any range in between, e.g., about 0.00001 mg/kg, about 0.00005 mg/kg, about 0.0001 mg/kg, about 0.0005 mg/kg, about 0.001 mg/kg, about 0.005 mg/kg, about 0.01 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg of the compound of Formula (I) (active).

The compound of Formula (I), or a pharmaceutically acceptable salt, polymorph, stereoisomer, or solvate thereof, may be administered at a psychedelic dose. For example, when administered by mouth, the dose range for a psychedelic dosing may range from about 0.083 mg/kg, about 0.09 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, and up to about 1 mg/kg, about 0.95 mg/kg, about 0.9 mg/kg, about 0.85 mg/kg, about 0.8 mg/kg, about 0.75 mg/kg, about 0.7 mg/kg, about 0.65 mg/kg, about 0.6 mg/kg, about 0.55 mg/kg of the compound of Formula (I) (active). Typically, psychedelic doses are administered once by mouth, with the possibility of repeat doses at least one week apart. In some instances, no more than 5 doses are given in any one course of treatment. Courses can be repeated as necessary, with or without a drug holiday. Such acute treatment regimens may be accompanied by psychotherapy, before, during, and/or after the psychedelic dose. These treatments are appropriate for a variety of mental health disorders disclosed herein, examples of which include, but are not limited to, major depressive disorder (MDD), therapy resistant depression (TRD), anxiety disorders, and substance use disorders (e.g., alcohol use disorder, opioid use disorder, amphetamine use disorder, nicotine use disorder, smoking, and cocaine use disorder).

The compound of Formula (I), or a pharmaceutically acceptable salt, polymorph, stereoisomer, or solvate thereof, may be administered at serotonergic, but sub-psychoactive concentrations to achieve durable therapeutic benefits, with decreased toxicity, and may thus be suitable for microdosing. For example, when administered by mouth, the dose range for sub-psychedelic dosing may range from about 0.00001 mg/kg, about 0.00005 mg/kg, about 0.0001 mg/kg, about 0.0005 mg/kg, about 0.001 mg/kg, about 0.005 mg/kg, about 0.006 mg/kg, about 0.008 mg/kg, about 0.009 mg/kg, about 0.01 mg/kg, and less than about 0.083 mg/kg, about 0.08 mg/kg, about 0.075 mg/kg, about 0.07 mg/kg, about 0.06 mg/kg, about 0.05 mg/kg, about 0.04 mg/kg, about 0.03 mg/kg, about 0.02 mg/kg of the compound of Formula (I) (active). Typically, sub-psychedelic doses are administered orally up to every day, for a treatment course (e.g., 1 month). However, there is no limitation on the number of doses at sub-psychedelic doses-dosing can be less frequent or more frequent as deemed appropriate. Courses can be repeated as necessary, with or without a drug holiday.

Sub-psychedelic dosing can also be carried out, for example, by transdermal delivery, subcutaneous administration, etc., via modified, controlled, slow, or extended release dosage forms, including, but not limited to, depot dosage forms, implants, patches, and pumps, which can be optionally remotely controlled. Here, doses would achieve similar blood levels as low oral dosing, but would nevertheless be sub-psychedelic.

Sub-psychedelic doses can be used, e.g., for the chronic treatment a variety of diseases or disorders disclosed herein, examples of which include, but are not limited to, inflammation, pain and neuroinflammation. In such settings where chronic administration is performed over extended periods of time, the stabilized forms of the compounds provided in the present disclosure become increasingly valuable.

The subjects treated herein may have a disease or disorder associated with a serotonin 5-$HT_2$ receptor.

In some embodiments, the disease or disorder is a neuropsychiatric disease or disorder or an inflammatory disease or disorder. In some embodiments, the neuropsychiatric disease or disorder is not schizophrenia or cognitive deficits in schizophrenia.

In some embodiments, the disease or disorder is a central nervous system (CNS) disorder, including, but not limited to, major depressive disorder (MDD), treatment-resistant depression (TRD), post-traumatic stress disorder (PTSD), bipolar and related disorders (including, but not limited to, bipolar I disorder, bipolar II disorder, cyclothymic disorder), obsessive-compulsive disorder (OCD), generalized anxiety disorder (GAD), social anxiety disorder, substance use disorders (including, but not limited to, alcohol use disorder, opioid use disorder, amphetamine use disorder, nicotine use disorder, smoking, and cocaine use disorder), eating disorders (including, but not limited to anorexia nervosa, bulimia nervosa, binge-eating disorder, etc.), Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, suicidal ideation, suicidal behavior, major depressive disorder with suicidal ideation or suicidal behavior, melancholic depression, atypical depression, dysthymia, non-suicidal self-injury disorder (NSSID), chronic fatigue syndrome, Lyme's disease, gambling disorder, paraphilic disorders (including, but not limited to, pedophilic disorder, exhibitionistic disorder, voyeuristic disorder, fetishistic disorder, sexual masochism or sadism disorder, and transvestic disorder, etc.), sexual dysfunction (e.g., low libido), peripheral neuropathy, and obesity.

In some embodiments, the disease or disorder is major depressive disorder (MDD).

In some embodiments, the disease or disorder is treatment-resistant depression (TRD).

In some embodiments, the disease or disorder is anxiety, e.g., generalized anxiety disorder (GAD) or social anxiety disorder.

In some embodiments, the disease or disorder is obsessive-compulsive disorder (OCD).

In some embodiments, the disease or disorder is cancer related depression and anxiety.

In some embodiments, the disease or disorder is headaches (e.g., cluster headache, migraine, etc.).

In some embodiments, the disease or disorder is alcohol use disorder. In some embodiments, the disease or disorder is smoking disorder and the therapy is used for smoking cessation.

In some embodiments, the disease or disorder includes conditions of the autonomic nervous system (ANS).

In some embodiments, the disease or disorder includes pulmonary disorders including asthma and chronic obstructive pulmonary disorder (COPD).

In some embodiments, the disease or disorder includes cardiovascular disorders including atherosclerosis.

The administering physician can provide a method of treatment that is prophylactic or therapeutic by adjusting the amount and timing of any of the compounds/salt forms described herein on the basis of observations of one or more symptoms of the disorder or condition being treated. In some embodiments, the subject is a mammal. In some embodiments, the mammal is a human.

Also disclosed herein is a method for decreasing time of therapeutic onset relative to a psilocybin-based drug comprising administering a therapeutically effective amount of a compound as disclosed herein (i.e., the compound of Formula (I), or a pharmaceutically acceptable salt, polymorph, stereoisomer, or solvate thereof) to a patient in need thereof.

Also disclosed herein is a method of reducing psychedelic side effects relative to a psilocybin-based drug comprising administering a therapeutically effective amount of a compound as disclosed herein (i.e., the compound of Formula (I), or a pharmaceutically acceptable salt, polymorph, stereoisomer, or solvate thereof) to a patient in need thereof.

The terms "hallucinogenic side effects" and "psychedelic side effects" are used in the present disclosure interchangeably to refer to unwanted and/or unintended secondary effects caused by the administration of a medicament to an individual resulting in subjective experiences being qualitatively different from those of ordinary consciousness. These experiences can include derealization, depersonalization, hallucinations and/or sensory distortions in the visual, auditory, olfactory, tactile, proprioceptive and/or interoceptive spheres and/or any other perceptual modifications, and/or any other substantial subjective changes in cognition, memory, emotion and consciousness.

In some embodiments, the administration of the compound of Formula (I), or a pharmaceutically acceptable salt, polymorph, stereoisomer, or solvate thereof causes no hallucinogenic and/or psychedelic side effects and/or less hallucinogenic and/or psychedelic side effects relative to a psilocybin-based drug. In some embodiments, the administration of the compound of Formula (I), or a pharmaceutically acceptable salt, polymorph, stereoisomer, or solvate thereof, alleviates, reduces, removes, and/or eliminates the hallucinogenic and/or psychedelic side effects caused by a psilocybin-based drug.

Also disclosed herein is a method of reducing dose related side-effects, e.g., nausea, relative to treatment with a psilocybin-based drug, comprising administering a therapeutically effective amount of a compound as disclosed herein (i.e., the compound of Formula (I), or a pharmaceutically acceptable salt, polymorph, stereoisomer, or solvate thereof) to a subject in need thereof. The compound of Formula (I), or a pharmaceutically acceptable salt, polymorph, stereoisomer, or solvate thereof has better brain penetration (i.e., a higher brain:plasma ratio) than that obtained from administration of psilocybin. As a result, the effective dosing for the compounds of the present disclosure can be lowered, thereby reducing dose related side effects such as nausea.

Also disclosed herein is a method of decreasing duration of therapeutic effect relative to a psilocybin-based drug comprising administering a therapeutically effective amount of a compound as disclosed herein (i.e., the compound of Formula (I), or a pharmaceutically acceptable salt, polymorph, stereoisomer, or solvate thereof) to a patient in need thereof.

Generally, a duration of therapeutic effect for a psilocybin-based drug is about 6-8 hours. In some embodiments, the duration of therapeutic effect of the compound of Formula (I) is less than the duration of therapeutic effect for a psilocybin-based drug. In some embodiments, the duration of therapeutic effect of the compound of Formula (I) is 7, 6, 5, 4, 3, 2, 1 hour or less, or 60, 50, 40, 30, 20, 10, 5 minutes or less. In some embodiments, the duration of therapeutic effect of the compound of Formula (I) is less than the duration of therapeutic effect of a psilocybin cased drug by 7, 6, 5, 4, 3, 2, 1 hour or less, or 60, 50, 40, 30, 20, 10, 5 minutes or less.

EXAMPLES

I. Analytical Methods

Differential Scanning Calorimetry (DSC)

DSC data were collected on a Mettler DSC 3+ equipped with a 34 position auto-sampler. The instrument was calibrated for energy and temperature using certified indium. Typically 0.5-3 mg of each sample, in a pin-holed aluminum pan, was heated at 10° C.·min$^{-1}$ from 30° C. to 300° C. A nitrogen purge at 50 mL·min$^{-1}$ was maintained over the sample. STARe v15.00 was used for instrument control and data processing.

X-Ray Powder Diffraction (XRPD)

X-Ray Powder Diffraction patterns were collected on a Bruker AXS D2 diffractometer using CuKα radiation (30 kV, 10 mA), θ-θ geometry, using a LynxEye detector from 5-42° 2θ.

The software used for data collection was DIFFRAC.SUITE and the data were analysed and presented using DIFFRAC EVA v 5.

The details of the data collection are:

Angular range: 5 to 42° 2θ

Step size: 0.024° 2θ

Collection time: 0.1 seconds per step.

Samples were run under ambient conditions and prepared as flat plate specimens using powder as received without grinding. Approximately 1-2 mg of the sample was lightly pressed on a silicon wafer to obtain a flat surface.

Gravimetric Vapor Sorption (GVS) Dynamic Vapor Sorption (DVS)

Sorption isotherms were obtained using a SMS DVS Intrinsic moisture sorption analyzer, controlled by SMS Analysis Suite software. The sample temperature was maintained at 25° C. throughout. The humidity was controlled by mixing streams of dry and wet nitrogen, with a total flow rate of 200 mL·min$^{-1}$. Relative humidity (RH) was measured by a calibrated Rotronic probe (dynamic range of 1.0-100% RH), located near the sample. Weight change (mass relaxation) of the sample as a function of % RH was constantly monitored by the microbalance (accuracy ±0.005 mg).

5-20 mg of sample was placed in a pre-tared stainless steel mesh basket under ambient conditions. The sample was loaded and unloaded at 40% RH and 25° C. (typical room conditions). A moisture sorption isotherm was performed as outlined below. The standard isotherm was performed at 25° C. using 10% RH intervals over a 0-90% RH range. The sample was recovered after completion of the isotherm and in some cases re-analyzed by XRPD. Parameters used during GVS/DVS acquisition are presented in Table 4.

TABLE 4

| Parameter | Value |
|---|---|
| RH Profile - Cycle 1 | 40-90, 90-0, 0-40 |
| RH Profile - Cycle 2 | 40-90, 90-0, 0-40 |
| Intervals (% RH) | 10 |
| Flow rate (mL · min$^{-1}$) | 200 |
| Temperature (° C.) | 25 |
| Stability (° C. · min$^{-1}$) | 0.2 |
| Sorption Time (hours) | 6 hour time out |

Nuclear Magnetic Resonance (NMR)

Solution phase $^1H$ NMR Spectra were obtained using a Bruker AVIIIHD NMR spectrometer, fitted with a 5 mm PABBO probe operating at 400.1326 MHz. Samples were prepared in $d_6$-DMSO, unless otherwise stated and referenced using a TMS internal standard.

Thermogravimetric Analysis (TGA)

TGA data were collected on a Mettler TGA 2 equipped with a 34 position auto-sampler. The instrument was temperature calibrated using certified isatherm and nickel. Typically 5-30 mg of each sample was loaded into a pin-holed aluminum pan and heated at 10° C.·min$^{-1}$ from 30° C. to 400° C. A nitrogen purge at 50 mL·min$^{-1}$ was maintained over the sample. STARe v15.00 was used for instrument control and data processing.

Ultra Performance Liquid Chromatography (UPLC)

Purity analysis was performed on a Waters Acquity system equipped with a diode array detector and MicroMass ZQ mass spectrometer using MassLynx software. The UPLC method parameters used for chemical purity analysis are presented in Table 5.

TABLE 5

| | |
|---|---|
| Sample Preparation: | 0.2-0.5 mg · mL$^{-1}$ in DMSO |
| Column: | BEH C18 1.7 μm 100 × 2.1 mm |
| Column Temperature (° C.): | 40 |
| Injection (μL): | 2 |
| Detection: | UV Diode array 200-500 nm |
| Wavelength, Bandwidth (nm) : | |
| Phase A: | 0.1% formic acid in water |
| Phase B: | 0.1% formic acid in acetonitrile |
| Flow Rate (mL · min$^{-1}$) | 0.4 |

| | Time (min) | % Phase A | % Phase B |
|---|---|---|---|
| Timetable: | 0 | 97 | 3 |
| | 0.4 | 97 | 3 |
| | 6.5 | 55 | 45 |
| | 7.0 | 55 | 45 |
| | 7.5 | 95 | 5 |
| | 8.0 | 95 | 5 |

High Resolution Mass Spectrometry (HRMS) and MS/MS

Samples were dissolved in acetonitrile:water (50:50) at 2 mg/mL and examined by LC-MS under the following conditions listed in Tables 6-8.

TABLE 6

| | |
|---|---|
| Instrumentation: | Waters Xevo G2 QTOF with Acquity LC system |
| Injection Volume (μL): | 1 |
| Column: | Acquity UPLC HSS T3 1.8 μm 50 × 2.1 mm |
| Mobile Phase: | A) HPLC Grade Water + 0.1% Formic Acid |
| | B) Acetonitrile + 0.1% Formic Acid |

| | Time (min) | Flow (mL/min) | % A | % B | Curve |
|---|---|---|---|---|---|
| Mobile Phase | Initial | 0.600 | 98.0 | 2.0 | |
| Gradient: | 1.00 | 0.600 | 98.0 | 2.0 | 6 |
| | 8.00 | 0.600 | 2.0 | 98.0 | 6 |

TABLE 6-continued

| | | | | | |
|---|---|---|---|---|---|
| | 9.00 | 0.600 | 2.0 | 98.0 | 6 |
| | 9.10 | 0.600 | 98.0 | 2.0 | 6 |
| | 10.00 | 0.600 | 98.0 | 2.0 | 6 |

TABLE 7

| | | |
|---|---|---|
| Tune Method | Ionisation Polarity | ESI + |
| | Analyser Mode | Resolution mode |
| | Capillary | 0.7 kV |
| | Sampling Cone | 35 V |
| | Extraction Cone | 4 V |
| | Source temperature | 100° C. |
| | Desolvation temperature | 500° C. |
| | Cone Gas Flow | 50 L · hr$^{-1}$ |
| | Desolvation Gas Flow | 900 L · hr$^{-1}$ |
| Lockspray | Analyte | Leucine Enkephalin |
| | Capillary | 3 kV |
| | Collision Energy | OFF |

TABLE 8

| | | |
|---|---|---|
| Scanning Conditions | Start Mass (Da): | 50 |
| | End Mass (Da): | 1200 |
| | Scan Time (s): | 0.1 |
| | Set Mass (Da): | $[M + H]^+$ |
| | Collision Energy (V): Ramp: | 10-30 |

II. Compounds and Salt Forms

Example 1 (Free Base)

3-(2-(bis(methyl-$d_3$)amino)ethyl-1,1,2,2-$d_4$)-1H-indol-4-ol (I-3; psilocin-$d_{10}$; PI-$d_{10}$)

Figure 1A:
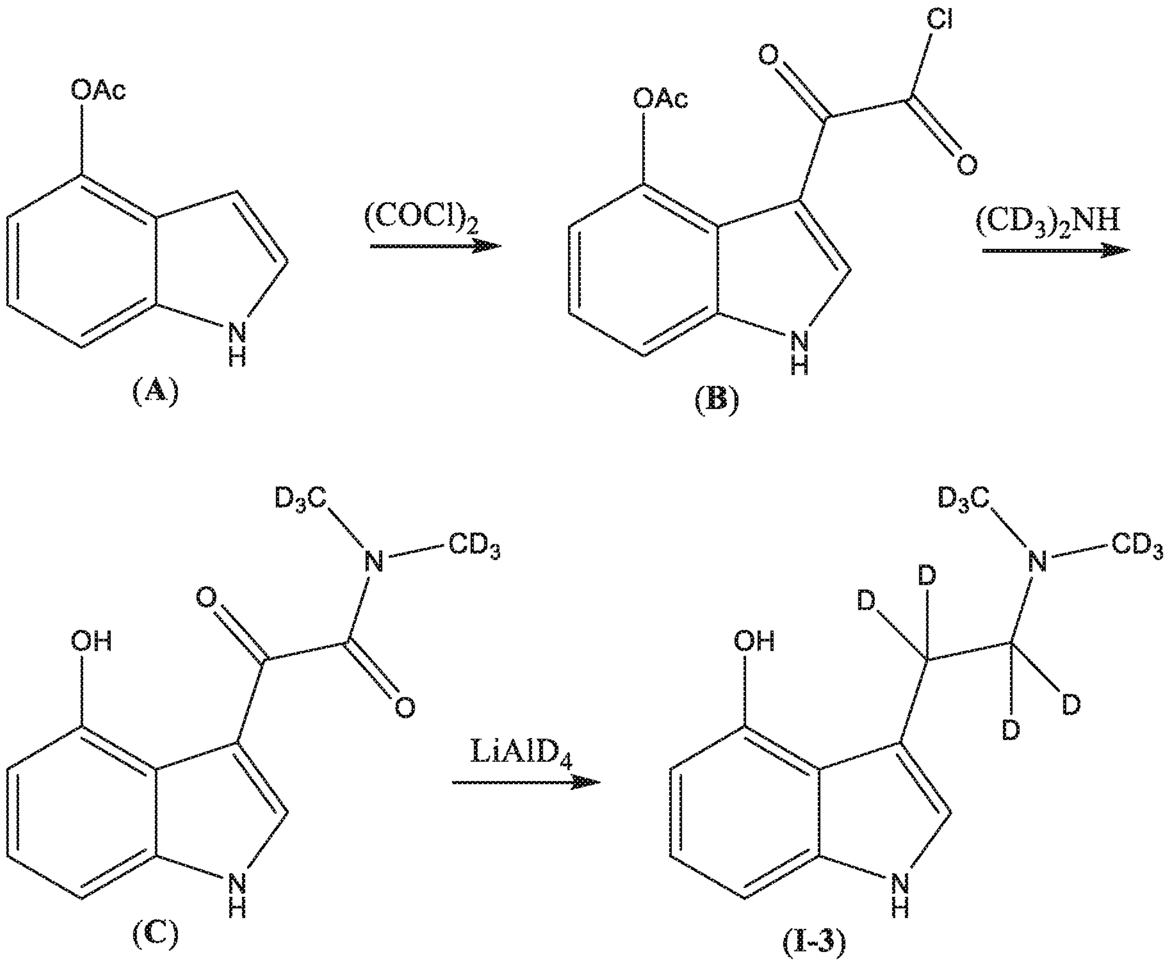
FIGS. 1A-ID show a synthetic route (FIG. 1A), a $^1H$ NMR spectrum (FIGS. 1B-1C), and a high resolution mass spectrometry (HRMS) spectrum (FIG. 1D) for compound I-3 (PI-$d_{10}$)
Figure 1B:
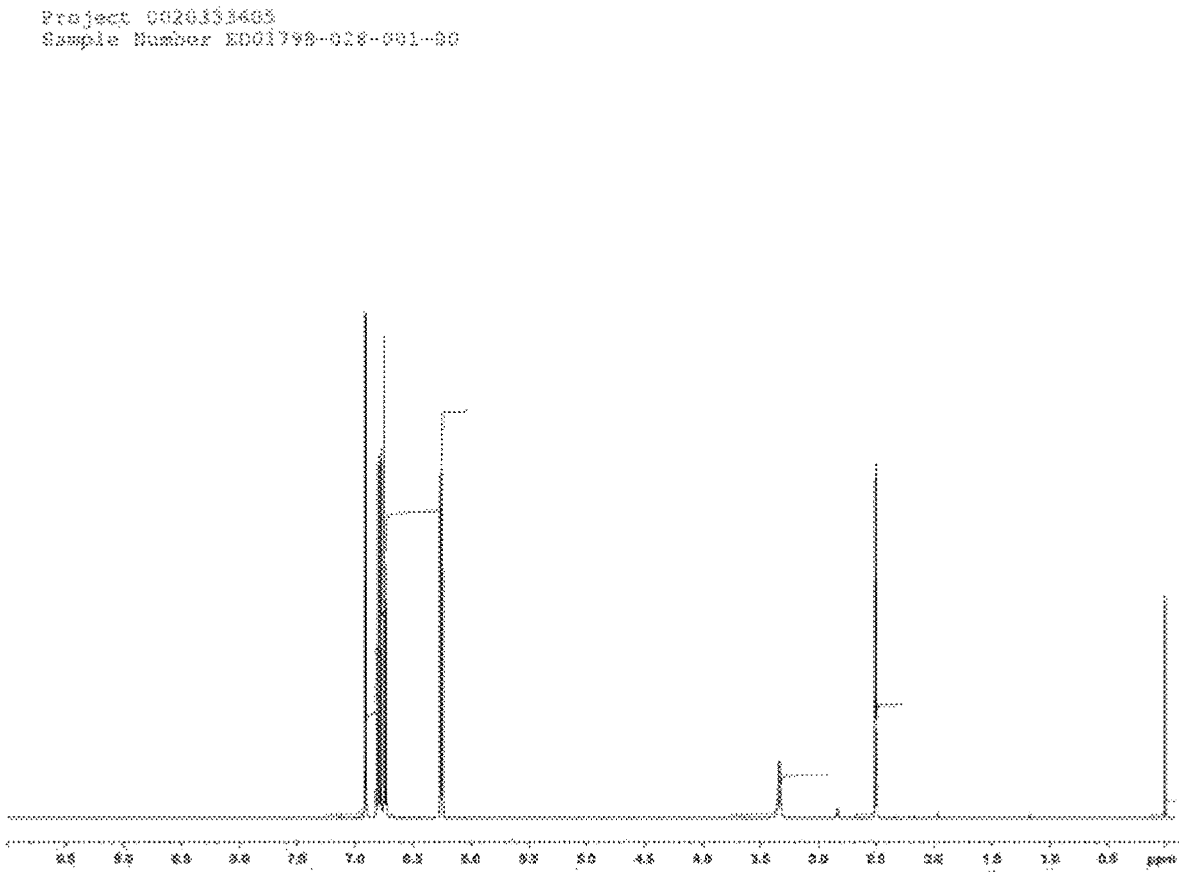
Figure 1C:
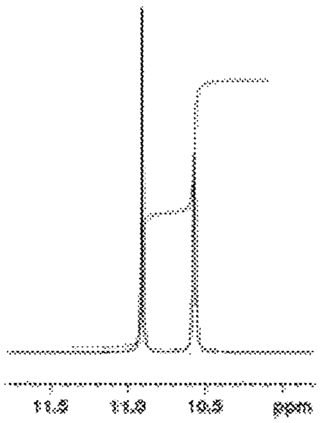
Figure 1D:
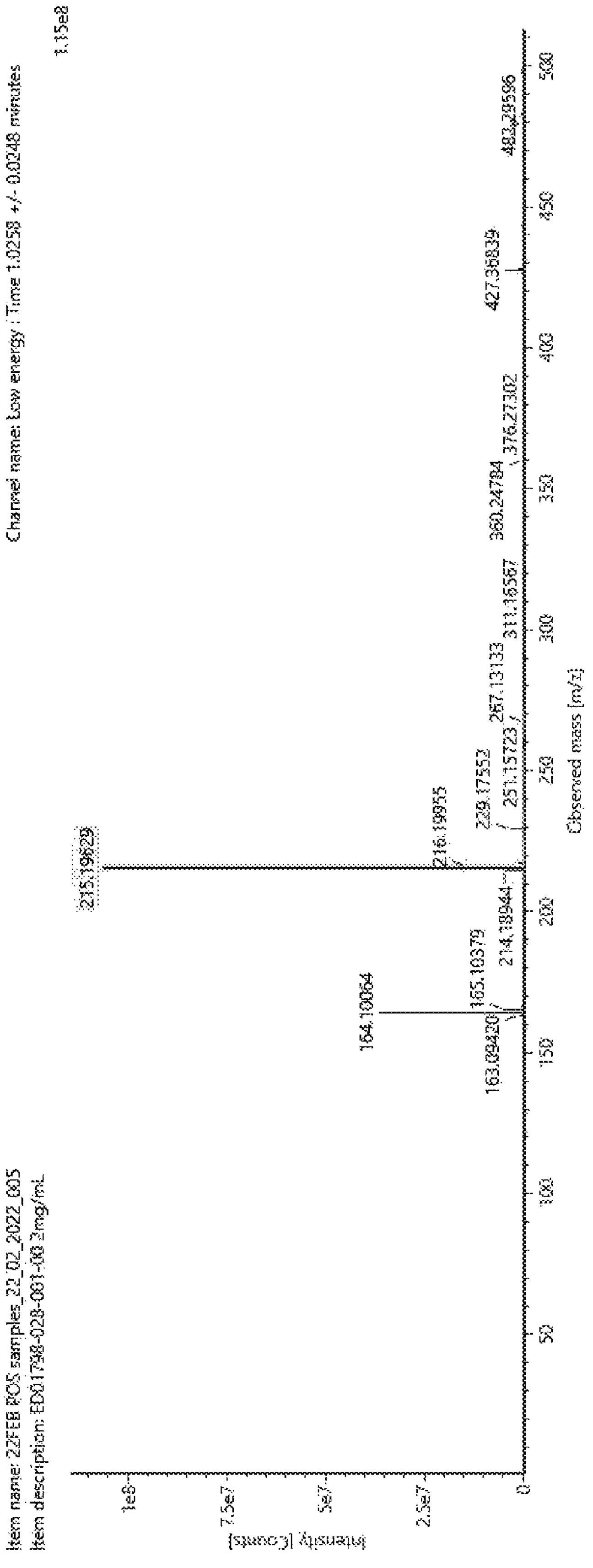

Compound 3-(2-(bis(methyl-$d_3$)amino)ethyl-1,1,2,2-$d_4$)-1H-indol-4-ol (I-3; PI-$d_{10}$) was synthesized according to FIG. 1A. 4-acetoxyindole was acylated using oxalyl chloride producing intermediate B as a yellow solid. Treatment of intermediate B with dimethyl-$d_6$-amine (Cambridge Isotopes Labs, Tewksbury, MA) resulted in amidation and de-acetylation to form intermediate C, which was then reduced by $LiAlD_4$ to form compound I-3 (free base). The structure of the final product with deuterium enrichment over 90% was confirmed by $^1H$ NMR (FIGS. 1B-1C) and HRMS (FIG. 1D). The tentative structure of molecular ion observed in HRMS is presented in Table 9.

TABLE 9

| Compound | Ion Observed | Proposed Formula | Calculated Mass | Tentative Structure | Error (mDa) |
|---|---|---|---|---|---|
| Psilocin-$d_{10}$ | 215.19629 | $C_{12}H_7D_{10}N_2O^+$ | 215.1963 | $[M + H]^+$ | −0.01 |

X-ray powder diffraction (XRPD) pattern of I-3 indicates the material is crystalline, with diffraction peaks of pattern 1 (FIG. 2A). FIGS. 2B and 2C show the zoomed in and annotated XRPD patterns of I-3. Table 10 shows the XRPD peak listing for I-3 (pattern 1).

TABLE 10

| Name | Caption (display) | Angle | d Value | Net Intensity | Rel. Intensity |
|---|---|---|---|---|---|
| Peak #1 | 7.582° | 7.582295 | 11.65008 | 861.3094 | 0.007792 |
| Peak #2 | 8.395° | 8.394759 | 10.52429 | 110533.8 | 1.000000 |
| Peak #3 | 9.647° | 9.646576 | 9.161201 | 269.5037 | 0.002438 |
| Peak #4 | 10.444° | 10.44383 | 8.46358 | 84.23746 | 0.000762 |
| Peak #5 | 11.319° | 11.3193 | 7.81087 | 32.57419 | 0.000295 |
| Peak #6 | 12.614° | 12.61394 | 7.011955 | 432.8757 | 0.003916 |
| Peak #7 | 13.372° | 13.3719 | 6.616152 | 84.5412 | 0.000765 |
| Peak #8 | 14.222° | 14.22235 | 6.222384 | 21.97205 | 0.000199 |
| Peak #9 | 15.157° | 15.15702 | 5.840713 | 744.3998 | 0.006735 |
| Peak #10 | 16.524° | 16.52404 | 5.360464 | 654.2328 | 0.005919 |
| Peak #11 | 16.787° | 16.78656 | 5.277219 | 74073.52 | 0.670143 |
| Peak #12 | 17.693° | 17.69319 | 5.008796 | 284.0384 | 0.002570 |
| Peak #13 | 19.468° | 19.46828 | 4.555921 | 423.9552 | 0.003836 |
| Peak #14 | 19.699° | 19.69928 | 4.503015 | 1017.259 | 0.009203 |
| Peak #15 | 20.901° | 20.90102 | 4.246741 | 389.4514 | 0.003523 |
| Peak #16 | 21.132° | 21.13205 | 4.200831 | 679.8422 | 0.006151 |
| Peak #17 | 21.859° | 21.85903 | 4.062737 | 85.95354 | 0.000778 |
| Peak #18 | 22.547° | 22.54694 | 3.940314 | 67.01072 | 0.000606 |
| Peak #19 | 23.699° | 23.6988 | 3.751339 | 942.5151 | 0.008527 |
| Peak #20 | 24.630° | 24.62965 | 3.611631 | 30.55703 | 0.000276 |
| Peak #21 | 25.034° | 25.03401 | 3.554202 | 51.79423 | 0.000469 |
| Peak #22 | 25.264° | 25.2645 | 3.522297 | 638.7632 | 0.005779 |
| Peak #23 | 26.867° | 26.86674 | 3.315764 | 360.7947 | 0.003264 |
| Peak #24 | 27.399° | 27.39855 | 3.252601 | 28.91455 | 0.000262 |
| Peak #25 | 27.929° | 27.92929 | 3.191985 | 54.06995 | 0.000489 |
| Peak #26 | 28.219° | 28.21871 | 3.159902 | 20.70195 | 0.000187 |
| Peak #27 | 28.871° | 28.87078 | 3.089999 | 43.83303 | 0.000397 |
| Peak #28 | 29.430° | 29.42954 | 3.03259 | 73.03846 | 0.000661 |
| Peak #29 | 30.120° | 30.11959 | 2.964665 | 34.19807 | 0.000309 |
| Peak #30 | 30.675° | 30.67536 | 2.912207 | 207.2589 | 0.001875 |
| Peak #31 | 31.373° | 31.37339 | 2.848986 | 91.50857 | 0.000828 |
| Peak #32 | 32.365° | 32.36467 | 2.763953 | 54.7266 | 0.000495 |
| Peak #33 | 33.880° | 33.88012 | 2.643708 | 132.8692 | 0.001202 |
| Peak #34 | 34.418° | 34.41825 | 2.603594 | 19.10025 | 0.000173 |
| Peak #35 | 34.792° | 34.7921 | 2.576469 | 20.48885 | 0.000185 |
| Peak #36 | 35.884° | 35.88435 | 2.500512 | 136.4738 | 0.001235 |
| Peak #37 | 36.254° | 36.25361 | 2.475885 | 28.93899 | 0.000262 |
| Peak #38 | 37.156° | 37.15607 | 2.417796 | 31.10832 | 0.000281 |
| Peak #39 | 38.200° | 38.20009 | 2.354083 | 34.23606 | 0.000310 |
| Peak #40 | 38.417° | 38.41659 | 2.341313 | 52.08007 | 0.000471 |

3-(2-(dimethylamino)ethyl)-1H-indol-4-ol (I-7/psilocin/psilocin-$d_0$/PI-$d_0$)

Compound I-7 (PI-$d_0$, free base) used in the below examples was characterized by X-ray powder diffraction (XRPD) as having an XRPD pattern of pattern 1 (see FIG. 3C). Table 11 shows the XRPD peak listing for I-7 (pattern 1).

TABLE 11

| Caption (display) | Angle | d Value | Net Intensity | Rel. Intensity |
|---|---|---|---|---|
| 7.563° | 7.563431 | 11.67909 | 44.11061 | 0.00672 |
| 8.375° | 8.374504 | 10.5497 | 6563.628 | 1 |
| 12.626° | 12.62642 | 7.005054 | 208.3727 | 0.031747 |
| 13.383° | 13.38263 | 6.610871 | 185.4812 | 0.028259 |
| 15.211° | 15.21114 | 5.820052 | 265.2301 | 0.040409 |
| 16.753° | 16.75303 | 5.287707 | 3690.068 | 0.562199 |
| 17.671° | 17.67111 | 5.015004 | 304.343 | 0.046368 |
| 19.668° | 19.66817 | 4.510068 | 2602.091 | 0.396441 |
| 21.112° | 21.11224 | 4.204728 | 864.1647 | 0.13166 |
| 21.863° | 21.86267 | 4.062068 | 148.0073 | 0.02255 |
| 22.201° | 22.20094 | 4.000934 | 80.56883 | 0.012275 |

TABLE 11-continued

| Caption (display) | Angle | d Value | Net Intensity | Rel. Intensity |
|---|---|---|---|---|
| 22.560° | 22.56038 | 3.937997 | 103.738 | 0.015805 |
| 23.711° | 23.71067 | 3.749489 | 1043.58 | 0.158994 |
| 24.592° | 24.59193 | 3.617084 | 48.51187 | 0.007391 |
| 25.415° | 25.41542 | 3.501722 | 60.87042 | 0.009274 |
| 26.820° | 26.81979 | 3.321463 | 226.2585 | 0.034472 |
| 27.357° | 27.35734 | 3.257406 | 63.70338 | 0.009706 |
| 27.921° | 27.92109 | 3.192905 | 111.1571 | 0.016935 |
| 28.228° | 28.22797 | 3.158886 | 18.08015 | 0.002755 |
| 29.253° | 29.25296 | 3.050493 | 70.03584 | 0.01067 |
| 30.653° | 30.65323 | 2.914259 | 174.6236 | 0.026605 |
| 31.364° | 31.3638 | 2.849835 | 103.4405 | 0.01576 |
| 32.401° | 32.40136 | 2.760907 | 58.739 | 0.008949 |
| 33.797° | 33.79747 | 2.649983 | 17.68047 | 0.002694 |
| 34.445° | 34.44516 | 2.601622 | 29.53493 | 0.0045 |
| 39.867° | 39.86696 | 2.259415 | 40.48755 | 0.006168 |

Example 2

Synthesis of benzenesulfonate salt of 3-(2-(dimethylamino)ethyl)-1H-indol-4-ol (I-7a)(benzenesulfonate salt of I-7/psilocin/psilocin-$d_0$/PI-$d_0$)

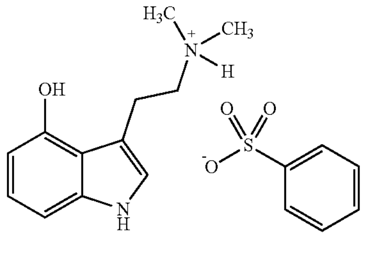

Compound I-7 (PI-$d_0$, free base)(10 mM) was dissolved in acetonitrile and treated with a solution of benzenesulfonic acid (10 mM) while being stirred at ambient temperature. Samples were shaken overnight at room temperature to produce I-7a (mono-benzenesulfonate salt of PI-do).

Figure 3D:
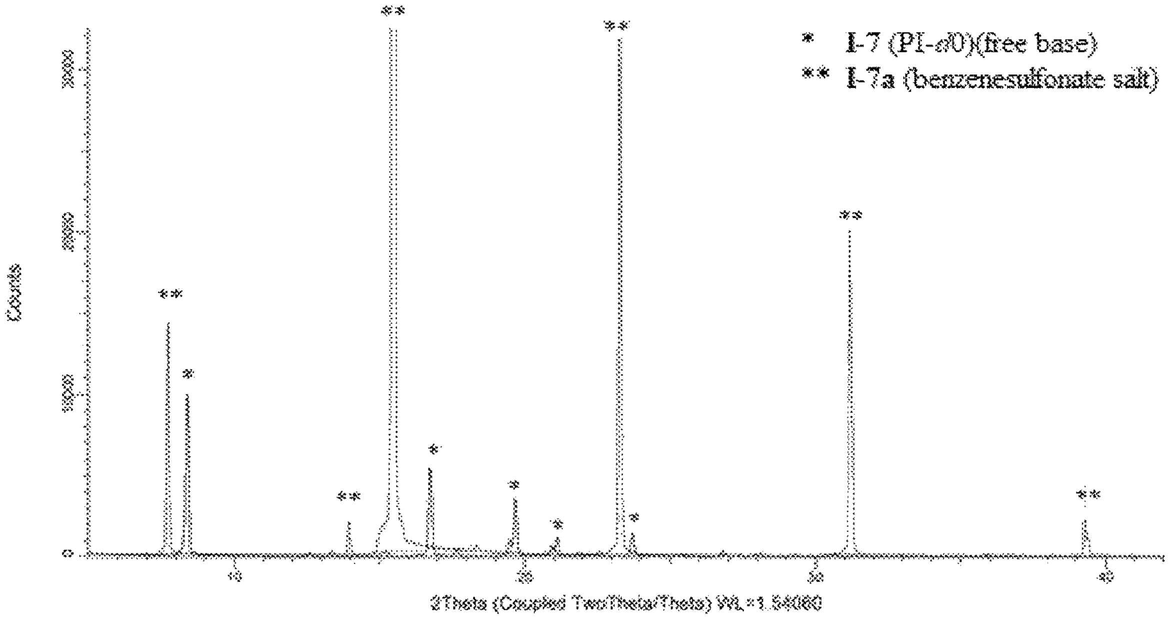

As shown in FIG. 3A, the X-ray powder diffraction (XRPD) pattern of I-7a indicates one crystalline polymorph was produced (pattern 1) having high crystallinity. FIG. 3B shows the zoomed in and annotated XRPD patterns of I-7a. FIG. 3C shows the XRPD pattern of I-7 (PI-$d_0$, free base) (pattern 1), and FIG. 3D shows a comparison between the XRPD patterns of I-7a (benzenesulfonate salt) and I-7 (PI-$d_0$, free base)(pattern 1). Table 12 shows the XRPD peak listing for I-7a (pattern 1).

TABLE 12

| Name | Caption (display) | Angle | d Value | Net Intensity | Rel. Intensity |
|---|---|---|---|---|---|
| Peak #1 | 7.002° | 7.00186 | 12.61448 | 24.92258 | 0.001100 |
| Peak #2 | 7.733° | 7.732948 | 11.42345 | 1731.93 | 0.076457 |
| Peak #3 | 11.768° | 11.76836 | 7.513811 | 77.21395 | 0.003409 |
| Peak #4 | 12.516° | 12.51581 | 7.066712 | 92.23495 | 0.004072 |
| Peak #5 | 12.882° | 12.88182 | 6.866737 | 12.68317 | 0.000560 |
| Peak #6 | 13.546° | 13.54551 | 6.531741 | 57.04026 | 0.002518 |
| Peak #7 | 13.968° | 13.96827 | 6.334989 | 229.514 | 0.010132 |
| Peak #8 | 14.788° | 14.78807 | 5.985592 | 86.10961 | 0.003801 |
| Peak #9 | 15.225° | 15.22511 | 5.814743 | 194.4308 | 0.008583 |
| Peak #10 | 15.474° | 15.47401 | 5.721769 | 22652.34 | 1.000000 |
| Peak #11 | 18.370° | 18.37028 | 4.825681 | 815.8047 | 0.036014 |
| Peak #12 | 19.737° | 19.73692 | 4.494512 | 37.58994 | 0.001659 |
| Peak #13 | 20.703° | 20.7033 | 4.286849 | 116.4809 | 0.005142 |
| Peak #14 | 21.050° | 21.04972 | 4.217076 | 68.59189 | 0.003028 |
| Peak #15 | 21.873° | 21.87293 | 4.060185 | 33.76218 | 0.001490 |
| Peak #16 | 21.982° | 21.98196 | 4.040294 | 270.1723 | 0.011927 |
| Peak #17 | 22.315° | 22.31468 | 3.980798 | 55.64486 | 0.002456 |
| Peak #18 | 22.639° | 22.63877 | 3.924538 | 158.6271 | 0.007003 |
| Peak #19 | 23.282° | 23.28249 | 3.817467 | 2953.931 | 0.130403 |
| Peak #20 | 23.775° | 23.77462 | 3.739549 | 179.0302 | 0.007903 |
| Peak #21 | 24.125° | 24.12521 | 3.685993 | 150.6518 | 0.006651 |
| Peak #22 | 25.193° | 25.19252 | 3.532198 | 48.53237 | 0.002142 |
| Peak #23 | 25.475° | 25.47532 | 3.493623 | 141.9634 | 0.006267 |
| Peak #24 | 25.931° | 25.93118 | 3.433232 | 49.37065 | 0.002179 |
| Peak #25 | 26.813° | 26.81276 | 3.322318 | 61.6441 | 0.002721 |
| Peak #26 | 27.778° | 27.77834 | 3.208987 | 27.04133 | 0.001194 |
| Peak #27 | 28.127° | 28.12704 | 3.169992 | 28.03019 | 0.001237 |
| Peak #28 | 30.866° | 30.86559 | 2.89469 | 52.91717 | 0.002336 |

TABLE 12-continued

| Name | Caption (display) | Angle | d Value | Net Intensity | Rel. Intensity |
|---|---|---|---|---|---|
| Peak #29 | 31.207° | 31.20687 | 2.863808 | 2039.447 | 0.090033 |
| Peak #30 | 32.941° | 32.94133 | 2.716873 | 58.67304 | 0.002590 |
| Peak #31 | 33.222° | 33.22205 | 2.694555 | 36.2762 | 0.001601 |
| Peak #32 | 33.698° | 33.69811 | 2.657569 | 31.60854 | 0.001395 |
| Peak #33 | 36.803° | 36.80291 | 2.440182 | 40.07982 | 0.001769 |
| Peak #34 | 38.668° | 38.66787 | 2.326675 | 22.73825 | 0.001004 |
| Peak #35 | 39.289° | 39.28912 | 2.291304 | 227.1359 | 0.010027 |

Figure 4:
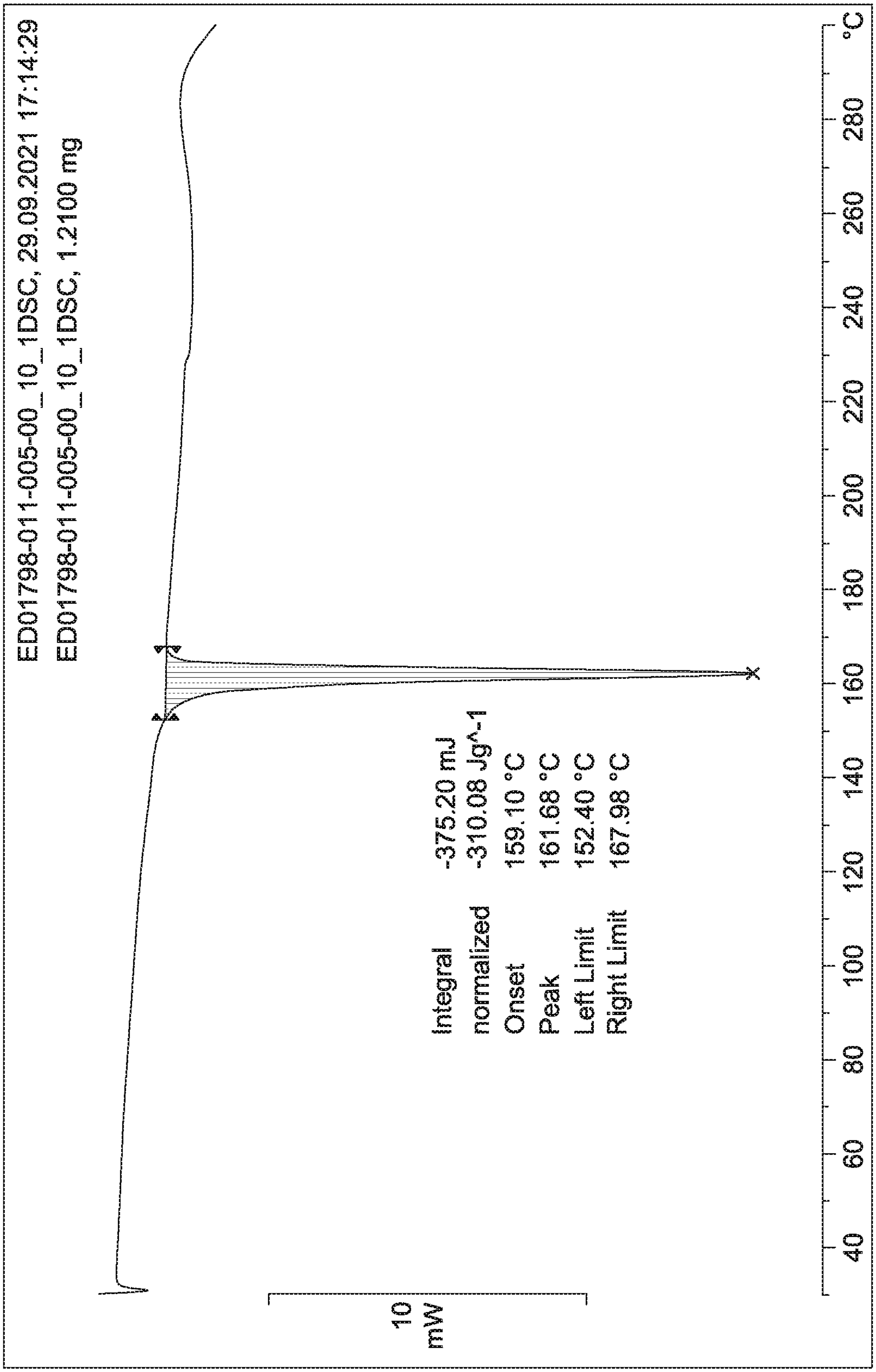

The DSC curve of I-7a is shown in FIG. 4 and it is evident that the salt has a high melt onset (159.10° C.) and peak (161.68° C.). Equally, no events were observed prior to the melt endotherm, indicating the absence of multiple physical forms in the sample, and also no conversion of physical forms prior to the melt.

Figure 5:
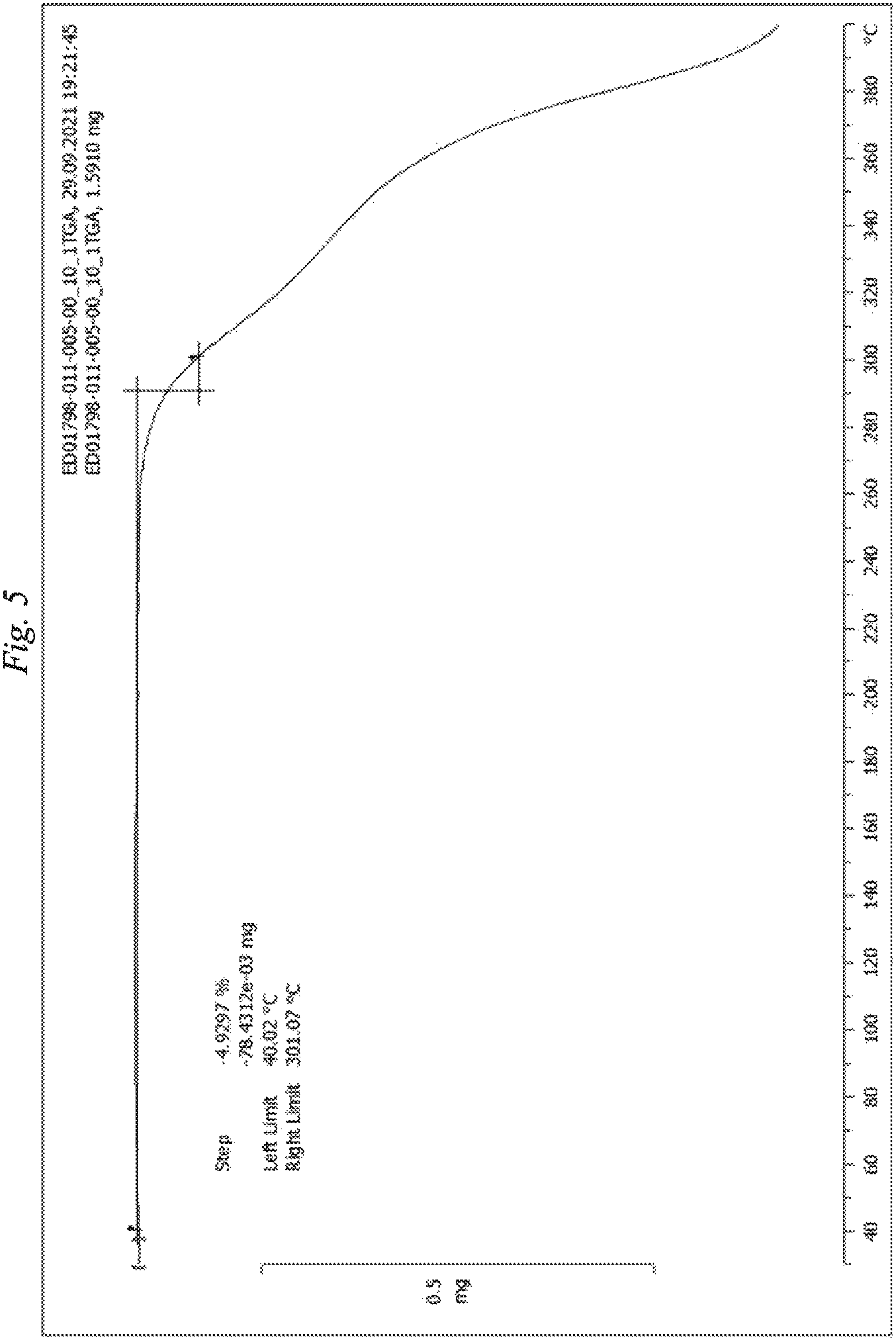

The thermogravimetric analysis (TGA) curve of I-7a is shown in FIG. 5 showed 95% mass remaining at 301° C. at a heating rate of 10° C./min.

Figure 6A:
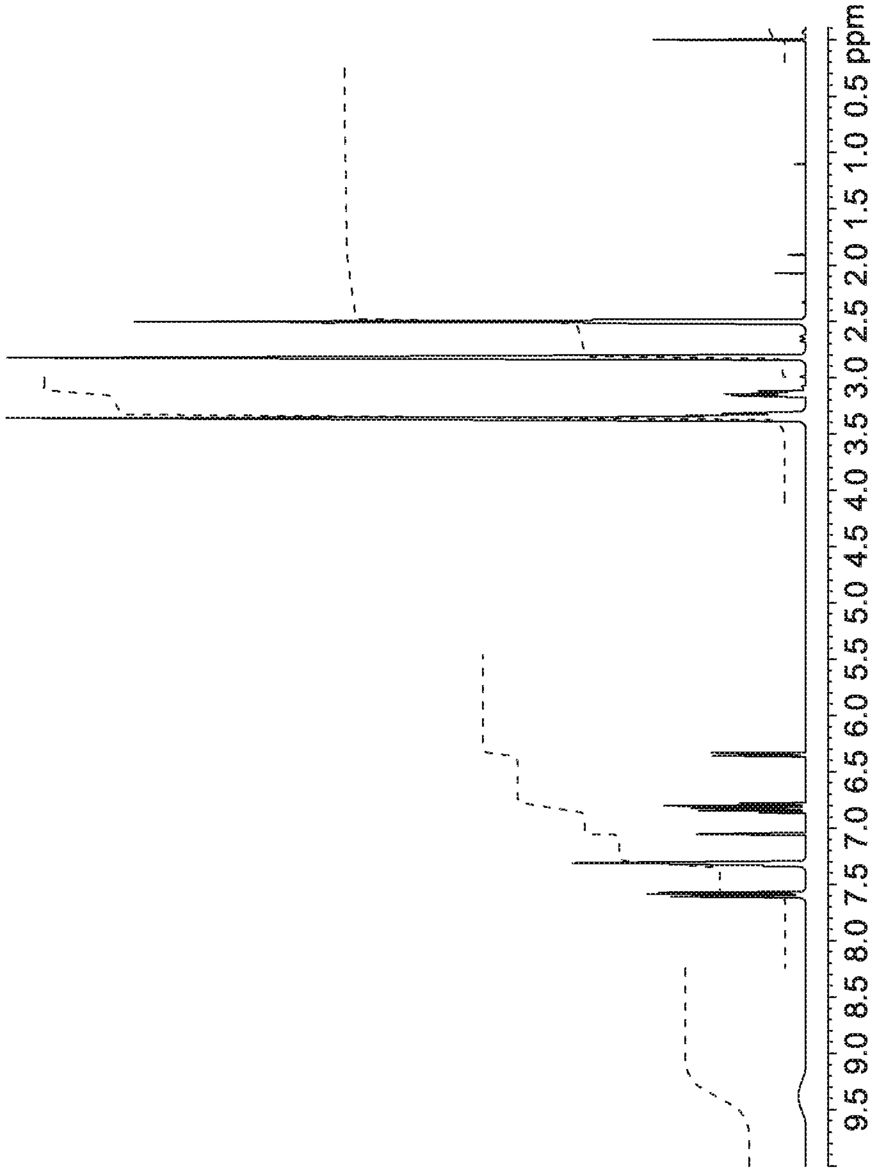
Figure 6B:
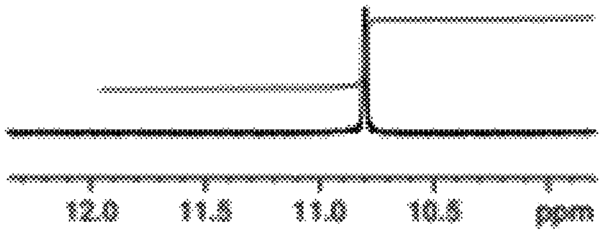

FIGS. 6A and 6B show a $^1$H NMR spectrum of I-7a, which indicates protonation and 1 molar equivalent of benzenesulfonate.

Figure 7:
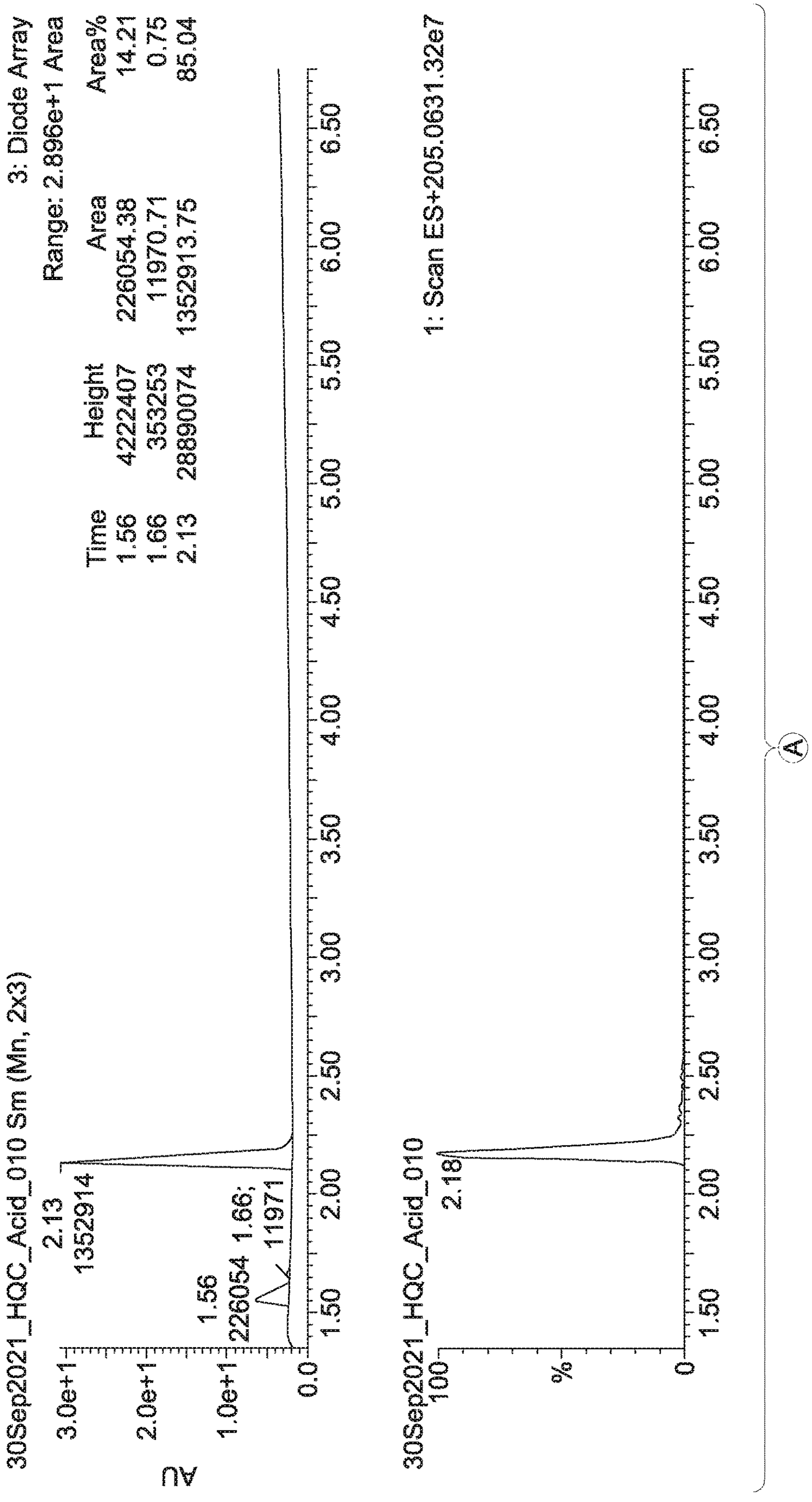
Figure 7:
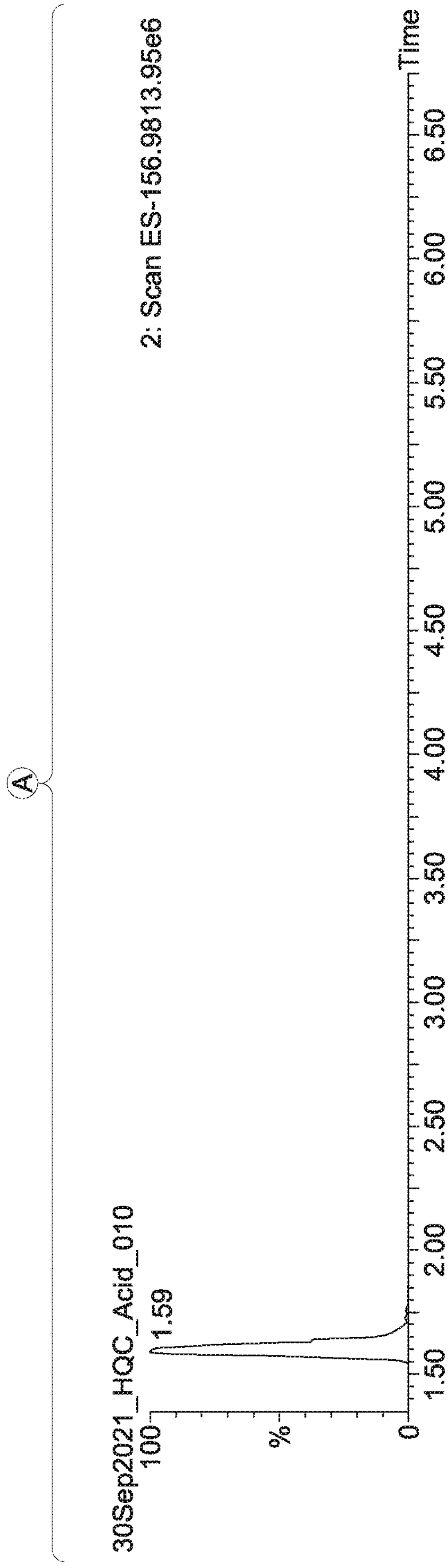

The UPLC chromatogram of I-7a (FIG. 7) indicates a purity including counterion of 99.2%.

Figure 8:
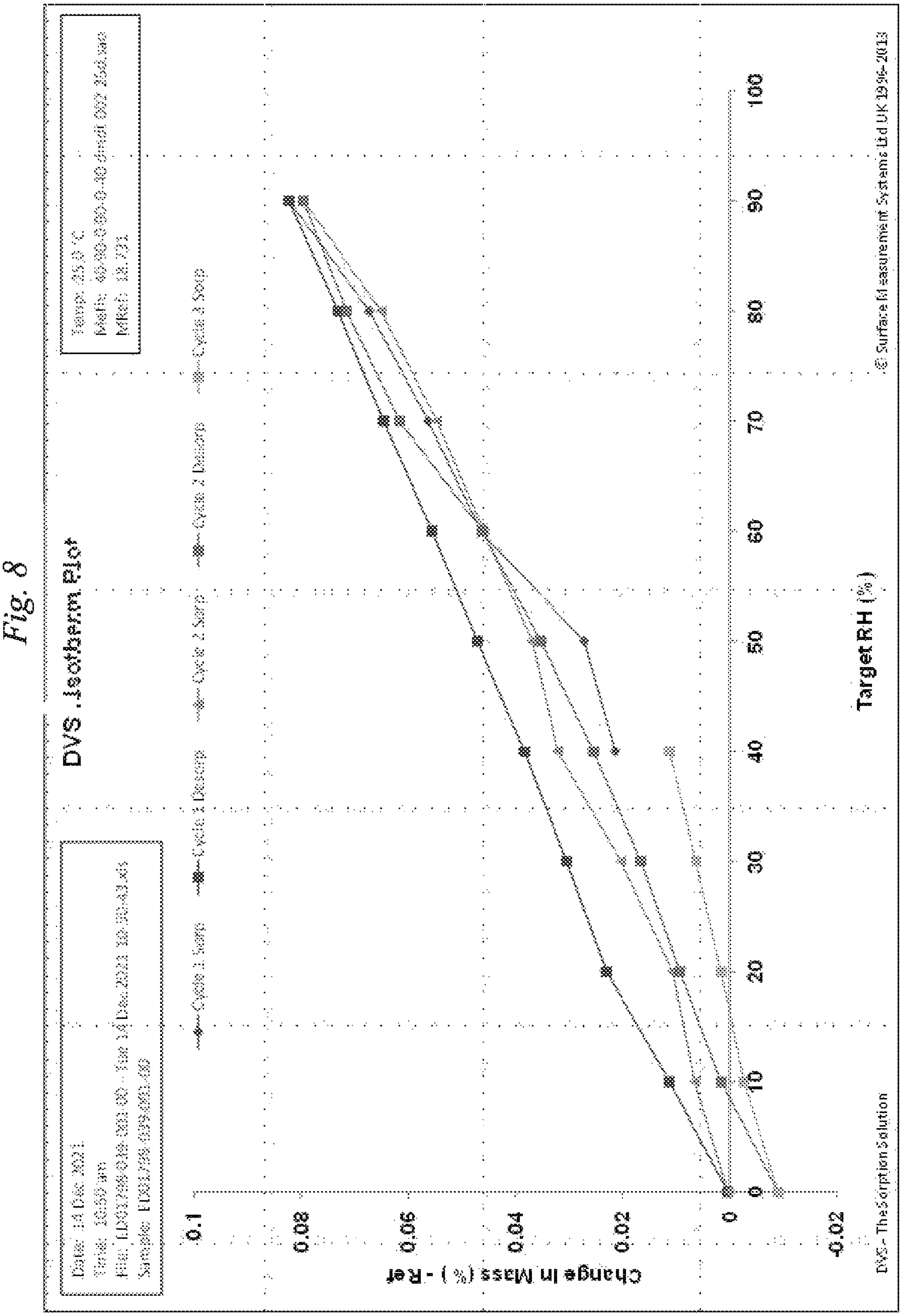

DVS isotherm plot of I-7a is shown in FIG. 8. There is no significant hygroscopicity and the acquisition of water was very low, even on exposure to elevated relative humidities (RH) of >90% RH, with a 0.08% mass increase over 0-90% RH range (second sorption cycle). The change in mass was low over the typical range of ambient relative humidities, and there was no evidence of physical form conversion throughout the cycle. This isotherm plot represents advantageous behavior for pharmaceutical development purposes.

Figure 9:
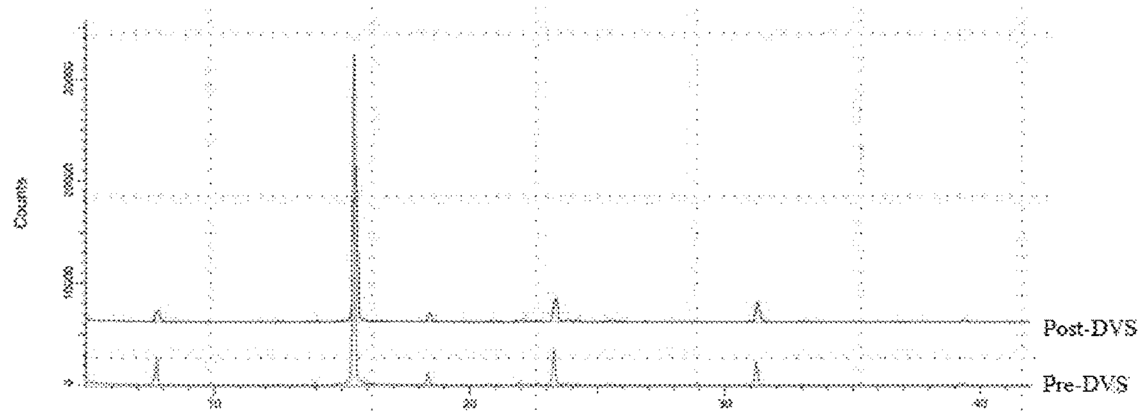
FIG. 9 shows the XRPD patterns of I-7a (pattern 1) pre- and post-DVS analysis.

FIG. 9 shows the XRPD pattern of I-7a after being subjected to the DVS conditions above (post-DVS) compared to the XRPD pattern before DVS (Pre-DVS), indicating that no changes to the crystal structure took place. There was also no loss of purity following DVS analysis according to $^1$H NMR and UPLC.

Figure 10:
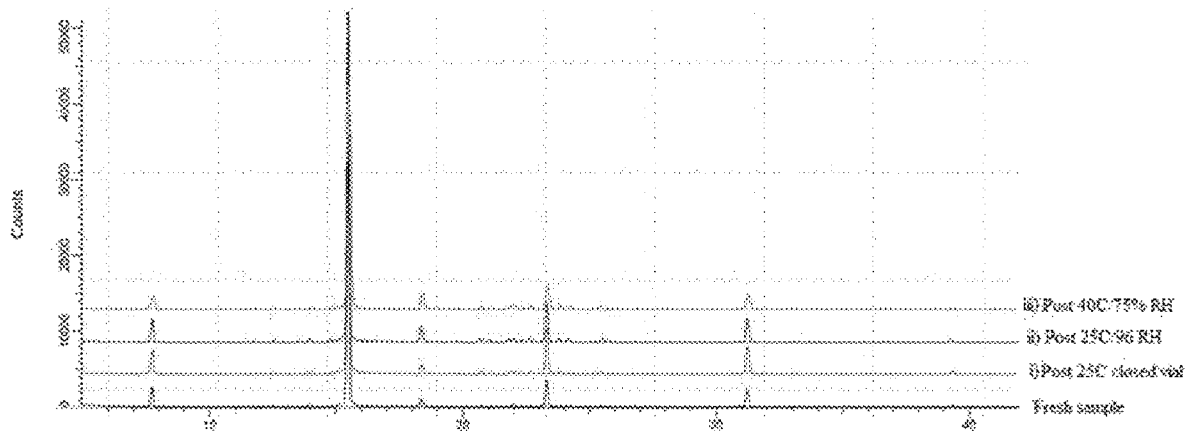
FIG. 10 shows the XRPD patterns of I-7a after storing solid samples for 22 days under the following conditions: i) 25° C., closed vial, ii) 25° C./96% RH, and iii) 40° C./75% RH, and comparing to fresh sample.

The storage stability of I-7a was also assessed by storing the solid samples for 22 days under the following conditions: i) 25° C., closed vial, ii) 25° C./96% RH, and iii) 40° C./75% RH, and comparing to fresh sample by XRPD. The results are presented in FIG. 10, which showed no change in form by XRPD post storage. There was also no loss of purity post storage for any of i) to iii) according to $^1$H NMR and UPLC.

Figure 11:
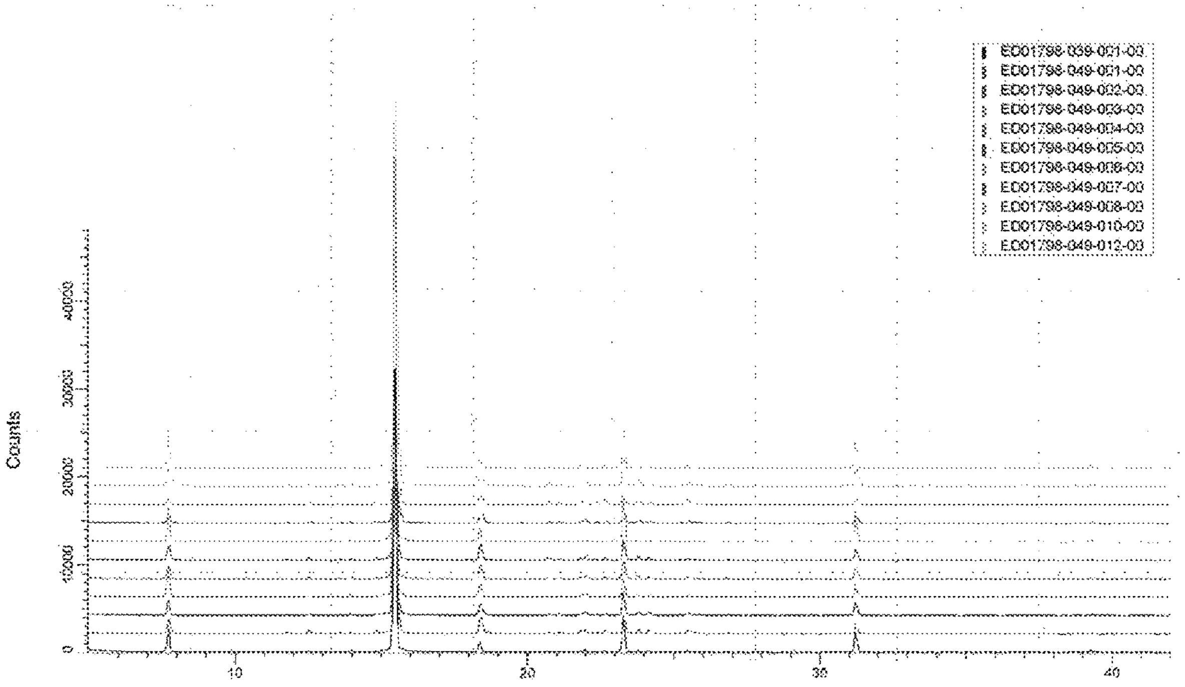
FIG. 11 shows the XRPD patterns of I-7a after maturation in 12 different solvents.

The benzenesulfonate salt (I-7a) was also subjected to maturation in 12 different solvents Briefly, 12 portions of I-7a (each ca.10 mg) were weighed into amber glass vials and treated with the following 12 solvents: TBME, acetone, chloroform, THF, ethyl acetate, ethanol, acetonitrile, heptane, water, toluene, 2-methoxyethanol, and benzyl alcohol. The resulting slurries were subjected to maturation with thermal cycling between room temperature and 50° C. (4 hours at each condition) for 3 days. Solids were then analysed by XRPD. All samples were isolated as solids and retained their initial crystalline form according to XRPD analysis (FIG. 11).

Example 3

Synthesis of tartrate salt of 3-(2-(dimethylamino)ethyl)-1H-indol-4-ol (I-7b)(tartrate salt of I-7/psilocin/psilocin-$d_0$/PI-$d_0$)

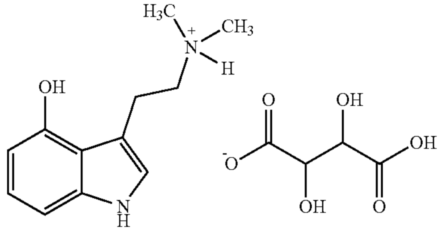

L-tartaric acid salt (1 eq). Compound I-7 (PI-$d_0$, free base)(10 mM) was dissolved in 1,4-dioxane, acetonitrile, or THF and treated with a solution of L-tartaric acid (10 mM) while being stirred at ambient temperature. Samples were shaken overnight at room temperature to produce I-7b (as a mono-L-tartrate salt of PI-$d_0$).

As shown in FIG. 12, the X-ray powder diffraction (XRPD) pattern indicates that two different crystalline polymorphs of I-7b were formed: a polymorph having pattern 1 (made from acetonitrile or THF), and a polymorph having pattern 2 (made from 1,4-dioxane). The XRPD peak listing of I-7b (pattern 1) is provided in Table 13.

TABLE 13

| Caption (display) | Angle | d Value | Net Intensity | Rel. Intensity |
|---|---|---|---|---|
| 6.798° | 6.798303 | 12.99172 | 81.18942 | 0.038823 |
| 11.360° | 11.36046 | 7.782664 | 38.20749 | 0.01827 |
| 12.764° | 12.76448 | 6.929597 | 187.3042 | 0.089565 |
| 13.535° | 13.53549 | 6.536554 | 359.2127 | 0.171768 |
| 14.837° | 14.83685 | 5.966021 | 518.4961 | 0.247934 |
| 15.973° | 15.97262 | 5.544258 | 221.2755 | 0.105809 |
| 16.351° | 16.35057 | 5.416944 | 88.56068 | 0.042348 |
| 17.367° | 17.36715 | 5.102086 | 2091.27 | 1 |
| 18.937° | 18.93699 | 4.682525 | 859.745 | 0.411111 |
| 20.168° | 20.16842 | 4.399317 | 729.6246 | 0.348891 |
| 20.929° | 20.92882 | 4.241163 | 299.6507 | 0.143287 |
| 21.946° | 21.94606 | 4.046822 | 686.9625 | 0.328491 |
| 22.719° | 22.71909 | 3.910844 | 1124.994 | 0.537948 |
| 23.604° | 23.6036 | 3.766255 | 214.5516 | 0.102594 |
| 23.814° | 23.81428 | 3.733409 | 211.4754 | 0.101123 |
| 24.874° | 24.87359 | 3.57676 | 376.8852 | 0.180218 |
| 25.609° | 25.60921 | 3.475661 | 285.7198 | 0.136625 |
| 26.745° | 26.74474 | 3.330612 | 251.1225 | 0.120081 |
| 27.111° | 27.11058 | 3.286493 | 138.8324 | 0.066387 |
| 27.558° | 27.55802 | 3.23414 | 68.66545 | 0.032834 |
| 28.653° | 28.65312 | 3.112975 | 232.9794 | 0.111406 |
| 29.630° | 29.63035 | 3.012493 | 176.5445 | 0.08442 |
| 31.129° | 31.12856 | 2.870833 | 132.7006 | 0.063455 |
| 31.567° | 31.56692 | 2.831959 | 106.4913 | 0.050922 |
| 32.180° | 32.18027 | 2.779369 | 100.1601 | 0.047894 |
| 33.073° | 33.0727 | 2.706382 | 58.33579 | 0.027895 |
| 34.096° | 34.09647 | 2.627426 | 68.95352 | 0.032972 |
| 34.460° | 34.46035 | 2.60051 | 147.7838 | 0.070667 |
| 36.226° | 36.22648 | 2.477677 | 73.88321 | 0.035329 |
| 37.497° | 37.49681 | 2.396604 | 137.836 | 0.06591 |
| 38.727° | 38.72692 | 2.323263 | 90.82414 | 0.04343 |
| 41.126° | 41.12576 | 2.193118 | 80.7093 | 0.038593 |

Figure 13:
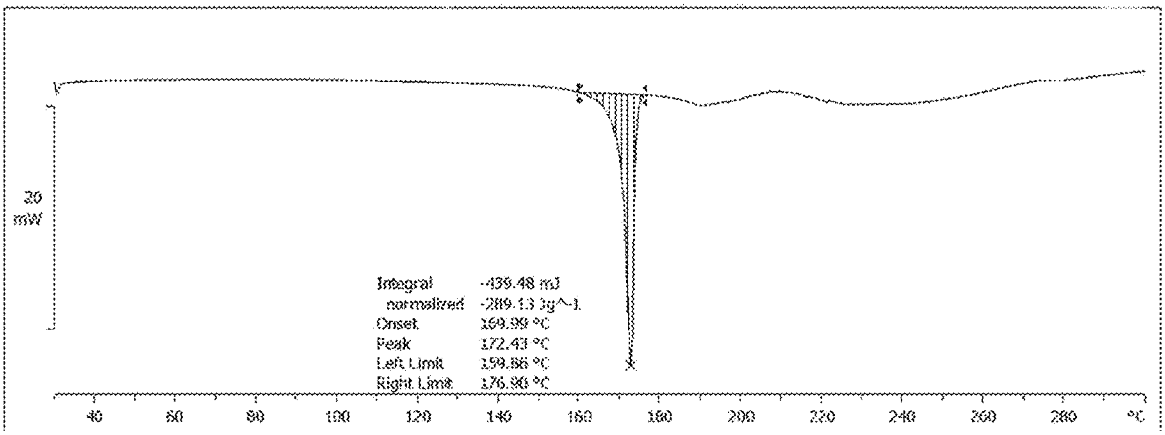
FIG. 13 shows the DSC curve of I-7b (polymorph of pattern 1)

The DSC curve of T-7b (polymorph of pattern 1) is shown in FIG. 13 and it is evident that the salt has a high melt onset (169.99° C.) and peak (172.43° C.). Equally, no events were observed prior to the melt endotherm, indicating the absence of multiple physical forms in the sample, and also no conversion of physical forms prior to the melt.

Figure 14:
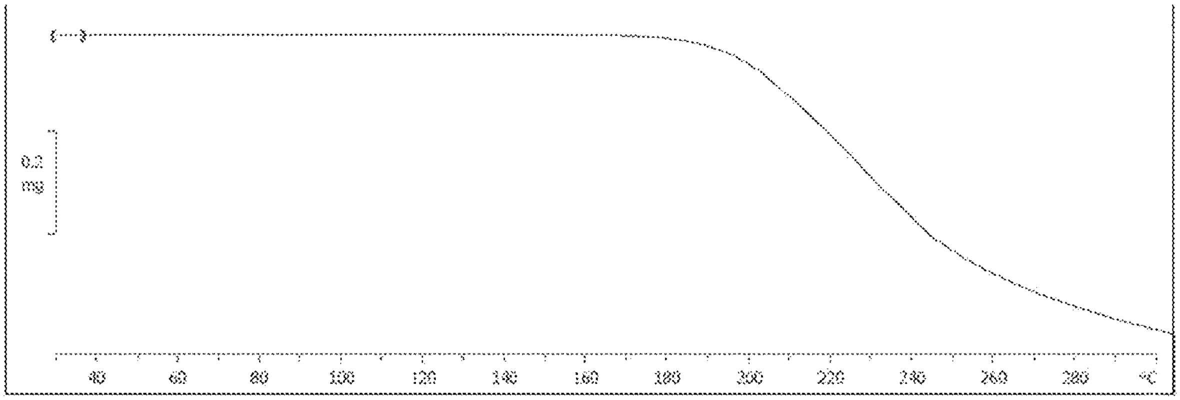
FIG. 14 shows the TGA curve of I-7b (polymorph of pattern 1)

The thermogravimetric analysis (TGA) curve of I-7b (polymorph of pattern 1) as shown in FIG. 14 showed no significant mass lost until about 180° C. at a heating rate of 10° C./min.

Figure 15A:
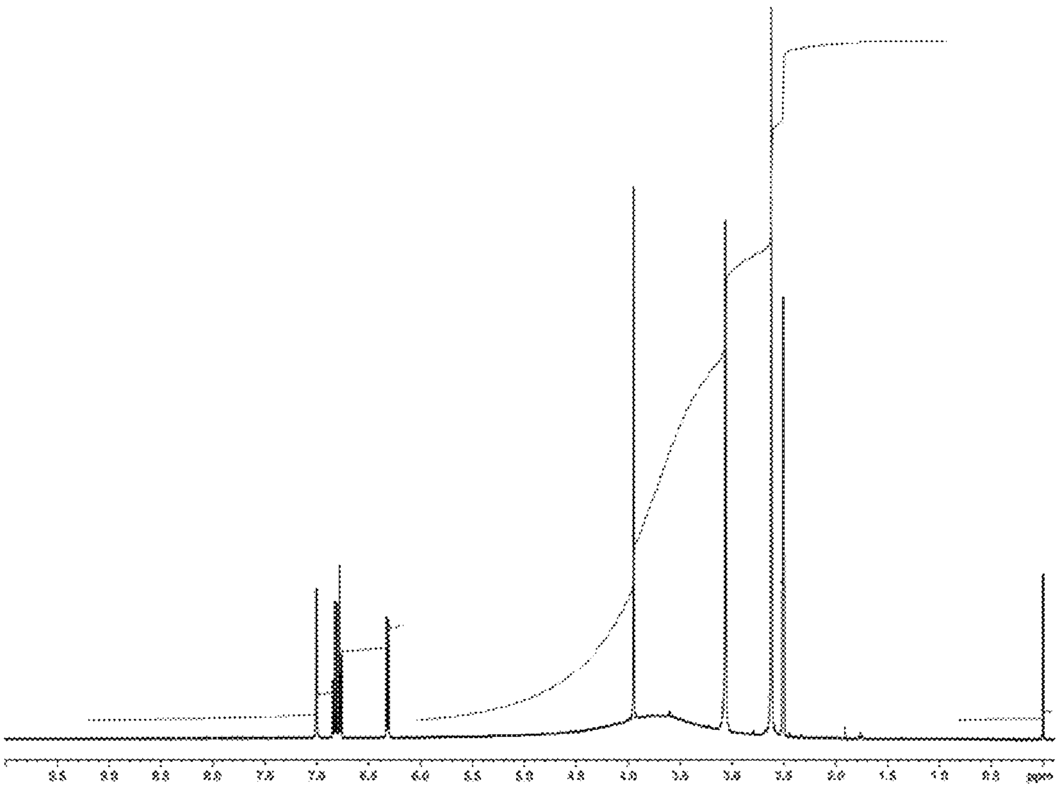
FIGS. 15A-15B show the $^1$H NMR spectrum of I-7b (polymorph of pattern 1)
Figure 15B:
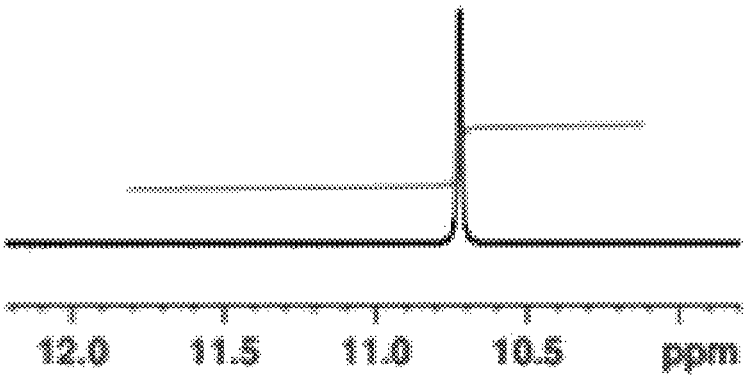

FIGS. 15A and 15B show a $^1$H NMR spectrum of I-7b (polymorph of pattern 1), which indicates protonation and 1 molar equivalent of L-tartrate.

Figure 16:
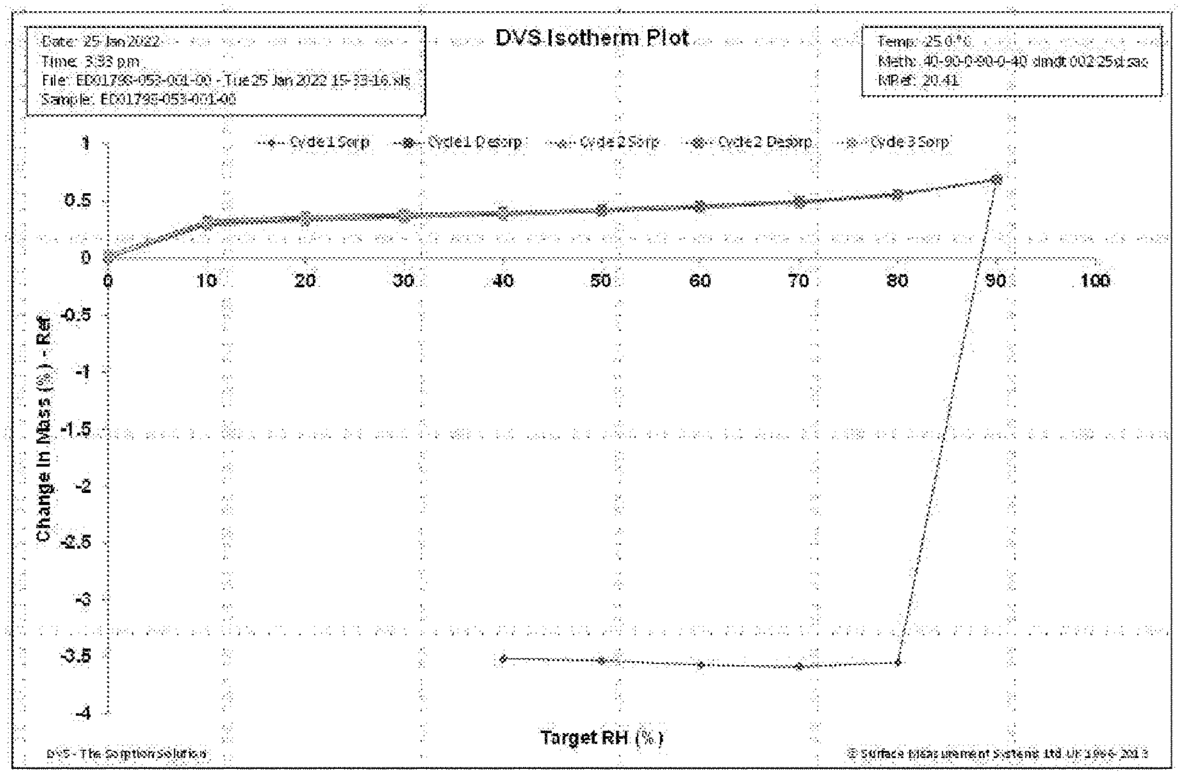
FIG. 16 shows a DVS isotherm plot of I-7b (polymorph of pattern 1)
Figure 17:
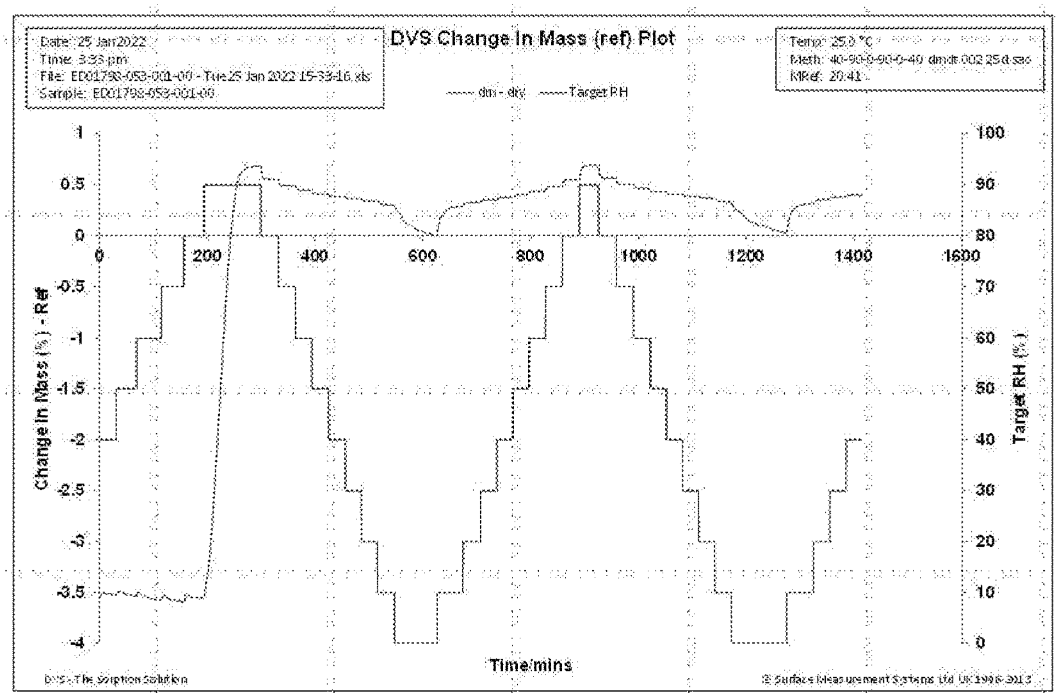
FIG. 17 shows a DVS change in mass plot of I-7b (polymorph of pattern 1)

In DVS experiments with polymorph of pattern 1 (FIG. 16), the first sorption cycle showed a large mass change (+4.2%, relative to 0% RH) between 80-90% RH, and a 0.7% mass increase over 0-90% RH range in the second sorption cycle. This can be seen in the DVS change in mass plot of FIG. 17.

Figure 18:
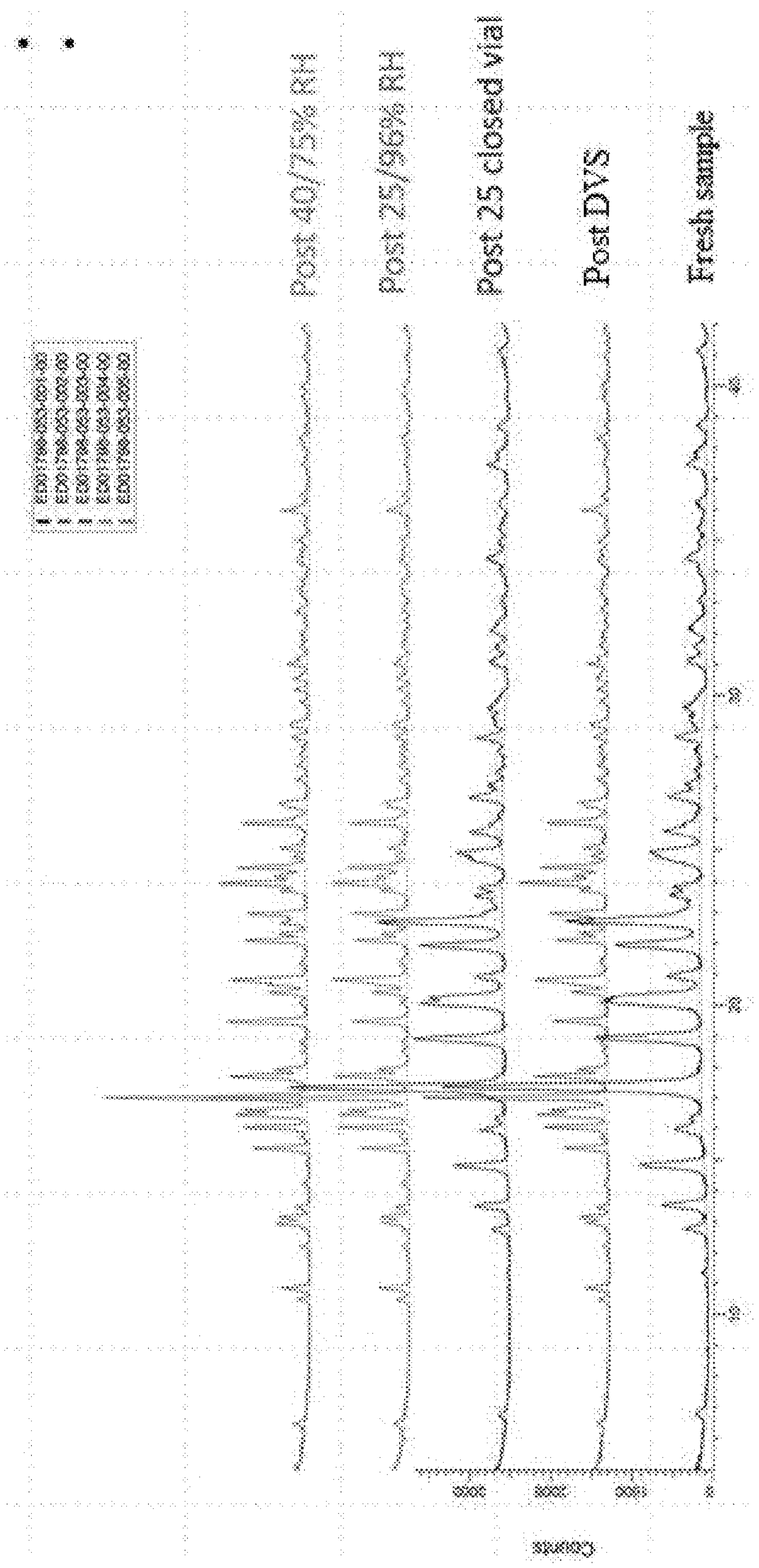
FIG. 18 shows the XRPD patterns of I-7b (polymorph of pattern 1) after storing solid samples for 22 days under the following conditions: i) 25° C., closed vial, ii) 25° C./96% RH, and iii) 40° C./75% RH, and comparing to fresh sample, with samples ii), iii) and post DVS indicating a change in form to polymorph of pattern 3.

The storage stability of I-7b was also assessed by storing the solid samples for 7 days under the following conditions: i) 25° C., closed vial, ii) 25° C./96% RH, iii) 40° C./75% RH, and comparing to fresh sample and the sample post DVS from above by XRPD. The results are presented in FIG. 18, which showed a change in form (formation of a hydrate; pattern 3) by XRPD post storage under elevated humidity conditions and post DVS. The sample stored at 25° C. in a closed vial showed no change by XRPD.

Figure 19A:
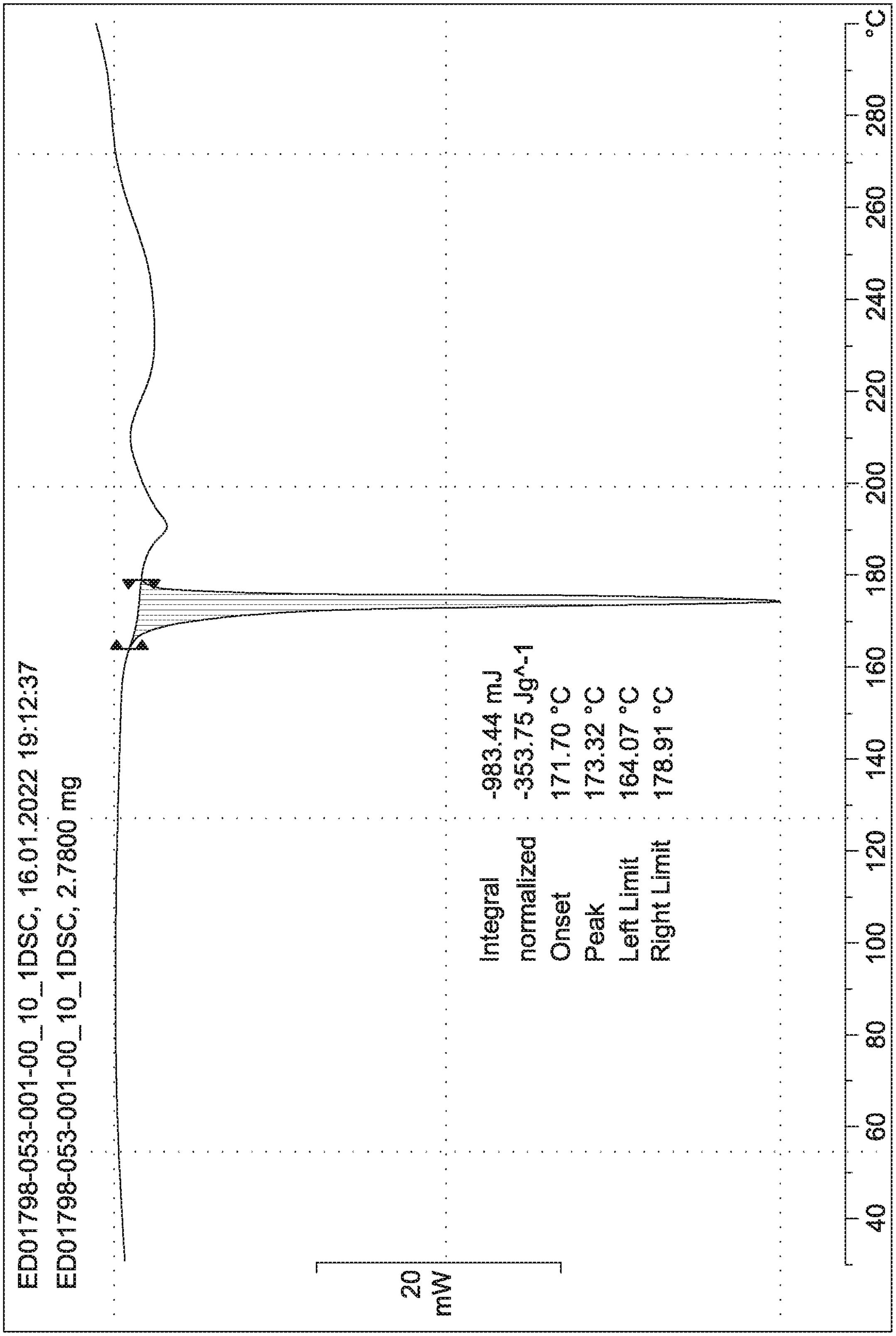
FIGS. 19A-19B show the DSC plots of I-7b (polymorph of pattern 1) pre-DVS (FIG. 19A) and post-DVS (FIG. 19B)
Figure 19B:
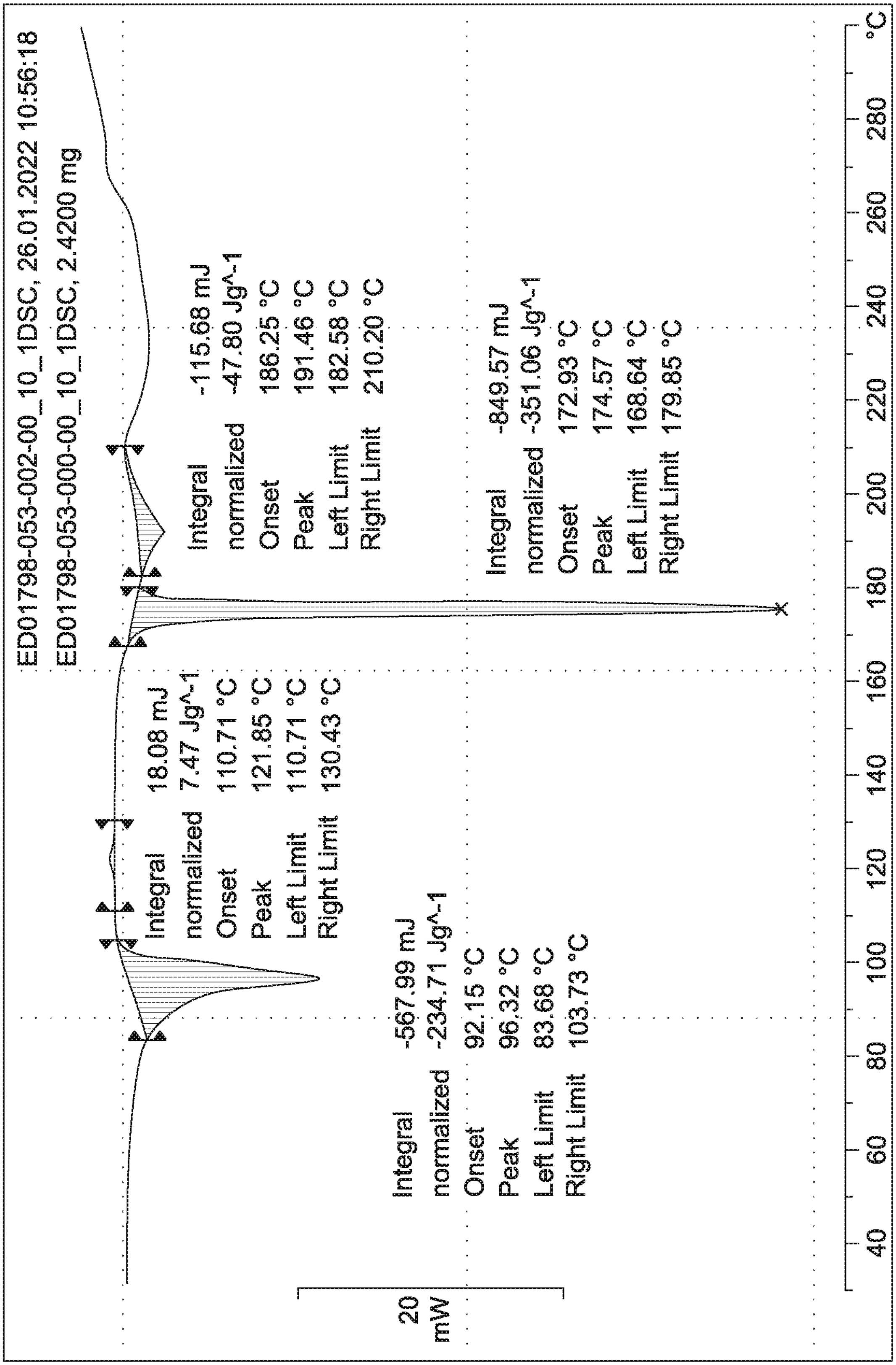
Figure 20A:
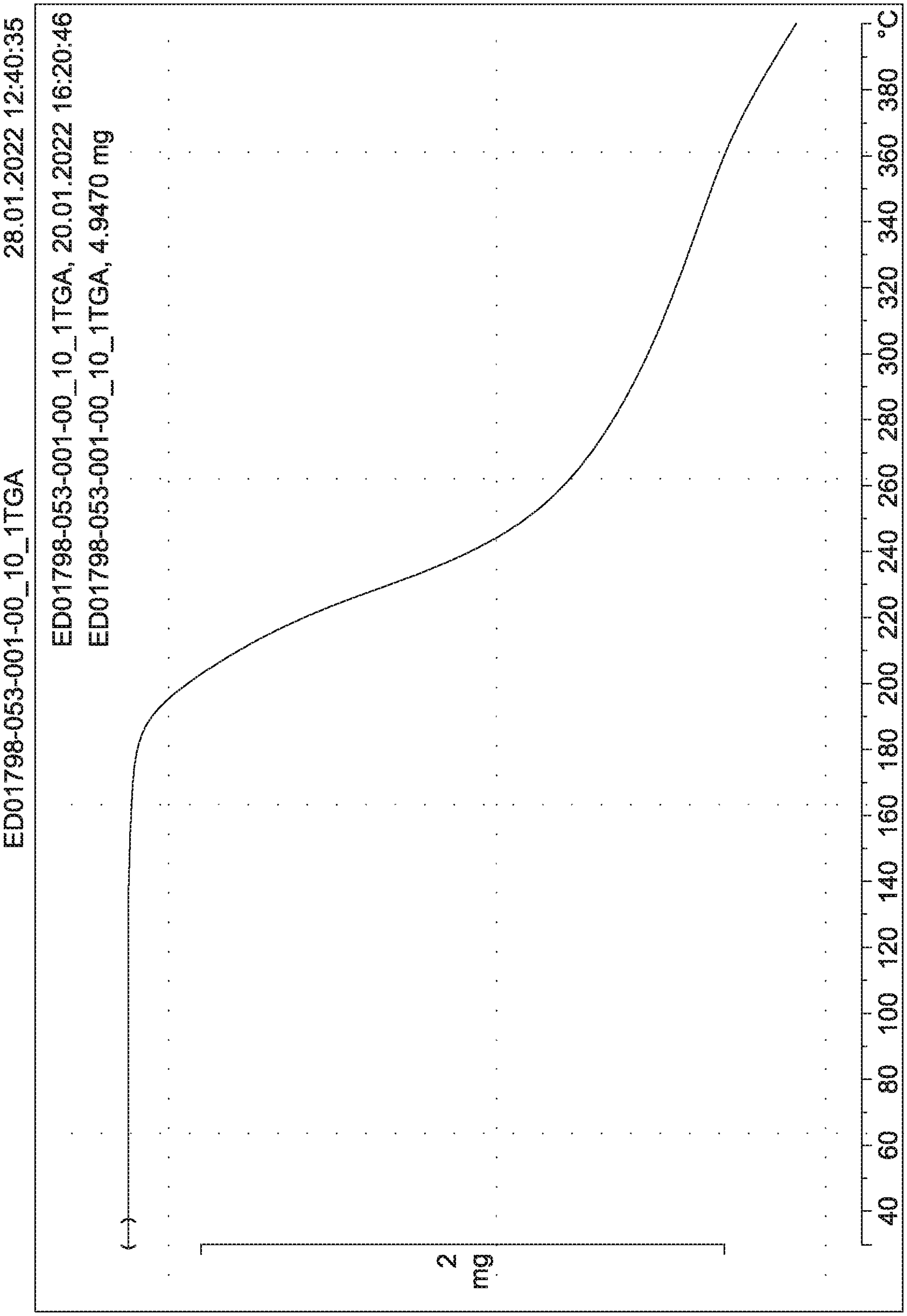
FIGS. 20A-20B show the TGA plots of I-7b (polymorph of pattern 1) pre-DVS (FIG. 20A) and post-DVS (FIG. 20B)
Figure 20B:
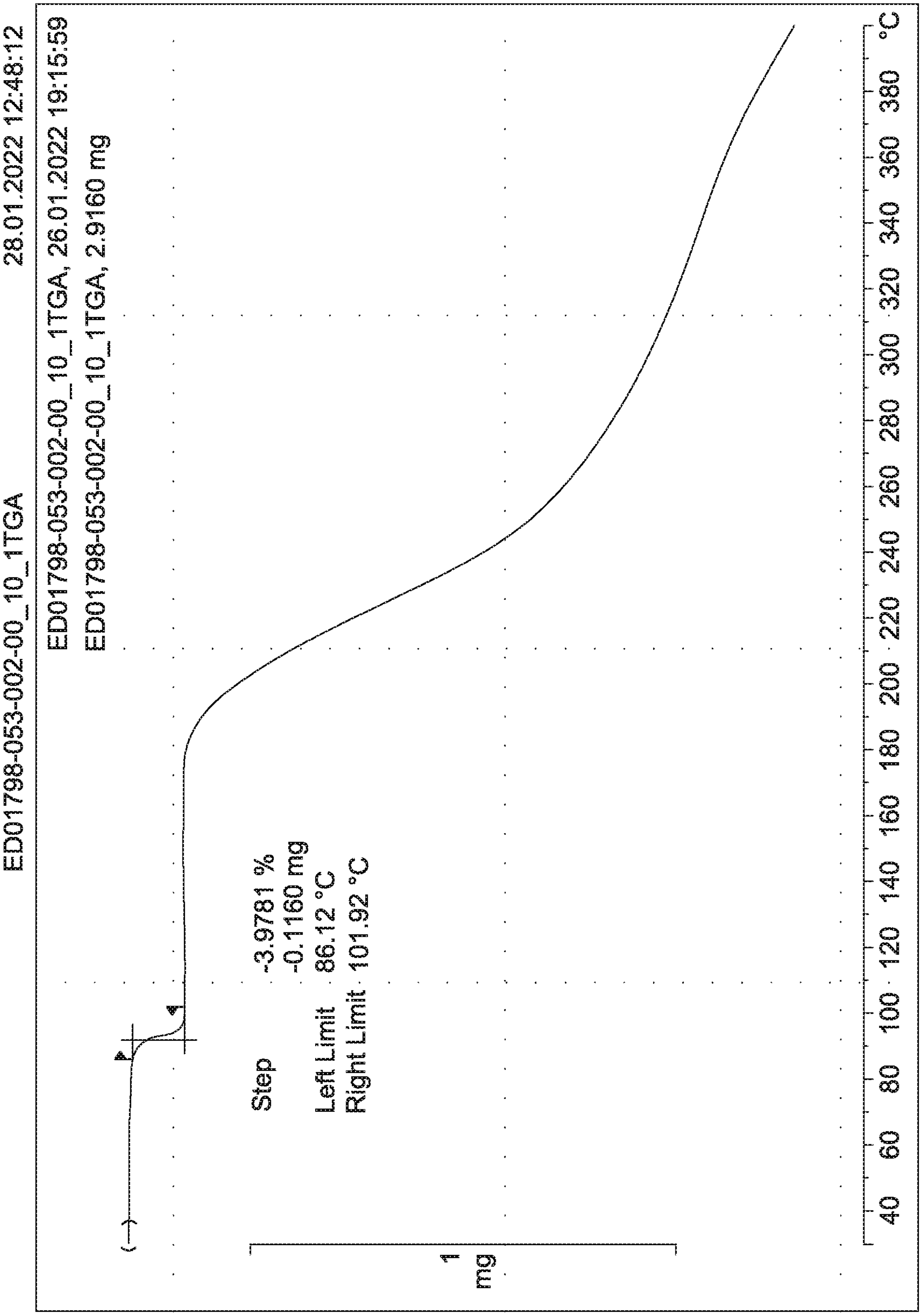

The changes to I-7b (polymorph of pattern 1) pre- and post-DVS can be seen in the DSC plots of FIG. 19A and FIG. 19B, respectively, as well as the TGA plots of pre- and post-DVS material in FIG. 20A and FIG. 20B, respectively.

Figure 21:
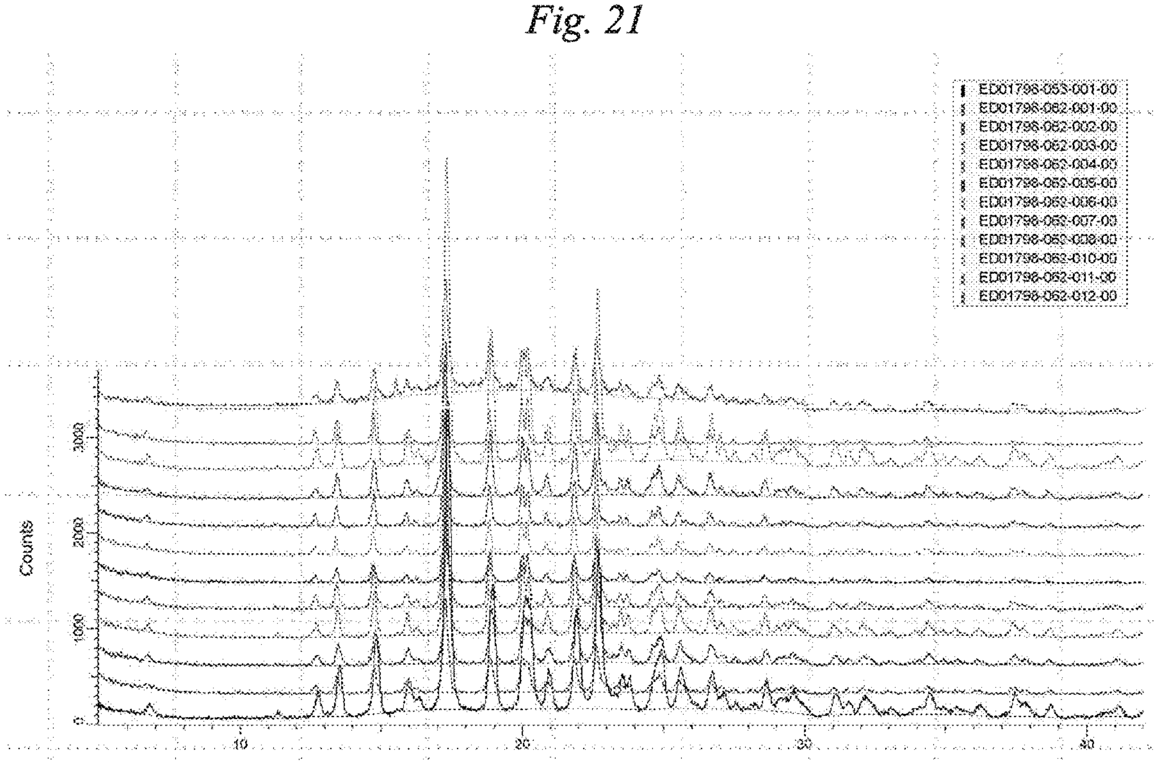
FIG. 21 shows the XRPD patterns of I-7b (polymorph of pattern 1) after maturation in 12 different solvents.

I-7b (polymorph of pattern 1) was also subjected to maturation in 12 different solvents following the procedure detailed in Example 2. All samples were isolated as solids and retained their initial crystalline form according to XRPD analysis (FIG. 21).

L-tartaric acid salt (0.5 eq). Compound I-7 (PI-$d_0$, free base)(10 mM) was dissolved in 1,4-dioxane or THF and treated with a solution of L-tartaric acid (5 mM) while being stirred at ambient temperature. Samples were shaken overnight at room temperature to produce I-7b (L-tartrate salt of PI-$d_0$).

Figure 22:
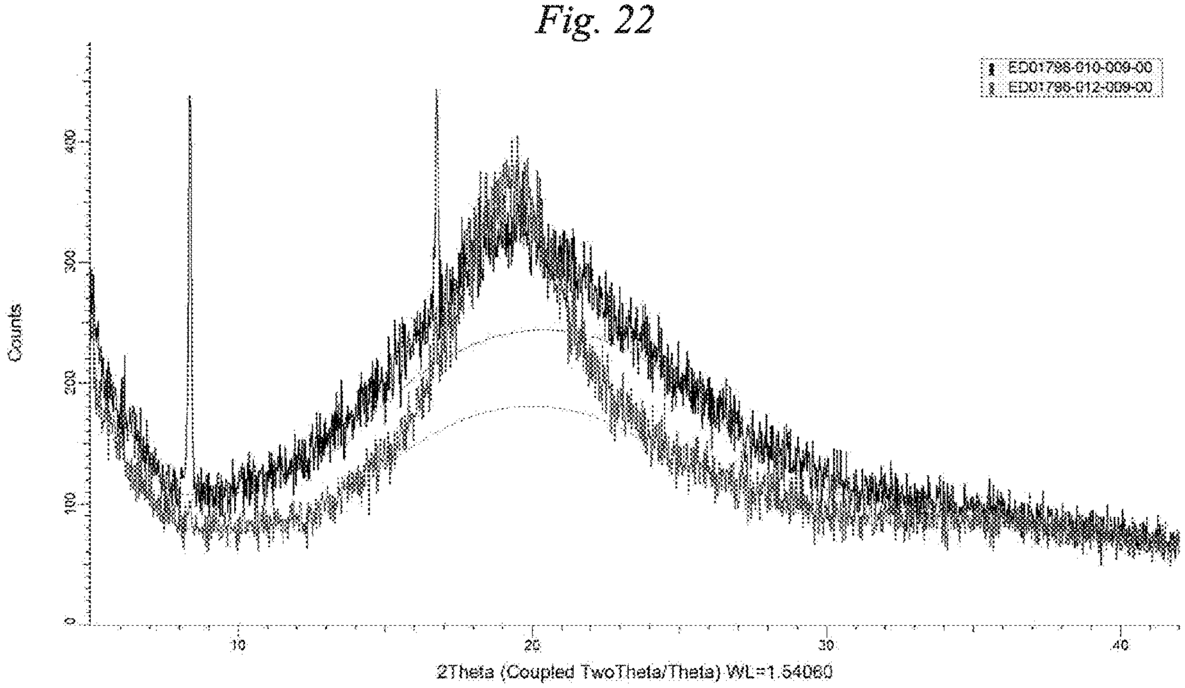
FIG. 22 shows the XRPD patterns of I-7b (amorphous) obtained from salt formation with 0.5 eq of L-tartaric acid from either 1,4-dioxane or THF.

As shown in FIG. 22, the X-ray powder diffraction (XRPD) pattern indicates that the obtained salts were largely amorphous, with only some weak diffraction peaks observed in the sample from THF.

Example 4

Synthesis of hemi-fumarate salt of 3-(2-(dimethylamino)ethyl)-1H-indol-4-ol (I-7c)(hemi-fumarate salt of I-7/psilocin/psilocin-$d_0$/PI-$d_0$)

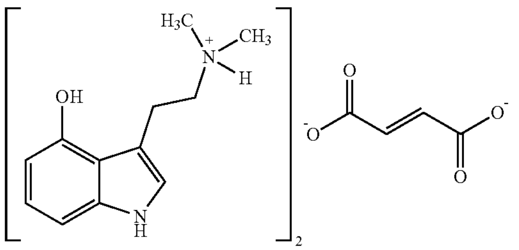

Compound I-7 (PI-$d_0$, free base)(10 mM) was dissolved in 1,4-dioxane, acetonitrile, or THF and treated with a solution of fumaric acid (0.25M solution in THF, 10 mM or 5 mM) while being stirred at ambient temperature. Samples were shaken overnight at room temperature to produce I-7c (as a hemi-fumarate salt of PI-$d_0$).

Figure 23:
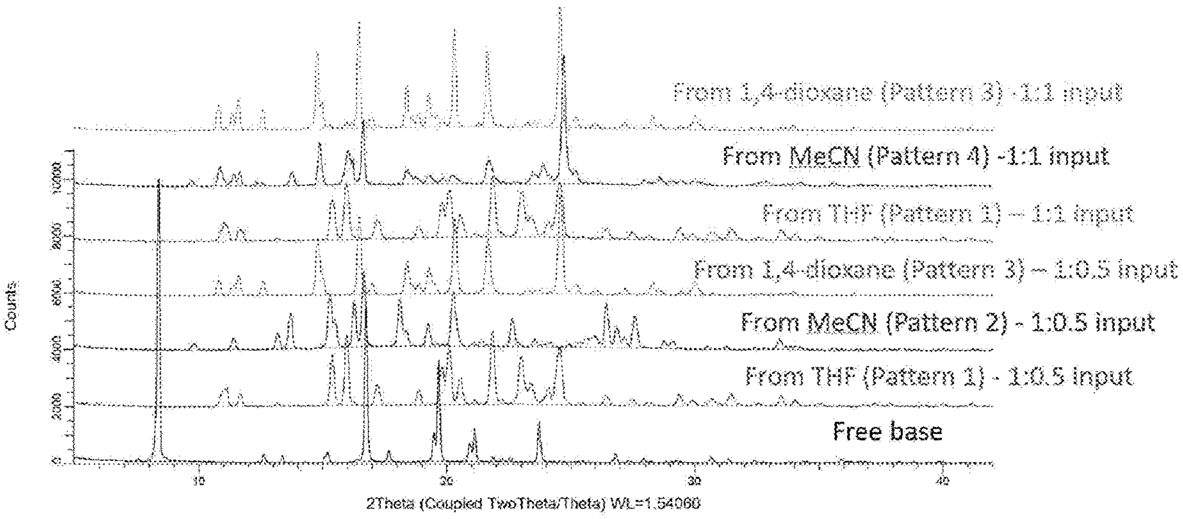
FIG. 23 shows the XRPD pattern of four different crystalline polymorphs of I-7c: a polymorph having pattern 1 (made from either 0.5 eq or 1 eq fumaric acid and THF), a polymorph having pattern 2 (made from 0.5 eq fumaric acid and acetonitrile), a polymorph having pattern 3 (made from either 0.5 eq or 1 eq fumaric acid in 1,4-dioxane), and a polymorph having pattern 4 (made from 1 eq fumaric acid in acetonitrile)

As shown in FIG. 23, the X-ray powder diffraction (XRPD) pattern indicates that four different crystalline polymorphs of I-7c were formed: a polymorph having pattern 1 (made from either 0.5 eq or 1 eq fumaric acid and THF), a polymorph having pattern 2 (made from 0.5 eq fumaric acid and acetonitrile), a polymorph having pattern 3 (made from either 0.5 eq or 1 eq fumaric acid in 1,4-dioxane), and a polymorph having pattern 4 (made from 1 eq fumaric acid in acetonitrile).

Figure 24:
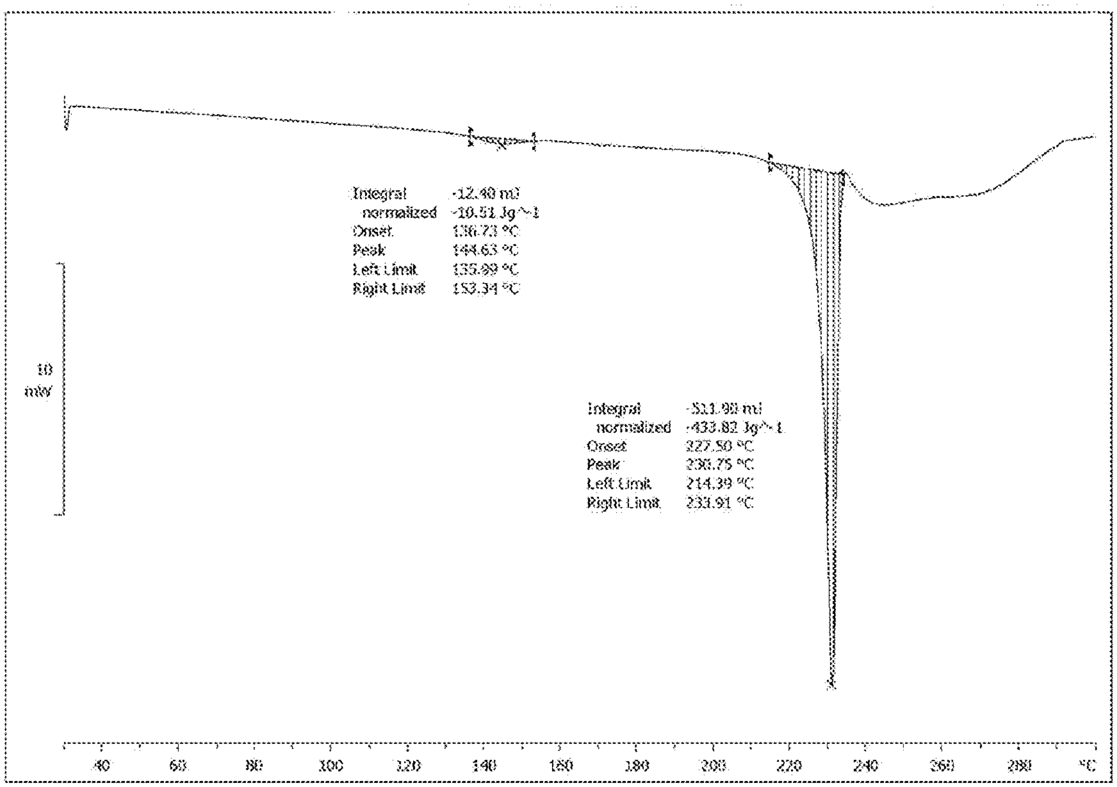
FIG. 24 shows a DSC of I-7c (polymorph of pattern 4)
Figure 25:
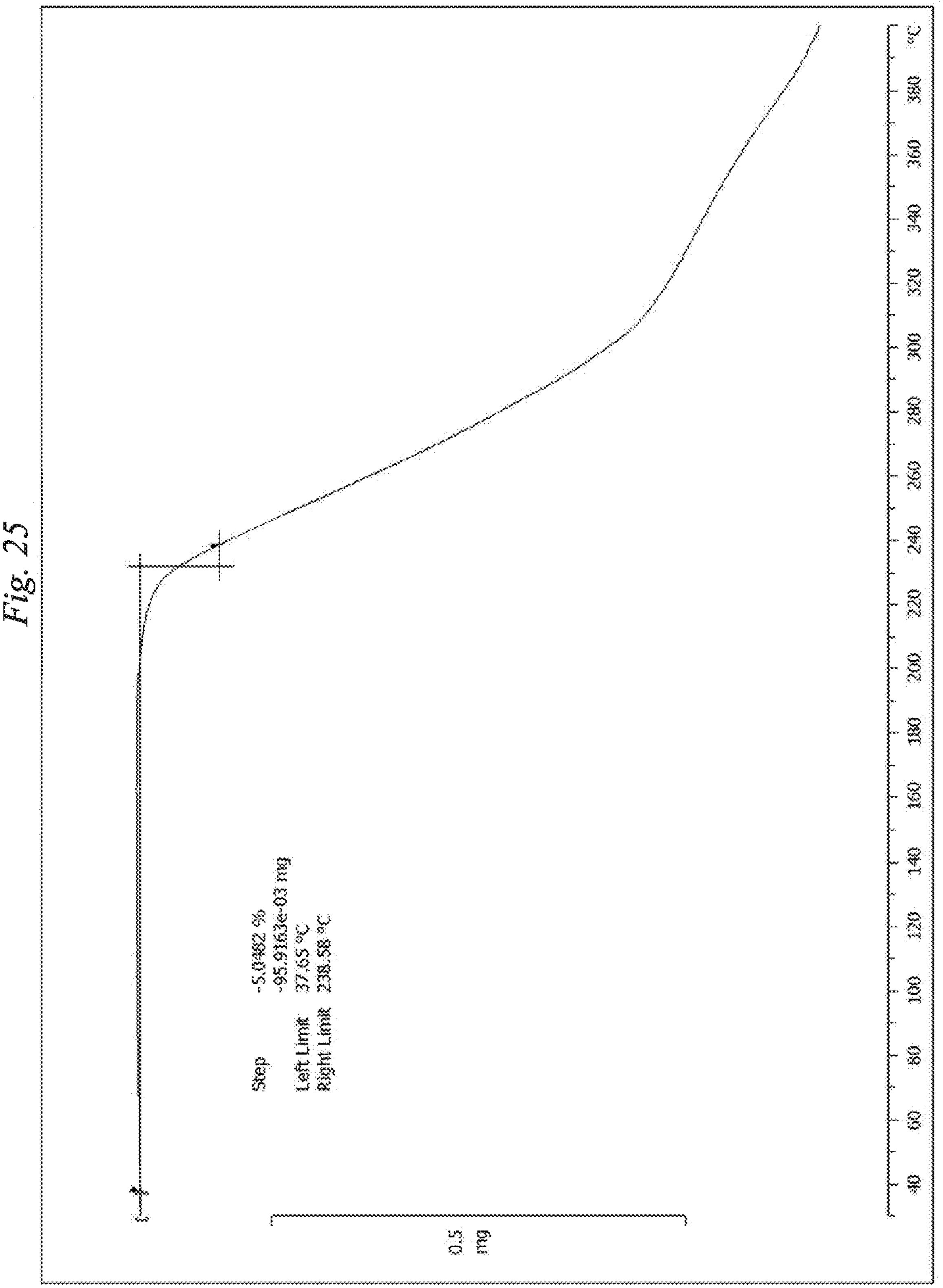
FIG. 25 shows a TGA of I-7c (polymorph of pattern 4)

The DSC of I-7c (polymorph of pattern 4) at 10° C./min shows a small endothermic event at 137° C. and an endothermic event of onset at about 228° C. (FIG. 24). Additionally, TGA of I-7c (polymorph of pattern 4) at 10° C./min shows no significant mass loss until about 220° C. and 95% mass remaining at 239° C. (FIG. 25).

Figure 26:
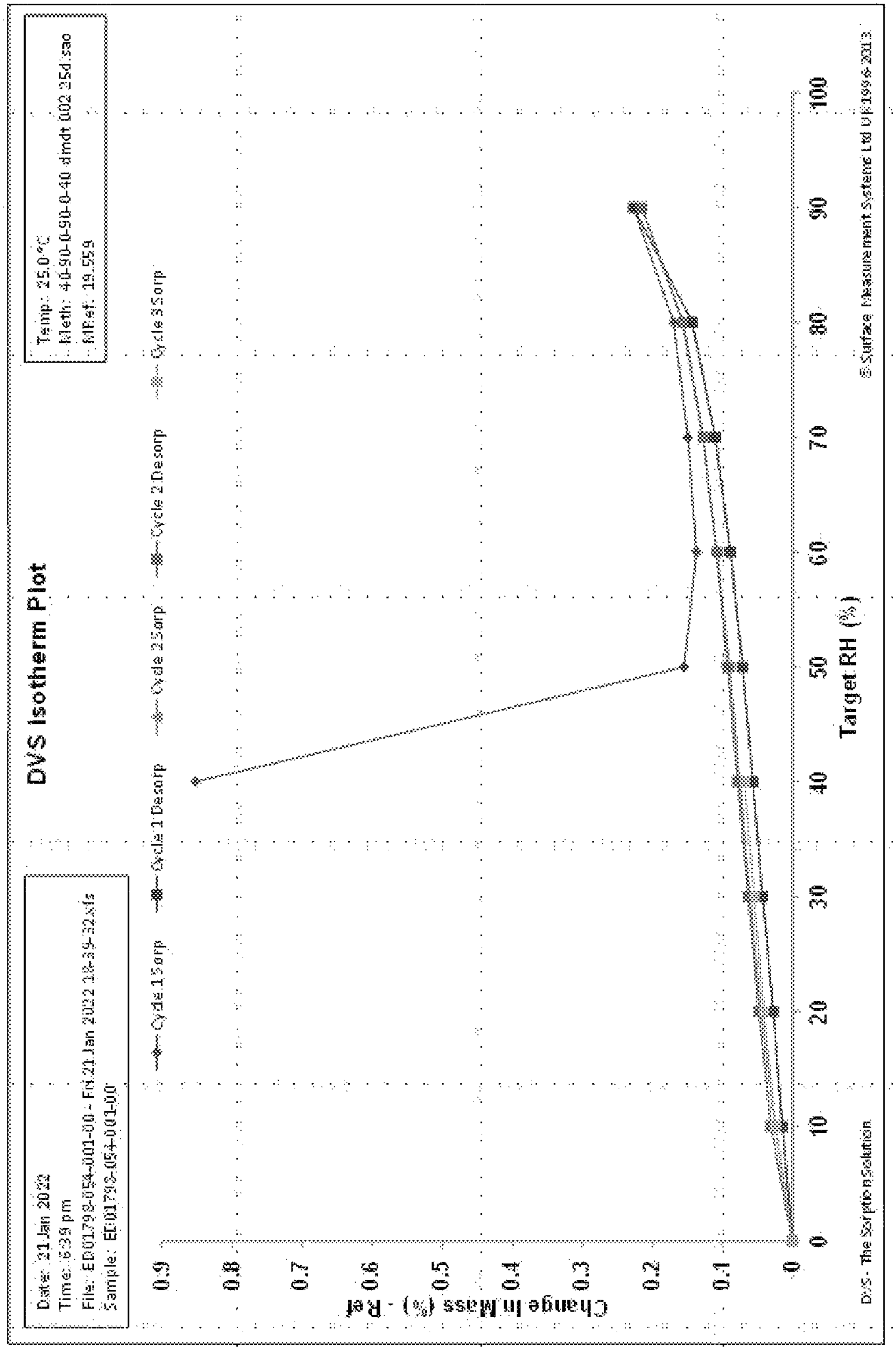
FIG. 26 shows a DVS of I-7c (polymorph of pattern 4)
Figure 27:
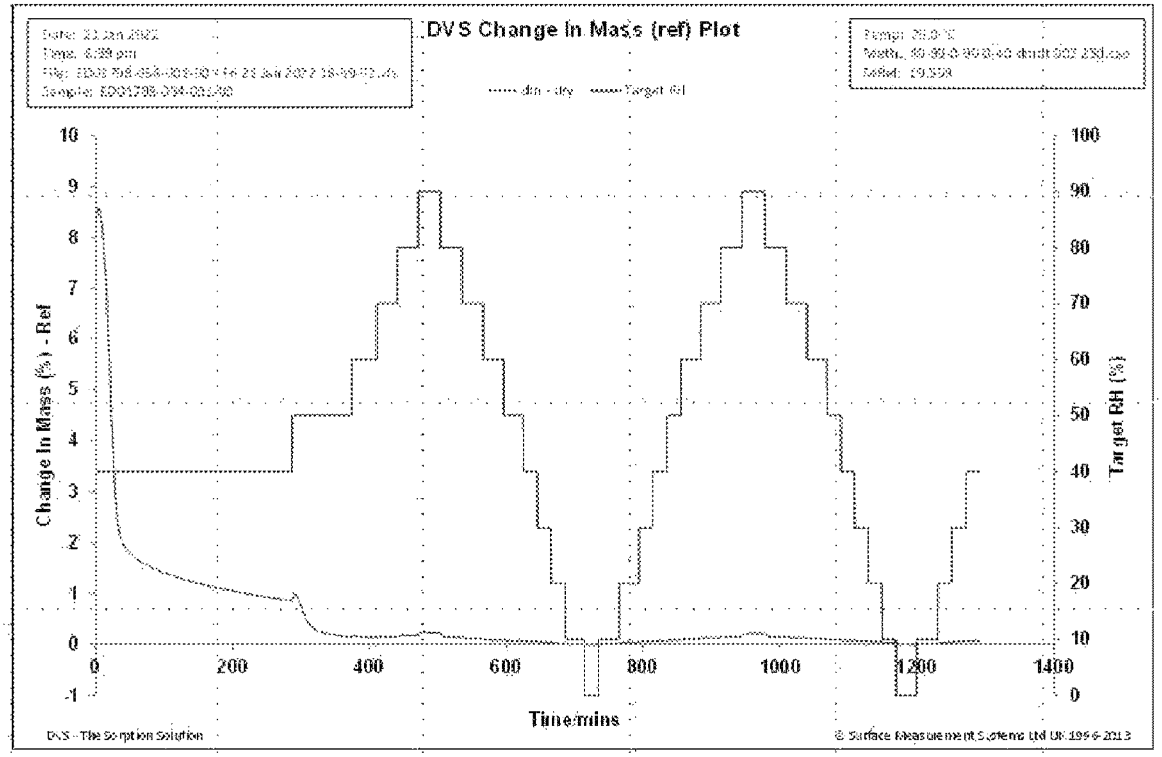
FIG. 27 shows a DVS change in mass plot of I-7c (polymorph of pattern 4)

DVS experiments with polymorph of pattern 4 (FIG. 26) initially showed a decrease in mass of about 0.7% between 40-60% RH, and a 0.2% mass increase over 0-90% RH range (second sorption cycle). This can also be seen in the DVS change in mass plot of FIG. 27.

Figure 29A:
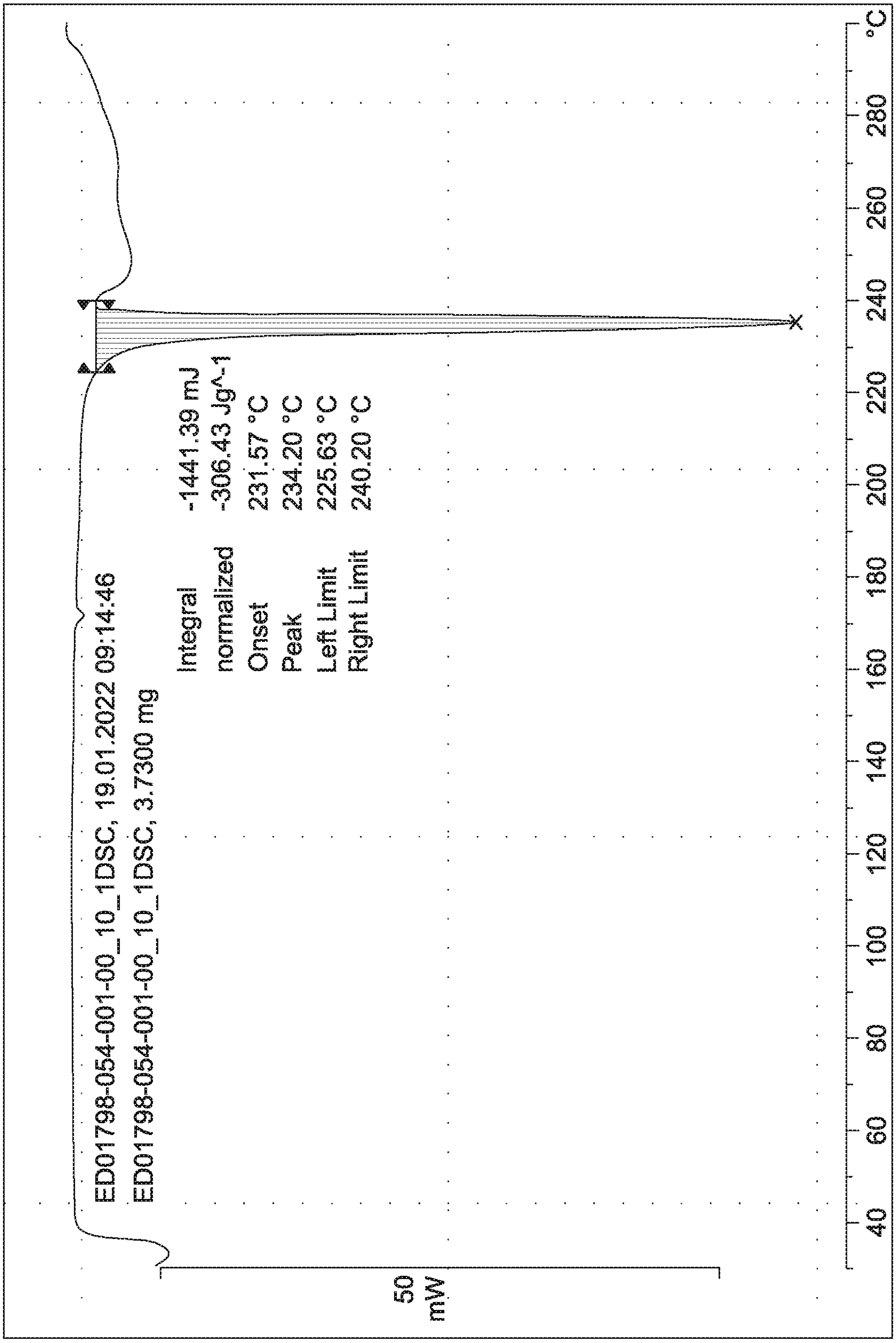
FIGS. 29A-29B show the DSC plot of I-7c pre-DVS (FIG. 29A, polymorph 5, obtained from scale-up using 1 eq fumaric acid in acetonitrile) and post-DVS (FIG. 29B, pattern 6)
Figure 29B:
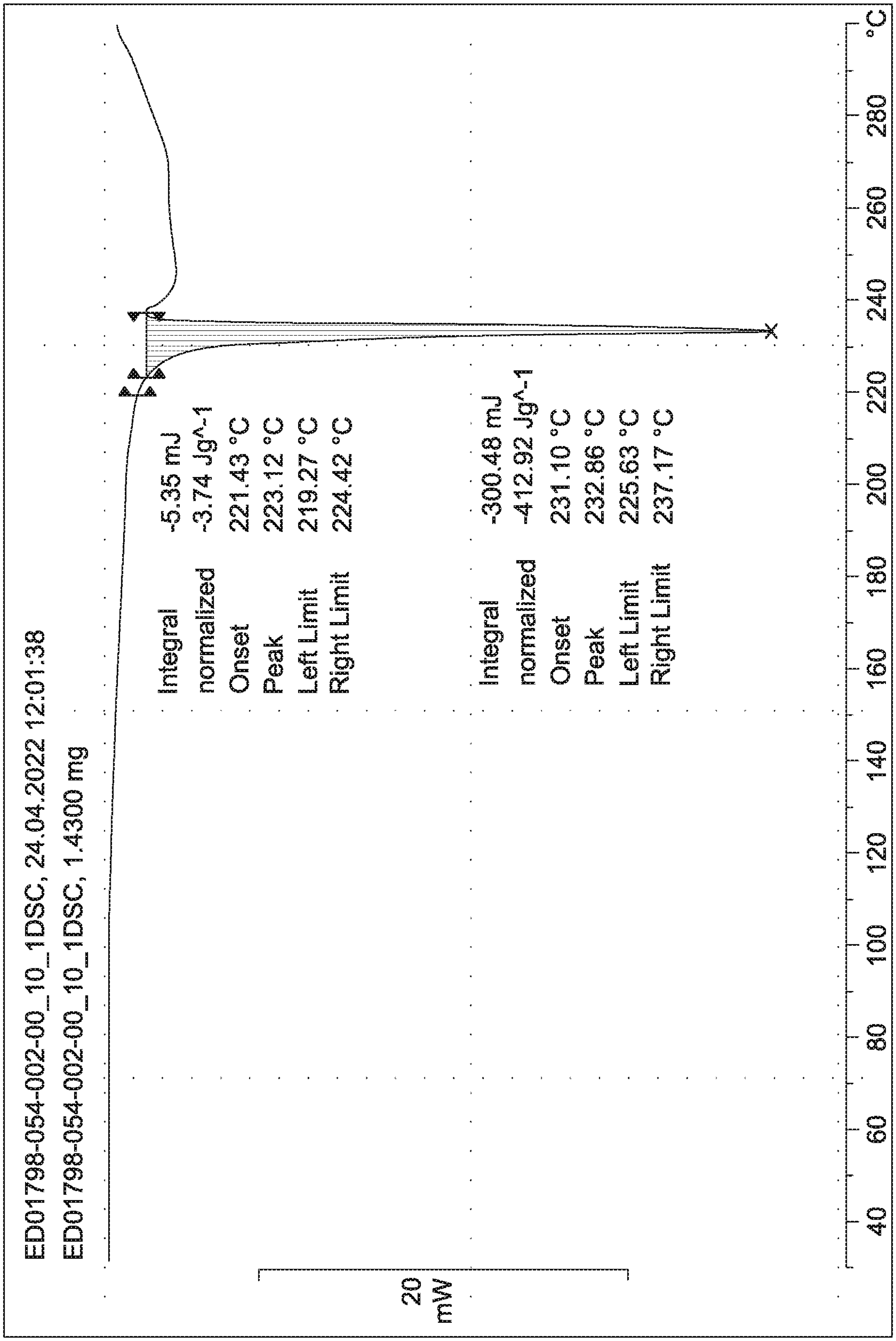
Figure 30A:
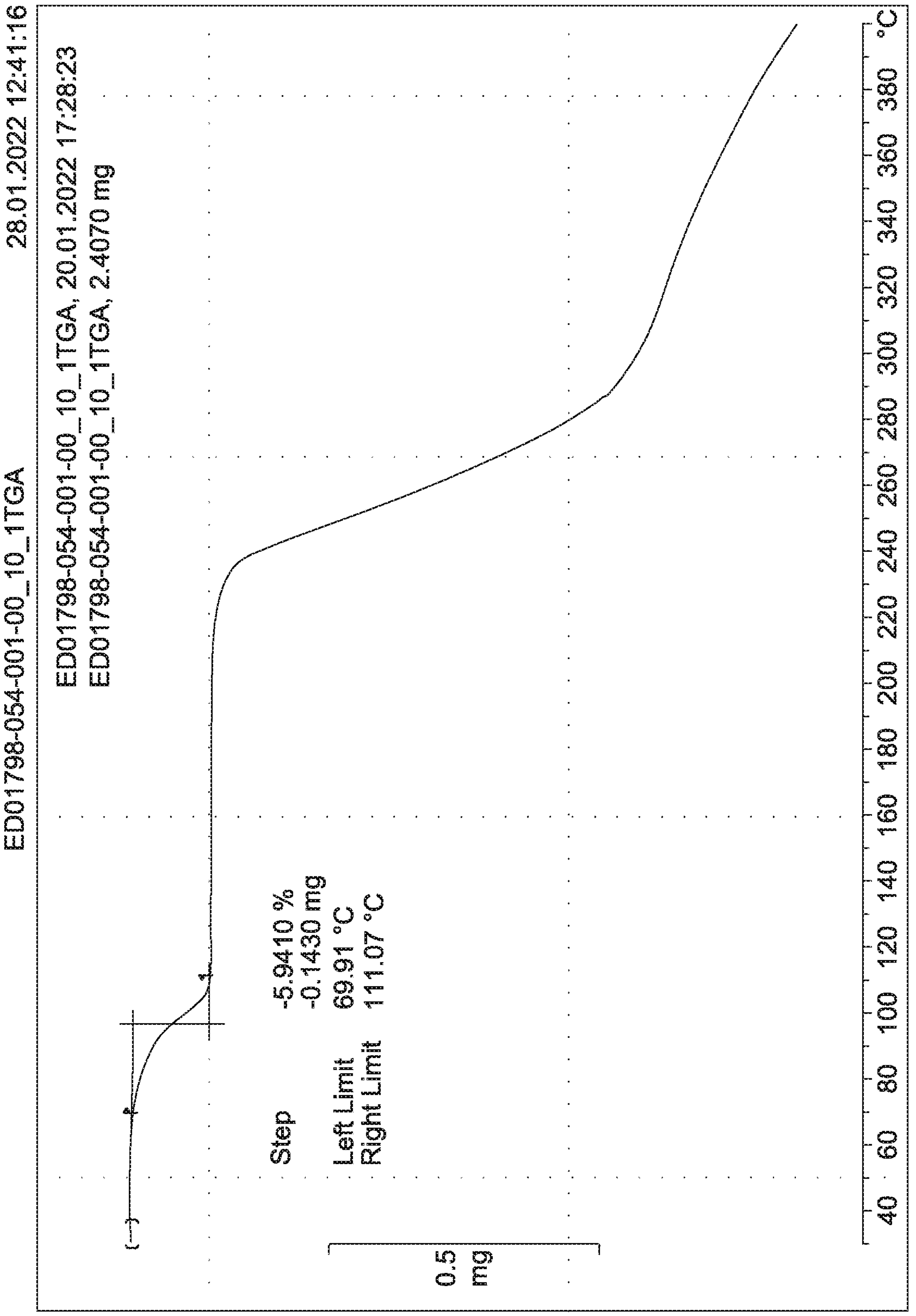
FIGS. 30A-30B show the TGA plot of I-7c pre-DVS (FIG. 30A, polymorph 5, obtained from scale-up using 1 eq fumaric acid in acetonitrile) and post-DVS (FIG. 30B, pattern 6)
Figure 30B:
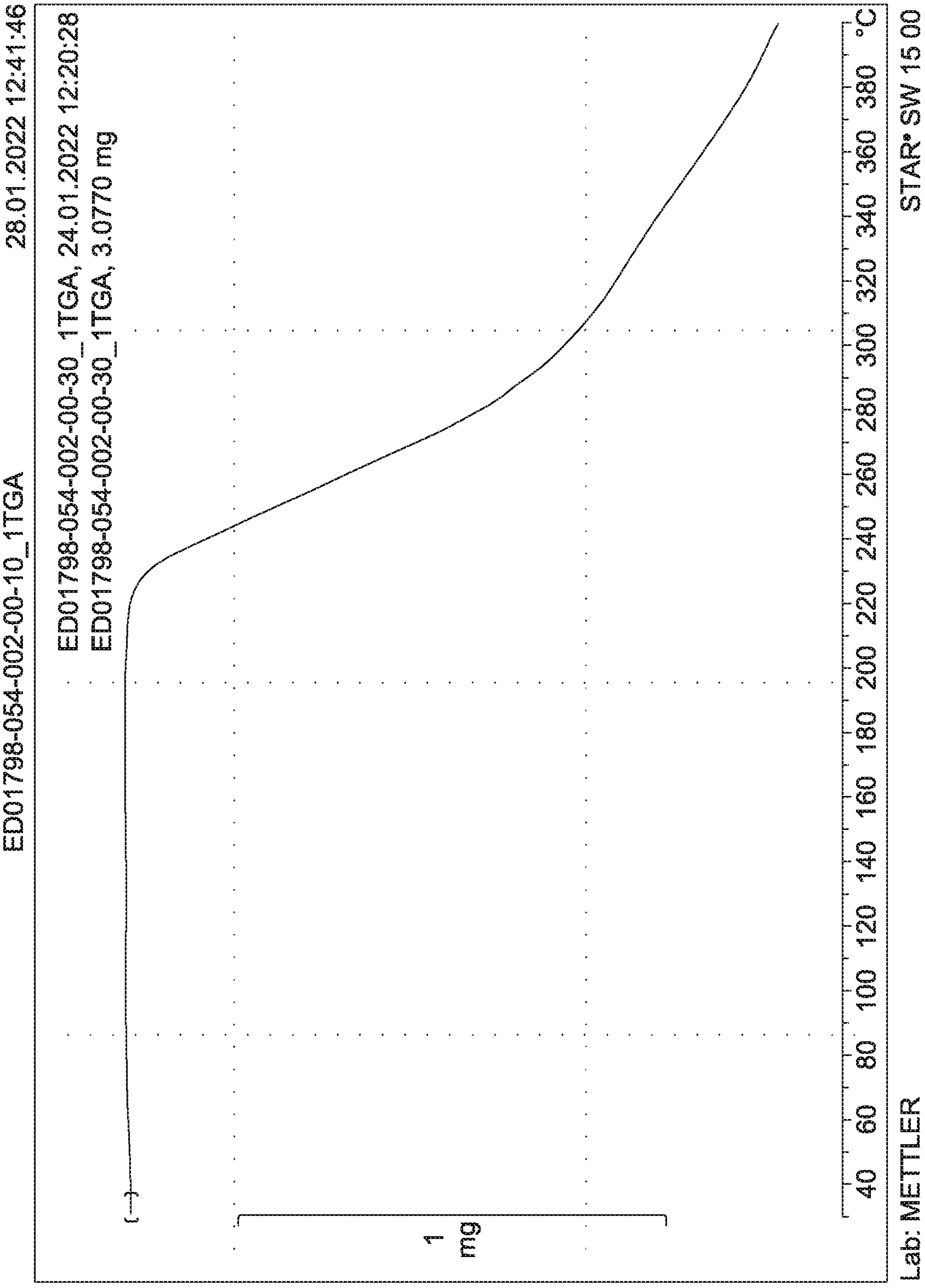

The changes to I-7c (polymorph of pattern 5, obtained from scale-up using 1 eq fumaric acid in acetonitrile seeded with I-7c of pattern 4, which was a moderately crystalline form) pre- and post-DVS can be seen in the XRPD pattern of FIG. 28, in the DSC plots of pre- and post-DVS material in FIG. 29A and FIG. 29B, respectively, as well as the TGA plots of pre- and post-DVS material in FIG. 30A and FIG. 30B, respectively. The TGA plot of pre-DVS material (FIG. 30A) shoed a step mass loss of 5.9%. The XRPD peak listing for I-7c (polymorph of pattern 5) is provided in Table 14.

TABLE 14

| Caption (display) | Angle | d Value | Net Intensity | Rel. Intensity |
|---|---|---|---|---|
| 8.483° | 8.483156 | 10.41482 | 202.1152 | 0.424545 |
| 8.733° | 8.733033 | 10.11738 | 44.55472 | 0.093588 |
| 11.080° | 11.08012 | 7.978936 | 307.0166 | 0.644891 |
| 11.351° | 11.35111 | 7.789053 | 333.765 | 0.701077 |
| 11.622° | 11.62241 | 7.607838 | 179.431 | 0.376896 |
| 12.615° | 12.61488 | 7.011438 | 55.97579 | 0.117578 |
| 13.258° | 13.25757 | 6.672949 | 73.79655 | 0.15501 |
| 14.977° | 14.97686 | 5.910563 | 476.075 | 1 |
| 15.557° | 15.55708 | 5.691403 | 143.6231 | 0.301682 |
| 16.089° | 16.0892 | 5.504347 | 217.2447 | 0.456324 |
| 16.319° | 16.31855 | 5.4275 | 276.0824 | 0.579914 |
| 16.606° | 16.60595 | 5.334209 | 136.2941 | 0.286287 |
| 17.013° | 17.01313 | 5.207448 | 40.47203 | 0.085012 |
| 18.928° | 18.92837 | 4.684638 | 213.0289 | 0.447469 |
| 18.884° | 18.88391 | 4.695568 | 260.5841 | 0.547359 |
| 19.429° | 19.42858 | 4.565141 | 179.7858 | 0.377642 |
| 19.734° | 19.73422 | 4.495121 | 92.05923 | 0.193371 |
| 20.643° | 20.64288 | 4.299259 | 119.3917 | 0.250783 |
| 21.484° | 21.4845 | 4.132707 | 65.13663 | 0.13682 |
| 22.067° | 22.0669 | 4.024933 | 166.4906 | 0.349715 |
| 23.433° | 23.43334 | 3.793233 | 203.0481 | 0.426504 |
| 24.466° | 24.46598 | 3.635419 | 62.75409 | 0.131816 |
| 24.885° | 24.88459 | 3.575203 | 316.7789 | 0.665397 |
| 26.740° | 26.73984 | 3.331212 | 29.87601 | 0.062755 |
| 27.900° | 27.89971 | 3.195303 | 75.67041 | 0.158946 |
| 28.557° | 28.55742 | 3.123189 | 112.5171 | 0.236343 |
| 29.523° | 29.52253 | 3.02325 | 32.91097 | 0.06913 |
| 32.888° | 32.88833 | 2.721131 | 55.0898 | 0.115717 |
| 34.183° | 34.18291 | 2.62098 | 91.18144 | 0.191528 |
| 36.808° | 36.8076 | 2.439882 | 17.00791 | 0.035725 |

Figure 31:
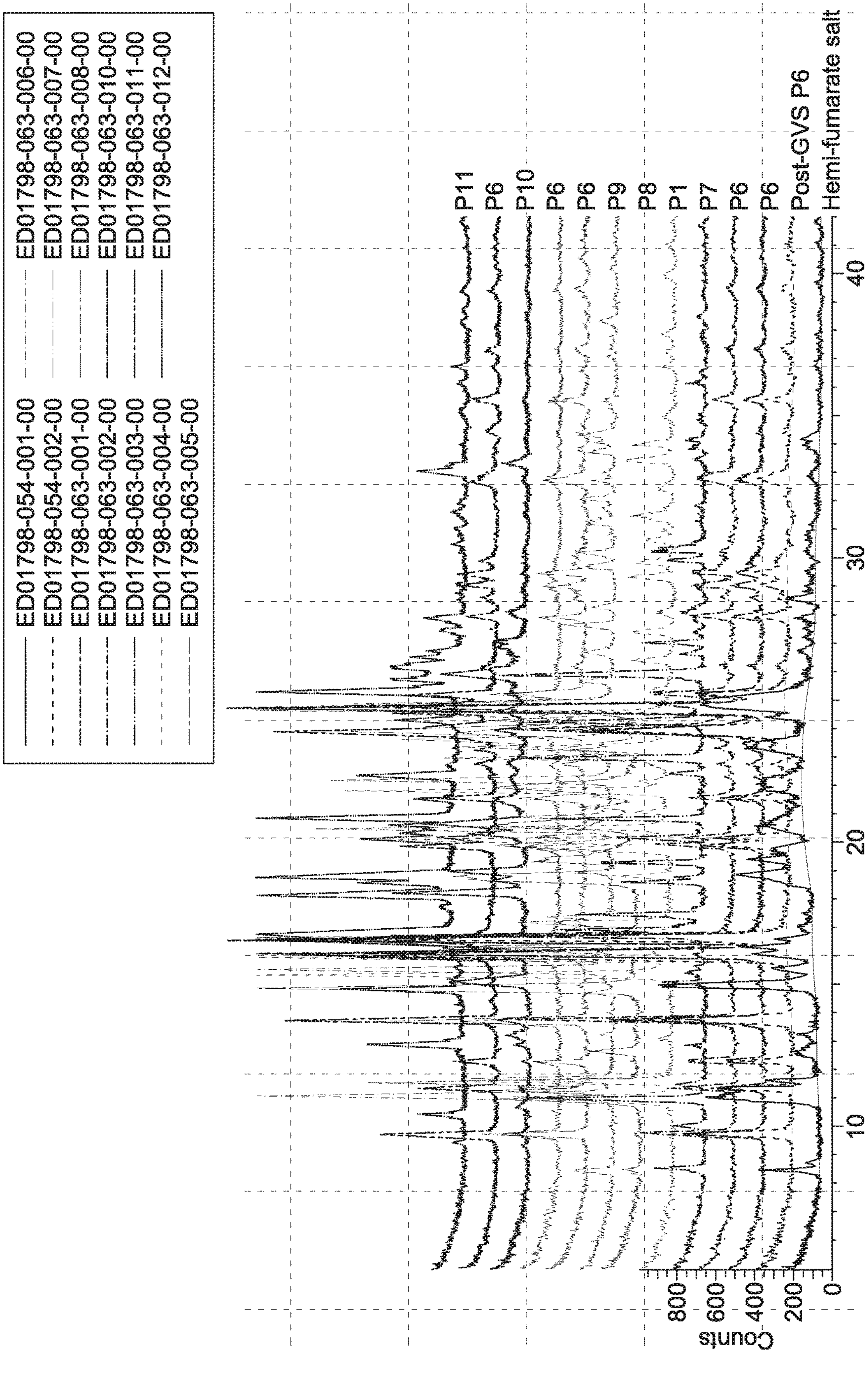
FIG. 31 shows the XRPD patterns of I-7c (polymorph of pattern 5) after maturation in 12 different solvents, forming polymorphs of patterns (P) 1, 6, 7, 8, 9, 10, and 11.

I-7c (polymorph of pattern 5) was also subjected to maturation in 12 different solvents following the procedure detailed in Example 2. All isolated solids showed complex polymorphism with multiple crystalline patterns obtained (polymorphs of patterns (P) 1, 6, 7, 8, 9, 10, and 11) according to XRPD analysis (FIG. 31).

Example 5

Synthesis of acetate salt of 3-(2-(dimethylamino) ethyl)-1H-indol-4-ol (I-7d)(acetate salt of I-7/psilocin/psilocin-$d_0$/PI-$d_0$)

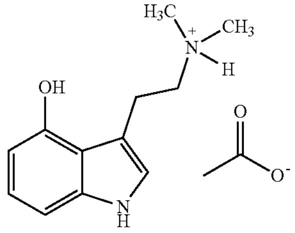

Compound I-7 (PI-$d_0$, free base)(10 mM) was dissolved in 1,4-dioxane or THF/heptane and treated with a solution of acetic acid (10 mM) while being stirred at ambient temperature. Samples were shaken overnight at room temperature to produce I-7d (acetate salt of PI-$d_0$).

Figure 32:
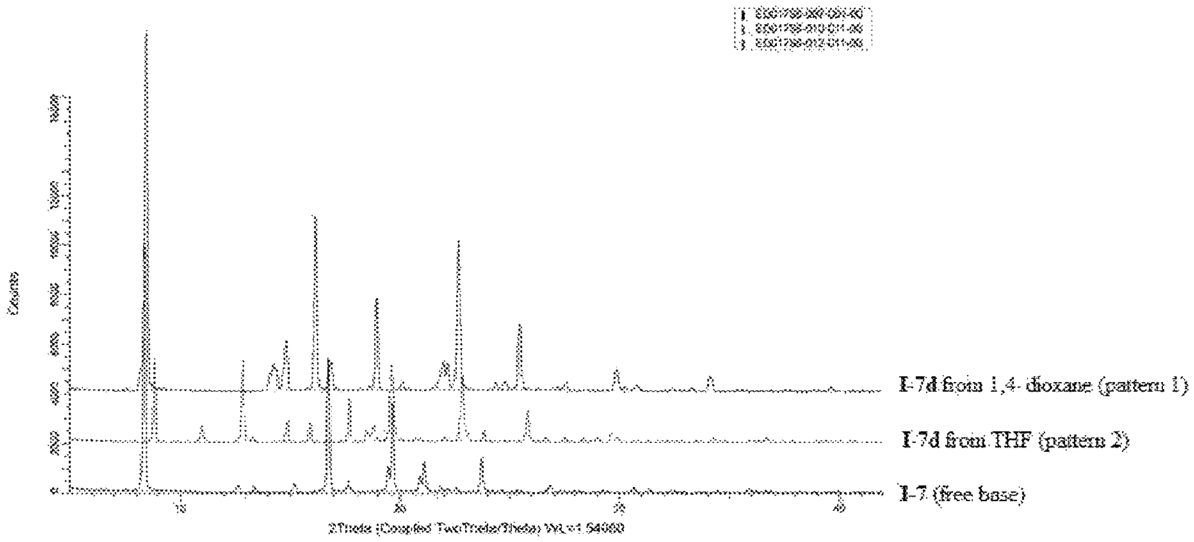
FIG. 32 shows the XRPD pattern of two different crystalline polymorphs of I-7d: a polymorph having pattern 1 (made from 1,4-dioxane), and a polymorph having pattern 2 (made from THF/heptane)

As shown in FIG. 32, the X-ray powder diffraction (XRPD) pattern indicates that two different crystalline polymorphs of I-7d were formed: a polymorph having pattern 1 (made from 1,4-dioxane), and a polymorph having pattern 2 (made from THF/heptane).

Figure 33:
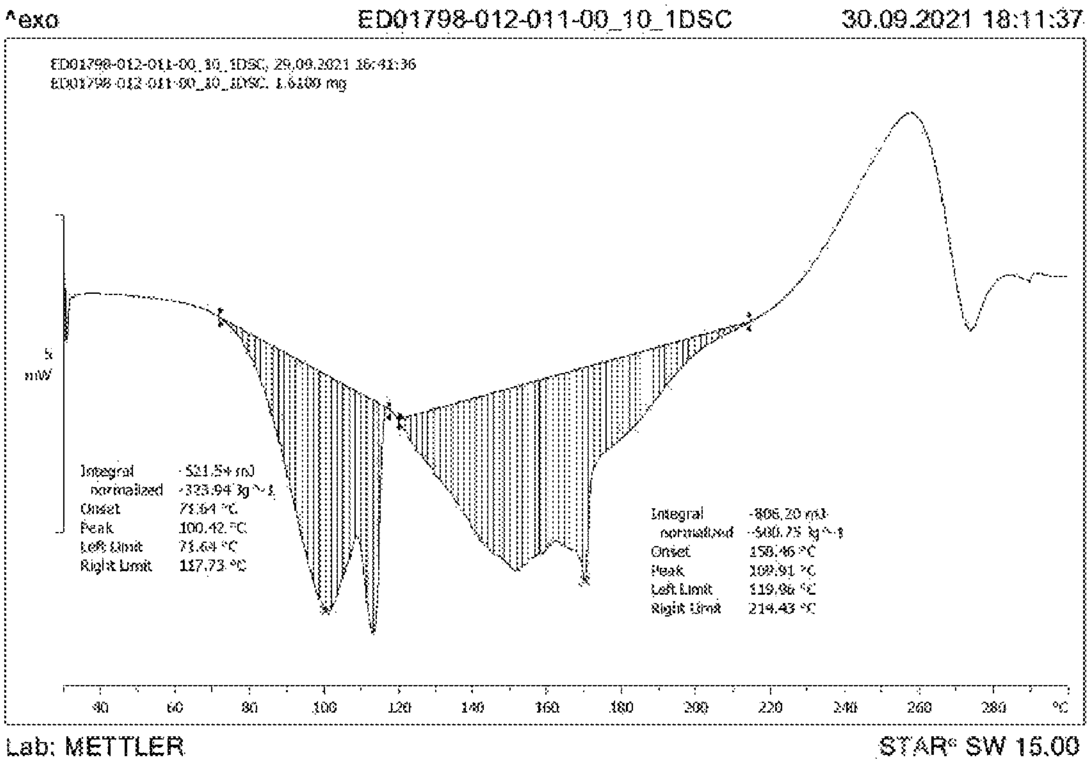
FIG. 33 shows the DSC curve of I-7d (polymorph of pattern 1)
Figure 34:
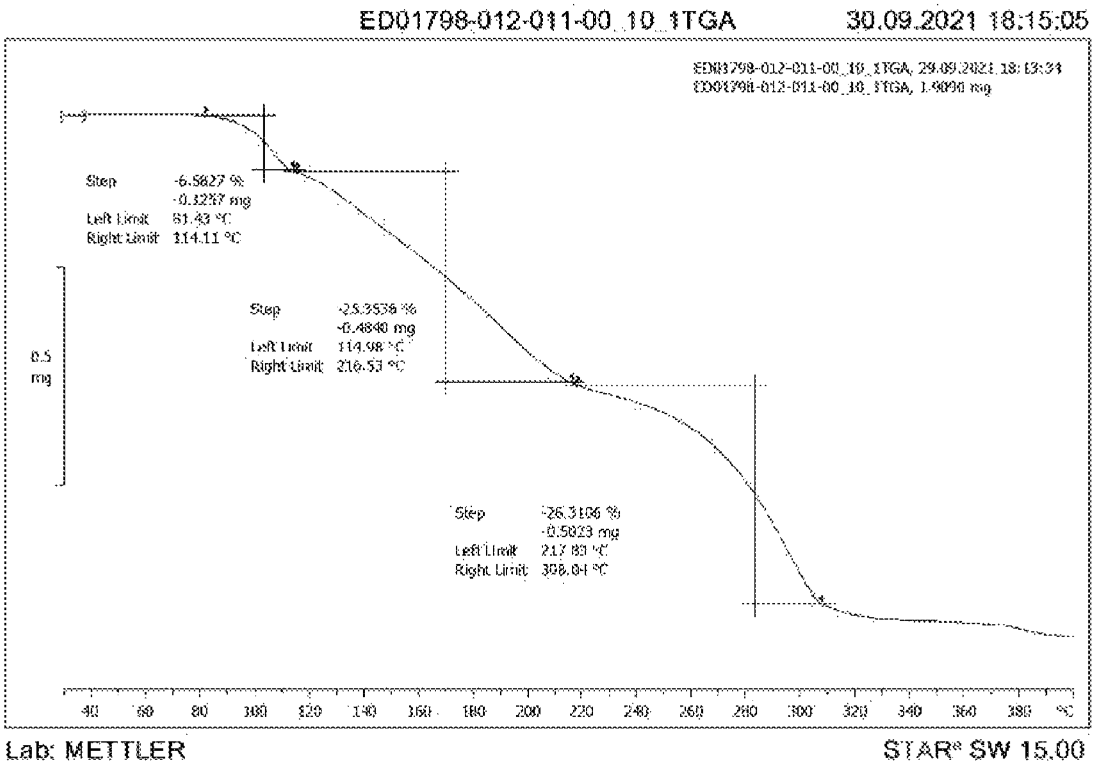
FIG. 34 shows the TGA plot of I-7d (polymorph of pattern 1)

The DSC curve of I-7d (polymorph of pattern 1) is shown in FIG. 33, which indicates the salt has multiple broad unresolved endotherms, with the earliest melt onset of (71.64° C.). The thermogravimetric analysis (TGA) curve of I-7d (polymorph of pattern 1) as shown in FIG. 34 showed about 6.5% mass loss between about 81 to 114° C., about 25% mass loss between about 115 to 216° C., and about 26% mass loss between about 217 to 308° C.

Figure 35:
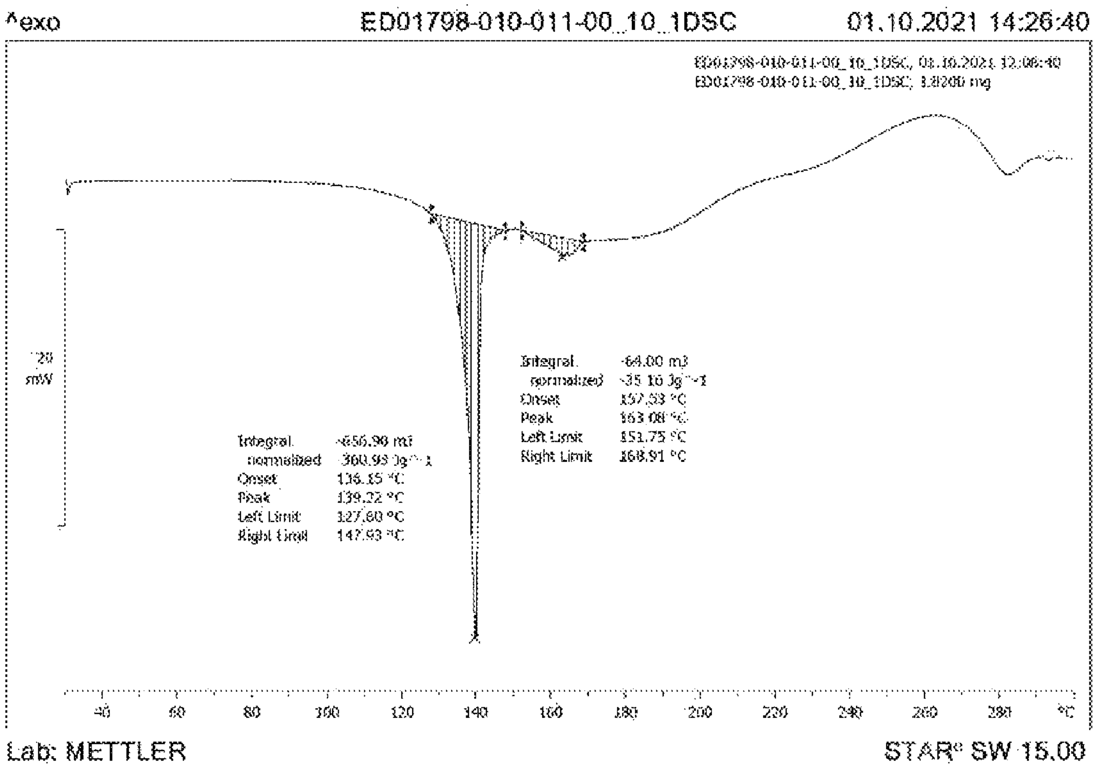
FIG. 35 shows the DSC curve of I-7d (polymorph of pattern 2)
Figure 36:
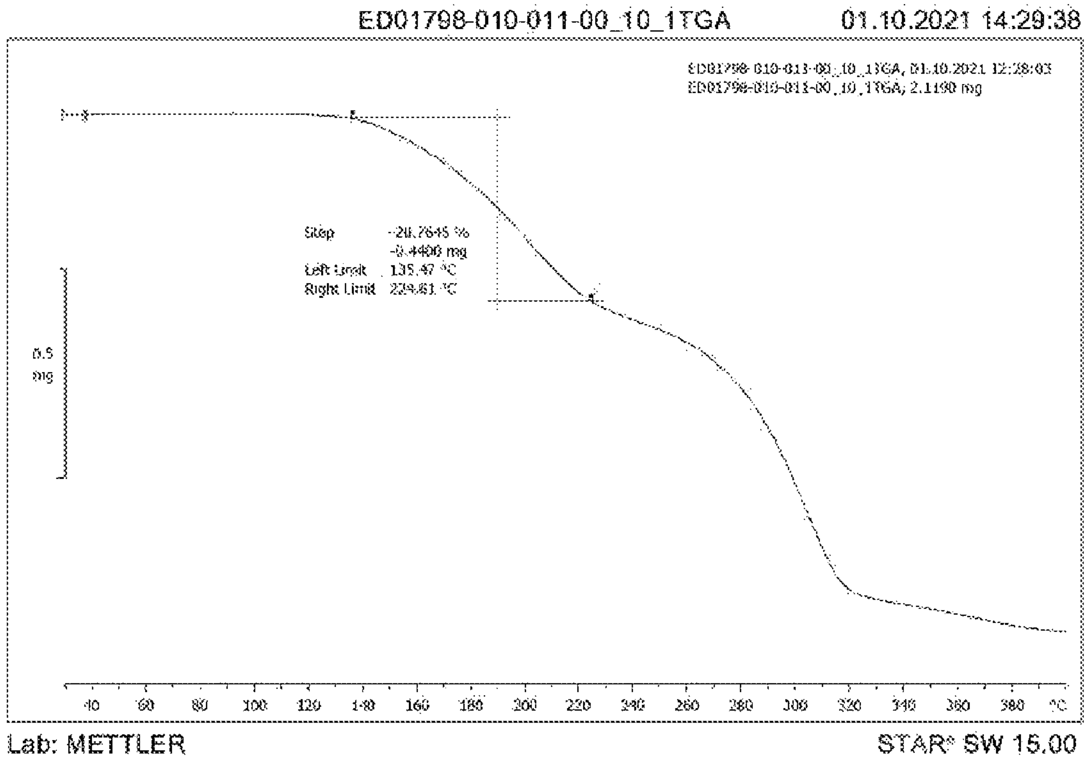
FIG. 36 shows the TGA curve of I-7d (polymorph of pattern 2)

The DSC curve of I-7d (polymorph of pattern 2) is shown in FIG. 35, which indicates the salt has a main endotherm with a melt onset of 136.15° C., higher than that of the polymorph of pattern 1. The thermogravimetric analysis (TGA) curve of I-7d (polymorph of pattern 2) as shown in FIG. 36 showed mass loss of about 20.7% between about 135 to 224° C.

Example 6

Synthesis of citrate salt of 3-(2-(dimethylamino) ethyl)-1H-indol-4-ol (I-7e)(citrate salt of I-7/psilocin/psilocin-$d_0$/PI-$d_0$)

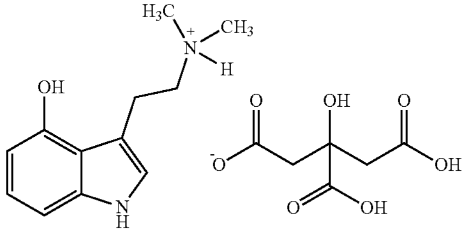

Compound I-7 (PI-$d_0$, free base)(10 mM) was dissolved in 1,4-dioxane and treated with a solution of citric acid (10 mM) while being stirred at ambient temperature. Samples were then freeze dried to provide I-7e (citrate salt of PI-$d_0$) as a white fluffy solid that was hygroscopic and rapidly became sticky.

The obtained salt was largely amorphous, with only some weak diffraction peaks in the X-ray powder diffraction (XRPD) pattern (FIG. 37).

Figure 38A:
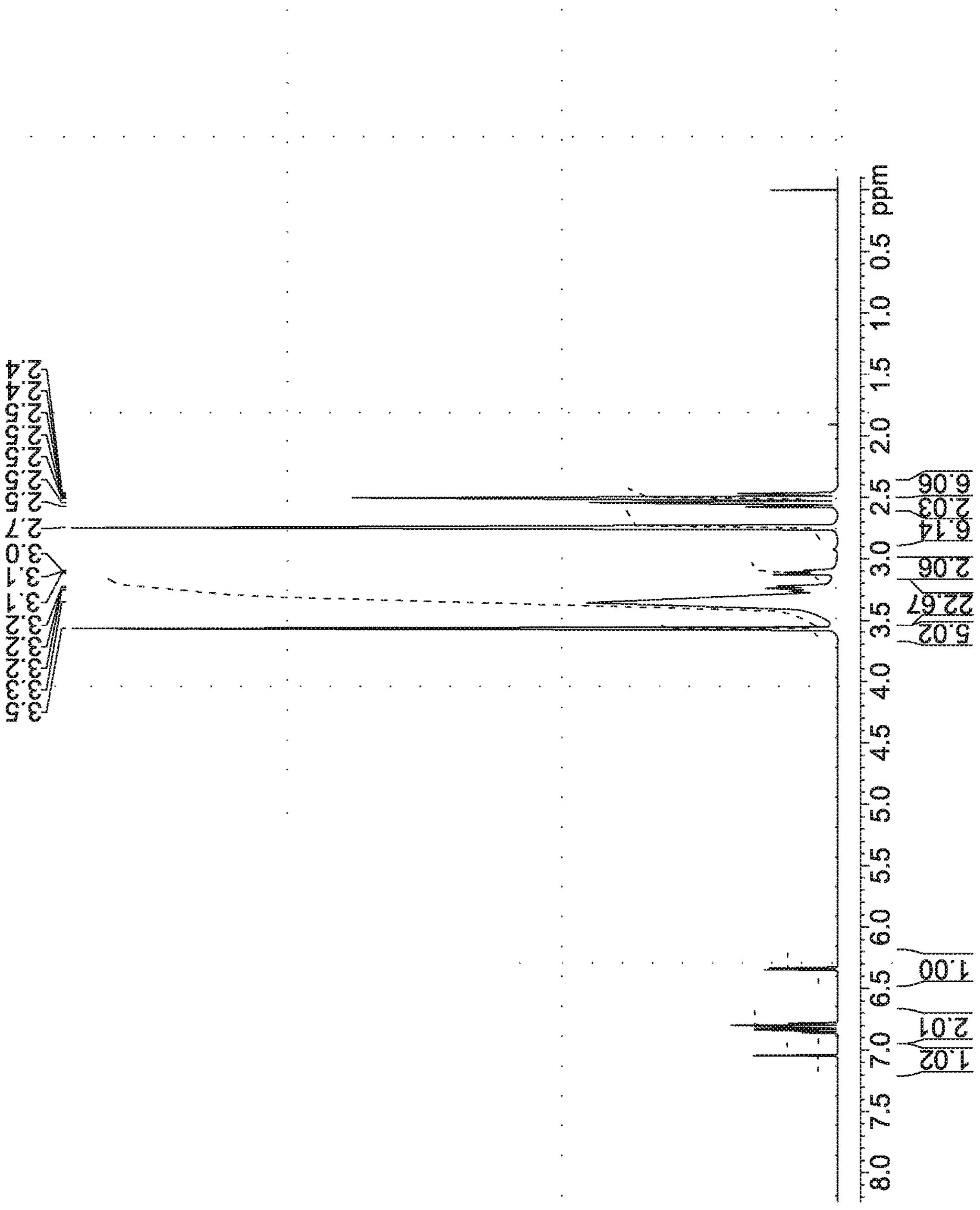
FIGS. 38A-38B shows the $^1$H NMR spectrum of I-7e.
Figure 38B:
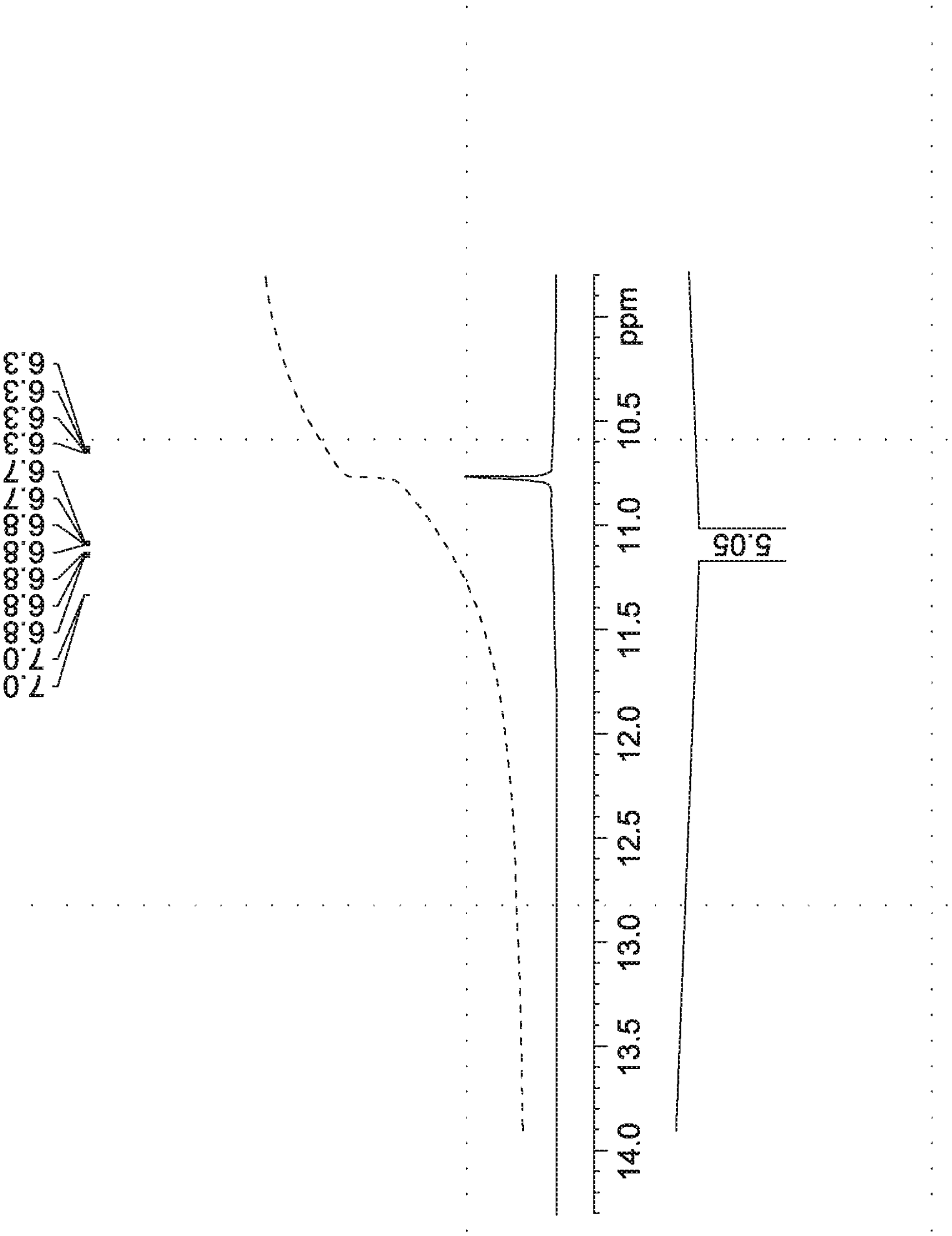

$^1$H NMR spectrum of I-7e (FIGS. 38A and 38B) shows protonation with citric acid (1 equivalent) along with 1,4-dioxane (0.6 mole equivalent).

Example 7

Synthesis of malonate salt of 3-(2-(dimethylamino)ethyl)-1H-indol-4-ol (I-7f)(malonate salt of I-7/psilocin/psilocin-$d_0$/PI-$d_0$)

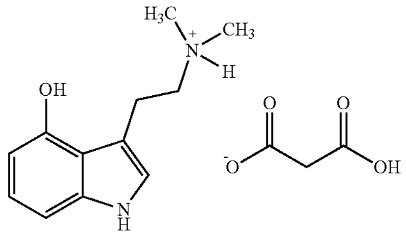

Compound I-7 (PI-$d_0$, free base)(10 mM) was dissolved in 1,4-dioxane or THF and treated with a solution of malonic acid (10 mM) while being stirred at ambient temperature. Samples were refrigerated to produce I-7f (malonate salt of PI-$d_0$).

Figure 39:
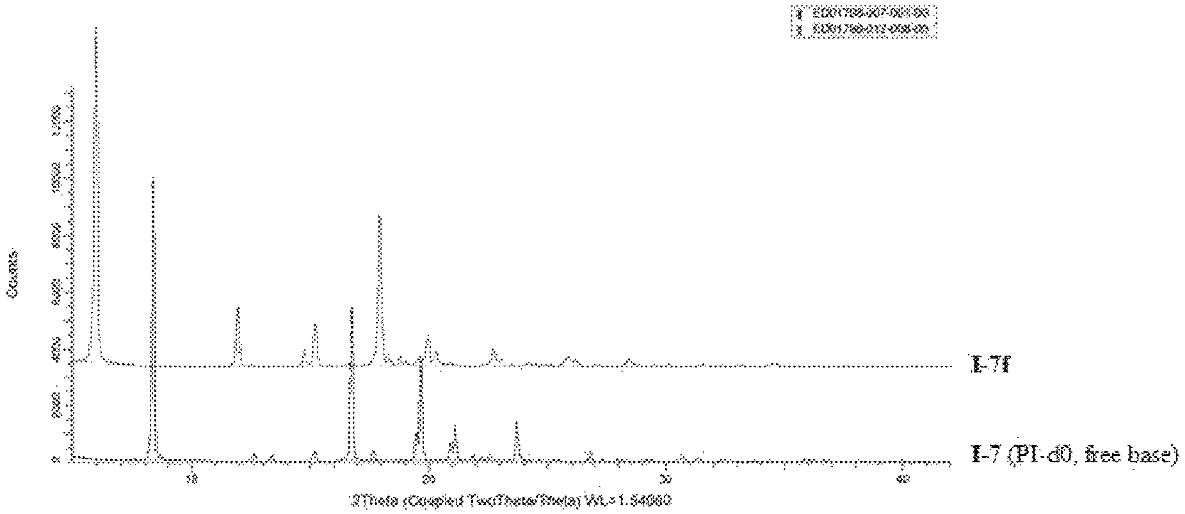
FIG. 39 shows the XRPD pattern of I-7f compared to free base.

As shown in FIG. 39, the X-ray powder diffraction (XRPD) pattern indicates the salt is crystalline, with only one polymorph observed.

Figure 40:
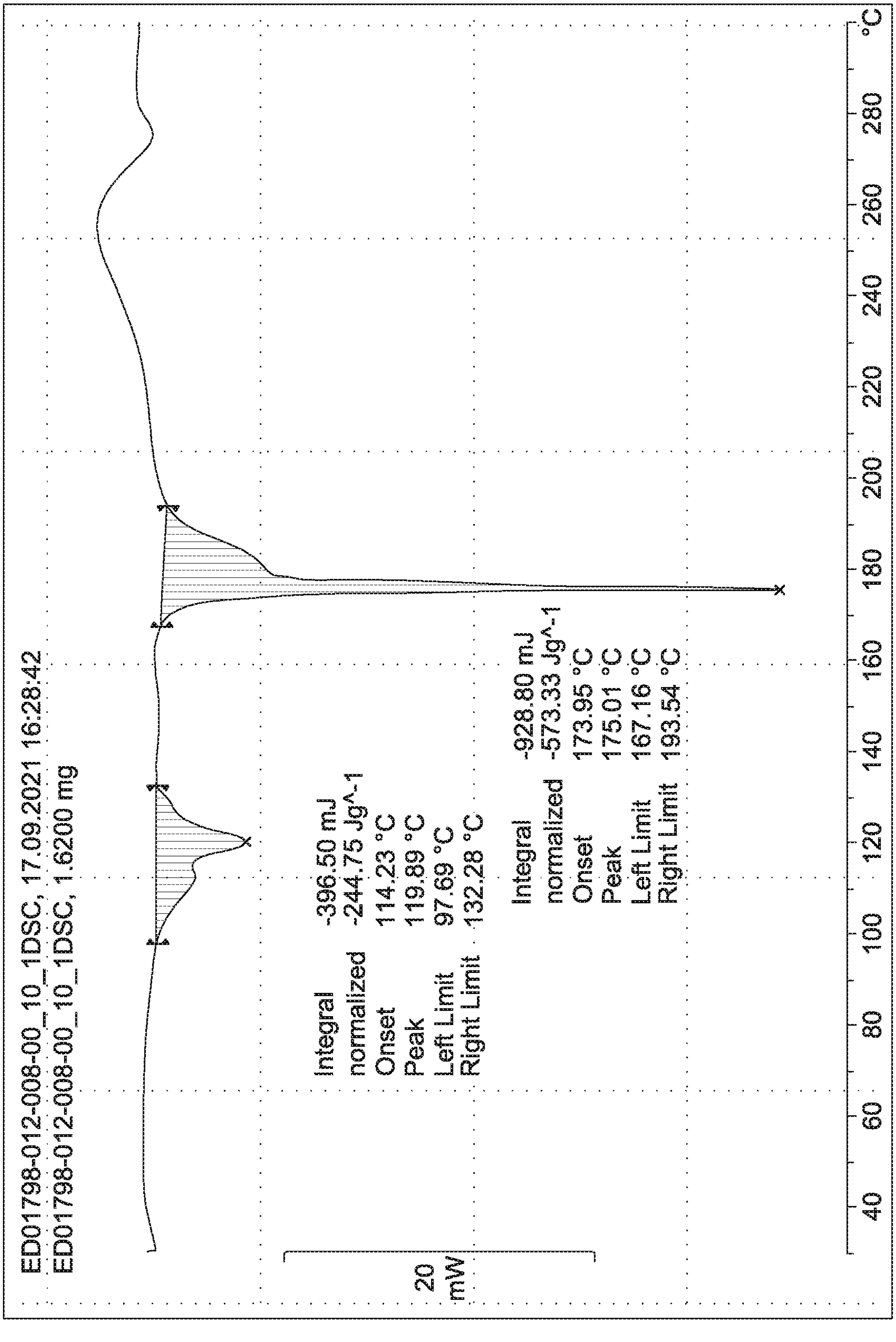
FIG. 40 shows the DSC curve of I-7f.
Figure 41:
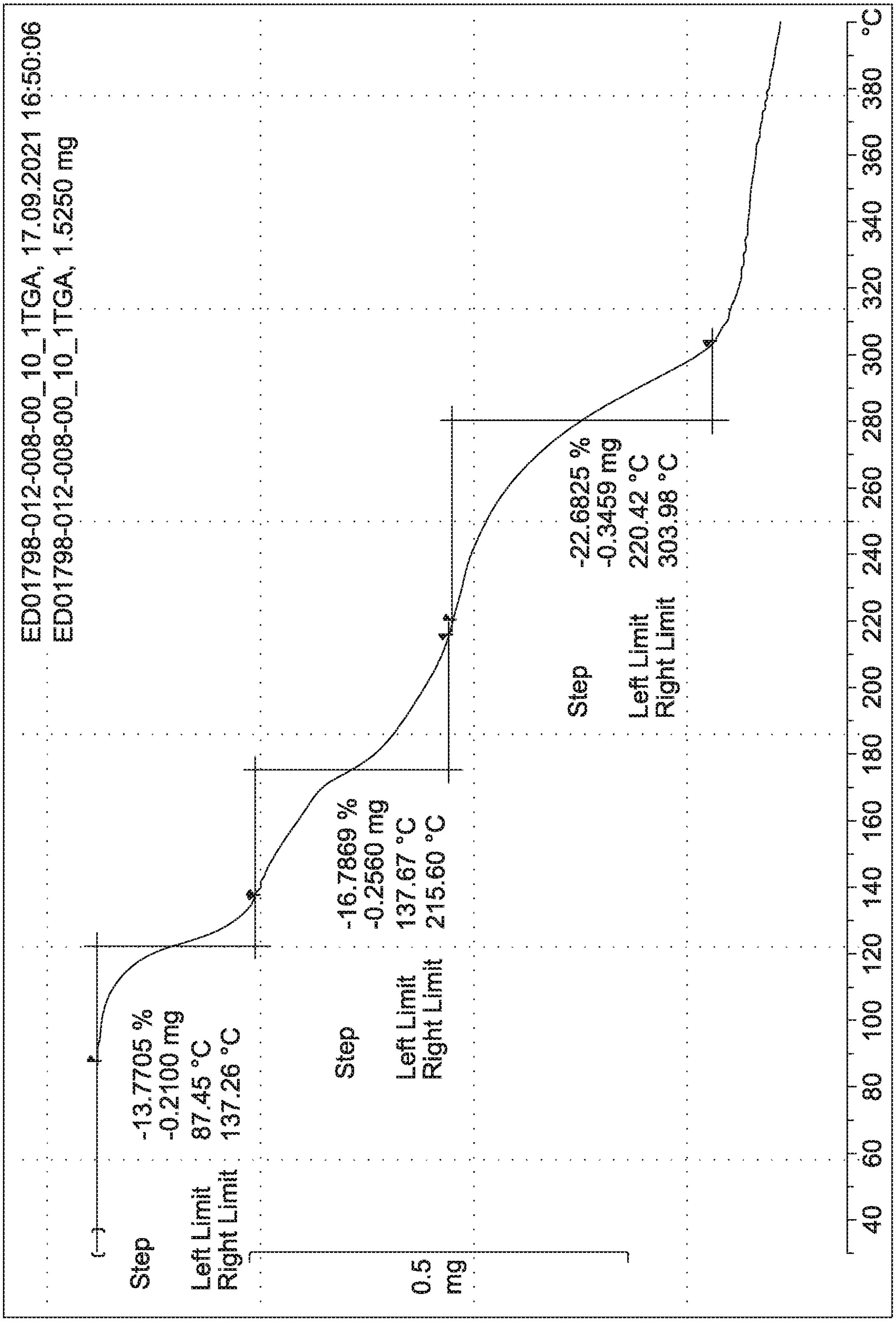
FIG. 41 shows the TGA plot of I-7f.

The DSC curve at 10° C./min shows a broad unresolved endothermic event between 98 to 132° C. and an unresolved endothermic event onset of 174° C. with a peak at 175° C. (FIG. 40). The TGA at 10° C./min shows 13.8% mass loss between 87 to 137° C., 16.8% between 138 to 215° C., and 22.7% between 220 to 304° C. (FIG. 41).

Example 8

Synthesis of fumarate salt of 3-(2-(dimethylamino)ethyl)-1H-indol-4-ol (I-7g)(fumarate salt of I-7/psilocin/psilocin-$d_0$/PI-$d_0$)

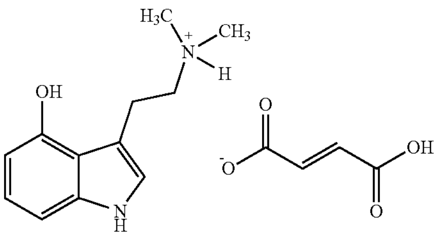

Compound I-7 (PI-$d_0$, free base)(10 mM) was dissolved in 1,4-dioxane, acetonitrile, or THF and treated with a solution of fumaric acid (10 mM) while being stirred at ambient temperature. Samples were refrigerated to produce I-7g (fumarate salt of PI-$d_0$).

Figure 42:
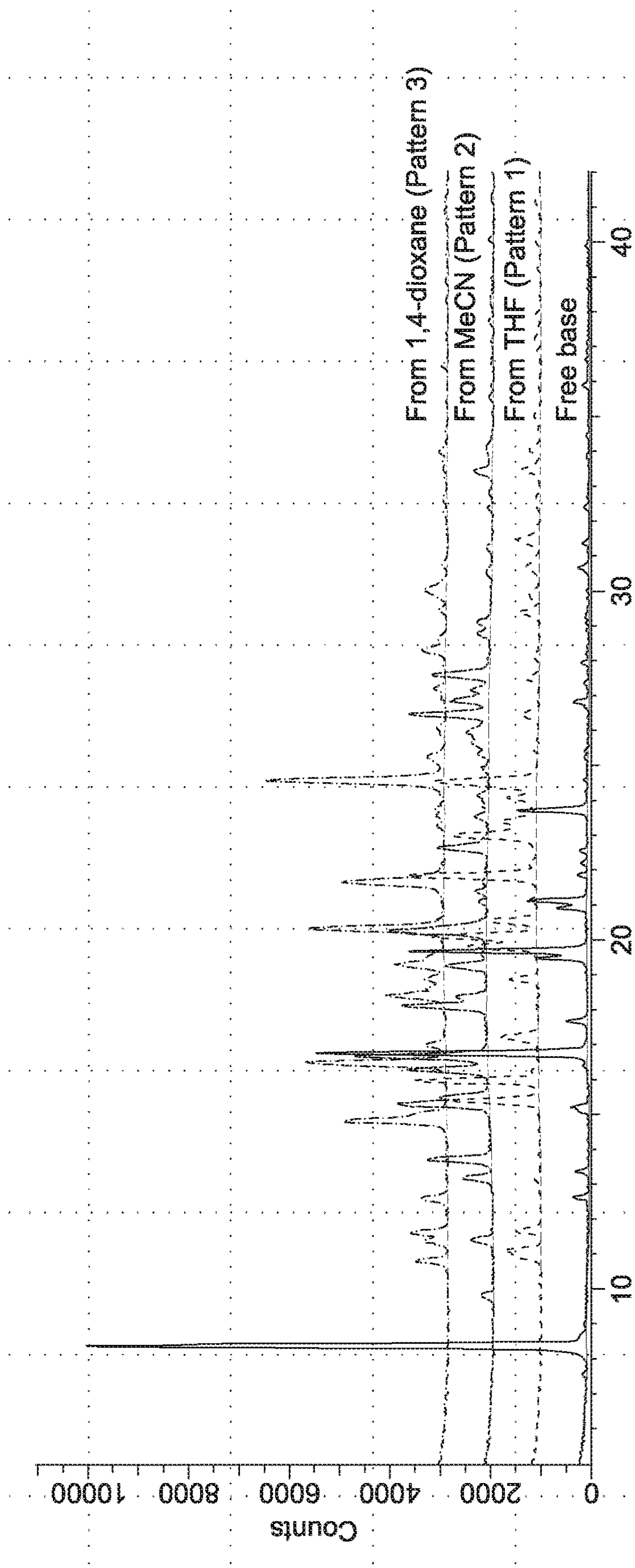
FIG. 42 shows the XRPD pattern of three different crystalline polymorphs of I-7g: a polymorph having pattern 1 (made from THF), a polymorph having pattern 2 (made from acetonitrile), a polymorph having pattern 3 (made from 1,4-dioxane)

As shown in FIG. 42, the X-ray powder diffraction (XRPD) pattern indicates that three different crystalline polymorphs of I-7g were formed: a polymorph having pattern 1 (made from THF), a polymorph having pattern 2 (made from acetonitrile), a polymorph having pattern 3 (made from 1,4-dioxane).

Figure 43:
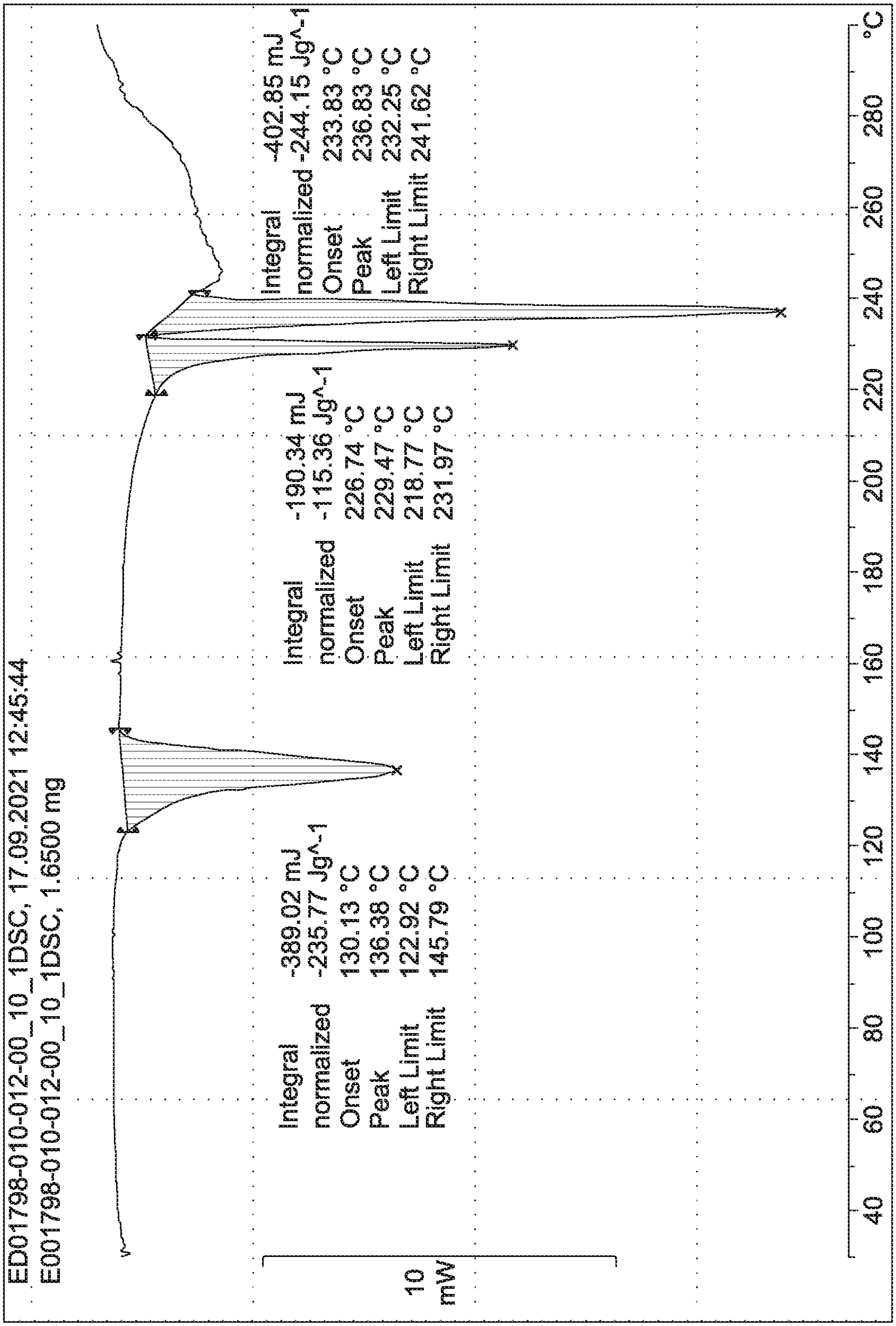
FIG. 43 shows the DSC curve of I-7g (polymorph of pattern 1)
Figure 44:
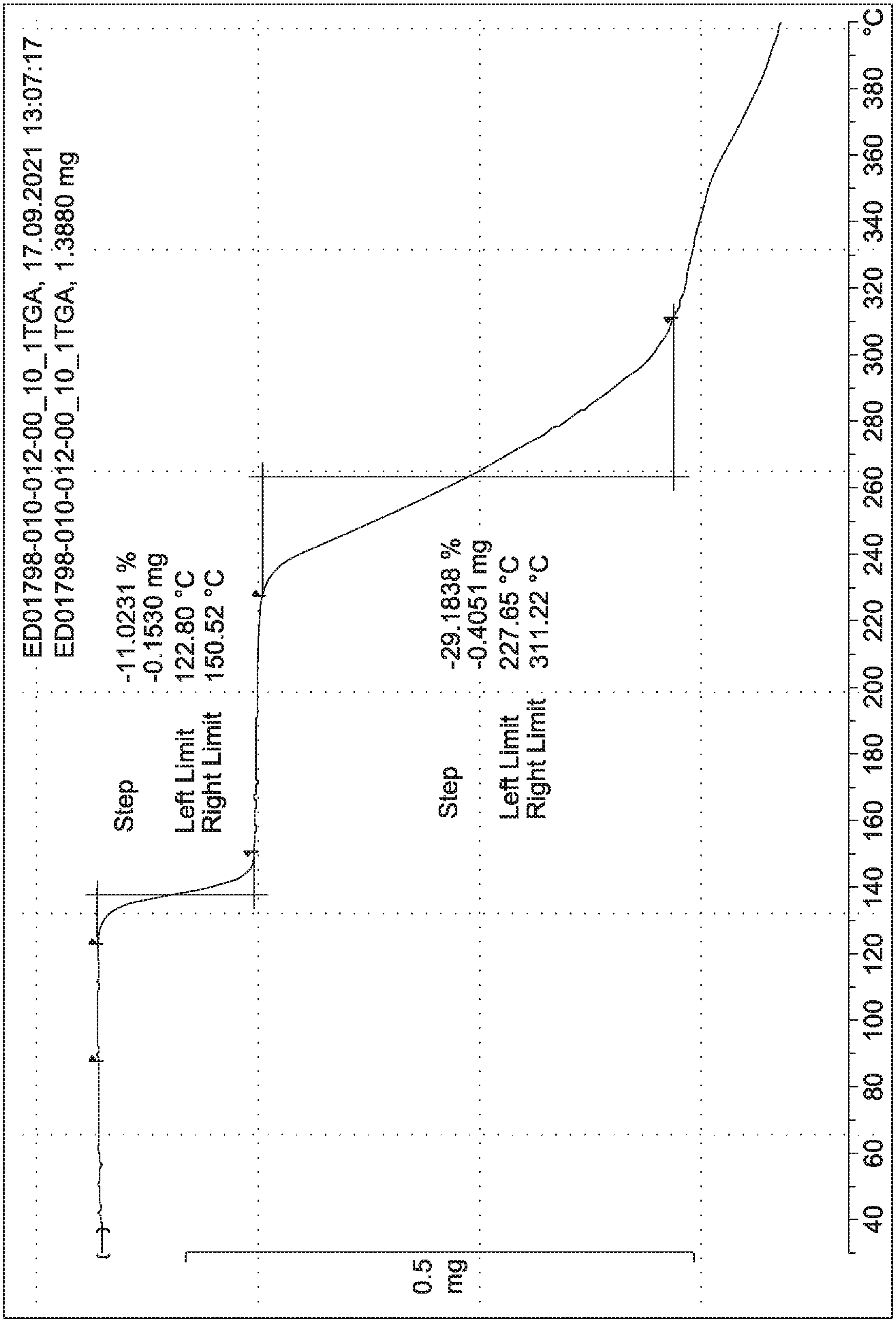
FIG. 44 shows the TGA plot of I-7g (polymorph of pattern 1)

The DSC curve of I-7g (polymorph of pattern 1) at 10° C./min is shown in FIG. 43, which shows an endothermic event onset at 130° C. (peak 136° C.) and further endothermic events of onset at 223° C. and 234° C. The thermogravimetric analysis (TGA) curve of I-7g (polymorph of pattern 1) at 10° C./min is shown in FIG. 44, which shows 11% mass loss between 123 to 151° C. and 29% mass loss between 228 to 311° C., corresponding to events in the DSC.

Figure 45:
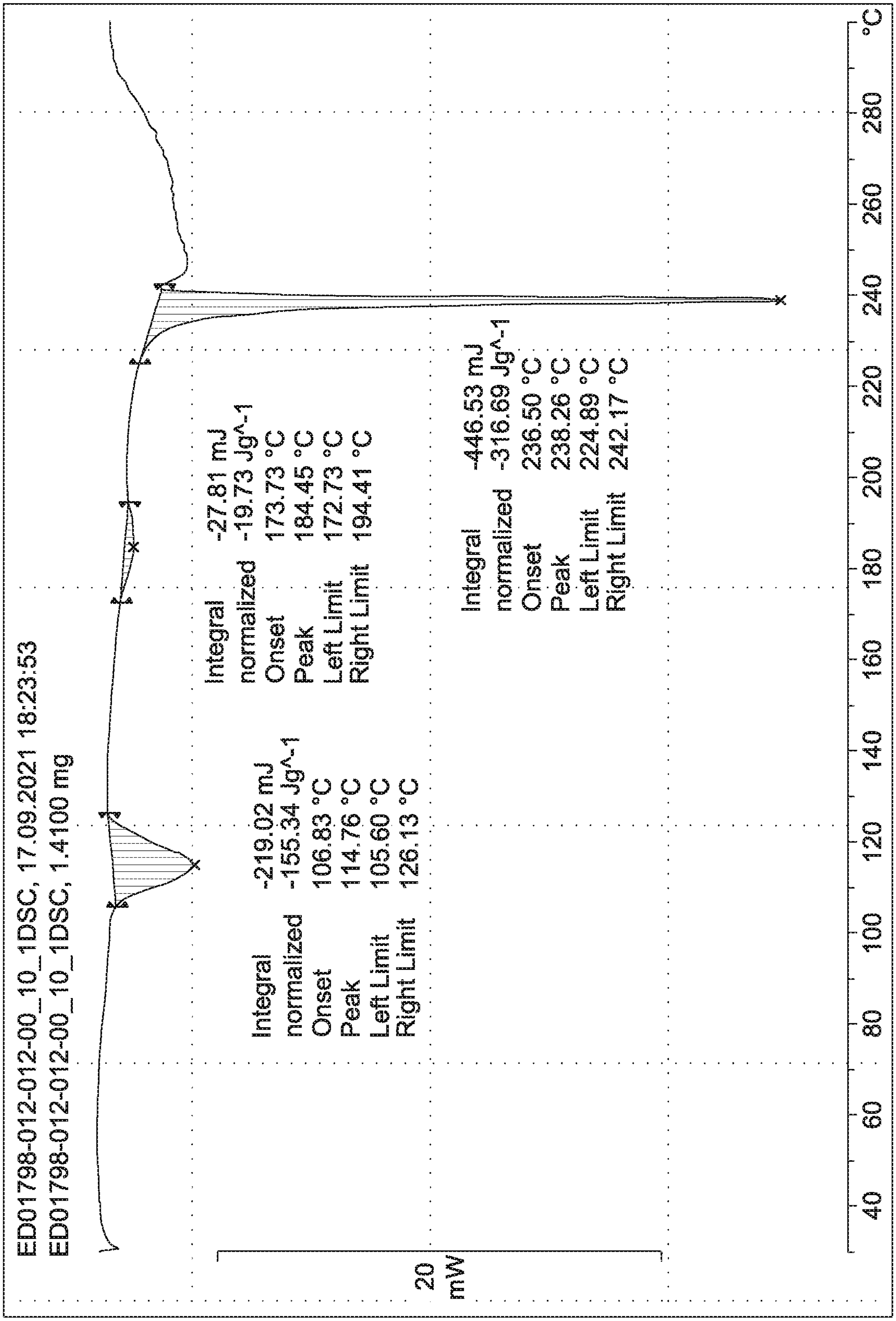
FIG. 45 shows the DSC curve of I-7g (polymorph of pattern 3)
Figure 46:
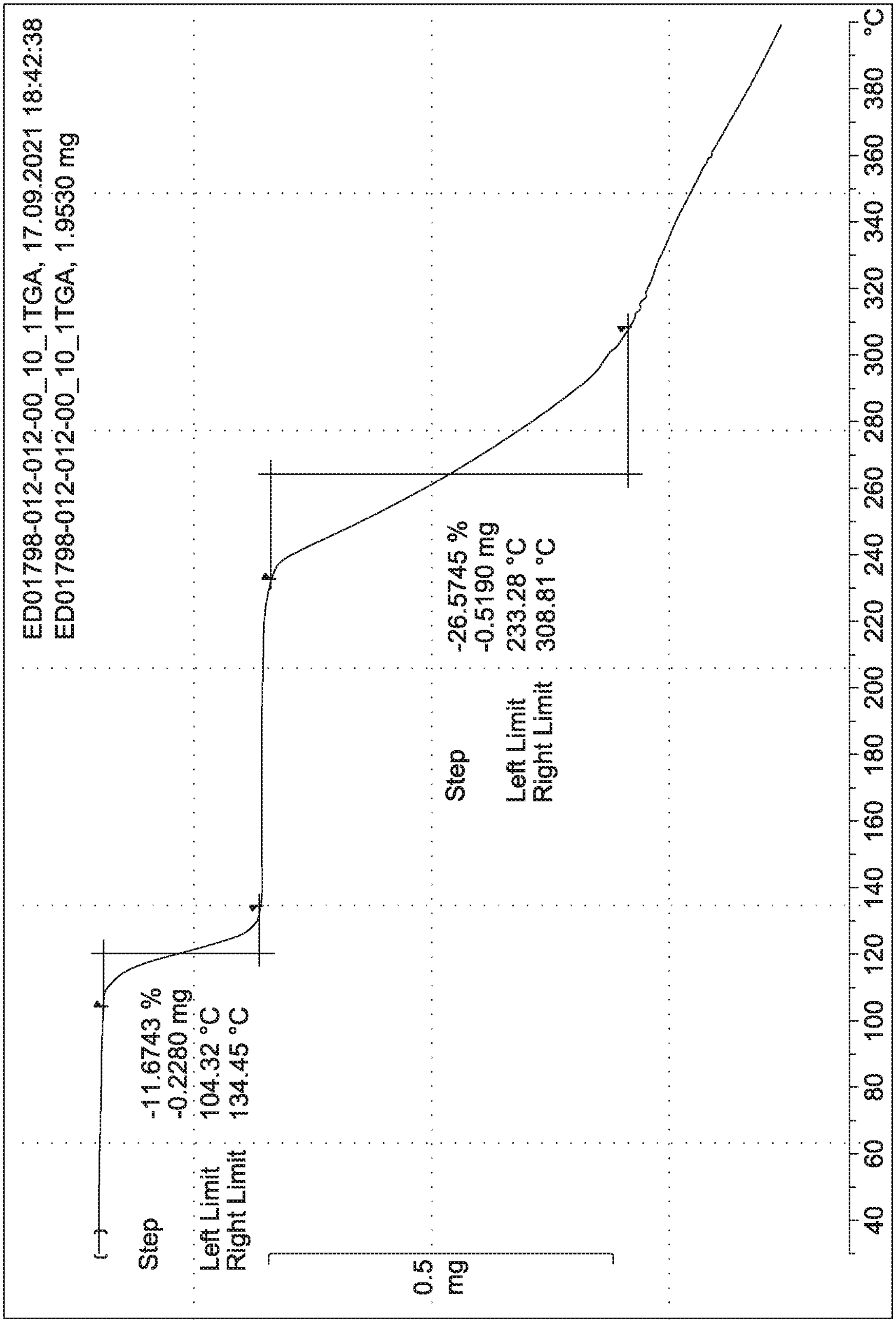
FIG. 46 shows the TGA plot of I-7g (polymorph of pattern 3)

The DSC curve of I-7g (polymorph of pattern 3) at 10° C./min is shown in FIG. 45, which shows a broad endothermic event onset at 107° C., a small shallow endothermic event of onset at 174° C., and an endothermic event of onset at 237° C. The thermogravimetric analysis (TGA) curve of I-7g (polymorph of pattern 3) at 10° C./min shows 11.7% mass loss between 104 to 134° C. and 27% mass loss between 233 to 309° C. (FIG. 46).

Example 9

Synthesis of succinate salt of 3-(2-(dimethylamino)ethyl)-1H-indol-4-ol (I-7h)(succinate salt of I-7/psilocin/psilocin-$d_0$/PI-$d_0$)

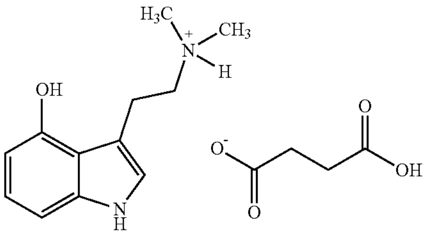

Compound I-7 (PI-$d_0$, free base)(10 mM) was dissolved in 1,4-dioxane or THF and treated with a solution of succinic acid (10 mM) while being stirred at ambient temperature. Samples were refrigerated to produce I-7h (succinate salt of PI-$d_0$).

Figure 47:
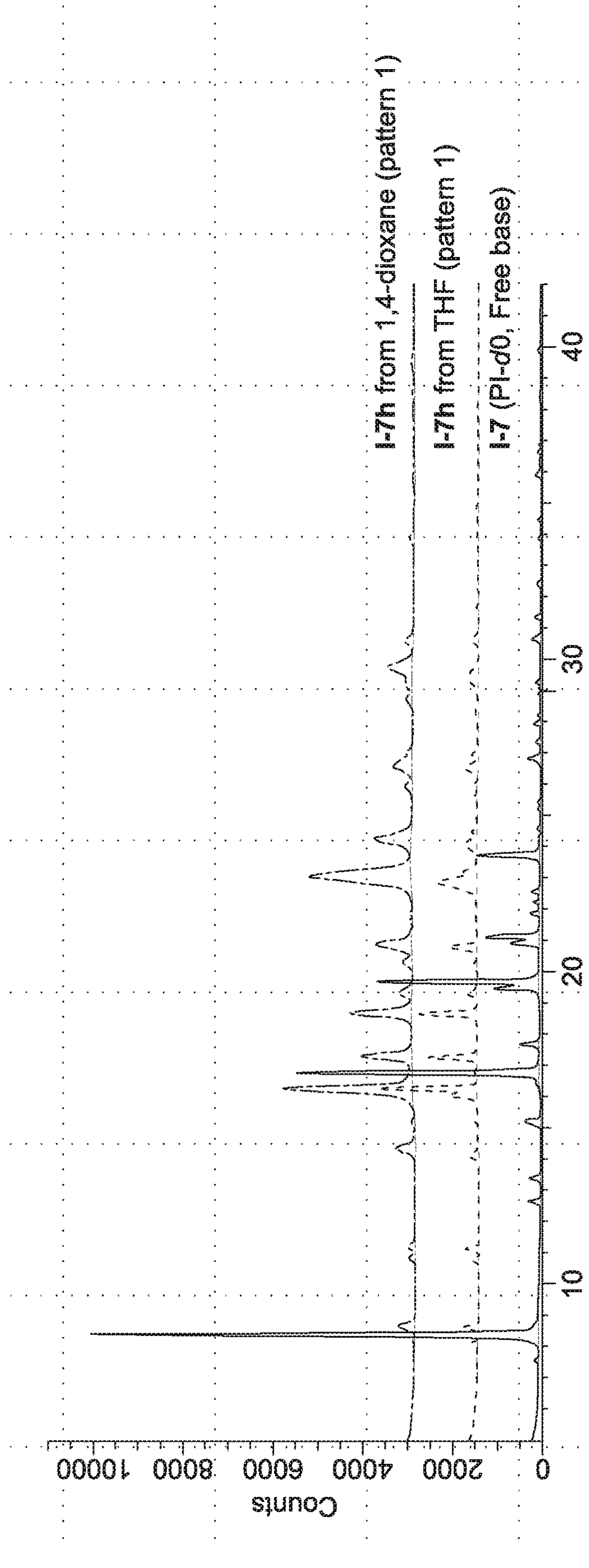
FIG. 47 shows the XRPD pattern of I-7h (polymorph of pattern 1) formed from either 1,4-dioxane or THF.

The X-ray powder diffraction (XRPD) pattern indicates that a single crystalline polymorph (pattern 1) was formed from either 1,4-dioxane or THF (FIG. 47).

Figure 48:
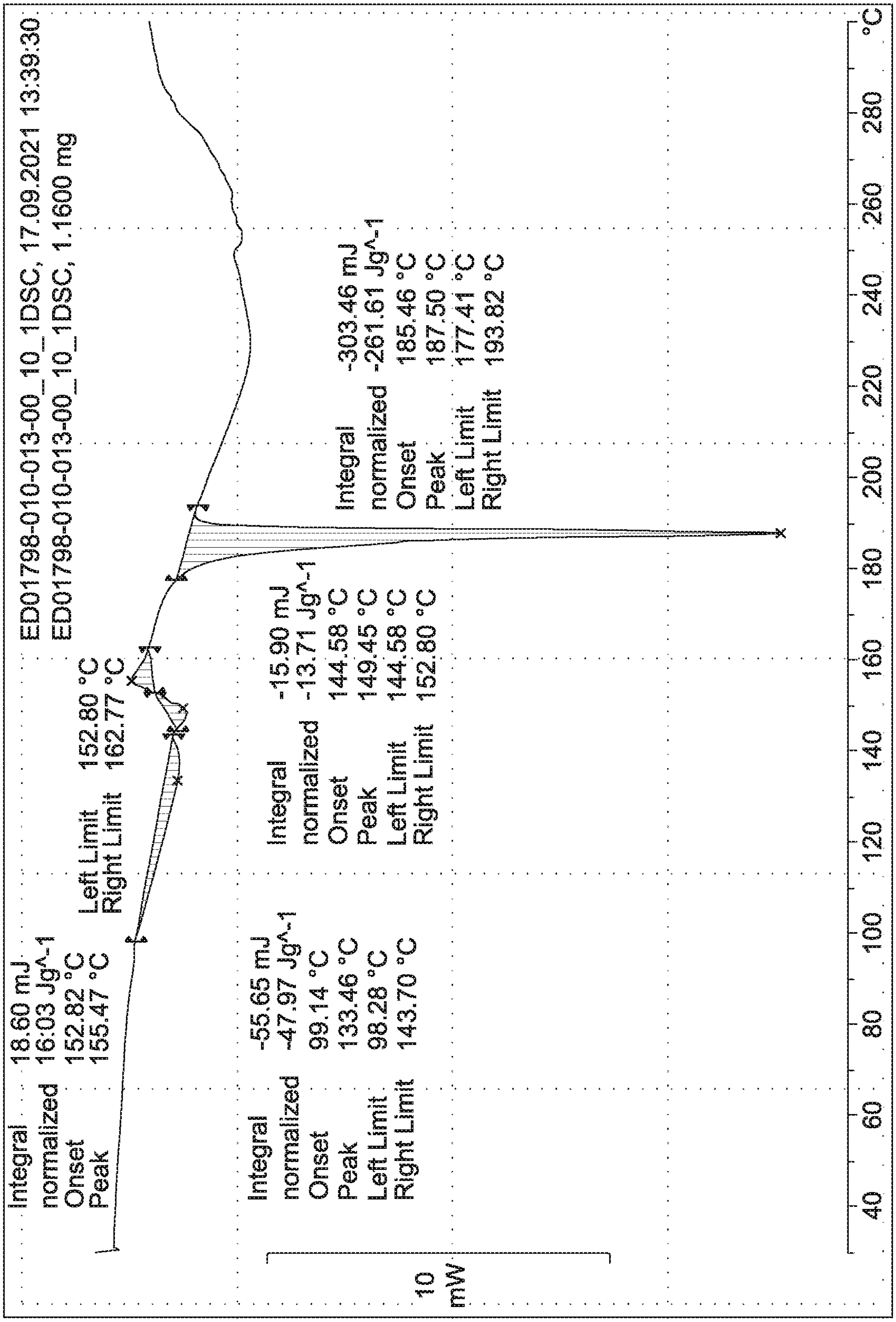
FIG. 48 shows the DSC curve of I-7h (polymorph of pattern 1)
Figure 49:
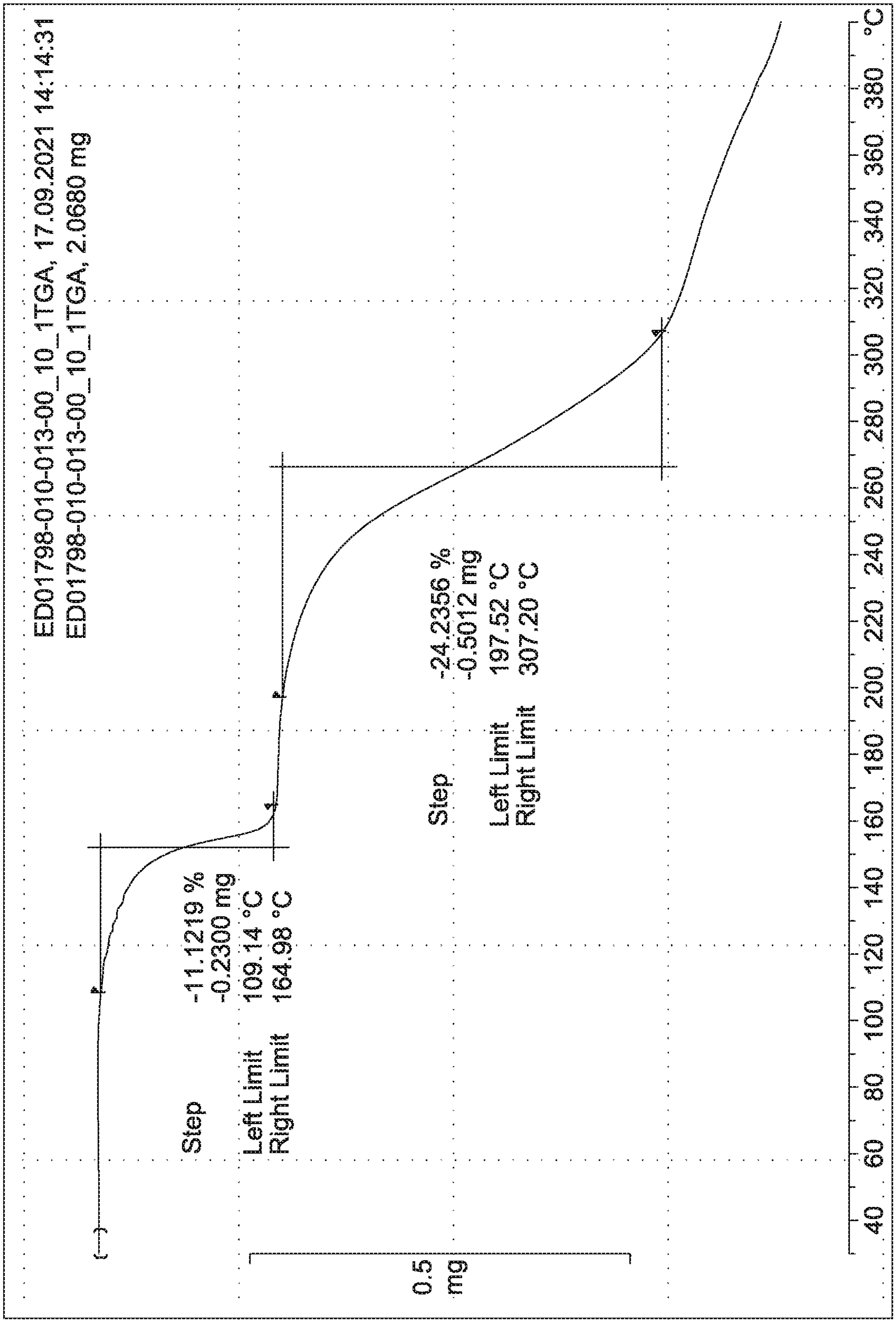
FIG. 49 shows TGA plot of I-7h (polymorph of pattern 1)

The DSC at 10° C./min shows several small events between 98 to 153° C. and an endothermic event of onset at about 185° C. (FIG. 48). TGA at 10° C./min shows about 11.1% mass loss between 109 to 165° C. and about 24% mass loss between 198 to 307° C. (FIG. 49).

Example 10

Synthesis of oxalate salt of 3-(2-(dimethylamino) ethyl)-1H-indol-4-ol (I-7i)(oxalate salt of I-7/psilocin/psilocin-$d_0$/PI-$d_0$)

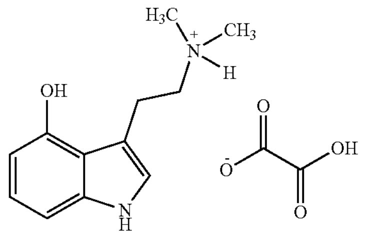

Compound I-7 (PI-$d_0$, free base)(10 mM) was dissolved in 1,4-dioxane, acetonitrile, or THF and treated with a solution of oxalic acid (10 mM or 5 mM) while being stirred at ambient temperature. Samples were refrigerated to produce I-7i (oxalate salt of PI-$d_0$).

Figure 50:
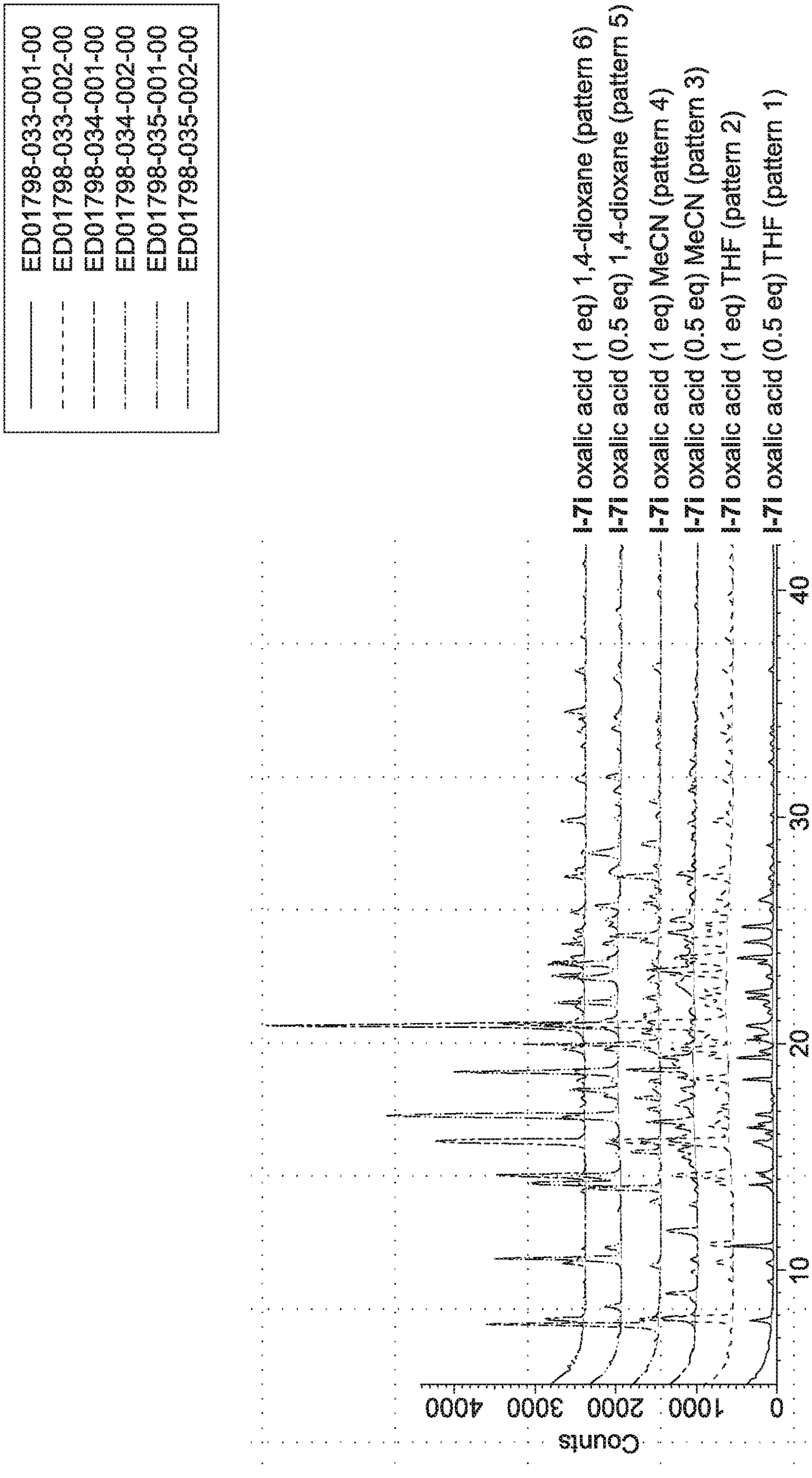
FIG. 50 shows the XRPD pattern of six different crystalline polymorphs of I-7i: a polymorph having pattern 1 (made from 0.5 eq oxalic acid and THF), a polymorph having pattern 2 (made from 1 eq oxalic acid and THF), a polymorph having pattern 3 (made from 0.5 eq oxalic acid and acetonitrile), a polymorph having pattern 4 (made from 1 eq oxalic acid and acetonitrile), a polymorph having pattern 5 (made from 0.5 eq oxalic acid and 1,4-dioxane), and a polymorph having pattern 6 (made from 1 eq oxalic acid and 1,4-dioxane)

As shown in FIG. 50, the X-ray powder diffraction (XRPD) pattern indicates that six different crystalline polymorphs of I-7i were formed: a polymorph having pattern 1 (made from 0.5 eq oxalic acid and THF), a polymorph having pattern 2 (made from 1 eq oxalic acid and THF), a polymorph having pattern 3 (made from 0.5 eq oxalic acid and acetonitrile), a polymorph having pattern 4 (made from 1 eq oxalic acid and acetonitrile), a polymorph having pattern 5 (made from 0.5 eq oxalic acid and 1,4-dioxane), and a polymorph having pattern 6 (made from 1 eq oxalic acid and 1,4-dioxane).

Figure 51:
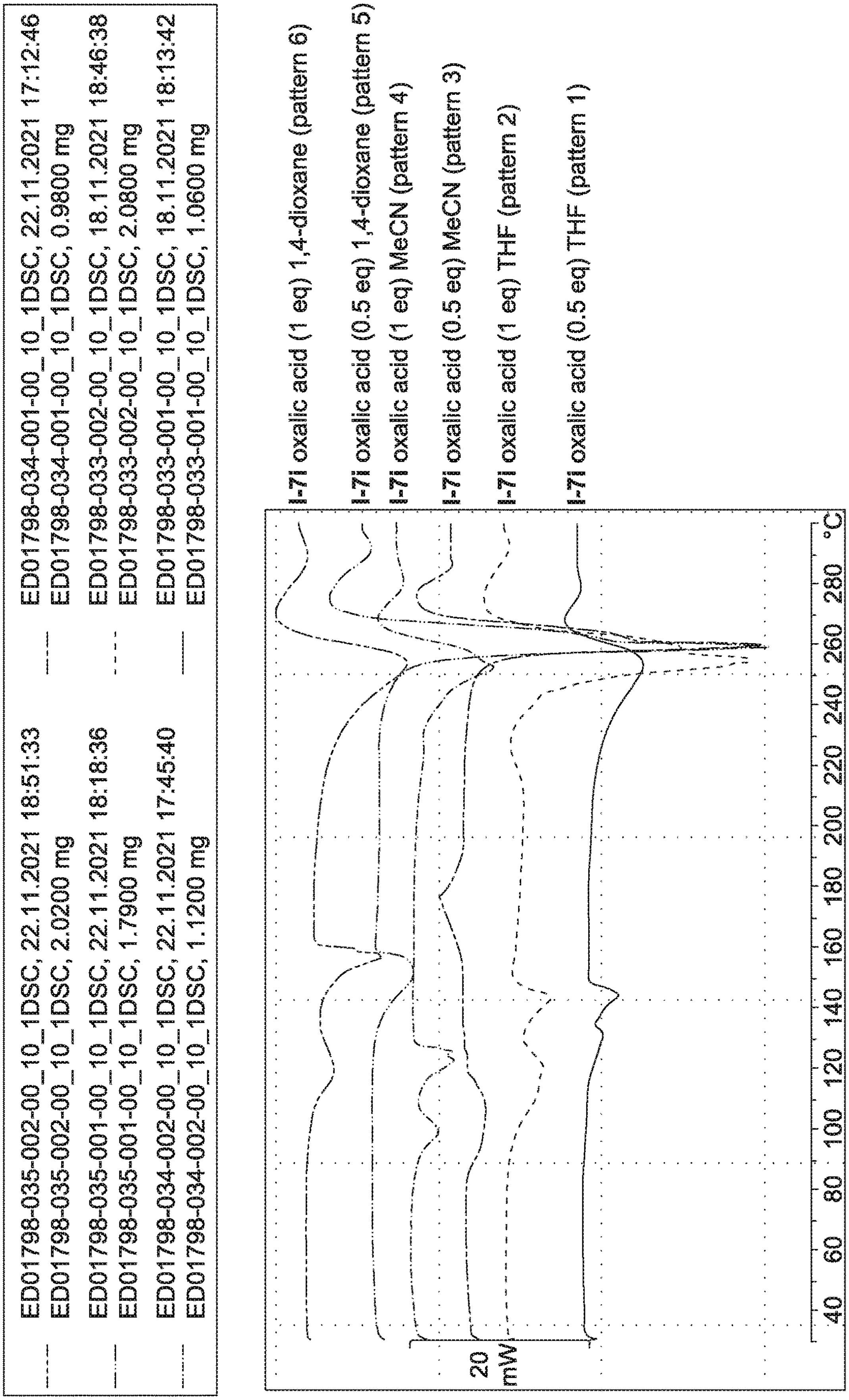
FIG. 51 shows the DSC curve of I-7i (polymorphs of patterns 1-6)
Figure 52:
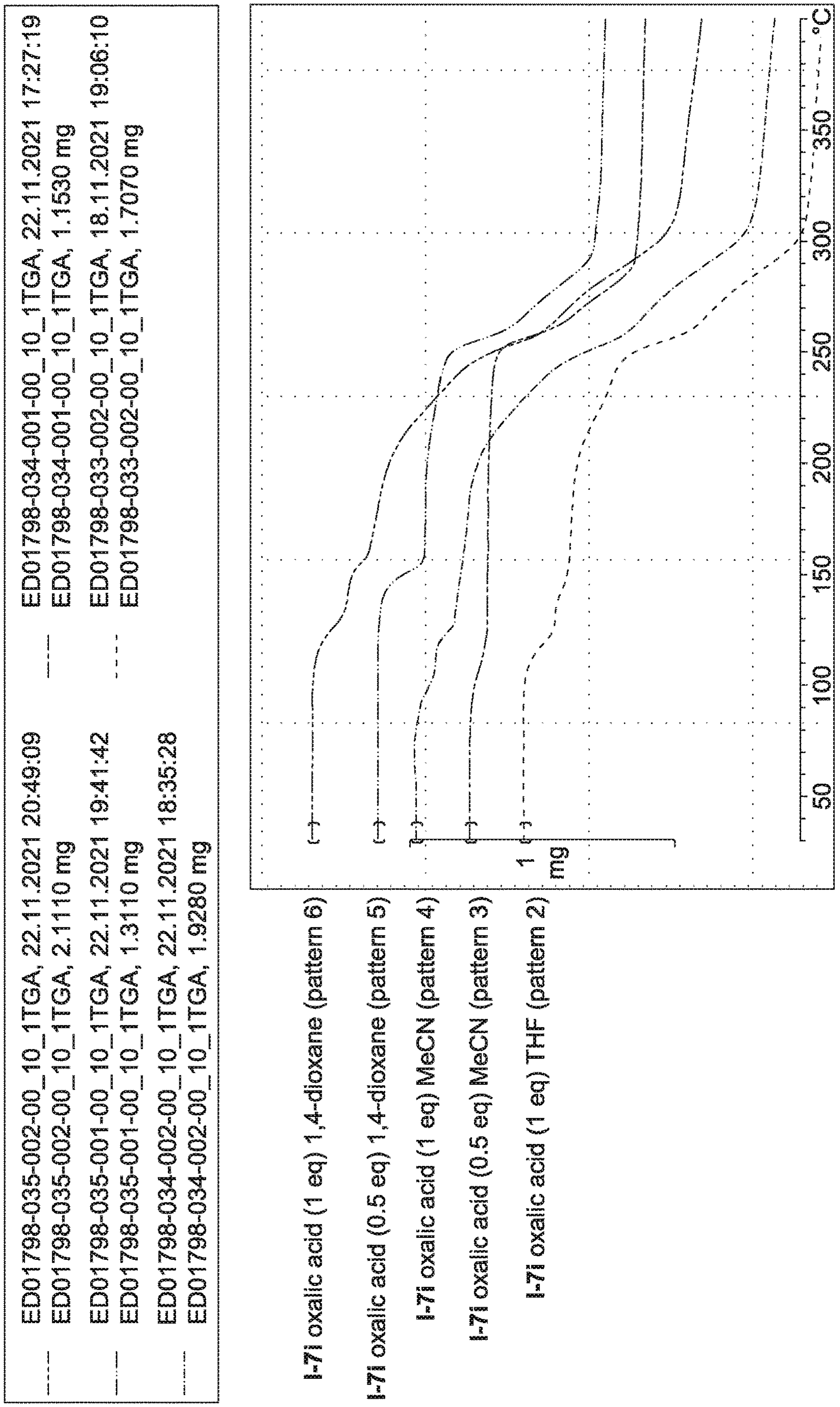
FIG. 52 shows the TGA plot of I-7i (polymorphs of patterns 2-6)

The DSC at 10° C./min shows that all solid crystalline material isolated from the various experiments were solvates, with several events showing in DSC (FIG. 51). Further, evidence that no anhydrous crystalline forms were isolated, the TGA shows several elements of mass loss (FIG. 52).

Example 11

Synthesis of benzoate salt of 3-(2-(dimethylamino) ethyl)-1H-indol-4-ol (I-7j)(benzoate salt of I-7/psilocin/psilocin-$d_0$/PI-$d_0$)

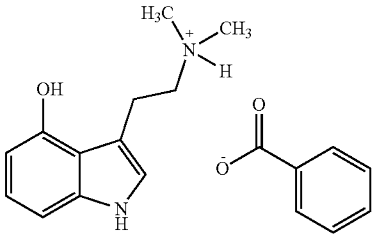

Compound I-7 (PI-$d_0$, free base)(10 mM) was dissolved in 1,4-dioxane, acetonitrile, or THF and treated with a solution of benzoic acid (10 mM) while being stirred at ambient temperature. Samples were refrigerated to produce I-7j (benzoate salt of PI-$d_0$).

As shown in FIGS. 53A, the X-ray powder diffraction (XRPD) pattern indicates the salt is crystalline, with only one polymorph observed regardless of which solvent was employed (pattern 1). FIG. 53B shows the annotated XRPD, and Table 15 shows the XRPD peak listing for I-7j (pattern 1).

TABLE 15

| Caption (display) | Angle | d Value | Gross Intensity | Rel. Intensity |
|---|---|---|---|---|
| 9.492° | 9.492038 | 9.310002 | 816.1553 | 0.234207 |
| 11.011° | 11.01083 | 8.028995 | 225.1465 | 0.046314 |
| 12.391° | 12.3913 | 7.137437 | 755.566 | 0.210192 |
| 13.440° | 13.4398 | 6.58288 | 292.8689 | 0.061474 |
| 14.609° | 14.60938 | 6.058398 | 1433.992 | 0.417304 |
| 15.432° | 15.43177 | 5.737337 | 182.47 | 0.016946 |
| 16.394° | 16.39421 | 5.402621 | 3297.966 | 1 |
| 18.259° | 18.25882 | 4.854886 | 2252.669 | 0.662731 |
| 18.967° | 18.96731 | 4.675109 | 3023.974 | 0.904632 |
| 19.356° | 19.35627 | 4.582032 | 977.581 | 0.255289 |
| 19.827° | 19.82713 | 4.474266 | 1207.459 | 0.328425 |
| 20.843° | 20.84305 | 4.25842 | 194.7453 | 0.010555 |
| 21.476° | 21.47557 | 4.134406 | 738.8857 | 0.187048 |
| 22.062° | 22.0625 | 4.025727 | 184.4619 | 0.012183 |
| 22.805° | 22.80468 | 3.89636 | 799.9279 | 0.203211 |
| 23.862° | 23.86174 | 3.726092 | 491.5757 | 0.103741 |
| 24.963° | 24.96308 | 3.56414 | 799.8894 | 0.201169 |
| 25.734° | 25.73424 | 3.459058 | 471.1698 | 0.096934 |
| 26.170° | 26.17029 | 3.402404 | 1669.852 | 0.47813 |
| 26.992° | 26.99244 | 3.300608 | 196.1326 | 0.015295 |
| 27.738° | 27.73771 | 3.213596 | 498.7095 | 0.115793 |
| 28.593° | 28.5934 | 3.119341 | 554.2463 | 0.136655 |
| 30.073° | 30.07312 | 2.969141 | 177.3094 | 0.020681 |
| 30.746° | 30.74603 | 2.905674 | 207.6318 | 0.030292 |
| 31.041° | 31.0409 | 2.878741 | 191.1328 | 0.02535 |
| 31.799° | 31.79946 | 2.811779 | 197.1789 | 0.02867 |
| 32.794° | 32.79412 | 2.728732 | 184.0209 | 0.026954 |
| 33.551° | 33.55059 | 2.668916 | 152.5839 | 0.019835 |
| 34.480° | 34.47956 | 2.599105 | 182.2929 | 0.030126 |
| 35.430° | 35.43034 | 2.531506 | 184.8386 | 0.031197 |
| 37.685° | 37.68499 | 2.385068 | 162.8452 | 0.024766 |
| 38.643° | 38.64258 | 2.328139 | 157.4924 | 0.022742 |

Figure 54:
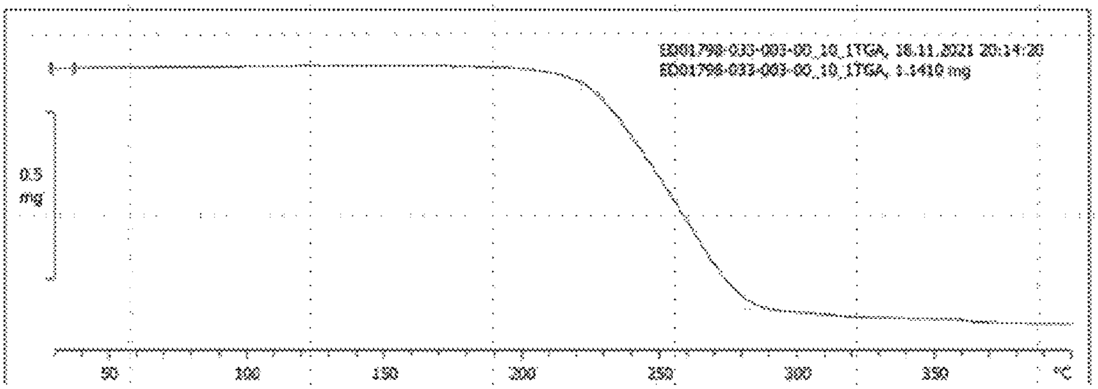
FIG. 54 shows the TGA plot of I-7j (polymorph of pattern 1)
Figure 55:
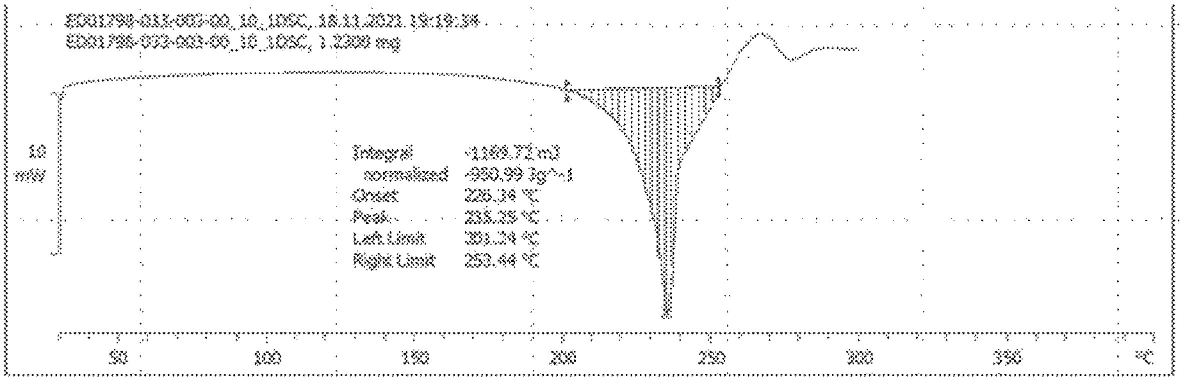
FIG. 55 shows the DSC curve of I-7j (polymorph of pattern 1)

The sample formed from THF was subjected to TGA analysis (FIG. 54), which indicated the crystalline form was stable until about 200° C. This mass loss in TGA associated with melt and decomposition in DSC (FIG. 55), which showed a high melt onset (226.3° C.) and peak (235.2° C.). Equally, no events were observed prior to the melt endotherm, indicating the absence of multiple physical forms in the sample, and also no conversion of physical forms prior to the melt. $^{1}$H NMR confirmed 1 equivalent of benzoic acid.

Figure 56:
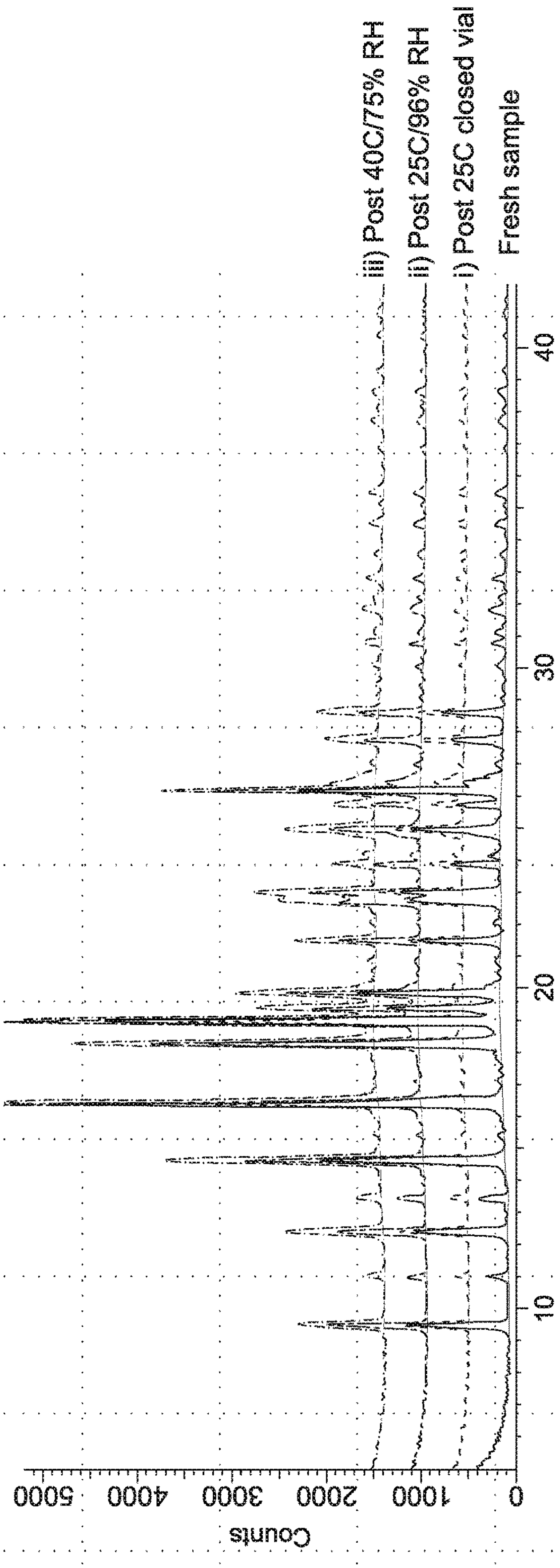
FIG. 56 shows the XRPD patterns of I-7j (polymorph of pattern 1) after storing solid samples for 22 days under the following conditions: i) 25° C., closed vial, ii) 25° C./96% RH, and iii) 40° C./75% RH, and comparing to fresh sample.

The storage stability of I-7j (sample from THF) was also assessed by storing the solid samples for 22 days under the following conditions: i) 25° C., closed vial, ii) 25° C./96% RH, and iii) 40° C./75% RH, and comparing to fresh sample by XRPD. The results are presented in FIG. 56, which showed no change in form by XRPD post storage. Further, no loss of purity was observed by 1H NMR and UPLC.

Figure 57:
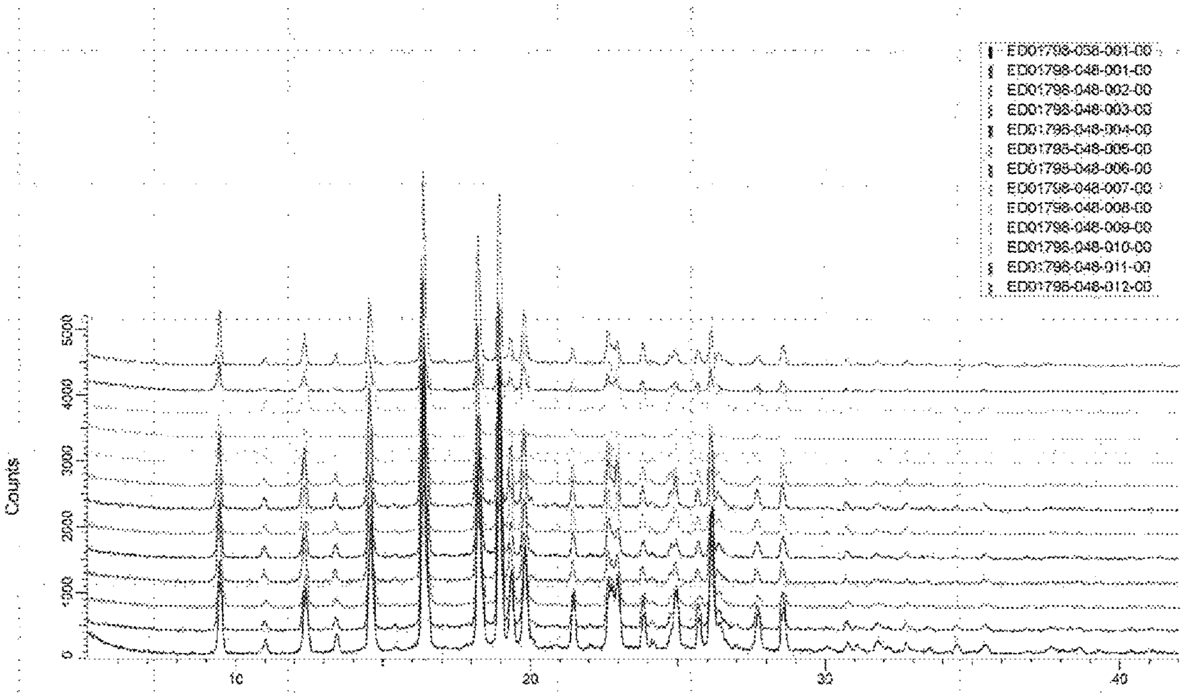
FIG. 57 shows the XRPD patterns of I-7j (polymorph of pattern 1) after maturation in 12 different solvents.

I-7j (sample from THF) was also subjected to maturation in 12 different solvents following the procedure detailed in Example 2. All samples were isolated as solids and retained their initial crystalline form according to XRPD analysis (FIG. 57).

Figure 58:
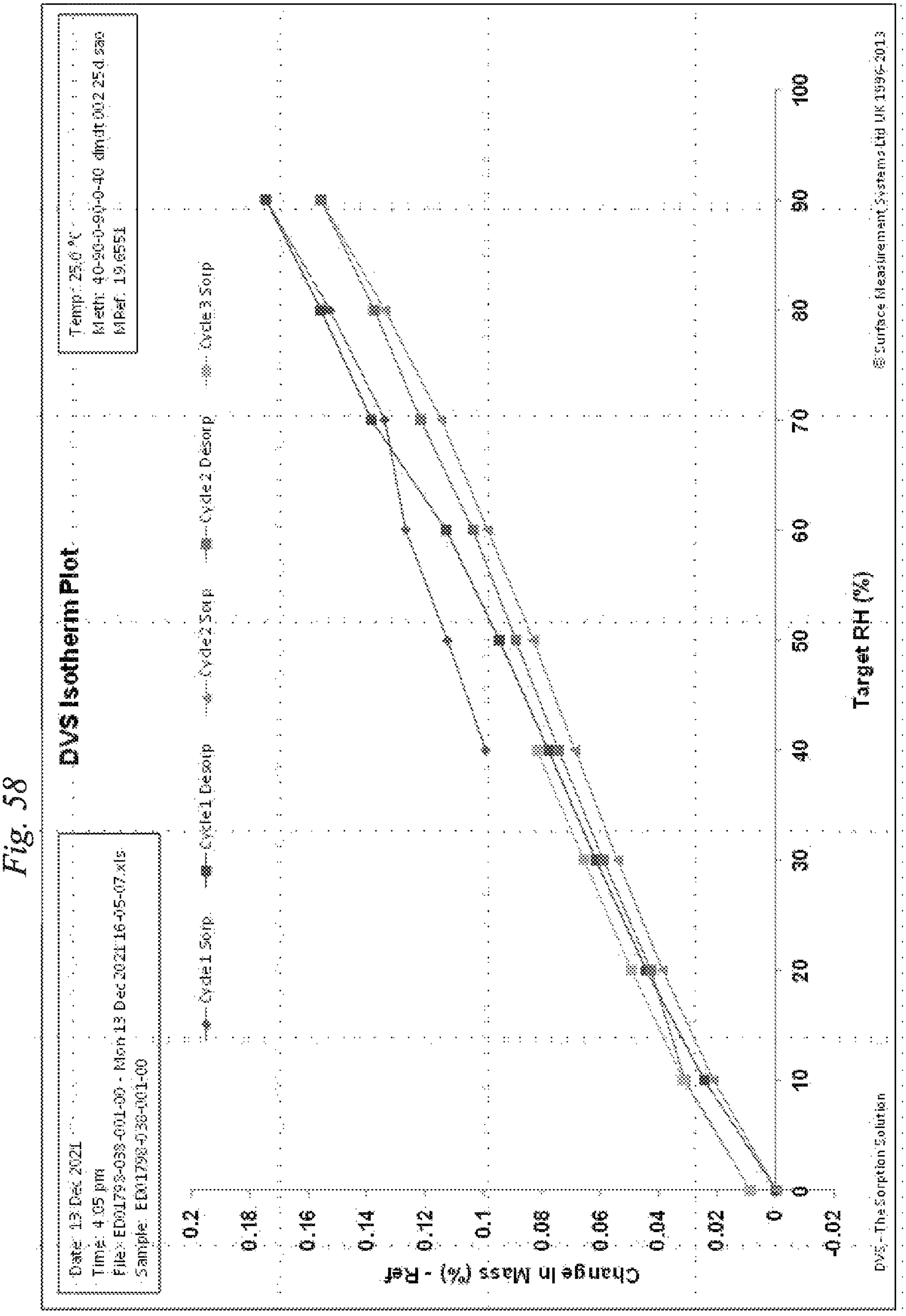
FIG. 58 shows the DVS isotherm of I-7j (polymorph of pattern 1)

DVS isotherm plot of I-7j (sample from THF) is shown in FIG. 58, which shows a 0.16% mass increase over 0-90% RH range (second sorption cycle).

Figure 59A:
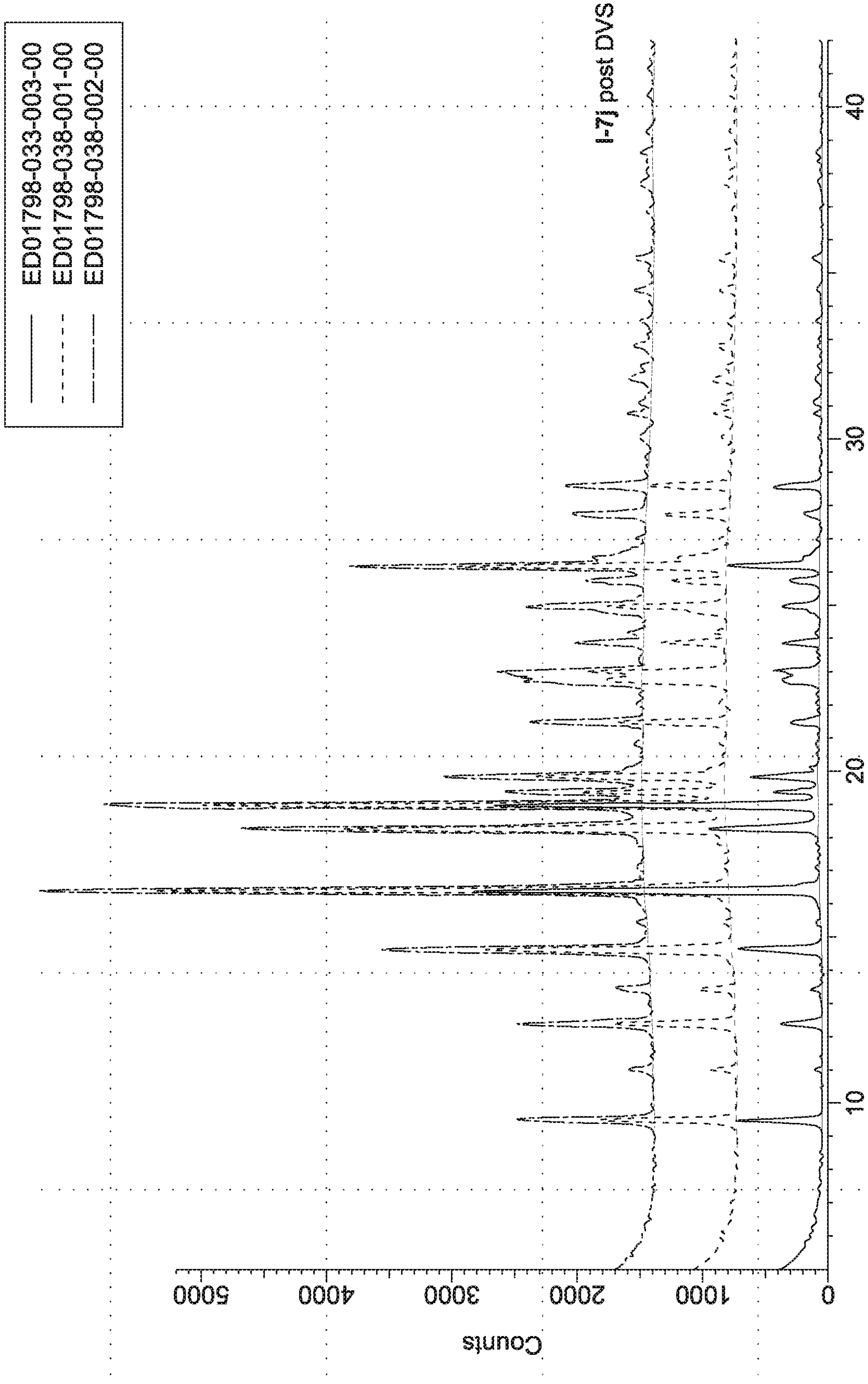
FIGS. 59A-59C show that no changes to I-7j (polymorph of pattern 1) took place after being subjected to DVS conditions (post-DVS) by XRPD (FIG. 59A, compared to pattern before DVS from material obtained from THF and acetonitrile) and by $^1$H NMR (FIGS. 59B and 59C)
Figure 59B:
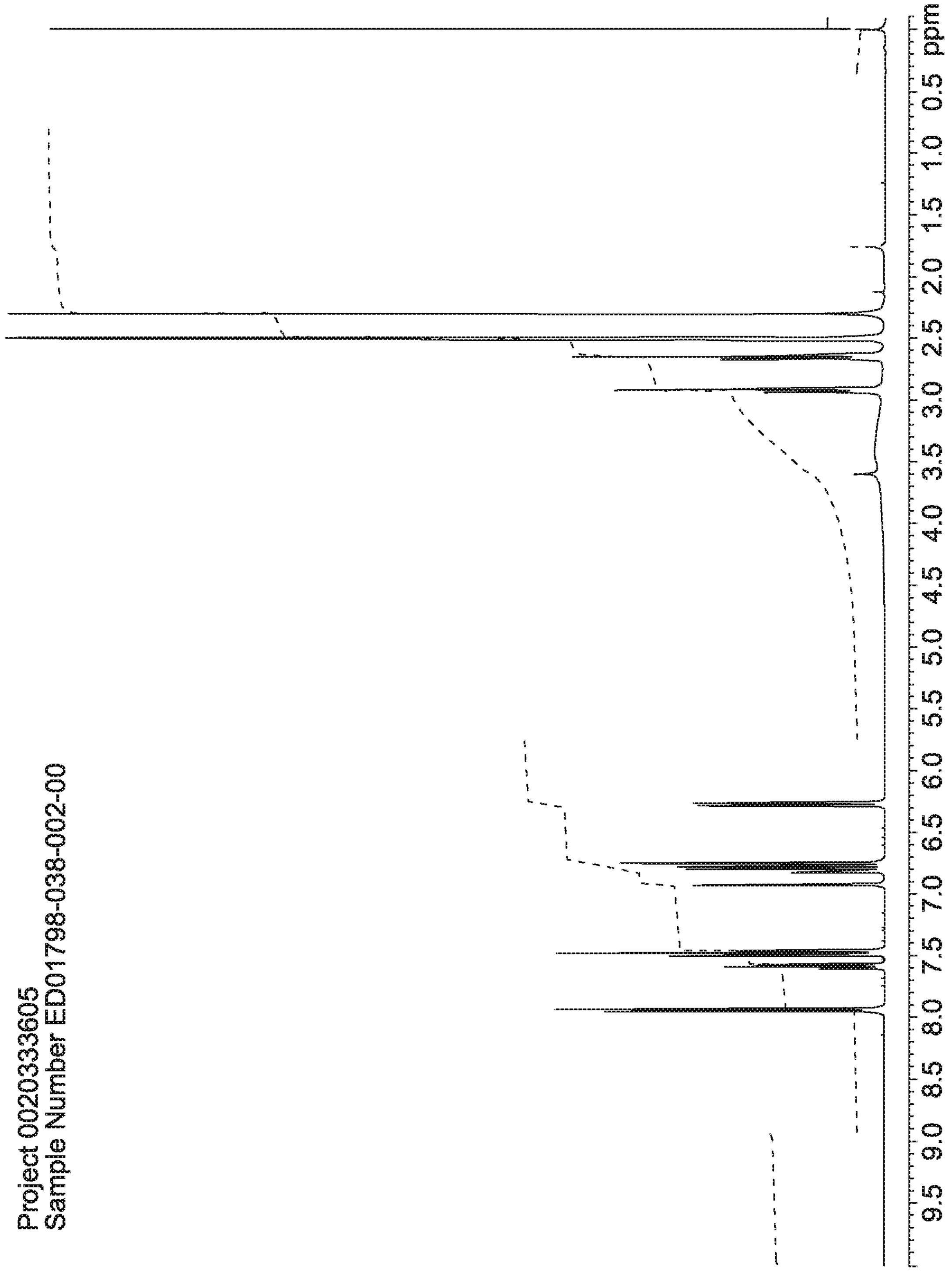
Figure 59C:
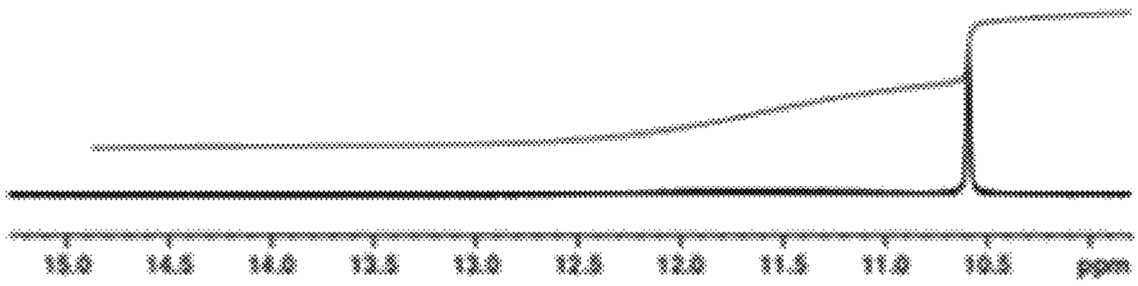

FIG. 59A shows the XRPD pattern of I-7j after being subjected to the DVS conditions above (post-DVS) compared to the XRPD pattern before DVS from material obtained from THF and acetonitrile (see FIG. 53A), indicating that no changes to the crystal structure took place. There was also no loss of purity following DVS analysis according to $^1$H NMR (FIGS. 59B-59C) and UPLC. $^1$H NMR was consistent with 1 eq of benzoic acid (0.97 eq).

This data represents advantageous behavior for pharmaceutical development purposes.

Example 12

Synthesis of salicylate salt of 3-(2-(dimethylamino)ethyl)-1H-indol-4-ol (I-7k)(salicylate salt of I-7/psilocin/psilocin-$d_0$/PI-$d_0$)

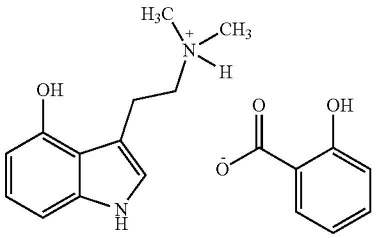

Compound I-7 (PI-$d_0$, free base)(10 mM) was dissolved in 1,4-dioxane/heptane, acetonitrile/TBME, or THF/heptane and treated with a solution of salicylic acid (10 mM) while being stirred at ambient temperature. Samples were refrigerated to produce I-7k (salicylate salt of PI-$d_0$).

Figure 60:
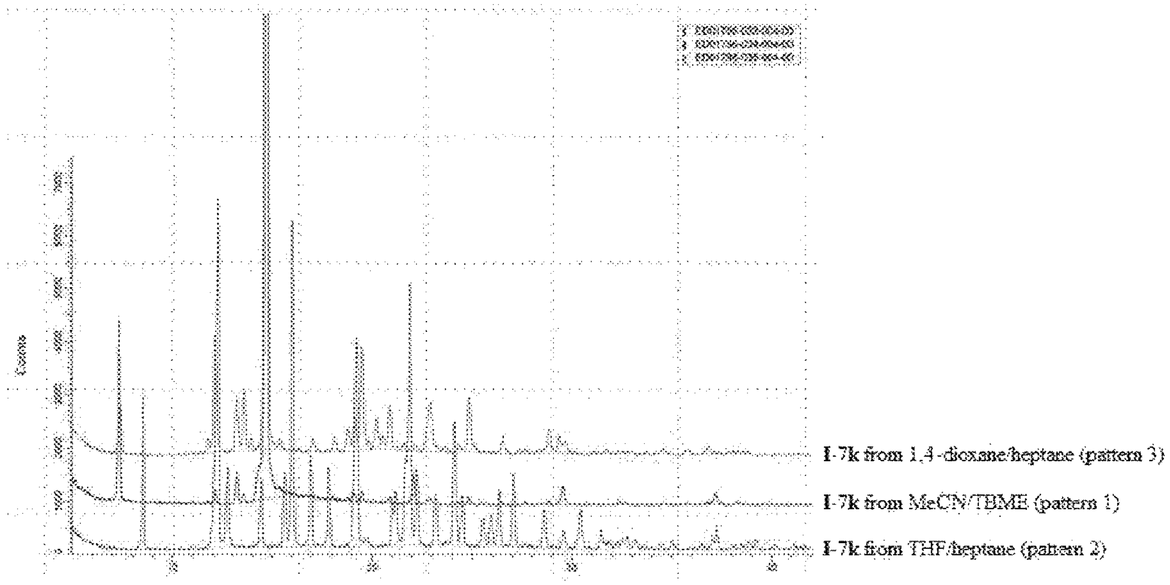
FIG. 60 shows the XRPD pattern of three different crystalline polymorphs of I-7k: a polymorph having pattern 1 (made from acetonitrile/TBME), a polymorph having pattern 2 (made from THF/heptane), and a polymorph having pattern 3 (made from 1,4-dioxane/heptane)

As shown in FIG. 60, the X-ray powder diffraction (XRPD) pattern indicates that three different crystalline polymorphs of I-7k were formed: a polymorph having pattern 1 (made from acetonitrile/TBME), a polymorph having pattern 2 (made from THF/heptane), and a polymorph having pattern 3 (made from 1,4-dioxane/heptane).

Figure 61:
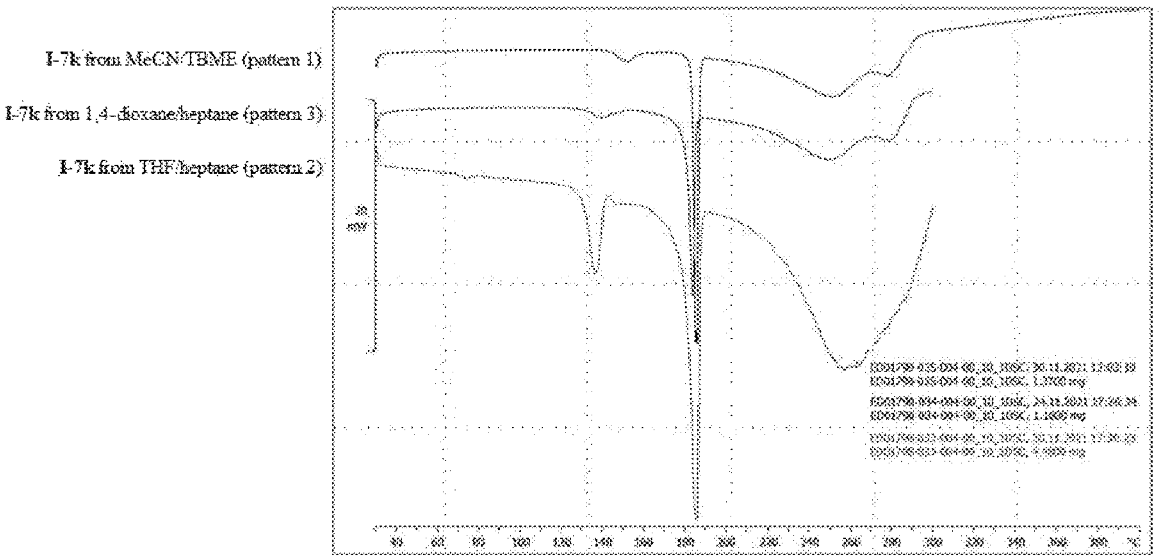
FIG. 61 shows the DSC curve of three different crystalline polymorphs of I-7k.
Figure 62:
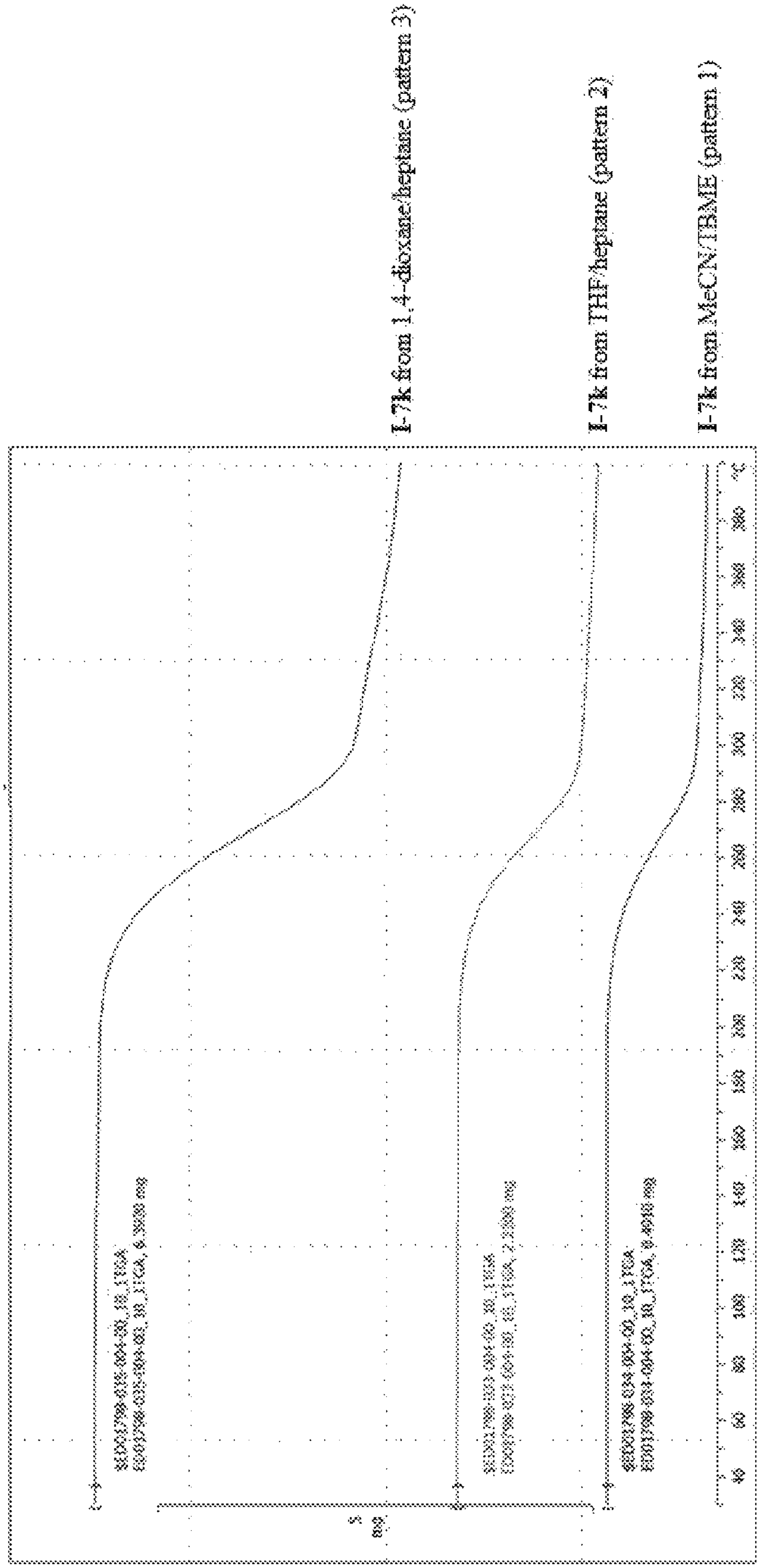
FIG. 62 shows the TGA plot of three different crystalline polymorphs of I-7k.

The DSC and TGA plots of these crystalline polymorphs are presented in FIGS. 61 and 62, respectively.

Example 13

Synthesis of benzenesulfonate salt of 3-(2-(bis(methyl-$d_3$)amino)ethyl-1,1,2,2-$d_4$)-1H-indol-4-ol (I-3a)(benzenesulfonate salt of I-3/psilocin-$d_{10}$/PI-$d_{10}$)

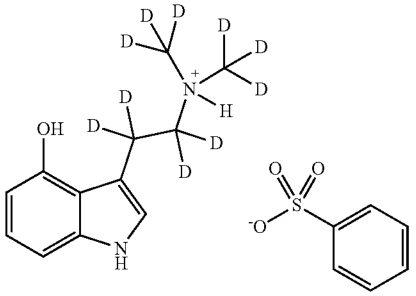

Compound I-3 (PI-$d_{10}$, free base)(10 mM) was dissolved in acetonitrile and treated with a solution of 1M benzenesulfonic acid in THF (10 mM). The resultant solution was treated with TBME and refrigerated. After several days, seeds of I-7a crystalline polymorph pattern 1 (see Example 2) were added. Crystals of I-3a (benzenesulfonate salt of PI-$d_{10}$) were slowly formed under refrigerated conditions.

Figure 63A:
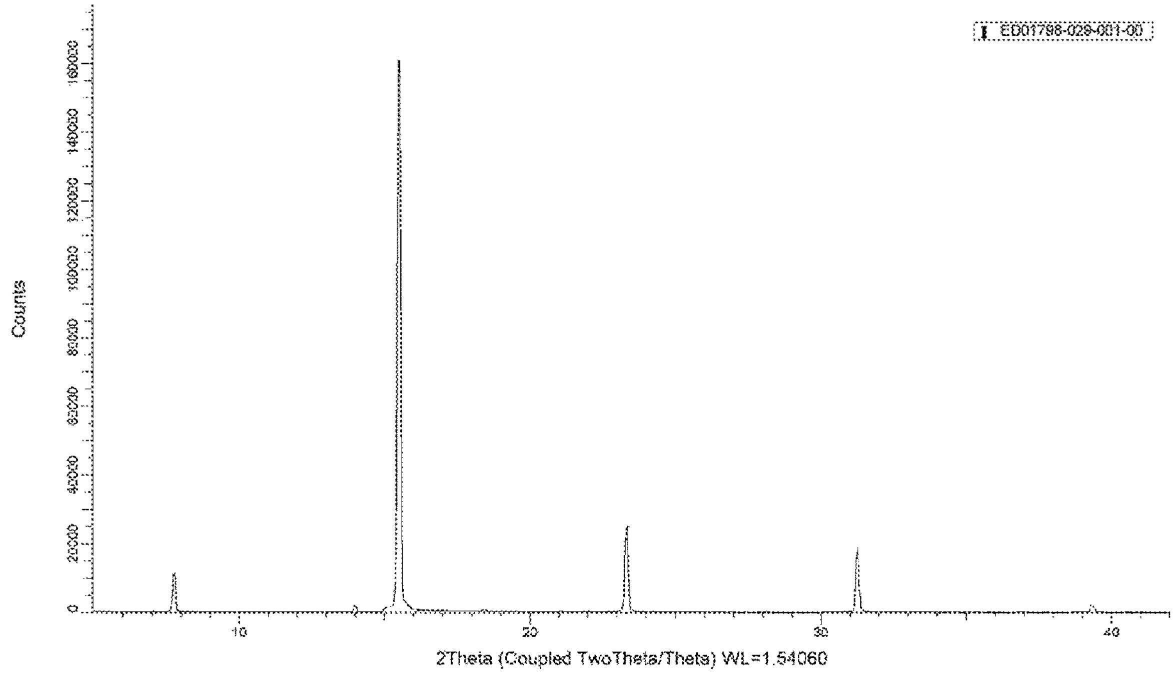
FIGS. 63A-63D show the XRPD pattern of I-3a (pattern 1) (FIG. 63A), zoomed in and annotated versions of the XRPD plot (FIGS. 63B-63C), and a comparative XRPD plot of I-3a (pattern 1) to I-7a seeds (FIG. 63D)
Figure 63B:
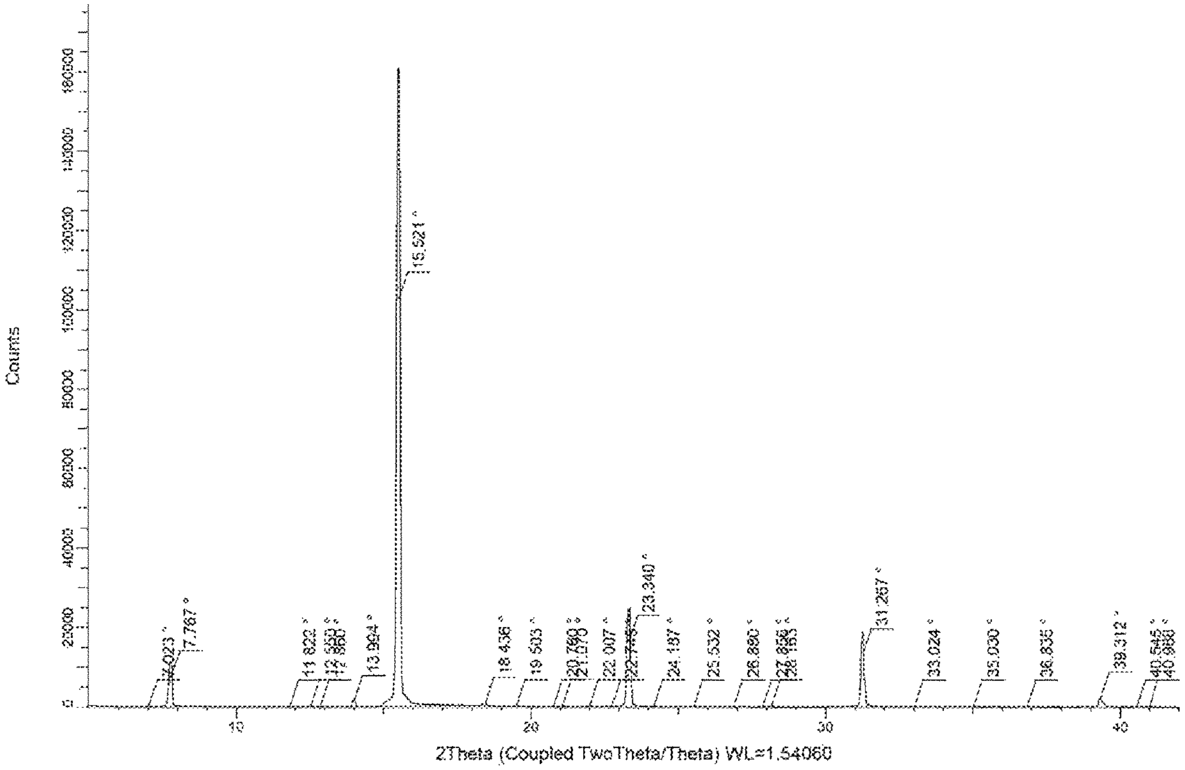
Figure 63C:
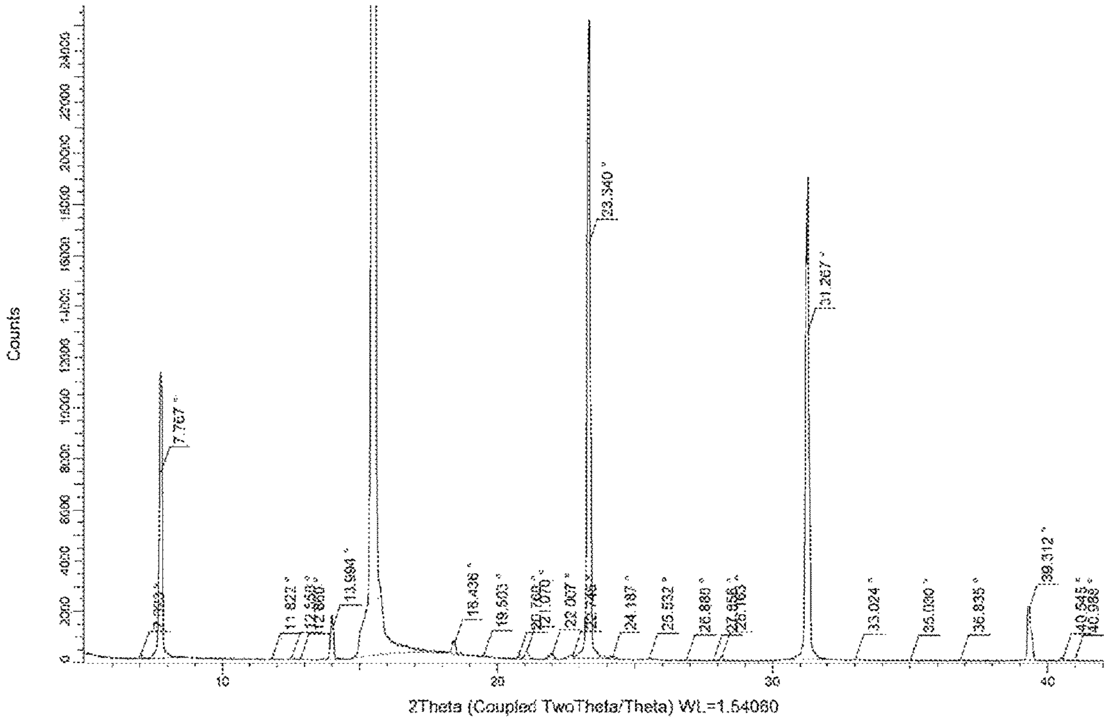
Figure 63D:
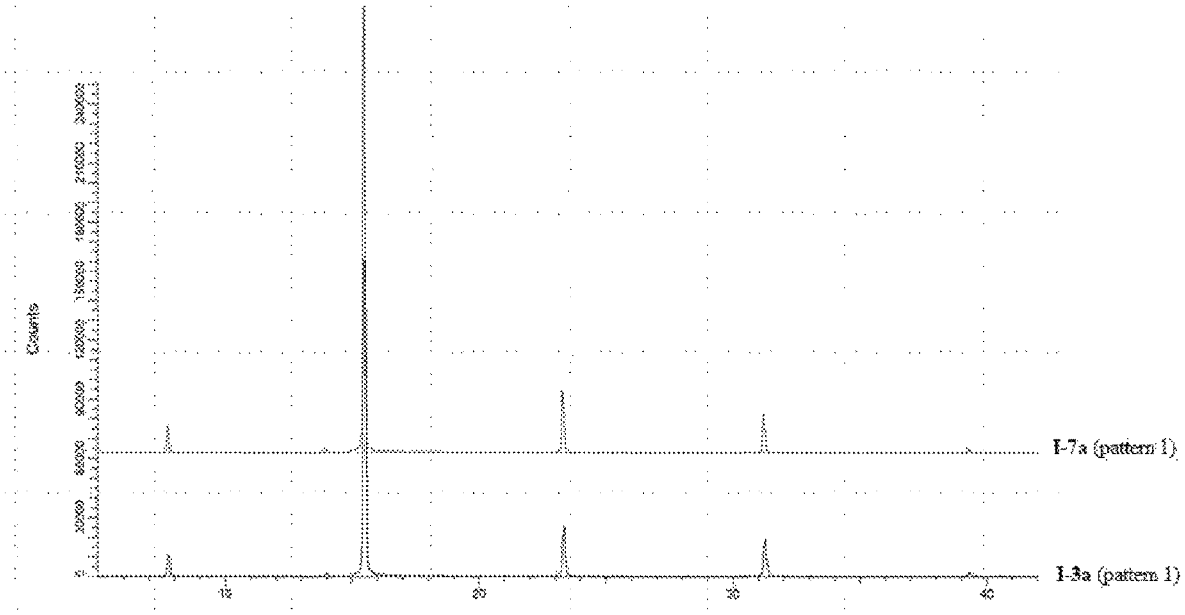

The X-ray powder diffraction (XRPD) pattern indicates that a single crystalline polymorph of I-3a was formed (pattern 1) (FIG. 63A). Zoomed in and annotated versions of the XRPD pattern are presented in FIGS. 63B-63C. FIG. 63D shows that the single crystalline polymorph of I-3a has the same pattern (pattern 1) as the I-7a seeds. Table 16 shows the XRPD peak listing for I-3a (pattern 1).

TABLE 16

| Name | Caption (display) | Angle | d Value | Net Intensity | Rel. Intensity |
|---|---|---|---|---|---|
| Peak #1 | 7.023° | 7.023418 | 12.57581 | 77.75247 | 0.000758426 |
| Peak #2 | 7.767° | 7.767084 | 11.37332 | 7314.893 | 0.07135213 |
| Peak #3 | 11.822° | 11.8224 | 7.479583 | 32.03899 | 0.00031252 |
| Peak #4 | 12.550° | 12.54997 | 7.047554 | 78.68196 | 0.000767493 |
| Peak #5 | 12.860° | 12.85957 | 6.878568 | 21.29807 | 0.000207749 |
| Peak #6 | 13.994° | 13.99379 | 6.323494 | 1152.819 | 0.01124502 |
| Peak #7 | 15.521° | 15.52119 | 5.704481 | 102518.2 | 1 |
| Peak #8 | 18.436° | 18.43564 | 4.808719 | 365.3079 | 0.003563346 |
| Peak #9 | 19.503° | 19.50339 | 4.547799 | 38.2632 | 0.000373233 |
| Peak #10 | 20.760° | 20.7598 | 4.275309 | 47.20708 | 0.000460475 |
| Peak #11 | 21.070° | 21.06976 | 4.21311 | 278.4323 | 0.00271593 |
| Peak #12 | 22.007° | 22.00676 | 4.035797 | 176.9576 | 0.001726109 |
| Peak #13 | 22.745° | 22.74485 | 3.906473 | 76.58357 | 0.000747024 |
| Peak #14 | 23.340° | 23.34011 | 3.808173 | 16264.17 | 0.1586466 |
| Peak #15 | 24.187° | 24.18713 | 3.676697 | 57.4707 | 0.00056059 |
| Peak #16 | 25.532° | 25.5316 | 3.486051 | 48.40523 | 0.000472162 |
| Peak #17 | 26.880° | 26.87974 | 3.314191 | 24.26286 | 0.000236669 |
| Peak #18 | 27.856° | 27.85616 | 3.200199 | 42.07394 | 0.000410405 |
| Peak #19 | 28.163° | 28.16311 | 3.166014 | 143.1989 | 0.001396815 |
| Peak #20 | 31.267° | 31.26673 | 2.858461 | 12789.69 | 0.1247553 |
| Peak #21 | 33.024° | 33.02377 | 2.710279 | 28.16152 | 0.000274698 |
| Peak #22 | 35.030° | 35.02954 | 2.559547 | 19.00768 | 0.000185408 |
| Peak #23 | 36.835° | 36.83464 | 2.438153 | 42.1271 | 0.000410923 |
| Peak #24 | 39.312° | 39.31247 | 2.289996 | 2013.023 | 0.01963576 |
| Peak #25 | 40.545° | 40.54509 | 2.223177 | 83.841 | 0.000817816 |
| Peak #26 | 40.988° | 40.98812 | 2.200164 | 15.99768 | 0.000156047 |

Figure 64A:
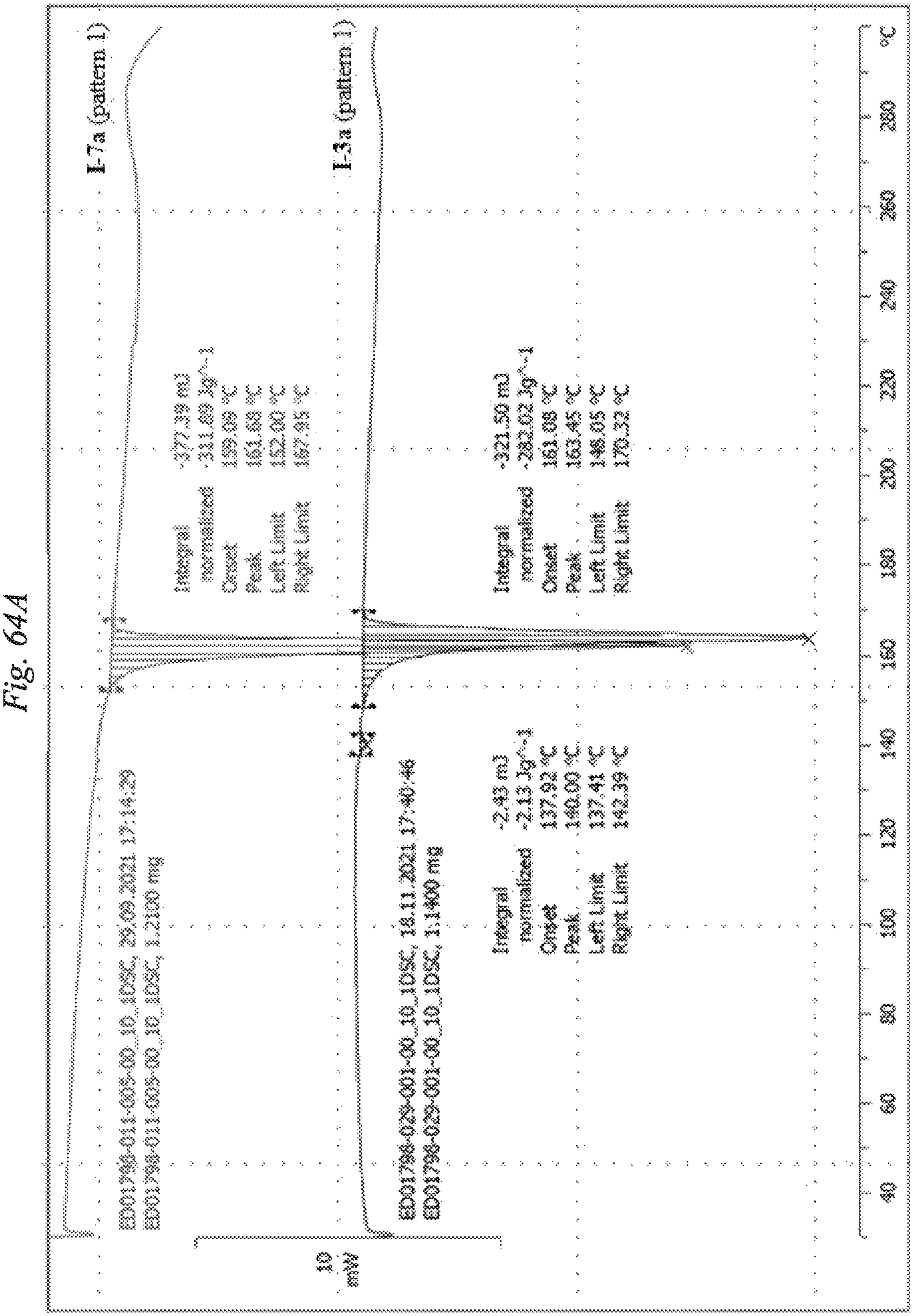
FIGS. 64A-64B show a comparison of I-3a (pattern 1) to I-7a seeds by DSC (FIG. 64A) and TGA (FIG. 64B)
Figure 64B:
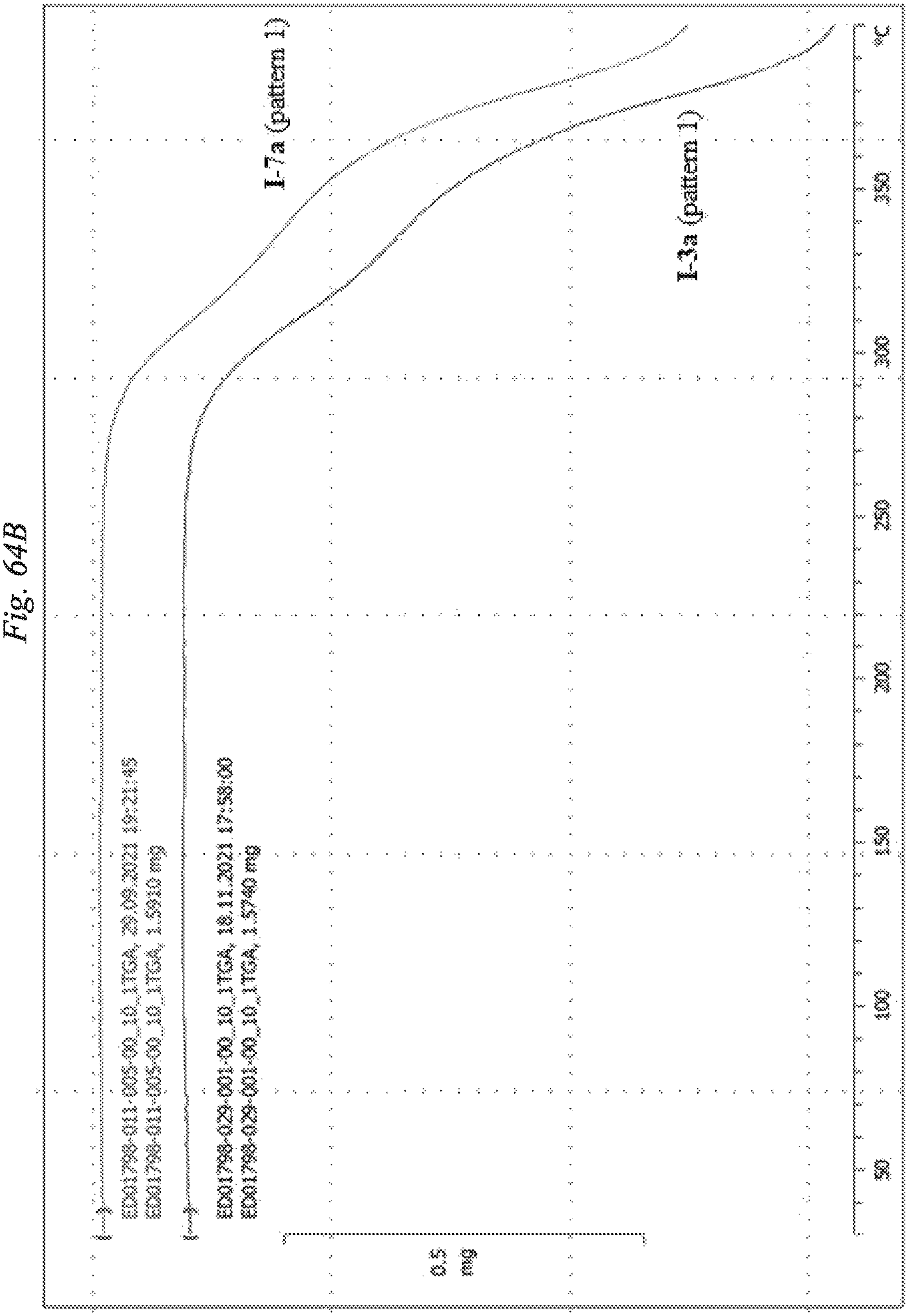

The DSC curve of I-3a is shown in FIG. 64A, compared to that of I-7a and it is evident that the salt has a high melt onset (161.08° C.) and peak (163.45° C.). One small event was observed prior to the melt endotherm with an onset of 137.92° C. The thermogravimetric analysis (TGA) curve of I-3a at 10° C./min is shown in FIG. 64B3, which is nearly identical to the TGA curve of I-7a.

Figure 65A:
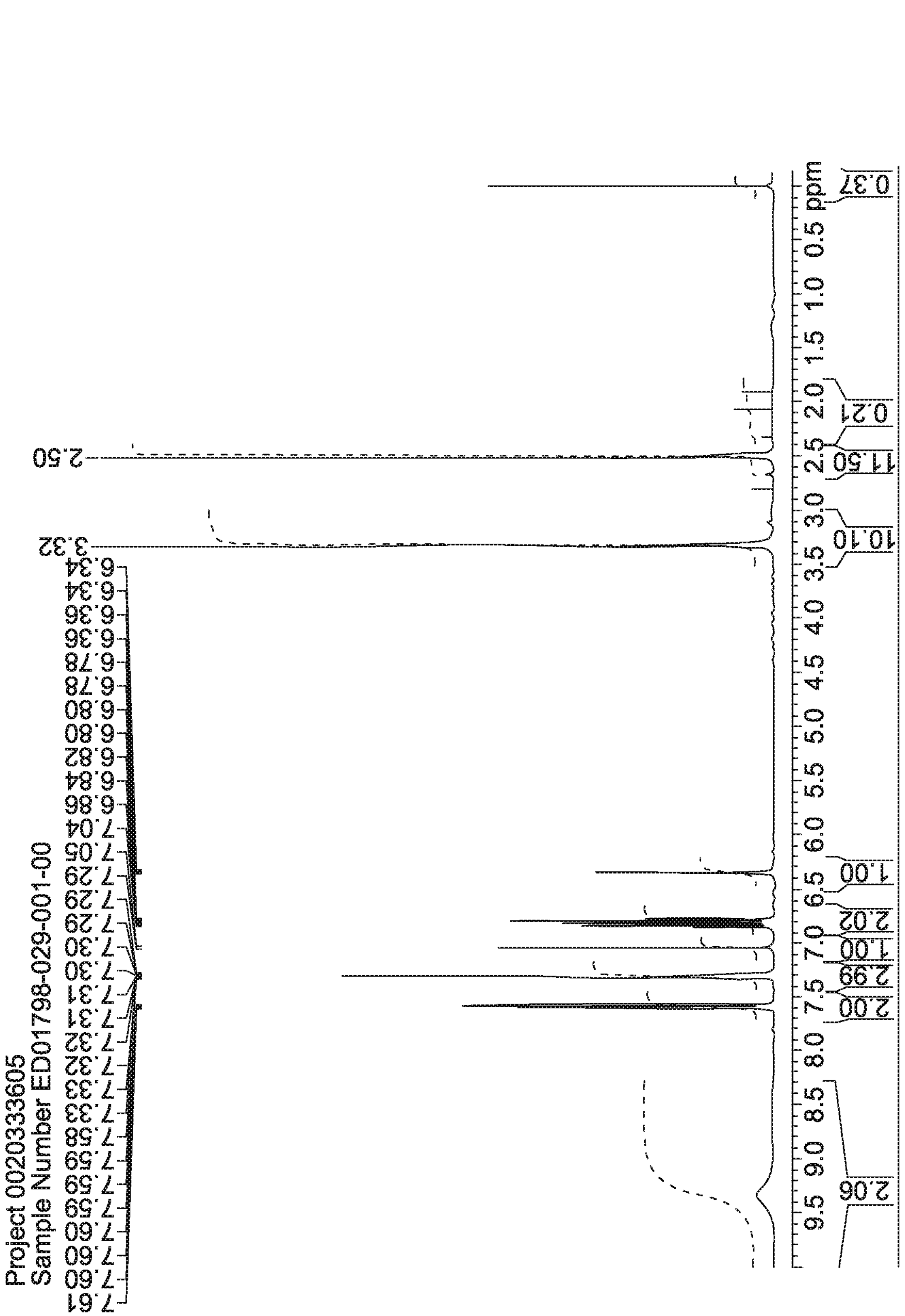
FIGS. 65A-65B shows the $^1H$ NMR spectrum of I-3a (pattern 1)
Figure 65B:
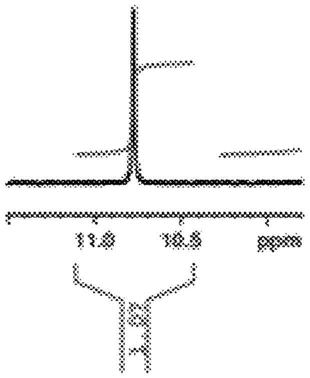

The identity of I-3a was also confirmed by $^1$H NMR (FIGS. 65A-65B).

Example 14

Synthesis of tartrate salt of 3-(2-(bis(methyl-$d_3$) amino)ethyl-1,1,2,2-$d_4$)-1H-indol-4-ol (I-3b)(tartrate salt of I-3/psilocin-$d_{10}$/PI-$d_{10}$)

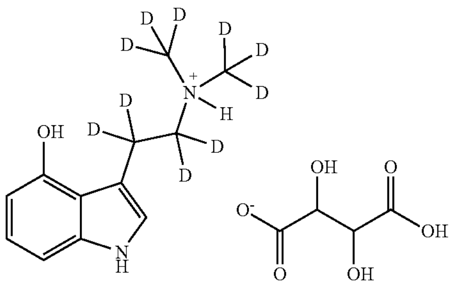

Non-seeded. Compound I-3 (PI-$d_{10}$, free base)(10 mM) was dissolved in THF and treated with a solution of L-tartaric acid (10 mM) while being stirred at ambient temperature. Samples were shaken overnight at room temperature to produce I-3b (as an L-tartrate salt of PI-$d_{10}$).

Figure 66:
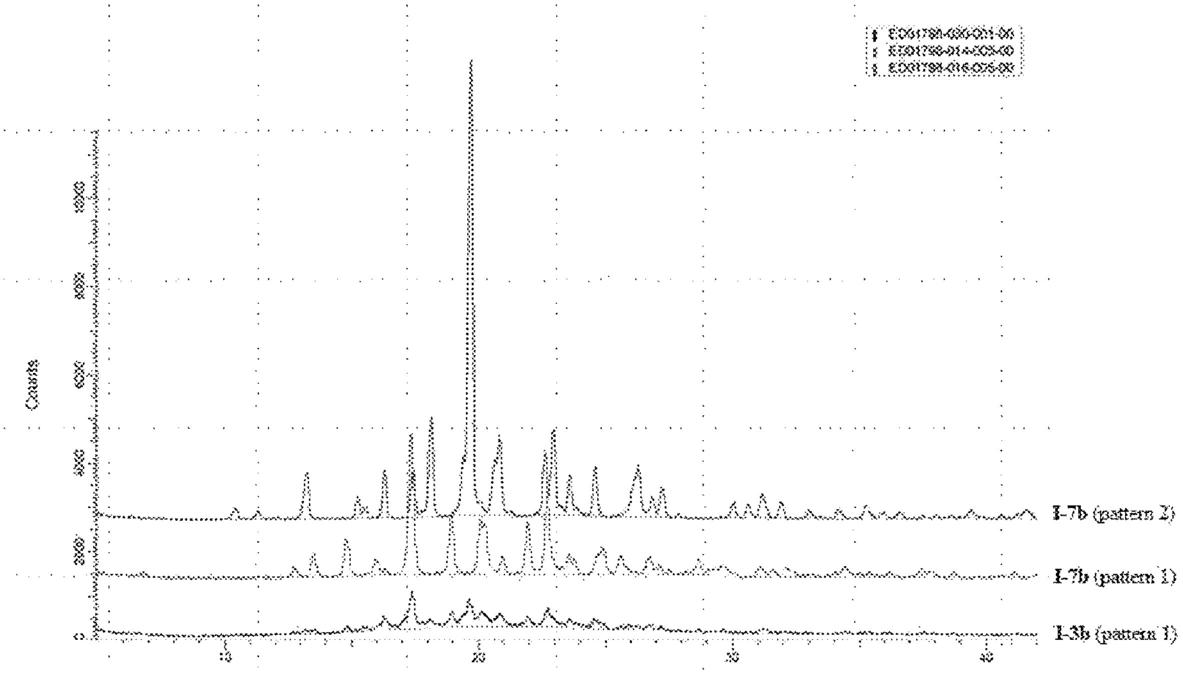
FIG. 66 shows the XRPD pattern of I-3b (pattern 1, obtained from non-seeded experiments) compared to crystalline polymorphs of I-7b of pattern 1 (from THF) and pattern 2 (from 1,4-dioxane)

As shown in FIG. 66, the X-ray powder diffraction (XRPD) pattern indicates that a single crystalline polymorph of I-3b was formed (pattern 1), although it was poorly crystalline compared to crystalline polymorphs of I-7b of pattern 1 (from THF) and pattern 2 (from 1,4-dioxane) (see Example 3).

Figure 67:
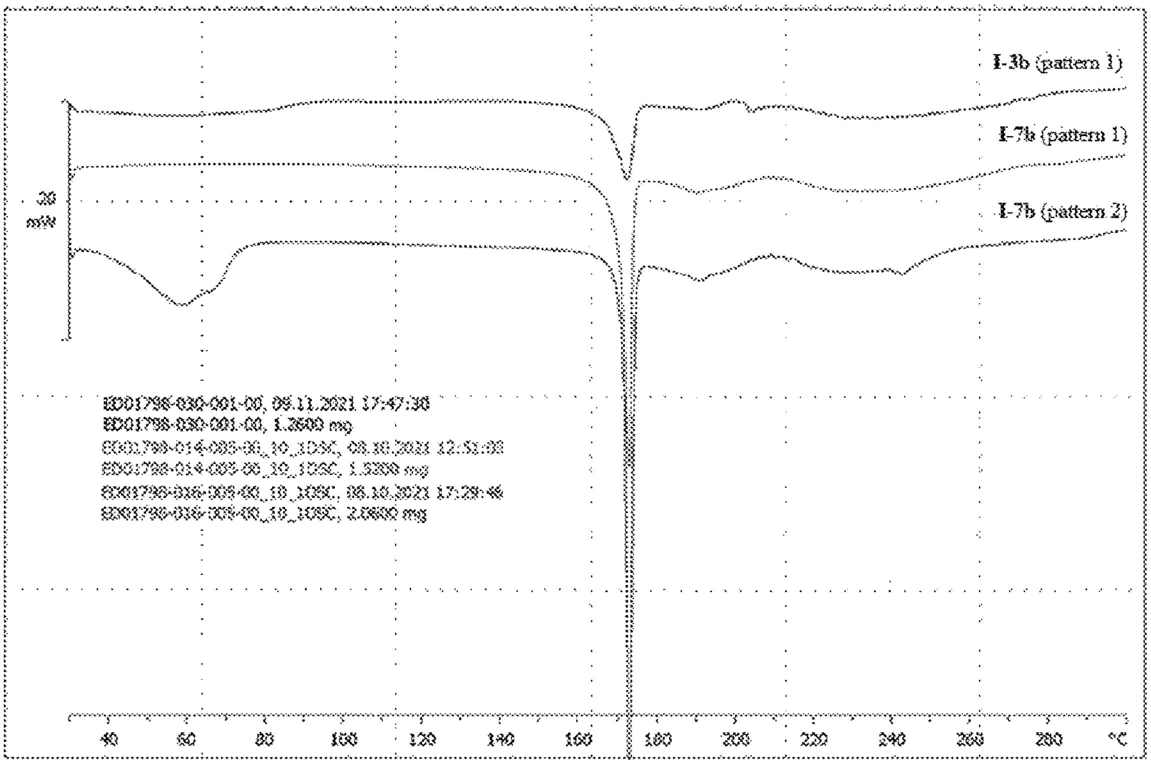
FIG. 67 shows DSC curve of I-3b (pattern 1, obtained from non-seeded experiments) compared to crystalline polymorphs of I-7b of pattern 1 (from THF) and pattern 2 (from 1,4-dioxane)
Figure 68:
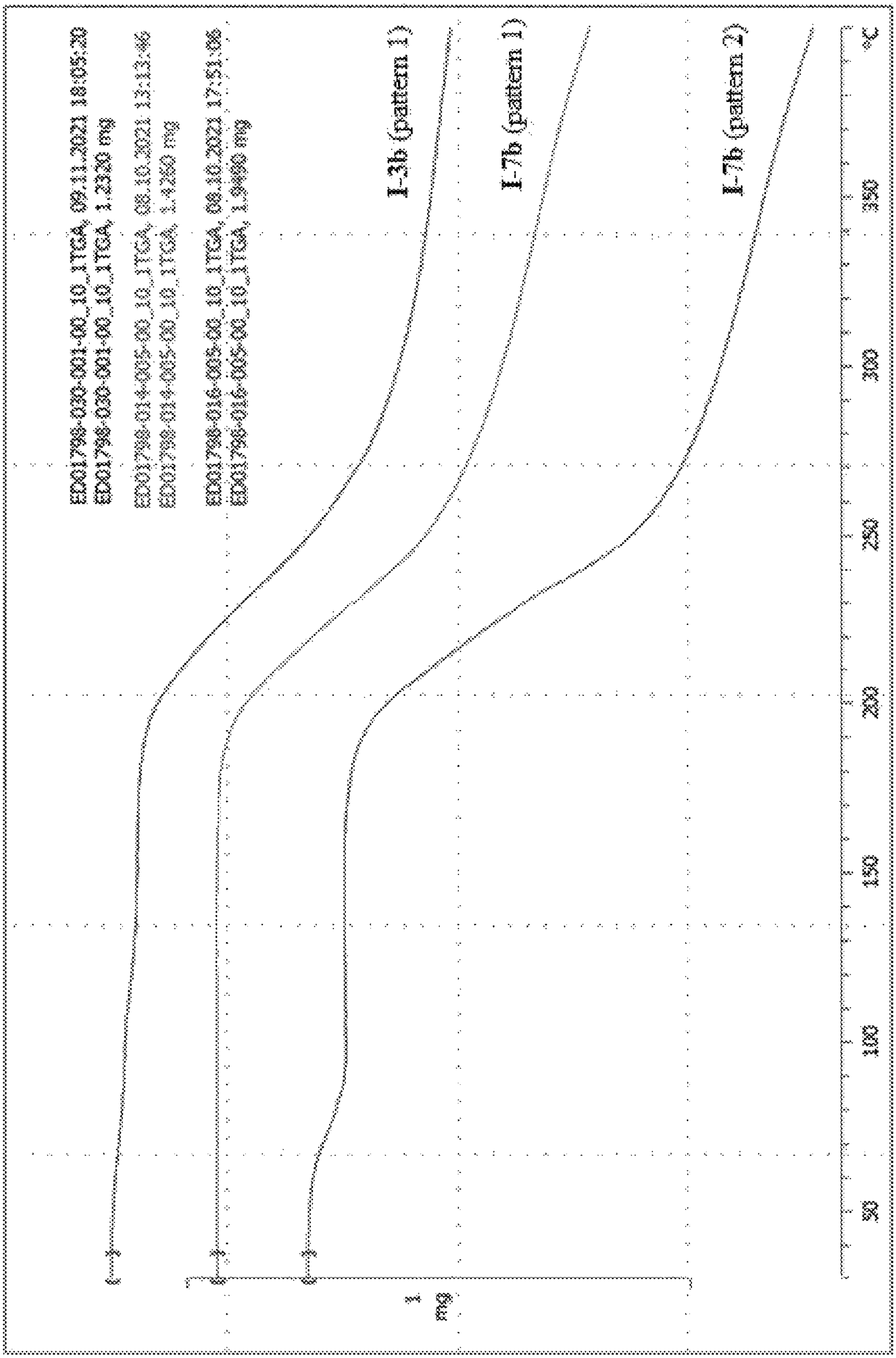
FIG. 68 shows the TGA plot of I-3b (pattern 1, obtained from non-seeded experiments) compared to crystalline polymorphs of I-7b of pattern 1 (from THF) and pattern 2 (from 1,4-dioxane)

The DSC curve of I-3b (pattern 1) at 10° C./min is shown in FIG. 67, compared to that of the polymorph patterns 1 and 2 of I-7b, and it is again evident that polymorph of I-3b (pattern 1) was poorly crystalline. The thermogravimetric analysis (TGA) curve of I-3b (pattern 1) at 10° C./min is shown in FIG. 68.

Seeded. Compound I-3 (PI-$d_{10}$, free base)(10 mM) was dissolved in THF or 1,4-dioxane and treated with a solution of L-tartaric acid (10 mM) while being stirred at ambient temperature. Samples were refrigerated. After several days, seeds of I-7b crystalline polymorph pattern 1 (see Example 3) were added and crystals of I-3b were slowly formed.

The X-ray powder diffraction (XRPD) pattern (FIGS. 69A-69B) indicates that the seeded experiment produced a single crystalline polymorph of I-3b (pattern 2), which was substantially the same as the seeds of crystalline polymorph of I-7b of pattern 1, and having a higher crystallinity compared to the crystalline polymorph of I-3b of pattern 1 obtained from the non-seeded experiments. Table 17 shows the XRPD peak listing for I-3b (pattern 2).

TABLE 17

| Name | Caption (display) | Angle | d Value | Net Intensity | Rel. Intensity |
|---|---|---|---|---|---|
| Peak #1 | 6.732° | 6.7315 | 13.1205 | 21.63181 | 0.01863163 |
| Peak #2 | 12.708° | 12.70753 | 6.960525 | 91.25528 | 0.0785988 |
| Peak #3 | 13.470° | 13.46988 | 6.568243 | 179.8262 | 0.1548855 |
| Peak #4 | 14.774° | 14.77353 | 5.991449 | 265.2903 | 0.2284964 |
| Peak #5 | 15.921° | 15.92107 | 5.562096 | 119.7453 | 0.1031374 |
| Peak #6 | 16.268° | 16.26759 | 5.444388 | 51.88243 | 0.04468669 |
| Peak #7 | 17.295° | 17.2945 | 5.123354 | 1161.026 | 1 |
| Peak #8 | 18.869° | 18.86872 | 4.699313 | 465.4803 | 0.4009213 |
| Peak #9 | 20.079° | 20.0787 | 4.418771 | 216.5187 | 0.186489 |
| Peak #10 | 20.208° | 20.20805 | 4.390777 | 379.5682 | 0.3269247 |
| Peak #11 | 20.877° | 20.87668 | 4.251637 | 136.9393 | 0.1179468 |
| Peak #12 | 21.894° | 21.89416 | 4.056297 | 343.8481 | 0.2961587 |
| Peak #13 | 22.657° | 22.65734 | 3.921363 | 598.8112 | 0.5157602 |
| Peak #14 | 23.491° | 23.49116 | 3.784026 | 184.869 | 0.1592289 |
| Peak #15 | 23.702° | 23.70229 | 3.750796 | 154.3493 | 0.1329421 |
| Peak #16 | 24.636° | 24.63617 | 3.610689 | 137.7375 | 0.1186342 |
| Peak #17 | 24.882° | 24.88205 | 3.575563 | 200.4769 | 0.1726721 |
| Peak #18 | 25.569° | 25.56915 | 3.481015 | 157.8053 | 0.1359188 |
| Peak #19 | 26.685° | 26.68466 | 3.337975 | 173.1976 | 0.1491763 |
| Peak #20 | 27.060° | 27.06003 | 3.292517 | 45.83561 | 0.03947853 |
| Peak #21 | 27.502° | 27.50171 | 3.240634 | 50.41544 | 0.04342317 |
| Peak #22 | 28.179° | 28.17879 | 3.164288 | 30.12094 | 0.02594337 |
| Peak #23 | 28.597° | 28.59672 | 3.118986 | 121.3689 | 0.1045359 |
| Peak #24 | 29.035° | 29.03487 | 3.072908 | 50.59545 | 0.04357821 |
| Peak #25 | 29.257° | 29.25673 | 3.050108 | 65.04179 | 0.05602094 |
| Peak #26 | 29.527° | 29.52666 | 3.022835 | 100.3665 | 0.08644637 |
| Peak #27 | 31.017° | 31.01673 | 2.880928 | 79.85507 | 0.06877972 |
| Peak #28 | 31.527° | 31.52703 | 2.835451 | 45.04162 | 0.03879466 |
| Peak #29 | 32.059° | 32.05877 | 2.789625 | 78.14873 | 0.06731004 |
| Peak #30 | 32.307° | 32.30659 | 2.768789 | 30.37478 | 0.02616201 |
| Peak #31 | 33.012° | 33.01181 | 2.711234 | 24.27336 | 0.02090681 |
| Peak #32 | 34.024° | 34.02446 | 2.632821 | 19.82419 | 0.01707471 |
| Peak #33 | 34.388° | 34.38762 | 2.605843 | 77.70146 | 0.0669248 |
| Peak #34 | 34.905° | 34.90529 | 2.568373 | 19.86779 | 0.01711226 |
| Peak #35 | 35.361° | 35.36144 | 2.53628 | 24.57932 | 0.02117033 |

TABLE 17-continued

| Name | Caption (display) | Angle | d Value | Net Intensity | Rel. Intensity |
|---|---|---|---|---|---|
| Peak #36 | 36.183° | 36.18279 | 2.480568 | 44.07069 | 0.03795839 |
| Peak #37 | 37.372° | 37.37207 | 2.404317 | 74.44651 | 0.06412129 |
| Peak #38 | 37.764° | 37.76379 | 2.380272 | 43.85532 | 0.03777289 |
| Peak #39 | 38.657° | 38.65681 | 2.327315 | 62.80877 | 0.05409762 |
| Peak #40 | 41.049° | 41.04871 | 2.197056 | 32.98244 | 0.028408 |

Figure 70:
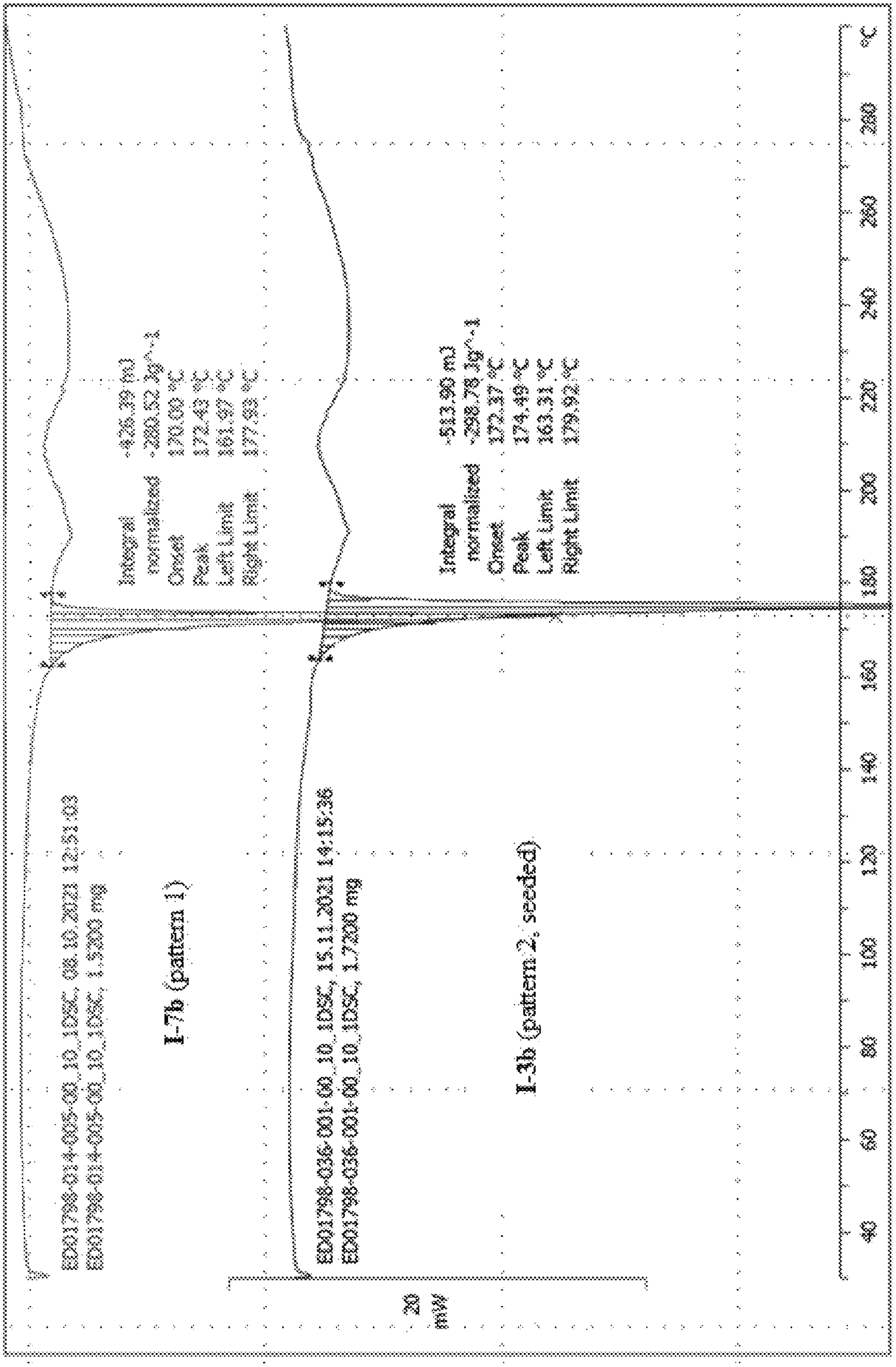
FIG. 70 shows the DSC curve of I-3b (pattern 2)
Figure 71:
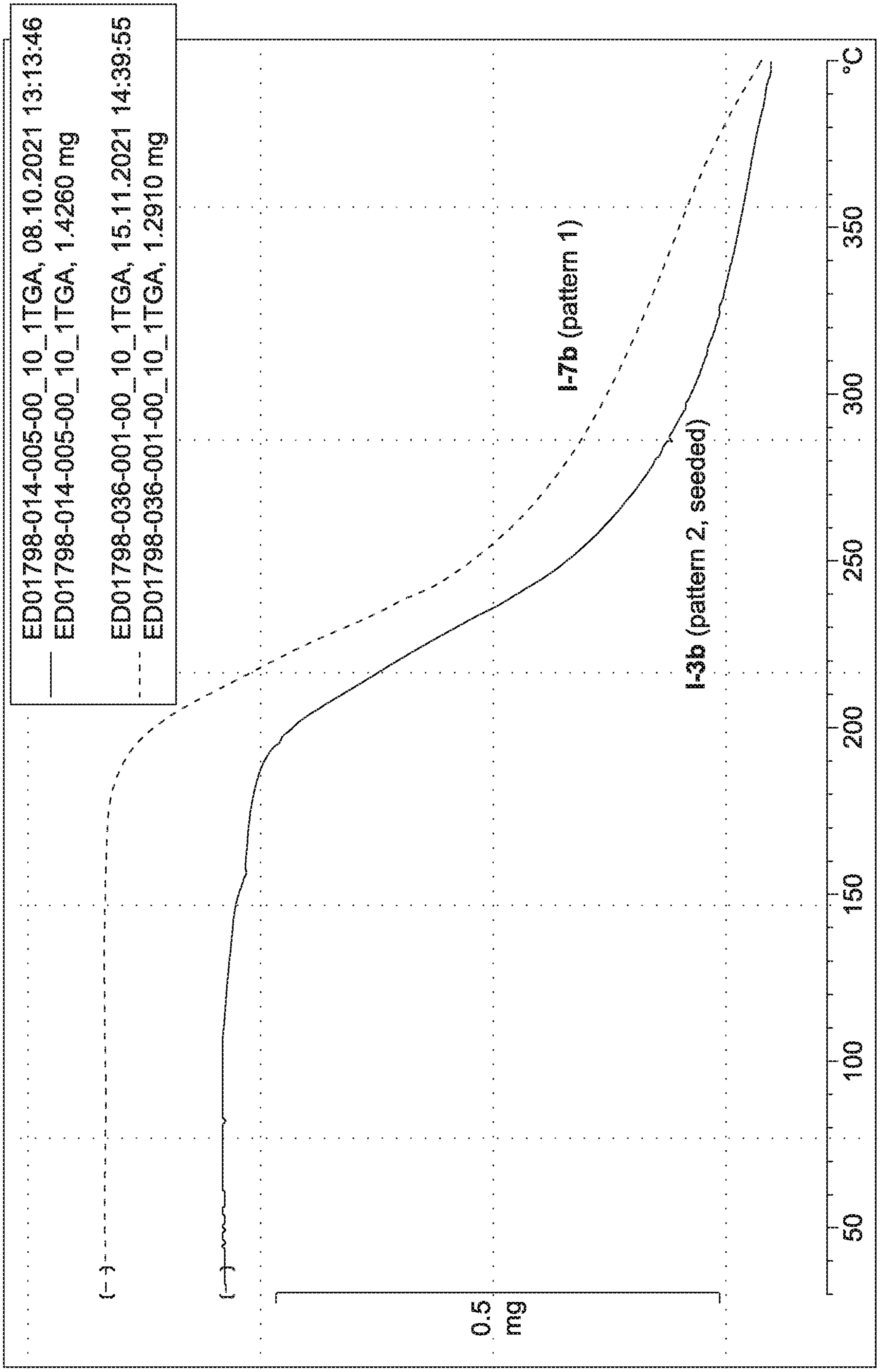
FIG. 71 shows the TGA plot of I-3b (pattern 2)

The DSC curve of I-3b (pattern 2) at 10° C./min is shown in FIG. 70, which shows a melt onset of 172.37° C. (peak 174.49° C.), similar to that of the polymorph pattern 1 of I-7b. The thermogravimetric analysis (TGA) curve of I-3b (pattern 2) at 10° C./min is shown in FIG. 71, which is also similar to that of I-7b (pattern 1).

Example 15

Synthesis of hemi-fumarate salt of 3-(2-(bis(methyl-$d_3$)amino)ethyl-1,1,2,2-$d_4$)-1H-indol-4-ol (I-3c)(hemi-fumarate salt of I-3/psilocin-$d_{10}$/PI-$d_{10}$)

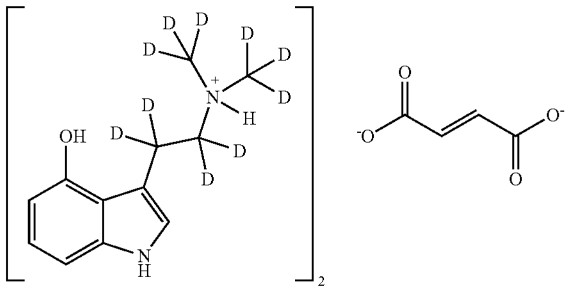

Non-seeded. Compound I-3 (PI-$d_{10}$, free base)(10 mM) was dissolved in acetonitrile or THF and treated with a solution of fumaric acid (10 mM) while being stirred at ambient temperature. Samples were shaken overnight at room temperature to produce I-3c (hemi-fumarate salt of PI-$d_{10}$).

Figure 72:
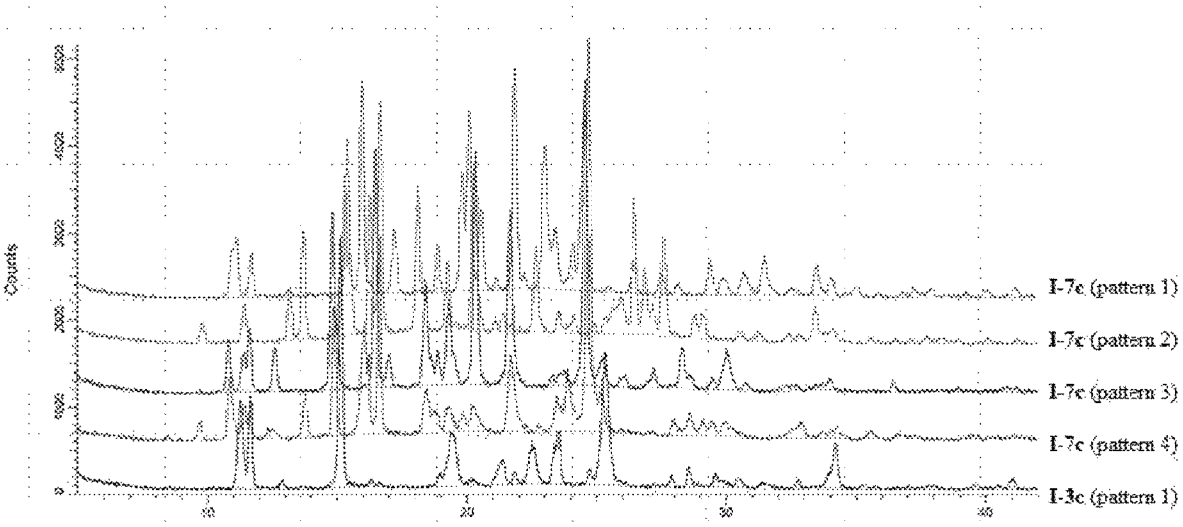
FIG. 72 shows the XRPD pattern of I-3c (pattern 1, obtained from non-seeded experiments) to the crystalline polymorphs of I-7c of patterns 1 through 4.

The X-ray powder diffraction (XRPD) pattern is presented in FIG. 72 comparing I-3c (pattern 1) to the crystalline polymorphs of I-7c of patterns 1 through 4 (see Example 4).

Figure 73:
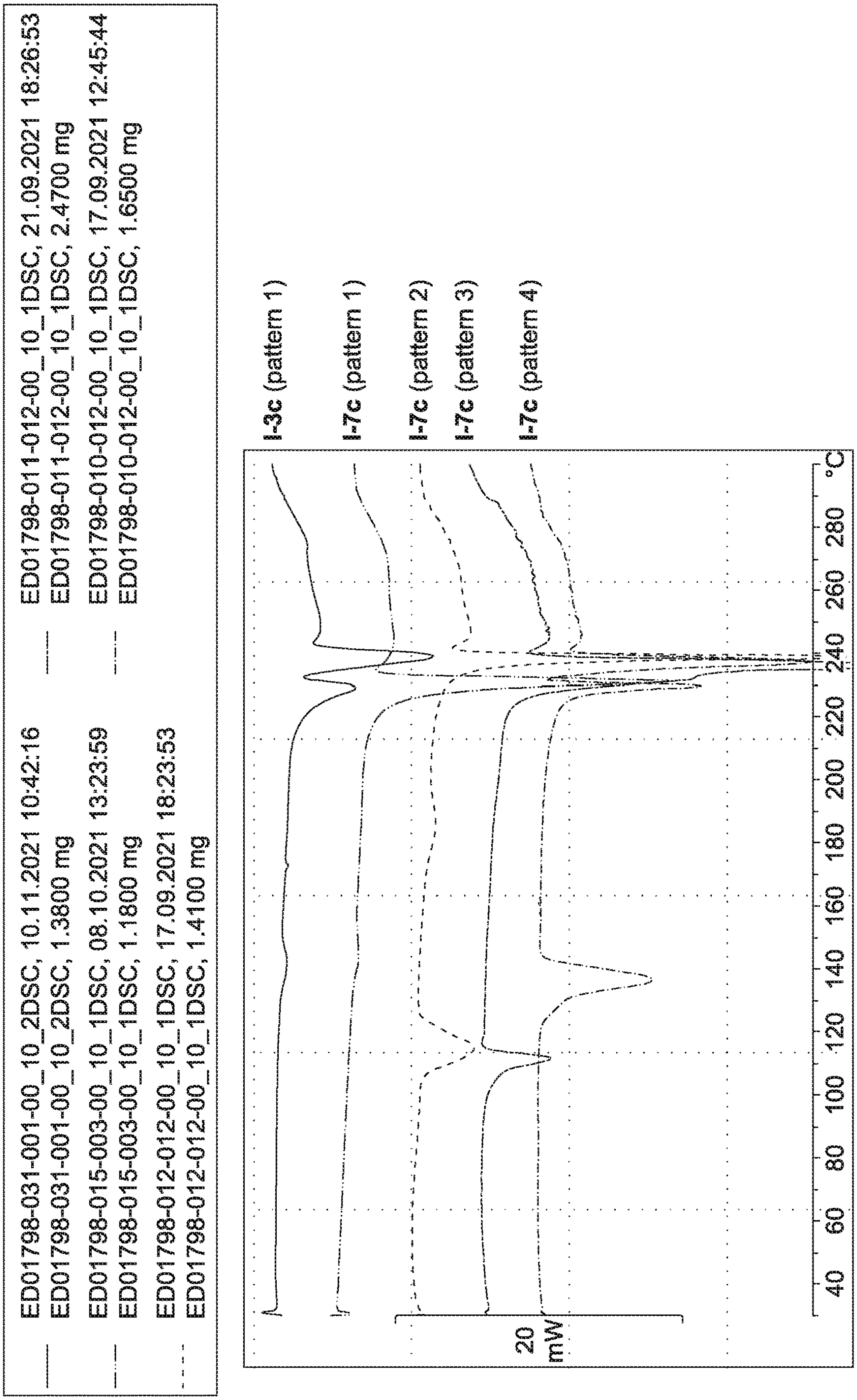
FIG. 73 shows the DSC curve of I-3c (pattern 1) compared to that of the polymorph patterns 1 through 4 of I-7c.
Figure 74:
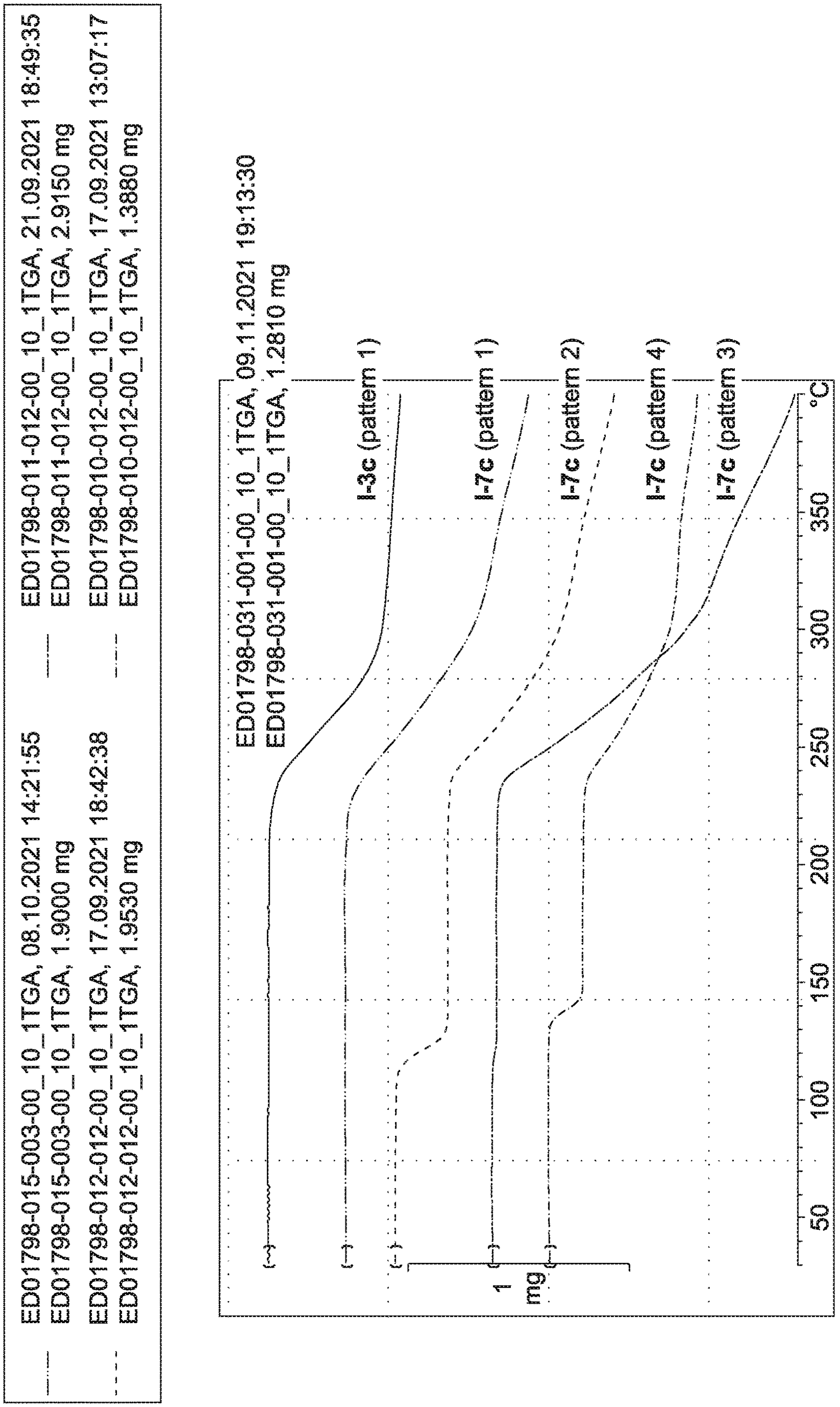
FIG. 74 shows the TGA plot of I-3c (pattern 1) compared to that of the polymorph patterns 1 through 4 of I-7c.

The DSC curve of I-3c (pattern 1) at 10° C./min is shown in FIG. 73, compared to that of the polymorph patterns 1 through 4 of I-7c, which indicates that I-3c (pattern 1) is likely to be a mixture of polymorphs. The thermogravimetric analysis (TGA) curve of I-3c (pattern 1) at 10° C./min is shown in FIG. 74.

Seeded. Compound I-3 (PI-$d_{10}$, free base)(10 mM) was dissolved in acetonitrile and treated with a solution of fumaric acid (10 mM) while being stirred at ambient temperature. Samples were shaken overnight at room temperature and then seeds of I-7c crystalline polymorph pattern 4 (see Example 4) were added and crystals of I-3c were slowly formed.

Figure 75:
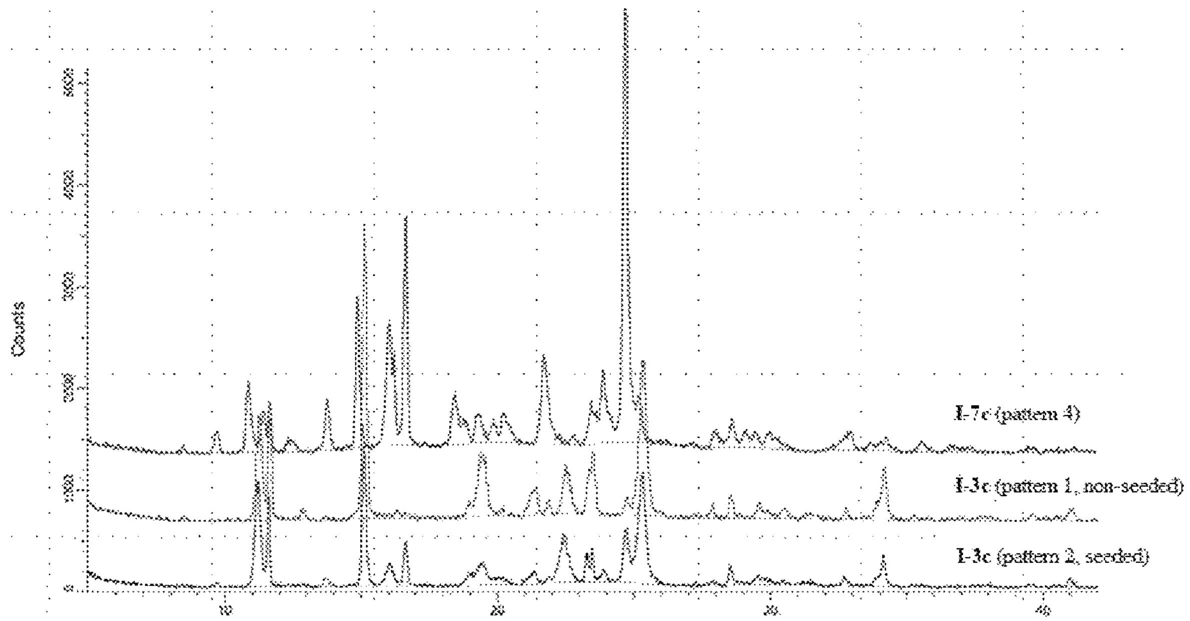
FIG. 75 shows the XRPD pattern of I-3c (pattern 2, obtained from seeded experiments) compared to crystalline polymorph of I-3c of pattern 1 obtained from the non-seeded experiments and the seeds of I-7c crystalline polymorph pattern 4.

The X-ray powder diffraction (XRPD) pattern (FIG. 75) indicates that the seeded experiment produced a single crystalline polymorph of I-3c (pattern 2) which was different from the crystalline polymorph of I-3c of pattern 1 obtained from the non-seeded experiments.

Figure 76:
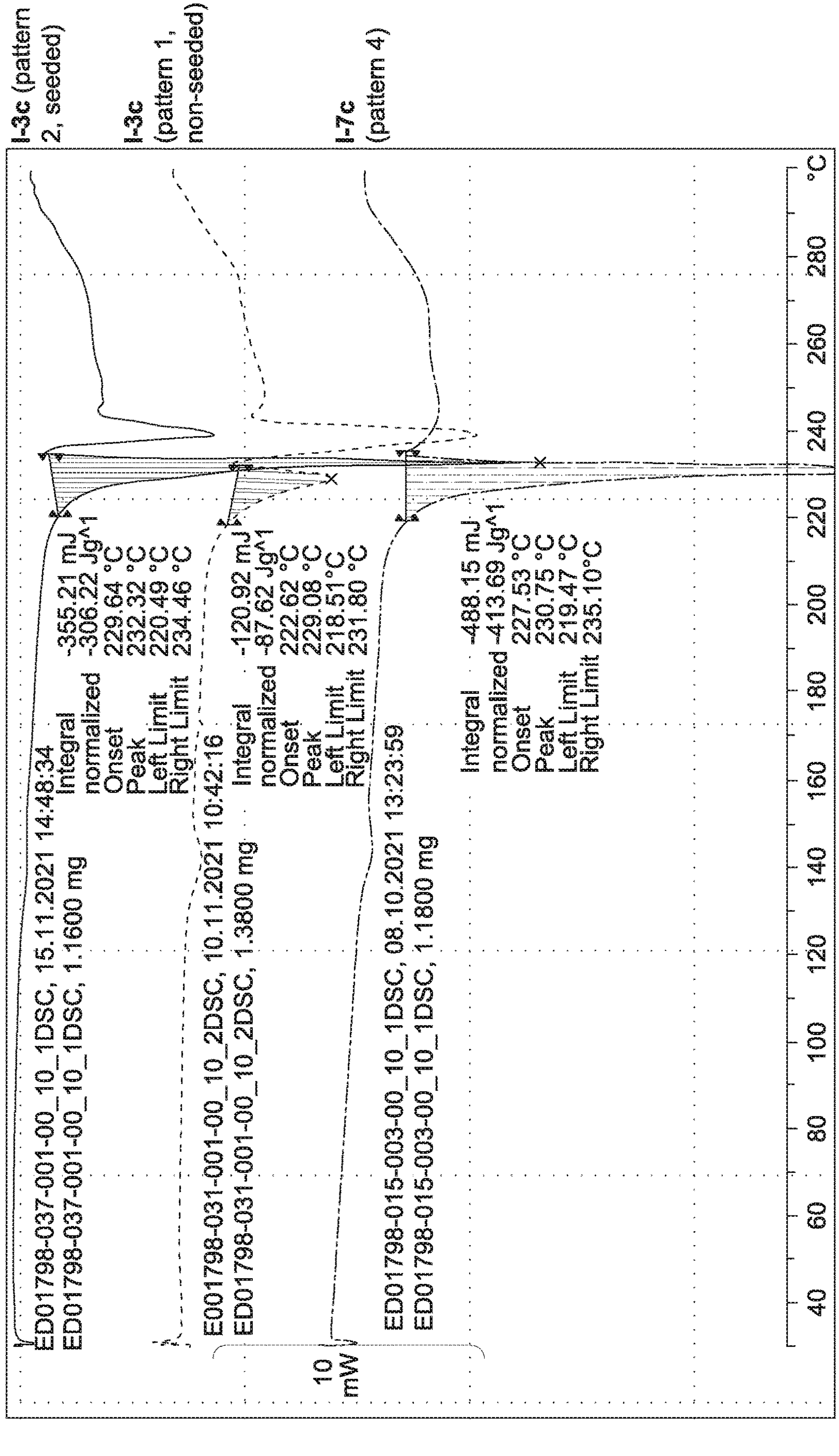
FIG. 76 shows the DSC curve of I-3c (pattern 2, obtained from seeded experiments) compared to crystalline polymorph of I-3c of pattern 1 obtained from the non-seeded experiments and the seeds of I-7c crystalline polymorph pattern 4.
Figure 77:
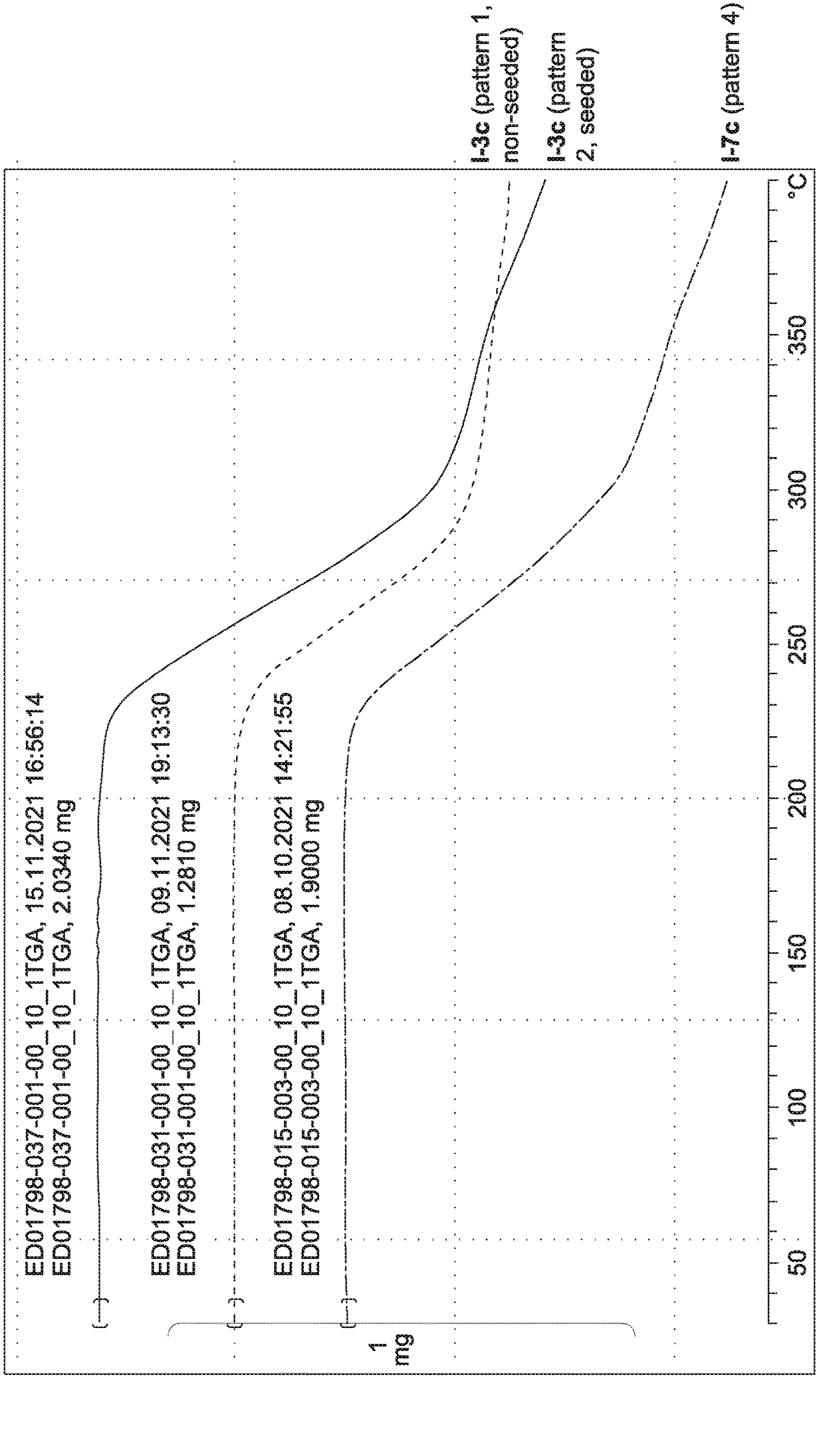
FIG. 77 shows the TGA plot of I-3c (pattern 2, obtained from seeded experiments) compared to crystalline polymorph of I-3c of pattern 1 obtained from the non-seeded experiments and the seeds of I-7c crystalline polymorph pattern 4.

The DSC curve of I-3c (pattern 2) at 10° C./min is shown in FIG. 76, which shows a first melt onset of 229.64° C. (peak 232.32° C.), but the analysis was complicated by polymorphisms issues. The thermogravimetric analysis (TGA) curve of I-3c (pattern 2) at 10° C./min is shown in FIG. 77, which is similar to that of I-7c (pattern 1) obtained from the non-seeded experiment.

Example 16

Synthesis of benzoate salt of 3-(2-(bis(methyl-$d_3$)amino)ethyl-1,1,2,2-$d_4$)-1H-indol-4-ol (I-3j)(benzoate salt of I-3/psilocin-$d_{10}$/PI-$d_{10}$)

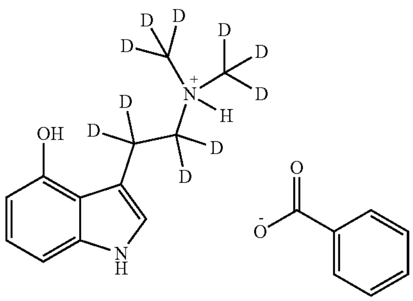

Compound I-3 (PI-$d_{10}$, free base)(10 mM) was dissolved in THF and treated with a solution of benzoic acid (10 mM in THF). Samples were stirred and then seeds of I-7j crystalline polymorph pattern 1 (see Example 11) were added at room temperature to produce crystals of I-3j.

As shown in FIGS. 78A-78B, the X-ray powder diffraction (XRPD) pattern indicates the I-3j salt is crystalline, with only one polymorph observed (pattern 1), which was the same as the pattern of the I-7j seed (FIG. 78C). Table 18 shows the XRPD peak listing for I-3j (pattern 1).

TABLE 18

| Caption (display) | Angle | d Value | Net Intensity | Rel. Intensity |
|---|---|---|---|---|
| 9.486° | 9.486166 | 9.315752 | 670.1039 | 0.22989 |
| 11.006° | 11.00646 | 8.032168 | 128.1829 | 0.043975 |
| 12.379° | 12.37882 | 7.144608 | 663.2478 | 0.227538 |
| 13.428° | 13.42827 | 6.588506 | 150.0904 | 0.051491 |
| 14.608° | 14.60809 | 6.058931 | 1259.188 | 0.431984 |
| 15.446° | 15.44628 | 5.73198 | 71.64919 | 0.02458 |
| 16.389° | 16.38903 | 5.404319 | 2914.894 | 1 |
| 18.247° | 18.2471 | 4.857978 | 1790.053 | 0.614106 |
| 18.977° | 18.97682 | 4.672788 | 2356.012 | 0.808267 |
| 19.346° | 19.34612 | 4.584413 | 686.9104 | 0.235655 |
| 19.831° | 19.83096 | 4.47341 | 856.2676 | 0.293756 |
| 20.868° | 20.8683 | 4.253326 | 51.75928 | 0.017757 |
| 21.447° | 21.4467 | 4.139906 | 473.447 | 0.162423 |
| 22.860° | 22.85971 | 3.887104 | 355.8473 | 0.122079 |

TABLE 18-continued

| Caption (display) | Angle | d Value | Net Intensity | Rel. Intensity |
|---|---|---|---|---|
| 23.878° | 23.87811 | 3.723574 | 292.7112 | 0.100419 |
| 24.944° | 24.94418 | 3.566798 | 571.3039 | 0.195995 |
| 25.737° | 25.73693 | 3.458703 | 237.9127 | 0.08162 |
| 26.144° | 26.14398 | 3.405768 | 1355.461 | 0.465012 |
| 26.341° | 26.3413 | 3.380702 | 164.0407 | 0.056277 |
| 26.990° | 26.98996 | 3.300906 | 45.78438 | 0.015707 |
| 27.708° | 27.70765 | 3.217014 | 286.3526 | 0.098238 |
| 28.595° | 28.59503 | 3.119166 | 340.7419 | 0.116897 |
| 30.048° | 30.04825 | 2.971541 | 43.63537 | 0.01497 |
| 30.763° | 30.76306 | 2.904104 | 92.80374 | 0.031838 |
| 31.127° | 31.12661 | 2.871009 | 64.86243 | 0.022252 |
| 31.839° | 31.83931 | 2.80835 | 90.03876 | 0.030889 |
| 32.800° | 32.8004 | 2.728225 | 61.20367 | 0.020997 |
| 34.460° | 34.45993 | 2.600541 | 49.32027 | 0.01692 |
| 35.444° | 35.44447 | 2.530529 | 70.97894 | 0.02435 |
| 37.725° | 37.7249 | 2.382637 | 42.98652 | 0.014747 |
| 38.597° | 38.59706 | 2.33078 | 75.10263 | 0.025765 |

Figure 79A:
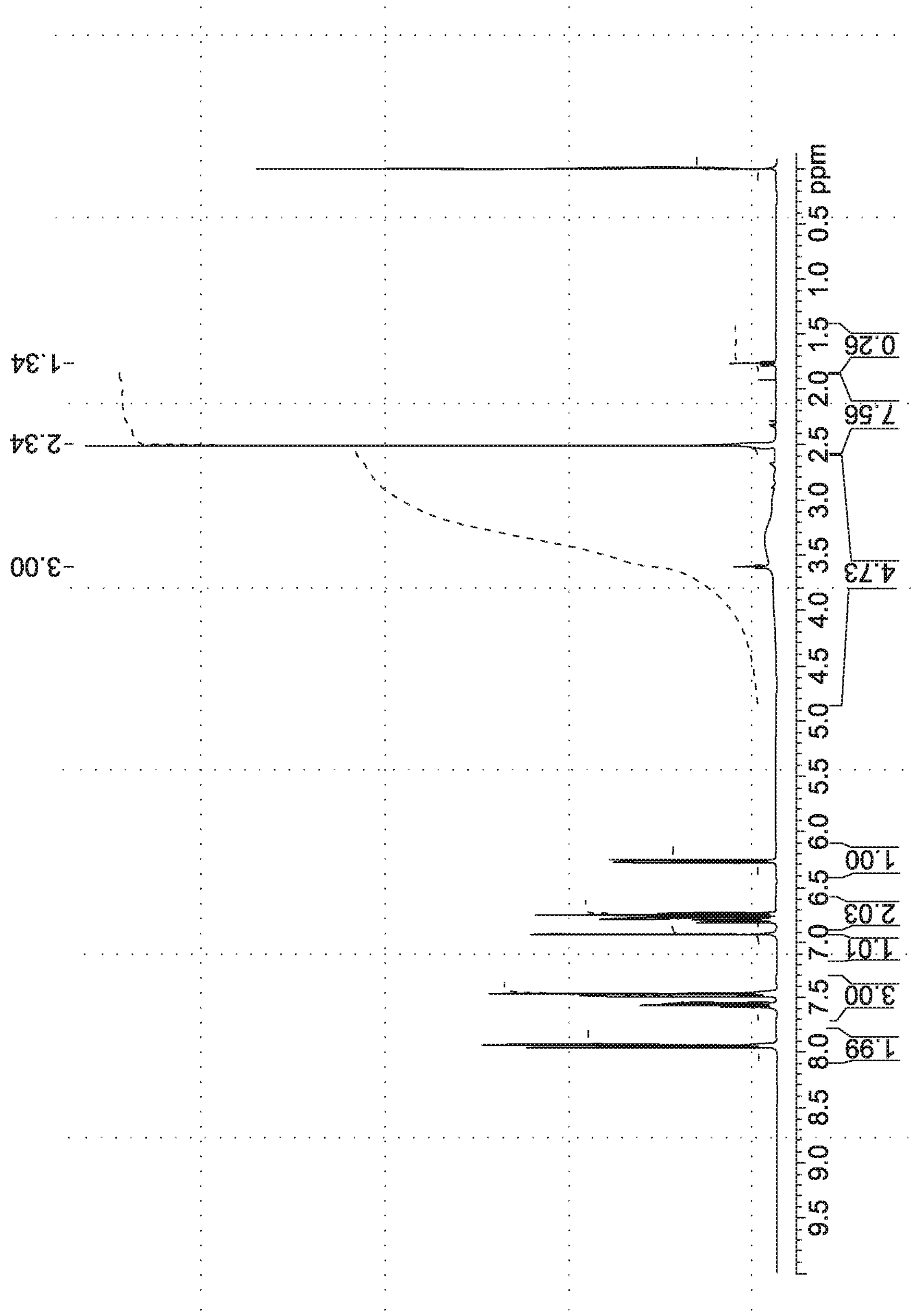
FIGS. 79A-79B show the $^1H$ NMR spectrum of I-3j (pattern 1)
Figure 79B:
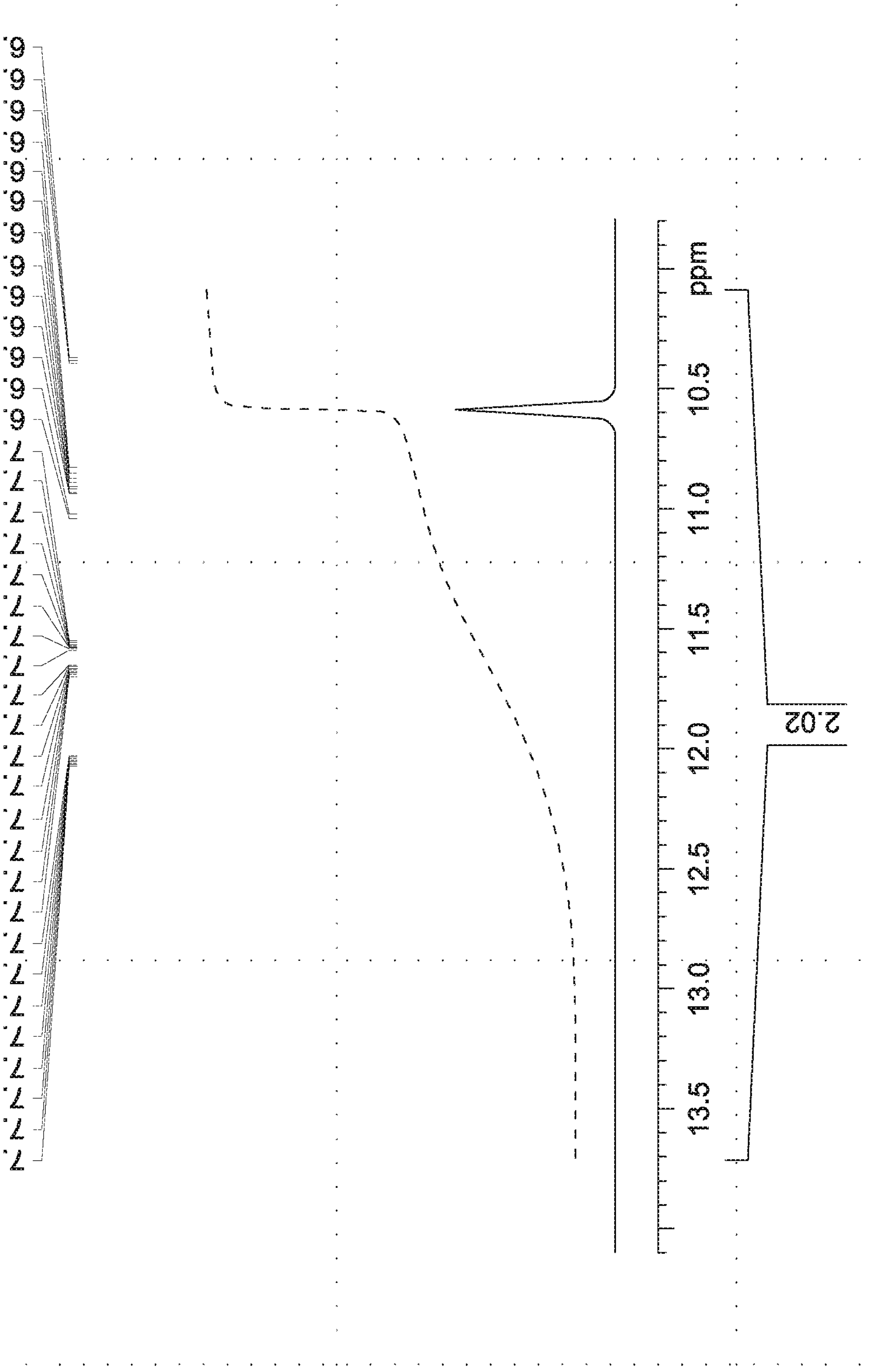

$^1H$ NMR confirmed 1 equivalent of benzoic acid (FIGS. 79A and 79B).

Figure 80:
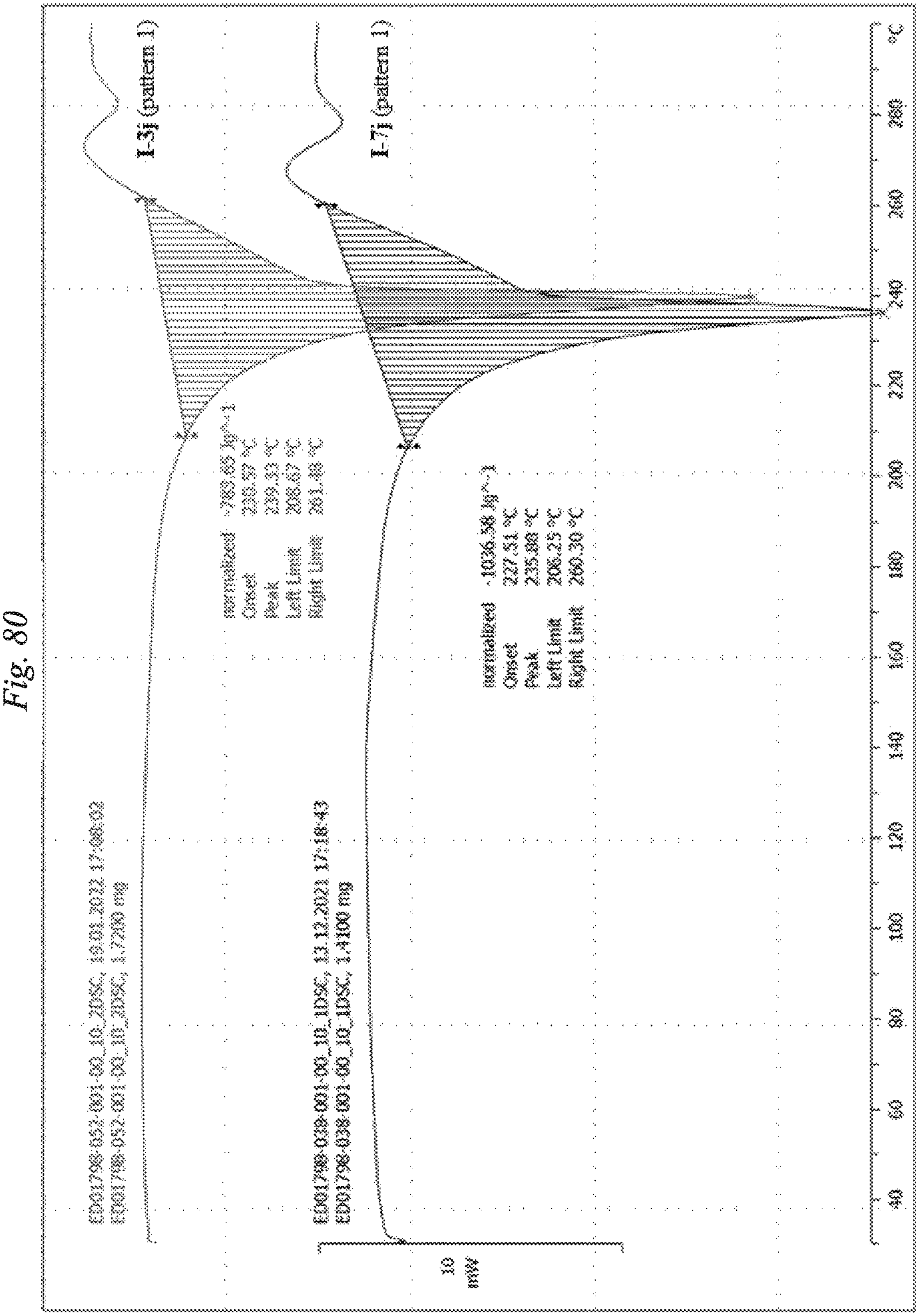
FIG. 80 shows the DSC plot of I-3j (pattern 1) compared to I-7j (pattern 1)

DSC of I-3j showed a high melt onset (230.57° C.) and peak (239.33° C.) (FIG. 80), with no events observed prior to the melt endotherm, indicating the absence of multiple physical forms in the sample, and also no conversion of physical forms prior to the melt, similar to the DSC of I-7j.

Figure 81:
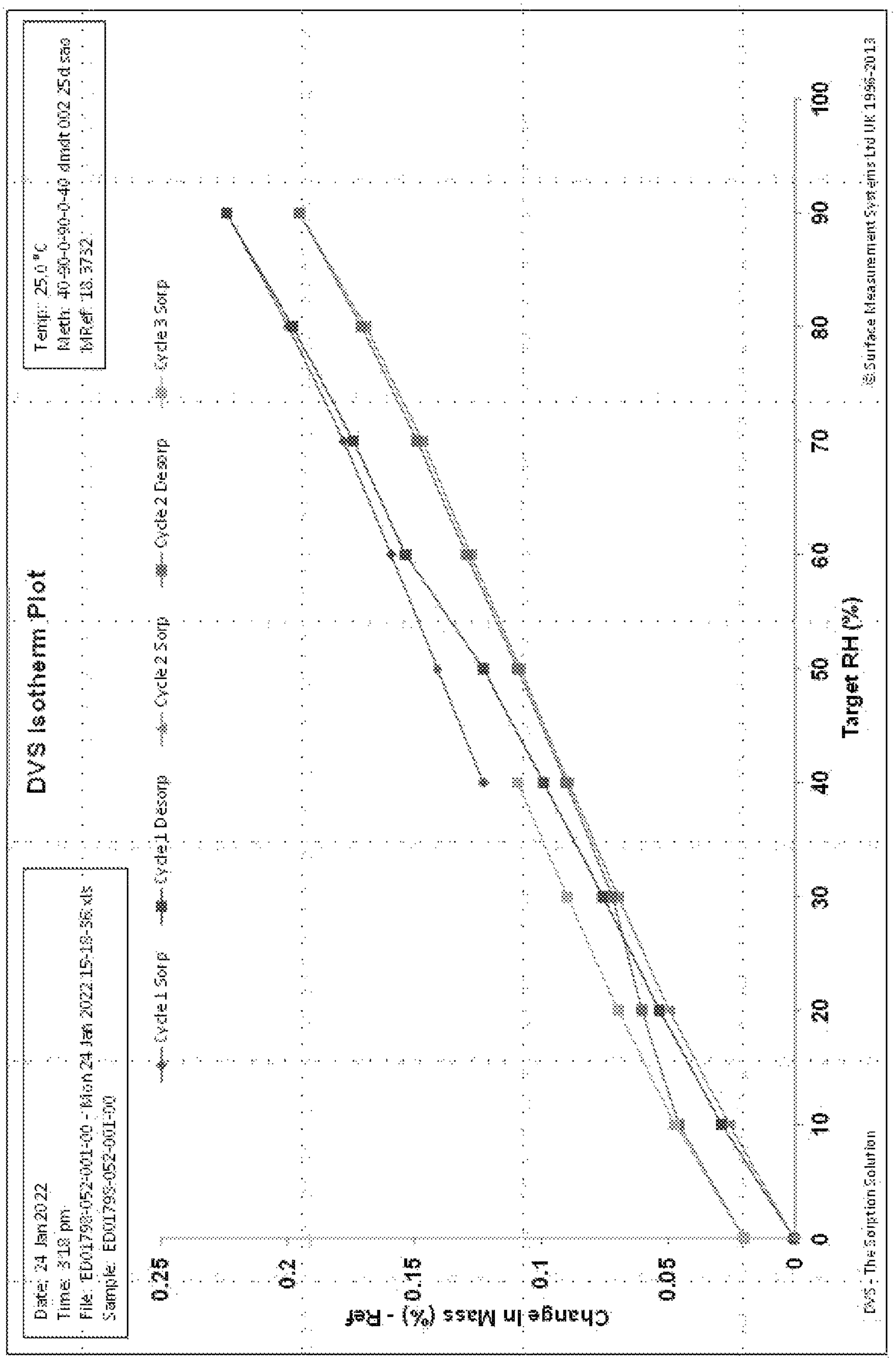
FIG. 81 shows the DVS isotherm plot of I-3j (pattern 1)
Figure 82:
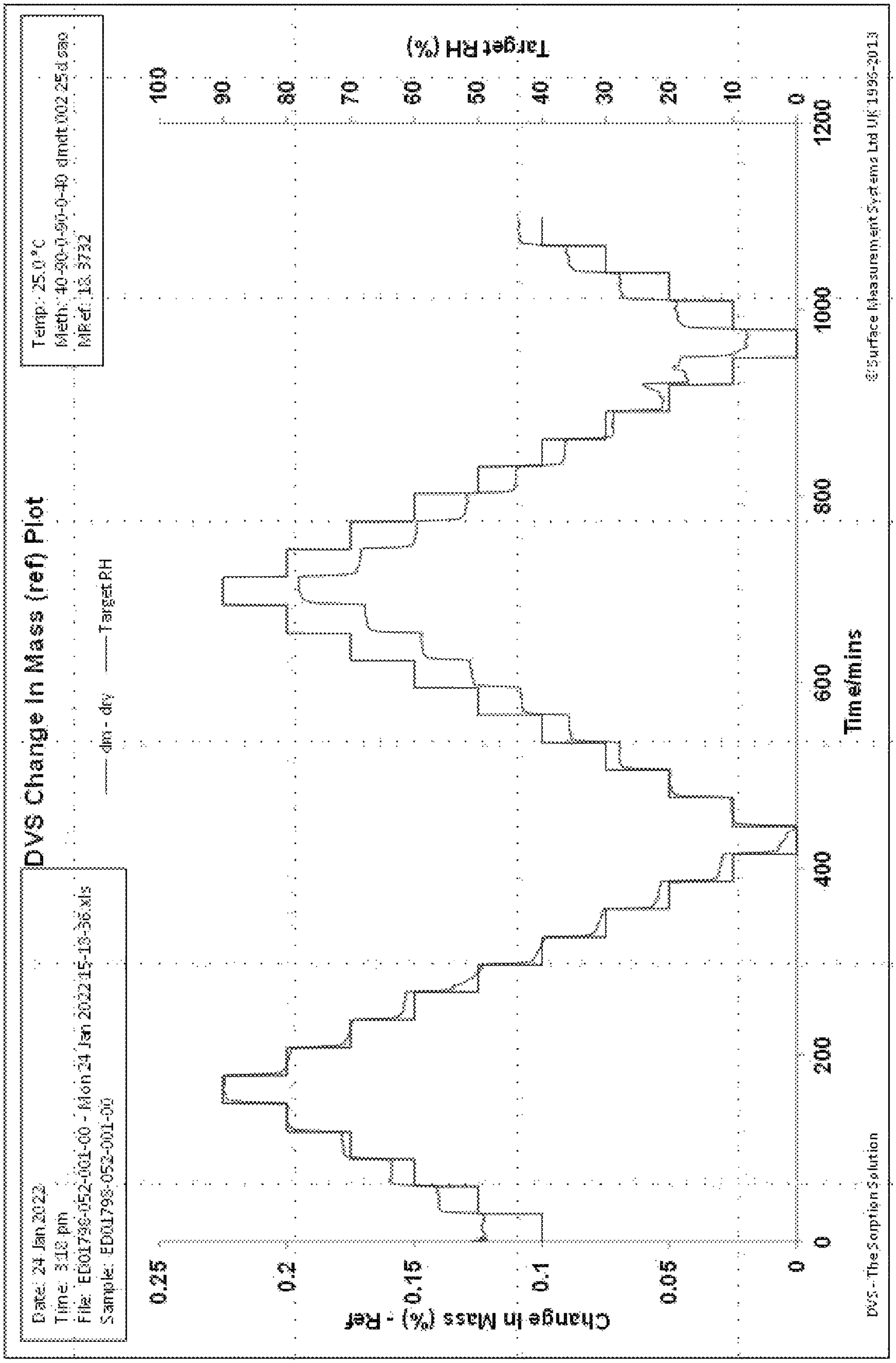
FIG. 82 shows the DVS change in mass plot of I-3j (pattern 1)

DVS isotherm plot of I-3j is shown in FIG. 81, which shows a 0.2% mass increase over 0-90% RH range (second sorption cycle), and thus the sample had no significant hygroscopicity, similar to I-7j which had a 0.16% mass increase over 0-90% RH range (second sorption cycle). This can be seen in the DVS change in mass plot of FIG. 82.

Figure 83:
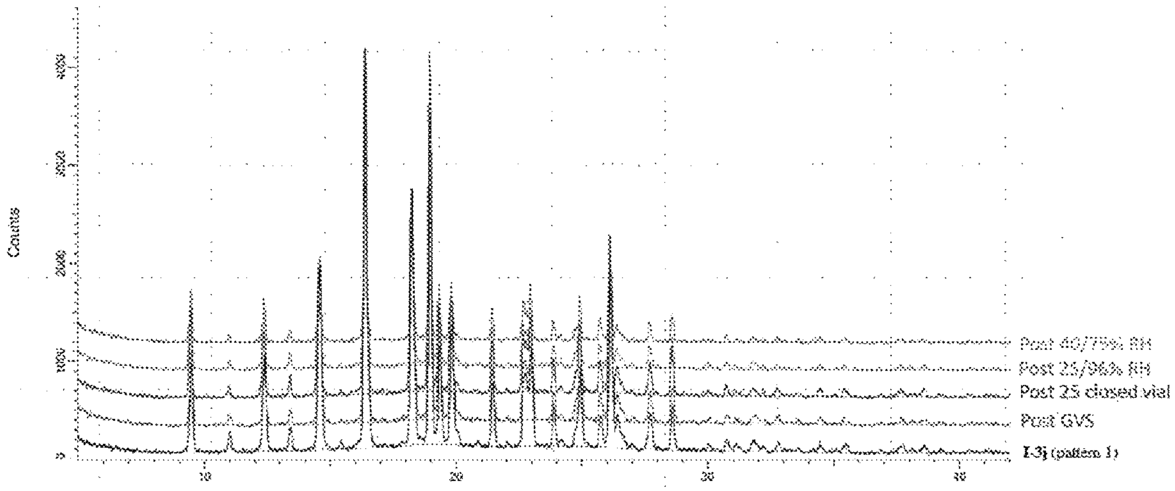
FIG. 83 shows the XRPD patterns of I-3j (polymorph of pattern 1) after storing solid samples for 22 days under the following conditions: i) 25° C., closed vial, ii) 25° C./96% RH, and iii) 40° C./75% RH, and comparing to fresh sample and post DVS sample.

The storage stability of I-3j was also assessed by storing the solid samples for 7 days under the following conditions: i) 25° C., closed vial, ii) 25° C./96% RH, and iii) 40° C./75% RH, and comparing to fresh sample and the sample post DVS from above by XRPD. The results are presented in FIG. 83, which showed no change in form by XRPD post storage or post DVS.

Figure 84:
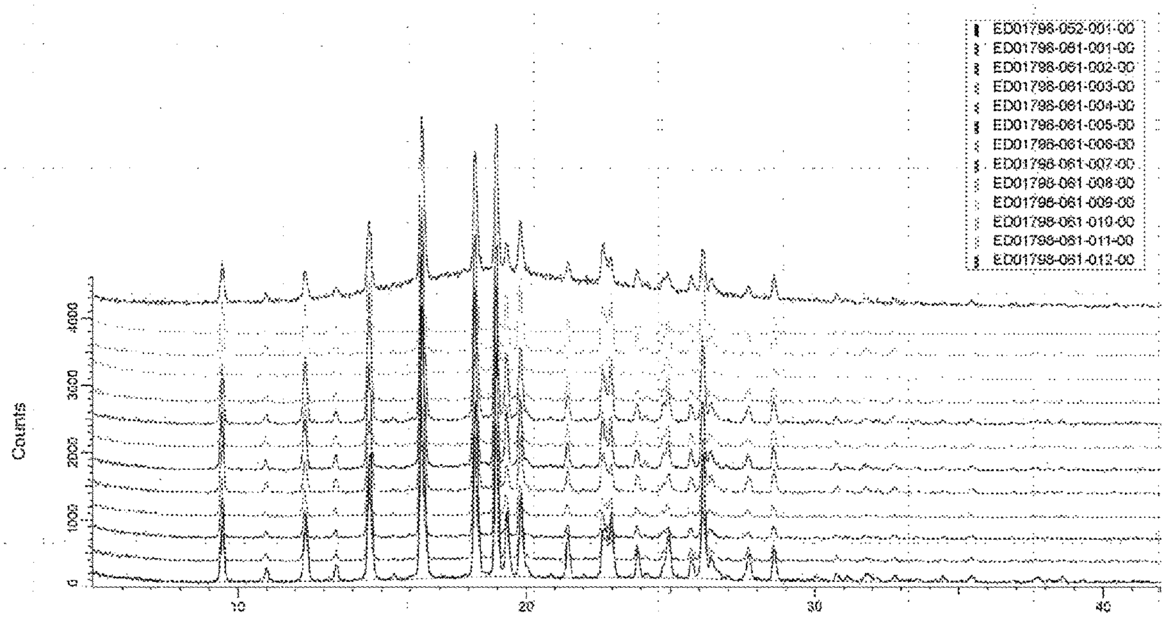
FIG. 84 shows the XRPD patterns of I-3j (polymorph of pattern 1) after maturation in 12 different solvents.

I-3j was also subjected to maturation in 12 different solvents following the procedure detailed in Example 2. All samples were isolated as solids and retained their initial crystalline form (pattern 1) according to XRPD analysis (FIG. 84), which was similar behavior to that observed for I-7j.

Together, this data represents advantageous behavior for pharmaceutical development purposes.

From the single crystals of I-3j grown from THF at room temperature, a suitable crystal was selected and mounted on a glass fiber with Fomblin® oil. This was then placed on a Rigaku Oxford Diffraction SuperNova diffractometer with a dual source (Cu at zero) collection. Using Olex2 (Dolomanov, O. V., Bourhis, L. J., Gildea, R. J, Howard, J. A. K. & Puschmann, H. 2009, J. Appl. Cryst. 42, 339-341), the structure was solved with the SHELXT (Sheldrick, G. M. 2015, Acta Cryst. A71, 3-8) structure solution program using Intrinsic Phasing and refined with the SHELXL (Sheldrick, G. M. 2015, Acta Cryst. C71, 3-8) refinement package using Least Squares minimization.

Figure 78D:
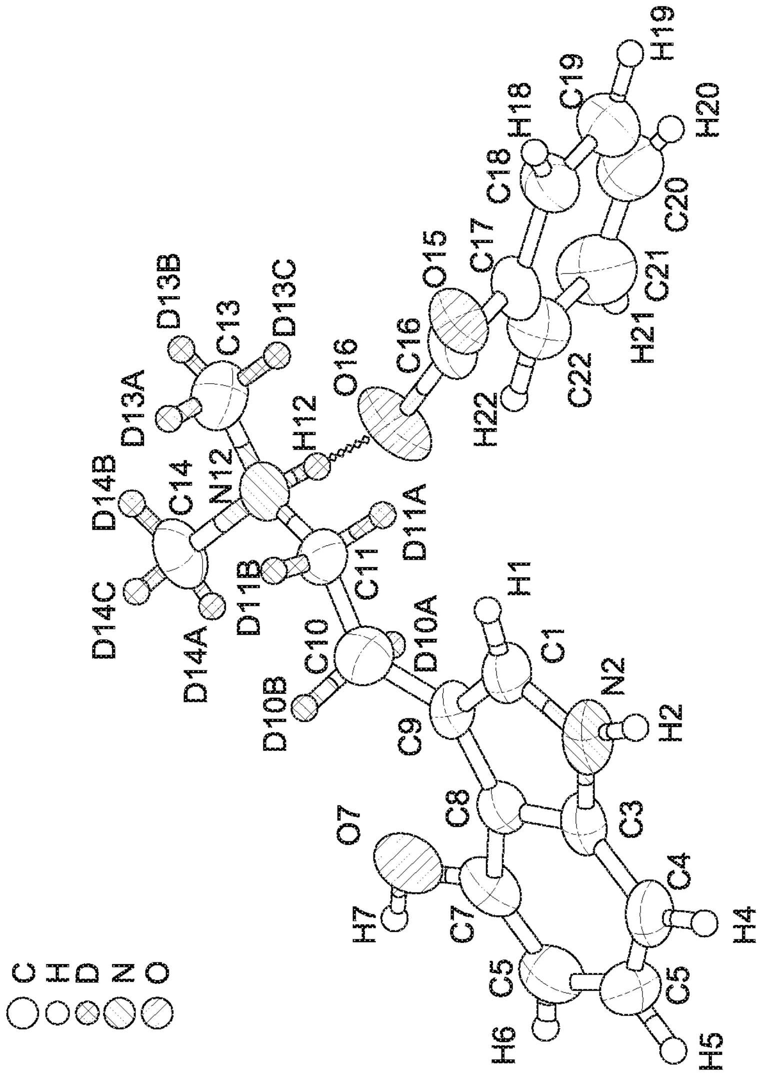

The solid-state structure of I-3j was generated. The asymmetric unit contains a protonated 4-hydroxy-N,N-dimethyltryptamine and a benzoate counter ion as shown in FIG. 78D, with four of each in the unit cell. The structure was refined containing both hydrogen and deuterium. There is interesting whole molecule disorder related by a 180-degree rotation about an axis through C5-C8 of the benzene ring.

Figure 78E:
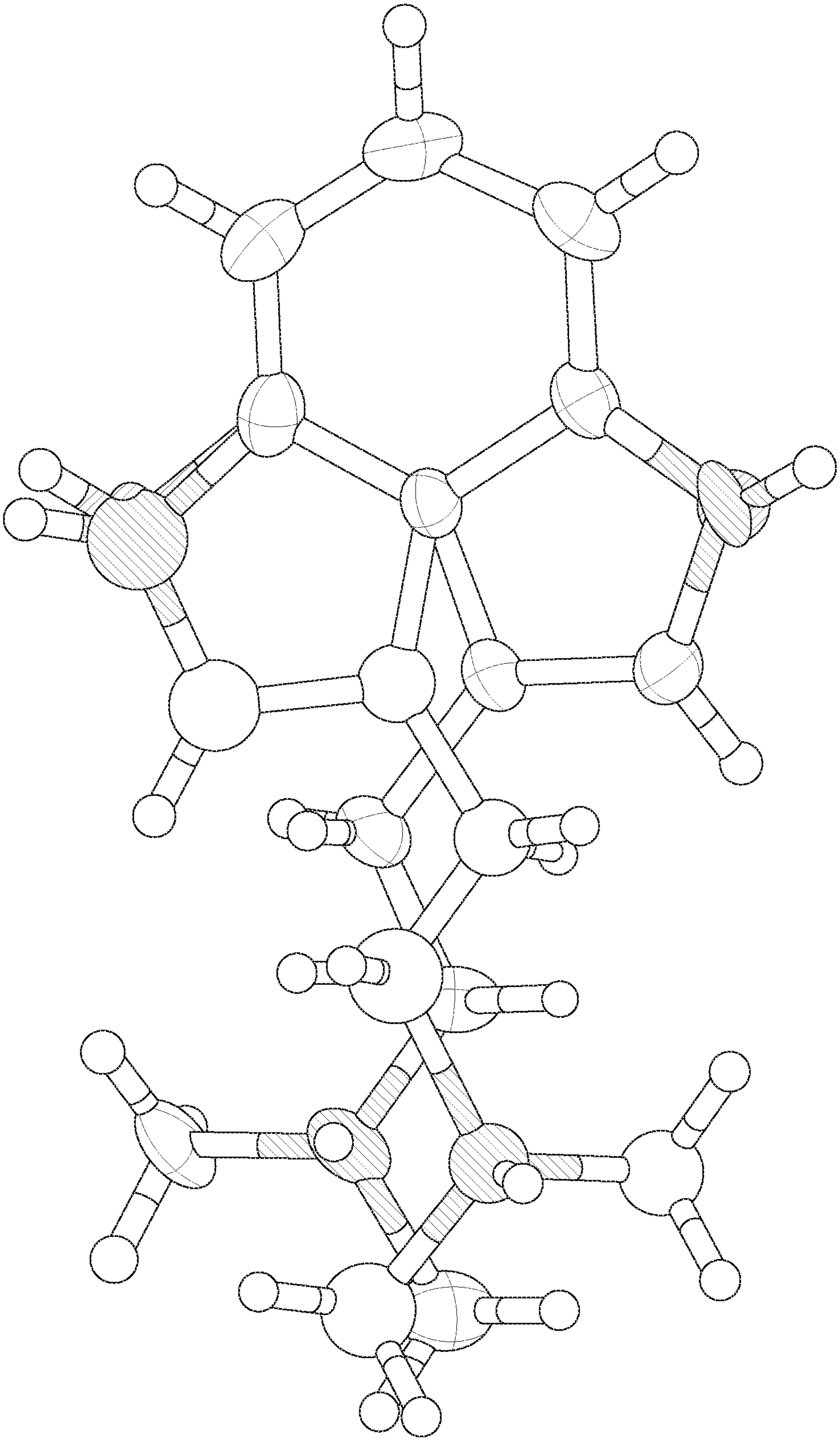

Many of the disordered components overlap but the disorder was modelled with both components sharing the orientation of the benzene ring but with different orientations of the 5 membered ring related by the above mentioned 180 degree rotation. The NH of the indole of one orientation maps onto the OH of the other orientation and vice versa. This disorder was traced right out to the dimethylamine unit. The occupancy of the two components were linked to a free variable which refined to 70:30 and this is depicted in FIG. 78E. The minor component was refined isotropically. Several distance and thermal parameter restraints were used to give the disordered components reasonable bond lengths and thermal parameters. The NHs and OH of the main component were located in a difference map. All NHs and OHs were placed at calculated positions for the refinement. They form short contacts listed in Table 19.

TABLE 19

| D-H | H . . . A | D . . . A | <(DHA) | Bond descriptor |
|---|---|---|---|---|
| 0.88 | 1.94 | 2.765(12) | 156.2 | N2^a—H2^a . . . O15_$1 |
| 0.84 | 1.86 | 2.657(4) | 157.8 | O7^a—H7^a . . . O16_$2 |
| 0.88 | 1.91 | 2.735(5) | 154.6 | N2A^b—H2A^b . . . O16_$2 |
| 1.00 | 1.68 | 2.677(5) | 174.6 | N12^a—H12^a . . . O16 |
| 1.00 | 1.76 | 2.757(11) | 174.3 | N12A^b—H12A^b . . . O15 |
| 0.84 | 1.95 | 2.77(3) | 164.2 | O7A^b—H7A^b . . . O15_$1 |

Symmetry operators used to generate symmetry equivalent atoms in above contact were $1 − X, 0.5 + Y, 0.5 − Z, $2 1 − X, 1 − Y, 1 − Z Crystal Data for $C_{19}H_{12}D_{10}N_2O_3$ (M=336.23 g/mol): monoclinic, space group $P2_1/c$ (no. 14), a=9.6406(2) Å, b=11.5042(3) Å, c=16.6070(3) Å, β=105.895(2)°, V=1771.42(8) Å3, Z=4, T=200(2) K, μ(CuKα)=0.673 mm-1, Dcalc=1.262 g/cm$^3$, 20733 reflections measured (9.474°≤2θ≤147.084°), 3542 unique (Rint=0.0256, Rsigma=0.0146) which were used in all calculations. The final $R_1$ was 0.0931 (I>2σ(I)) and $wR_2$ was 0.2289 (all data).

A complete summary of the geometry coordinates is shown in Tables 20-27. The proposed crystal structure has a very high degree of certainty and is consistent with expectation in accordance with the determined counter-ion stoichiometry.

TABLE 20

| Crystal structure and data refinement | |
|---|---|
| Empirical formula | $C_{19}H_{12}D_{10}N_2O_3$ |
| Formula weight | 336.45 |
| Temperature/K | 200(2) |
| Crystal system | monoclinic |
| Space group | P21/c |
| a/Å | 9.6406(2) |
| b/Å | 11.5042(3) |
| c/Å | 16.6070(3) |
| α/° | 90 |
| β/° | 105.895(2) |
| γ/° | 90 |
| Volume/Å3 | 1771.42(8) |
| Z | 4 |
| ρcalcg/cm3 | 1.262 |
| μ/mm−1 | 0.673 |
| F(000) | 696.0 |
| Crystal size/mm3 | 0.2 × 0.1 × 0.08 colourless block |
| Radiation | CuKα (% = 1.54184) |
| 2Θ range for data collection/° | 9.474 to 147.084 |
| Index ranges | −11 ≤ h ≤ 11, −14 ≤ k ≤ 14, −20 ≤ L ≤ 19 |
| Reflections collected | 20733 |
| Independent reflections | 3542 [Rint = 0.0256, Rsigma = 0.0146] |
| Data/restraints/parameters | 3542/42/252 |
| Goodness-of-fit on F2 | 1.091 |
| Final R indexes [I >= 2σ (I)] | R1 = 0.0931, wR2 = 0.2265 |

TABLE 20-continued

| Crystal structure and data refinement | |
|---|---|
| Final R indexes [all data] | R1 = 0.0967, wR2 = 0.2289 |
| Largest diff. peak/hole / e Å−3 | 0.71/−0.49 |

TABLE 21

Fractional Atomic Coordinates (×$10^4$) and Equivalent Isotropic Displacement Parameters ($Å^2$ × 10)

| Atom | x | y | z | U(eq) |
|---|---|---|---|---|
| O15 | 2746(2) | 1021(2) | 3472.8(13) | 61.4(6) |
| O16 | 4532(3) | 1971(3) | 4306.1(16) | 81.6(9) |
| N2 | −870(17) | 5612(16) | 3089(9) | 61(4) |
| O7 | 3346(4) | 6541(4) | 5052(2) | 66.5(16) |
| C17 | 5015(3) | 923(3) | 3182.1(18) | 53.1(7) |
| C8 | 1183(3) | 6146(2) | 4057.1(16) | 47.0(7) |
| C9A | 1665(6) | 5056(2) | 4430(4) | 63(3) |
| CIA | 3032(8) | 5225(5) | 5015(6) | 88(4) |
| N2A | 3395(5) | 6420(5) | 5003(4) | 107(7) |
| C7 | 2252(3) | 6989(3) | 4411(2) | 60.9(8) |
| C3 | 7(3) | 6525(3) | 3381.6(17) | 51.4(7) |
| C16 | 4034(3) | 1329(3) | 3684.5(18) | 52.5(7) |
| C18 | 4668(4) | −43(3) | 2671(2) | 64.6(9) |
| C4 | −91(4) | 7661(3) | 3093(2) | 65.6(9) |
| C5 | 1004(5) | 8422(3) | 3490(3) | 75.4(11) |
| C22 | 6291(4) | 1498(4) | 3219(3) | 75.1(10) |
| C19 | 5573(6) | 427(4) | 2214(3) | 83.2(12) |
| N12 | 2647(5) | 2173(4) | 5220(2) | 64.8(12) |
| C6 | 2157(5) | 8090(3) | 4129(3) | 72.7(10) |
| C9 | 866(5) | 4966(4) | 4172(2) | 54.4(11) |
| C20 | 6821(6) | 152(4) | 2251(3) | 92.7(15) |
| C11 | 1512(7) | 2982(4) | 4840(3) | 59.3(13) |
| D11A | 1037.97 | 2708.05 | 4265.52 | 71 |
| D11B | 782.26 | 2954.6 | 5159 | 71 |
| C21 | 7177(6) | 1118(4) | 2748(3) | 95.4(15) |
| C1 | −368(6) | 4695(4) | 3593(3) | 58.9(12) |
| C13 | 1978(9) | 999(6) | 5293(5) | 78.4(18) |
| D13A | 1338.46 | 1065.96 | 5658.81 | 118 |
| D13B | 2741.76 | 434.52 | 5530.58 | 118 |
| D13C | 1421.26 | 737.61 | 4736.69 | 118 |
| C10 | 1926(7) | 4168(4) | 4791(3) | 71.8(15) |
| D10A | 2853.42 | 4175.66 | 4642.86 | 86 |
| D10B | 2107.74 | 4512.86 | 5356.82 | 86 |
| C14 | 3512(7) | 2589(5) | 6062(3) | 77.4(17) |
| D14A | 4096.13 | 3259.06 | 5992.82 | 116 |
| D14B | 4146.58 | 1962.38 | 6348.64 | 116 |
| D14C | 2860.13 | 2816.22 | 6394.9 | 116 |
| N12A | 1714(12) | 1809(9) | 4767(7) | 67(3) |
| C10A | 1218(13) | 3891(10) | 4312(8) | 60(3) |
| D10C | 320.32 | 3794.24 | 4484.27 | 72 |
| D10D | 997.79 | 3700.67 | 3708.36 | 72 |
| C14A | 158(14) | 1525(13) | 4485(9) | 77(4) |
| D14D | 37.23 | 704.2 | 4322.84 | 116 |
| D14E | −311.53 | 2012.24 | 4003.48 | 116 |
| D14F | −282.48 | 1670.23 | 4942.03 | 116 |
| C13A | 2620(20) | 1110(20) | 5464(14) | 94(7) |
| D13D | 3618.95 | 1391.71 | 5598.04 | 140 |
| D13E | 2587.35 | 293.87 | 5297.95 | 140 |
| D13F | 2257.49 | 1192.6 | 5957.61 | 140 |
| C11A | 2200(20) | 3155(15) | 4741(13) | 96(4) |
| D11C | 2540.44 | 3439.76 | 5324.35 | 115 |
| D11D | 3038.14 | 3176.97 | 4502.73 | 115 |
| O7A | −1010(30) | 5600(30) | 3127(19) | 55(6) |

TABLE 22

Anisotropic displacement parameters ($Å^2$ × $10^3$)

| Atom | U11 | U22 | U33 | U23 | U13 | U12 |
|---|---|---|---|---|---|---|
| O15 | 48.3(12) | 80.2(16) | 49.9(12) | −9.1(11) | 3.7(9) | −7.2(11) |
| O16 | 62.0(15) | 117(2) | 65.6(15) | −42.9(15) | 17.6(12) | −25.5(15) |
| N2 | 45(4) | 89(6) | 38(3) | 14(2) | −9(3) | 0(3) |

TABLE 22-continued

Anisotropic displacement parameters ($Å^2$ × $10^3$)

| Atom | U11 | U22 | U33 | U23 | U13 | U12 |
|---|---|---|---|---|---|---|
| O7 | 49(2) | 71(2) | 61(2) | −20.4(18) | −15.0(15) | −0.7(16) |
| C17 | 56.8(17) | 60.1(18) | 38.9(14) | 5.2(13) | 7.1(12) | 3.7(14) |
| C8 | 46.8(15) | 52.7(16) | 37.7(13) | −2.8(12) | 5.1(11) | 2.0(12) |
| C7 | 57.5(18) | 68(2) | 55.2(17) | −16.8(16) | 12.6(14) | −3.6(16) |
| C3 | 50.2(16) | 66.7(19) | 36.2(13) | 4.7(13) | 9.9(12) | 5.3(14) |
| C16 | 54.1(17) | 61.2(18) | 37.0(14) | −2.0(13) | 3.4(12) | −2.2(14) |
| C18 | 74(2) | 64(2) | 50.9(17) | 4.2(15) | 8.9(16) | 7.5(17) |
| C4 | 74(2) | 77(2) | 45.8(16) | 13.9(16) | 16.7(15) | 25.5(19) |
| C5 | 114(3) | 49.5(19) | 73(2) | 2.2(17) | 42(2) | 2(2) |
| C22 | 79(3) | 75(2) | 79(2) | −7(2) | 35(2) | −10(2) |
| C19 | 116(4) | 75(3) | 62(2) | −4.3(19) | 29(2) | 18(3) |
| N12 | 85(3) | 65(3) | 39.1(18) | 0.8(17) | 8.0(19) | 29(2) |
| C6 | 86(3) | 62(2) | 75(2) | −14.7(18) | 29(2) | −17.8(19) |
| C9 | 63(3) | 56(3) | 32.9(19) | 2.1(17) | −6.4(18) | 2(2) |
| C20 | 127(4) | 85(3) | 87(3) | 15(2) | 66(3) | 25(3) |
| C11 | 84(3) | 55(3) | 55(2) | 12(2) | 45(2) | 10(2) |
| C21 | 99(3) | 92(3) | 119(4) | −1(3) | 70(3) | −7(3) |
| C1 | 73(3) | 55(3) | 43(2) | 2.7(19) | 7(2) | −13(2) |
| C13 | 97(6) | 76(4) | 68(4) | 11(3) | 33(4) | 2(4) |
| C10 | 91(4) | 57(3) | 48(2) | 2(2) | −14(3) | 11(3) |
| C14 | 92(4) | 91(4) | 36(2) | 1(2) | −4(2) | 34(3) |

TABLE 23

Bond lengths

| Atom | Atom | Length/Å | Atom | Atom | Length/Å |
|---|---|---|---|---|---|
| O15 | C16 | 1.246(4) | C3 | O7A | 1.43(3) |
| O16 | C16 | 1.253(4) | C18 | C19 | 1.377(6) |
| N2 | C3 | 1.352(17) | C4 | C5 | 1.392(6) |
| N2 | C1 | 1.352(17) | C5 | C6 | 1.365(6) |
| O7 | C7 | 1.377(5) | C22 | C21 | 1.378(6) |
| C17 | C16 | 1.497(5) | C19 | C20 | 1.362(7) |
| C17 | C18 | 1.383(5) | N12 | C11 | 1.443(6) |
| C17 | C22 | 1.383(5) | N12 | C13 | 1.516(9) |
| C8 | C9A | 1.4200 | N12 | C14 | 1.496(6) |
| C8 | C7 | 1.4200 | C9 | C1 | 1.345(6) |
| C8 | C3 | 1.427(4) | C9 | C10 | 1.539(6) |
| C8 | C9 | 1.416(5) | C20 | C21 | 1.370(7) |
| C9A | C1A | 1.4200 | C11 | C10 | 1.431(8) |
| C9A | C10A | 1.405(12) | N12A | C14A | 1.481(17) |
| C1A | N2A | 1.4200 | N12A | C13A | 1.48(2) |
| N2A | C7 | 1.4200 | N12A | C11A | 1.62(2) |
| C7 | C6 | 1.344(5) | C10A | C11A | 1.33(2) |
| C3 | C4 | 1.386(5) | | | |

TABLE 24

Bond angles

| Atom | Atom | Atom | Angle/° | Atom | Atom | Atom | Angle/° |
|---|---|---|---|---|---|---|---|
| C3 | N2 | C1 | 107.5(8) | O15 | C16 | C17 | 119.1(3) |
| C18 | C17 | C16 | 120.6(3) | O16 | C16 | C17 | 119.1(3) |
| C18 | C17 | C22 | 118.3(3) | C19 | C18 | C17 | 120.9(4) |
| C22 | C17 | C16 | 121.0(3) | C3 | C4 | C5 | 117.3(3) |
| C9A | C8 | C3 | 135.0(3) | C6 | C5 | C4 | 122.8(3) |
| C7 | C8 | C9A | 108.0 | C21 | C22 | C17 | 120.3(4) |
| C7 | C8 | C3 | 116.6(3) | C20 | C19 | C18 | 120.2(4) |
| C9 | C8 | C7 | 139.3(3) | C11 | N12 | C13 | 108.7(5) |
| C9 | C8 | C3 | 104.1(2) | C11 | N12 | C14 | 111.4(4) |
| C8 | C9A | C1A | 108.0 | C14 | N12 | C13 | 110.5(5) |
| C10A | C9A | C8 | 136.9(6) | C7 | C6 | C5 | 119.9(4) |
| C10A | C9A | C1A | 114.7(6) | C8 | C9 | C10 | 122.2(4) |
| N2A | C1A | C9A | 108.0 | C1 | C9 | C8 | 107.9(4) |
| C1A | N2A | C7 | 108.0 | C1 | C9 | C10 | 129.4(4) |
| O7 | C7 | C8 | 112.3(3) | C19 | C20 | C21 | 119.8(4) |
| C8 | C7 | N2A | 108.0 | C10 | C11 | N12 | 116.7(5) |
| C6 | C7 | 07 | 125.9(3) | C20 | C21 | C22 | 120.5(4) |
| C6 | C7 | C8 | 121.8(3) | C9 | C1 | N2 | 111.0(8) |

TABLE 24-continued

| Bond angles | | | | | | | |
|---|---|---|---|---|---|---|---|
| Atom | Atom | Atom | Angle/° | Atom | Atom | Atom | Angle/° |
| C6 | C7 | N2A | 129.9(3) | C11 | C10 | C9 | 117.5(5) |
| N2 | C3 | C8 | 109.3(6) | C14A | N12A | C11A | 118.6(11) |
| N2 | C3 | C4 | 129.1(6) | C13A | N12A | C14A | 117.3(12) |
| C8 | C3 | O7A | 109.7(12) | C13A | N12A | C11A | 115.1(14) |
| C4 | C3 | C8 | 121.6(3) | C11A | C10A | C9A | 112.8(13) |
| C4 | C3 | O7A | 128.6(12) | C10A | C11A | N12A | 117.0(15) |
| O15 | | C16 | | O16 | | 121.8(3) | |

TABLE 25

| Hydrogen bonds | | | | | | |
|---|---|---|---|---|---|---|
| D | H | A | d(D-H)/Å | d(H-A)/Å | d(D-A)/Å | D-H-A/° |
| N2 | H2 | O15[1] | 0.88 | 1.94 | 2.765(12) | 156.2 |
| O7 | H7 | O16[2] | 0.84 | 1.86 | 2.657(4) | 157.8 |
| N2A | H2A | O16[2] | 0.88 | 1.91 | 2.735(5) | 154.6 |
| N12 | H12 | O16 | 1.00 | 1.68 | 2.677(5) | 174.6 |
| N12A | H12A | O15 | 1.00 | 1.76 | 2.757(11) | 174.3 |
| O7A | H7A | O15[1] | 0.84 | 1.95 | 2.77(3) | 164.2 |

[1]-X, ½ + Y, ½-Z;
[2]1-X, 1-Y, 1-Z

TABLE 26

| Hydrogen Atom Coordinates (Å × $10^4$) and Isotropic Displacement Parameters ($Å^2$ × $10^3$) | | | | |
|---|---|---|---|---|
| Atom | x | y | z | U(eq) |
| H2 | −1628.75 | 5615.1 | 2649.87 | 74 |
| H7 | 3853.1 | 7086.72 | 5313.46 | 100 |
| H1A | 3604.02 | 4641.02 | 5354.36 | 105 |
| H2A | 4188.78 | 6749.65 | 5308.8 | 128 |
| H18 | 3794.52 | −447.67 | 2635.49 | 78 |
| H4 | −875.14 | 7909.18 | 2642.63 | 79 |
| H5 | 947.53 | 9208.16 | 3307.27 | 90 |
| H22 | 6557.96 | 2158.3 | 3571.61 | 90 |
| H19 | 5326.1 | −1097.93 | 1870.56 | 100 |
| H12 | 3301.85 | 2092.76 | 4848.79 | 97 |
| H6 | 2891.82 | 8634.68 | 4374.4 | 87 |
| H20 | 7442.52 | −111.75 | 1933.85 | 111 |
| H21 | 8041.09 | 1528.28 | 2768.33 | 115 |
| H1 | −825.73 | 3956.74 | 3545.65 | 71 |
| H12A | 2037.03 | 1487.8 | 4289 | 140(70) |
| H7A | −1412.87 | 5655.14 | 2612.09 | 82 |

TABLE 27

| Atomic occupancy | | | | | |
|---|---|---|---|---|---|
| Atom | Occupancy | Atom | Occupancy | Atom | Occupancy |
| N2 | 0.702(4) | H2 | 0.702(4) | O7 | 0.702(4) |
| H7 | 0.702(4) | C9A | 0.298(4) | C1A | 0.298(4) |
| H1A | 0.298(4) | N2A | 0.298(4) | H2A | 0.298(4) |
| N12 | 0.702(4) | H12 | 0.702(4) | C9 | 0.702(4) |
| C11 | 0.702(4) | D11A | 0.702(4) | D11B | 0.702(4) |
| C1 | 0.702(4) | H1 | 0.702(4) | C13 | 0.702(4) |
| D13A | 0.702(4) | D13B | 0.702(4) | D13C | 0.702(4) |
| C10 | 0.702(4) | D10A | 0.702(4) | D10B | 0.702(4) |
| C14 | 0.702(4) | D14A | 0.702(4) | D14B | 0.702(4) |

TABLE 27-continued

| Atomic occupancy | | | | | |
|---|---|---|---|---|---|
| Atom | Occupancy | Atom | Occupancy | Atom | Occupancy |
| D14C | 0.702(4) | N12A | 0.298(4) | H12A | 0.298(4) |
| C10A | 0.298(4) | D10C | 0.298(4) | D10D | 0.298(4) |
| C14A | 0.298(4) | D14D | 0.298(4) | D14E | 0.298(4) |
| D14F | 0.298(4) | C13A | 0.298(4) | D13D | 0.298(4) |
| D13E | 0.298(4) | D13F | 0.298(4) | C11A | 0.298(4) |
| D11C | 0.298(4) | D11D | 0.298(4) | O7A | 0.298(4) |
| H7A | | | 0.298(4) | | |

III. Free Base Compound Forms

Figure 85:
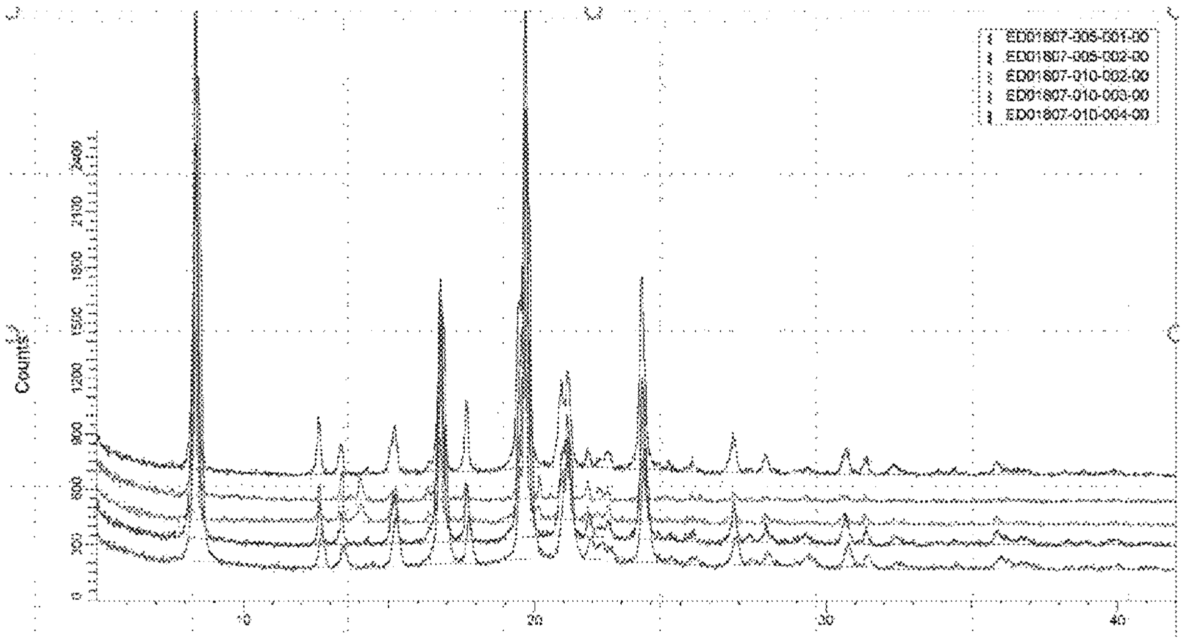
FIG. 85 shows XRPD diffraction peaks of compound I-3 (pattern 1) obtained from crash cooling and freeze-drying solutions of I-3 (PI-$d_{10}$, free base) in 1,4-dioxane, t-BuOH, 1,4-dioxane/water, MeCN/water.
Figure 86:
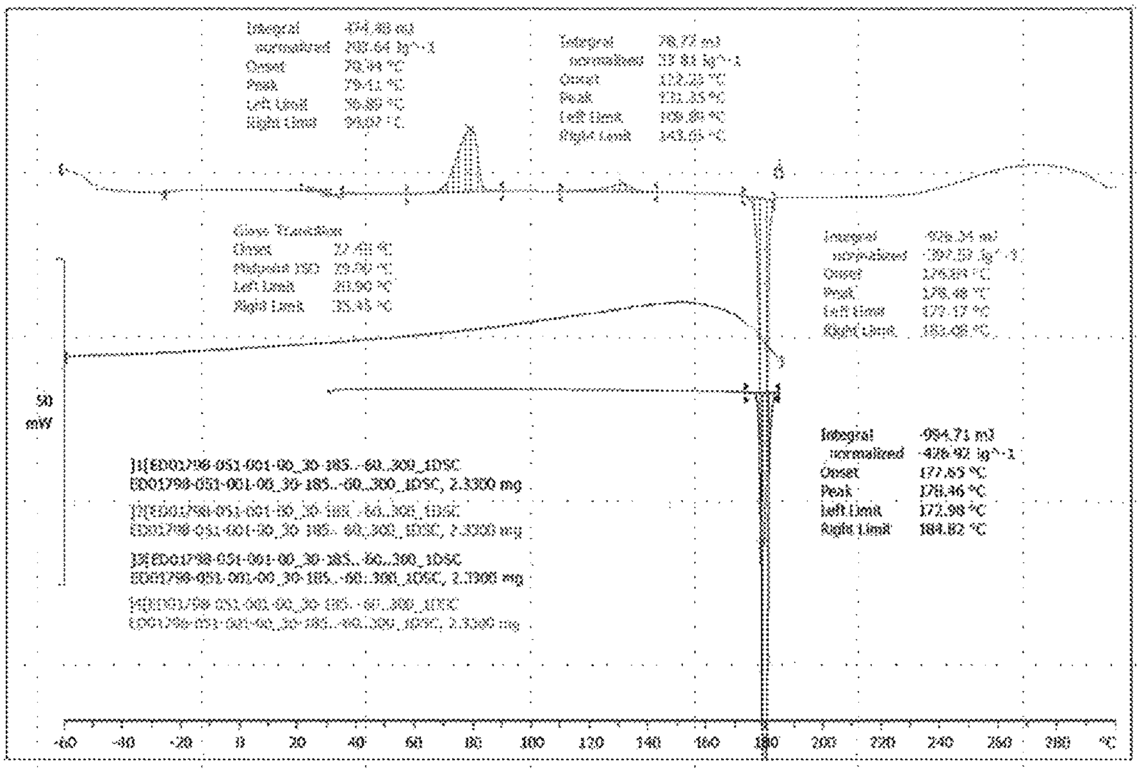
FIG. 86 shows a DSC plot of compound I-3 (PI-$d_{10}$, free base)(pattern 1)

As described in Example 1, I-3 (PI-$d_{10}$, free base) was only isolated as a crystalline solid having an XRPD diffraction pattern 1 (see FIGS. 2A-2C). Attempts were made to prepare an amorphous form of I-3 (PI-$d_{10}$, free base) using a variety of techniques using the crystalline form (pattern 1) as input. The following techniques were tried but were not successful in the preparation of amorphous material:

i) Crash cooling/freeze drying. Crash cooling and freeze-drying solutions of I-3 (PI-$d_{10}$, free base) in 1,4-dioxane, t-BuOH, 1,4-dioxane/water, MeCN/water all gave material that still showed XRPD diffraction peaks of Pattern 1 (FIG. 85).

ii) Fast evaporation. Fast evaporation of a solution of I-3 (PI-$d_{10}$, free base) in dichloromethane (DCM) gave a crystalline material that still showed diffraction peaks of pattern 1.

iii) Anti-solvent precipitation. The addition of concentrated solutions of I-3 (PI-$d_{10}$, free base) in either dimethylformamide (DMF) or dimethylsulfoxide (DMSO) to water did not result in precipitation. Instead, solutions were formed which became dark within 4 hours, signifying degradation Next, a melt/crash cooling technique was investigated. An initial cyclic DSC experiment was conducted in which a portion of the crystalline input of I-3 (PI-$d_{10}$, free base) was heated to 185° C. (beyond the melting point with endothermic event onset at 178° C.) and then rapidly cooled to −60° C. The sample was then heated to 300° C. at 10° C./min. As can be seen in the DSC plot (FIG. 86), I-3 (PI-$d_{10}$, free base) showed a glass transition onset at about 27° C. and 2 exothermic events (onset at 70° C. and 122° C.) prior to the endothermic event onset at 177° C.

Figure 87:
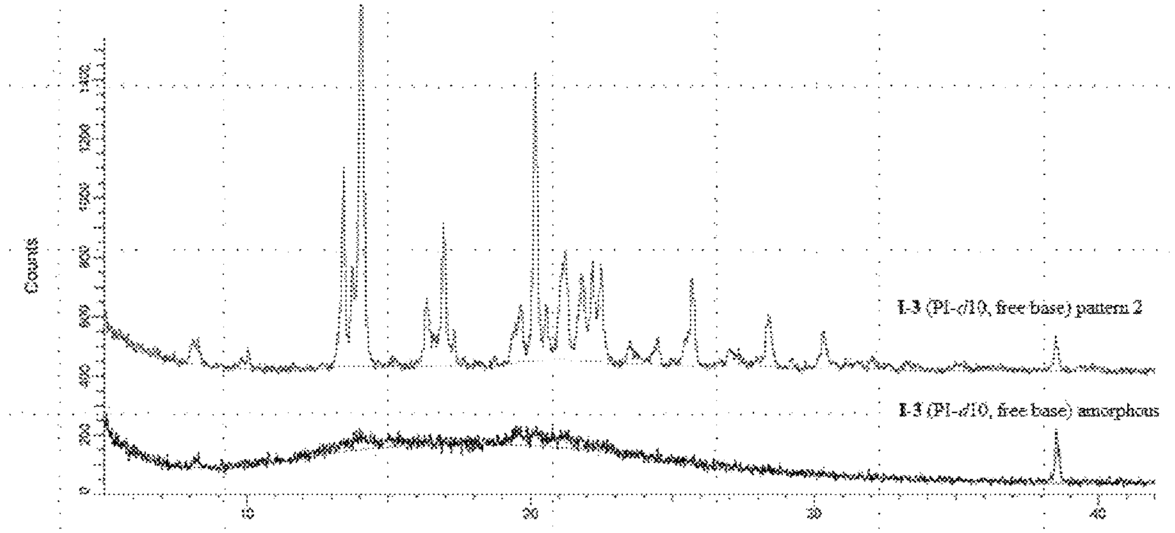
FIG. 87 shows an XRPD of the amorphous form of compound I-3 (PI-$d_{10}$, free base) obtained from melt/crash cooling experiment (>185° C./30° C.) in DSC compared to the XRPD pattern of compound I-3 (pattern 2) which resulted from the amorphous form crystallizing overnight upon standing.

A melt/crash cooling experiment (>185° C./30° C.) was then conducted by heating I-3 (PI-$d_{10}$, free base) in DSC beyond the melting point (to 185° C.) and then rapidly cooled to 30° C. The resulting sample was then analyzed by XRPD, which indicated an amorphous form of I-3 (PI-$d_{10}$, free base) was successfully prepared (FIG. 87). The amorphous material was not stable for prolonged periods, and crystallized overnight to crystal polymorph pattern 2, which was different from the crystalline polymorph pattern 1 used as input in the experiment (FIG. 87).

In summary, attempts to prepare amorphous psilocin-$d_{10}$ (I-3) by crash cooling/freeze drying or fast evaporation gave only crystalline material. Attempts to prepare amorphous psilocin-$d_{10}$ (I-3) by anti-solvent precipitation by addition to water did not yield solid material. Amorphous psilocin-$d_{10}$ (I-3) was successfully prepared by DSC melt/crash cooling (>185° C./30° C.). The amorphous form was unstable upon standing and reverted to a new crystalline form (pattern 2). The amorphous material shows a low glass transition temperature (27° C.).

Preparation of I-3 crystalline pattern 2 by DSC. Eleven portions of I-3 (pattern 1) (each ca. 40 mg) were weighed into 100 μL aluminum DSC pans and the following DSC experiment was performed on each one. (The sample was heated from 30 to 185° C. at 10° C./min, held at 185° C. for 5 minutes, rapidly cooled at −100° C./min to 0° C., heated to 90° C. at 10° C./min and then cooled at 10° C./min to 30° C.) After the experiments the DSC pans were opened and the contents scraped out. A portion of each was analyzed by XRPD to check that Pattern 2 had formed. The eleven samples were then combined to give Psilocin-$d_{10}$ free base crystals of Pattern 2 as a white solid (356 mg).

FIG. 88 shows the X-ray powder diffraction (XRPD) pattern of I-3 (pattern 2) from the DSC scale-up experiment, with FIG. 89 showing the annotated XRPD version. Table 28 shows the XRPD peak listing for I-3 (pattern 2).

TABLE 28

| Name | Caption (display) | Angle | d Value | Net Intensity | Rel. Intensity |
|---|---|---|---|---|---|
| Peak #1 | 8.124° | 8.123984 | 10.87445 | 1288.204 | 0.5911127 |
| Peak #2 | 8.357° | 8.357478 | 10.57115 | 409.2122 | 0.1877734 |
| Peak #3 | 10.059° | 10.05879 | 8.78668 | 89.95876 | 0.04127898 |
| Peak #4 | 12.630° | 12.63015 | 7.002995 | 40.84302 | 0.01874146 |
| Peak #5 | 13.420° | 13.41959 | 6.592748 | 323.3918 | 0.1483934 |
| Peak #6 | 13.743° | 13.74308 | 6.438281 | 159.5939 | 0.07323217 |
| Peak #7 | 14.053° | 14.05272 | 6.297107 | 739.7607 | 0.3394507 |
| Peak #8 | 15.220° | 15.22 | 5.816685 | 167.2829 | 0.07676034 |
| Peak #9 | 16.272° | 16.27205 | 5.442906 | 523.0821 | 0.2400244 |
| Peak #10 | 16.763° | 16.76291 | 5.284614 | 195.402 | 0.08966326 |
| Peak #11 | 16.954° | 16.95446 | 5.225336 | 235.4412 | 0.1080359 |
| Peak #12 | 17.328° | 17.32756 | 5.113654 | 48.59261 | 0.02229748 |
| Peak #13 | 17.662° | 17.66165 | 5.017669 | 71.53699 | 0.03282586 |
| Peak #14 | 18.062° | 18.06191 | 4.907367 | 97.47566 | 0.04472823 |
| Peak #15 | 18.742° | 18.74222 | 4.730745 | 32.0491 | 0.01470623 |
| Peak #16 | 19.413° | 19.41254 | 4.568877 | 745.5985 | 0.3421295 |
| Peak #17 | 19.658° | 19.65764 | 4.512459 | 521.7926 | 0.2394327 |
| Peak #18 | 20.172° | 20.17238 | 4.398462 | 2179.287 | 1 |
| Peak #19 | 20.836° | 20.8364 | 4.259765 | 152.215 | 0.06984623 |
| Peak #20 | 21.267° | 21.26686 | 4.174506 | 317.3733 | 0.1456317 |
| Peak #21 | 21.833° | 21.83276 | 4.067565 | 271.5293 | 0.1245954 |
| Peak #22 | 22.213° | 22.21281 | 3.998823 | 157.6812 | 0.07235449 |
| Peak #23 | 22.504° | 22.50401 | 3.947733 | 245.7072 | 0.1127466 |
| Peak #24 | 23.334° | 23.3343 | 3.809107 | 73.21411 | 0.03359544 |
| Peak #25 | 23.701° | 23.70123 | 3.750961 | 125.4296 | 0.05755533 |
| Peak #26 | 24.385° | 24.3849 | 3.647322 | 65.75739 | 0.0301738 |
| Peak #27 | 25.431° | 25.43138 | 3.49956 | 94.61557 | 0.04341583 |
| Peak #28 | 25.721° | 25.72122 | 3.46078 | 232.2516 | 0.1065723 |
| Peak #29 | 26.049° | 26.04914 | 3.417951 | 68.57748 | 0.03146784 |
| Peak #30 | 27.291° | 27.29145 | 3.265122 | 29.86893 | 0.01370582 |
| Peak #31 | 28.368° | 28.36801 | 3.14361 | 86.29607 | 0.0395983 |
| Peak #32 | 30.349° | 30.3493 | 2.942747 | 108.3302 | 0.04970898 |
| Peak #33 | 30.656° | 30.65631 | 2.913972 | 42.82265 | 0.01964984 |
| Peak #34 | 31.337° | 31.33691 | 2.85222 | 18.87493 | 0.008661055 |
| Peak #35 | 31.538° | 31.53802 | 2.834489 | 34.52836 | 0.01584388 |
| Peak #36 | 32.091° | 32.09148 | 2.786855 | 70.13274 | 0.0321815 |
| Peak #37 | 35.870° | 35.86994 | 2.501483 | 26.79949 | 0.01229736 |
| Peak #38 | 38.514° | 38.51409 | 2.33561 | 153.147 | 0.07027388 |
| Peak #39 | 41.361° | 41.36089 | 2.181192 | 26.51964 | 0.01216895 |

IV. Fatty Acid Salt Forms

Materials. Super Refined® oleic acid commercially available from Croda. Caprylic (octanoic) acid, stearic acid, capric (decanoic) acid, myristic acid, lauric acid, and sodium stearate commercially available from Sigma-Aldrich. Linoleic acid and sodium oleate commercially available from Sigma.

Example 17

Synthesis of laurate salt of 3-(2-(bis(methyl-$d_3$)amino)ethyl-1,1,2,2-$d_4$)-1H-indol-4-ol (I-3m) (laurate salt of I-3/psilocin-$d_{10}$/PI-$d_{10}$)

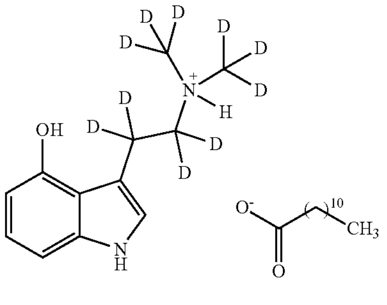

Compound I-3 (PI-$d_{10}$, free base)(ca. 50 mg) was dissolved in chloroform (ca. 25 mg/mL) in a glass vial. 1 molar equivalent of 1M lauric acid in chloroform was added to the free base solution and the sample was stirred at room temperature overnight. The solvent was then removed using a Biotage® V-10 evaporator. The resulting material was scraped and stored at −20° C. to induce crystallization. Crystals of I-3m were produced, which were then stored at 5° C. prior to analysis.

Figure 90:
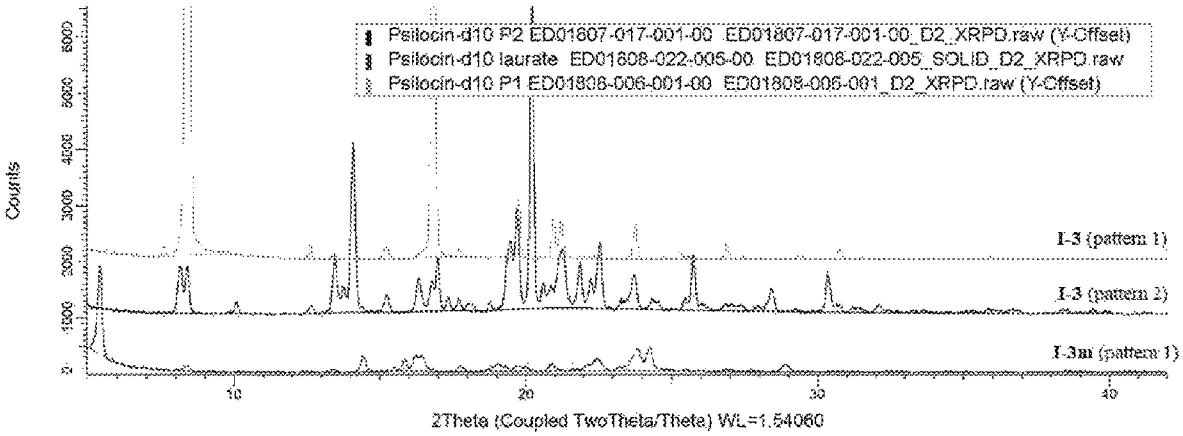
FIG. 90 shows the XRPD pattern of I-3m (pattern 1) compared to diffraction patterns 1 and 2 of the free base I-3.

As shown in FIG. 90, the X-ray powder diffraction (XRPD) pattern indicates the I-3m salt is crystalline, with only one polymorph observed (pattern 1), which was different from the diffraction patterns 1 and 2 of the free base I-3.

Example 18

Synthesis of linoleate salt of 3-(2-(bis(methyl-$d_3$)amino)ethyl-1,1,2,2-$d_4$)-1H-indol-4-ol (I-3n) (linoleate salt of I-3/psilocin-$d_{10}$/PI-$d_{10}$)

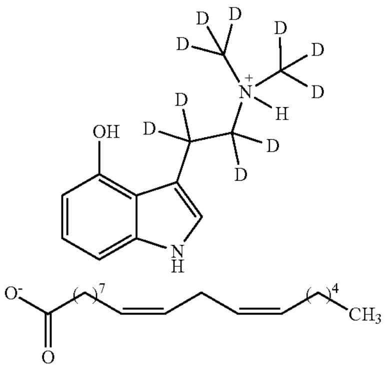

Compound I-3 (PI-$d_{10}$, free base)(ca. 50 mg) was dissolved in chloroform (ca. 25 mg/mL) in a glass vial. 1 molar equivalent of 1M linoleic acid (commercially available from Aldrich) in chloroform was added to the free base solution and the sample was stirred at room temperature overnight. The solvent was then removed using a Biotage® V-10 evaporator. The resulting material was scraped and stored at −20° C. to induce crystallization. Crystals of I-3n were produced, which were then stored at 5° C. prior to analysis.

Figure 91:
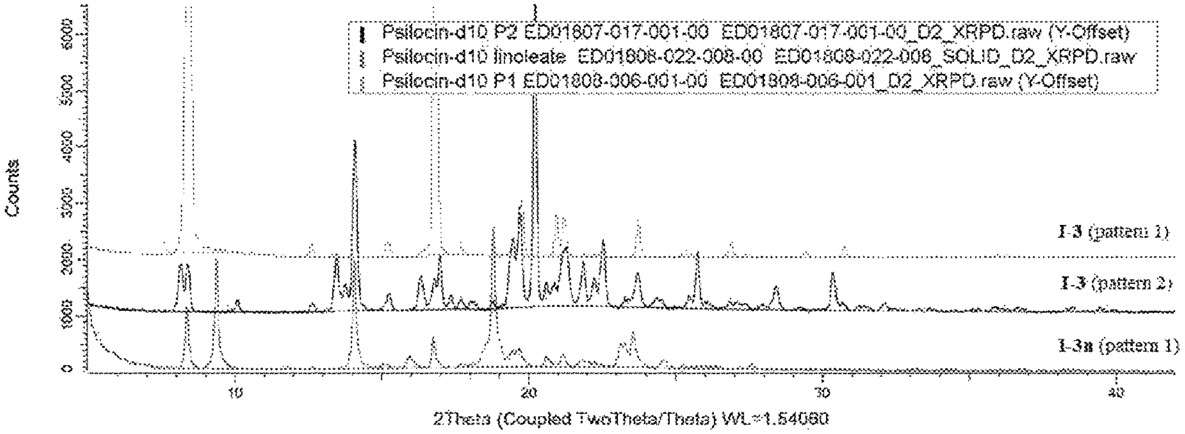
FIG. 91 shows the XRPD pattern of I-3n (pattern 1) compared to diffraction patterns 1 and 2 of the free base I-3.

As shown in FIG. 91, the X-ray powder diffraction (XRPD) pattern indicates the I-3n salt is crystalline, with only one polymorph observed (pattern 1), which was different from the diffraction patterns 1 and 2 of the free base I-3.

Example 19

Synthesis of myristate salt of 3-(2-(bis(methyl-$d_3$)amino)ethyl-1,1,2,2-$d_4$)-1H-indol-4-ol (I-3o) (myristate salt of I-3/psilocin-$d_{10}$/PI-$d_{10}$)

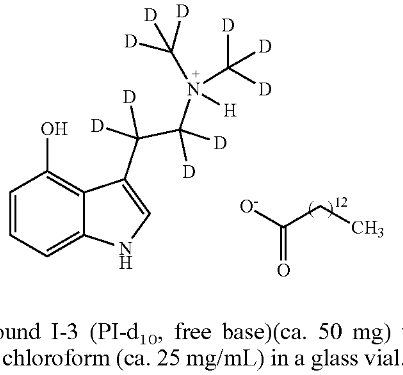

Compound I-3 (PI-$d_{10}$, free base)(ca. 50 mg) was dissolved in chloroform (ca. 25 mg/mL) in a glass vial. 1 molar equivalent of 1M myristic acid in chloroform was added to the free base solution and the sample was stirred at room temperature overnight. The solvent was then removed using a Biotage® V-10 evaporator. The resulting material was scraped and stored at −20° C. to induce crystallization. Crystals of I-3o were produced, which were then stored at 5° C. prior to analysis.

Figure 92:
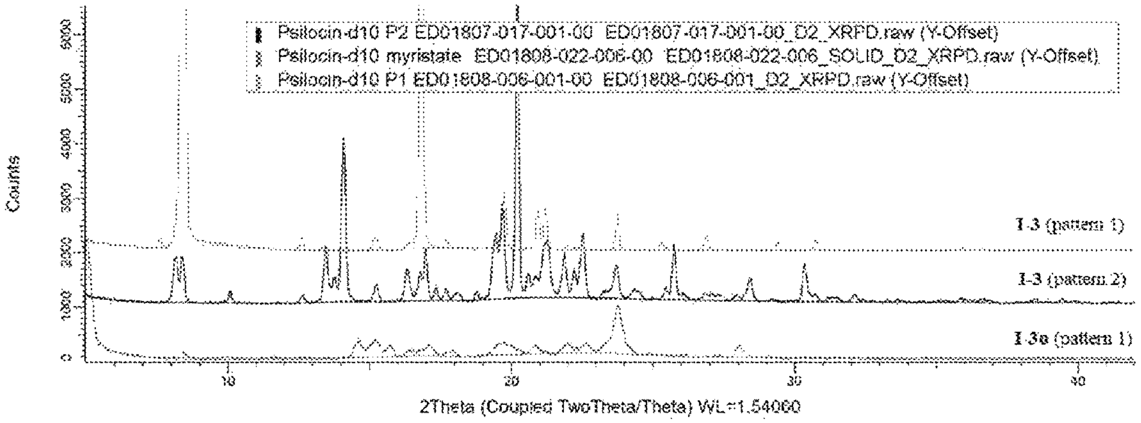
FIG. 92 shows the XRPD pattern of I-3o (pattern 1) compared to diffraction patterns 1 and 2 of the free base I-3.

As shown in FIG. 92, the X-ray powder diffraction (XRPD) pattern indicates the I-3o salt is poorly crystalline, with only one polymorph observed (pattern 1), which was different from the diffraction patterns 1 and 2 of the free base I-3.

Example 20

Synthesis of caprate salt of 3-(2-(bis(methyl-$d_3$)amino)ethyl-1,1,2,2-$d_4$)-1H-indol-4-ol (I-3p) (caprate salt of I-3/psilocin-$d_{10}$/PI-$d_{10}$)

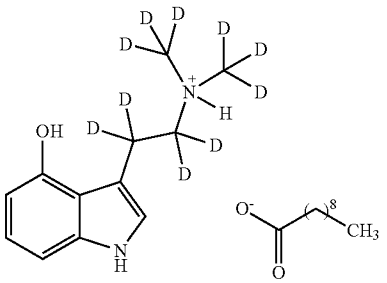

Compound I-3 (PI-$d_{10}$, free base)(ca. 50 mg) was dissolved in chloroform (ca. 25 mg/mL) in a glass vial. 1 molar equivalent of 1M capric acid in chloroform was added to the free base solution and the sample was stirred at room temperature overnight. The solvent was then removed using a Biotage® V-10 evaporator. The resulting material was scraped and stored at −20° C. to induce crystallization. Crystals of I-3p were produced, which were then stored at 5° C. prior to analysis.

Figure 93:
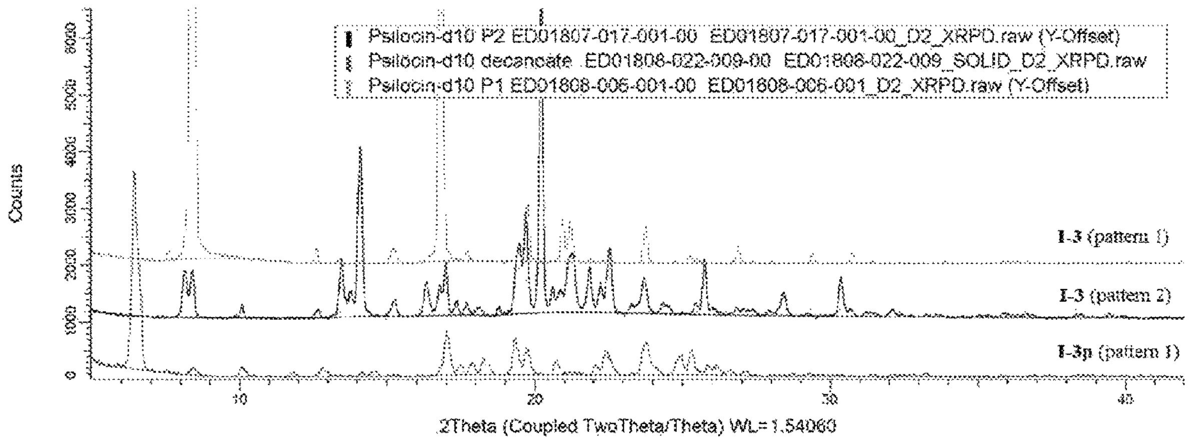
FIG. 93 shows the XRPD pattern of I-3p (pattern 1) compared to diffraction patterns 1 and 2 of the free base I-3.

As shown in FIG. 93, the X-ray powder diffraction (XRPD) pattern indicates the I-3p salt is crystalline, with only one polymorph observed (pattern 1), which was different from the diffraction patterns 1 and 2 of the free base I-3.

Example 21

Synthesis of stearate salt of 3-(2-(bis(methyl-$d_3$)amino)ethyl-1,1,2,2-$d_4$)-1H-indol-4-ol (I-3q) (stearate salt of I-3/psilocin-$d_{10}$/PI-$d_{10}$)

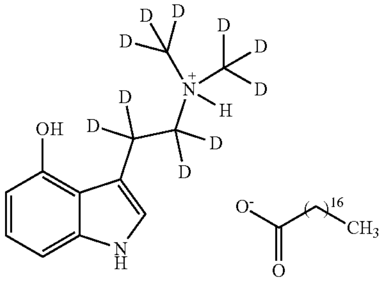

Compound I-3 (PI-$d_{10}$, free base)(ca. 50 mg) was dissolved in chloroform (ca. 25 mg/mL) in a glass vial. 1 molar equivalent of 0.5 M stearic acid (commercially available stearic acid or stearic acid obtained by desalting sodium stearate with 1M HCl) in chloroform was added to the free base solution and the sample was stirred at room temperature overnight. The solvent was then removed using a Biotage® V-10 evaporator. The resulting material was scraped and stored at −20° C. to induce crystallization. Crystals of I-3q were produced, which were then stored at 5° C. prior to analysis.

Figure 94:
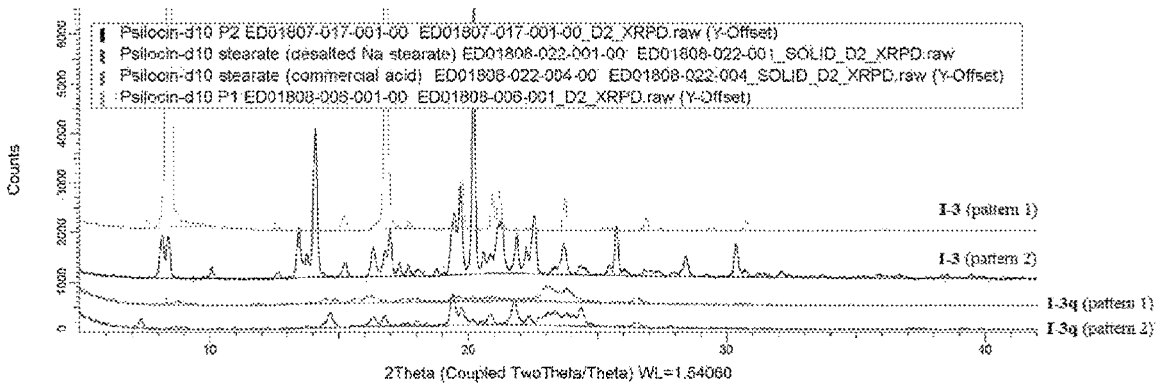
FIG. 94 shows the XRPD pattern of two different polymorphs of I-3q (pattern 1 obtained from commercially available stearic acid, and pattern 2 obtained from desalting sodium stearate) compared to the diffraction patterns 1 and 2 of the free base I-3.

As shown in FIG. 94, the X-ray powder diffraction (XRPD) pattern indicates that two different polymorphs were formed: pattern 1 obtained from commercially available stearic acid, and pattern 2 obtained from desalting sodium stearate. Both polymorphs of I-3q were poorly crystalline and different from the diffraction patterns 1 and 2 of the free base I-3.

Example 22

Synthesis of oleate salt of 3-(2-(bis(methyl-$d_3$)amino)ethyl-1,1,2,2-$d_4$)-1H-indol-4-ol (I-3r) (oleate salt of I-3/psilocin-$d_{10}$/PI-$d_{10}$)

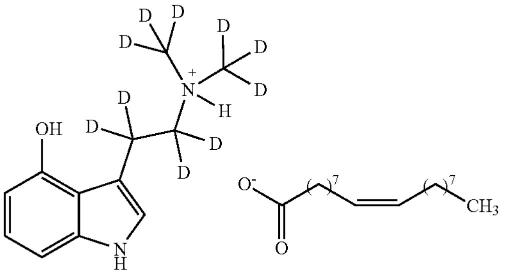

Compound I-3 (PI-$d_{10}$, free base)(ca. 50 mg) was dissolved in chloroform (ca. 25 mg/mL) in a glass vial. 1 molar equivalent of 1M oleic acid (commercially available Super Refined® oleic acid or oleic acid obtained by desalting sodium oleate with 1M HCl) in chloroform was added to the free base solution and the sample was stirred at room temperature overnight. The solvent was then removed using a Biotage® V-10 evaporator. The resulting material was scraped and stored at −20° C. to induce crystallization. Crystals of I-3r were produced, which were then stored at 5° C. prior to analysis.

Figure 95:
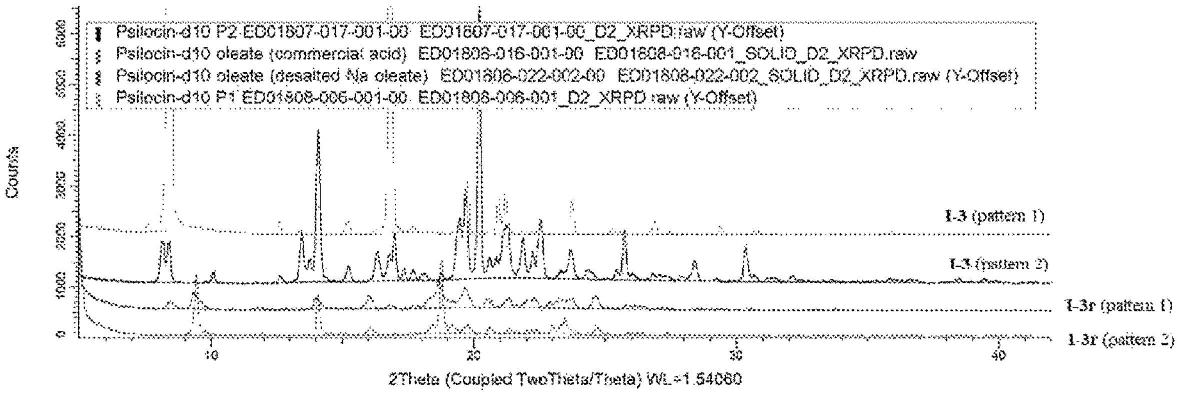
FIG. 95 shows the XRPD pattern of two different polymorphs of I-3r (pattern 1 obtained from desalting sodium oleate, and pattern 2 obtained from commercially available oleic acid) compared to the diffraction patterns 1 and 2 of the free base I-3.

As shown in FIG. 95, the X-ray powder diffraction (XRPD) pattern indicates that two different polymorphs were formed: pattern 1 obtained from desalting sodium oleate, and pattern 2 obtained from commercially available oleic acid. Polymorph of pattern 1 of I-3r was poorly crystalline. Polymorph of pattern 2 of I-3r was crystalline. Both polymorphs of I-3r were different from the diffraction patterns 1 and 2 of the free base I-3.

Example 23

Synthesis of caprylate salt of 3-(2-(bis(methyl-$d_3$)amino)ethyl-1,1,2,2-$d_4$)-1H-indol-4-ol (I-3s) (caprylate salt of I-3/psilocin-$d_{10}$/PI-$d_{10}$)

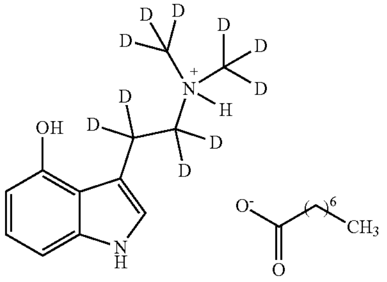

Compound I-3 (PI-$d_{10}$, free base)(ca. 50 mg) was dissolved in chloroform (ca. 25 mg/mL) in a glass vial. 1 molar equivalent of 1M caprylic acid in chloroform was added to the free base solution and the sample was stirred at room temperature overnight. The solvent was then removed using a Biotage® V-10 evaporator. The resulting material was scraped and stored at −20° C. to induce crystallization. Crystals of I-3s were produced, which were then stored at 5° C. prior to analysis.

Figure 96:
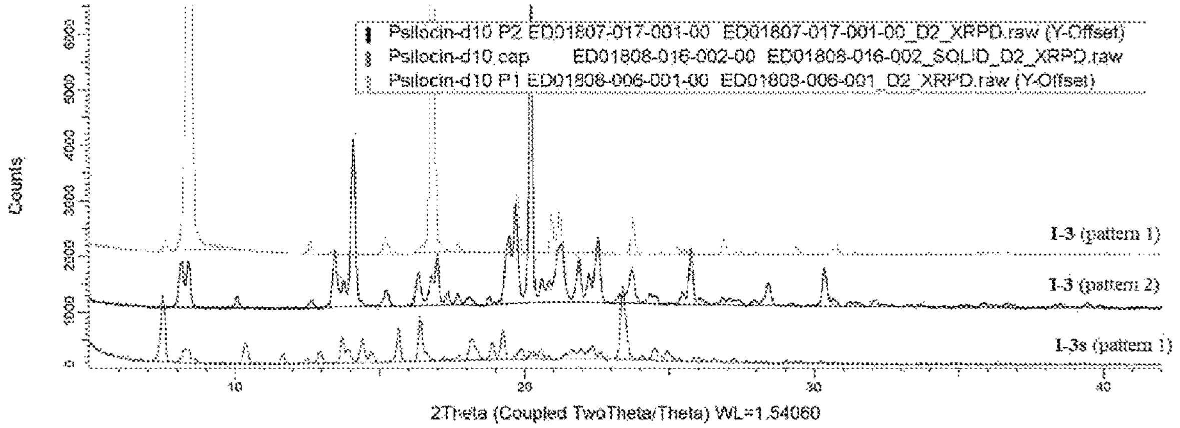
FIG. 96 shows the XRPD pattern of I-3s (pattern 1) compared to diffraction patterns 1 and 2 of the free base I-3.
Figure 97:
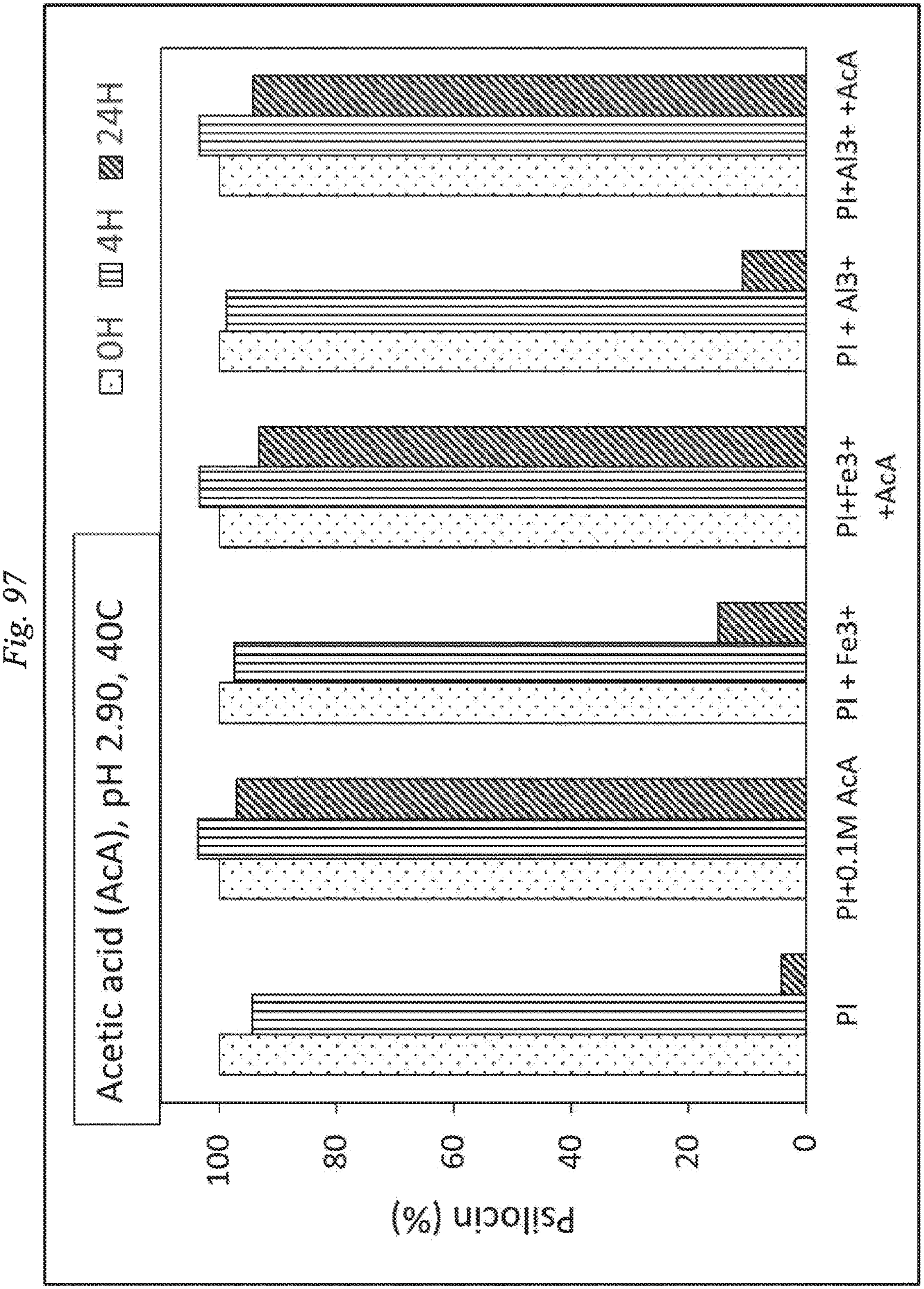
FIG. 97 shows the stability of I-7 (PI-$d_0$) over 24 hours in 0.1 M solutions of acetic acid, with or without metal ions, compared to those solutions without acetic acid, at 40° C.
Figure 98:
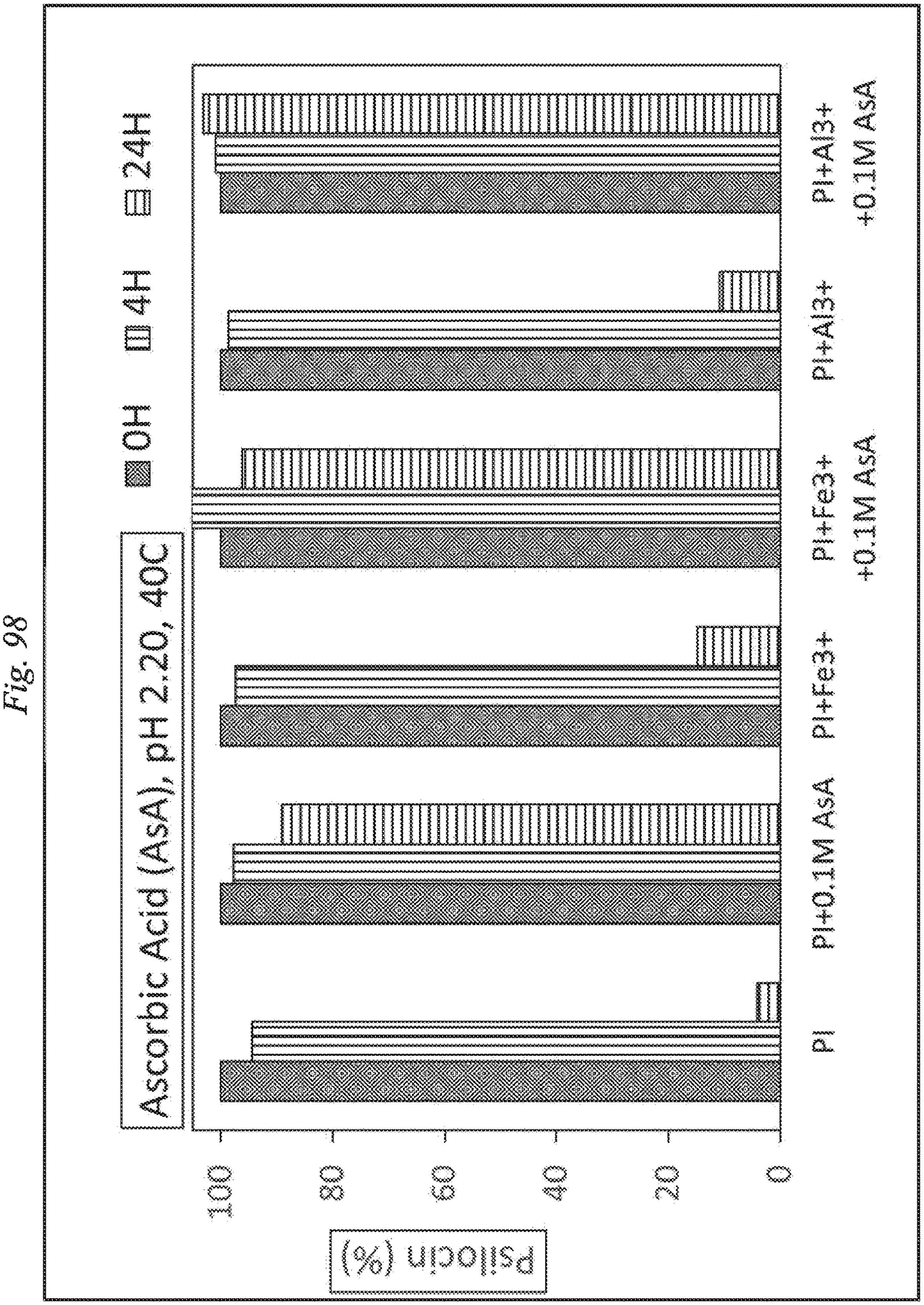
FIG. 98 shows the stability of I-7 (PI-$d_0$) over 24 hours in 0.1 M solutions of ascorbic acid, with or without metal ions, compared to those solutions without ascorbic acid, at 40° C.
Figure 99:
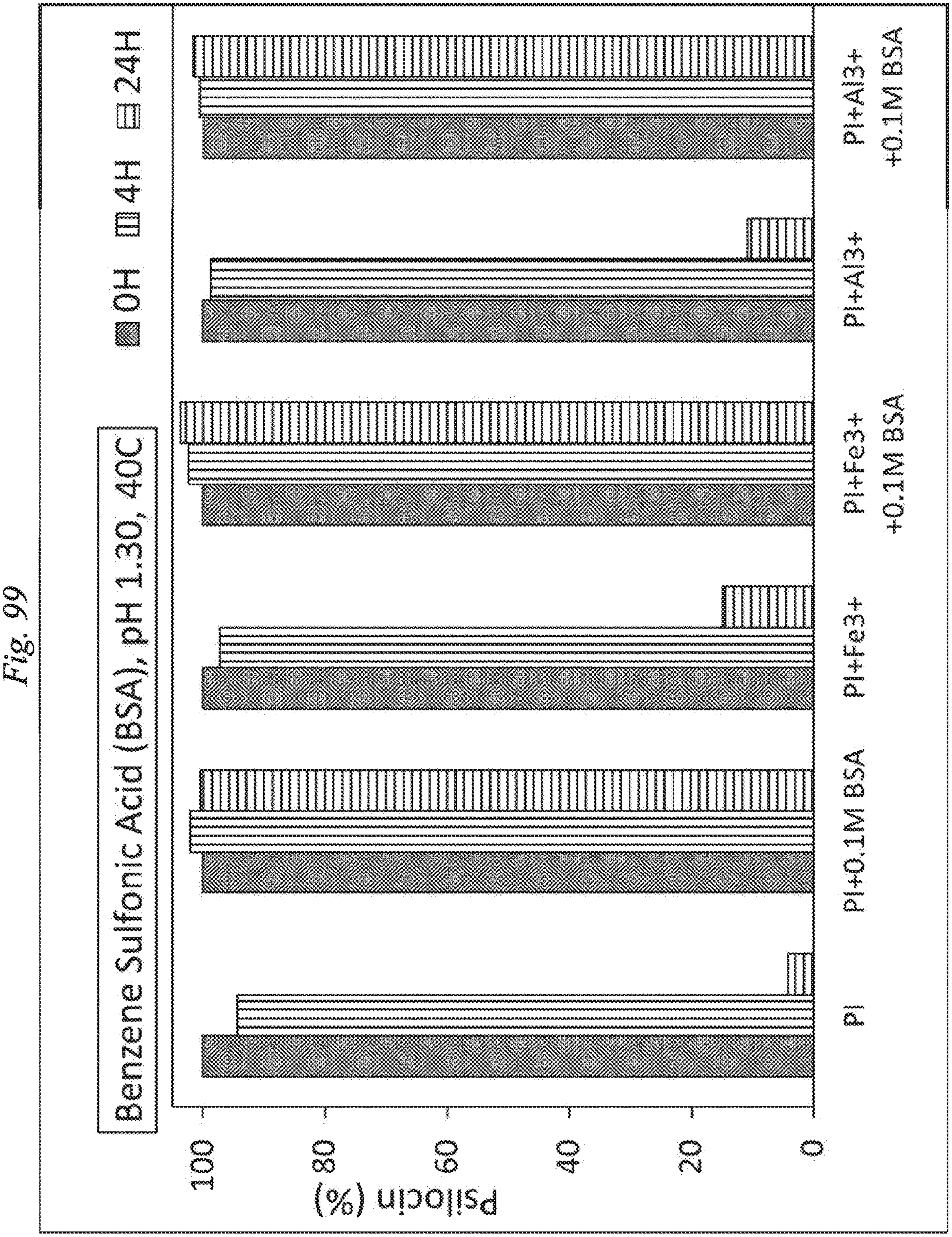
FIG. 99 shows the stability of I-7 (PI-$d_0$) over 24 hours in 0.1 M solutions of benzenesulfonic acid, with or without metal ions, compared to those solutions without benzenesulfonic acid, at 40° C.
Figure 100:
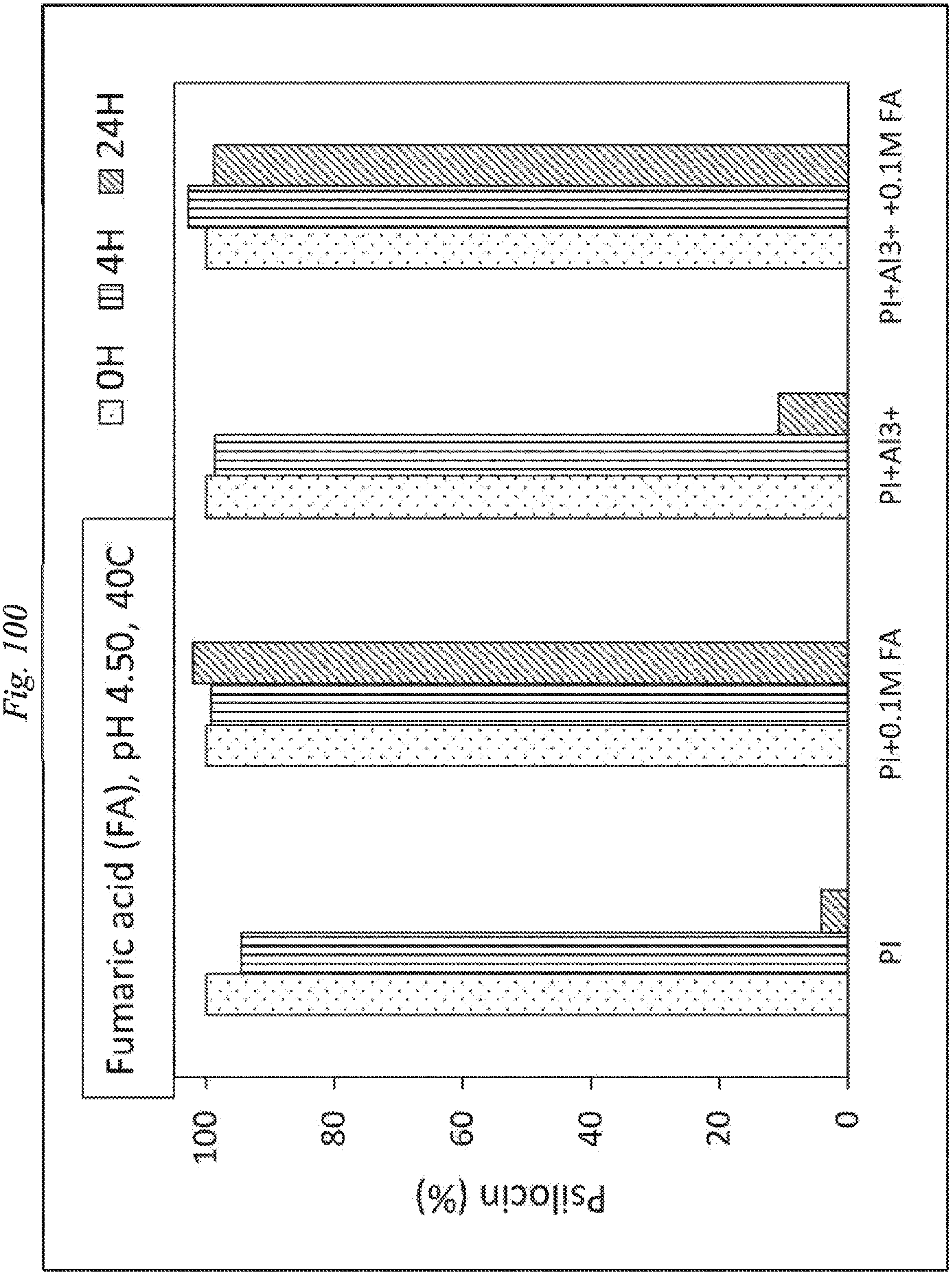
FIG. 100 shows the stability of I-7 (PI-$d_0$) over 24 hours in 0.1 M solutions of fumaric acid, with or without metal ions, compared to those solutions without fumaric acid, at 40° C.
Figure 101:
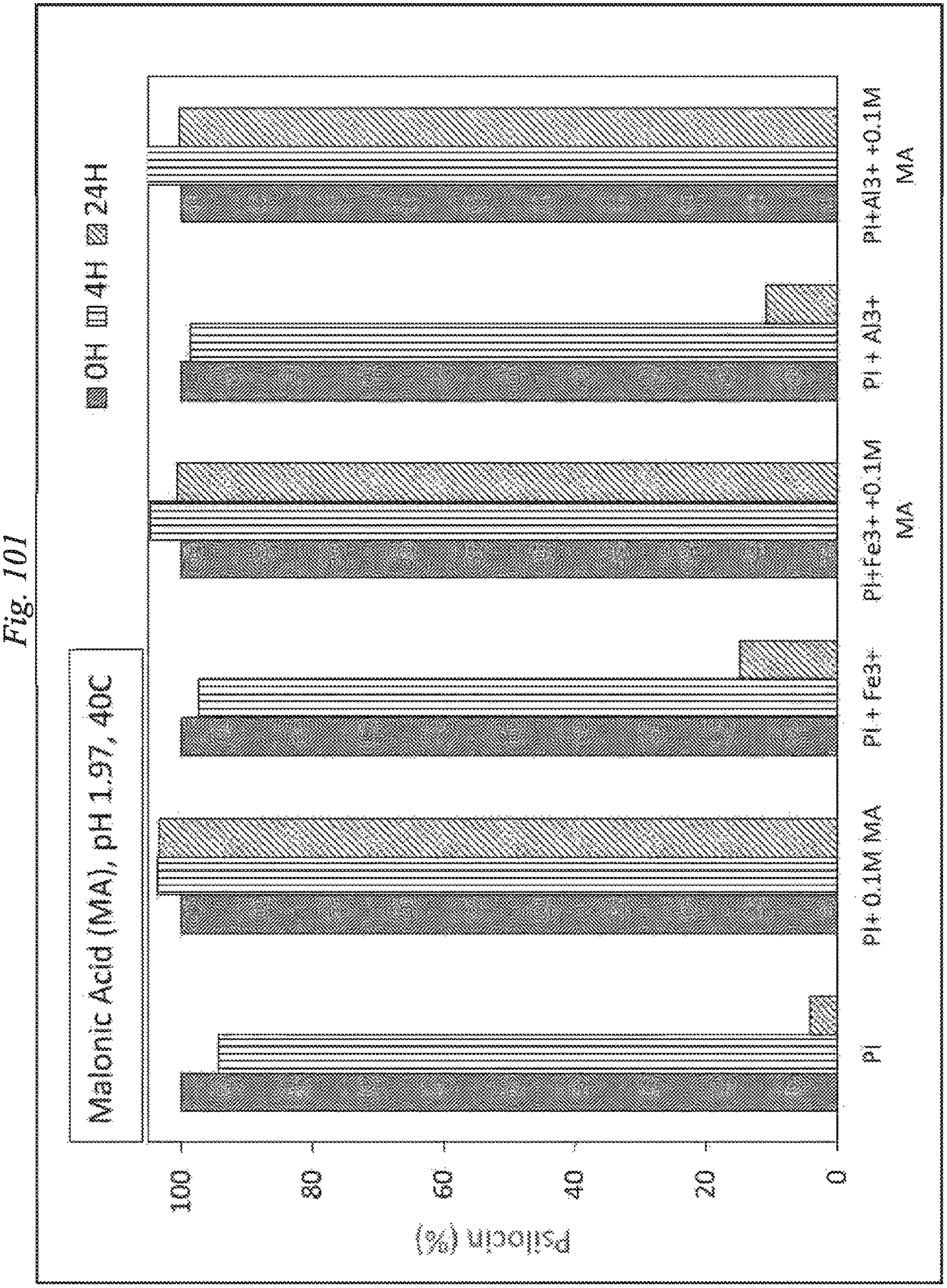
FIG. 101 shows the stability of I-7 (PI-$d_0$) over 24 hours in 0.1 M solutions of malonic acid, with or without metal ions, compared to those solutions without malonic acid, at 40° C.
Figure 102:
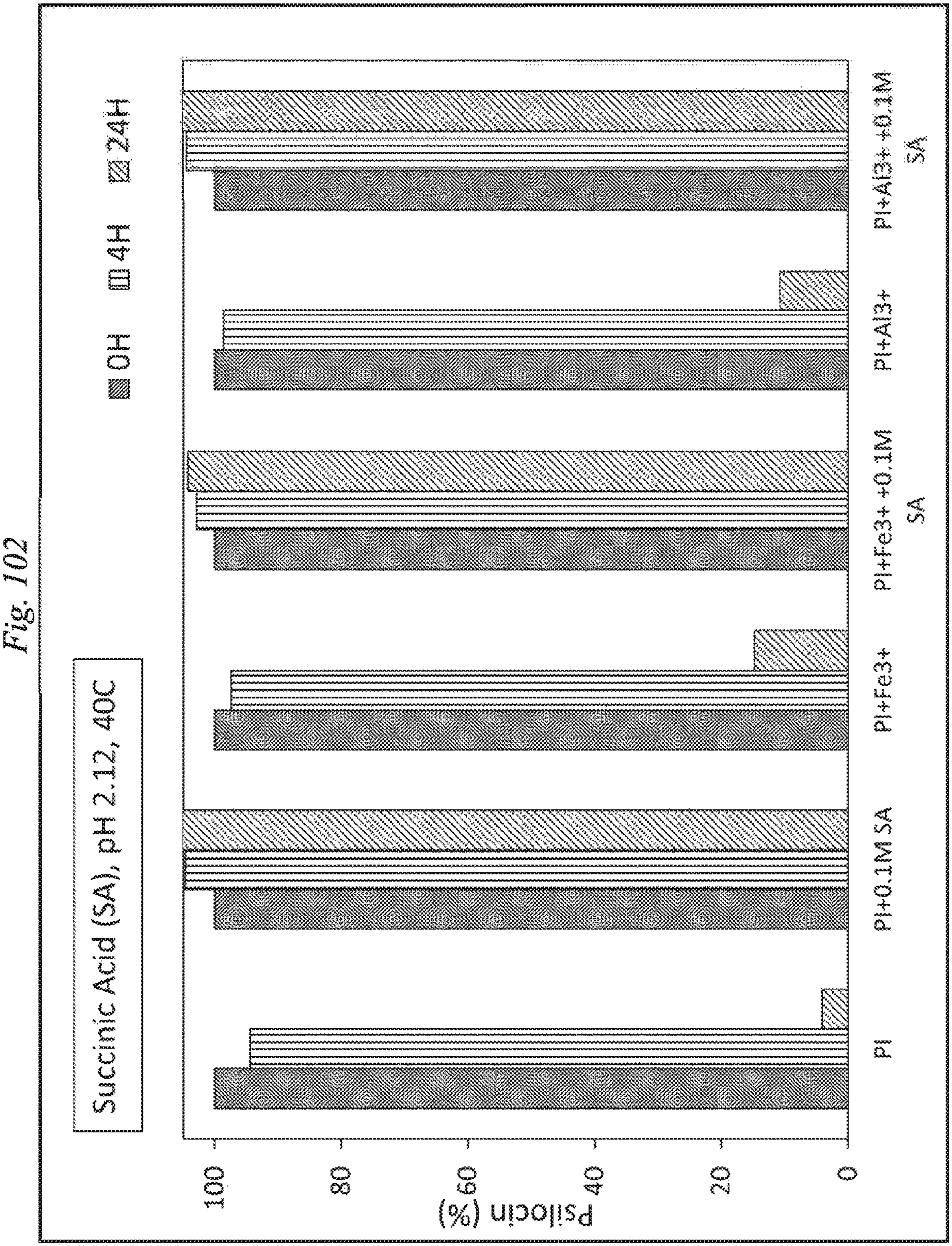
FIG. 102 shows the stability of I-7 (PI-$d_0$) over 24 hours in 0.1 M solutions of succinic acid, with or without metal ions, compared to those solutions without succinic acid, at 40° C.
Figure 103:
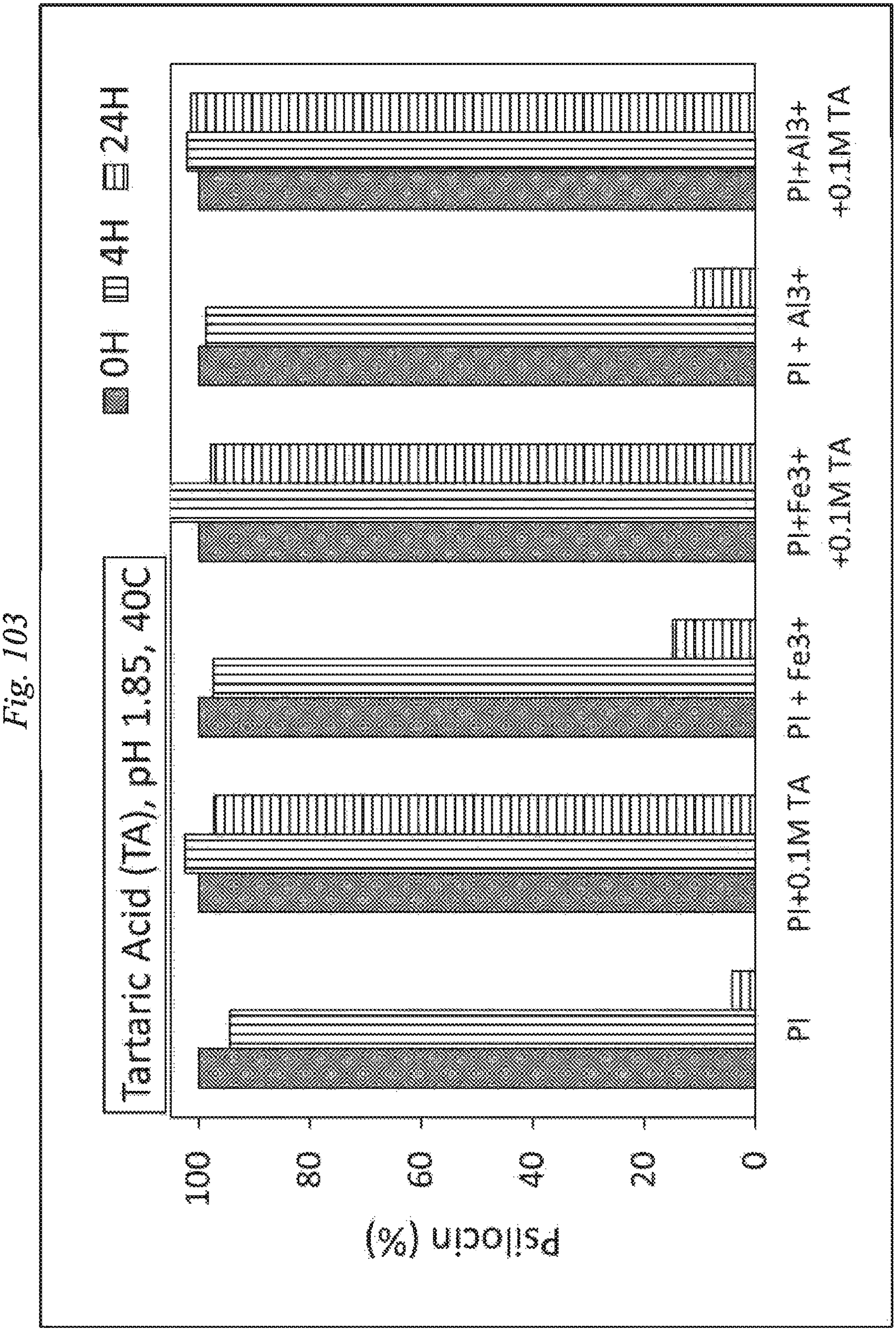
FIG. 103 shows the stability of I-7 (PI-$d_0$) over 24 hours in 0.1 M solutions of tartaric acid, with or without metal ions, compared to those solutions without tartaric acid, at 40° C.
Figure 104:
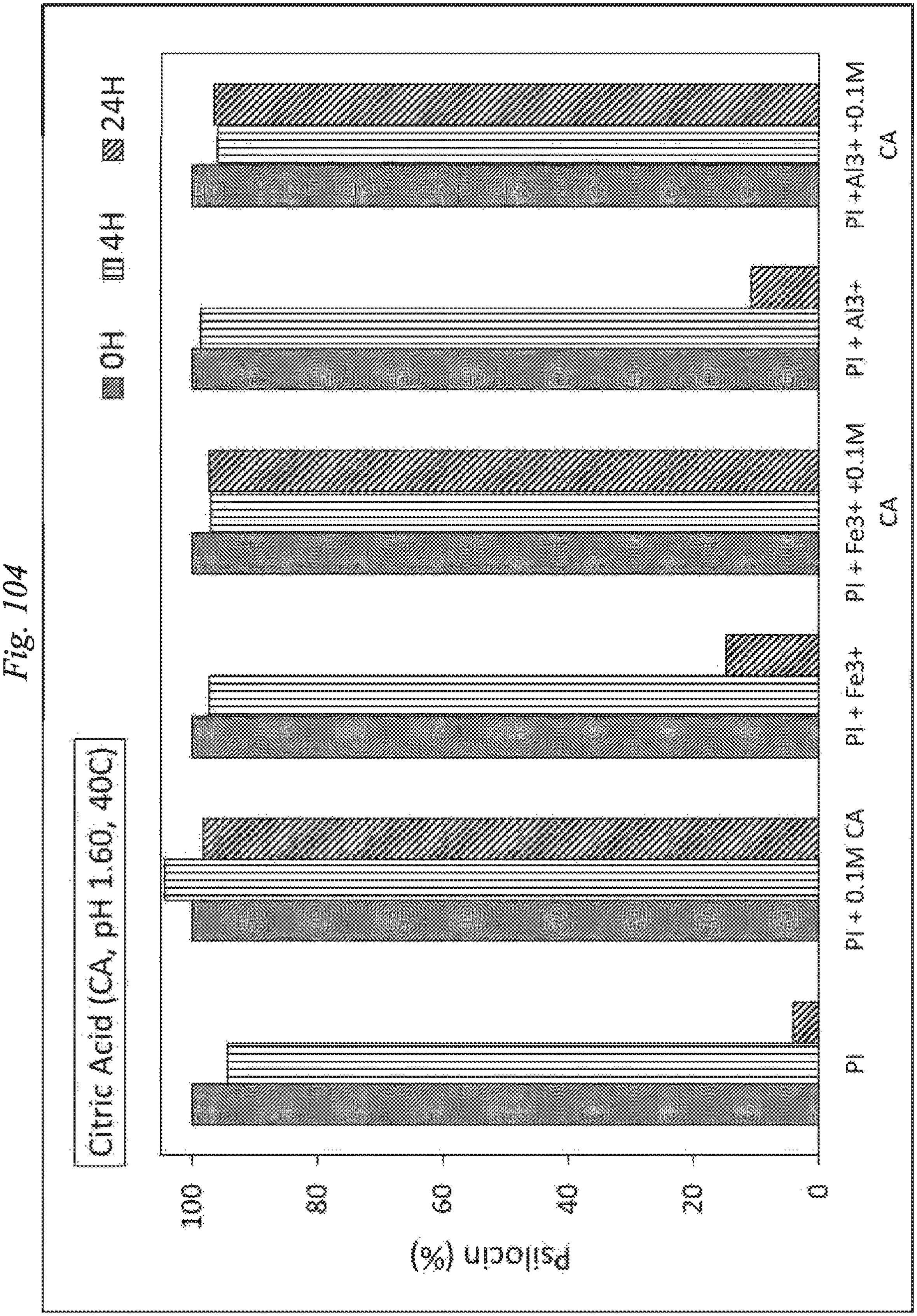
FIG. 104 shows the stability of I-7 (PI-$d_0$) over 24 hours in 0.1 M solutions of citric acid, with or without metal ions, compared to those solutions without citric acid, at 40° C.

As shown in FIG. 96, the X-ray powder diffraction (XRPD) pattern indicates the I-3s salt is crystalline, with only one polymorph observed (pattern 1), which was different from the diffraction patterns 1 and 2 of the free base I-3.

Lipid solubility assessment. Approximately 2-5 mg of test item was added to 0.5 mL of each excipient. The excipients used were corn oil (mixture of unsaturated triglycerides, from Mazola), Crodamol® GTCC (medium chain glyceride, from Croda), and Maisine® CC (mixture of unsaturated mono-, di-, and triglycerides, from Gattefosse). Samples were shaken at room temperature overnight (ca. 18 hours) on an orbital shaker. Where significant solid was present, samples were centrifugated (12500 rpm, 3 min) prior to sampling. A 100 μL aliquot of sample was spiked with 100 μL of internal standard (2 mg/mL benzophenone in 1:1 2-propanol/acetonitrile). The resulting sample was diluted with diluent (resultant ten-fold dilution). For corn oil the diluent was 3:1 2-propanol/acetonitrile. For Crodamol® GTCC and Maisine® CC, the diluent was 1:1 2-propanol/acetonitrile. The samples were analysed by UPLC. Table 29 presents the lipid solubility data.

TABLE 29

| Chain length | | Salt Concentration (mg/mL) | | |
| --- | --- | --- | --- | --- |
| of fatty acid | Test item | Corn oil | GTCC | Maisine CC |
| N/A | I-3 | 0.40 | 1.93 | 1.08 |
| C8 | I-3s | >1.16 | >0.90 | >2.67 |
| C10 | I-3p | 0.40 | 1.33 | 2.17 |
| C12 | I-3m | 0.83 | 2.19 | >1.04 |
| C14 | I-30 | 0.87 | 2.12 | 3.59 |
| C18 | I-3q (pattern 2) | 0.65 | 1.08 | 3.05 |
| | I-3q (pattern 1) | 0.64 | 1.17 | 2.48 |

TABLE 29-continued

| Chain length | | Salt Concentration (mg/mL) | | |
|---|---|---|---|---|
| of fatty acid | Test item | Corn oil | GTCC | Maisine CC |
| C18, (18:1) | I-3r (pattern 1) | 0.71 | 3.03 | >4.02 |
| | I-3r (pattern 2) | 1.01 | >0.57 | >1.91 |
| C18, (18:2) | I-3n | 1.29 | 3.10 | >2.37 |

V. Psilocin Solution Stability Studies

Materials and Methods.

Psilocin (I-7/PI/psilocin-$d_0$/PI-$d_0$) (free base) (1 mg/ml in acetonitrile:water 1:1, non-schedule) was purchased from Cayman Chemicals. Ascorbic acid (AsA), acetic acid (AcA), tartaric acid (TA), fumaric acid (FA), citric acid (CA), malic acid (MA), benzenesulfonic acid (BSA), stearic acid (SA), sodium citrate dihydrate, monosodium phosphate hydrate, disodium phosphate were purchased from Sigma Aldrich. Aluminum (III) chloride ($AlCl_3$) and iron (III) chloride ($FeCl_3$) were purchased from Sigma Aldrich. Antioxidants, i.e., ethylenediaminetetraacetic acid (EDTA), ascorbic acid (AsA), L-cysteine (Cys), sodium metabisulfite ($NamBiSO_3$) and propyl gallate (PG) were purchased from Sigma Aldrich. Hydroxypropyl-β-cyclodextrin (CAVASOL® W7 HP, CAVITRON® W7 HP7) and methyl-β-cyclodextrin (CAVASOL® W7 M) were provided by DuPont.

The following chromatographic conditions were used:

| | | | |
|---|---|---|---|
| Column | Stationary Phase | ZorbaxSB 18 3.5 mm | |
| | Material/Dimensions | Stainless steel, 4.6 × 150 mm | |
| | Mobile Phase A | Water:TFA (100:0.1 v/v) | |
| | Mobile Phase B | ACN:TFA (100:0.1 v/v) | |
| | Time (Min) | % A | % B |
| Gradient Time | 0.0 | 95 | 5 |
| | 1.0 | 95 | 5 |
| | 21 | 60 | 40 |
| | 27 | 5 | 95 |
| | 31 | 5 | 95 |
| | 34 | 95 | 5 |
| | 36 | 95 | 5 |
| | Flow rate | 0.8 mL/min | |
| | Column Temp | 30° C. | |
| | Injection Vol | 10 μL | |
| | Needle wash | Diluent | |
| | Detection wavelength | 269 nm | |
| | Run Time | 36 min | |

Diluent. The diluent used in the below studies was prepared as follows: 100 mL of acetonitrile (ACN) was mixed with 800 mL of water and 100 mL of 1.0 M citric acid and mixed well to prepare 1 L of diluent.

Stability Studies in Acid Solutions (PI Salt Solutions)

The stability of psilocin in 0.1 M solutions of various acids was tested. Furthermore, psilocin stability was explored in the presence of metal ions ($Fe^{3+}$ and $Al^{3+}$), both with and without the presence of the acids.

Test solutions: To prepare the test solutions, 0.1 M solutions of AsA, AcA, TA, FA, CA, MA, BSA, and SA were prepared in DI water. 10 μM solutions of $AlCl_3$ and $FeCl_3$ were prepared in the above solutions. Typically, the psilocin solution was mixed with the 0.1 M acid solution, with or without metal ions, and incubated at 40° C. for designated timepoints (0, 2, 4, 6, 8, 18, 24H). The samples were diluted (1:1) with the diluent before submitting to chromatography to determine the % psilocin remaining.

Results: As can be seen from the results presented in FIGS. 97-104, the solution stability of psilocin (free base) without acid was poor, with nearly all psilocin being degraded within 24 hours. The presence of $Fe^{3+}$ and $Al^{3+}$ metal ions in the solutions without acid also resulted in significant psilocin degradation. To the contrary, all tested acid solutions of psilocin (solution-phase salts of psilocin) provided excellent stability for up to 24, the highest time point tested, at 40° C. The stabilizing effect of the various acids was seen in both the acid solutions and those doped with the metal salts.

Stability Studies in Citric Acid Solution

The stability of psilocin in the presence of citric acid was tested at 4° C., 23° C., and 40° C. Furthermore, psilocin stability was explored in the presence of metal ions ($Fe^{3+}$ and $Al^{3+}$), both with and without the presence of citric acid.

Stock solutions: A 0.2 mg/ml stock solution of citric acid was prepared in DI water with a pH of 3.2. 20 μM stock solutions of $AlCl_3$ and $FeCl_3$ were freshly prepared in the above prepared 0.2 mg/ml citric acid solution.

Test solutions: To prepare the test solutions, psilocin solution (1 mg/ml) was mixed with (i) 0.2 mg/ml citric acid solution (1:1 v/v), (ii) 20 μM $FeCl_3$, and (iii) 20 μM $AlCl_3$ in 1:1 v/v ratio. The samples were incubated at 4° C., 23° C., and 40° C. for designated timepoints (0, 2, 4, 6, 8, 18, 24H). The samples were diluted (1:1) with the diluent before submitting to chromatography to determine the % psilocin remaining.

Figure 105:
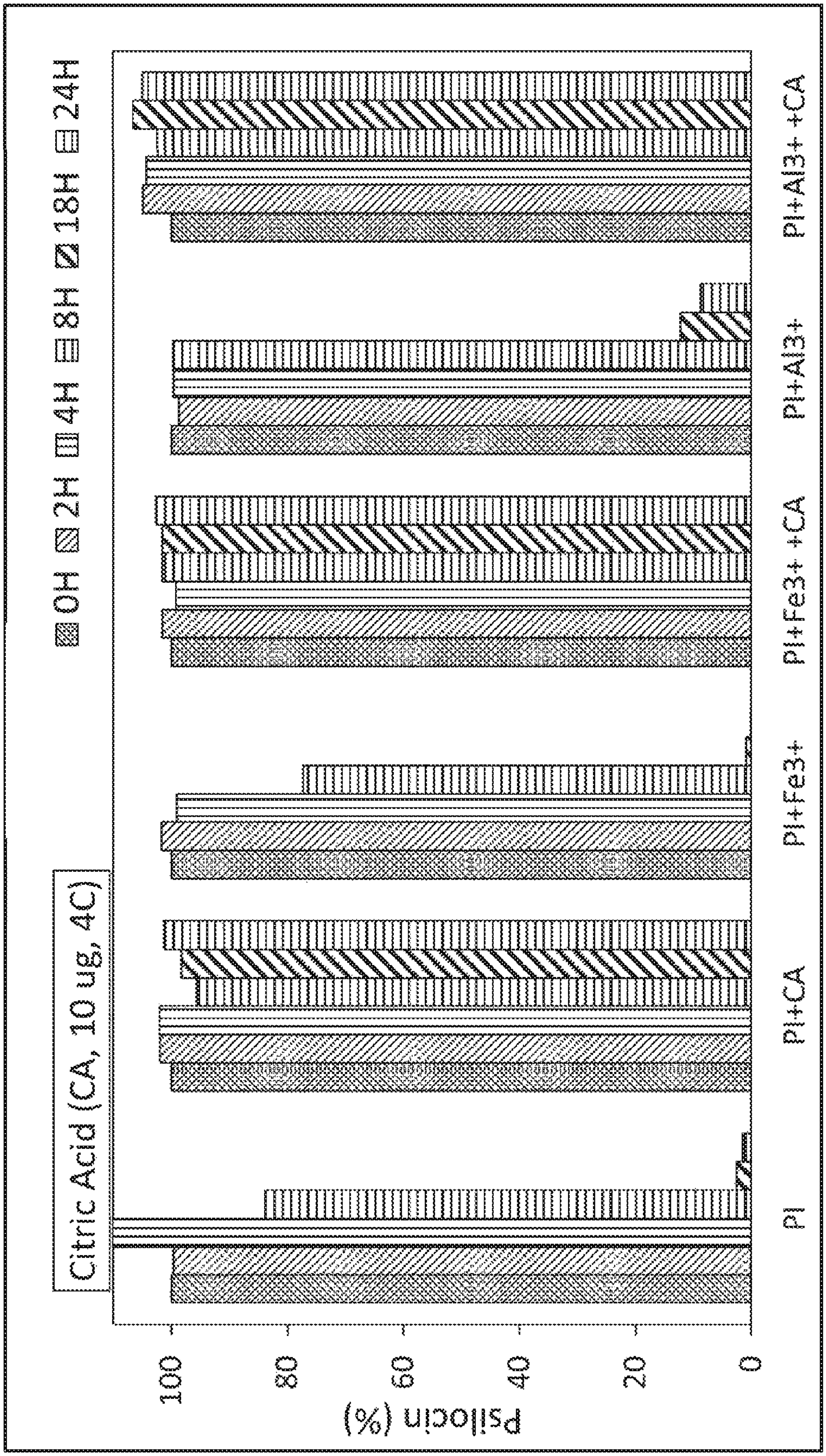
FIG. 105 shows the stability of I-7 (PI-$d_0$) over 24 hours in dilute solutions of citric acid, with or without metal ions, compared to those solutions without citric acid, at 4° C.
Figure 106:
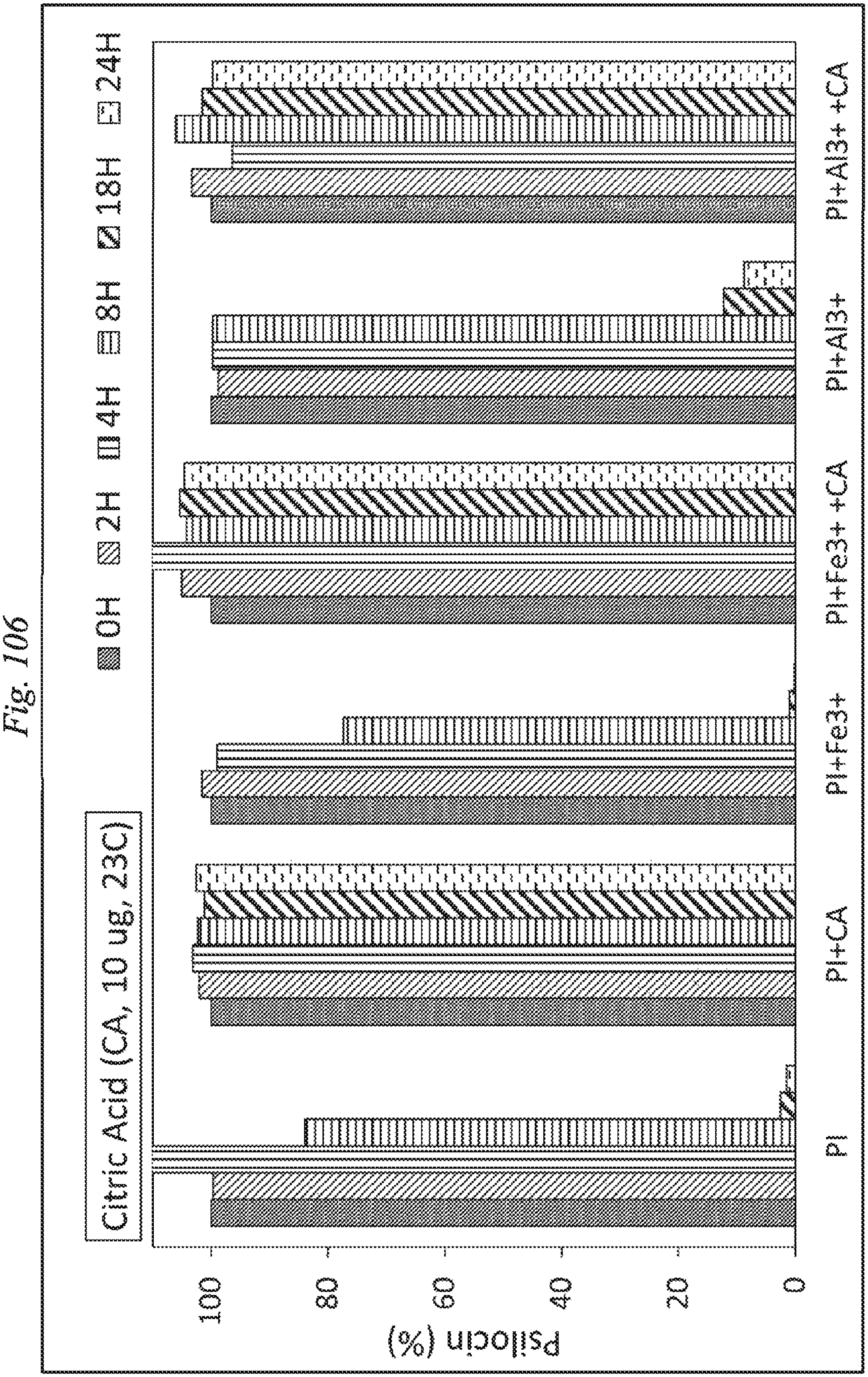
FIG. 106 shows the stability of I-7 (PI-$d_0$) over 24 hours in dilute solutions of citric acid, with or without metal ions, compared to those solutions without citric acid, at 23° C.
Figure 107:
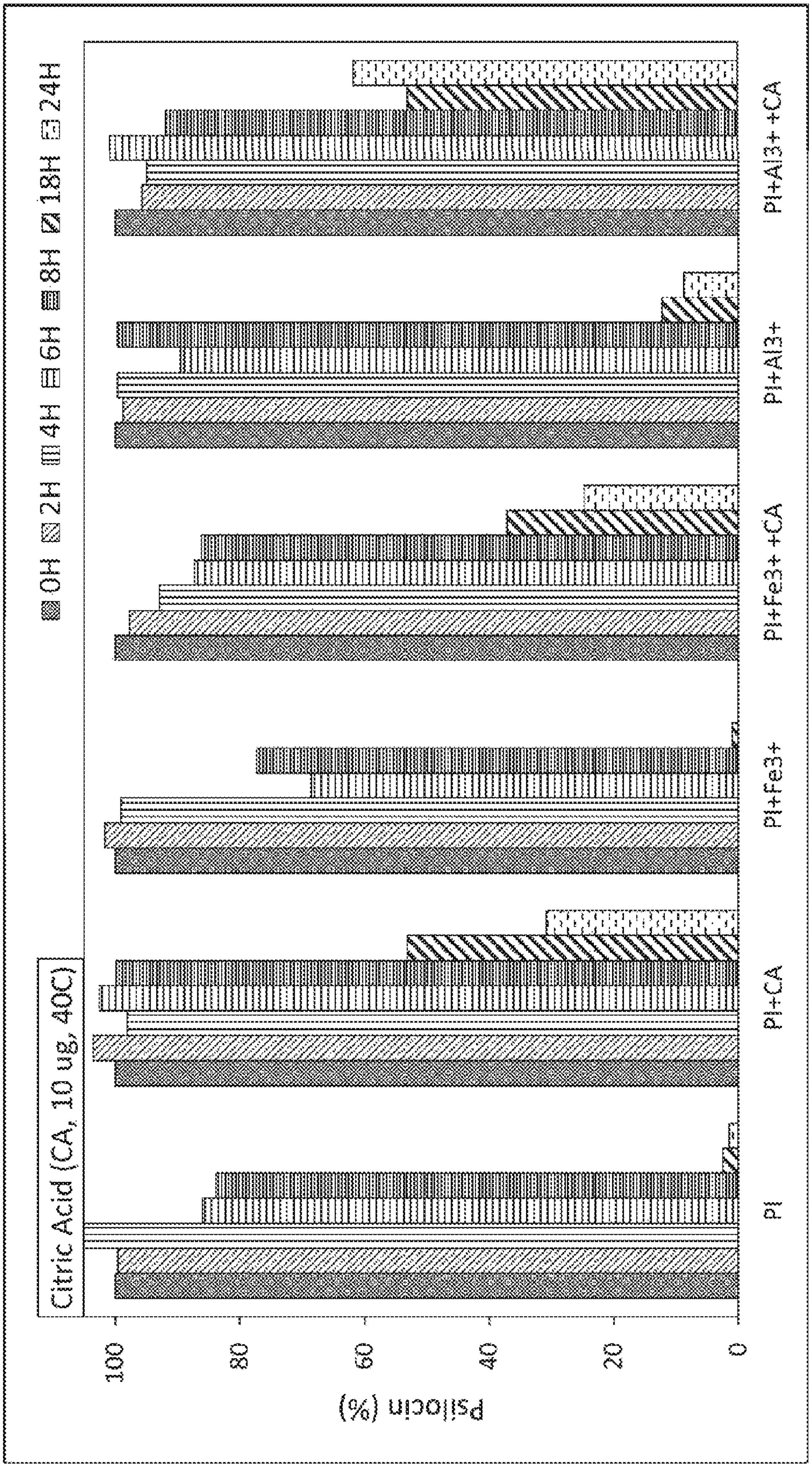
FIG. 107 shows the stability of I-7 (PI-$d_0$) over 24 hours in dilute solutions of citric acid, with or without metal ions, compared to those solutions without citric acid, at 40° C.

Results: As can be seen from the results presented in FIGS. 105-107, the solution stability of psilocin (free base) in solutions without citric acid was poor, with nearly all psilocin being degraded by the 18 hour time point at all temperatures tested. The presence of $Fe^{3+}$ and $Al^{3+}$ metal ions in these solutions without citric acid also resulted in significant psilocin degradation. However, even the addition of small quantities of citric acid (10 μg), forming solution-phase citrate salts of psilocin with a pH of 3.2, greatly enhanced the stability of psilocin at 4° C. and room temperature (23° C.). Psilocin stabilization at 40° C. with small quantities of citric acid was not efficient at the 24 hour time point (30%, FIG. 107), but provided increased protection compared to solutions without citric acid. A similar behavior was observed in the presence of trace metals.

Stability Studies in Sodium Citrate Buffer

The stability of psilocin in the presence of 0.1 M sodium citrate buffer was tested at 4° C., 23° C., and 40° C. Furthermore, psilocin stability was explored in the presence of metal ions ($Fe^{3+}$ and $Al^{3+}$), both with and without the presence of sodium citrate buffer.

Preparation of 0.1 M sodium citrate buffer (pH 6.01): 2.427 g of sodium citrate dihydrate and 0.336 g of citric acid were dissolved in 80 ml of DI water. The pH was adjusted to 6.0 using a 1 M NaOH solution. The final volume was adjusted to 100 ml.

Test solutions: 20 μM stock solutions of $AlCl_3$ and $FeCl_3$ were freshly prepared in above prepared 0.1 M sodium citrate buffer. Psilocin (1 mg/ml) was mixed with (i) 0.1 M sodium citrate buffer (1:1 v/v), (ii) 10 μM $FeCl_3$, and (iii) 10 μM $AlCl_3$ in 1:1 v/v ratio. The samples were incubated at 4° C., room temperature (RT, 23° C.), and 40° C. for designated timepoints (0, 2, 4, 6, 8, 18, 24H). The samples were diluted (1:1) with the diluent before submitting to chromatography to determine the % psilocin remaining.

Figure 108A:
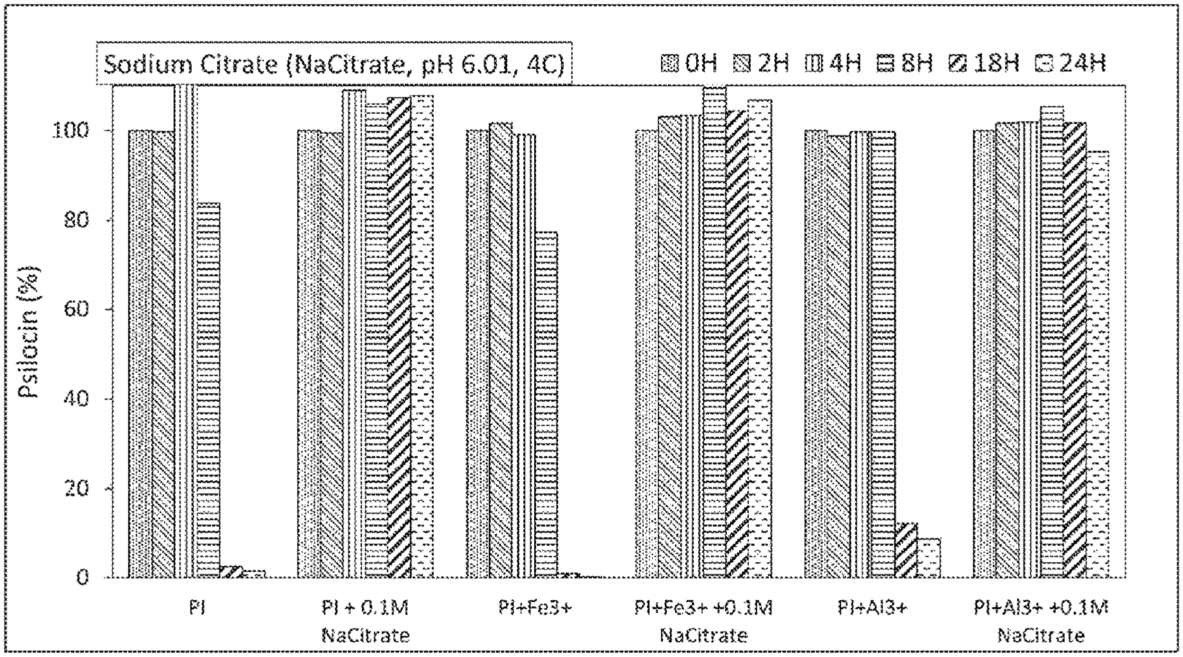
FIGS. 108A-108C shows the stability of I-7 (PI-$d_0$) over 24 hours in 0.1M solutions of sodium citrate buffer, with or without metal ions, compared to those solutions without sodium citrate buffer, at 4° C.
Figure 108B:
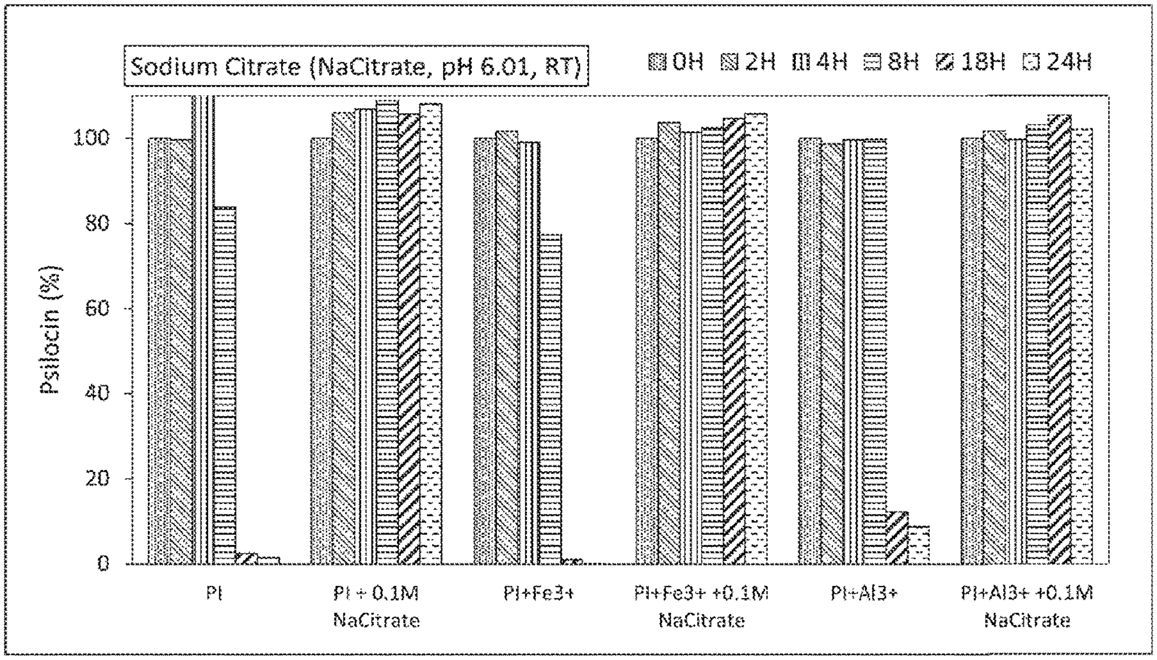
Figure 108C:
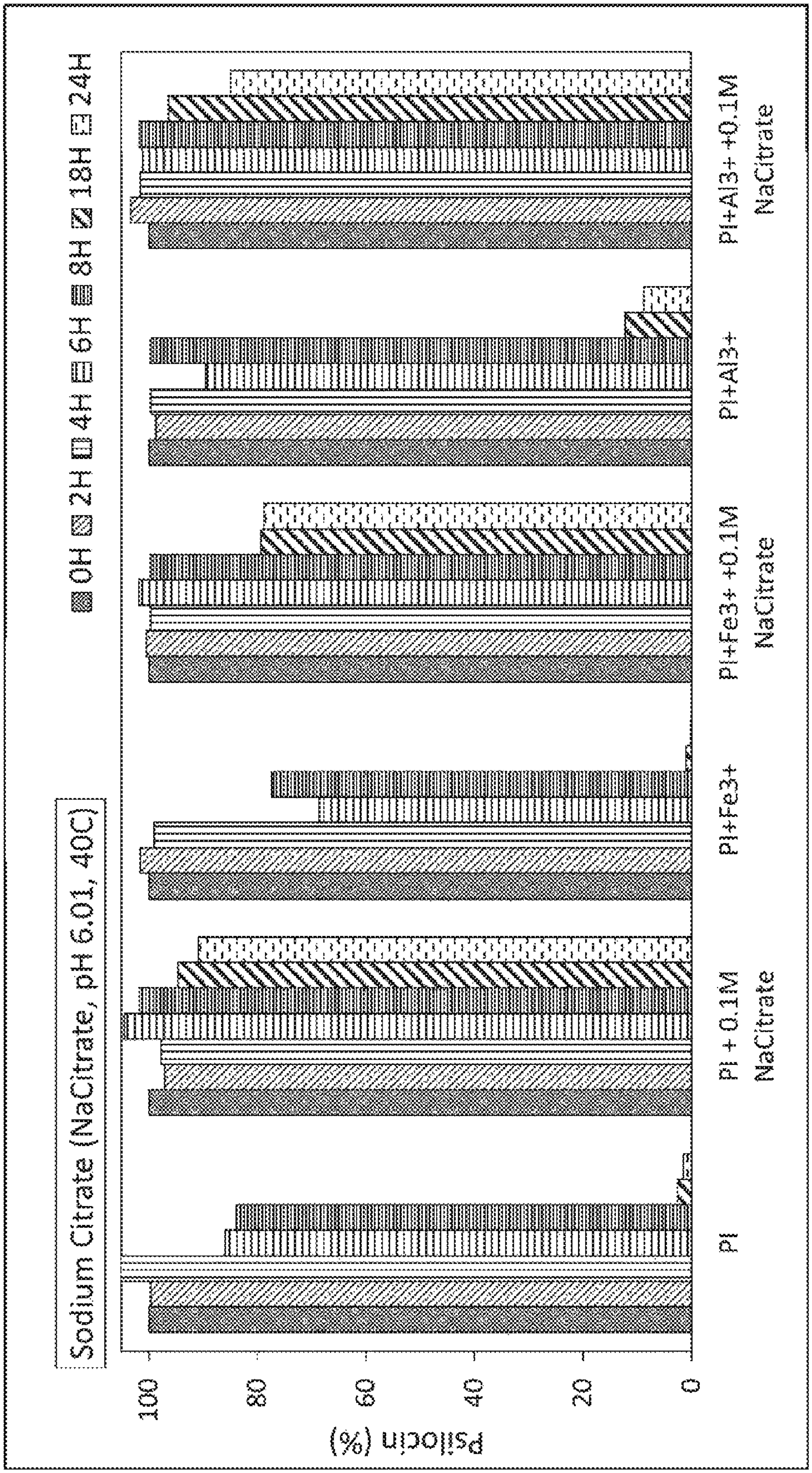

Results: As seen from FIGS. 108A-108C, the solution stability of psilocin (free base) without sodium citrate buffer was poor, with nearly all psilocin being degraded by the 18 hour time point at all temperatures tested. The presence of $Fe^{3+}$ and $Al^{3+}$ metal ions in these non-citrate buffered solutions also resulted in significant psilocin degradation. Conversely, 0.1 M sodium citrate buffer greatly stabilized psilocin at 4° C. and room temperature. Furthermore, no detrimental effects on psilocin were observed due to metal salts ($Fe^{3+}$ and $Al^{3+}$) in the citrate buffer. A minimal degradation (10-15%) of psilocin was observed at the higher temperature (40° C.) condition.

Stability Comparison Between Sodium Citrate and Phosphate Buffer

The effect of buffer type and pH on the stability of psilocin was assessed.

Preparation of 0.1 M sodium citrate buffer (pH 6.01): 2.427 g of sodium citrate dihydrate and 0.336 g of citric acid were dissolved in 80 ml of DI water. The pH was adjusted to 6.0 using a 1 M NaOH solution. The final volume was adjusted to 100 ml.

Preparation of 0.1 M phosphate buffer (pH 6.0 and pH 7.5): Monosodium phosphate (0.339 g, 0.002 moles) and disodium phosphate (2.021 g, 0.014 moles) were dissolved in 80 ml water and the pH was adjusted as necessary using sodium hydroxide or phosphoric acid. The volume was adjusted to 100 ml using water.

Test solutions: Psilocin (1 mg/ml) was mixed with (i) 0.1 M sodium citrate buffer (pH 6.01), (ii) 0.1 M phosphate buffer (pH 6.0), and (iii) 0.1 M phosphate buffer (pH 7.5) in a 1:1 v/v ratio. The samples were incubated at 40° C. for designated timepoints (0, 2, 4, 6, 8, 18, 24H) and diluted (1:1) with the diluent before submitting to chromatography to determine the % psilocin remaining.

Figure 109:
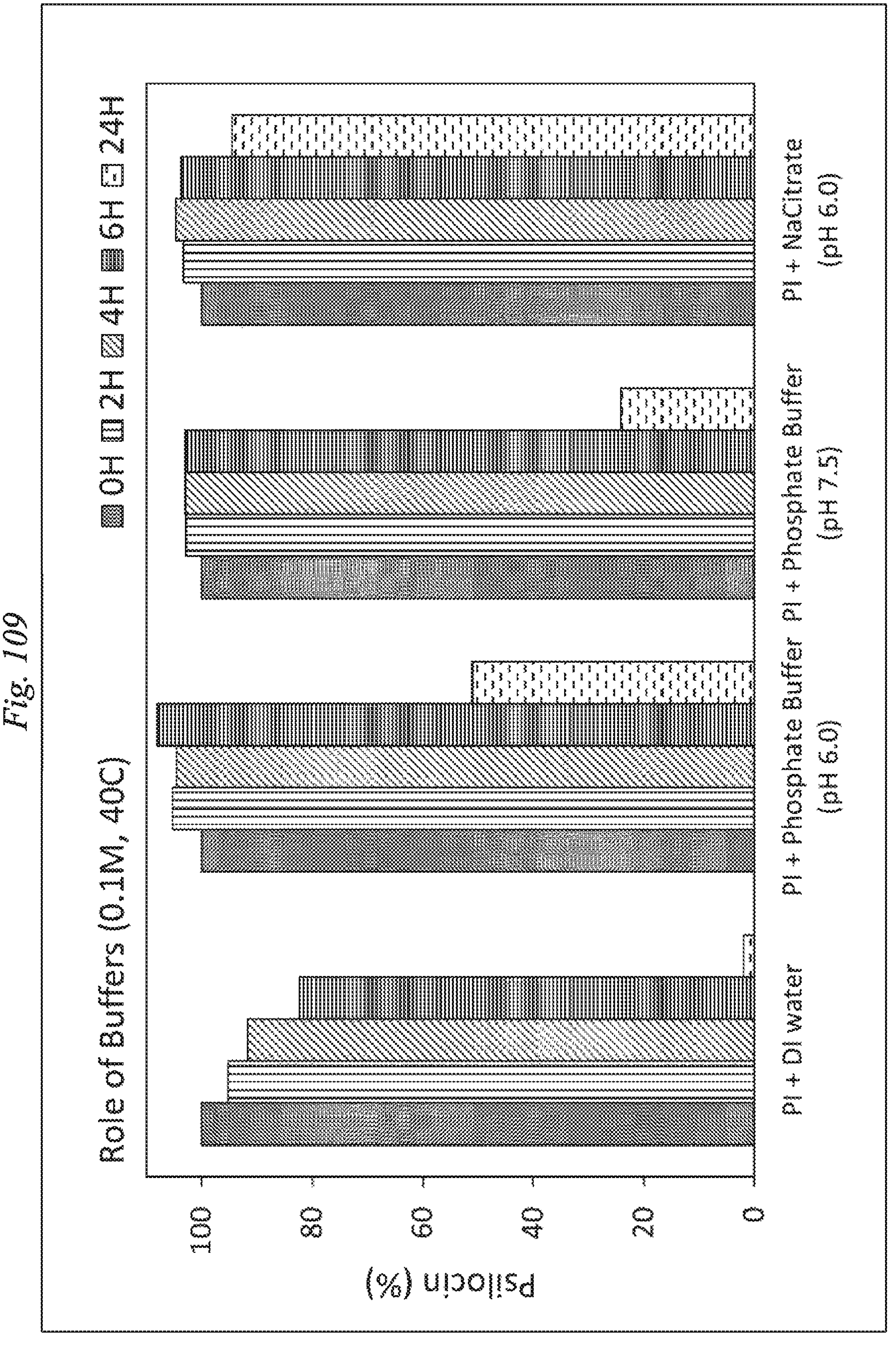
FIG. 109 shows the stability of I-7 (PI-$d_0$) over 24 hours in 0.1M solutions of phosphate buffer (pH 6.0), phosphate buffer (pH 7.5), and sodium citrate buffer (6.0) at 40° C.

Results: The role of the different buffer solutions and pH on psilocin stability can be seen in FIG. 109. Overall, both phosphate and citrate buffers (pH 6.01 and pH 7.5) provided better stability to psilocin than water at 40° C. after 24 hours. Phosphate buffer at pH 6.0 provided better stability than at pH 7.5. Comparing the two different buffers with the same pH value, citrate buffer (95% efficiency) outperformed phosphate buffer (50%) in stabilizing psilocin at 40° C.

Long Term Stability Studies with Citric Acid and Sodium Citrate Buffer

The long-term stability (up to 25 days) of psilocin in a citric acid solution (0.1 M, pH 1.60) and a sodium citrate buffer (0.1 M, pH 6.01) at 4° C. and 23° C. was assessed.

Preparation of 0.1 M sodium citrate buffer (pH 6.01): 2.427 g of sodium citrate dihydrate and 0.336 g of citric acid were dissolved in 80 ml of DI water. The pH was adjusted to 6.0 using a 1 M NaOH solution. The final volume was adjusted to 100 ml.

Preparation of 0.1 M citric acid solution (pH 1.60): 0.1 M solution of citric acid was prepared in DI water without any pH adjustment.

Test solutions: Psilocin (1 mg/ml) was mixed with (i) sodium citrate buffer (0.1 M, pH 6.01) and (ii) citric acid solution (0.1 M, pH 1.60) in 1:1 v/v. The samples were stored at 4° C. and 23° C., and aliquots were sampled at designated timepoints (days 0, 7, 17, and 25). The samples were diluted (1:1) with the diluent before submitting to chromatography to determine the % psilocin remaining.

Figure 110:
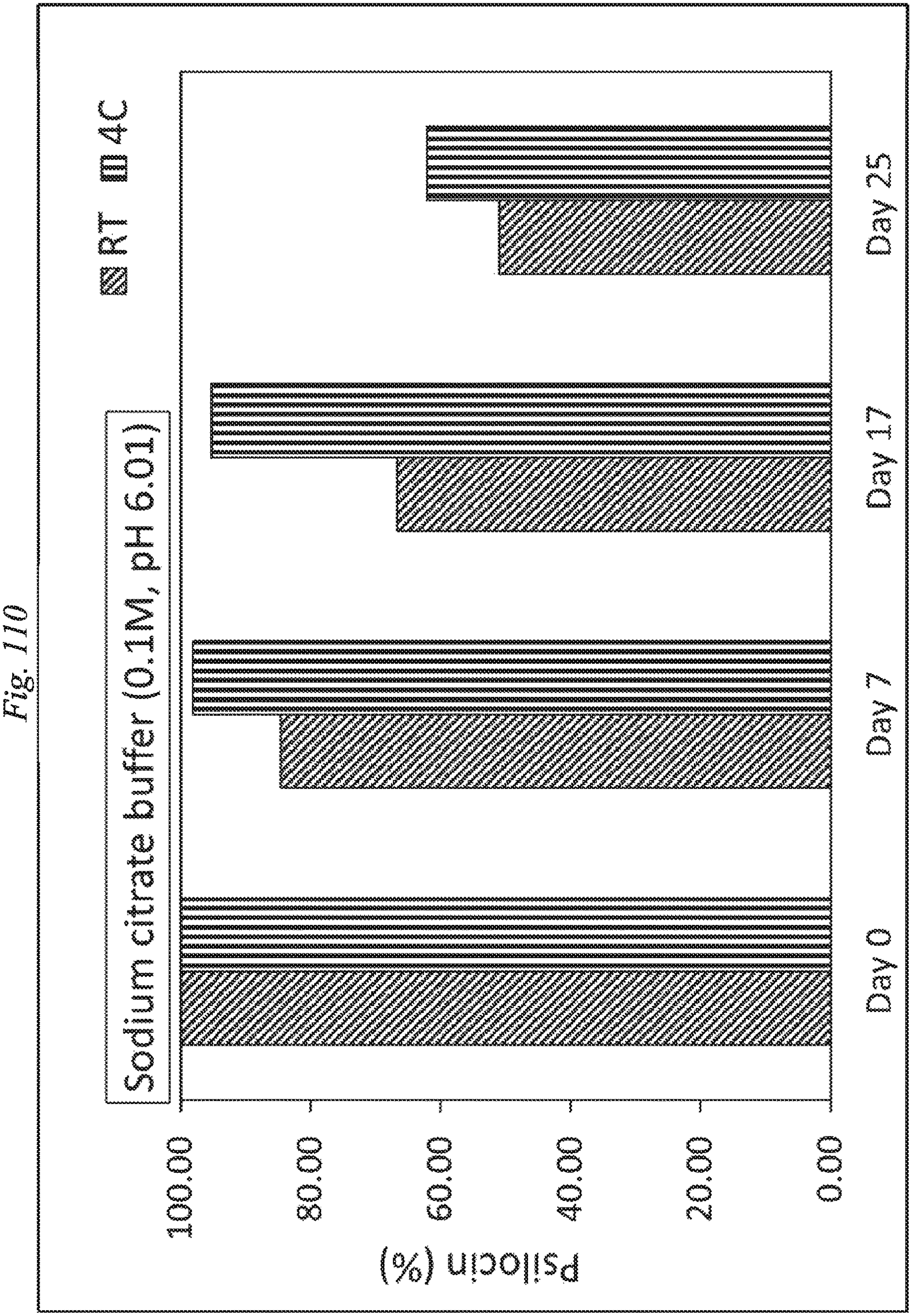
FIG. 110 shows the long-term stability (up to 25 days) of I-7 (PI-$d_0$) in a sodium citrate buffer (0.1 M, pH 6.01) at 4° C. and 23° C.
Figure 111:
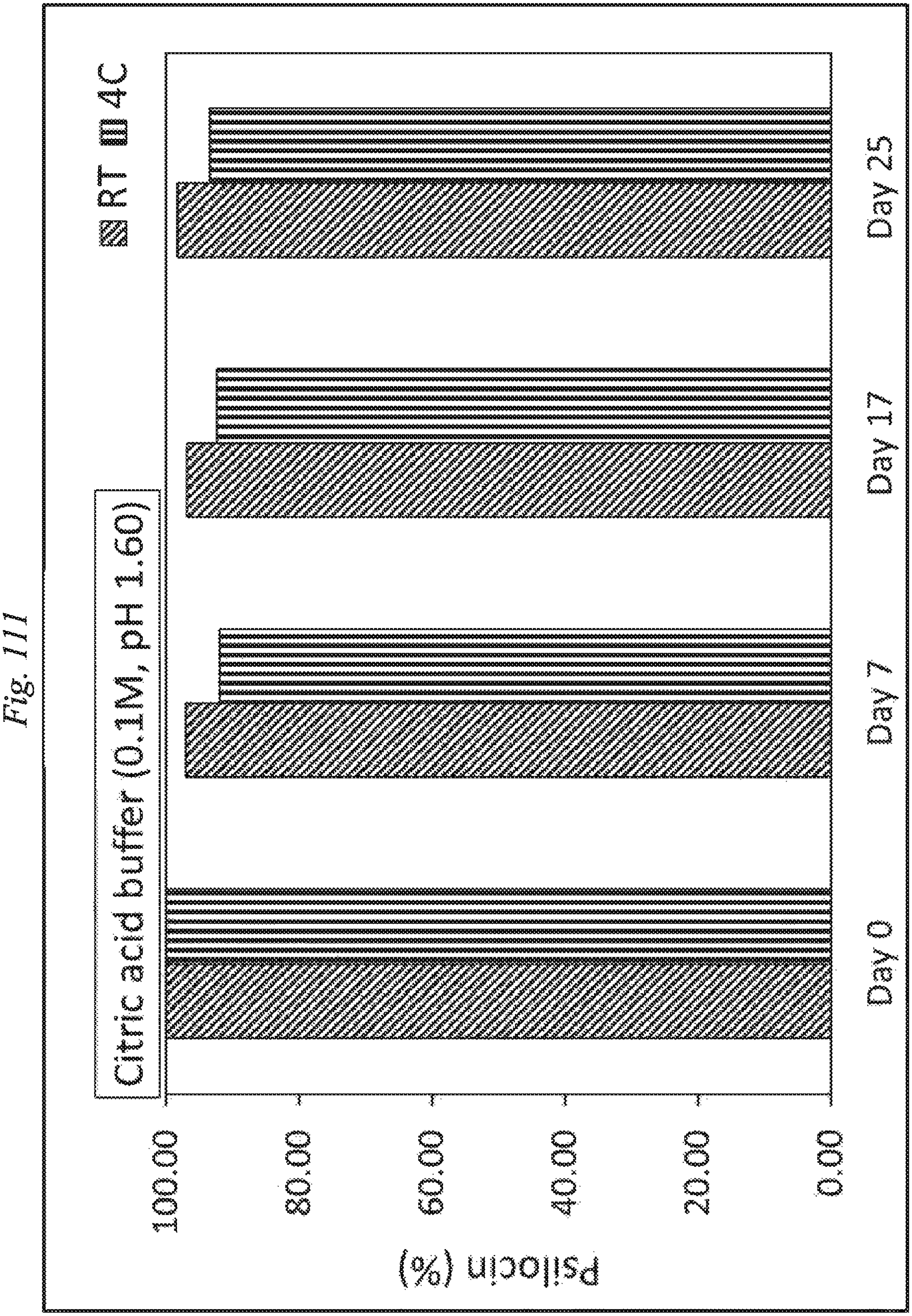
FIG. 111 shows the long-term stability (up to 25 days) of I-7 (PI-$d_0$) in a citric acid solution (0.1 M, pH 1.60) at 4° C. and 23° C.
Figure 112:
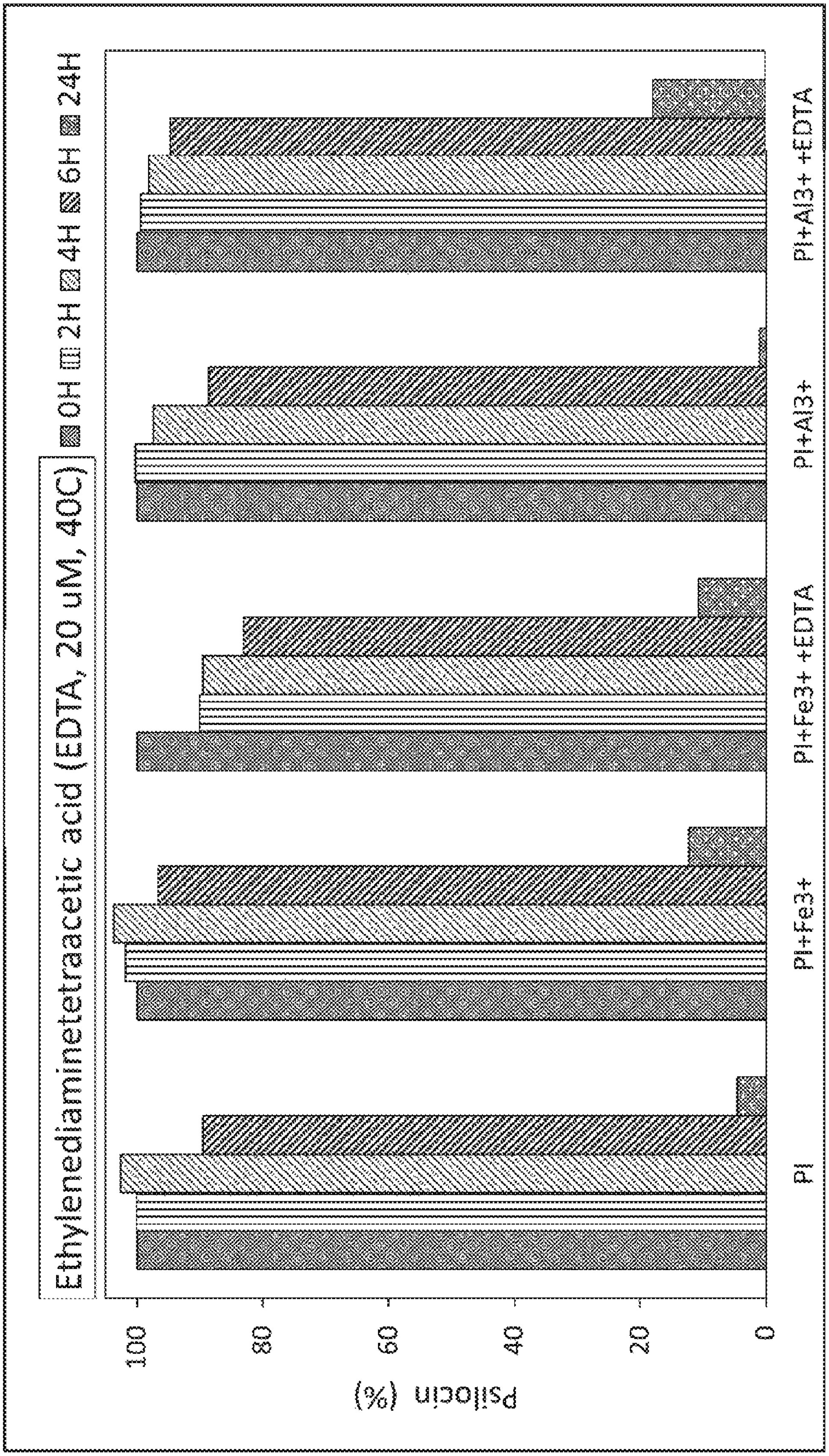
FIG. 112 shows the stability of I-7 (PI-$d_0$) over 24 hours in 20 μM solutions of ethylenediaminetetraacetic acid (EDTA), with or without metal ions, compared to those solutions without ethylenediaminetetraacetic acid (EDTA), at 40° C.
Figure 113:
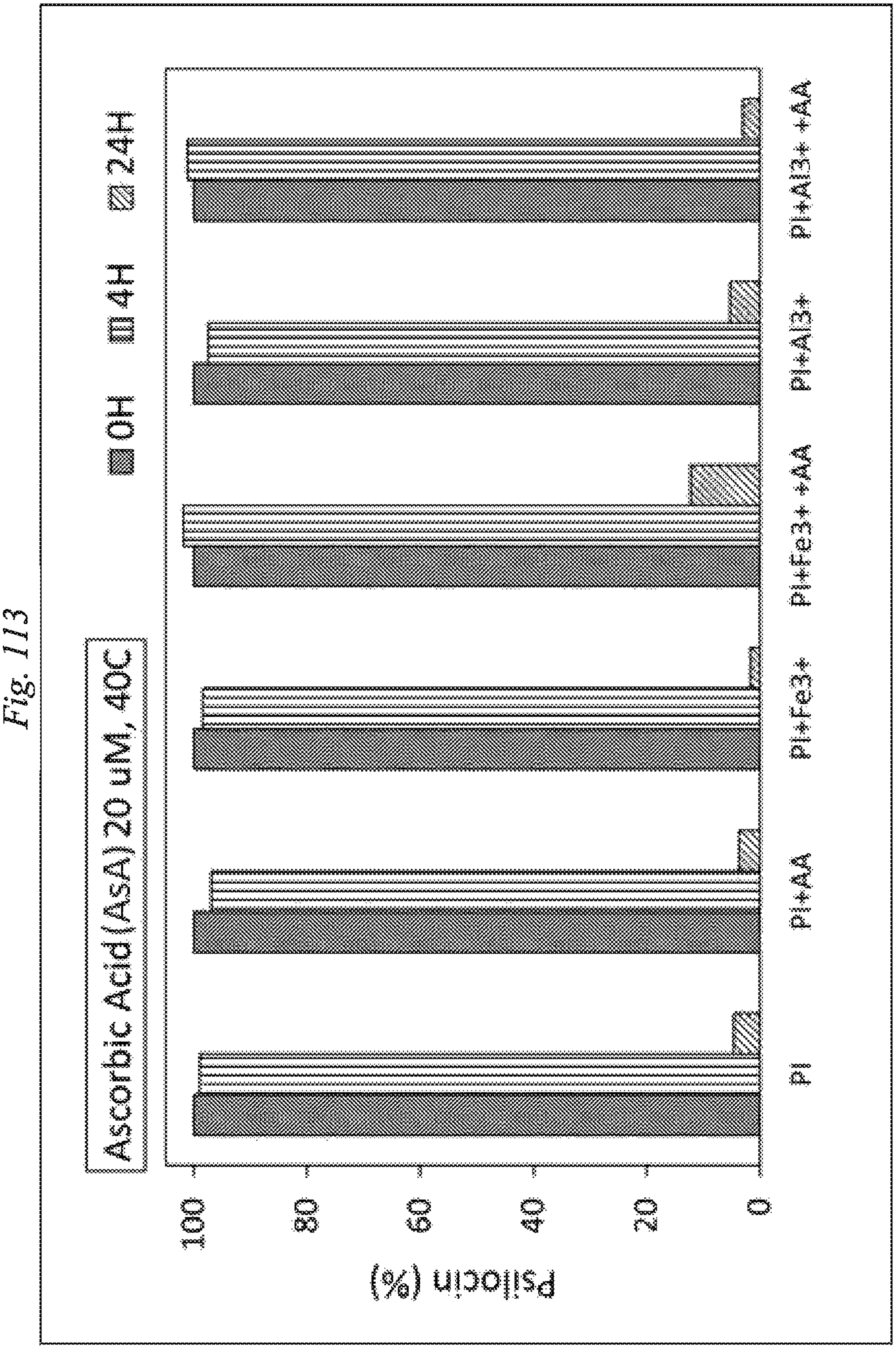
FIG. 113 shows the stability of I-7 (PI-$d_0$) over 24 hours in 20 μM solutions of ascorbic acid, with or without metal ions, compared to those solutions without ascorbic acid, at 40° C.
Figure 114:
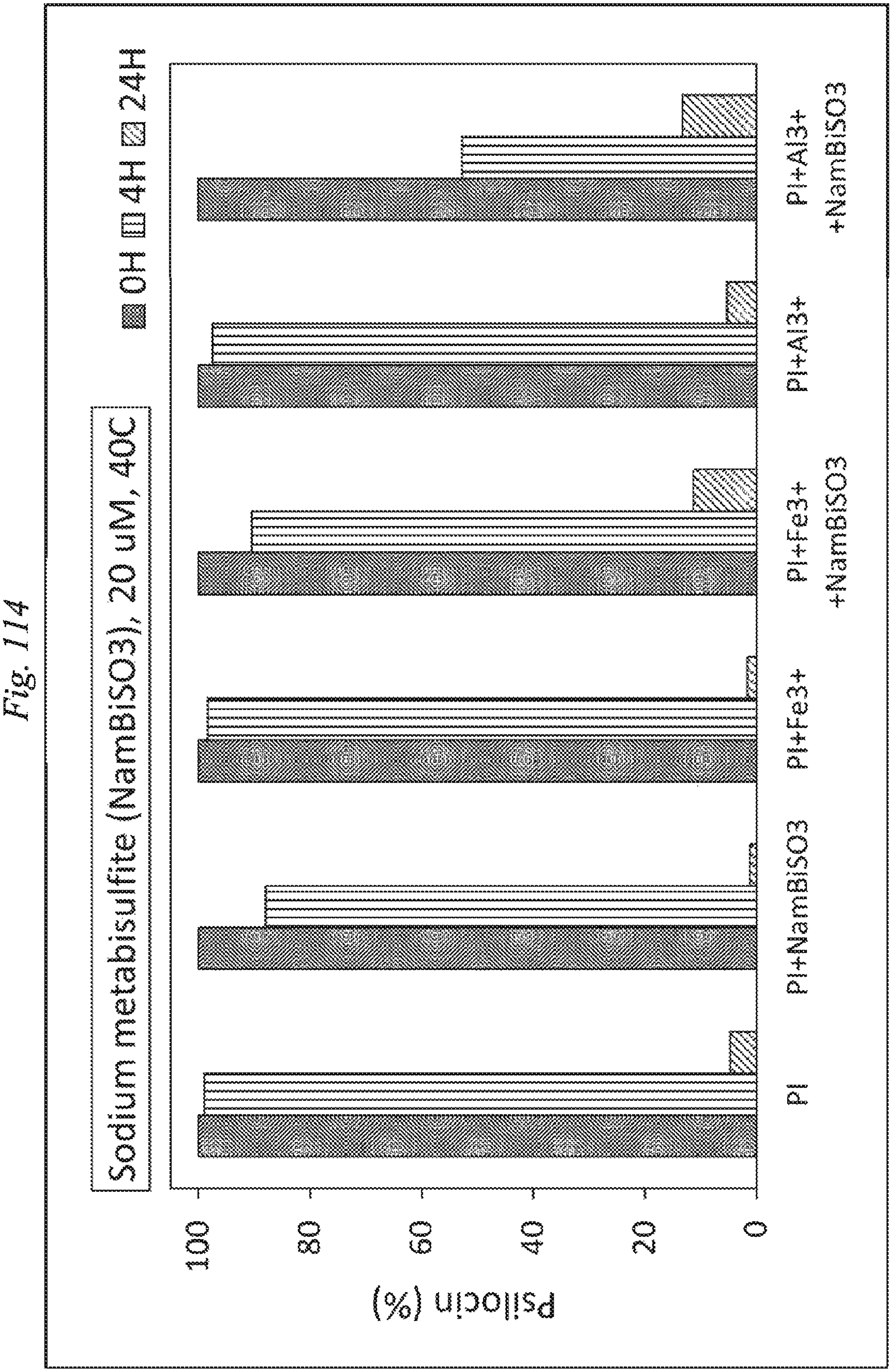
FIG. 114 shows the stability of I-7 (PI-$d_0$) over 24 hours in 20 μM solutions of sodium metabisulfite, with or without metal ions, compared to those solutions without sodium metabisulfite, at 40° C.
Figure 115:
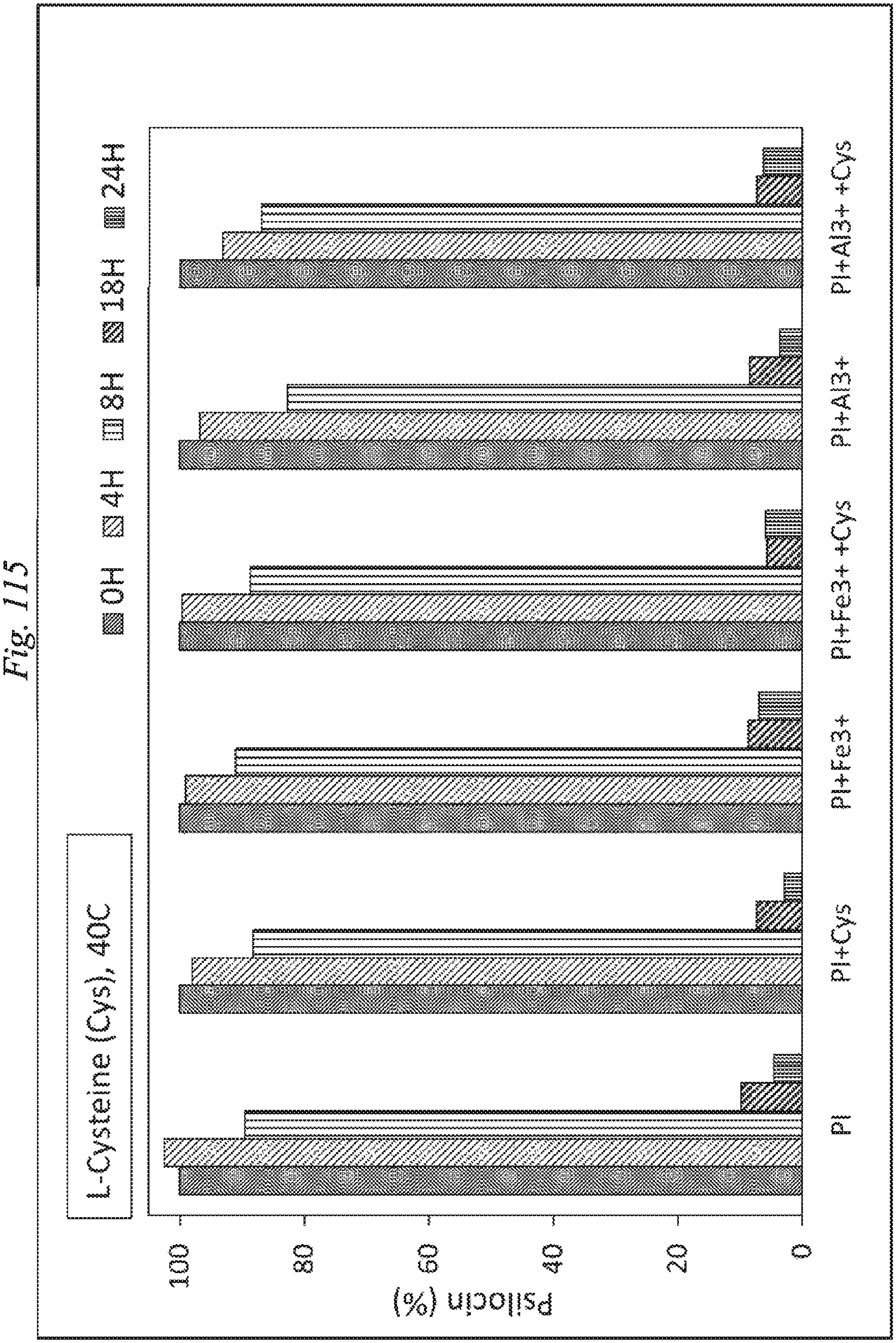
FIG. 115 shows the stability of I-7 (PI-$d_0$) over 24 hours in 20 μM solutions of L-cysteine, with or without metal ions, compared to those solutions without L-cysteine, at 40° C.
Figure 116:
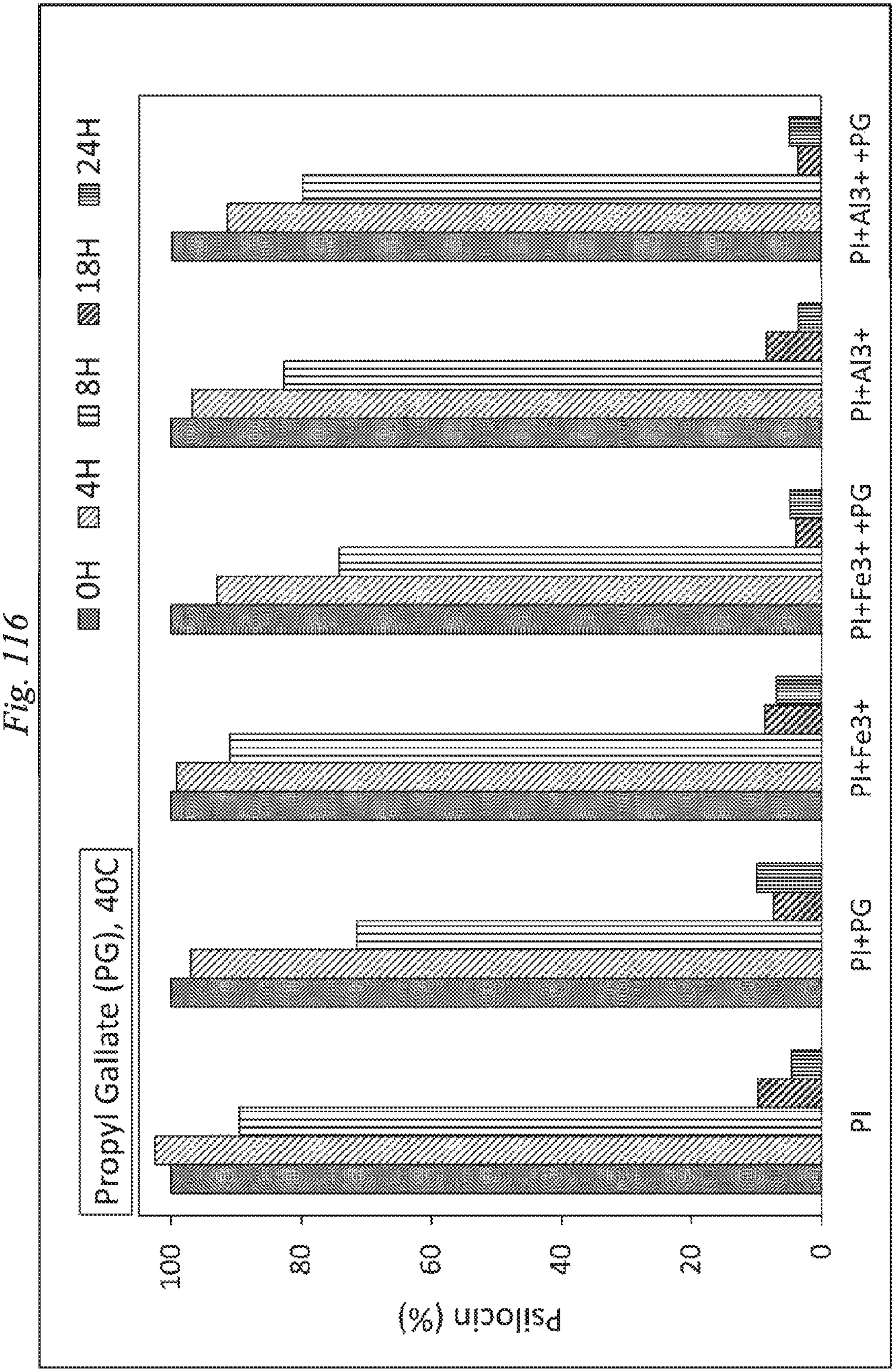
FIG. 116 shows the stability of I-7 (PI-$d_0$) over 24 hours in 20 μM solutions of propyl gallate, with or without metal ions, compared to those solutions without propyl gallate, at 40° C.

Results: The role of the different buffer solutions on psilocin stability can be seen in FIGS. 110-111. Overall, lower pH (citric acid buffer, pH 1.60) provides the highest level of stabilization to psilocin for both room temperature (23° C.) and 4° C., with only minimal degradation occurring across all 25 day time points at either temperature. Psilocin remained stable for up to 17 days in sodium citrate buffer (pH 6.01) in cold storage (4° C.), but considerable degradation occurred in between the day 17 and 25 day time points. At room temperature, degradation of psilocin began within a week in the sodium citrate buffer conditions.

Stability Studies with Antioxidants

The role of antioxidants in providing stability against metal induced degradation (e.g., oxidation) of psilocin was examined.

Test solutions: 40 μM stock solutions of EDTA, AsA, Cys, $NamBiSO_3$, and PG were prepared in DI water. 20 μM stock solutions of $AlCl_3$ and $FeCl_3$ were freshly prepared in DI water. Typically, antioxidant was premixed with metal salt in a 1:1 v/v before introducing psilocin. The solution mix was incubated at 40° C. for the designated timepoints (0, 2, 4, 6, 8, 18, 24H). The samples were diluted (1:1) with the diluent before submitting to chromatography to determine the % psilocin remaining.

Results: As is evident from FIGS. 112-116, none of the antioxidants tested were able to provide stability to psilocin base against metal salts under the tested accelerated degradation conditions.

Stability Studies with Cyclodextrin Complexes

The role of cyclodextrin complexes in providing stability against metal induced degradation (e.g., oxidation) of psilocin was examined at elevated temperature (40° C.).

Test solutions: Cyclodextrin and metals salt ($AlCl_3$ and $FeCl_3$) solutions were prepared in DI water. Typically, psilocin solution (1 mg/ml) was mixed with a 2% (w/w) cyclodextrin in 1:1 (v/v) and incubated at 40° C. for designated timepoints (0, 4, and 24H). Metal salts (10 μM) were also coincubated with the psilocin/cyclodextrin mixture under similar conditions mentioned above. The test samples were diluted (1:1) with the diluent before submitting to chromatography to determine the % psilocin remaining.

Figure 117:
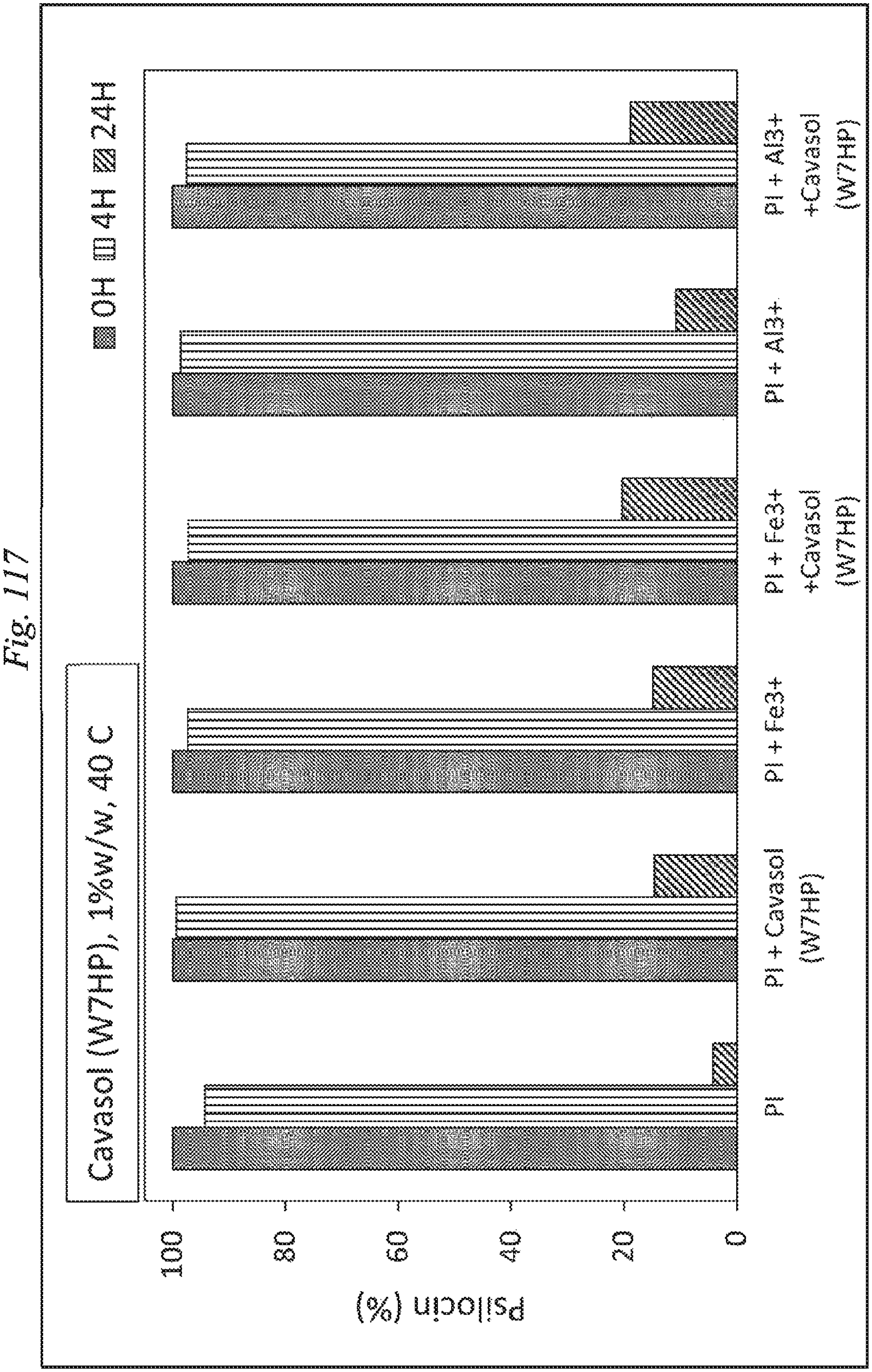
FIG. 117 shows the stability of I-7 (PI-$d_0$) over 24 hours in 1% w/w solutions of CAVASOL® W7 HP, with or without metal ions, compared to those solutions without CAVASOL® W7 HP, at 40° C.
Figure 118:
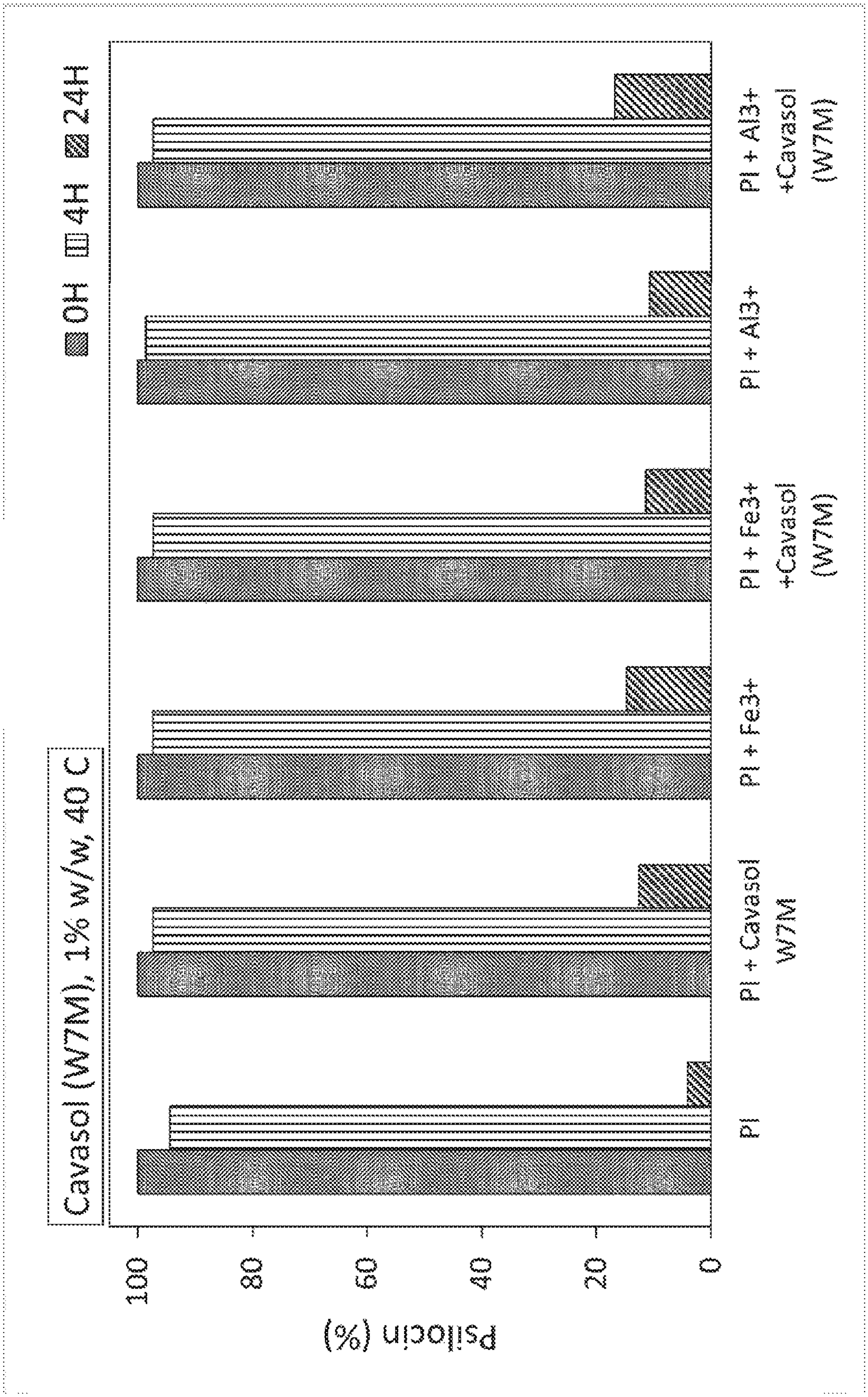
FIG. 118 shows the stability of I-7 (PI-$d_0$) over 24 hours in 1% w/w solutions of CAVASOL® W7 M, with or without metal ions, compared to those solutions without CAVASOL® W7 M, at 40° C.
Figure 119:
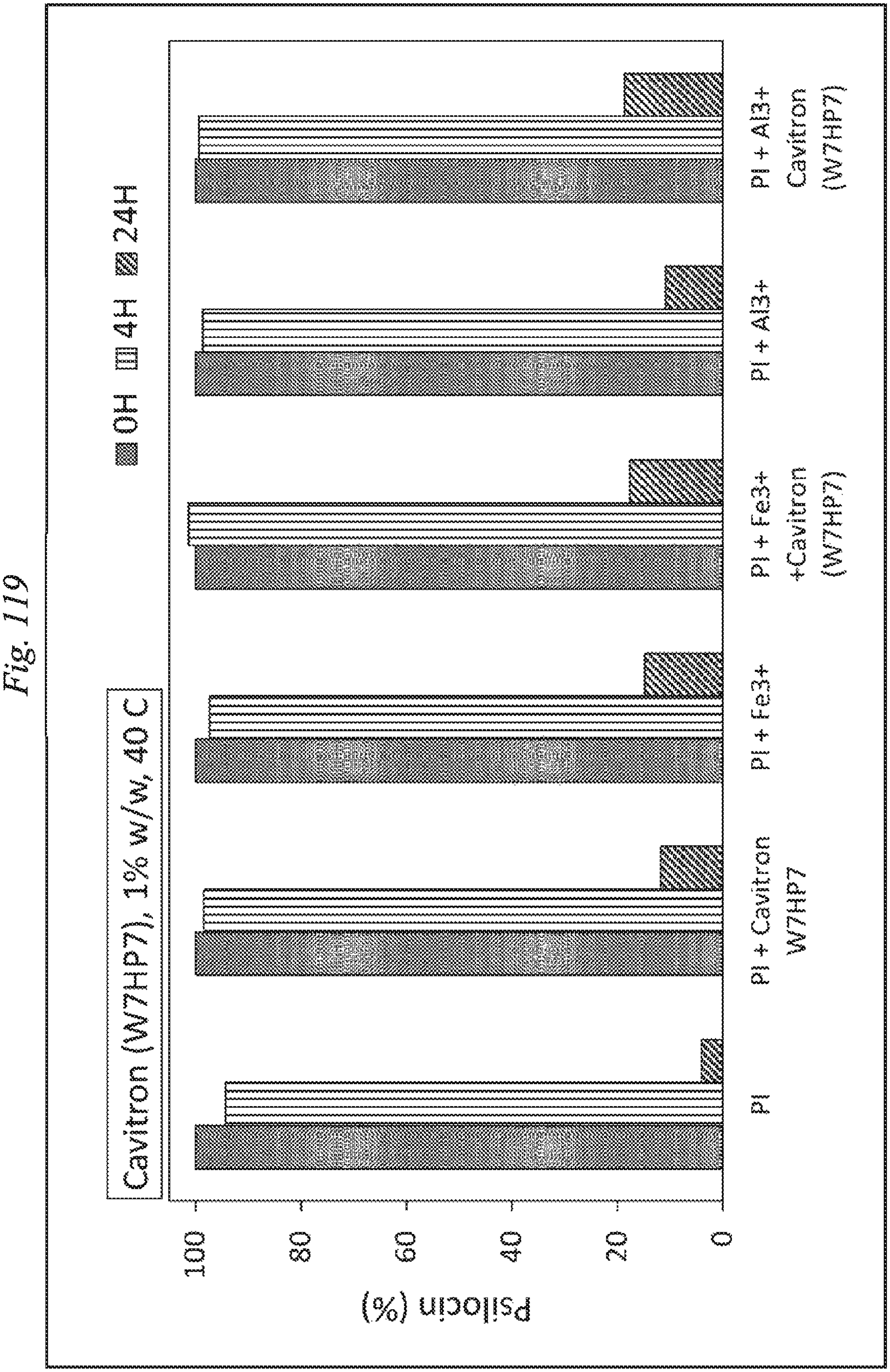

Results: As is evident from FIGS. 117-119, cyclodextrins did not impart stability to psilocin against high temperature (40° C.) or metal induced degradation.

VI. Simulated Gastric Fluid and Water Solubility Studies

The solubility of free bases, I-3 (PI-$d_{10}$)(pattern 1) and I-7 (PI-$d_0$)(pattern1), and salts, I-3j (pattern 1), I-7a (pattern 1), I-7b (pattern 1), I-7c (pattern 5), I-7j (pattern 1) were determined in FaSSGF (Fasted State Simulated Gastric Fluid) and in water.

Preparation of solutions: Solubility tests in FaSSGF were carried out at 37° C. and in water at room temperature for 2 hour and 6 hour timepoints. 50 mg solid was added to 0.5 mL media and incubated on an orbital shaker for 6 hours. (For free base in water 20 mg samples were used). Slurry/solution was sampled at 2 and 6 hours and aliquots were filtered through 0.45 micron PTFE filters. The filtrate was diluted 500 fold with the appropriate (same) media and injected on to UPLC. Table 30 provides the details of the FaSSGF media.

TABLE 30

| | | Component concentration, mM | | | |
|---|---|---|---|---|---|
| Media | pH | Taurocholate | Phospholipids | Sodium | Chloride |
| FaSSGF | 1.6 | 0.08 | 0.02 | 34 | 59 |

Chromatographic conditions. Aqueous solubility was determined by suspending sufficient compound in water or media to give a maximum final concentration of ≥100 mg·mL$^{-1}$ of the salt form of the compound. (For free base in water ≥40 mg·mL$^{-1}$). Solubility was calculated in QuanLynx using the peak areas determined by integration of the peak found at the same retention time as the principal peak in the standard injection. Results were calculated based on a standard calibration curve of appropriate free base. Values quoted are for the free base component of each salt and are average of two (n=2) determinations. The method parameters used are presented in Table 31.

TABLE 31

| | | | |
|---|---|---|---|
| Instrumentation | Waters Acquity I class with Quattro-Micro mass spectrometer and PDAdetector | | |
| Column | BEH C18 1.7 μm 2.1 × 100 mm | | |
| Mobile Phase A | 0.1% aqueous formic acid | | |
| Mobile Phase B | 0.1% formic acid in acetonitrile | | |
| Flow Rate (mL · min$^{-1}$) | 0.4 | | |
| | Time (mins) | % A | % B |
| Gradient Program | 0.0 | 95 | 5 |
| | 0.1 | 95 | 5 |
| | 1.5 | 5 | 95 |
| | 1.9 | 5 | 95 |
| | 2 | 95 | 5 |
| | 2.75 | 95 | 5 |
| Injection Volume (μL) | 1 | | |
| Detectors | UV, diode array 200-500 nm<br>MS, mass 100-800 in ES$^+$ | | |
| Data Analysis | Peak area percentage (APCT) with an integration threshold of 0.2% (relative) | | |

Results: The results are presented in Table 32 and also graphically in FIGS. 120-121. It was observed that salts were generally more soluble than free base and that the solubility in FaSSGF was generally higher than in water. The solubility in FaSSGF (2h) was in the order: I-7<I-7j<I-3<I-3j<I-7a<I-7b=I-7c. Solubility for the free base in FaSSGF decreased at 6h compared to at 2h probably due to decomposition (discoloration observed over time). The following solubility trend was observed in water: I-7<I-3<I-7j<I-3j<I-7a<I-7c<I-7b.

TABLE 32

| Solubility (mg/mL) | FaSSGF 2 hours | FaSSGF 6 hours | Water 2 hours | Water 6 hours |
|---|---|---|---|---|
| I-3 (PI-$d_{10}$ free base)(pattern 1) | 10.63 | 4.50 | 0.71 | 0.74 |
| I-7 (PI-$d_0$ free base)(pattern1) | 8.54 | 3.60 | 0.53 | 0.56 |

TABLE 32-continued

| Solubility (mg/mL) | FaSSGF 2 hours | FaSSGF 6 hours | Water 2 hours | Water 6 hours |
|---|---|---|---|---|
| I-7j (pattern 1) | 10.10 | 9.79 | 2.43 | 2.58 |
| I-7a (pattern 1) | 31.71 | 29.11 | 15.46 | 17.49 |
| I-3j (pattern 1) | 12.65 | 12.79 | 3.38 | 3.70 |
| I-7b (pattern 1) | 42.41* | 42.81* | 41.95 | 45.08 |
| I-7c (pattern 5) | 51.51* | 52.25* | 32.94 | 34.78 |

*samples became visually clear with no solid remaining in FaSSGF, so solubility is equal to or greater than the recorded value

VII. Compositions/Formulations

Immediate Release (IR) Dosage Form

Immediate release (IR) tablets were formulated with psilocin benzoate (I-7j) (crystalline pattern 1) at a dose of 5.0 mg free base (equivalent to 6.3712 mg of benzoate salt form), with a tablet weight of 80 mg.

Table 33 is a list of materials used for the IR tablet formulations. Tables 34 and 35 provides two different formulations prepared with varying excipients.

TABLE 33

| Material | Type | Manufacturer | Functionality |
|---|---|---|---|
| Psilocin benzoate (I-7j) | — | — | API |
| Carboxymethylcellulose, sodium | Ac-Di-Sol ® SD-711 | Dupont | Disintegrant |
| Microcrystalline cellulose | Avicel ® PH-102 | Dupont | Diluent |
| Magnesium stearate | | Avantor | Lubricant |
| Mannitol | Pearlitol ® SD 100 | Roquette | Diluent |
| Crospovidone | Polyplasdone ® Ultra | Ashland | Disintegrant |
| Sodium stearyl fumarate | PRUV ® | JRS | Lubricant |

TABLE 34

| Lot: FS22-001-1A | | |
|---|---|---|
| Material | % w/w | Per tablet (mg) |
| Psilocin benzoate (I-7j) | 7.964 | 6.3712 |
| Microcrystalline cellulose | 88.536 | 70.8288 |
| Carboxymethylcellulose, sodium | 3.000 | 2.4000 |
| Magnesium stearate | 0.500 | 0.4000 |
| Total | 100.000 | 80.000 |

TABLE 35

| Lot: FS22-001-1B | | |
|---|---|---|
| Material | % w/w | Per tablet (mg) |
| Psilocin benzoate (I-7j) | 7.964 | 6.3712 |
| Mannitol | 88.036 | 70.4288 |

TABLE 35-continued

| Lot: FS22-001-1B | | |
|---|---|---|
| Material | % w/w | Per tablet (mg) |
| Crospovidone | 3.000 | 2.4000 |
| Sodium stearyl fumarate | 1.000 | 0.8000 |
| Total | 100.000 | 80.000 |

Procedure. To prepare Lot: FS22-001-1A, approximately 2 g of psilocin benzoate (I-7j) was delumped by passing it through a 20 mesh sieve and was set aside. Sodium carboxymethylcellulose was delumped by passing through the same 20 mesh sieve and was set aside. The sieve was 'dry washed' with all of the dispensed microcrystalline cellulose and set aside. Approximately half of the microcrystalline cellulose was charged in a Turbula blender bottle and was blended for 1 minute to coat the surfaces of the bottle. In order, 1.00 g of the psilocin benzoate (I-7j), sodium carboxymethyl cellulose, and the remainder of the microcrystalline cellulose was charged into the Turbula bottle and blended for 15 minutes. Magnesium stearate was delumped through a 40 mesh sieve and charged into the center of the blend in the Turbula bottle (a hole was dug, the lubricant was added, and the added lubricant was covered over). Blended for 5 minutes. The resulting blend was characterized for bulk and manual tapped density. The 7 mm tooling was inserted into a Carver press and the final blend was compressed at 2 kN, 5 kN, and 8 kN compression levels, which is approximately 500, 1,000, and 1,500 lbs on the Carver press, by weighing out individual aliquots of blend and compressing at the tablet weight of 80 mg.

To prepare Lot: FS22-001-1B, crospovidone was delumped by passing through a 20 mesh sieve and was set aside. The sieve was 'dry washed' with all of the dispensed mannitol and set aside. Approximately half of the mannitol was charged in a Turbula blender bottle and was blended for 1 minute to coat the surfaces of the bottle. Sodium stearyl fumarate was delumped through a 40 mesh sieve and set aside. In order, 1.00 g of the previously delumped psilocin benzoate (I-7j)(from protocol above), crospovidone, sodium stearyl fumarate, and the remainder of the mannitol was charged into the Turbula bottle and blended for 15 minutes. The resulting blend was characterized for bulk and manual tapped density. The 7 mm tooling was inserted into a Carver press and the final blend was compressed at 2 kN, 5 kN, and 8 kN compression levels, which is approximately 500, 1,000, and 1,500 lbs on the Carver press, by weighing out individual aliquots of blend and compressing at the tablet weight of 80 mg.

Orally Disintegrating Tablet (ODT) Dosage Form

Orally disintegrating tablets (ODT) were formulated with psilocin (I-7) as API and either L-tartaric acid or citric acid in Zydis® (Catalent) ODT format, along with a placebo. Six active batches were made using stock mixes at pH 4.5 sub-batched and adjusted to different pH points. Three dose strengths were treated as dose proportional, with wet fill weights of 250 mg, 500 mg, and 1,000 mg for 5 mg, 10 mg, and 20 mg dose strengths, respectively.

Table 36 provides formulation details for stock pre-mix batches 1 and 2 (Z5193/133/1 & 2) and placebo batch (Z5193/133/3). Table 37 provides formulation details for sub-batches Z5193/133/1a-c & 2a-c.

TABLE 36

| | Batch number | | |
|---|---|---|---|
| Material | Z5193/133/1 (stock pre-mix 1) % w/w | Z5193/133/2 (stock pre-mix 1) % w/w | Z5193/133/1 (Placebo batch) % w/w |
| Purified water | 79.00 | 79.00 | 90.49 |
| Gelatin EP/USP/JP (fish HMW) | 5.00 | 5.00 | 5.00 |
| Mannitol EP/USP | 4.00 | 4.00 | 4.00 |
| Psilocin (I-7) | 2.00 | 1.99 | — |
| Citric acid anhydrous EP/USP | 1.28 | — | 0.51 |
| Tartaric acid | — | 1.57 | — |
| Total | 91.28 | 91.56 | 100.00 |

TABLE 37

| Batch number | 1a | 1b | 1c | 2a | 2b | 2c |
|---|---|---|---|---|---|---|
| Material | % w/w | % w/w | % w/w | % w/w | % w/w | % w/w |
| Citric acid anhydrous EP/USP | 1.22 | — | — | — | — | — |
| Tartaric acid | — | — | — | 1.11 | — | — |
| 5% w/w NaOH solution | — | — | 5.99 | — | 3.69 | 6.84 |
| Purified water | 7.50 | 8.72 | 2.73 | 7.33 | 4.75 | 1.60 |
| Total | 100 | 100 | 100 | 100 | 100 | 100 |

To prepare, all excipients were dispensed. Gelatin and mannitol were added to the purified water and the solution was heated to 60° C. and held for 10 min, while being stirred. The solution was cooled to 12° C. and psilocin was added for preparing active batches. The stock mixes were aliquoted into sub-batches. As indicated, the pH of each sub-batch was adjusted as necessary using a pH modifier (sodium hydroxide). Final water was then added.

Mix pH was measured according to solution hold (SH) times: at the end of mixing (SH0) and again at 24 and 48 hours, SH24 and SH48, with the pH of all acidic batches remaining stable, as shown in Table 38. This stability demonstrates suitability for a commercial manufacturing process, where stability up to a 48-hour solution hold time would typically be required. For the alkaline batches, a trend towards more acidic pH over time was observed, which is typical of alkaline Zydis® formulations. Results for placebo are not given as the properties of the placebo formulation are equivalent to batch 1b.

TABLE 38

| Batch ID | pH Modifier | Batch pH at SH0 | Batch pH at SH24 | Batch pH at SH48 |
|---|---|---|---|---|
| 1a | Citric acid | 3.55 | 3.55 | 3.61 |
| 1b | Citric acid | 4.53 | 4.50 | 4.55 |
| 1c | Citric acid/NaOH | 7.64 | 7.56 | 7.42 |
| 2a | Tartaric acid | 3.02 | 3.13 | 3.10 |
| 2b | Tartaric acid/NaOH | 4.42 | 4.33 | 4.37 |
| 2c | Tartaric acid/NaOH | 8.11 | 7.94 | 7.75 |

Significant color changes were observed in the formulations over time; this was especially significant in formulations under alkaline conditions. For both acid modifiers, the most acidic condition was consistent in color over 48 hours, but at pH 4.5, both citric acid and tartaric acid formulations saw some darkening; this was more pronounced for the tartaric acid formulation, which was similarly darkened to the alkaline condition by 48 hours. None of the mixes demonstrated precipitation of API over time Dosing and Freezing: The resulting products were dosed into blister pockets with a wet dose weight of 250 mg or 500 mg (proportional dosing). The product was frozen at −90° C. for 4 minutes. The frozen product was placed in a freezer (0° C.) for storage for ≥12 hours.

Freeze Drying: the frozen product was dried in a freeze dryer at a shelf temperature of 0° C. for 12 hours. The dried product was stored in dry storage cabinets at either ambient, fridge (2-8° C.) or freezer (<−20° C.) temperatures.

Finished product analysis. FIGS. 122-124 show the TGA, DSC, and XRPD of I-7 (pattern 1)(API) used in the ODT formulations, respectively. FIGS. 125-128 show the TGA, DSC, XRPD, and appearance, respectively, of the ODT dosage form formed from batch 1a (SH24) formulated with the citrate salt of psilocin at pH 3.55. FIGS. 129-131 show the DSC, XRPD, and appearance, respectively, of the ODT dosage form formed from batch 1b (SH24) formulated with the citrate salt of psilocin at pH 4.50. FIGS. 132-134 show the DSC, XRPD, and appearance, respectively, of the ODT dosage form formed from batch 1c (SH24) formulated with the citrate salt of psilocin at pH 7.56. FIGS. 135-137 show the DSC, XRPD, and appearance, respectively, of the ODT dosage form formed from batch 2a (SH24) formulated with the tartrate salt of psilocin at pH 3.13. FIGS. 138-140 show the DSC, XRPD, and appearance, respectively, of the ODT dosage form formed from batch 2b (SH24) formulated with the tartrate salt of psilocin at pH 4.33. FIGS. 141-142 show the DSC and XRPD, respectively, of the ODT dosage form formed from batch 2c (SH24) formulated with the tartrate salt of psilocin at pH 7.94. FIGS. 143-145 show the TGA, DSC and XRPD, respectively, of the placebo ODT dosage form.

ODT unit dispersion testing was performed, whereby the units were placed bottom surface facing down in a beaker filled with purified water at 20° C.±5° C. The length of time for the unit to disperse was timed using a calibrated stopwatch. This process is carried out for five units in total. The mean dispersion times for various ODT units is presented in Table 39.

TABLE 39

| | Mean dispersion time (n = 5) (seconds) | | |
|---|---|---|---|
| Batch | SH0 | SH24 | SH48 |
| 1a 5 mg | <5 | <8 | <20 |
| 1a 10 mg | <6 | <11 | <16 |
| 1b 5 mg | <18 | <17 | <47 |
| 1a 10 mg | <12 | <16 | <34 |
| 1c 5 mg | <20 | <15 | <43 |
| 1c 10 mg | <32 | <23 | <30 |
| 2a 5 mg | <8 | <12 | <31 |
| 2a 10 mg | <12 | <15 | <35 |
| 2b 5 mg | <30 | <34 | <35 |
| 2b 10 mg | <47 | <48 | <15 |
| 2c 5 mg | <2 | — | <3 |
| 2c 10 mg | <4 | <41 | <9 |

VIII. In Vivo Studies

Psilocin-$d_0$/Psilocin-$d_{10}$ and Psilocybin PK Comparative Study in Rats

The pharmacokinetics and bioavailability of psilocybin, psilocin (PI-$d_0$), and psilocin-$d_{10}$) in the rat was investigated following oral gavage and intravenous (bolus) administrations.

The study was designed as shown below in Table 40 to determine if psilocin/psilocin-$d_{10}$ provides a clinical therapeutic PK profile of fast onset and short duration of action in rats.

TABLE 40

| Group | Treatment | Route | Dose (mg/kg) | Formulated concentration (mg/mL) | Volume dose (mL/kg) |
|---|---|---|---|---|---|
| 1 | Psilocin + psilocin-d10 | Intravenous (bolus) | 1 + 1 | 1 | 1 |
| 2 | Psilocin + psilocin-d10 | Oral gavage | 5 + 5 | 1 | 5 |
| 3 | Psilocybin | Intravenous (bolus) | 2.8 | 2.8 | 1 |
| 4 | Psilocybin | Oral gavage | 14 | 1.4 | 10 |

Formulations. The vehicle was 0.1 M citrate buffer pH 6 for Groups 1 and 2 and water for injection for Groups 3 and 4.

To make the citrate (0.1M) buffer pH 6 vehicle for Groups 1 and 2, citric acid mono-anhydrous and tri-sodium citrate dihydrate were weighed out and dissolved in in water for injection (sterile) to 90% final volume. The pH was checked and adjusted to 6.00±0.1 using NaOH or HCl as require and was then made to final volume and magnetically stirred until visually homogenous. The final pH of the vehicle was adjusted to 6.00±0.1 if required and filtered using 0.22 m PVDF filter. The required amount of test item was weighed and, using aseptic techniques for the IV preparation, the test item was transferred to a suitable container. The weighing container was rinsed using no more than 15% of final volume of vehicle. It was then made up to 90% of the final volume with the vehicle using sonication and magnetic stirring. The pH was checked and adjusted to 6.00±0.1 using citric acid, then made up to final volume with vehicle. It was stirred for a minimum of 20 minutes using a magnetic stirrer, and whilst under magnetic stirring, the final pH and SG was checked and recorded. The formulation was then transferred quantitatively to final dispensing container (Amber glass). Prepared on the day of administration and stored refrigerated pending transfer to the animal unit. Formulations were brought to room temperature prior to use.

To make the water vehicle for Groups 3 and 4, the required amount of test item was weighed and, using aseptic techniques for the IV preparation, the test item was transferred to a suitable container. The required volume of water for injection was added and place on a magnetic stirrer. The IV formulation was filtered using 0.22 m PVDF filter. Formulations were prepared on the day administration and stored refrigerated pending transfer to the animal unit. Formulations were brought to room temperature prior to use.

Animals. Hsd:Sprague Dawley rats from Envigo RMS Limited; 38 males (including 2 spare animals). Spare animals were removed from the study room after treatment commenced. Rats were given a Teklad 2014C diet, non-restricted. All rats were 7-10 weeks of age at the start of treatment and weight 281 to 319 g.

Administration. Groups 1 and 3 were given an intravenous (bolus) injection (once) in the Lateral tail vein, with a new sterile disposable needle per animal. Treated at constant doses in mg/kg, with a volume dose of 1 mL/kg body weight, calculated from the most recent recorded scheduled body weight. Groups 2 and 4 were dosed by oral gavage (once), using a suitably graduated syringe and a flexible cannula inserted via the mouth. Treated at constant doses in mg/kg, with a volume dose of 5 mL/kg body weight for Group 2 and 10 mL/kg body weight for Group 4, calculated from the most recently recorded scheduled body weight.

Pharmacokinetics. Venous blood samples were taken from animals at the following times in relation to dosing: 0, 5, 15, 30 min, 1, 2, 4 h. Brain samples were taken from animals euthanized at the following time intervals in relation to dosing: 15, 30 min, 1, 2, 4 h (IV); 4 h (Oral). The jugular vein was used as the blood sample site. Terminal bleeds were taken via the sublingual vein to provide larger blood volumes. $K_2$EDTA was used as anticoagulant. Blood was collected onto wet ice ($K_2$EDTA tubes). Samples were allowed to stand on wet ice for a minimum of 5 minutes to fully cool, and then harvested to plasma using a refrigerated centrifuge. Centrifugation was performed at 2000 g for 10 minutes at 4° C. Cellular fractions were discarded. After end of centrifugation the samples were returned to wet ice ready for separation. Two/50 μL (serial) or 400 μL (terminal) aliquots were taken per sample, sampled accurately using a calibrated pipette. Samples were mixed 1:1 v/v with ascorbic acid 200 mM stabilizer solution (50 μL pre-spiked to the plasma tubes). 50 μL (serial) or 400 μL (terminal), of plasma was measured accurately using a calibrated pipette and transferred to a plasma tube pre-spiked with 50 μL (serial) or 400 μL (terminal) of stabilizer and was inverted several times to mix thoroughly. Mixing was completed within 30 minutes of plasma separation. Noncompartmental analysis using Phoenix® WinNonlin® was applied to the composite plasma and brain tissue concentration data for Groups 1 and 3 and the individual plasma concentration data for Groups 2 and 4.

Results. The mean pharmacokinetic parameters are summarized in Table 41.

TABLE 41

| Analyte | Matrix | Dose Group | Dose Level (mg/kg) | $C_{max}$ (ng/mL) | $T_{max}$ (h) | $AUC_{0-t}$ (h * ng/mL) | $t_{1/2}$ (h) | CL (mL/h/kg) | $V_{ss}$ (mL/kg) |
|---|---|---|---|---|---|---|---|---|---|
| Psilocin | Plasma | 1 | 1 + 1 | 353 | IAD | 165 | 0.788 | 5910 | 5740 |
| | | 2 | 5 + 5 | 35.2 | 1.67 | 62.0 | NA | — | — |
| | | 3 | 2.8 | 1090 | IAD | 461 | 0.771 | — | — |
| | | 4 | 14 | 116 | 1.33 | 370 | NA | — | — |
| | Brain | 1 | 1 + 1 | 1380 | 0.250 | 1670 | 0.971 | — | — |
| | | 3 | 2.8 | 1940 | 0.500 | 3530 | 0.867 | — | — |
| Psilocin-$d_{10}$ | Plasma | 1 | 1 + 1 | 308 | IAD | 145 | 0.861 | 6680 | 7020 |
| | | 2 | 5+5 | 50.1 | 1.67 | 87.2 | NA | — | — |
| | | 3 | 2.8 | NC | NC | NC | NC | — | — |
| | | 4 | 14 | NC | NC | NC | NC | — | — |
| | Brain | 1 | 1 + 1 | 973 | 0.250 | 1530 | 1.27 | — | — |
| | | 3 | 2.8 | NC | NC | NC | NC | — | — |
| Psilocybin | Plasma | 1 | 1 + 1 | 0.583 | 2.00 | NR | NR | — | — |
| | | 2 | 5 + 5 | NA | NA | NA | NA | — | — |
| | | 3 | 2.8 | 28700 | IAD | 1910 | NR | NR | NR |
| | | 4 | 14 | 2.88 | 0.528 | 6.54 | NA | — | — |
| | Brain | 1 | 1 + 1 | 2.29 | 4.00 | 6.95 | $NR^a$ | — | — |
| | | 3 | 2.8 | 15.0 | 0.250 | 39.2 | $NR^b$ | — | — |

IAD Immediately after dosing.

NA Not applicable.

NC Not calculated as all concentrations were below the limit of quantitation.

NR Not reportable as there was only one measurable concentration.

$NR^a$ Not reportable due to the lack of a distinct elimination phase.

$NR^b$ Not reportable due to an inability to characterize the elimination phase.

Groups 1 and 2 were dosed psilocin + psilocin-d10 intravenously and by oral gavage, respectively. Groups 3 and 4 were dosed psilocybin intravenously and by oral gavage, respectively.

FIGS. 146-147 compare oral bioavailability of psilocin and psilocybin in rats. Psilocybin is not orally bioavailable in rats (<0.1%). By comparison, co-dosing of PI-$d_0$ and PI-$d_{10}$ was found to provide oral bioavailabilities of 7.52 and 12.1%, for PI-$d_0$ and PI-$d_{10}$, respectively. FIG. 148 compares psilocin plasma levels after oral psilocin and oral psilocybin. Oral psilocybin is enzymatically converted to psilocin, thereby adding to variability to psilocin plasma concentrations. Oral psilocin does not have the time-delay effect that burdens psilocybin. Oral psilocin does not go through an enzymatic step that allows for less variation in plasma concentrations than oral psilocybin. Oral psilocin exhibits a faster onset and shorter duration of effect.

FIGS. 149-150 compares brain and plasma concentration-time profiles after IV dosing. FIG. 149 shows that despite high plasma psilocybin levels, brain concentrations are low after IV dosing. FIG. 150 shows that psilocin (PI-tot) brain concentrations are high compared to plasma concentrations, i.e., psilocin rat brain exposure was much higher than corresponding psilocin plasma levels.

FIG. 151 compares brain levels of PI-tot (PI-$d_0$+PI-$d_{10}$) after IV co-dosing of PI-$d_0$ and PI-$d_{10}$, and of brain levels of PI after IV administration of psilocybin (PY). For IV co-dosing of PI-$d_0$ and PI-$d_{10}$, brain PI-tot peak concentrations occurred at or before the first sample was taken at 0.25 hr. PI peak levels were at 0.5 hr after PY dosing. It is believed that PI after PY peak levels lag due to metabolism of PY to PI, contributing to slower onset.

The better brain penetration (higher brain:plasma ratio) achieved from administration of psilocin and deuterated psilocin (PI-$d_0$ and PI-$d_{10}$) allows for lower effective dosing regimens which would also reduce dose related side-effects, e.g., nausea.

Psilocin-$d_{10}$ Pharmacokinetics Study in Dogs Following Oral Gavage and Intravenous (Bolus) Administrations The pharmacokinetics and bioavailability of psilocin-$d_{10}$ in dogs were investigated following oral gavage and intravenous (bolus) administrations. The study was designed as shown below in Table 42.

TABLE 42

| Phase* | Treatment | Route | Dose (mg/kg) | Formulated concentration (mg/mL)** | Volume dose (mL/kg) | Number/Sex of animals | Animal numbers |
|---|---|---|---|---|---|---|---|
| A | Psilocin-$d_{10}$ | Intravenous (bolus | 0.2 | 0.2 | 1.0 | 3F | 60, 61, 723 |
| B | Psilocin-$d_{10}$ | Oral gavage | 1.0 | 0.2 | 5.0 | 3F | 60, 61, 723 |

*7-day stagger between dose administration.

**As supplied, assumes a target volume dose of 5 mL/kg PO, and 1 mL/kg IV

Formulations. The vehicle was 0.1 M citrate buffer pH 6. To make the vehicle, citric acid mono-anhydrous and tri-sodium citrate dehydrate were weighed out and dissolved in in water for injection (sterile) to 90% final volume. The pH was checked and adjusted to 6.00±0.1 using NaOH as required, then made to final volume and magnetically stirred until visually homogenous. The final pH of the vehicle was adjusted to 6.00±0.1 when required and filtered using a 0.22 m PVDF filter. The required amount of test item was weighed out and, using aseptic techniques for the IV preparation, the weighing was transferred to a suitable container and the weighing container rinsed using no more than 15% of final volume of vehicle. This was made up to 90% of the final volume with the vehicle and stirred using magnetic stirring. The pH was checked and no adjustments were required, therefore the formulation was made up to final volume with vehicle. The vehicle was then stirred for a minimum of 20 minutes using a magnetic stirrer and, whilst under magnetic stirring, the final pH and SG were checked and recorded. The formulation was then transferred quantitatively to final dispensing containers (Amber glass). Formulations were prepared on the day of administration and stored refrigerated pending transfer to the animal unit. Formulations were brought to room temperature prior to use.

Animals. Purebred beagle dogs from Marshall BioResources; 3 non-naïve females. Dogs were given a Teklad 2025C Dog Maintenance Diet, 400-500 grams daily. All dogs were 16-20 months of age at the start of treatment and at a weight 8.1 to 9.5 kg.

Administration. Phase A animals were given an intravenous (bolus) injection (once), one hour before feeding in the left or right cephalic vein, with a new sterile disposable needle per animal. Treated at constant doses in mg/kg, with a volume dose of 1 mL/kg body weight, calculated from the most recent recorded scheduled body weight. Phase B animals were dosed by oral gavage (once), one hour before feeding, using a suitably graduated syringe and a rubber catheter inserted via the mouth and down the esophagus. Treated at constant doses in mg/kg, with a volume dose of 5 mL/kg body weight, calculated from the most recently recorded scheduled body weight.

Pharmacokinetics. Psilocin is extremely prone to phenolic oxidation in plasma samples and degradation is extremely rapid in plasma. Therefore, ascorbic acid addition to plasma was required to prevent oxidation and stabilise this analyte. Stabilised incurred plasma samples were then divided into single-use aliquots to avoid repeated freeze-thaw cycles and prolonged bench-top exposure. The analytes have acceptable stability in whole blood on wet ice for the short duration required to process the samples to plasma and stabilise the plasma. To stabilize psilocin-$d_{10}$ in plasma, a solution of ascorbic acid 200 mM was prepared fresh on the day of use and was added 1:1 (v/v) to control plasma and the harvested plasma from incurred samples. Handling of matrix samples on wet ice was also used. Venous blood samples were obtained from all animals at the following times in relation to dosing: pre-dose (0), 0.25, 0.5, 1, 2, 4, 8 and 24 h. The jugular vein was used as the blood sample site, 1.5 mL blood volume. $K_2$EDTA was used as anticoagulant. Blood was collected onto wet ice ($K_2$EDTA tubes). Samples were allowed to stand on wet ice for a minimum of 5 minutes to fully cool, and then harvested to plasma using a refrigerated centrifuge. Centrifugation was performed at 2000 g for 10 minutes at 4° C. within 60 minutes of collection. Cellular fractions were discarded. After end of centrifugation, the samples were returned to wet ice ready for separation. Three/~200 µL aliquots were taken per sample, sampled accurately using a calibrated pipette. Plasma tubes used were 0.5 mL, pre spiked with 200 µL of ascorbic acid 200 mM. Ascorbic acid was prepared fresh on the day of use by dissolving 1.76 g of ascorbic acid in 50 mL water, the solution was mixed thoroughly. The solution was stored in amber glass at room temperature and used within 24 hours. Samples were mixed 1:1 v/v with ascorbic acid 200 mM stabilizer solution (50 µL pre-spiked to the plasma tubes). 200 µL of plasma was transferred and measured accurately using a calibrated pipette to a plasma tube pre-spiked with 200 µL of stabilizer and inverted several times to mix thoroughly. Mixing was completed within 30 minutes of plasma separation. The ratio of stabilizer to plasma was 1:1 (v/v); and the addition was checked for accuracy: If the volume of plasma recovered was found to be lower than 200 µL taken, then the amount of stabilizer was adjusted accordingly by removing a volume of stabilizer equal to the difference from the tube using a second calibrated pipette, prior to adding the plasma. Noncompartmental analysis using Phoenix® WinNonlin® was applied to the individual plasma concentration data.

Results. The mean pharmacokinetic parameters for phase A are summarized in Table 43, and the mean pharmacokinetic parameters for phase B are summarized in Table 44.

TABLE 43

Individual and Mean Pharmacokinetic Parameters for Psilocin-$d_{10}$ in Female Dog Plasma following a Single Intravenous (Bolus) Administration

| Phase | Dose Level (mg/kg) | Animal | $C_0$ (ng/ml) | $C_{max}$ (ng/ml) | DN $C_{max}$ (ng/ml)/ (mg/kg) | $T_{max}$ (h) | $AUC_{0-t}$ (h * ng/ mL) | $AUC_{0-inf}$ (h * ng/ ml) | DN $AUC_{0-inf}$ (h * ng/mL)/ (mg/kg) | $t_{1/2}$ (h) | CL (mL/ h/kg) | $V_{ss}$ (mL/ kg) |
|---|---|---|---|---|---|---|---|---|---|---|---|---|
| Phase A | 0.20 | 60F | 69.5 | 45.9 | 230 | 0.250 | 67.0 | 73.3 | 366 | 1.16 | 2730 | 3960 |
| | | 61F | 40.5 | 43.9 | 220 | 0.500 | 80.7 | 95.8 | 479 | 1.55 | 2090 | 4280 |
| | | 723F | 62.0 | 47.7 | 239 | 0.250 | 85.8 | 99.9 | 500 | 1.41 | 2000 | 3790 |
| | | Mean | 57.3 | 45.8 | 229 | 0.333 | 77.8 | 89.6 | 448 | 1.37 | 2270 | 4010 |
| | | SD | 15.1 | 1.90 | 9.50 | 0.144 | 9.73 | 14.3 | 71.7 | 0.195 | 398 | 248 |
| | | CV % | 26.3 | 4.15 | 4.15 | 43.3 | 12.5 | 16.0 | 16.0 | 14.2 | 17.5 | 6.18 |
| | | Median | 62.0 | 45.9 | 230 | 0.250 | 80.7 | 95.8 | 479 | 1.41 | 2090 | 3960 |
| | | Min | 40.5 | 43.9 | 220 | 0.250 | 67.0 | 73.3 | 366 | 1.16 | 2000 | 3790 |
| | | Max | 69.5 | 47.7 | 239 | 0.500 | 85.8 | 99.9 | 500 | 1.55 | 2730 | 4280 |
| | | N | 3 | 3 | 3 | 3 | 3 | 3 | 3 | 3 | 3 | 3 |

TABLE 44

Individual and Mean Pharmacokinetic Parameters for Psilocin-$d_{10}$ in Female Dog Plasma following a Single Oral (Gavage) Administration

| Phase | Dose Level (mg/kg) | Animal | $C_{max}$ (ng/ml) | DN $C_{max}$ (ng/ml)/ (mg/kg) | $T_{max}$ (h) | $AUC_{0-t}$ (h * ng/ mL) | $AUC_{0-inf}$ (h * ng/ ml) | DN $AUC_{0-inf}$ (h * ng/mL)/ (mg/kg) | $t_{1/2}$ (h) | F (%) |
|---|---|---|---|---|---|---|---|---|---|---|
| Phase B | 1.00 | 60F | 132 | 132 | 0.500 | 359 | 374 | 374 | 1.82 | 102 |
| | | 61F | 179 | 179 | 0.500 | 399 | 414 | 414 | 1.69 | 86.5 |
| | | 723F | 126 | 126 | 0.500 | 404 | 426 | 426 | 1.80 | 85.2 |
| | | Mean | 146 | 146 | 0.500 | 387 | 405 | 405 | 1.77 | 91.3 |
| | | SD | 29.0 | 29.0 | 0.00 | 24.9 | 27.1 | 27.1 | 0.0684 | 9.40 |
| | | CV % | 19.9 | 19.9 | 0.00 | 6.42 | 6.71 | 6.71 | 3.86 | 10.3 |
| | | Median | 132 | 132 | 0.500 | 399 | 414 | 414 | 1.80 | 86.5 |
| | | Min | 126 | 126 | 0.500 | 359 | 374 | 374 | 1.69 | 85.2 |
| | | Max | 179 | 179 | 0.500 | 404 | 426 | 426 | 1.82 | 102 |
| | | N | 3 | 3 | 3 | 3 | 3 | 3 | 3 | 3 |

F Bioavailability.
NA Not applicable.

The exposure of psilocin-$d_{10}$, as assessed by mean $C_{max}$ and $AUC_{0-t}$ values, was 45.8 ng/mL and 146 ng/mL ($C_{max}$) and 77.8 h*ng/mL and 387 h*ng/mL ($AUC_{0-t}$) when dosed intravenously and orally, respectively. The mean oral bioavailability of psilocin-$d_{10}$ at 1 mg/kg was 91.3%. Clearance (CL) was 2270 mL/h/kg, which is similar to the liver blood flow in a 10 kg dog (1854 mL/h/kg), indicating that psilocin-$d_{10}$ extraction by the liver is a major route of drug clearance. The volume of distribution at steady state ($V_{SS}$) was 4010 mL/kg, which exceeded the total body water of a 10 kg dog (604 mL/kg), indicating that psilocin-$d_{10}$ is highly distributed to the tissues following intravenous administration.

FIG. 152A shows plasma PK profile following IV and oral administration of psilocin-$d_{10}$. FIG. 152B shows that oral dosing of psilocin-$d_{10}$ to dogs yielded a fast onset and high bioavailability with elimination similar to an IV dose of psilocin-$d_{10}$. Peak plasma psilocin-$d_{10}$ levels occurred at 0.5 hr after oral administration. The last detectable plasma level after oral administration was at 9 hr. The % F of 91.3% indicates that nearly all the given oral dose was distributed to the systemic circulation. Elimination half-lives were similar between IV (1.35 hr) and oral (1.77 hr) doses.

Pharmacokinetics of Psilocin-$d_{10}$ and Psilocybin in the Male Beagle Dog Following Oral Administration by Powder in Capsule (PIC) or Orally Disintegrating Tablet (ODT)

The pharmacokinetic profile of psilocin-$d_{10}$ and psilocin from psilocybin after oral administration in oral disintegrating tablets (ODTs) or powder in capsule (PIC) dosage forms to male beagle dogs was compared.

Animals. Six, non-naïve, male Beagle dogs aged ca 2-5 years and weighing ca 10-15 kg at dosing were used. These animals were supplied by a recognized supplier of laboratory animals and are currently held as part of a colony (997433). Following study completion, animals were returned to the colony for further use.

Housing. Animals were housed and maintained according to established procedures as detailed in the appropriate Standard Operating Procedures (SOPs). Animals were uniquely identified by tattoo or by microchip. During the pre-trial holding periods, the animals were group housed in caging appropriate to the species. The dogs were housed singly for up to 4 h per day and in this period, had access to their daily ration of diet. The dogs were exercised during the study. Animals were checked regularly throughout the duration of the study. Any clinical signs were closely monitored and recorded. Animals had access to 200-400 g/day of Special Diet Services (SDS) D3 (E) SQC diet throughout the study. Mains quality tap water was available ad libitum.

Test items. Orally disintegration tablet (ODT) dosage forms were prepared from a stock mix having the following composition; water (86.5% w/w), gelatin (5% w/w, EP/USP/JP (Fish HMW)), mannitol (4% w/w, EP/USP), API (either psilocin-$d_{10}$ or psilocybin) (2% w/w), citric acid (2.5% w/w, anhydrous EP/USP). Typically, a mixture of gelatin and mannitol was prepared in water and the solution was heated to 60° C. for 10 min. The solution was cooled to 12° C. followed by addition of API. Finally, the pH was adjusted to the desired level. The solution was dosed into blister pockets and subjected to lyophilization by freezing at −90° C. for 4 minutes, placing the frozen product in a freezer (0° C.) for storage for ≥12 hours, and drying in a freeze dryer at a shelf temperature of 0° C. for 12 hours. Powder in capsule (PIC) dosage forms were prepared using 5 mg of either dry I-3 (psilocin-$d_{10}$)(pattern 1)(free base) or psilocybin as powder inside a capsule.

the psilocin-$d_{10}$ ODT and capsule groups were analyzed for psilocin-$d_{10}$. Plasma samples from the psilocybin ODT and capsule groups were analyzed for psilocybin and psilocin (psilocin-$d_0$).

Pharmacokinetic parameters. Noncompartmental pharmacokinetic parameters were determined from the psilocin-$d_{10}$ plasma concentration-time profiles using commercially available software (Phoenix® WinNonlin®).

Results. The data relating to the individual PK parameters are presented in Table 45.

TABLE 45

| Formulation | Compound Dosed | Analyte | Stats | T1/2 (hr) | Tmax (hr) | Cmax (ng/ml) | AUClast (hr * ng/ mL) | AUCINF_obs (hr * ng/mL) | Vz_F_obs (mL/kg) | Cl_F_obs (mL/kg/hr) |
|---|---|---|---|---|---|---|---|---|---|---|
| ODT | Psilocybin | Psilocin | Mean | 1.99 | 0.333 | 28.9 | 71.8 | 76.8 | 19200 | 6660 |
| | | | SD | 0.458 | 0.129 | 5.75 | 13.3 | 13.2 | 5570 | 1030 |
| PIC | Psilocybin | Psilocin | Mean | 1.66 | 0.708 | 41 | 89 | 93 | 13200 | 5520 |
| | | | SD | 0.183 | 0.641 | 11.6 | 16.5 | 17 | 2710 | 926 |
| ODT | Psilocin- | Psilocin- | Mean | 1.99 | 0.542 | 67.2 | 199 | 213 | 6900 | 2420 |
| | $d_{10}$ | $d_{10}$ | SD | 0.182 | 0.246 | 12.2 | 41.1 | 45 | 1090 | 436 |
| PIC | Psilocin- | Psilocin- | Mean | 2.01 | 1.08 | 60 | 181 | 195 | 7600 | 2610 |
| | $d_{10}$ | $d_{10}$ | SD | 0.19 | 0.492 | 11.5 | 29.7 | 31.9 | 1570 | 394 |
| | PI-d10/PI-PY | | ODT | 1.00 | | 2.33 | 2.77 | 2.77 | 0.36 | 0.36 |
| | | | PIC | 1.21 | | 1.46 | 2.03 | 2.10 | 0.58 | 0.47 |

*Psilocybin dose of 0.5 mg/kg is equivalent to 0.377 mg/kg of PI-$d_{10}$; The values in the table have not been correct to a PI-$d_{10}$ mg/kg equivalent dose Dose levels.

Psilocin-$d_{10}$ as ODT contains 5 mg of active; nominal 0.5 mg/kg active

Psilocin-$d_{10}$ as PIC contains 5 mg of active; nominal 0.5 mg/kg active

Psilocybin as ODT contains 5 mg of active; nominal 0.5 mg/kg active

Psilocybin as PIC contains 5 mg of active; nominal 0.5 mg/kg active

Experimental design. This is a cross over study with at least a 7-day washout period between oral administrations. Animals received 5 mg of each test item either via ODT or by PIC. Each animal received a dose level of ca 0.5 mg/kg, but may vary according to the most recent bodyweight of each animal. Bodyweights were recorded for each animal prior to dosing. Oral administration was performed with either an ODT or PIC containing either psilocin-$d_{10}$ or psilocybin. Capsules were placed at the back of the throat and the animals were encouraged to swallow. A flush of 5 mL of water was given if required. Orally disintegrating tablets were placed under the tongue (sublingual). Animal's mouth were held closed for 10 seconds to ensure the tablet was fully dissolved.

Sampling collection. PK samples (ca 1 mL) were collected from the jugular vein by venepuncture into tubes containing $K_2$EDTA anticoagulant at the following sampling times: Pre-dose, 0.083 (5 min), 0.16 (10 min), 0.25, 0.5, 60, 120, 240 min, 8 and 24 hrs post-dose. Immediately following collection, samples were inverted to ensure mixing with anti-coagulant and placed on wet ice. As soon as practically possible, plasma were generated by centrifugation (2500 g, 10 min, 4° C.). All plasma generated was transferred from $K_2$EDTA tube to aliquot A (per animal/timepoint). Then, 300 µL of plasma and 300 µL (1:1 (v/v)) of 200 mM ascorbic acid were decanted into Aliquot B and stored in a freezer set to maintain a temperature of −65° C., until analysis.

Bioanalysis. Plasma samples were analyzed using an established LC-MS/MS assay (BQL were set at zero prior to Cmax; BQL undefined after Cmax). Plasma samples from The results are also graphically represented in FIGS. 153A-153B, which show the plasma concentration-time profiles for PI after psilocybin dosing and psilocin-$d_{10}$ (ODT and PIC dosage forms), respectively, FIG. 154 showing the exposure comparison between psilocybin and psilocin-$d_{10}$ as assessed by Cmax, and FIG. 155 showing the exposure comparison between psilocybin and psilocin-$d_{10}$ as assessed by AUCinf.

As can be seen from these graphs, psilocin-$d_{10}$ and psilocin after psilocybin ODT formulation exposure is not significantly ($p>0.5$) different than PIC exposure. The ODTs produced a faster onset of action compared to PIC dosage forms as measured by time to maximum plasma concentrations—the time to maximum plasma concentration was twice as fast after ODT compared to PIC (psilocin-$d_{10}$ median Tmax was 0.5 and 1 hr, ODT and PIC, respectively; psilocin after psilocybin median Tmax was 0.25 and 0.5 hr, ODT and PIC, respectively). However, psilocin-$d_{10}$ exposure was found to be twice as high as psilocin exposure after administration of psilocybin, independent of formulation.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

Accordingly, the preceding merely illustrates the principles of the methods and compositions. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the following.

The invention claimed is:

1. A crystalline pharmaceutically acceptable salt of a compound of Formula (I), as determined by X-ray powder diffraction, or a stereoisomer, or solvate thereof (I)

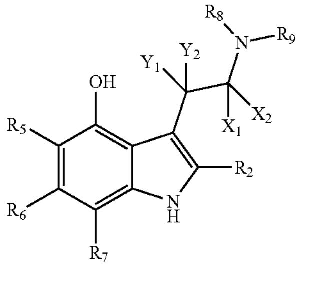

wherein:

$R_2$, $R_5$, $R_6$, and $R_7$ are independently selected from the group consisting of hydrogen and deuterium, $R_8$ and $R_9$ are independently selected from the group consisting of —$CH_3$ and —$CD_3$, $X_1$ and $X_2$ are deuterium, and $Y_1$ and $Y_2$ are independently selected from the group consisting of hydrogen and deuterium.

2. The crystalline pharmaceutically acceptable salt of claim 1, wherein $R_8$ and $R_9$ are —$CH_3$.

3. The crystalline pharmaceutically acceptable salt of claim 1, wherein $R_8$ and $R_9$ are —$CD_3$.

4. The crystalline pharmaceutically acceptable salt of claim 1, wherein $Y_1$ and $Y_2$ are deuterium.

5. The crystalline pharmaceutically acceptable salt of claim 1, wherein $Y_1$ and $Y_2$ are hydrogen.

6. The crystalline pharmaceutically acceptable salt of claim 1, wherein the compound of Formula (I) is selected from the group consisting of:

(I-1)

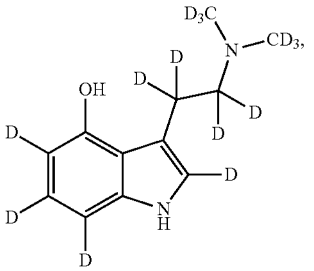

(I-2)

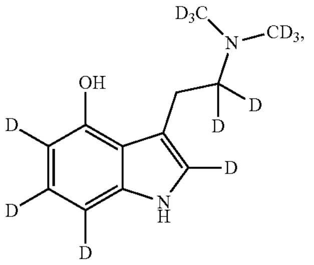

(I-3)

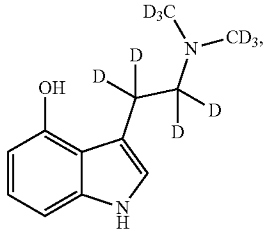

(I-4)

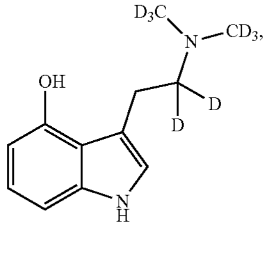

-continued (I-5)

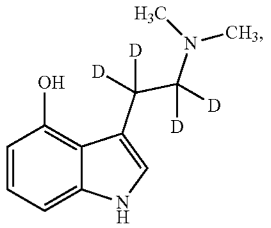

and (I-6)

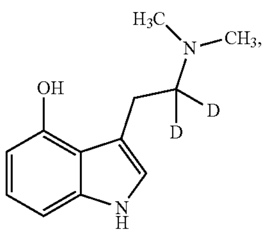

7. The crystalline pharmaceutically acceptable salt of claim 1, wherein the compound of Formula (I) is (I-3)

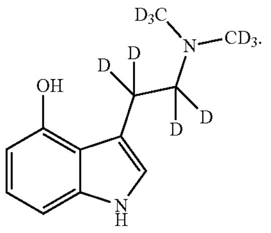

8. The crystalline pharmaceutically acceptable salt of claim 1, which is a crystalline benzenesulfonate salt of the compound of Formula (I).

9. The crystalline pharmaceutically acceptable salt of claim 1, which is a crystalline benzoate salt of the compound of Formula (I).

10. The crystalline pharmaceutically acceptable salt of claim 1, which is a crystalline tartrate salt of the compound of Formula (I).

11. The crystalline pharmaceutically acceptable salt of claim 1, which is a crystalline benzenesulfonate salt of 3-(2-(bis(methyl-$d_3$) amino) ethyl-1,1,2,2-$d_4$)-1H-indol-4-ol (I-3a).

12. The crystalline pharmaceutically acceptable salt of claim 11, wherein the crystalline benzenesulfonate salt of 3-(2-(bis(methyl-$d_3$) amino) ethyl-1,1,2,2-$d_4$)-1H-indol-4-ol (I-3a) is characterized by an X-ray powder diffraction pattern containing at least three characteristic peaks at diffraction angles (2θ±0.2°) selected from the group consisting of 7.023°, 7.767°, 11.822°, 12.550°, 12.860°, 13.994°, 15.521°, 18.436°, 19.503°, 20.760°, 21.070°, 22.007°, 22.745°, 23.340°, 24.187°, 25.532°, 26.880°, 27.856°, 28.163°, 31.267°, 33.024°, 35.030°, 36.835°, 39.312°, 40.545°, and 40.988°.

13. The crystalline pharmaceutically acceptable salt of claim 1, which is a crystalline benzoate salt of 3-(2-(bis (methyl-$d_3$) amino) ethyl-1,1,2,2-$d_4$)-1H-indol-4-ol (I-3j).

14. The crystalline pharmaceutically acceptable salt of claim 13, wherein the crystalline benzoate salt of 3-(2-(bis(methyl-$d_3$) amino) ethyl-1,1,2,2-$d_4$)-1H-indol-4-ol (I-3j) is characterized by an X-ray powder diffraction pattern containing at least three characteristic peaks at diffraction angles (2θ±0.2°) selected from the group consisting of 9.486°, 11.006°, 12.379°, 13.428°, 14.608°, 15.446°, 16.389°, 18.247°, 18.977°, 19.346°, 19.831°, 20.868°, 21.447°, 22.860°, 23.878°, 24.944°, 25.737°, 26.144°, 26.341°, 26.990°, 27.708°, 28.595°, 30.048°, 30.763°, 31.127°, 31.839°, 32.800°, 34.460°, 35.444°, 37.725°, and 38.597°.

15. The crystalline pharmaceutically acceptable salt of claim 1, which is a crystalline tartrate salt of 3-(2-(bis (methyl-$d_3$) amino) ethyl-1,1,2,2-$d_4$)-1H-indol-4-ol (I-3b).

16. The crystalline pharmaceutically acceptable salt of claim 15, wherein the crystalline tartrate salt of 3-(2-(bis (methyl-$d_3$) amino) ethyl-1,1,2,2-$d_4$)-1H-indol-4-ol (I-3b) is characterized by an X-ray powder diffraction pattern containing at least three characteristic peaks at diffraction angles (2θ±0.2°) selected from the group consisting of 6.732°, 12.708°, 13.470°, 14.774°, 15.921°, 16.268°, 17.295°, 18.869°, 20.079°, 20.208°, 20.877°, 21.894°, 22.657°, 23.491°, 23.702°, 24.636°, 24.882°, 25.569°, 26.685°, 27.060°, 27.502°, 28.179°, 28.597°, 29.035°, 29.257°, 29.527°, 31.017°, 31.527°, 32.059°, 32.307°, 33.012°, 34.024°, 34.388°, 34.905°, 35.361°, 36.183°, 37.372°, 37.764°, 38.657°, and 41.049°.

17. The crystalline pharmaceutically acceptable salt of claim 1, wherein the crystalline pharmaceutically acceptable salt of the compound of Formula (I) has a water solubility from about 1 mg/mL to about 400 mg/mL.

18. A crystalline compound of Formula (I), or a stereoisomer or a solvate thereof (I)

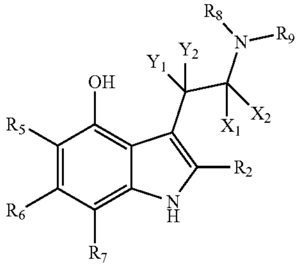

wherein:

$R_2$, $R_5$, $R_6$, and $R_7$ are independently selected from the group consisting of hydrogen and deuterium, $R_8$ and $R_9$ are independently selected from the group consisting of —$CH_3$ and —$CD_3$, $X_1$ and $X_2$ are deuterium, and $Y_1$ and $Y_2$ are independently selected from the group consisting of hydrogen and deuterium.

19. The crystalline compound of claim 18, which is crystalline form of 3-(2-(bis(methyl-$d_3$) amino) ethyl-1,1,2, 2-$d_4$)-1H-indol-4-ol (I-3) characterized by an X-ray powder diffraction pattern containing at least three characteristic peaks at diffraction angles (2θ±0.2°) selected from the group consisting of 7.582°, 8.395°, 9.647°, 10.444°, 11.319° 12.614°, 13.372°, 14.222°, 15.157°, 16.524°, 16.787°, 17.693°, 19.468°, 19.699°, 20.901°, 21.132°, 21.859°, 22.547°, 23.699°, 24.630°, 25.034°, 25.264°, 26.867°, 27.399°, 27.929°, 28.219°, 28.871°, 29.430°, 30.120°, 30.675°, 31.373°, 32.365°, 33.880°, 34.418°, 34.792°, 35.884°, 36.254°, 37.156°, 38.200°, and 38.417°.

20. The crystalline compound of claim 18, which is crystalline form of 3-(2-(bis(methyl-$d_3$) amino) ethyl-1,1,2,2-$d_4$)-1H-indol-4-ol (I-3) characterized by an X-ray powder diffraction pattern containing at least three characteristic peaks at diffraction angles (2θ±0.2°) selected from the group consisting of 8.124°, 8.357°, 10.059°, 12.630°, 13.420°, 13.743°, 14.053°, 15.220°, 16.272°, 16.763°, 16.954°, 17.328°, 17.662°, 18.062°, 18.742°, 19.413°, 19.658°, 20.172°, 20.836°, 21.267°, 21.833°, 22.213°, 22.504°, 23.334°, 23.701°, 24.385°, 25.431°, 25.721°, 26.049°, 27.291°, 28.368°, 30.349°, 30.656°, 31.337°, 31.538°, 32.091°, 35.870°, 38.514°, and 41.361°.

21. A citrate salt of a compound of Formula (I), as determined by X-ray powder diffraction, or a stereoisomer, or solvate thereof (I)

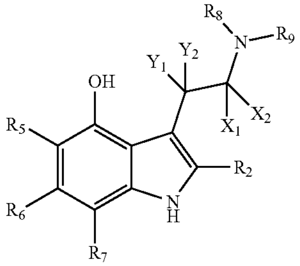

wherein:

$R_2$, $R_5$, $R_6$, and $R_7$ are independently selected from the group consisting of hydrogen or deuterium, $R_8$ and $R_9$ are independently selected from the group consisting of $-CH_3$ and $-CD_3$, $X_1$ and $X_2$ are deuterium, and $Y_1$ and $Y_2$ are independently selected from the group consisting of hydrogen and deuterium.

22. The citrate salt of claim 21, which is a citrate salt of 3-(2-(bis(methyl-$d_3$) amino) ethyl-1,1,2,2-$d_4$)-1H-indol-4-ol (I-3e).

23. The citrate salt of claim 22, wherein the citrate salt of 3-(2-(bis(methyl-$d_3$) amino) ethyl-1,1,2,2-$d_4$)-1H-indol-4-ol (I-3e) is amorphous by X-ray powder diffraction.

* * * * *